US007309760B2

(12) United States Patent
O'Brien et al.

(10) Patent No.: US 7,309,760 B2
(45) Date of Patent: Dec. 18, 2007

(54) REPEAT SEQUENCES OF THE CA125 GENE AND THEIR USE FOR DIAGNOSTIC AND THERAPEUTIC INTERVENTIONS

(75) Inventors: Timothy J. O'Brien, Little Rock, AR (US); John B. Beard, Little Rock, AR (US); Lowell J. Underwood, Little Rock, AR (US)

(73) Assignee: The Board of Trustees of the University of Arkansas, Little Rock, AK (US)

( * ) Notice: Subject to any disclaimer, the term of this patent is extended or adjusted under 35 U.S.C. 154(b) by 1003 days.

(21) Appl. No.: 09/965,738

(22) Filed: Sep. 27, 2001

(65) Prior Publication Data

US 2003/0143667 A1 Jul. 31, 2003

Related U.S. Application Data

(60) Provisional application No. 60/284,175, filed on Apr. 17, 2001, provisional application No. 60/299,380, filed on Jun. 19, 2001.

(51) Int. Cl.
*C07K 1/00* (2006.01)
*C07K 16/00* (2006.01)
(52) U.S. Cl. .................................... 530/350; 530/387.1
(58) Field of Classification Search ................ 530/350
See application file for complete search history.

(56) References Cited

U.S. PATENT DOCUMENTS

| 6,335,194 B1 | 1/2002 | Bennett et al. | ............. 435/375 |
| 6,451,602 B1 | 9/2002 | Popoff et al. | ............... 435/375 |

FOREIGN PATENT DOCUMENTS

| EP | 0 288 082 | 10/1988 |
| WO | WO 00/36107 | 6/2000 |
| WO | WO 02/092836 | 11/2002 |

OTHER PUBLICATIONS

Accession No. AA640072, GenBank nucleotide sequence database, Oct. 27, 1997.
"More than 15 years of CA125: What is known about the antigen, its structure and its function" T.J. O'Brien, et al. The International Journal of Biological Markers, vol. 13, No. 4, pp. 188-195.
"Isolation and Characterization of Ovarian Cancer Antigen CA125 Using a New Monoclonal Antibody (VK-8): Identification as a Mucin-type Molecule" Kenneth O. Lloyd, et al. Int. J. Cancer: 71, 842-850 (1997).
"Immunohistochemical Characterization of 22 Monoclonal Antibodies against the CA125 Antigen 2nd Report from the ISOBM TD-1 Workshop" M. Nap, et al. Tumor Biol. 1996: 17: 325-331.
"Human Mucin Gene MUC5B, the 10.7-kb Large Central Exon Encodes Various Alternate Subdomains Resulting in a Super-repeat" Jean-Luc Desseyn, et al. The Journal of Biological Chemistry, vol. 272, No. 6, Issue of Feb. 7, pp. 3168-3178 (1997).
"Isolation of the Murine Nbr1 Gene Adjacent to the Murine Brca1 Gene" Julie Chambers, et al. Genomics 38, 305-313 (1996).
http://www.ncbi.nim.nih.gov/entrez/viewer.fcgi?db=nucleotide &val=2566012 "Nucleotide" Lee Helman, M.D., et al. NCBI Sequence Viewer.
"Molecular Cloning of the CA125 Ovarian Cancer Antigen" Beatrice W.T. Yin, et al. The Journal of Biological Chemistry, vol. 276, No. 29, Issue of Jul. 20, pp. 27371-27375 (2001).
"The CA125 Gene: An Extracellular Superstructure Dominated by Repeat Sequences" Timothy J. O'Brien, et al. Tumor Biol. 2001; 22: 348-366.
"The CA125 Gene: A Newly Discovered Extension of the Glycosylated N-Terminal Domain Doubles the Size of This Extracellular Superstructure" Timothy J. O'Brien, et al. Tumor Biol 2002; 23: 154-169.
Bast RC et al., A radioimmunoassy using a monoclonal antibody to monitor the course of epithelial ovarian cancer, *N Engl J Med.* 309:883-887 (1983).
Bon GC et al., Serum tumer marker immunoassays in gynecologic oncology: Establishment of reference values, *Am J Obstet. Gynecol.* 174:107-114 (1996).
Clemons-Miller, A et al. Intrathecal Cytotoxic T-Cell Immunotherapy for Metastatic Leptomeningeal Melanoma. *Clinical Cancer Research* 7:917s-924s, Mar. 2001 (Suppl.).
Desseyn JL et al., Human mucin gene MUC5B, the 10.7-kb large central exon encodes various alternate subdomains resulting in a super-repeat. Structural evidence for a 11p15.5 gene family, *J Biol. Chem.* 272(6):3168-3178 (1997).
Fendrick, JL et al. Characterization of CA 125 Synthesized by the Human Epithelial Amnion WISH Cell Line. *Tumor Biol* 1993; 14:310-318.
Fendrick, JL et al. CA125 Phosphorylation Is Associated with Its Secretion from the WISH Human Amnion Cell Line. *Tumor Biol* 1997; 18:278-289.
Foon, KA et al., Are solid tumor anti-idotype vaccines ready for prime time?, *Clinical Cancer Research* 7:1112-1115 (2001).
Gendler SJ et al., Epithelial mucin genes, *Annu. Rev. Physiol.* 57:607-634 (1995).

(Continued)

*Primary Examiner*—Shanon Foley
*Assistant Examiner*—Peter J. Reddig
(74) *Attorney, Agent, or Firm*—Cyr & Associates, P.A.

(57) ABSTRACT

The CA125 gene has been cloned and multiple repeat sequences as well as the carboxy terminus have been identified. The CA125 molecule comprises three major domains: an extracellular amino terminal domain (Domain 1); a large multiple repeat domain (Domain 2); and a carboxy terminal domain (Domain 3) which includes a transmembrane anchor with a short cytoplasmic domain. The amino terminal domain has numerous O-glycosylation sites. Domain 2 is a repeat domain comprising homologous repeat units of 156 amino acids. More than 60 repeat units have been identified, sequenced, and contiguously placed in the CA125 domain structure. The repeat units are the sites of OC125 and M11 antibody binding. The CA125 molecule is anchored at its carboxy terminal through a transmembrane domain and a short cytoplasmic tail.

1 Claim, 17 Drawing Sheets

OTHER PUBLICATIONS

Gum Jr., JR, Mucin genes and the proteins they encode: Structure, diversity and regulation, *Am J Respir. Cell Mol. Biol.* 7:557-564 (1992).

Gum JR, Human Mucin Glycoproteins: Varied Structures Predict Diverse Properties and Specific Functions. Biochemical Society Transactions. 23(4):795-799, 1995.

Hardardottir H et al., Distribution of CA125 in embryonic tissue and adult derivatives of the fetal periderm, *Am J Obstet. Gynecol.* 163;6(1):1925-1931 (1990).

Konish I et al., Epidermal growth factor enhances secretion of the ovarian tumor-associated cancer antigen CA125 from the human amnion WISH cell line, *J Soc. Gynecol. Invest.* 1:89-96 (1994).

Lloyd Ko et al., Synthesis and secretion of the ovarian cancer antigen CA125 by the human cancer cell line NIH: OVCAR-3, *Tumor Biology* 22, 77-82 (2001).

Lloyd Ko et al., Isolation and characterization of ovarian cancer antigen CA125 using a new monoclonal antibody (VK-8): Identification as a ucin-type molecule, *Int. J. Cancer*, 71:842-850 (1997).

Marshall E, DNA Sequencing: Genome teams adjust to shotgun marriage, *Science* 292:1982-1983 (2001).

Nap M et al., Immunohistochemical characterization of 22 monoclonal antibodies against the CA125 antigen: $2^{nd}$ report from the ISOBM TD-1 workshop, Tumor Biology 17:325-331 (1996).

Nustad K et al., CA125—epitopes and molecular size, *Int. J of Biolog. Markers*, 13(4)196-199 (1998).

Nustad K et al., Specificity and affinity of 26 monoclonal antibodies against the CA125 antigen: First report from the ISOBM TD-1 workshop *Tumor Biology* 17:196-219 (1996).

O'Brien, TJ et al. CA 125 Antigen in Human Amniotic Fluid and Fetal Membranes. *Am J Obstet Gynecol* 155:50-55 Jul. 1986.

O'Brien, TJ et al. New Monoclonal Antibodies Identify the Glycoprotein Carrying the CA 125 Epitope. *Am J Obstet Gynecol* 1991; 165-1857-64.

O'Brien, TJ et al. More Than 15 Years of CA 125: What Is Known about the Antigen, Its Structure and Its Function. *The International Journal of Biological Markers* 13:188-195 (1998).

Quirk, JR et al. CA 125 in Tissues and Amniotic Fluid During Pregnancy. *Am J Obstet Gynecol* 159:655-649 (1988).

Santin, AD et al. Induction of Ovarian Tumor-Specific CD8+ Cytotoxic T Lymphocytes by Acid-Eluted Peptitde-Pulsed Autologous Dendritic Cells. *Obstetrics & Gynecology* 2000; 96:422-30.

Santin, AD et al. In vitro Induction of Tumor-Specific Human Lymphocyte Antigen Class I-Restricted CD8+ Cytotoxic T Lymphocytes by Ovarian Tumor Antigen-Pulsed Autologous Dendritic Cells from Patients with Advanced Ovarian Cancer. *Am J Obstet Gynecol* 2000; 183:601-9.

Shigesmasa, K, et al. p21: a Monitor of p53 Dysfunction in Ovarian Neoplasia. International Journal of Gynecologic Cancer 7:296-303, 1997.

Shigesmasa, K, et al. p16 Overexpression: A Potential Early Indicator of Transormation in Ovarian Carcinoma. J Soc Gynecol Invest 4:95-102, 1997.

Verma M et al., Mucin genes: Structure, expression and regulation, *Glycoconjugate J.* 11:172-179 (1994).

Wagner, U. et al. Immunological Responses to the Tumor-Associated Antigen CA125 in Patients with Advanced Ovarian Cancer Induced by the Murine Monoclonal Anti-Idiotype Vaccine ACA125. *HYBRIDOMA* 16:33-40 (1997).

Wagner U et al., Immunological consolidation of ovarian carcinoma recurrences with monoclonal anti-idiotype antibody ACA125: Immune responses and survival in palliative treatment, *Clin. Cancer Res.* 7:1112-1115 (2001).

Williams, SJ et al. MUC13, a Novel Human Cell Surface Mucin Expressed by Epithelial and Hemopoietic Cells. The Journal of Biological Chemistry 276(21):18327-18336, 2001.

Yin Twt et al., Molecular cloning of the CA125 ovarian cancer antigen. Identification as a new mucin (MUC16), *J Biol. Chem.* 276:27371-27375 (2001).

Zurawski VR et al., Tissue distribution and characteristics of the CA125 antigen, *Cancer Rev.* 11-12:102-118 (1998).

U.S. Appl. No. 10/715,066, filed Nov. 17, 2003, O'Brien et al.

U.S. Appl. No. 10/475,117, filed Oct. 16, 2003, O'Brien et al.

O'Brien, et al. "The CA125 Gene: An Extracellular Superstructure Dominated by Repeat Sequences" Tumor Biology, vol. 22, 2001 pp. 348-366.

Argueso, et al. "MUC16 Mucin is Expressed by the Human Ocular Surface Epithelia and Carries the H185 Carbohydrate Epitope" Invest Ophthalmol Vis Sci Jun. 2003;44(6):2487-95.

Figure 3 (SEQ ID NOS: 158, 159, 160, and 161)

Figure 5 (SEQ ID NO: 150)

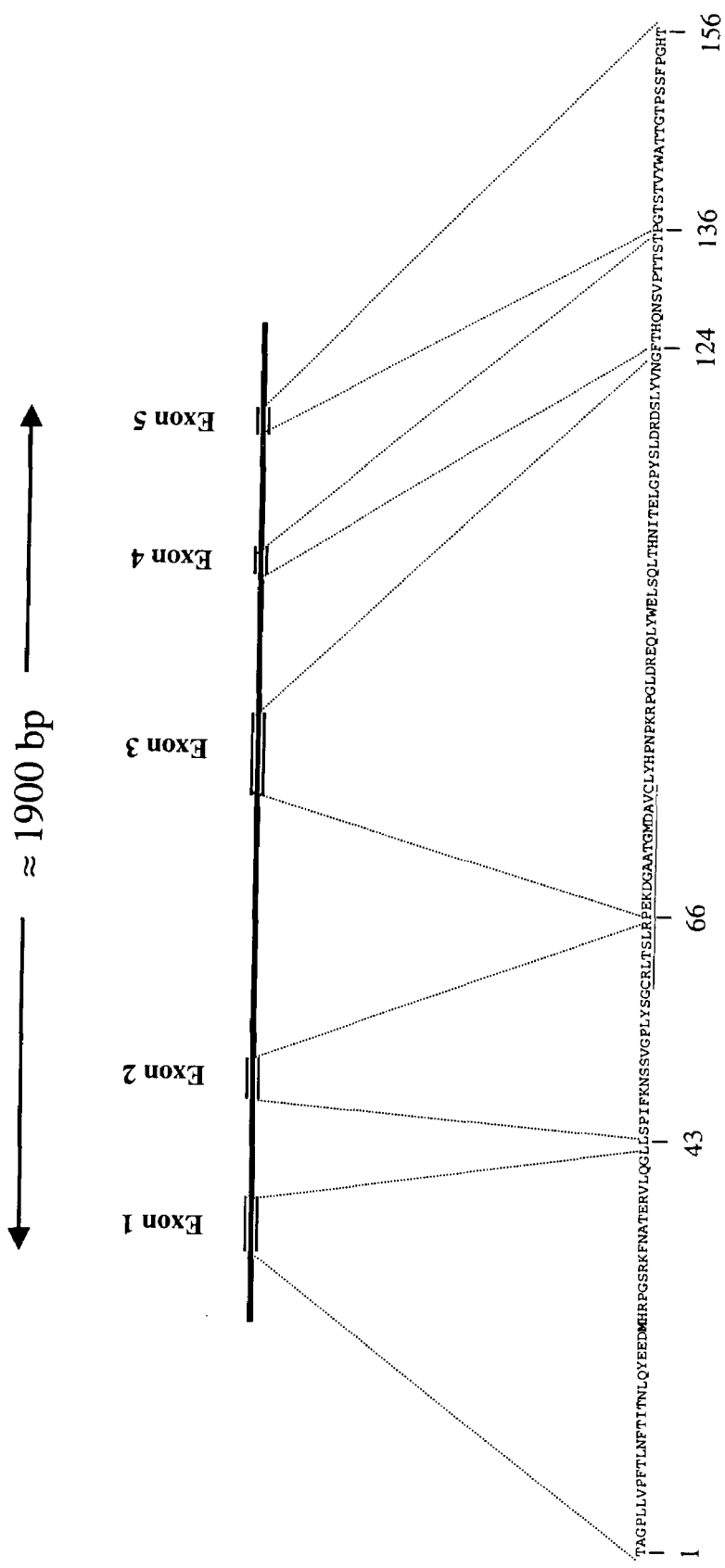
Figure 7B (SEQ ID NO: 163)

Exon 1

```
1                                          42
ATVPFMVPFTLNFTITNLQYEEDMRHPGSRKFNATERELQGL (SEQ ID NO: 164)
TAVPLLVPFTLNFTITNLQYGEDMRHPGSRKFNTTERVLQGL (SEQ ID NO: 165)
VPGPLLVPFTLNFTITNLQYEEAMRHPGSRKFNTTERVLQGL (SEQ ID NO: 166)
APGPLLVPFTLNFTITNLQYEEDMRHPGSRKFSTTERVLQGL (SEQ ID NO: 167)
APGPLLVPFTLNFTITNLQYEEDMRHPGSRKFNTTERVLQGL (SEQ ID NO: 168)
APGPLLVPFTLNFTITNLQYEVDMRHPGSRKFNTTERVLQGL (SEQ ID NO: 169)
SAGPLLVPFTLNFTITNLQYEEDMRHPGSRKFNTTERVLQGL (SEQ ID NO: 170)
AAGPLLMPFTLNFTITNLQYEEDMRRTGSRKFNTMESVLQGL (SEQ ID NO: 171)
TASPLLVLFTINCTITNLQYEEDMRRTGSRKFNTMESVLQGL (SEQ ID NO: 172)
AAGPLLVPFTLNFTITNLQYGEDMGHPGSRKFNTTERVLQGL (SEQ ID NO: 173)
TAGPLLIPFTLNFTITNLQYGEDMGHPGSRKFNTTERVLQGL (SEQ ID NO: 174)
TAGPLLVPFTLNFTITNLQYGEDMGHPGSRKFNTTERVLQGL (SEQ ID NO: 175)
TAGPLLVLFTLNFTITNLKYEEDMHRPGSRKFNTTERVLQTL (SEQ ID NO: 176)
TAGPLLVPFTLNFTITNLQYEEDMHRPGSRKFNATERVLQGL (SEQ ID NO: 177)
TAGPLLVPFTLNFTITNLQYEEDMHRPGSRRFNTTERVLQGL (SEQ ID NO: 178)
TAGPLLVPFTLNFTITNLQYEEDMHRPGSRKFNTTERVLQGL (SEQ ID NO: 179)
APVPLLIPFTLNFTITNLQYEEDMHRPGSRKFNTTERVLQGL (SEQ ID NO: 180)
ATGPVLLPFTLNFTITNLQYEEDMHRPGSRKFNTTERVLQGL (SEQ ID NO: 181)
AAGPLLVPFTLNFTITNLQYEEDMHHPGSRKFNTTERVLQGL (SEQ ID NO: 182)
SAGPLLVPFTLNFTITNLQYEEDMHHPGSRKFNTTERVLQGL (SEQ ID NO: 183)
TASPLLVLFTINFTITNQRYEENMHHPGSRKFNTTERVLQGL (SEQ ID NO: 184)
TASPLLVLFTINFTITNLRYEENMHHPGSRKFNTTERVLQGL (SEQ ID NO: 185)
EPGPLLIPFTFNFTITNLHYEENMQHPGSRKFNTTERVLQGL (SEQ ID NO: 186)
EPGPLLIPFTFNFTITNLRYEENMQHPGSRKFNTTERVLQGL (SEQ ID NO: 187)
APVPLLIPFTLNFTITNLHYEENMQHPGSRKFNTTERVLQGL (SEQ ID NO: 188)
APVPLLIPFTLNFTITDLHYEENMQHPGSRKFNTTERVLQGL (SEQ ID NO: 189)
AASPLLVLFTLNGTITNLRYEENMQHPGSRKFNTTERVLQGL (SEQ ID NO: 190)
TAGPLLVPFTLNFTITNLKYEEDMHCPGSRKFNTTERVLQSL (SEQ ID NO: 191)
AASHLLILFTLNFTITNLRYEENMW.PGSRKFNTTERVLQGL (SEQ ID NO: 192)
TGVVSEEPFTLNFTINNLRYMADMGQPGSLKFNITDNVMKHL (SEQ ID NO: 193)
AMGYHLKTLTLNFTISNLQYSPDMGKGSATFNSTEGVLQHLL (SEQ ID NO: 194)
```

Figure 7C

Exon 2

```
43                      65
LKPLFRNSSLEYLYSGCRLASLR   (SEQ ID NO: 195)
LKPLFKNTSVSSLYSGCRLTLLR   (SEQ ID NO: 196)
LKPLFKNTSVGPLYSGCRLTLLR   (SEQ ID NO: 197)
LKPLFKSTSVGPLYSGCRLTLLR   (SEQ ID NO: 198)
LKPLFKSTSVGPLYSSCRLTLLR   (SEQ ID NO: 199)
LKPLFKNTSVGPLYSGCRLTSLR   (SEQ ID NO: 200)
LGPIFKNTSVGPLYSGCRLTSLR   (SEQ ID NO: 201)
LGPMFKNTSVGLLYSGCRLTLLR   (SEQ ID NO: 202)
LGPMFKNTSVGPLYSGCRLTLLR   (SEQ ID NO: 203)
LGPMFKNTSVGPLYSGCRLTSLR   (SEQ ID NO: 204)
LGPLFKNSSVGPLYSGCRLISLR   (SEQ ID NO: 205)
LGPLFKNSSVDPLYSGCRLTSLR   (SEQ ID NO: 206)
LSPIFKNSSVGPLYSGCRLTSLR   (SEQ ID NO: 207)
LSPIFKNTSVGPLYSGCRLTLLR   (SEQ ID NO: 208)
LSPLFQRSSLGARYTGCRVIALR   (SEQ ID NO: 209)
LRPLFKNTSVSSLYSGCRLTLLR   (SEQ ID NO: 210)
LRPLFKNTSVGPLYSGSRLTLLR   (SEQ ID NO: 211)
LRPLFKNTSIGPLYSSCRLTLLR   (SEQ ID NO: 212)
LRPLFKSTSVGPLYSGCRLTLLR   (SEQ ID NO: 213)
LRPVFKNTSVGLLYSGCRLTLLR   (SEQ ID NO: 214)
LRPVFKNTSVGPLYSGCRLTLLR   (SEQ ID NO: 215)
LRSLFKSTSVGPLYSGCRLTLLR   (SEQ ID NO: 216)
LRSLFKSTSVGPLYSGCRLTSLR   (SEQ ID NO: 217)
LTPLFKNTSVGPLYSGCRLTLLR   (SEQ ID NO: 218)
LTPLFRNTSVSSLYSGCRLTLLR   (SEQ ID NO: 219)
LMPLFKNTSVSSLYSGCRLTLLR   (SEQ ID NO: 220)
RPLFQKSSM.GPFYLGCQLISLR   (SEQ ID NO: 221)
```

Figure 7C

Exon 3

```
66                                                                 123
PEKDSSAMAVDAICTHRPDPEDLGLDRERLYWELSNLTNGIQELGPYTLDRNSLYVNG (SEQ ID NO: 222)
PEKDGAATGVDAICTHRLDPKSPGLNREQLYWELSKLTNDIEELGPYTLDRNSLYVNG (SEQ ID NO: 223)
PKKDGAATGVDAICTHRLDPKSPGLNREQLYWELSKLTNDIEELGPYTLDRNSLYVNG (SEQ ID NO: 224)
PEKDGTATGVDAICTHHPDPKSPRLDREQLYWELSQLTHNITELGHYALDNDSLFVNG (SEQ ID NO: 225)
PEKDGEATGVDAICTHRPDPTGPGLDREQLYLELSQLTHSITELGPYTLDRDSLYVNG (SEQ ID NO: 226)
PEKDGAATGMDAVCLYHPNPKRPGLDREQLYWELSQLTHNITELGPYSLDRDSLYVNG (SEQ ID NO: 227)
PEKDGAATGMDAVCLYHPNPKRPGLDREQLYCELSQLTHNITELGPYSLDRDSLYVNG (SEQ ID NO: 228)
PEKDGAATRVDAACTYRPDPKSPGLDREQLYWELSQLTHSITELGPYTLDRVSLYVNG (SEQ ID NO: 229)
PKKDGAATKVDAICTYRPDPKSPGLDREQLYWELSQLTHSITELGPYTQDRDSLYVNG (SEQ ID NO: 230)
PKKDGAATKVDAICTYRPDPKSPGLDREQLYWELSQLTHSITELGPYTQDRDSLYNVG (SEQ ID NO: 231)
PEKDGAATRVDAVCTHRPDPKSPGLDRERLYWKLSQLTHGITELGPYTLDRHSLYVNG (SEQ ID NO: 232)
PEKDGVATRVDAICTHRPDPKIPGLDRQQLYWELSQLTHSITELGPYTLDRDSLYVNG (SEQ ID NO: 233)
SEKDGAATGVDAICIHHLDPKSPGLNRERLYWELSQLTNGIKELGPYTLDRNSLYVNG (SEQ ID NO: 234)
SEKDGAATGVDAICTHRLDPKSPGLDREQLYWELSQLTNGIKELGPYTLDRNSLYVNG (SEQ ID NO: 235)
SEKDGAATGVDAICTHRLDPKSPGVDREQLYWELSQLTNGIKELGPYTLDRNSLYVNG (SEQ ID NO: 236)
SEKDGAATGVDAICTHRVDPKSPGVDREQLYWELSQLTNGIKELGPYTLDRNSLYVNG (SEQ ID NO: 237)
SEKDGAATGVDAICTHHLNPQSPGLDREQLYWQLSQMTNGIKELGPYTLDRNSLYVNG (SEQ ID NO: 238)
PEKRGAATGVDTICTHRLDPLNPGLDREQLYWELSKLTRGIIELGPYLLDRGSLYVNG (SEQ ID NO: 239)
PEKNGAATGMDAICSHRLDPKSPGLNREQLYWELSQLTHGIKELGPYTLDRNSLYVNG (SEQ ID NO: 240)
PEKNGAATGMDAICSHRLDPKSPGLDREQLYWELSQLTHGIKELGPYTLDRNSLYVNG (SEQ ID NO: 241)
PEKHGAATGVDAICTLRLDPTGPGLDRERLYWELSQLTNSVTELGPYTLDRDSLYVNG (SEQ ID NO: 242)
PEKHGAATGVDAICTLRLDPTGPGLDRERLYWELSQLTNSITELGPYTLDRDSLYVNG (SEQ ID NO: 243)
PEKHEAATGVDTICTHRVDPIGPGLDRERLYWELSQLTNSITELGPYTLDRDSLYVNG (SEQ ID NO: 244)
PEKQEAATGVDTICTHRVDPIGPGLDRERLYWELSQLTNSITELGPYTLDRDSLYVNG (SEQ ID NO: 245)
PEKQEAATGVDTICTHRVDPIGPGLDRERLYWELSQLTNSITELGPYTLDRDSLYVDG (SEQ ID NO: 246)
PEKDKAATRVDAICTHHPDPQSPGLNREQLYWELSQLTHGITELGPYTLDRDSLYVDG (SEQ ID NO: 247)
SVKNGAETRVDLLCTYLQPLSGPGLPIKQVFHELSQQTHGITRLGPYSLDKDSLYLNG (SEQ ID NO: 248)
PEKDGAATGVDTTCTYHPDPVGPGLDIQQLYWELSQLTHGVTQLGFYVLDRDSLFING (SEQ ID NO: 249)
```

Figure 7C

| Exon 4 | | Exon 5 | |
|---|---|---|---|
| 124        135 | | 136                   156 | |
| FTHRSSMPTTST | (SEQ ID NO: 250) | PGTSTVDVGTSGTPSSSPSPT | (SEQ ID NO: 278) |
| FTHRSSMPTTSI | (SEQ ID NO: 251) | PGTSTVDLRTSGTPSSLSSPTIM | (SEQ ID NO: 279) |
| FTHRTSVPTSST | (SEQ ID NO: 252) | PGTSTVDLGTSGTPFSLPSPA | (SEQ ID NO: 280) |
| FTHRTSVPTTST | (SEQ ID NO: 253) | PGTSTVDLG.SGTPSSLPSPT | (SEQ ID NO: 281) |
| FTHRSSVPTTSS | (SEQ ID NO: 254) | PGTSTVDLG.SGTPSLPSSPT | (SEQ ID NO: 282) |
| FTHRSSVSTTST | (SEQ ID NO: 255) | PGTSTVDLGTSGTPSSLPSPT | (SEQ ID NO: 283) |
| FTHRSSVAPTST | (SEQ ID NO: 256) | PGTPTVDLGTSGTPVSKPGPS | (SEQ ID NO: 284) |
| FTHRSSGLTTST | (SEQ ID NO: 257) | PWTSTVDLGTSGTPSPVPSPT | (SEQ ID NO: 285) |
| FTHRSFGLTTST | (SEQ ID NO: 258) | PGTSTVYWATTGTPSSFPGHT | (SEQ ID NO: 286) |
| FTHRSSFLTTST | (SEQ ID NO: 259) | PGTSTVHLATSGTPSSLPGHT | (SEQ ID NO: 287) |
| FTHRNFVPITST | (SEQ ID NO: 260) | PGTSTVHLATSGTPSPLPGHT | (SEQ ID NO: 288) |
| FTHRSSVPTTSI | (SEQ ID NO: 261) | PDTSTMHLATSRTPASLSGPT | (SEQ ID NO: 289) |
| FTHQSSVSTTST | (SEQ ID NO: 262) | PGTSAVHLETSGTPASLPGHT | (SEQ ID NO: 290) |
| FTHQTSAPNTST | (SEQ ID NO: 263) | PGTSAVHLETTGTPSSFPGHT | (SEQ ID NO: 291) |
| FTHQTFAPNTST | (SEQ ID NO: 264) | PGTSTVHLGTSETPSSLPRPI | (SEQ ID NO: 292) |
| FTHQNSVPTTST | (SEQ ID NO: 265) | PGTSIVNLGTSGIPPSLPETT | (SEQ ID NO: 293) |
| FTHQSSMTTTRT | (SEQ ID NO: 266) | PGTFTVQPETSETPSSLPGPT | (SEQ ID NO: 294) |
| FTHWIPVPTSST | (SEQ ID NO: 267) | PGTPTVDLGTSGTPVSKPGPS | (SEQ ID NO: 295) |
| FTHWSPIPTTST | (SEQ ID NO: 268) | PGTPTVYLGASKTPASIFGPS | (SEQ ID NO: 296) |
| FTHWSSGLTTST | (SEQ ID NO: 269) | PKPATTFLPPLSEATT..... | (SEQ ID NO: 297) |
| FHPRSSVPTTST | (SEQ ID NO: 270) | QINFHIVNWNLSNPDPTSSEY | (SEQ ID NO: 298) |
| FNPRSSVPTTST | (SEQ ID NO: 271) | | |
| FNPWSSVPTTST | (SEQ ID NO: 272) | | |
| FTQRSSVPTTSI | (SEQ ID NO: 273) | | |
| FTQRSSVPTTST | (SEQ ID NO: 274) | | |
| FTQRSSVPTTSV | (SEQ ID NO: 275) | | |
| YNEPGLDEPPTT | (SEQ ID NO: 276) | | |
| YAPQNLSIRGEY | (SEQ ID NO: 277) | | |

Figure 7C

```
   1  MEHITKIPNE AAHRGTIRPV KGPQTSTSPA SPKGLHTGGT KRMETTTTAL         901  ISATFPTVPE SPHESEATAS WVTHPAVTST TVPRTTPNYS HSEPDTTPSI
  51  KTTTTALKTT SRATLTTSVY TPTLGTLTPL NASRQMASTI LTEMMITTPY         951  ATSPGAEATS DFPTITVSPD VPDMVTSQVT SSGTDTSITI PTLTLSSGEP
 101  VFPDVPETTS SLATSLGAET STALPRTTPS VLNRESETTA SLVSRSGAER        1001  ETTTSFITYS ETHTSSAIPT LPVSPGASKM LTSLVISSGT DSTTTFPTLT
 151  SPVIQTLDVS SSEPDTTASW VIHPAETIPT VSKTTPNFFH SELDTVSSTA        1051  ETPYEPETTA IQLIHPAETN TMVPRTTPKF SHSKSDTTLP VAITSPGEA
 201  TSHGADVSSA IPTNISPSEL DALTPLVTIS GTDTSTTFPT LTKSPHETET        1101  SSAVSTTTIS PDMSDLVTSL VPSSGTDTST TFPTLSETPY EPETTATWLT
 251  RTTWLTHPAE TSSTIPRTIP NFSHHESDAT PSIATSPGAE TSSAIPIMTV        1151  HPAETSTTVS GTIPNFSHRG SDTAPSMVTS PGVDTRSGVP TTTIPPSIPG
 301  SPGAEDLVTS QVTSSGTDRN MTIPTLTLSP GEPKTIASLV THPEAQTSSA        1201  VVTSQVTSSA TDTSTAIPTL TPSPGEPETT ASSATHPGTQ TGFTVPIRTV
 351  IPTSTISPAV SRLVTSMVTS LAAKTSTTNR ALTNSPGEPA QTVSLVTHPA        1251  PSSEPDTMAS WVTHPPQTST PVSRTTSSFS HSSPDATPVM ATSPRTEASS
 401  QTSPTTVPWTT SIFFHSKSDT TPSMTTSHGA ESSSAVPTPT VSTEVPGVVT        1301  AVLTTISPGA PEMVTSQITS SGAATSTTVP TLTHSPGMPE TTALLSTHPR
 451  PLVTSSRAVI STTIPILTLS PGEPETTPSM ATSHGEASS AIPTPTVSPG          1351  TETSKTFPAS TVFPQVSETT ASLTIRPGAE TSTALPTQTT SSLFTLLVTG
 501  VPGVVTSLVT SSRAVTSTTI PILTFSLGEP ETTPSMATSH GTEAGSAVPT        1401  TSRVDLSPTA SPGVSAKTAP LSTHPGTETS TMIPTSTLSL GLLETTGLLA
 551  VLPEVPGMVT SLVASSRAVT STTLPTLTLS PGEPETTPSM ATSHGAEASS        1451  TSSAETSTS TLTLTVSPAV SGLSSASITT DKPQTVTSWN TETSPSVTSV
 601  TVPTVSPEVP GVVTSLVTSS SGVNSTSIPT LILSPGELET TPSMATSHGA        1501  GPPEFSRTVT GTTMLIPSE MPTPPKTSHG EGVSPTTILR TTMVEATNLA
 651  EASSAVPTPT VSPGVSGVVT PLVTSSRAVT STTIPILTLS SSEPETTPSM        1551  TTGSSPTVAK TTTTFNTLAG SLFTPLTTPG MSTLASESVT SRTSYNHRSW
 701  ATSHGVEASS AVLTVSPEVP GMVTSLVTSS RAVTSTTIPT LTISSDEPET        1601  ISTTSSYNRR YWTPATSPV TSTFSPGIST QSIPSSTAAT VPFMVPFTLN
 751  TTSLVTHSEA KMISAIPTLA VSPTVQGLVT SLVTSSGSET SAFSNLTVAS        1651  FTITNLQYEE DMRHPGSRKF NATERELQGL LKPLFRNSSL EYLYSGCRLA
 801  SQPETIDSWV AHPGTEASSV VPTLTVSTGE PFTNISLVTH PAESSSTLPR        1701  SLRPEKDSSA MAVDAICTHR PDPEDLGLDR ERLYWELSNL TNGIQELGPY
 851  TTSRFSHSEL DTMPSTVTSP EAESSSAIST TISPGIPGVL TSLVTSSGRD        1751  TLDRNSLYVN GFTHRSSMPT TSTPGTSTVD VGTSGTPSSS PSPT
```

Figure 8B (SEQ ID NO: 299)

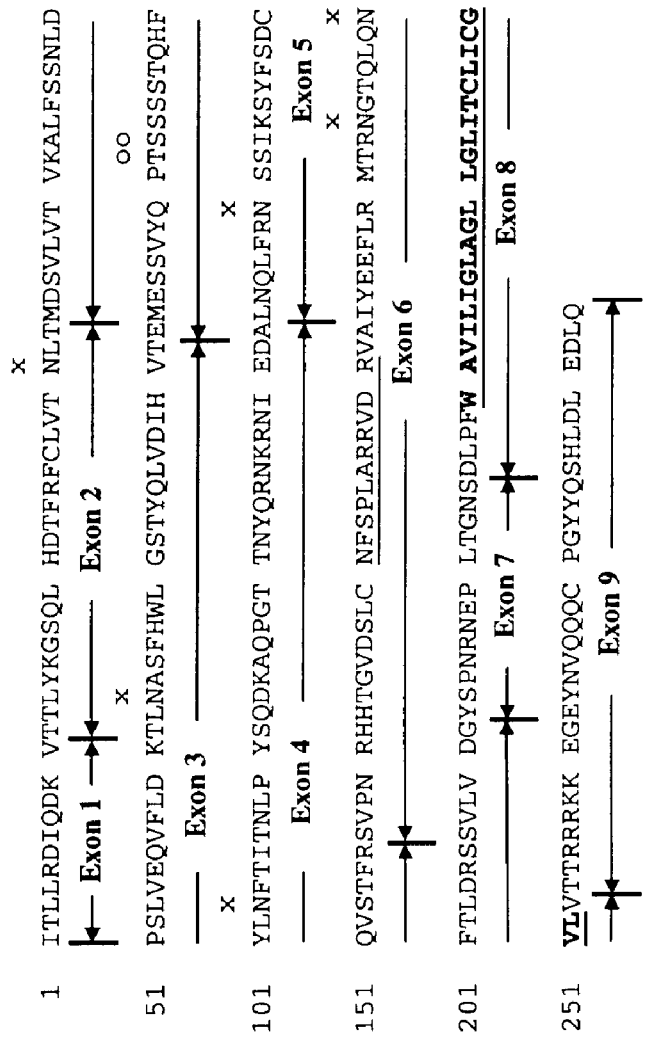
Figure 9B (SEQ ID NO: 300)

SEQUENCE LISTING

<160> NUMBER OF SEQ ID NOS: 308

<210> SEQ ID NO 1
<211> LENGTH: 13
<212> TYPE: PRT
<213> ORGANISM: Homo sapiens

<400> SEQUENCE: 1

Gln His Pro Gly Ser Arg Lys Phe Lys Thr Thr Glu Gly
1               5                   10

<210> SEQ ID NO 2
<211> LENGTH: 11
<212> TYPE: PRT
<213> ORGANISM: Homo sapiens

```
<400> SEQUENCE: 2

Phe Leu Thr Val Glu Arg Val Leu Gln Gly Leu
1               5                   10

<210> SEQ ID NO 3
<211> LENGTH: 8
<212> TYPE: PRT
<213> ORGANISM: Homo sapiens

<400> SEQUENCE: 3

Asp Thr Tyr Val Gly Pro Leu Tyr
1               5

<210> SEQ ID NO 4
<211> LENGTH: 8
<212> TYPE: PRT
<213> ORGANISM: Homo sapiens

<400> SEQUENCE: 4

Asp Gly Ala Ala Asn Gly Val Asp
1               5

<210> SEQ ID NO 5
<211> LENGTH: 240
<212> TYPE: DNA
<213> ORGANISM: Homo sapiens
<220> FEATURE:
<221> NAME/KEY: CDS
<222> LOCATION: (1)..(240)
<223> OTHER INFORMATION:

<400> SEQUENCE: 5 cgt cga cct ggc tct aga aag ttt aac acc acg gag aga gtc ctt cag      48
Arg Arg Pro Gly Ser Arg Lys Phe Asn Thr Thr Glu Arg Val Leu Gln
1               5                   10                  15 ggt ctg ctc agg cct gtg ttc aag aac acc agt gtt ggc cct ctg tac      96
Gly Leu Leu Arg Pro Val Phe Lys Asn Thr Ser Val Gly Pro Leu Tyr
            20                  25                  30 tct ggc tgc aga ctg acc ttg ctc agg ccc aag aag gat ggg gca gcc     144
Ser Gly Cys Arg Leu Thr Leu Leu Arg Pro Lys Lys Asp Gly Ala Ala
        35                  40                  45 acc aaa gtg gat gcc atc tgc acc tac cgc cct gat ccc aaa agc cct     192
Thr Lys Val Asp Ala Ile Cys Thr Tyr Arg Pro Asp Pro Lys Ser Pro
    50                  55                  60 gga ctg gac aga gag cag cta tac tgg gag ctg agc cag ggt gat gca     240
Gly Leu Asp Arg Glu Gln Leu Tyr Trp Glu Leu Ser Gln Gly Asp Ala
65                  70                  75                  80

<210> SEQ ID NO 6
<211> LENGTH: 80
<212> TYPE: PRT
<213> ORGANISM: Homo sapiens

<400> SEQUENCE: 6

Arg Arg Pro Gly Ser Arg Lys Phe Asn Thr Thr Glu Arg Val Leu Gln
1               5                   10                  15

Gly Leu Leu Arg Pro Val Phe Lys Asn Thr Ser Val Gly Pro Leu Tyr
            20                  25                  30

Ser Gly Cys Arg Leu Thr Leu Leu Arg Pro Lys Lys Asp Gly Ala Ala
        35                  40                  45

Thr Lys Val Asp Ala Ile Cys Thr Tyr Arg Pro Asp Pro Lys Ser Pro
    50                  55                  60
```

```
Gly Leu Asp Arg Glu Gln Leu Tyr Trp Glu Leu Ser Gln Gly Asp Ala
65                  70                  75                  80
```

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
ggagagggtt ctgcagggtc                                          20

<210> SEQ ID NO 8
<211> LENGTH: 6
<212> TYPE: PRT
<213> ORGANISM: Artificial Sequence
<220> FEATURE:
<223> OTHER INFORMATION: Synthetic Primer

<400> SEQUENCE: 8

```
Glu Arg Val Leu Gln Gly
1               5
```

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
gtgaatggta tcaggagagg                                          20

<210> SEQ ID NO 10
<211> LENGTH: 6
<212> TYPE: PRT
<213> ORGANISM: Artificial Sequence
<220> FEATURE:
<223> OTHER INFORMATION: Synthetic Primer

<400> SEQUENCE: 10

```
Pro Leu Leu Ile Pro Phe
1               5
```

<210> SEQ ID NO 11
<211> LENGTH: 131
<212> TYPE: PRT
<213> ORGANISM: Homo sapiens

<400> SEQUENCE: 11

```
Glu Arg Val Leu Gln Gly Leu Leu Arg Ser Leu Phe Lys Ser Thr Ser
1               5                   10                  15

Val Gly Pro Leu Tyr Ser Gly Cys Arg Leu Thr Leu Leu Arg Pro Glu
                20                  25                  30

Lys Asp Gly Thr Ala Thr Gly Val Asp Ala Ile Cys Thr His His Pro
            35                  40                  45

Asp Pro Lys Ser Pro Arg Leu Asp Arg Glu Gln Leu Tyr Trp Glu Leu
        50                  55                  60

Ser Gln Leu Thr His Asn Ile Thr Glu Leu Gly Pro Tyr Ala Leu Asp
65                  70                  75                  80

Asn Asp Ser Leu Phe Val Asn Gly Phe Thr His Arg Ser Ser Val Ser
                85                  90                  95
```

```
Thr Thr Ser Thr Pro Gly Thr Pro Val Tyr Leu Gly Ala Ser Lys
                100                 105                 110

Thr Pro Ala Ser Ile Phe Gly Pro Ser Ala Ala Ser Pro Leu Leu Ile
            115                 120                 125

Pro Phe Thr
        130

<210> SEQ ID NO 12
<211> LENGTH: 130
<212> TYPE: PRT
<213> ORGANISM: Homo sapiens

<400> SEQUENCE: 12

Glu Arg Val Leu Gln Gly Leu Leu Met Pro Leu Phe Lys Asn Thr Ser
1               5                   10                  15

Val Ser Ser Leu Tyr Ser Gly Cys Arg Leu Thr Leu Arg Pro Glu
                20                  25                  30

Lys Asp Gly Ala Ala Thr Arg Ala Asp Ala Val Cys Thr His Arg Pro
            35                  40                  45

Asp Pro Lys Ser Pro Gly Leu Asp Arg Glu Arg Leu Tyr Trp Lys Leu
    50                  55                  60

Ser Gln Leu Thr His Gly Ile Thr Glu Leu Gly Pro Tyr Thr Leu Asp
65                  70                  75                  80

Arg His Ser Leu Tyr Val Asn Gly Phe Thr His Gln Ser Ser Met Thr
                85                  90                  95

Thr Thr Arg Thr Pro Asp Thr Ser Met His Leu Ala Thr Ser Arg
                100                 105                 110

Thr Pro Ala Ser Leu Ser Gly Pro Thr Thr Ala Ser Pro Leu Leu Ile
            115                 120                 125

Pro Phe
    130

<210> SEQ ID NO 13
<211> LENGTH: 132
<212> TYPE: PRT
<213> ORGANISM: Homo sapiens

<400> SEQUENCE: 13

Glu Arg Val Leu Gln Gly Leu Leu Gly Pro Ile Phe Lys Asn Thr Ser
1               5                   10                  15

Val Gly Pro Leu Tyr Ser Gly Cys Arg Leu Thr Ser Leu Arg Ser Glu
                20                  25                  30

Lys Asp Gly Ala Ala Thr Gly Val Asp Ala Ile Cys Ile His Arg Leu
            35                  40                  45

Asp Pro Lys Ser Pro Gly Leu Asn Arg Glu Gln Leu Tyr Trp Glu Leu
    50                  55                  60

Ser Lys Leu Thr Asn Asp Ile Glu Glu Leu Gly Pro Tyr Thr Leu Asp
65                  70                  75                  80

Arg Asn Ser Leu Tyr Val Asn Gly Phe Thr His Gln Ser Ser Val Ser
                85                  90                  95

Thr Thr Ser Thr Pro Gly Thr Ser Thr Val Asp Leu Arg Thr Ser Gly
                100                 105                 110

Thr Pro Ser Ser Leu Ser Ser Pro Thr Ile Met Ala Ala Gly Pro Leu
            115                 120                 125

Leu Ile Pro Phe
        130
```

```
<210> SEQ ID NO 14
<211> LENGTH: 130
<212> TYPE: PRT
<213> ORGANISM: Homo sapiens

<400> SEQUENCE: 14

Glu Arg Val Leu Gln Gly Leu Leu Gly Pro Met Phe Lys Asn Thr Ser
1               5                   10                  15

Val Gly Leu Leu Tyr Ser Gly Cys Arg Leu Thr Leu Leu Arg Pro Glu
            20                  25                  30

Lys Asn Gly Ala Ala Thr Gly Met Asp Ala Ile Cys Ser His Arg Leu
        35                  40                  45

Asp Pro Lys Ser Pro Gly Leu Asn Arg Glu Gln Leu Tyr Trp Glu Leu
    50                  55                  60

Ser Gln Leu Thr His Gly Ile Lys Glu Leu Gly Pro Tyr Thr Leu Asp
65                  70                  75                  80

Arg Asn Ser Leu Tyr Val Asn Gly Phe Thr His Arg Ser Ser Val Ala
                85                  90                  95

Pro Thr Ser Thr Pro Gly Thr Ser Thr Val Asp Leu Gly Thr Ser Gly
            100                 105                 110

Thr Pro Ser Ser Leu Pro Ser Pro Thr Thr Ala Val Pro Leu Leu Ile
        115                 120                 125

Pro Phe
    130

<210> SEQ ID NO 15
<211> LENGTH: 130
<212> TYPE: PRT
<213> ORGANISM: Homo sapiens

<400> SEQUENCE: 15

Glu Arg Val Leu Gln Gly Leu Leu Gly Pro Leu Phe Lys Asn Ser Ser
1               5                   10                  15

Val Gly Pro Leu Tyr Ser Gly Cys Arg Leu Ile Ser Leu Arg Ser Glu
            20                  25                  30

Lys Asp Gly Ala Ala Thr Gly Val Asp Ala Ile Cys Thr His His Leu
        35                  40                  45

Asn Pro Gln Ser Pro Gly Leu Asp Arg Glu Gln Leu Tyr Trp Gln Leu
    50                  55                  60

Ser Gln Met Thr Asn Gly Ile Lys Glu Leu Gly Pro Tyr Thr Leu Asp
65                  70                  75                  80

Arg Asn Ser Leu Tyr Val Asn Gly Phe Thr His Arg Ser Ser Gly Leu
                85                  90                  95

Thr Thr Ser Thr Pro Trp Thr Ser Thr Val Asp Leu Gly Thr Ser Gly
            100                 105                 110

Thr Pro Ser Pro Val Pro Ser Pro Thr Thr Ala Gly Pro Phe Leu Ile
        115                 120                 125

Pro Phe
    130

<210> SEQ ID NO 16
<211> LENGTH: 130
<212> TYPE: PRT
<213> ORGANISM: Homo sapiens

<400> SEQUENCE: 16

Glu Arg Val Leu Gln Gly Leu Leu Arg Pro Leu Phe Lys Ser Thr Ser
```

-continued

```
               1               5              10              15
        Ala Gly Pro Leu Tyr Ser Gly Cys Arg Leu Thr Leu Arg Pro Glu
                       20              25              30

Lys His Gly Ala Ala Thr Gly Val Asp Ala Ile Cys Thr Leu Arg Leu
                       35              40              45

Asp Pro Thr Gly Pro Gly Leu Asp Arg Glu Arg Leu Tyr Trp Glu Leu
               50              55              60

Ser Gln Leu Thr Asn Ser Val Thr Glu Leu Gly Pro Tyr Thr Leu Asp
        65              70              75              80

Arg Asp Ser Leu Tyr Val Asn Gly Phe Thr His Arg Ser Ser Val Pro
                       85              90              95

Thr Thr Ser Ile Pro Gly Thr Ser Ala Val His Leu Glu Thr Ser Gly
                       100             105             110

Thr Pro Ala Ser Leu Pro Gly His Thr Ala Pro Gly Pro Leu Leu Ile
                       115             120             125

Pro Phe
               130
```

<210> SEQ ID NO 17
<211> LENGTH: 130
<212> TYPE: PRT
<213> ORGANISM: Homo sapiens

<400> SEQUENCE: 17

```
        Glu Arg Val Leu Gln Gly Leu Leu Lys Pro Leu Phe Lys Ser Thr Ser
        1               5              10              15

Val Gly Pro Leu Tyr Ser Gly Cys Arg Leu Thr Leu Arg Pro Glu
                       20              25              30

Lys Arg Gly Ala Ala Thr Gly Val Asp Thr Ile Cys Thr His Arg Leu
                       35              40              45

Asp Pro Leu Asn Pro Gly Leu Asp Arg Glu Gln Leu Tyr Trp Glu Leu
               50              55              60

Ser Lys Leu Thr Arg Gly Ile Ile Glu Leu Gly Pro Tyr Thr Leu Asp
        65              70              75              80

Arg Asp Ser Leu Tyr Val Asn Gly Phe Thr His Arg Ser Ser Val Pro
                       85              90              95

Thr Thr Ser Ile Pro Gly Thr Ser Ala Val His Leu Glu Thr Ser Gly
                       100             105             110

Thr Pro Ala Ser Leu Pro Gly His Ile Val Pro Gly Pro Leu Leu Ile
                       115             120             125

Pro Phe
               130
```

<210> SEQ ID NO 18
<211> LENGTH: 131
<212> TYPE: PRT
<213> ORGANISM: Homo sapiens

<400> SEQUENCE: 18

```
        Glu Arg Val Leu Gln Gly Leu Leu Thr Pro Leu Phe Lys Asn Thr Ser
        1               5              10              15

Val Gly Pro Leu Tyr Ser Gly Cys Arg Leu Thr Leu Arg Pro Glu
                       20              25              30

Lys Gln Glu Ala Ala Thr Gly Val Asp Thr Ile Cys Thr His Arg Val
                       35              40              45

Asp Pro Ile Gly Pro Gly Leu Asp Arg Glu Arg Leu Tyr Trp Glu Leu
```

```
            50                  55                  60
Ser Gln Leu Thr Asn Ser Ile Thr Glu Leu Gly Pro Tyr Thr Leu Asp
 65                  70                  75                  80

Arg Asp Ser Leu Tyr Val Asp Gly Phe Asn Pro Trp Ser Ser Val Pro
                 85                  90                  95

Thr Thr Ser Thr Pro Gly Thr Ser Val His Leu Ala Thr Ser Gly
                100                 105                 110

Thr Pro Ser Pro Leu Pro Gly His Thr Ala Pro Val Pro Leu Leu Ile
            115                 120                 125

Pro Phe Thr
    130

<210> SEQ ID NO 19
<211> LENGTH: 131
<212> TYPE: PRT
<213> ORGANISM: Homo sapiens

<400> SEQUENCE: 19

Glu Arg Val Leu Gln Gly Leu Leu Lys Pro Leu Phe Lys Asn Thr Ser
 1               5                  10                  15

Val Gly Pro Leu Tyr Ser Gly Cys Arg Leu Thr Leu Arg Pro Glu
                20                  25                  30

Lys His Glu Ala Ala Thr Gly Val Asp Thr Ile Cys Thr His Arg Leu
            35                  40                  45

Asp Pro Leu Asn Pro Gly Leu Asp Arg Glu Gln Leu Tyr Trp Glu Leu
        50                  55                  60

Ser Lys Leu Thr Arg Gly Ile Ile Glu Leu Gly Pro Tyr Leu Leu Asp
 65                  70                  75                  80

Arg Gly Ser Leu Tyr Val Asn Gly Phe Thr His Arg Asn Phe Val Pro
                 85                  90                  95

Ile Thr Ser Thr Pro Gly Thr Ser Thr Val His Leu Gly Thr Ser Glu
                100                 105                 110

Thr Pro Ser Ser Leu Pro Arg Pro Ile Val Pro Gly Pro Leu Leu Val
            115                 120                 125

Pro Phe Thr
    130

<210> SEQ ID NO 20
<211> LENGTH: 130
<212> TYPE: PRT
<213> ORGANISM: Homo sapiens

<400> SEQUENCE: 20

Glu Arg Val Leu Gln Gly Leu Leu Ser Pro Ile Phe Lys Asn Ser Ser
 1               5                  10                  15

Val Gly Pro Leu Tyr Ser Gly Cys Arg Leu Thr Ser Leu Arg Pro Glu
                20                  25                  30

Lys Asp Gly Ala Ala Thr Gly Met Asp Ala Val Cys Leu Tyr His Pro
            35                  40                  45

Asn Pro Lys Arg Pro Gly Leu Asp Arg Glu Gln Leu Tyr Trp Glu Leu
        50                  55                  60

Ser Gln Leu Thr His Asn Ile Thr Glu Leu Gly Pro Tyr Ser Leu Asp
 65                  70                  75                  80

Arg Asp Ser Leu Tyr Val Asn Gly Phe Thr His Gln Asn Ser Val Pro
                 85                  90                  95

Thr Thr Ser Thr Pro Gly Thr Ser Thr Val Tyr Trp Ala Thr Thr Gly
```

```
                100             105             110
Thr Pro Ser Ser Phe Pro Gly His Thr Glu Pro Gly Pro Leu Leu Ile
        115                 120                 125

Pro Phe
    130

<210> SEQ ID NO 21
<211> LENGTH: 131
<212> TYPE: PRT
<213> ORGANISM: Homo sapiens

<400> SEQUENCE: 21

Glu Arg Val Leu Gln Gly Leu Leu Arg Pro Leu Phe Lys Asn Thr Ser
1               5                   10                  15

Ile Gly Pro Leu Tyr Ser Ser Cys Arg Leu Thr Leu Leu Arg Pro Glu
            20                  25                  30

Lys Asp Lys Ala Ala Thr Arg Val Asp Ala Ile Cys Thr His His Pro
        35                  40                  45

Asp Pro Gln Ser Pro Gly Leu Asn Arg Glu Gln Leu Tyr Trp Glu Leu
    50                  55                  60

Ser Gln Leu Thr His Gly Ile Thr Glu Leu Gly Pro Tyr Thr Leu Asp
65                  70                  75                  80

Arg Asp Ser Leu Tyr Val Asp Gly Phe Thr His Trp Ser Pro Ile Pro
                85                  90                  95

Thr Thr Ser Thr Pro Gly Thr Ser Ile Val Asn Leu Gly Thr Ser Gly
            100                 105                 110

Ile Pro Pro Ser Leu Pro Glu Thr Thr Ala Thr Gly Pro Leu Leu Ile
        115                 120                 125

Pro Phe Thr
    130

<210> SEQ ID NO 22
<211> LENGTH: 282
<212> TYPE: PRT
<213> ORGANISM: Homo sapiens

<400> SEQUENCE: 22

Glu Arg Val Leu Gln Gly Leu Leu Lys Pro Leu Phe Arg Asn Ser Ser
1               5                   10                  15

Leu Glu Tyr Leu Tyr Ser Gly Cys Arg Leu Ala Ser Leu Arg Pro Glu
            20                  25                  30

Lys Asp Ser Ser Ala Met Ala Val Asp Ala Ile Cys Thr His Arg Pro
        35                  40                  45

Asp Pro Glu Asp Leu Gly Leu Asp Arg Glu Arg Leu Tyr Trp Glu Leu
    50                  55                  60

Ser Asn Leu Thr Asn Gly Ile Gln Glu Leu Gly Pro Tyr Thr Leu Asp
65                  70                  75                  80

Arg Asn Ser Leu Tyr Val Asn Gly Phe Thr His Arg Ser Ser Met Pro
                85                  90                  95

Thr Thr Ser Thr Pro Gly Thr Ser Val Asp Val Gly Thr Ser Gly
            100                 105                 110

Thr Pro Ser Ser Pro Ser Pro Thr Thr Ala Gly Pro Leu Leu Met
        115                 120                 125

Pro Phe Thr Leu Asn Phe Thr Ile Thr Asn Leu Gln Tyr Glu Glu Asp
    130                 135                 140

Met Arg Arg Thr Gly Ser Arg Lys Phe Asn Thr Met Glu Arg Val Leu
```

```
                145                 150                 155                 160
Gln Gly Leu Leu Ser Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
                180                 185                 190

Ala Thr Gly Met Asp Ala Val Cys Leu Tyr His Pro Asn Pro Lys Arg
                195                 200                 205

Pro Gly Leu Asp Arg Glu Gln Leu Tyr Trp Glu Leu Ser Gln Leu Thr
                210                 215                 220

His Asn Ile Thr Glu Leu Gly Pro Tyr Ser Leu Asp Arg Asp Ser Leu
225                 230                 235                 240

Tyr Val Asn Gly Phe Thr His Gln Asn Ser Val Pro Thr Thr Ser Thr
                245                 250                 255

Pro Gly Thr Ser Thr Val Tyr Trp Ala Thr Gly Thr Pro Ser Ser
                260                 265                 270

Phe Pro Gly His Thr Glu Pro Gly Pro Leu
                275                 280

<210> SEQ ID NO 23
<211> LENGTH: 286
<212> TYPE: PRT
<213> ORGANISM: Homo sapiens

<400> SEQUENCE: 23

Glu Arg Val Leu Gln Gly Leu Leu Lys Pro Leu Phe Arg Asn Ser Ser
1               5                   10                  15

Leu Glu Tyr Leu Tyr Ser Gly Cys Arg Leu Ala Ser Leu Arg Pro Glu
                20                  25                  30

Lys Asp Ser Ser Ala Met Ala Val Asp Ala Ile Cys Thr His Arg Pro
            35                  40                  45

Asp Pro Glu Asp Leu Gly Leu Asp Arg Glu Arg Leu Tyr Trp Glu Leu
        50                  55                  60

Ser Asn Leu Thr Asn Gly Ile Gln Glu Leu Gly Pro Tyr Thr Leu Asp
65                  70                  75                  80

Arg Asn Ser Leu Tyr Val Asn Gly Phe Thr His Arg Ser Ser Gly Leu
                85                  90                  95

Thr Thr Ser Thr Pro Trp Thr Ser Val Asp Leu Gly Thr Ser Gly
                100                 105                 110

Thr Pro Ser Pro Val Pro Ser Pro Thr Thr Ala Gly Pro Leu Leu Ile
            115                 120                 125

Pro Phe Thr Leu Asn Phe Thr Ile Thr Asn Leu Gln Tyr Glu Glu Asn
        130                 135                 140

Met Gly His Pro Gly Ser Arg Lys Phe Asn Ile Met Glu Arg Val Leu
145                 150                 155                 160

Gln Gly Leu Leu Met Pro Leu Phe Lys Asn Thr Ser Val Ser Ser Leu
                165                 170                 175

Tyr Ser Gly Cys Arg Leu Thr Leu Leu Arg Pro Glu Lys Asp Gly Ala
                180                 185                 190

Ala Thr Arg Val Asp Ala Val Cys Thr Gln Arg Pro Asp Pro Lys Ser
            195                 200                 205

Pro Gly Leu Asp Arg Glu Arg Leu Tyr Trp Lys Leu Ser Gln Leu Thr
        210                 215                 220

His Gly Ile Thr Glu Leu Gly Pro Tyr Thr Leu Asp Arg His Ser Leu
225                 230                 235                 240
```

```
Tyr Val Asn Gly Leu Thr His Gln Ser Ser Met Thr Thr Arg Thr
                245                 250                 255

Pro Asp Thr Ser Thr Met His Leu Ala Thr Ser Arg Thr Pro Ala Ser
            260                 265                 270

Leu Ser Gly Pro Thr Thr Ala Ser Pro Leu Leu Ile Pro Phe
        275                 280                 285

<210> SEQ ID NO 24
<211> LENGTH: 250
<212> TYPE: PRT
<213> ORGANISM: Homo sapiens

<400> SEQUENCE: 24

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
            20                  25                  30

Lys Arg Gly Ala Ala Thr Gly Val Asp Thr Ile Cys Thr His Arg Leu
        35                  40                  45

Asp Pro Leu Asn Pro Gly Leu Asp Arg Glu Gln Leu Tyr Trp Glu Leu
    50                  55                  60

Ser Lys Leu Thr Arg Gly Ile Ile Glu Leu Gly Pro Tyr Leu Leu Asp
65                  70                  75                  80

Arg Gly Ser Leu Tyr Val Asn Gly Phe Thr His Arg Thr Ser Val Pro
                85                  90                  95

Thr Thr Ser Thr Pro Gly Thr Ser Thr Val Asp Leu Gly Thr Ser Gly
            100                 105                 110

Thr Pro Phe Ser Leu Pro Ser Pro Ala Thr Ala Gly Pro Leu Leu Val
        115                 120                 125

Leu Phe Thr Leu Asn Phe Thr Ile Thr Asn Leu Lys Tyr Glu Glu Asp
    130                 135                 140

Met His Arg Pro Gly Ser Arg Lys Phe Asn Thr Thr Glu Arg Val Leu
145                 150                 155                 160

Gln Thr Leu Leu Gly Pro Met Phe Lys Asn Thr Ser Val Gly Leu Leu
                165                 170                 175

Tyr Ser Gly Cys Arg Leu Thr Leu Leu Arg Ser Glu Lys Asp Gly Ala
            180                 185                 190

Ala Thr Gly Val Asp Ala Ile Cys Thr His Arg Leu Asp Pro Lys Ser
        195                 200                 205

Pro Gly Val Asp Arg Glu Gln Leu Tyr Trp Glu Leu Ser Gln Leu Thr
    210                 215                 220

Asn Gly Ile Lys Glu Leu Gly Pro Tyr Thr Leu Asp Arg Asn Ser Leu
225                 230                 235                 240

Tyr Val Asn Gly Phe Thr His Trp Ile Pro
                245                 250

<210> SEQ ID NO 25
<211> LENGTH: 286
<212> TYPE: PRT
<213> ORGANISM: Homo sapiens

<400> SEQUENCE: 25

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
            20                  25                  30
```

```
Lys Arg Gly Ala Ala Thr Gly Val Asp Thr Ile Cys Thr His Arg Leu
            35                  40                  45

Asp Pro Leu Asn Pro Gly Leu Asp Arg Glu Gln Leu Tyr Trp Glu Leu
        50                  55                  60

Ser Lys Leu Thr Arg Gly Ile Ile Glu Leu Gly Pro Tyr Leu Leu Asp
65                  70                  75                  80

Arg Gly Ser Leu Tyr Val Asn Gly Phe Thr His Arg Asn Phe Val Pro
                85                  90                  95

Ile Thr Ser Thr Pro Gly Thr Ser Thr Val His Leu Gly Thr Ser Glu
            100                 105                 110

Thr Pro Ser Ser Leu Pro Arg Pro Ile Val Pro Gly Pro Leu Leu Ile
        115                 120                 125

Pro Phe Thr Ile Asn Phe Thr Ile Thr Asn Leu Arg Tyr Glu Glu Asn
130                 135                 140

Met His His Pro Gly Ser Arg Lys Phe Asn Ile Met Glu Arg Val Leu
145                 150                 155                 160

Gln Gly Leu Leu Gly Pro Leu Phe Lys Asn Ser Ser Val Gly Pro Leu
                165                 170                 175

Tyr Ser Gly Cys Arg Leu Ile Ser Leu Arg Ser Glu Lys Asp Gly Ala
            180                 185                 190

Ala Thr Gly Val Asp Ala Ile Cys Thr His His Leu Asn Pro Gln Ser
        195                 200                 205

Pro Gly Leu Asp Arg Glu Gln Leu Tyr Trp Gln Leu Ser Gln Met Thr
210                 215                 220

Asn Gly Ile Lys Glu Leu Gly Pro Tyr Thr Leu Asp Arg Asn Ser Leu
225                 230                 235                 240

Tyr Val Asn Gly Phe Thr His Arg Ser Ser Gly Leu Thr Thr Ser Thr
                245                 250                 255

Pro Trp Thr Ser Thr Val Asp Leu Gly Thr Ser Gly Thr Pro Ser Pro
            260                 265                 270

Val Pro Ser Pro Thr Thr Ala Gly Pro Leu Leu Ile Pro Phe
        275                 280                 285

<210> SEQ ID NO 26
<211> LENGTH: 286
<212> TYPE: PRT
<213> ORGANISM: Homo sapiens

<400> SEQUENCE: 26

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
            20                  25                  30

Lys Arg Gly Ala Ala Thr Gly Val Asp Thr Ile Cys Thr His Arg Leu
            35                  40                  45

Asp Pro Leu Asn Pro Gly Leu Asp Arg Glu Gln Leu Tyr Trp Glu Leu
        50                  55                  60

Ser Lys Leu Thr Arg Gly Ile Ile Glu Leu Gly Pro Tyr Leu Leu Asp
65                  70                  75                  80

Arg Gly Ser Leu Tyr Val Asn Gly Phe Ser Arg Gln Ser Ser Met Thr
                85                  90                  95

Thr Thr Arg Thr Pro Asp Thr Ser Thr Met His Leu Ala Thr Ser Arg
            100                 105                 110

Thr Pro Ala Ser Leu Ser Gly Pro Thr Thr Ala Ser Pro Leu Leu Ile
        115                 120                 125
```

-continued

```
Pro Phe Thr Leu Asn Phe Thr Ile Thr Asn Leu Gln Tyr Glu Glu Asn
    130                 135                 140

Met Gly His Pro Gly Ser Arg Lys Phe Asn Ile Met Glu Arg Val Leu
145                 150                 155                 160

Gln Gly Leu Leu Asn Pro Ile Phe Lys Asn Ser Ser Val Gly Pro Leu
                165                 170                 175

Tyr Ser Gly Cys Arg Leu Thr Ser Leu Lys Pro Glu Lys Asp Gly Ala
            180                 185                 190

Ala Thr Gly Met Asp Ala Val Cys Leu Tyr His Pro Asn Pro Lys Arg
            195                 200                 205

Pro Gly Leu Asp Arg Glu Gln Leu Tyr Trp Glu Leu Ser Gln Leu Thr
    210                 215                 220

His Gly Ile Lys Glu Leu Gly Pro Tyr Thr Leu Asp Arg Asn Ser Leu
225                 230                 235                 240

Tyr Val Asn Gly Phe Thr His Arg Ser Ser Val Ala Pro Thr Ser Thr
                245                 250                 255

Pro Gly Thr Ser Thr Val Asp Leu Gly Thr Ser Gly Thr Pro Ser Ser
            260                 265                 270

Leu Pro Ser Pro Thr Thr Ala Val Pro Leu Leu Ile Pro Phe
            275                 280                 285
```

<210> SEQ ID NO 27
<211> LENGTH: 286
<212> TYPE: PRT
<213> ORGANISM: Homo sapiens

<400> SEQUENCE: 27

```
Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
                20                  25                  30

Lys Arg Gly Ala Ala Thr Gly Val Asp Thr Ile Cys Thr His Arg Leu
            35                  40                  45

Asp Pro Leu Asn Pro Gly Leu Asp Arg Glu Gln Leu Tyr Trp Glu Leu
    50                  55                  60

Ser Lys Leu Thr Arg Gly Ile Ile Glu Leu Gly Pro Tyr Leu Leu Asp
65                  70                  75                  80

Arg Asp Ser Leu Tyr Val Asn Gly Phe Thr His Arg Ser Ser Val Pro
                85                  90                  95

Thr Thr Ser Ile Pro Gly Thr Ser Ala Val His Leu Glu Thr Phe Gly
            100                 105                 110

Thr Pro Ala Ser Leu His Gly His Thr Ala Pro Gly Pro Val Leu Val
            115                 120                 125

Pro Phe Thr Leu Asn Phe Thr Ile Thr Asn Leu Gln Tyr Glu Glu Asp
    130                 135                 140

Met Arg His Pro Gly Ser Arg Lys Phe Asn Thr Thr Glu Arg Val Leu
145                 150                 155                 160

Gln Gly Leu Leu Lys Pro Leu Phe Lys Ser Thr Ser Val Gly Pro Leu
                165                 170                 175

Tyr Ser Gly Cys Arg Leu Thr Leu Leu Arg Pro Glu Lys Arg Gly Ala
            180                 185                 190

Ala Thr Gly Val Asp Thr Ile Cys Thr His Arg Leu Asp Pro Leu Asn
            195                 200                 205

Pro Gly Leu Asp Arg Glu Gln Leu Tyr Trp Glu Leu Ser Lys Leu Thr
```

```
                    210                 215                 220
Arg Gly Ile Ile Glu Leu Gly Pro Tyr Leu Leu Asp Arg Gly Ser Leu
225                 230                 235                 240

Tyr Val Asn Gly Phe Thr His Arg Asn Phe Val Pro Ile Thr Ser Thr
                245                 250                 255

Pro Gly Thr Ser Thr Val His Leu Gly Thr Ser Glu Thr Pro Ser Ser
            260                 265                 270

Leu Pro Arg Pro Ile Val Pro Gly Pro Leu Leu Ile Pro Phe
        275                 280                 285

<210> SEQ ID NO 28
<211> LENGTH: 286
<212> TYPE: PRT
<213> ORGANISM: Homo sapiens

<400> SEQUENCE: 28

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
                20                  25                  30

Lys His Gly Ala Ala Thr Gly Val Asp Ala Ile Cys Thr Leu Arg Leu
            35                  40                  45

Asp Pro Thr Gly Pro Gly Leu Asp Arg Glu Arg Leu Tyr Trp Glu Leu
        50                  55                  60

Ser Gln Leu Thr Asn Ser Val Thr Glu Leu Gly Pro Tyr Thr Leu Asp
65                  70                  75                  80

Arg Asp Ser Leu Tyr Val Asn Gly Phe Thr His Arg Ser Ser Val Pro
                85                  90                  95

Thr Thr Ser Ile Pro Gly Thr Ser Ala Val His Leu Glu Thr Ser Gly
            100                 105                 110

Thr Pro Ala Ser Leu Pro Gly His Thr Ala Pro Gly Pro Leu Leu Val
            115                 120                 125

Pro Phe Thr Leu Asn Phe Thr Ile Thr Asn Leu Gln Tyr Glu Glu Asp
        130                 135                 140

Met Arg His Pro Gly Ser Arg Lys Phe Asn Thr Thr Glu Arg Val Leu
145                 150                 155                 160

Gln Gly Leu Leu Lys Pro Leu Phe Lys Ser Thr Ser Val Gly Pro Leu
                165                 170                 175

Tyr Ser Gly Cys Arg Leu Thr Leu Leu Arg Pro Glu Lys Arg Gly Ala
            180                 185                 190

Ala Thr Gly Val Asp Thr Ile Cys Thr His Arg Leu Asp Pro Leu Asn
            195                 200                 205

Pro Gly Leu Asp Arg Glu Gln Leu Tyr Trp Glu Leu Ser Lys Leu Thr
        210                 215                 220

Arg Gly Ile Ile Glu Leu Gly Pro Tyr Leu Leu Asp Arg Gly Ser Leu
225                 230                 235                 240

Tyr Val Asn Gly Phe Thr His Arg Asn Phe Val Pro Ile Thr Ser Thr
                245                 250                 255

Pro Gly Thr Ser Thr Val His Leu Gly Thr Ser Glu Thr Pro Ser Ser
            260                 265                 270

Leu Pro Arg Pro Ile Val Pro Gly Pro Leu Leu Ile Pro Phe
        275                 280                 285

<210> SEQ ID NO 29
<211> LENGTH: 281
```

```
<212> TYPE: PRT
<213> ORGANISM: Homo sapiens

<400> SEQUENCE: 29

Glu Arg Val Leu Gln Gly Leu Leu Thr Pro Leu Phe Lys Asn Thr Ser
1               5                   10                  15

Val Gly Pro Leu Tyr Ser Gly Cys Arg Leu Thr Leu Arg Pro Glu
            20                  25                  30

Lys Gln Glu Ala Ala Thr Gly Val Asp Thr Ile Cys Thr His Arg Val
            35                  40                  45

Asp Pro Ile Gly Pro Gly Leu Asp Arg Glu Arg Leu Tyr Trp Glu Leu
50                  55                  60

Ser Gln Leu Thr Asn Ser Ile Thr Glu Leu Gly Pro Tyr Thr Leu Asp
65                  70                  75                  80

Arg Asp Ser Leu Tyr Val Asn Gly Phe Asn Pro Trp Ser Ser Val Pro
                85                  90                  95

Thr Thr Ser Thr Pro Gly Thr Ser Thr Val His Leu Ala Thr Ser Gly
            100                 105                 110

Thr Pro Ser Ser Leu Pro Gly His Thr Ala Pro Val Pro Leu Leu Ile
            115                 120                 125

Pro Phe Thr Leu Asn Phe Thr Ile Thr Asn Leu His Tyr Glu Glu Asn
130                 135                 140

Met Gln His Pro Gly Ser Arg Lys Phe Asn Thr Thr Glu Arg Val Leu
145                 150                 155                 160

Gln Gly Leu Leu Lys Pro Leu Phe Lys Ser Thr Ser Val Gly Pro Leu
                165                 170                 175

Tyr Ser Gly Cys Arg Leu Thr Leu Leu Arg Pro Glu Lys His Gly Ala
            180                 185                 190

Ala Thr Gly Val Asp Ala Ile Cys Thr His Arg Leu Asp Pro Lys Ser
            195                 200                 205

Pro Gly Val Asp Arg Glu Gln Leu Tyr Trp Glu Leu Ser Gln Leu Thr
            210                 215                 220

Asn Gly Ile Lys Glu Leu Gly Pro Tyr Thr Leu Asp Arg Asn Ser Leu
225                 230                 235                 240

Tyr Val Asn Gly Phe Thr His Trp Ile Pro Val Pro Thr Ser Ser Thr
                245                 250                 255

Pro Gly Thr Ser Thr Val Asp Leu Gly Ser Gly Thr Pro Ser Ser Leu
            260                 265                 270

Pro Ser Pro Thr Thr Ala Gly Pro Leu
            275                 280

<210> SEQ ID NO 30
<211> LENGTH: 217
<212> TYPE: PRT
<213> ORGANISM: Homo sapiens

<400> SEQUENCE: 30

Glu Arg Val Leu Gln Gly Leu Leu Arg Pro Leu Phe Lys Asn Thr Ser
1               5                   10                  15

Ile Gly Pro Leu Tyr Ser Ser Cys Arg Leu Thr Leu Leu Arg Pro Glu
            20                  25                  30

Lys Asp Lys Ala Ala Thr Arg Val Asp Ala Ile Cys Thr His His Pro
            35                  40                  45

Asp Pro Gln Ser Pro Gly Leu Asn Arg Glu Gln Leu Tyr Trp Glu Leu
50                  55                  60
```

```
Ser Gln Leu Thr His Gly Ile Thr Glu Leu Gly Pro Tyr Thr Leu Asp
 65                  70                  75                  80

Arg Asp Ser Leu Tyr Val Asp Gly Phe Thr His Trp Ser Pro Ile Pro
                 85                  90                  95

Thr Thr Ser Thr Pro Gly Thr Ser Ile Val Asn Leu Gly Thr Ser Gly
            100                 105                 110

Ile Pro Pro Ser Leu Pro Glu Thr Thr Ala Thr Gly Pro Leu Leu Ile
            115                 120                 125

Pro Phe Thr Pro Asn Phe Thr Ile Thr Asn Leu Gln Tyr Glu Glu Asp
130                 135                 140

Met Arg Arg Thr Gly Ser Arg Lys Phe Asn Thr Met Glu Arg Val Leu
145                 150                 155                 160

Gln Gly Leu Leu Ser Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
                180                 185                 190

Ala Thr Gly Met Asp Ala Val Cys Leu Tyr His Pro Asn Pro Lys Arg
            195                 200                 205

Pro Gly Leu Asp Arg Glu Gln Leu Tyr
        210                 215

<210> SEQ ID NO 31
<211> LENGTH: 286
<212> TYPE: PRT
<213> ORGANISM: Homo sapiens

<400> SEQUENCE: 31

Glu Arg Val Leu Gln Gly Leu Leu Arg Pro Val Phe Lys Asn Thr Ser
 1               5                  10                  15

Val Gly Pro Leu Tyr Ser Gly Cys Arg Leu Thr Leu Leu Arg Pro Lys
                20                  25                  30

Lys Asp Gly Ala Ala Thr Lys Val Asp Ala Ile Cys Thr Tyr Arg Pro
            35                  40                  45

Asp Pro Lys Ser Pro Gly Leu Asp Arg Glu Gln Leu Tyr Trp Glu Leu
 50                  55                  60

Ser Gln Leu Thr His Ser Ile Thr Glu Leu Gly Pro Tyr Thr Leu Asp
 65                  70                  75                  80

Arg Asp Ser Leu Tyr Val Asn Gly Phe Thr Gln Arg Ser Ser Val Pro
                 85                  90                  95

Thr Thr Ser Ile Pro Gly Thr Pro Thr Val Asp Leu Gly Thr Ser Gly
            100                 105                 110

Thr Pro Val Ser Lys Pro Gly Pro Ser Ala Ala Ser Pro Leu Leu Val
            115                 120                 125

Pro Phe Thr Leu Asn Phe Thr Ile Thr Asn Leu Gln Tyr Glu Glu Asp
130                 135                 140

Met His Arg Pro Gly Ser Arg Lys Phe Asn Ala Thr Glu Arg Val Leu
145                 150                 155                 160

Gln Gly Leu Leu Ser Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
                180                 185                 190

Ala Thr Gly Met Asp Ala Val Cys Leu Tyr His Pro Asn Pro Lys Arg
            195                 200                 205

Pro Gly Leu Asp Arg Glu Gln Leu Tyr Trp Glu Leu Ser Gln Leu Thr
        210                 215                 220
```

-continued

```
His Asn Ile Thr Glu Leu Gly Pro Tyr Ser Leu Asp Arg Asp Ser Leu
225                 230                 235                 240

Tyr Val Asn Gly Phe Thr His Gln Ser Ser Met Thr Thr Arg Thr
            245                 250                 255

Pro Asp Thr Ser Thr Met His Leu Ala Thr Ser Arg Thr Pro Ala Ser
            260                 265                 270

Leu Ser Gly Pro Thr Thr Ala Ser Pro Leu Leu Ile Pro Phe
            275                 280                 285

<210> SEQ ID NO 32
<211> LENGTH: 288
<212> TYPE: PRT
<213> ORGANISM: Homo sapiens

<400> SEQUENCE: 32

Glu Arg Val Leu Gln Gly Leu Leu Gly Pro Met Phe Lys Asn Thr Ser
1               5                   10                  15

Val Gly Leu Leu Tyr Ser Gly Cys Arg Leu Thr Leu Leu Arg Pro Lys
            20                  25                  30

Lys Asp Gly Ala Ala Thr Lys Val Asp Ala Ile Cys Thr Tyr Arg Pro
        35                  40                  45

Asp Pro Lys Ser Pro Gly Leu Asp Arg Glu Gln Leu Tyr Trp Glu Leu
    50                  55                  60

Ser Gln Leu Thr His Ser Ile Thr Glu Leu Gly Pro Tyr Thr Leu Asp
65                  70                  75                  80

Arg Asp Ser Leu Tyr Val Asn Gly Phe Thr Gln Arg Ser Ser Val Pro
                85                  90                  95

Thr Thr Ser Ile Pro Gly Thr Pro Thr Val Asp Leu Gly Thr Ser Gly
            100                 105                 110

Thr Pro Val Ser Lys Pro Gly Pro Ser Ala Ala Ser Pro Leu Leu Ile
            115                 120                 125

Pro Phe Thr Ile Asn Phe Thr Ile Thr Asn Leu Arg Tyr Glu Glu Asn
    130                 135                 140

Met Gly His Pro Gly Ser Arg Lys Phe Asn Ile Met Glu Arg Val Leu
145                 150                 155                 160

Gln Gly Leu Leu Lys Pro Leu Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Gly Val Asp Ala Ile Cys Thr His Arg Leu Asp Pro Lys Ser
        195                 200                 205

Pro Gly Leu Asn Arg Glu Gln Leu Tyr Trp Glu Leu Ser Lys Leu Thr
    210                 215                 220

Asn Asp Ile Glu Glu Leu Gly Pro Tyr Thr Leu Asp Arg Asn Ser Leu
225                 230                 235                 240

Tyr Val Asn Gly Phe Thr His Gln Ser Ser Val Ser Thr Ser Thr
            245                 250                 255

Pro Gly Thr Ser Thr Val Asp Leu Arg Thr Ser Gly Thr Pro Ser Ser
            260                 265                 270

Leu Ser Ser Pro Thr Ile Met Ala Gly Pro Leu Leu Ile Pro Phe
            275                 280                 285

<210> SEQ ID NO 33
<211> LENGTH: 284
<212> TYPE: PRT
```

<213> ORGANISM: Homo sapiens

<400> SEQUENCE: 33

```
Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Arg Pro Glu
            20                  25                  30

Lys Asp Gly Ala Ala Thr Gly Met Asp Ala Val Cys Leu Tyr His Pro
            35                  40                  45

Asn Pro Lys Arg Pro Gly Leu Asp Arg Glu Gln Leu Tyr Cys Glu Leu
        50                  55                  60

Ser Gln Leu Thr His Asp Ile Thr Glu Leu Gly Pro Tyr Ser Leu Asp
65                  70                  75                  80

Arg Asp Ser Leu Tyr Val Asn Gly Phe Thr His Gln Asn Ser Val Pro
                85                  90                  95

Thr Thr Ser Thr Pro Gly Thr Ser Thr Val Tyr Trp Ala Thr Thr Gly
            100                 105                 110

Thr Pro Ser Ser Phe Pro Gly His Thr Glu Pro Gly Pro Leu Leu Ile
            115                 120                 125

Pro Phe Thr Phe Asn Phe Thr Ile Thr Asn Leu His Tyr Glu Glu Asn
        130                 135                 140

Met Gln His Pro Gly Ser Arg Lys Phe Asn Thr Thr Glu Arg Val Leu
145                 150                 155                 160

Gln Gly Leu Leu Lys Pro Leu Phe Lys Asn Thr Ser Val Gly Pro Leu
                165                 170                 175

Tyr Ser Gly Cys Arg Leu Thr Leu Leu Arg Pro Glu Lys His Glu Ala
            180                 185                 190

Ala Thr Gly Val Asp Thr Ile Cys Thr His Arg Val Asp Pro Ile Gly
            195                 200                 205

Pro Gly Leu Asp Arg Glu Arg Leu Tyr Trp Glu Leu Ser Gln Leu Thr
        210                 215                 220

Asn Ser Ile His Glu Leu Gly Pro Tyr Thr Leu Asp Arg Asp Ser Leu
225                 230                 235                 240

Tyr Val Asn Gly Phe Asn Pro Arg Ser Ser Val Pro Thr Thr Ser Thr
                245                 250                 255

Pro Gly Thr Ser Thr Val His Leu Ala Thr Ser Gly Thr Pro Ser Ser
            260                 265                 270

Leu Pro Gly His Thr Ala Pro Val Pro Leu Leu Ile
        275                 280
```

<210> SEQ ID NO 34
<211> LENGTH: 288
<212> TYPE: PRT
<213> ORGANISM: Homo sapiens

<400> SEQUENCE: 34

```
Glu Arg Val Leu Gln Gly Leu Leu Ser Pro Ile Ser Lys Asn Ser Ser
1               5                   10                  15

Val Gly Pro Leu Tyr Ser Gly Cys Arg Leu Thr Ser Leu Arg Pro Glu
            20                  25                  30

Lys Asp Gly Ala Ala Thr Gly Met Asp Ala Val Cys Leu Tyr His Pro
            35                  40                  45

Asn Pro Lys Arg Pro Gly Leu Asp Arg Glu Gln Leu Tyr Trp Glu Leu
        50                  55                  60

Ser Gln Leu Thr His Asn Ile Thr Glu Leu Gly Pro Tyr Ser Leu Asp
```

```
                65                  70                  75                  80
Arg Asp Ser Leu Tyr Val Asn Gly Phe Thr His Gln Asn Ser Val Pro
                    85                  90                  95

Thr Thr Ser Thr Pro Gly Thr Ser Thr Val Tyr Trp Ala Thr Thr Gly
                100                 105                 110

Thr Pro Ser Ser Phe Pro Gly His Thr Glu Pro Gly Pro Leu Leu Ile
                115                 120                 125

Pro Phe Thr Val Asn Phe Thr Ile Thr Asn Leu Arg Tyr Glu Glu Asn
            130                 135                 140

Met His His Pro Gly Ser Arg Lys Phe Asn Thr Thr Glu Arg Val Leu
145                 150                 155                 160

Gln Gly Leu Leu Arg Pro Val Phe Lys Asn Thr Ser Val Gly Pro Leu
                165                 170                 175

Tyr Ser Gly Cys Arg Leu Thr Leu Leu Arg Pro Lys Lys Asp Gly Ala
                180                 185                 190

Ala Thr Lys Val Asp Ala Ile Cys Thr Tyr Arg Pro Asp Pro Lys Ser
                195                 200                 205

Pro Gly Leu Asp Arg Glu Gln Leu Tyr Trp Glu Leu Ser Lys Leu Thr
            210                 215                 220

Asn Asp Ile Glu Glu Leu Gly Pro Tyr Thr Leu Asp Arg Asn Ser Leu
225                 230                 235                 240

Tyr Val Asn Gly Phe Thr His Gln Ser Ser Val Ser Thr Thr Ser Thr
                245                 250                 255

Pro Gly Thr Ser Thr Val Asp Leu Arg Thr Ser Gly Thr Pro Ser Ser
            260                 265                 270

Leu Ser Ser Pro Thr Ile Met Ala Ala Gly Pro Leu Leu Ile Pro Phe
                275                 280                 285

<210> SEQ ID NO 35
<211> LENGTH: 274
<212> TYPE: PRT
<213> ORGANISM: Homo sapiens

<400> SEQUENCE: 35

Glu Arg Val Leu Gln Gly Leu Leu Ser Pro Ile Phe Lys Asn Ser Ser
1               5                   10                  15

Val Gly Ser Leu Tyr Ser Gly Cys Arg Leu Thr Leu Leu Arg Pro Glu
                20                  25                  30

Lys Asp Gly Ala Ala Thr Arg Val Asp Ala Val Cys Thr His Arg Pro
                35                  40                  45

Asp Pro Lys Ser Pro Gly Leu Asp Arg Glu Arg Leu Tyr Trp Lys Leu
            50                  55                  60

Ser Gln Leu Thr His Gly Ile Thr Glu Leu Gly Pro Tyr Thr Leu Asp
65                  70                  75                  80

Arg His Ser Leu Tyr Val Asn Gly Phe Thr His Gln Ser Ser Met Thr
                85                  90                  95

Thr Thr Arg Thr Pro Asp Thr Ser Met His Leu Ala Thr Ser Arg
                100                 105                 110

Thr Pro Ala Ser Leu Ser Gly Pro Thr Thr Ala Ser Pro Leu Leu Val
                115                 120                 125

Leu Phe Thr Ile Asn Phe Thr Ile Thr Asn Gln Arg Tyr Glu Glu Asn
            130                 135                 140

Met His Pro Gly Ser Arg Lys Phe Asn Thr Thr Glu Arg Val Leu
145                 150                 155                 160
```

```
Gln Gly Leu Leu Arg Pro Val Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Lys Val Asp Ala Ile Cys Thr Tyr Arg Pro Asp Pro Lys Ser
        195                 200                 205

Pro Gly Leu Asp Arg Glu Gln Leu Tyr Trp Glu Leu Ser Gln Leu Thr
    210                 215                 220

His Ser Ile Thr Glu Leu Gly Pro Tyr Thr Gln Asp Arg Asp Ser Leu
225                 230                 235                 240

Tyr Val Asn Gly Phe Thr His Arg Ser Ser Val Pro Thr Thr Ser Ile
                245                 250                 255

Pro Gly Thr Ser Ala Val His Leu Glu Thr Ser Gly Thr Pro Ala Ser
            260                 265                 270

Leu Pro

<210> SEQ ID NO 36
<211> LENGTH: 386
<212> TYPE: PRT
<213> ORGANISM: Homo sapiens

<400> SEQUENCE: 36

Glu Arg Val Leu Gln Gly Leu Leu Gly Pro Met Phe Lys Asn Thr Ser
1               5                   10                  15

Val Gly Leu Leu Tyr Ser Gly Cys Arg Leu Thr Leu Leu Arg Pro Glu
                20                  25                  30

Lys Arg Gly Ala Ala Thr Gly Val Asp Thr Ile Cys Thr His Arg Leu
            35                  40                  45

Asp Pro Leu Asn Pro Gly Leu Asp Arg Glu Gln Leu Tyr Trp Glu Leu
        50                  55                  60

Ser Lys Leu Thr Arg Gly Ile Ile Glu Leu Gly Pro Tyr Leu Leu Asp
65                  70                  75                  80

Arg Gly Ser Leu Tyr Val Asn Gly Phe Thr His Arg Asn Phe Val Pro
                85                  90                  95

Ile Thr Ser Thr Pro Gly Thr Ser Thr Val His Leu Gly Thr Ser Glu
                100                 105                 110

Thr Pro Ser Ser Leu Pro Arg Pro Ile Val Pro Gly Pro Leu Leu Val
            115                 120                 125

Pro Phe Thr Leu Asn Phe Thr Ile Thr Asn Leu Gln Tyr Glu Glu Ala
    130                 135                 140

Met Arg His Pro Gly Ser Arg Lys Phe Asn Thr Thr Glu Arg Val Leu
145                 150                 155                 160

Gln Gly Leu Leu Arg Pro Leu Phe Lys Asn Thr Ser Val Ser Ser Leu
                165                 170                 175

Tyr Ser Gly Cys Arg Leu Thr Leu Leu Arg Pro Glu Lys Asp Gly Ala
            180                 185                 190

Ala Thr Arg Val Asp Ala Ala Cys Thr Tyr Arg Pro Asp Pro Lys Ser
        195                 200                 205

Pro Gly Leu Asp Arg Glu Gln Leu Tyr Trp Glu Leu Ser Gln Leu Thr
    210                 215                 220

His Ser Ile Thr Glu Leu Gly Pro Tyr Thr Leu Asp Arg Val Ser Leu
225                 230                 235                 240

Tyr Val Asn Gly Phe Asn Pro Arg Ser Ser Val Pro Thr Thr Ser Thr
                245                 250                 255
```

```
Pro Gly Thr Ser Thr Val His Leu Ala Thr Ser Gly Thr Pro Ser Ser
            260                 265                 270

Leu Pro Gly His Thr Ala Pro Val Pro Leu Leu Ile Pro Phe Thr Leu
        275                 280                 285

Asn Phe Thr Ile Thr Asn Leu Gln Tyr Glu Glu Asp Met Arg His Pro
    290                 295                 300

Gly Ser Arg Lys Phe Asn Thr Met Glu Arg Val Leu Gln Gly Leu Leu
305                 310                 315                 320

Arg Pro Leu Phe Lys Asn Thr Ser Ile Gly Pro Leu Tyr Ser Ser Cys
            325                 330                 335

Arg Leu Thr Leu Leu Arg Pro Glu Lys Asp Lys Ala Ala Thr Arg Val
            340                 345                 350

Asp Ala Ile Cys Thr His His Pro Asp Pro Gln Ser Pro Gly Leu Asn
            355                 360                 365

Arg Glu Gln Leu Tyr Trp Glu Leu Ser Gln Leu Thr His Gly Ile Thr
        370                 375                 380

Glu Leu
385

<210> SEQ ID NO 37
<211> LENGTH: 438
<212> TYPE: PRT
<213> ORGANISM: Homo sapiens

<400> SEQUENCE: 37

Glu Arg Val Leu His Gly Leu Leu Thr Pro Leu Phe Lys Asn Thr Arg
1               5                   10                  15

Val Gly Pro Leu Tyr Ser Gly Cys Arg Leu Thr Leu Leu Arg Pro Glu
            20                  25                  30

Lys Gln Glu Ala Ala Thr Gly Val Asp Thr Ile Cys Thr His Arg Val
        35                  40                  45

Asp Pro Ile Gly Pro Gly Leu Asp Arg Glu Arg Leu Tyr Trp Glu Leu
    50                  55                  60

Ser Gln Leu Thr Asn Ser Ile Thr Glu Leu Gly Pro Tyr Thr Leu Asp
65                  70                  75                  80

Arg Asp Ser Leu Tyr Val Asn Gly Phe Asn Pro Trp Ser Ser Val Pro
            85                  90                  95

Thr Thr Ser Thr Pro Gly Thr Ser Thr Val His Leu Ala Thr Ser Gly
            100                 105                 110

Thr Pro Ser Ser Leu Pro Gly His Thr Ala Pro Val Pro Leu Leu Ile
        115                 120                 125

Pro Phe Thr Leu Asn Phe Thr Ile Thr Asn Leu His Tyr Glu Glu Asn
    130                 135                 140

Met Gln His Pro Gly Ser Arg Lys Phe Asn Thr Thr Glu Arg Val Leu
145                 150                 155                 160

Gln Gly Leu Leu Lys Pro Leu Phe Lys Asn Thr Ser Val Gly Pro Leu
            165                 170                 175

Tyr Ser Gly Cys Arg Leu Thr Leu Phe Lys Pro Glu Lys His Glu Ala
            180                 185                 190

Ala Thr Gly Val Asp Ala Ile Cys Thr Leu Arg Leu Asp Pro Thr Gly
        195                 200                 205

Pro Gly Leu Asp Arg Glu Arg Leu Tyr Trp Glu Leu Ser Gln Leu Thr
    210                 215                 220

Asn Ser Val Thr Glu Leu Gly Pro Tyr Thr Leu Asp Arg Asp Ser Leu
225                 230                 235                 240
```

```
Tyr Val Asn Gly Phe Thr His Arg Ser Ser Val Pro Thr Thr Ser Ile
                245                 250                 255

Pro Gly Thr Ser Ala Val His Leu Glu Thr Ser Gly Thr Pro Ala Ser
            260                 265                 270

Leu Pro Gly His Thr Ala Pro Gly Pro Leu Leu Ile Pro Phe Thr Leu
        275                 280                 285

Asn Phe Thr Ile Thr Asn Leu Gln Tyr Glu Glu Asp Met Arg Arg Thr
    290                 295                 300

Gly Ser Arg Lys Phe Asn Thr Met Glu Arg Val Leu Gln Gly Leu Leu
305                 310                 315                 320

Lys Pro Leu Phe Lys Ser Thr Ser Val Gly Pro Leu Tyr Ser Gly Cys
                325                 330                 335

Arg Leu Thr Leu Leu Arg Pro Glu Lys Arg Gly Ala Ala Thr Gly Val
            340                 345                 350

Asp Thr Ile Cys Thr His Arg Leu Asp Pro Leu Asn Pro Gly Leu Asp
        355                 360                 365

Arg Glu Gln Leu Tyr Trp Glu Leu Ser Lys Leu Thr Arg Gly Ile Ile
    370                 375                 380

Glu Leu Gly Pro Tyr Leu Leu Asp Arg Gly Ser Leu Tyr Val Asn Gly
385                 390                 395                 400

Phe Thr His Arg Asn Phe Val Pro Ile Thr Ser Thr Pro Gly Thr Ser
                405                 410                 415

Thr Val His Leu Gly Thr Ser Glu Ile His Pro Ser Leu Pro Arg Pro
            420                 425                 430

Ile Val Pro Gly Pro Leu
        435

<210> SEQ ID NO 38
<211> LENGTH: 420
<212> TYPE: PRT
<213> ORGANISM: Homo sapiens

<400> SEQUENCE: 38

Gly Pro Leu Tyr Ser Gly Cys Arg Leu Thr Ser Leu Arg Pro Glu Lys
1               5                   10                  15

Asp Gly Ala Ala Thr Gly Met Asp Ala Val Cys Leu Tyr His Pro Asn
            20                  25                  30

Pro Lys Arg Pro Gly Leu Asp Arg Glu Gln Leu Tyr Trp Glu Leu Ser
        35                  40                  45

Gln Leu Thr His Asn Ile Thr Glu Leu Gly Pro Tyr Ser Leu Asp Arg
    50                  55                  60

Asp Ser Leu Tyr Val Asn Gly Phe Thr His Gln Asn Ser Val Pro Thr
65                  70                  75                  80

Thr Ser Thr Pro Gly Thr Ser Thr Val Tyr Trp Ala Thr Thr Gly Thr
                85                  90                  95

Pro Ser Ser Phe Pro Gly His Thr Glu Pro Gly Pro Leu Leu Ile Pro
            100                 105                 110

Phe Thr Leu Asn Phe Thr Ile Thr Asn Leu Gln Tyr Glu Glu Asn Met
        115                 120                 125

Gly His Pro Gly Ser Arg Lys Phe Asn Ile Thr Glu Ser Val Leu Gln
    130                 135                 140

Gly Leu Leu Thr Pro Leu Phe Lys Asn Ser Ser Val Gly Pro Leu Tyr
145                 150                 155                 160

Ser Gly Cys Arg Leu Ile Ser Leu Arg Ser Glu Lys Asp Gly Ala Ala
```

```
            165                 170                 175
Thr Gly Val Asp Ala Ile Cys Thr His His Leu Asn Pro Gln Ser Pro
            180                 185                 190

Gly Leu Asp Arg Glu Gln Leu Tyr Trp Gln Leu Ser Gln Met Thr Asn
            195                 200                 205

Gly Ile Lys Glu Leu Gly Pro Tyr Thr Leu Asp Arg Asp Ser Leu Tyr
            210                 215                 220

Val Asn Gly Phe Thr His Arg Ser Leu Gly Leu Thr Thr Ser Thr Pro
225                 230                 235                 240

Trp Thr Ser Thr Val Asp Leu Gly Thr Ser Gly Thr Pro Ser Pro Val
                245                 250                 255

Pro Ser Pro Thr Thr Ala Gly Pro Leu Leu Ile Pro Phe Thr Leu Asn
                260                 265                 270

Phe Thr Ile Thr Asn Leu Gln Tyr Glu Glu Asn Met Gly His Pro Gly
                275                 280                 285

Ser Arg Lys Phe Asn Ile Met Glu Arg Val Leu Gln Gly Leu Leu Arg
                290                 295                 300

Pro Val Phe Lys Asn Thr Ser Val Gly Pro Leu Tyr Ser Gly Cys Arg
305                 310                 315                 320

Leu Thr Leu Leu Arg Pro Lys Lys Asp Gly Ala Ala Thr Lys Val Asp
                325                 330                 335

Ala Ile Cys Thr Tyr Arg Pro Asp Pro Lys Ser Pro Gly Leu Asp Arg
                340                 345                 350

Glu Gln Leu Tyr Trp Glu Leu Ser Gln Leu Thr His Ser Ile Thr Glu
                355                 360                 365

Leu Gly Pro Tyr Thr Leu Asp Arg Asp Ser Leu Tyr Val Asn Gly Phe
                370                 375                 380

Thr Gln Arg Ser Ser Val Pro Thr Thr Ser Ile Pro Gly Thr Pro Thr
385                 390                 395                 400

Val Asp Leu Gly Thr Ser Gly Thr Pro Val Ser Lys Pro Gly Pro Ser
                405                 410                 415

Ala Ala Ser Pro
                420

<210> SEQ ID NO 39
<211> LENGTH: 439
<212> TYPE: PRT
<213> ORGANISM: Homo sapiens

<400> SEQUENCE: 39

Glu Arg Val Leu Gln Gly Pro Leu Ser Pro Ile Phe Lys Asn Ser Ser
1               5                   10                  15

Val Gly Pro Leu Tyr Ser Gly Cys Arg Leu Thr Ser Leu Arg Pro Glu
                20                  25                  30

Lys Asp Gly Ala Ala Thr Gly Met Asp Ala Val Cys Leu Tyr His Pro
                35                  40                  45

Asn Pro Lys Arg Pro Gly Leu Asp Arg Glu Gln Leu Tyr Trp Glu Leu
                50                  55                  60

Ser Gln Leu Thr His Asn Ile Thr Glu Leu Gly Pro Tyr Ser Leu Asp
65                  70                  75                  80

Arg Asp Ser Leu Tyr Val Asn Gly Phe Thr His Gln Asn Ser Val Pro
                85                  90                  95

Thr Thr Ser Thr Pro Gly Thr Ser Thr Val Tyr Trp Ala Thr Thr Gly
                100                 105                 110
```

```
Thr Pro Ser Ser Phe Pro Gly His Thr Glu Pro Gly Pro Leu Leu Ile
        115                 120                 125

Pro Phe Thr Leu Asn Phe Thr Ile Thr Asn Leu Gln Tyr Glu Glu Asn
130                 135                 140

Met Gly His Pro Gly Ser Arg Lys Phe Asn Ile Thr Glu Arg Val Leu
145                 150                 155                 160

Gln Gly Leu Leu Asn Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
            180                 185                 190

Ala Thr Gly Met Asp Ala Val Cys Leu Tyr His Pro Asn Pro Lys Arg
        195                 200                 205

Pro Gly Leu Asp Arg Glu Gln Leu Tyr Cys Glu Leu Ser Gln Leu Thr
    210                 215                 220

His Asn Ile Thr Glu Leu Gly Pro Tyr Ser Leu Asp Arg Asp Ser Leu
225                 230                 235                 240

Tyr Val Asn Gly Phe Thr His Gln Asn Ser Val Pro Thr Thr Ser Thr
                245                 250                 255

Pro Gly Thr Ser Thr Val Tyr Trp Ala Thr Thr Gly Thr Pro Ser Ser
            260                 265                 270

Phe Pro Gly His Thr Glu Pro Gly Pro Leu Leu Ile Pro Phe Thr Leu
        275                 280                 285

Asn Phe Thr Ile Thr Asn Leu Gln Tyr Glu Glu Asp Met Arg Arg Thr
    290                 295                 300

Gly Ser Arg Lys Phe Asn Thr Met Glu Arg Val Leu Gln Gly Leu Leu
305                 310                 315                 320

Lys Pro Leu Phe Lys Ser Thr Ser Val Gly Pro Leu Tyr Ser Gly Cys
                325                 330                 335

Arg Leu Thr Leu Leu Arg Pro Glu Lys His Gly Ala Ala Thr Gly Val
            340                 345                 350

Asp Ala Ile Cys Thr Leu Arg Leu Asp Pro Thr Gly Pro Gly Leu Asp
        355                 360                 365

Arg Glu Arg Leu Tyr Trp Glu Leu Ser Gln Leu Thr Asn Ser Val Thr
    370                 375                 380

Glu Leu Gly Pro Tyr Thr Leu Asp Arg Asp Ser Leu Tyr Val Asn Gly
385                 390                 395                 400

Phe Thr His Arg Ser Ser Val Pro Thr Thr Ser Ile Pro Gly Thr Ser
                405                 410                 415

Ala Val His Leu Glu Thr Ser Gly Thr Pro Ala Ser Leu Pro Gly His
            420                 425                 430

Thr Ala Pro Gly Pro Leu Leu
        435

<210> SEQ ID NO 40
<211> LENGTH: 424
<212> TYPE: PRT
<213> ORGANISM: Homo sapiens

<400> SEQUENCE: 40

Thr Ser Val Gly Pro Leu Tyr Ser Gly Cys Arg Leu Thr Leu Leu Arg
1               5                   10                  15

Ser Glu Lys Asp Gly Ala Ala Thr Gly Val Asp Ala Ile Tyr Thr His
                20                  25                  30

Arg Leu Asp Pro Lys Ser Pro Gly Val Asp Arg Glu Gln Leu Tyr Trp
            35                  40                  45
```

```
Glu Leu Ser Gln Leu Thr Asn Gly Ile Lys Glu Leu Gly Pro Tyr Thr
 50                  55                  60

Leu Asp Arg Asn Ser Leu Tyr Val Asn Gly Phe Thr His Gln Thr Ser
 65                  70                  75                  80

Ala Pro Asn Thr Ser Thr Pro Gly Thr Ser Thr Val Asp Leu Gly Thr
                 85                  90                  95

Ser Gly Thr Pro Ser Ser Leu Pro Ser Pro Thr Ser Ala Gly Pro Leu
            100                 105                 110

Leu Ile Pro Phe Thr Ile Asn Phe Thr Ile Thr Asn Leu Arg Tyr Glu
            115                 120                 125

Glu Asn Met His His Pro Gly Ser Arg Lys Phe Asn Thr Met Glu Arg
130                 135                 140

Val Leu Gln Gly Leu Leu Lys Pro Leu Phe Lys Ser Thr Ser Val Gly
145                 150                 155                 160

Pro Leu Tyr Ser Gly Cys Arg Leu Thr Leu Leu Arg Pro Glu Lys Asp
                165                 170                 175

Gly Val Ala Thr Arg Val Asp Ala Ile Cys Thr His Arg Pro Asp Pro
            180                 185                 190

Lys Ile Pro Gly Leu Asp Arg Gln Gln Leu Tyr Trp Glu Leu Ser Gln
            195                 200                 205

Leu Thr His Ser Ile Thr Glu Leu Gly Pro Tyr Thr Leu Asp Arg Asp
210                 215                 220

Ser Leu Tyr Val Asn Gly Phe Thr Gln Arg Ser Ser Val Pro Thr Thr
225                 230                 235                 240

Ser Thr Pro Gly Thr Phe Thr Val Gln Pro Glu Thr Ser Glu Thr Pro
                245                 250                 255

Ser Ser Leu Pro Gly Pro Thr Ala Thr Gly Pro Val Leu Leu Pro Phe
            260                 265                 270

Thr Leu Asn Phe Thr Ile Ile Asn Leu Gln Tyr Glu Glu Asp Met His
            275                 280                 285

Arg Pro Gly Ser Arg Lys Phe Asn Thr Thr Glu Arg Val Leu Gln Gly
290                 295                 300

Leu Leu Lys Pro Leu Phe Lys Ser Thr Ser Val Gly Pro Leu Tyr Ser
305                 310                 315                 320

Gly Cys Arg Leu Thr Leu Leu Arg Pro Glu Lys His Gly Ala Ala Thr
                325                 330                 335

Gly Val Asp Ala Ile Cys Thr Leu Arg Leu Asp Pro Thr Gly Pro Gly
            340                 345                 350

Leu Asp Arg Glu Arg Leu Tyr Trp Glu Leu Ser Gln Leu Thr Asn Ser
            355                 360                 365

Ile Thr Glu Leu Gly Pro Tyr Thr Leu Asp Arg Asp Ser Leu Tyr Val
370                 375                 380

Asn Gly Phe Asn Pro Trp Ser Ser Val Pro Thr Thr Ser Thr Pro Gly
385                 390                 395                 400

Thr Ser Thr Val His Leu Ala Thr Ser Gly Thr Pro Ser Ser Leu Pro
                405                 410                 415

Gly His Thr Ala Pro Val Pro Leu
            420

<210> SEQ ID NO 41
<211> LENGTH: 418
<212> TYPE: PRT
<213> ORGANISM: Homo sapiens
```

-continued

<400> SEQUENCE: 41

```
Thr Leu Leu Arg Pro Lys Lys Asp Gly Val Ala Thr Gly Val Asp Ala
1               5                   10                  15

Ile Cys Thr His Arg Leu Asp Pro Lys Ser Pro Gly Leu Asn Arg Glu
            20                  25                  30

Gln Leu Tyr Trp Glu Leu Ser Lys Leu Thr Asn Asp Ile Glu Glu Leu
        35                  40                  45

Gly Pro Tyr Thr Leu Asp Arg Asn Ser Leu Tyr Val Asn Gly Phe Thr
    50                  55                  60

His Gln Ser Ser Val Ser Thr Thr Ser Thr Pro Gly Thr Ser Thr Val
65                  70                  75                  80

Asp Leu Arg Thr Ser Gly Thr Pro Ser Ser Leu Ser Ser Pro Thr Ile
                85                  90                  95

Met Ala Ala Gly Pro Leu Leu Ile Pro Phe Thr Ile Asn Phe Thr Ile
            100                 105                 110

Thr Asn Leu Arg Tyr Glu Glu Asn Met His His Pro Gly Ser Arg Lys
        115                 120                 125

Phe Asn Thr Met Glu Arg Val Leu Gln Gly Leu Leu Met Pro Leu Phe
    130                 135                 140

Lys Asn Thr Ser Val Ser Ser Leu Tyr Ser Gly Cys Arg Leu Thr Leu
145                 150                 155                 160

Leu Arg Pro Glu Lys Asp Gly Ala Ala Thr Arg Val Asp Ala Val Cys
                165                 170                 175

Thr His Arg Pro Asp Pro Lys Ser Pro Gly Leu Asp Arg Glu Arg Leu
            180                 185                 190

Tyr Trp Lys Leu Ser Gln Leu Thr His Gly Ile Thr Glu Leu Gly Pro
        195                 200                 205

Tyr Thr Leu Asp Arg Asn Ser Leu Tyr Val Asn Gly Phe Thr His Arg
    210                 215                 220

Ser Ser Met Pro Thr Thr Ser Thr Pro Gly Thr Ser Thr Val Asp Val
225                 230                 235                 240

Gly Thr Ser Gly Thr Pro Ser Ser Ser Pro Ser Pro Thr Thr Ala Gly
                245                 250                 255

Pro Leu Leu Met Pro Phe Thr Leu Asn Phe Thr Ile Thr Asn Leu Gln
            260                 265                 270

Tyr Glu Glu Asp Met Arg Arg Thr Gly Ser Arg Lys Phe Asn Thr Met
        275                 280                 285

Glu Arg Val Leu Gln Gly Leu Leu Lys Pro Leu Phe Lys Ser Thr Ser
    290                 295                 300

Val Gly Pro Leu Tyr Ser Gly Cys Arg Leu Thr Leu Leu Arg Pro Glu
305                 310                 315                 320

Lys His Gly Ala Ala Thr Gly Val Asp Ala Ile Cys Thr Leu Arg Leu
                325                 330                 335

Asp Pro Thr Gly Pro Gly Leu Asp Arg Glu Arg Leu Tyr Trp Glu Leu
            340                 345                 350

Ser Gln Leu Thr Asn Ser Val Thr Glu Leu Gly Pro Tyr Thr Leu Asp
        355                 360                 365

Arg Asp Ser Leu Tyr Val Asn Gly Phe Thr His Arg Ser Ser Val Pro
    370                 375                 380

Thr Thr Ser Ile Pro Gly Thr Ser Ala Val His Leu Glu Thr Ser Gly
385                 390                 395                 400

Thr Pro Ala Ser Leu Pro Gly His Thr Ala Pro Gly Pro Leu Leu Ile
                405                 410                 415
```

Pro Phe

<210> SEQ ID NO 42
<211> LENGTH: 443
<212> TYPE: PRT
<213> ORGANISM: Homo sapiens

<400> SEQUENCE: 42

```
Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
            20                  25                  30

Lys Asp Gly Val Ala Thr Arg Val Asp Ala Ile Cys Thr His Arg Pro
        35                  40                  45

Asp Pro Lys Ile Pro Gly Leu Asp Arg Gln Gln Leu Tyr Trp Glu Leu
    50                  55                  60

Ser Gln Leu Thr His Ser Ile Thr Glu Leu Pro Tyr Thr Leu Asp
65                  70                  75                  80

Arg Asp Ser Leu Tyr Val Asn Gly Phe Thr Gln Arg Ser Ser Val Pro
                85                  90                  95

Thr Thr Ser Thr Pro Gly Thr Phe Thr Val Gln Pro Glu Thr Ser Glu
            100                 105                 110

Thr Pro Ser Ser Leu Pro Gly Pro Thr Ala Thr Gly Pro Val Leu Leu
        115                 120                 125

Pro Phe Thr Leu Asn Phe Thr Ile Ile Asn Leu Gln Tyr Glu Glu Asp
    130                 135                 140

Met His Arg Pro Gly Ser Arg Lys Phe Asn Thr Thr Glu Arg Val Leu
145                 150                 155                 160

Gln Gly Leu Leu Met Pro Leu Phe Lys Asn Thr Ser Val Gly Pro Leu
                165                 170                 175

Tyr Ser Gly Cys Arg Leu Thr Leu Leu Arg Pro Glu Lys Gln Glu Ala
            180                 185                 190

Ala Thr Gly Val Asp Thr Ile Cys Thr His Arg Leu Asp Pro Ser Glu
        195                 200                 205

Pro Gly Leu Asp Arg Glu Gln Leu Tyr Trp Glu Leu Ser Gln Leu Thr
    210                 215                 220

Asn Ser Ile Thr Glu Leu Gly Pro Tyr Thr Leu Asp Arg Asp Ser Leu
225                 230                 235                 240

Tyr Val Asn Gly Phe Thr His Ser Gly Val Leu Cys Pro Pro Ser
                245                 250                 255

Ile Leu Gly Ile Phe Thr Val Gln Pro Glu Thr Phe Glu Thr Pro Ser
            260                 265                 270

Ser Leu Pro Gly Pro Thr Ala Thr Gly Pro Val Leu Leu Pro Phe Thr
        275                 280                 285

Leu Asn Phe Thr Ile Ile Asn Leu Gln Tyr Glu Glu Asp Met His Arg
    290                 295                 300

Pro Gly Ser Arg Lys Phe Asn Thr Thr Glu Arg Val Leu Gln Gly Leu
305                 310                 315                 320

Leu Met Pro Leu Phe Lys Asn Thr Ser Val Gly Pro Leu Tyr Ser Gly
                325                 330                 335

Cys Arg Leu Thr Leu Leu Arg Pro Glu Lys Gln Glu Ala Ala Thr Gly
            340                 345                 350

Val Asp Thr Ile Cys Thr His Arg Val Asp Pro Ile Gly Pro Gly Leu
        355                 360                 365
```

-continued

Asp Arg Glu Arg Leu Tyr Trp Glu Leu Ser Gln Leu Thr Asn Ser Ile
        370                 375                 380

Thr Glu Leu Gly Pro Tyr Thr Leu Asp Arg Asp Ser Leu Tyr Val Asn
385                 390                 395                 400

Gly Phe Asn Pro Trp Ser Ser Val Pro Thr Thr Ser Thr Pro Gly Thr
                405                 410                 415

Ser Thr Val His Leu Ala Thr Ser Gly Thr Pro Ser Ser Leu Pro Gly
            420                 425                 430

His Thr Ala Pro Val Pro Leu Leu Ile Pro Phe
        435                 440

<210> SEQ ID NO 43
<211> LENGTH: 442
<212> TYPE: PRT
<213> ORGANISM: Homo sapiens

<400> SEQUENCE: 43

Glu Arg Val Leu Gln Gly Leu Leu Lys Pro Leu Phe Arg Asn Ser Ser
1               5                   10                  15

Leu Glu Tyr Leu Tyr Ser Gly Cys Arg Leu Ala Ser Leu Arg Pro Glu
            20                  25                  30

Lys Asp Ser Ser Ala Met Ala Val Asp Ala Ile Cys Thr His Arg Pro
        35                  40                  45

Asp Pro Glu Asp Leu Gly Leu Asp Arg Glu Arg Leu Tyr Trp Glu Leu
    50                  55                  60

Ser Asn Leu Thr Asn Gly Ile Gln Glu Leu Gly Pro Tyr Thr Leu Asp
65                  70                  75                  80

Arg Asn Ser Leu Tyr Val Asn Gly Phe Thr His Arg Ser Ser Met Pro
                85                  90                  95

Thr Thr Ser Thr Pro Gly Thr Ser Thr Val Asp Val Gly Thr Ser Gly
            100                 105                 110

Thr Pro Ser Ser Ser Pro Ser Pro Thr Thr Ala Gly Pro Leu Leu Met
        115                 120                 125

Pro Phe Thr Leu Asn Phe Thr Ile Thr Asn Leu Gln Tyr Glu Glu Asp
    130                 135                 140

Met Arg Arg Thr Gly Ser Arg Lys Phe Asn Thr Met Glu Ser Val Leu
145                 150                 155                 160

Gln Gly Leu Leu Lys Pro Leu Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Gly Val Asp Ala Ile Cys Thr His Arg Leu Asp Pro Lys Ser
        195                 200                 205

Pro Gly Leu Asn Arg Glu Gln Leu Tyr Trp Glu Leu Ser Lys Leu Thr
    210                 215                 220

Asn Asp Ile Glu Glu Val Gly Pro Tyr Thr Leu Asp Arg Asn Ser Leu
225                 230                 235                 240

Tyr Val Asn Gly Phe Thr His Arg Ser Phe Val Ala Pro Thr Ser Thr
                245                 250                 255

Leu Gly Thr Ser Thr Val Asp Leu Gly Thr Ser Gly Thr Pro Ser Ser
            260                 265                 270

Leu Pro Ser Pro Thr Thr Gly Val Pro Leu Leu Ile Pro Phe Thr Leu
        275                 280                 285

Asn Phe Thr Ile Thr Asn Leu Gln Tyr Glu Glu Asn Met Gly His Pro

```
              290                 295                 300
Gly Ser Arg Lys Phe Asn Ile Met Glu Arg Val Leu Gln Gly Leu Leu
305                 310                 315                 320

Met Pro Leu Phe Lys Asn Thr Ser Val Ser Ser Leu Tyr Ser Gly Cys
                325                 330                 335

Arg Leu Thr Leu Leu Arg Pro Glu Lys Asp Gly Ala Ala Thr Arg Val
                340                 345                 350

Val Ala Val Cys Thr His Arg Pro Asp Pro Lys Ser Pro Gly Leu Asp
                355                 360                 365

Arg Glu Arg Leu Tyr Trp Lys Leu Ser Gln Leu Thr His Gly Ile Thr
                370                 375                 380

Glu Leu Gly Pro Tyr Thr Leu Asp Arg His Ser Leu Tyr Val Asn Gly
385                 390                 395                 400

Phe Thr His Gln Ser Ser Met Thr Thr Thr Arg Thr Pro Asp Thr Ser
                405                 410                 415

Thr Met His Leu Ala Thr Ser Arg Thr Pro Ala Ser Leu Ser Gly Pro
                420                 425                 430

Thr Thr Ala Ser Pro Leu Leu Ile Pro Phe
                435                 440

<210> SEQ ID NO 44
<211> LENGTH: 442
<212> TYPE: PRT
<213> ORGANISM: Homo sapiens

<400> SEQUENCE: 44

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
                20                  25                  30

Lys Arg Gly Ala Ala Thr Gly Val Asp Thr Ile Cys Thr His Arg Leu
                35                  40                  45

Asp Pro Leu Asn Pro Gly Leu Asp Arg Glu Gln Leu Tyr Trp Glu Leu
                50                  55                  60

Ser Lys Leu Thr Arg Gly Ile Ile Glu Leu Gly Pro Tyr Leu Leu Asp
65              70                  75                  80

Arg Gly Ser Leu Tyr Val Asn Gly Phe Thr His Arg Asn Phe Val Pro
                85                  90                  95

Ile Thr Ser Thr Pro Gly Thr Ser Thr Val His Leu Gly Thr Ser Glu
                100                 105                 110

Thr Pro Ser Ser Leu Pro Arg Pro Ile Val Pro Gly Pro Leu Leu Ile
                115                 120                 125

Pro Phe Thr Leu Asn Phe Thr Ile Thr Asn Leu Gln Tyr Glu Glu Asn
                130                 135                 140

Met Gly His Pro Gly Ser Arg Lys Phe Asn Ile Thr Glu Arg Val Leu
145                 150                 155                 160

Gln Gly Leu Leu Lys Pro Leu Phe Arg Asn Ser Ser Leu Glu Tyr Leu
                165                 170                 175

Tyr Ser Gly Cys Arg Leu Thr Ser Leu Arg Pro Glu Lys Asp Ser Ser
                180                 185                 190

Thr Met Ala Val Asp Ala Ile Cys Thr His Arg Pro Asp Pro Glu Asp
                195                 200                 205

Leu Gly Leu Asp Arg Glu Arg Leu Tyr Trp Glu Leu Ser Asn Leu Thr
210                 215                 220
```

```
Asn Gly Ile Gln Glu Leu Gly Pro Tyr Thr Leu Asp Arg Asn Ser Leu
225                 230                 235                 240

Tyr Val Asn Gly Phe Thr His Arg Ser Phe Met Pro Thr Thr Ser Thr
                245                 250                 255

Leu Gly Thr Ser Thr Val Asp Val Gly Thr Ser Gly Thr Pro Ser Ser
            260                 265                 270

Ser Pro Ser Pro Thr Thr Ala Gly Pro Leu Leu Met Pro Phe Thr Leu
        275                 280                 285

Asn Phe Thr Ile Thr Asn Leu Gln Tyr Glu Glu Asp Met Arg Arg Thr
    290                 295                 300

Gly Ser Arg Lys Phe Asn Thr Met Glu Ser Val Leu Gln Gly Leu Leu
305                 310                 315                 320

Lys Pro Leu Phe Lys Asn Thr Ser Val Gly Pro Leu Tyr Ser Gly Cys
                325                 330                 335

Arg Leu Thr Leu Leu Arg Pro Lys Lys Asp Gly Ala Ala Thr Gly Val
            340                 345                 350

Asp Ala Ile Cys Thr His Arg Leu Asp Pro Lys Ser Pro Gly Leu Asn
        355                 360                 365

Arg Glu Gln Leu Tyr Trp Glu Leu Ser Lys Leu Thr Asn Asp Ile Glu
370                 375                 380

Glu Leu Gly Pro Tyr Thr Leu Asp Arg Asn Ser Leu Tyr Val Asn Gly
385                 390                 395                 400

Phe Thr His Gln Ser Ser Val Ser Thr Thr Ser Thr Pro Gly Thr Ser
                405                 410                 415

Thr Val Asp Pro Arg Thr Ser Gly Thr Pro Ser Ser Leu Ser Ser Pro
            420                 425                 430

Thr Ile Met Ala Ala Gly Pro Leu Leu Ile
            435                 440

<210> SEQ ID NO 45
<211> LENGTH: 379
<212> TYPE: PRT
<213> ORGANISM: Homo sapiens

<400> SEQUENCE: 45

Glu Arg Val Leu Gln Gly Leu Leu Gly Pro Met Phe Lys Asn Thr Ser
1               5                   10                  15

Val Gly Leu Leu Tyr Ser Gly Cys Arg Leu Thr Leu Leu Arg Pro Glu
                20                  25                  30

Lys Asn Gly Ala Ala Thr Gly Met Asp Ala Ile Cys Ser His Arg Leu
            35                  40                  45

Asp Pro Lys Ser Pro Gly Leu Asn Arg Glu Gln Leu Tyr Trp Glu Leu
        50                  55                  60

Ser Gln Leu Thr His Gly Ile Lys Glu Leu Gly Pro Tyr Thr Leu Asp
65                  70                  75                  80

Arg Asn Ser Leu Tyr Val Asn Gly Phe Thr His Arg Ser Ser Val Ala
                85                  90                  95

Pro Thr Ser Thr Pro Gly Thr Ser Thr Val Asp Leu Gly Thr Ser Gly
            100                 105                 110

Thr Pro Ser Ser Leu Pro Ser Pro Thr Thr Ala Val Pro Leu Leu Ile
        115                 120                 125

Pro Phe Thr Leu Asn Phe Thr Ile Thr Asn Leu Lys Tyr Glu Glu Asp
    130                 135                 140

Met His Cys Pro Gly Ser Arg Lys Phe Asn Thr Thr Glu Arg Val Leu
145                 150                 155                 160
```

```
Gln Ser Leu Phe Gly Pro Met Phe Lys Asn Thr Ser Val Gly Pro Leu
                165                 170                 175
Tyr Ser Gly Cys Arg Leu Thr Leu Phe Arg Ser Glu Lys Asp Gly Ala
            180                 185                 190
Ala Thr Gly Val Asp Ala Ile Cys Thr His Arg Leu Asp Pro Lys Ser
        195                 200                 205
Pro Gly Val Asp Arg Glu Gln Leu Tyr Trp Glu Leu Ser Gln Leu Thr
    210                 215                 220
Asn Gly Ile Lys Glu Leu Gly Pro Tyr Thr Leu Asp Arg Asn Ser Leu
225                 230                 235                 240
Tyr Val Asn Gly Phe Thr His Gln Thr Ser Ala Pro Asn Thr Ser Thr
                245                 250                 255
Pro Gly Thr Ser Thr Val Asp Leu Gly Thr Ser Gly Thr Pro Ser Ser
            260                 265                 270
Leu Pro Ser Pro Thr Ser Ala Gly Pro Leu Leu Val Pro Phe Thr Leu
        275                 280                 285
Asn Phe Thr Ile Thr Asn Leu Gln Tyr Glu Glu Asp Met Arg Arg Thr
    290                 295                 300
Gly Ser Arg Lys Phe Asn Thr Met Glu Ser Val Leu Gln Gly Leu Leu
305                 310                 315                 320
Lys Pro Leu Phe Lys Asn Thr Ser Val Gly Pro Leu Tyr Ser Gly Cys
                325                 330                 335
Arg Leu Thr Leu Leu Arg Pro Glu Lys Asp Gly Ala Ala Thr Gly Val
            340                 345                 350
Asp Ala Ile Cys Thr His Arg Leu Asp Pro Lys Ser Pro Gly Leu Asn
        355                 360                 365
Arg Glu Gln Leu Tyr Trp Glu Leu Ser Lys Leu
    370                 375

<210> SEQ ID NO 46
<211> LENGTH: 439
<212> TYPE: PRT
<213> ORGANISM: Homo sapiens
<220> FEATURE:
<221> NAME/KEY: MISC_FEATURE
<222> LOCATION: (1)..(439)
<223> OTHER INFORMATION: Any "X" = any amino acid

<400> SEQUENCE: 46

Glu Arg Val Leu Gln Gly Leu Leu Lys Pro Leu Phe Lys Ser Thr Ser
1               5                   10                  15
Val Gly Pro Leu Tyr Ser Gly Cys Arg Leu Thr Leu Leu Arg Pro Glu
                20                  25                  30
Lys His Gly Ala Ala Thr Gly Val Asp Ala Ile Cys Thr Leu Arg Leu
            35                  40                  45
Asp Pro Thr Gly Pro Gly Leu Asp Arg Glu Arg Leu Tyr Trp Glu Leu
        50                  55                  60
Ser Gln Leu Thr Asn Ser Val Thr Glu Leu Gly Pro Tyr Thr Leu Asp
65                  70                  75                  80
Arg Asp Ser Leu Tyr Val Asn Gly Phe Thr His Arg Ser Ser Val Pro
                85                  90                  95
Thr Thr Ser Ile Pro Gly Thr Ser Ala Val His Leu Glu Thr Ser Gly
            100                 105                 110
Thr Pro Ala Ser Leu Pro Gly His Thr Ala Pro Gly Pro Leu Leu Ile
        115                 120                 125
```

```
Pro Phe Thr Leu Asn Phe Thr Ile Thr Asn Leu His Tyr Glu Glu Asn
    130                 135                 140

Met Gln His Pro Gly Ser Arg Lys Phe Asn Thr Met Glu Arg Val Leu
145                 150                 155                 160

Gln Gly Cys Leu Val Pro Cys Ser Arg Asn Thr Asn Val Gly Leu Leu
                165                 170                 175

Tyr Ser Gly Cys Arg Leu Thr Leu Leu Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Gly Pro Tyr Thr Leu Asp Arg Asn Ser Leu
225                 230                 235                 240

Tyr Val Asn Gly Phe Thr His Arg Ser Ser Val Ala Pro Thr Ser Thr
                245                 250                 255

Pro Gly Thr Ser Thr Val Asp Leu Gly Thr Ser Gly Thr Pro Ser Ser
            260                 265                 270

Leu Pro Ser Pro Thr Thr Val Pro Leu Leu Val Pro Phe Thr Leu Asn
        275                 280                 285

Phe Thr Ile Thr Asn Leu Gln Tyr Gly Glu Asp Met Arg His Pro Gly
    290                 295                 300

Ser Arg Lys Phe Asn Thr Thr Glu Arg Val Leu Gln Gly Leu Leu Gly
305                 310                 315                 320

Pro Leu Phe Lys Asn Ser Ser Val Gly Pro Leu Tyr Ser Gly Cys Arg
                325                 330                 335

Leu Ile Ser Leu Arg Ser Glu Lys Asp Gly Ala Ala Thr Gly Val Asp
            340                 345                 350

Ala Ile Cys Thr His His Leu Asn Pro Gln Ser Pro Gly Leu Asp Arg
        355                 360                 365

Glu Gln Leu Tyr Trp Gln Leu Ser Gln Val Thr Asn Gly Ile Lys Glu
    370                 375                 380

Leu Gly Pro Tyr Thr Leu Asp Arg Asn Ser Leu Tyr Val Asn Gly Phe
385                 390                 395                 400

Thr His Arg Ser Ser Gly Leu Thr Thr Ser Thr Pro Trp Thr Ser Thr
                405                 410                 415

Val Asp Leu Gly Thr Ser Gly Thr Pro Ser Pro Val Pro Ser Pro Thr
            420                 425                 430

Thr Ala Gly Pro Leu Leu Ile
        435

<210> SEQ ID NO 47
<211> LENGTH: 1366
<212> TYPE: PRT
<213> ORGANISM: Homo sapiens

<400> SEQUENCE: 47

Glu Arg Val Leu Gln Gly Leu Leu Lys Pro Leu Phe Arg Asn Ser Ser
1               5                   10                  15

Leu Glu Tyr Leu Tyr Ser Gly Cys Arg Leu Ala Ser Leu Arg Pro Glu
            20                  25                  30

Lys Asp Ser Ser Ala Met Ala Val Asp Ala Ile Cys Thr His Arg Pro
        35                  40                  45

Asp Pro Glu Asp Leu Gly Leu Asp Arg Glu Arg Leu Tyr Trp Glu Leu
    50                  55                  60
```

```
Ser Asn Leu Thr Asn Gly Ile Gln Glu Leu Gly Pro Tyr Thr Leu Asp
 65                  70                  75                  80

Arg Asn Ser Leu Tyr Val Asn Gly Phe Thr His Arg Ser Ser Met Pro
                 85                  90                  95

Thr Thr Ser Thr Pro Gly Thr Ser Val Asp Val Gly Thr Ser Gly
            100                 105                 110

Thr Pro Ser Ser Pro Ser Pro Thr Ala Gly Pro Leu Leu Met
            115                 120             125

Pro Phe Thr Leu Asn Phe Thr Ile Thr Asn Leu Gln Tyr Glu Glu Asp
130                 135                 140

Met Arg Arg Thr Gly Ser Arg Lys Phe Asn Thr Met Glu Arg Val Leu
145                 150                 155                 160

Gln Gly Pro Leu Ser Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
            180                 185                 190

Ala Thr Gly Met Asp Ala Val Cys Leu Tyr His Pro Asn Pro Lys Arg
            195                 200                 205

Pro Gly Leu Asp Arg Glu Gln Leu Tyr Trp Glu Leu Ser Gln Leu Thr
210                 215                 220

His Asn Ile Thr Glu Leu Gly Pro Tyr Ser Leu Asp Arg Asp Ser Leu
225                 230                 235                 240

Tyr Val Asn Gly Phe Thr His Gln Asn Ser Val Pro Thr Thr Ser Thr
                245                 250                 255

Pro Gly Thr Ser Thr Val Tyr Trp Ala Thr Gly Thr Pro Ser Ser
            260                 265                 270

Phe Pro Gly His Thr Glu Pro Gly Pro Leu Leu Ile Pro Phe Thr Leu
            275                 280                 285

Asn Phe Thr Ile Thr Asn Leu Gln Tyr Glu Glu Asn Met Gly His Pro
290                 295                 300

Gly Ser Arg Lys Phe Asn Ile Thr Glu Arg Val Leu Gln Gly Leu Leu
305                 310                 315                 320

Asn Pro Ile Phe Lys Asn Ser Ser Val Gly Pro Leu Tyr Ser Gly Cys
                325                 330                 335

Arg Leu Thr Ser Leu Arg Pro Glu Lys Asp Gly Ala Ala Thr Gly Met
            340                 345                 350

Asp Ala Val Cys Leu Tyr His Pro Asn Pro Lys Arg Pro Gly Leu Asp
            355                 360                 365

Arg Glu Gln Leu Tyr Cys Glu Leu Ser Gln Leu Thr His Asn Ile Thr
370                 375                 380

Glu Leu Gly Pro Tyr Ser Leu Asp Arg Asp Ser Leu Tyr Val Asn Gly
385                 390                 395                 400

Phe Thr His Gln Asn Ser Val Pro Thr Thr Ser Thr Pro Gly Thr Ser
                405                 410                 415

Thr Val Tyr Trp Ala Thr Thr Gly Thr Pro Ser Ser Phe Pro Gly His
            420                 425                 430

Thr Glu Pro Gly Pro Leu Leu Ile Pro Phe Thr Leu Asn Phe Thr Ile
            435                 440                 445

Thr Asn Leu Gln Tyr Glu Glu Asp Met Arg Arg Thr Gly Ser Arg Lys
            450                 455                 460

Phe Asn Thr Met Glu Arg Val Leu Gln Gly Leu Leu Lys Pro Leu Phe
465                 470                 475                 480
```

```
Lys Ser Thr Ser Val Gly Pro Leu Tyr Ser Gly Cys Arg Leu Thr Leu
                485                 490                 495

Leu Arg Pro Glu Lys His Gly Ala Ala Thr Gly Val Asp Ala Ile Cys
            500                 505                 510

Thr Leu Arg Leu Asp Pro Thr Gly Pro Gly Leu Asp Arg Glu Arg Leu
        515                 520                 525

Tyr Trp Glu Leu Ser Gln Leu Thr Asn Ser Val Thr Glu Leu Gly Pro
    530                 535                 540

Tyr Thr Leu Asp Arg Asp Ser Leu Tyr Val Asn Gly Phe Thr His Arg
545                 550                 555                 560

Ser Ser Val Pro Thr Thr Ser Ile Pro Gly Thr Ser Ala Val His Leu
                565                 570                 575

Glu Thr Ser Gly Thr Pro Ala Ser Leu Pro Gly His Thr Ala Pro Gly
            580                 585                 590

Pro Leu Leu Val Pro Phe Thr Leu Asn Phe Thr Ile Thr Asn Leu Gln
        595                 600                 605

Tyr Glu Glu Asp Met Arg His Pro Gly Ser Arg Lys Phe Asn Thr Thr
    610                 615                 620

Glu Arg Val Leu Gln Gly Leu Leu Lys Pro Leu Phe Lys Ser Thr Ser
625                 630                 635                 640

Val Gly Pro Leu Tyr Ser Gly Cys Arg Leu Thr Leu Leu Arg Pro Glu
                645                 650                 655

Lys Arg Gly Ala Ala Thr Gly Val Asp Thr Ile Cys Thr His Arg Leu
            660                 665                 670

Asp Pro Leu Asn Pro Gly Leu Asp Arg Glu Gln Leu Tyr Trp Glu Leu
        675                 680                 685

Ser Lys Leu Thr Arg Gly Ile Ile Glu Leu Gly Pro Tyr Leu Leu Asp
    690                 695                 700

Arg Gly Ser Leu Tyr Val Asn Gly Phe Thr His Arg Asn Phe Val Pro
705                 710                 715                 720

Ile Thr Ser Thr Pro Gly Thr Ser Thr Val His Leu Gly Thr Ser Glu
                725                 730                 735

Thr Pro Ser Ser Leu Pro Arg Pro Ile Val Pro Gly Pro Leu Leu Ile
            740                 745                 750

Pro Phe Thr Leu Asn Phe Thr Ile Thr Asn Leu Gln Tyr Glu Glu Asn
        755                 760                 765

Met Gly His Pro Gly Ser Arg Lys Phe Asn Ile Thr Glu Arg Val Leu
    770                 775                 780

Gln Gly Leu Leu Lys Pro Leu Phe Arg Asn Ser Ser Leu Glu Tyr Leu
785                 790                 795                 800

Tyr Ser Gly Cys Arg Leu Ala Ser Leu Arg Pro Glu Lys Asp Ser Ser
                805                 810                 815

Ala Met Ala Val Asp Ala Ile Cys Thr His Arg Pro Asp Pro Glu Asp
            820                 825                 830

Leu Gly Leu Asp Arg Glu Arg Leu Tyr Trp Glu Leu Ser Asn Leu Thr
        835                 840                 845

Asn Gly Ile Gln Glu Leu Gly Pro Tyr Thr Leu Asp Arg Asn Ser Leu
    850                 855                 860

Tyr Val Asn Gly Phe Thr His Arg Ser Ser Met Pro Thr Thr Ser Thr
865                 870                 875                 880

Pro Gly Thr Ser Thr Val Asp Val Gly Thr Ser Gly Thr Pro Ser Ser
                885                 890                 895

Ser Pro Ser Pro Thr Thr Ala Gly Pro Leu Leu Met Pro Phe Thr Leu
```

-continued

```
              900                 905                 910
Asn Phe Thr Ile Thr Asn Leu Gln Tyr Glu Glu Asp Met Arg Arg Thr
        915                 920                 925
Gly Ser Arg Lys Phe Asn Thr Met Glu Ser Val Leu Gln Gly Leu Leu
        930                 935                 940
Lys Pro Leu Phe Lys Asn Thr Ser Val Gly Pro Leu Tyr Ser Gly Cys
945                 950                 955                 960
Arg Leu Thr Leu Leu Arg Pro Lys Lys Asp Gly Ala Ala Thr Gly Val
                965                 970                 975
Asp Ala Ile Cys Thr His Arg Leu Asp Pro Lys Ser Pro Gly Leu Asn
                980                 985                 990
Arg Glu Gln Leu Tyr Trp Glu Leu Ser Lys Leu Thr Asn Asp Ile Glu
                995                1000                1005
Glu Val Gly Pro Tyr Thr Leu Asp Arg Asn Ser Leu Tyr Val Asn
        1010                1015                1020
Gly Phe Thr His Arg Ser Phe Val Ala Pro Thr Ser Thr Leu Gly
        1025                1030                1035
Thr Ser Thr Val Asp Leu Gly Thr Ser Gly Thr Pro Ser Ser Leu
        1040                1045                1050
Pro Ser Pro Thr Thr Gly Val Pro Leu Leu Ile Pro Phe Thr Leu
        1055                1060                1065
Asn Phe Thr Ile Thr Asn Leu Gln Tyr Glu Glu Asn Met Gly His
        1070                1075                1080
Pro Gly Ser Arg Lys Phe Asn Ile Met Glu Arg Val Leu Gln Gly
        1085                1090                1095
Leu Leu Ser Pro Ile Phe Lys Asn Ser Ser Val Gly Ser Leu Tyr
        1100                1105                1110
Ser Gly Cys Arg Leu Thr Leu Leu Arg Pro Glu Lys Asp Gly Ala
        1115                1120                1125
Ala Thr Arg Val Asp Ala Val Cys Thr His Arg Pro Asp Pro Lys
        1130                1135                1140
Ser Pro Gly Leu Asp Arg Glu Arg Leu Tyr Trp Lys Leu Ser Gln
        1145                1150                1155
Leu Thr His Gly Ile Ile Glu Leu Gly Pro Tyr Thr Leu Asp Arg
        1160                1165                1170
His Ser Phe Tyr Val Asn Gly Phe Thr His Gln Ser Ser Met Thr
        1175                1180                1185
Thr Thr Arg Thr Pro Asp Thr Ser Thr Met His Leu Ala Thr Ser
        1190                1195                1200
Arg Thr Pro Ala Ser Leu Ser Gly Pro Thr Thr Ala Ser Pro Leu
        1205                1210                1215
Leu Val Leu Phe Thr Ile Asn Phe Thr Ile Thr Asn Gln Arg Tyr
        1220                1225                1230
Glu Glu Asn Met His His Pro Gly Ser Arg Lys Phe Asn Thr Thr
        1235                1240                1245
Glu Arg Val Leu Gln Gly Leu Leu Arg Pro Val Phe Lys Asn Thr
        1250                1255                1260
Ser Val Gly Pro Leu Tyr Ser Gly Cys Arg Leu Thr Leu Leu Arg
        1265                1270                1275
Pro Lys Lys Asp Gly Ala Ala Thr Lys Val Asp Ala Ile Cys Thr
        1280                1285                1290
Tyr Arg Pro Asp Pro Lys Ser Pro Gly Leu Asp Arg Glu Gln Leu
        1295                1300                1305
```

```
Tyr Trp Glu Leu Ser Gln Leu Thr His Ser Ile Thr Glu Leu Gly
    1310                1315                1320

Pro Tyr Thr Gln Asp Arg Asp Ser Leu Tyr Val Asn Gly Phe Thr
    1325                1330                1335

His Arg Ser Ser Val Pro Thr Thr Ser Ile Pro Gly Thr Ser Ala
    1340                1345                1350

Val His Leu Glu Thr Ser Gly Thr Pro Ala Ser Leu Pro
    1355                1360                1365

<210> SEQ ID NO 48
<211> LENGTH: 1148
<212> TYPE: PRT
<213> ORGANISM: Homo sapiens

<400> SEQUENCE: 48

Met Pro Leu Phe Lys Asn Thr Ser Val Ser Ser Leu Tyr Ser Gly Cys
1               5                   10                  15

Arg Leu Thr Leu Leu Arg Pro Glu Lys Asp Gly Ala Ala Thr Arg Val
            20                  25                  30

Asp Ala Val Cys Thr His Arg Pro Asp Pro Lys Ser Pro Gly Leu Asp
        35                  40                  45

Arg Glu Arg Leu Tyr Trp Lys Leu Ser Gln Leu Thr His Gly Ile Ile
    50                  55                  60

Glu Leu Gly Pro Tyr Thr Leu Asp Arg His Ser Phe Tyr Val Asn Gly
65                  70                  75                  80

Phe Thr His Gln Ser Ser Met Thr Thr Thr Arg Thr Pro Asp Thr Ser
                85                  90                  95

Thr Met His Leu Ala Thr Ser Arg Thr Pro Ala Ser Leu Ser Gly Pro
            100                 105                 110

Thr Thr Ala Ser Pro Leu Leu Val Leu Phe Thr Ile Asn Phe Thr Ile
        115                 120                 125

Thr Asn Gln Arg Tyr Glu Glu Asn Met His His Pro Gly Ser Arg Lys
    130                 135                 140

Phe Asn Thr Thr Glu Arg Val Leu Gln Gly Leu Leu Arg Pro Val Phe
145                 150                 155                 160

Lys Asn Thr Ser Val Gly Pro Leu Tyr Ser Gly Cys Arg Leu Thr Leu
                165                 170                 175

Leu Arg Pro Lys Lys Asp Gly Ala Ala Thr Lys Val Asp Ala Ile Cys
            180                 185                 190

Thr Tyr Arg Pro Asp Pro Lys Ser Pro Gly Leu Asp Arg Glu Gln Leu
    195                 200                 205

Tyr Trp Glu Leu Ser Gln Leu Thr His Ser Ile Thr Glu Leu Gly Pro
    210                 215                 220

Tyr Thr Gln Asp Arg Asp Ser Leu Tyr Val Asn Gly Phe Thr His Arg
225                 230                 235                 240

Ser Ser Val Pro Thr Thr Ser Ile Pro Gly Thr Ser Ala Val His Leu
                245                 250                 255

Glu Thr Ser Gly Thr Pro Ala Ser Leu Pro Gly Pro Ser Ala Ala Ser
            260                 265                 270

Pro Leu Leu Val Leu Phe Thr Leu Asn Phe Thr Ile Thr Asn Leu Arg
        275                 280                 285

Tyr Glu Glu Asn Met Gln His Pro Gly Ser Arg Lys Phe Asn Thr Thr
    290                 295                 300

Glu Arg Val Leu Gln Gly Leu Leu Arg Ser Leu Phe Lys Ser Thr Ser
```

-continued

```
            305                 310                 315                 320
        Val Gly Pro Leu Tyr Ser Gly Cys Arg Leu Thr Leu Arg Pro Glu
                        325                 330                 335
        Lys Asp Gly Thr Ala Thr Gly Val Asp Ala Ile Cys Thr His His Pro
                        340                 345                 350
        Asp Pro Lys Ser Pro Arg Leu Asp Arg Glu Gln Leu Tyr Trp Glu Leu
                        355                 360                 365
        Ser Gln Leu Thr His Asn Ile Thr Glu Leu Gly His Tyr Ala Leu Asp
                370                 375                 380
        Asn Asp Ser Leu Phe Val Asn Gly Phe Thr His Arg Ser Ser Val Ser
        385                 390                 395                 400
        Thr Thr Ser Thr Pro Gly Thr Pro Thr Val Tyr Leu Gly Ala Ser Lys
                        405                 410                 415
        Thr Pro Ala Ser Ile Phe Gly Pro Ser Ala Ser His Leu Leu Ile
                        420                 425                 430
        Leu Phe Thr Leu Asn Phe Thr Ile Thr Asn Leu Arg Tyr Glu Glu Asn
                        435                 440                 445
        Met Trp Pro Gly Ser Arg Lys Phe Asn Thr Thr Glu Arg Val Leu Gln
                        450                 455                 460
        Gly Leu Leu Arg Pro Leu Phe Lys Asn Thr Ser Val Gly Pro Leu Tyr
        465                 470                 475                 480
        Ser Gly Ser Arg Leu Thr Leu Leu Arg Pro Glu Lys Asp Gly Glu Ala
                        485                 490                 495
        Thr Gly Val Asp Ala Ile Cys Thr His Arg Pro Asp Pro Thr Gly Pro
                        500                 505                 510
        Gly Leu Asp Arg Glu Gln Leu Tyr Leu Glu Leu Ser Gln Leu Thr His
                        515                 520                 525
        Ser Ile Thr Glu Leu Gly Pro Tyr Thr Leu Asp Arg Asp Ser Leu Tyr
                530                 535                 540
        Val Asn Gly Phe Thr His Arg Ser Ser Val Pro Thr Thr Ser Thr Gly
        545                 550                 555                 560
        Val Val Ser Glu Glu Pro Phe Thr Leu Asn Phe Thr Ile Asn Asn Leu
                        565                 570                 575
        Arg Tyr Met Ala Asp Met Gly Gln Pro Gly Ser Leu Lys Phe Asn Ile
                        580                 585                 590
        Thr Asp Asn Val Met Lys His Leu Leu Ser Pro Leu Phe Gln Arg Ser
                        595                 600                 605
        Ser Leu Gly Ala Arg Tyr Thr Gly Cys Arg Val Ile Ala Leu Arg Ser
                        610                 615                 620
        Val Lys Asn Gly Ala Glu Thr Arg Val Asp Leu Leu Cys Thr Tyr Leu
        625                 630                 635                 640
        Gln Pro Leu Ser Gly Pro Gly Leu Pro Ile Lys Gln Val Phe His Glu
                        645                 650                 655
        Leu Ser Gln Gln Thr His Gly Ile Thr Arg Leu Gly Pro Tyr Ser Leu
                        660                 665                 670
        Asp Lys Asp Ser Leu Tyr Leu Asn Gly Tyr Asn Glu Pro Gly Leu Asp
                        675                 680                 685
        Glu Pro Pro Thr Thr Pro Lys Pro Ala Thr Thr Phe Leu Pro Pro Leu
                        690                 695                 700
        Ser Glu Ala Thr Thr Ala Met Gly Tyr His Leu Lys Thr Leu Thr Leu
        705                 710                 715                 720
        Asn Phe Thr Ile Ser Asn Leu Gln Tyr Ser Pro Asp Met Gly Lys Gly
                        725                 730                 735
```

```
Ser Ala Thr Phe Asn Ser Thr Glu Gly Val Leu Gln His Leu Leu Arg
        740                 745                 750

Pro Leu Phe Gln Lys Ser Ser Met Gly Pro Phe Tyr Leu Gly Cys Gln
        755                 760                 765

Leu Ile Ser Leu Arg Pro Glu Lys Asp Gly Ala Ala Thr Gly Val Asp
        770                 775                 780

Thr Thr Cys Thr Tyr His Pro Asp Pro Val Gly Pro Gly Leu Asp Ile
785                 790                 795                 800

Gln Gln Leu Tyr Trp Glu Leu Ser Gln Leu Thr His Gly Val Thr Gln
                805                 810                 815

Leu Gly Phe Tyr Val Leu Asp Arg Asp Ser Leu Phe Ile Asn Gly Tyr
                820                 825                 830

Ala Pro Gln Asn Leu Ser Ile Arg Gly Glu Tyr Gln Ile Asn Phe His
                835                 840                 845

Ile Val Asn Trp Asn Leu Ser Asn Pro Asp Pro Thr Ser Ser Glu Tyr
        850                 855                 860

Ile Thr Leu Leu Arg Asp Ile Gln Asp Lys Val Thr Thr Leu Tyr Lys
865                 870                 875                 880

Gly Ser Gln Leu His Asp Thr Phe Arg Phe Cys Leu Val Thr Asn Leu
                885                 890                 895

Thr Met Asp Ser Val Leu Val Thr Val Lys Ala Leu Phe Ser Ser Asn
        900                 905                 910

Leu Asp Pro Ser Leu Val Glu Gln Val Phe Leu Asp Lys Thr Leu Asn
        915                 920                 925

Ala Ser Phe His Trp Leu Gly Ser Thr Tyr Gln Leu Val Asp Ile His
        930                 935                 940

Val Thr Glu Met Glu Ser Ser Val Tyr Gln Pro Thr Ser Ser Ser Ser
945                 950                 955                 960

Thr Gln His Phe Tyr Leu Asn Phe Thr Ile Thr Asn Leu Pro Tyr Ser
                965                 970                 975

Gln Asp Lys Ala Gln Pro Gly Thr Thr Asn Tyr Gln Arg Asn Lys Arg
                980                 985                 990

Asn Ile Glu Asp Ala Leu Asn Gln Leu Phe Arg Asn Ser Ser Ile Lys
        995                 1000                1005

Ser Tyr Phe Ser Asp Cys Gln Val Ser Thr Phe Arg Ser Val Pro Asn
        1010                1015                1020

Asn Arg His His Thr Gly Val Asp Ser Leu Cys Asn Phe Ser Pro
        1025                1030                1035

Leu Ala Arg Arg Val Asp Arg Val Ala Ile Tyr Glu Glu Phe Leu
        1040                1045                1050

Arg Met Thr Arg Asn Gly Thr Gln Leu Gln Asn Phe Thr Leu Asp
        1055                1060                1065

Arg Ser Ser Val Leu Val Asp Gly Tyr Ser Pro Asn Arg Asn Glu
        1070                1075                1080

Pro Leu Thr Gly Asn Ser Asp Leu Pro Phe Trp Ala Val Ile Leu
        1085                1090                1095

Ile Gly Leu Ala Gly Leu Leu Gly Leu Ile Thr Cys Leu Ile Cys
        1100                1105                1110

Gly Val Leu Val Thr Thr Arg Arg Arg Lys Lys Glu Gly Glu Tyr
        1115                1120                1125

Asn Val Gln Gln Gln Cys Pro Gly Tyr Tyr Gln Ser His Leu Asp
        1130                1135                1140
```

-continued

Leu Glu Asp Leu Gln
    1145

<210> SEQ ID NO 49
<211> LENGTH: 6833
<212> TYPE: DNA
<213> ORGANISM: Homo sapiens

<400> SEQUENCE: 49

| | | | | | |
|---|---|---|---|---|---|
| gagagggttc | tgcagggtct | gctcaaaccc | ttgttcagga | atagcagtct | ggaataccte | 60 |
| tattcaggct | gcagactagc | ctcactcagg | ccagagaagg | atagctcagc | catggcagtg | 120 |
| gatgccatct | gcacacatcg | ccctgaccct | gaagacctcg | gactggacag | agagcgactg | 180 |
| tactgggagc | tgagcaatct | gacaaatggc | atccaggagc | tgggccccta | caccctggac | 240 |
| cggaacagtc | tctatgtcaa | tggtttcacc | catcgaagct | ctatgcccac | caccagcact | 300 |
| cctgggacct | ccacagtgga | tgtgggaacc | tcagggactc | catcctccag | ccccagcccc | 360 |
| acgactgctg | gccctctcct | gatgccgttc | accctcaact | tcaccatcac | caacctgcag | 420 |
| tacgaggagg | acatgcgtcg | cactggctcc | aggaagttca | acaccatgga | gagggttctg | 480 |
| cagggtccgc | ttagtcccat | attcaagaac | tccagtgttg | ccctctgta | ctctggctgc | 540 |
| agactgacct | ctctcaggcc | cgagaaggat | ggggcagcaa | ctggaatgga | tgctgtctgc | 600 |
| ctctaccacc | ctaatcccaa | aagacctggg | ctggacagag | agcagctgta | ctgggagcta | 660 |
| agccagctga | cccacaacat | cactgagctg | gcccctaca | gcctggacag | ggacagtctc | 720 |
| tatgtcaatg | gtttcaccca | tcagaactct | gtgcccacca | ccagtactcc | tgggacctcc | 780 |
| acagtgtact | gggcaaccac | tgggactcca | tccteettee | ccggccacac | agagcctggc | 840 |
| cctctcctga | taccattcac | gctcaacttc | accatcacta | acctacagta | tgaggagaac | 900 |
| atgggtcacc | ctggctccag | gaagttcaac | atcacggaga | gggttctgca | gggtctgctt | 960 |
| aatcccattt | tcaagaactc | cagtgttggc | cctctgtact | ctggctgcag | actgacctct | 1020 |
| ctcaggcccg | agaaggatgg | ggcagcaact | ggaatggatg | ctgtctgcct | ctaccaccct | 1080 |
| aatcccaaaa | gacctgggct | ggacagagag | cagctgtact | gcgagctaag | ccagctgacc | 1140 |
| cacaacatca | ctgagctggg | ccctacagc | ttggacaggg | acagtcttta | tgtcaatggt | 1200 |
| ttcacccatc | agaactctgt | gcccaccacc | agtactcctg | ggacctccac | agtgtactgg | 1260 |
| gcaaccactg | ggactccatc | tccttccc | ggccacacag | agcctggccc | tctcctgata | 1320 |
| ccattcaccc | tcaacttcac | catcaccaac | ctgcagtacg | aggaggacat | gcgtcgcact | 1380 |
| ggctccagga | agttcaacac | catggagagg | ttctgcagg | gtctgctcaa | gcccttgttc | 1440 |
| aagagcacca | cgttggccc | tctgtactct | ggctgcagac | tgaccttgct | cagacctgag | 1500 |
| aaacatgggg | cagccactgg | agtggacgcc | atctgcaccc | tccgccttga | tcccactggt | 1560 |
| cctggactgg | acagagagcg | ctatactgg | gagctgagcc | agctgaccaa | cagcgttaca | 1620 |
| gagctgggcc | cctacaccct | ggacagggac | agtctctatg | tcaatggctt | cacccatcgg | 1680 |
| agctctgtgc | caaccaccag | tattcctggg | acctctgcag | tgcacctgga | aacctctggg | 1740 |
| actccagcct | ccctccctgg | ccacacagcc | ctggccctc | tcctggtgcc | attcacccte | 1800 |
| aacttcacta | tcaccaacct | gcagtatgag | gaggacatgc | gtcaccctgg | ttccaggaag | 1860 |
| ttcaacacca | cggagagagt | cctgcagggt | ctgctcaagc | ccttgttcaa | gagcaccagt | 1920 |
| gttggccctc | tgtactctgg | ctgcagactg | accttgctca | ggcctgaaaa | acgtggggca | 1980 |
| gccaccggcg | tggacaccat | ctgcactcac | cgccttgacc | ctctaaaccc | tggactggac | 2040 |

```
agagagcagc tatactggga gctgagcaaa ctgacccgtg gcatcatcga gctgggcccc    2100
tacctcctgg acagaggcag tctctatgtc aatggtttca cccatcggaa ctttgtgccc    2160
atcaccagca ctcctgggac ctccacagta cacctaggaa cctctgaaac tccatcctcc    2220
ctacctagac ccatagtgcc tggccctctc ctgataccat tcacactcaa cttcaccatc    2280
actaacctac agtatgagga gaacatgggt caccctggct ccaggaagtt caacatcacg    2340
gagagggttc tgcagggtct gctcaaaccc ttgttcagga atagcagtct ggaataccctc   2400
tattcaggct gcagactaac ctcactcagg ccagagaagg atagctcaac catggcagtg    2460
gatgccatct gcacacatcg ccctgaccct gaagacctcg gactggacag agagcgactg    2520
tactgggagc tgagcaatct gacaaatggc atccaggagc tgggccccta caccctggac    2580
cggaacagtc tctatgtcaa tggtttcacc catcgaagct ctatgccccac caccagcact   2640
cctgggacct ccacagtgga tgtgggaacc tcagggactc catcctccag ccccagcccc    2700
acgactgctg gccctctcct gatgccgttc accctcaact tcaccatcac caacctgcag    2760
tacgaggagg acatgcgtcg cactggctcc aggaagttca acaccatgga gagtgtcctg    2820
cagggtctgc tcaagccctt gttcaagaac accagtgttg gccctctgta ctctggctgc    2880
agattgacct tgctcaggcc caagaaagat ggggcagcca ctggagtgga tgccatctgc    2940
acccaccgcc ttgaccccaa aagccctgga ctcaacaggg agcagctgta ctgggagtta    3000
agcaaactga ccaatgacat tgaagaggtg ggcccctaca ccttggacag gaacagtctc    3060
tatgtcaatg gtttcaccca tcggagcttt gtggccccca ccagcactct ggggacctcc    3120
acagtggacc ttgggacctc agggactcca tcctccctcc ccagcccaca acaggtgtt    3180
cctctcctga taccattcac actcaacttc accatcacta acctacagta tgaggagaac    3240
atgggtcacc ctggctccag gaagttcaac atcatggaga gggttctgca gggtctgctt    3300
atgcccttgt tcaagaacac cagtgtcagc tctctgtact ctggttgcag actgaccttg    3360
ctcaggcctg agaaggatgg ggcagccacc agagtggttg ctgtctgcac ccatcgtcct    3420
gacccccaaa agccctggac tggacagagag cggctgtact ggaagctgag ccagctgacc    3480
cacggcatca ctgagctggg cccctacacc ctggacaggc acagtctcta tgtcaatggt    3540
ttcacccatc agagctctat gacgaccacc agaactcctg atacctccac aatgcacctg    3600
gcaacctcga gaactccagc ctccctgtct ggacctacga ccgccagccc tctcctgata    3660
ccattcacaa ttaacttcac catcactaac ctgcggtatg aggagaacat gcatcaccct    3720
ggctctagaa agtttaacac cacggagaga gtccttcagg gtctgctcag gctgtgttc     3780
aagaacacca gtgttggccc tctgtactct ggctgcagac tgaccttgct caggcccaag    3840
aaggatgggg cagccaccaa agtggatgcc atctgcacct accgccctga tcccaaaagc    3900
cctggactgg acagagagca gctatactgg gagctgagcc agctaaccca cagcatcact    3960
gagctgggcc cctacaccct ggacagggac agtctctatg tcaatggttt cacacagcgg    4020
agctctgtgc ccaccactag cattcctggg accccacag tggacctggg aacatctggg     4080
actccagttt ctaaacctgg tccctcggct gccagccctc tcctggtgct attcactctc    4140
aacttcacca tcaccaacct gcggtatgag gagaacatgc agcaccctgg ctccaggaag    4200
ttcaacacca cggagagggt ccttcagggc ctgctcaggt ccctgttcaa gagcaccagt    4260
gttggccctc tgtactctgg ctgcagactg actttgctca ggcctgaaaa ggatgggaca    4320
gccactggag tggatgccat ctgcacccac caccctgacc caaaagccc taggctggac     4380
agagagcagc tgtattggga gctgagccag ctgacccaca atatcactga gctgggccac    4440
```

```
tatgccctgg acaacgacag cctctttgtc aatggtttca ctcatcggag ctctgtgtcc    4500
accaccagca ctcctgggac ccccacagtg tatctgggag catctaagac tccagcctcg    4560
atatttggcc cttcagctgc cagccatctc ctgatactat tcaccctcaa cttcaccatc    4620
actaacctgc ggtatgagga gaacatgtgg cctggctcca ggaagttcaa cactacagag    4680
agggtccttc agggcctgct aaggcccttg ttcaagaaca ccagtgttgg ccctctgtac    4740
tctggctcca ggctgacctt gctcaggcca gagaaagatg gggaagccac cggagtggat    4800
gccatctgca cccaccgccc tgaccccaca ggccctgggc tggacagaga gcagctgtat    4860
ttggagctga gccagctgac ccacagcatc actgagctgg gcccctacac actggacagg    4920
gacagtctct atgtcaatgg tttcacccat cggagctctg tacccaccac cagcaccggg    4980
gtggtcagcg aggagccatt cacactgaac ttcaccatca acaacctgcg ctacatggcg    5040
gacatgggcc aacccggctc cctcaagttc aacatcacag acaacgtcat gaagcacctg    5100
ctcagtcctt tgttccagag gagcagcctg ggtgcacggt acacaggctg cagggtcatc    5160
gcactaaggt ctgtgaagaa cggtgctgag acacgggtgg acctcctctg cacctacctg    5220
cagcccctca gcggcccagg tctgcctatc aagcaggtgt ccatgagcct gagccagcag    5280
acccatggca tcacccggct gggccctac tctctggaca agacagcct ctaccttaac    5340 ggttacaatg aacctggtct agatgagcct cctacaactc ccaagccagc caccacattc    5400
ctgcctcctc tgtcagaagc cacaacagcc atggggtacc acctgaagac cctcacactc    5460
aacttcacca tctccaatct ccagtattca ccagatatgg gcaagggctc agctacattc    5520
aactccaccg aggggtcct tcagcacctg ctcagaccct tgttccagaa gagcagcatg    5580
ggccccttct acttgggttg ccaactgatc tccctcaggc tgagaagga tggggcagcc    5640 actggtgtgg acaccacctg cacctaccac cctgaccctg tgggccccgg gctggacata    5700
cagcagcttt actgggagct gagtcagctg acccatggtg tcacccaact gggcttctat    5760
gtcctggaca gggatagcct cttcatcaat ggctatgcac cccagaattt atcaatccgg    5820
ggcgagtacc agataaattt ccacattgtc aactggaacc tcagtaatcc agaccccaca    5880
tcctcagagt acatcacccct gctgagggac atccaggaca aggtcaccac actctacaaa    5940
ggcagtcaac tacatgacac attccgcttc tgcctggtca ccaacttgac gatggactcc    6000
gtgttggtca ctgtcaaggc attgttctcc tccaatttgg accccagcct ggtggagcaa    6060
gtctttctag ataagaccct gaatgcctca ttccattggc tgggctccac ctaccagttg    6120
gtggacatcc atgtgacaga aatggagtca tcagtttatc aaccaacaag cagctccagc    6180
acccagcact ctacccgaa tttcaccatc accaacctac catattccca ggacaaagcc    6240
cagccaggca ccaccaatta ccagaggaac aaaaggaata ttgaggatgc gctcaaccaa    6300
ctcttccgaa acagcagcat caagagttat tttttctgact gtcaagtttc aacattcagg    6360
tctgtcccca acaggcacca caccggggtg gactccctgt gtaacttctc gccactggct    6420
cggagagtag acagagttgc catctatgag gaatttctgc ggatgacccg gaatggtacc    6480
cagctgcaga acttcaccct ggacaggagc agtgtccttg tggatgggta ttctcccaac    6540
agaaatgagc ccttaactgg gaattctgac cttcccttct gggctgtcat cttcatcggc    6600
ttggcaggac tcctgggact catcacatgc ctgatctgcg gtgtcctggt gaccacccgc    6660
cggcggaaga aggaaggaga atacaacgtc cagcaacagt gcccaggcta ctaccagtca    6720
cacctagacc tggaggatct gcaatgactg gaacttgccg gtgcctgggg tgcctttccc    6780
```

-continued ccagccaggg tccaaagaag cttggctggg gcagaaataa accatattgg tcg            6833

<210> SEQ ID NO 50
<211> LENGTH: 2248
<212> TYPE: PRT
<213> ORGANISM: Homo sapiens

<400> SEQUENCE: 50

```
Glu Arg Val Leu Gln Gly Leu Leu Lys Pro Leu Phe Arg Asn Ser Ser
1               5                   10                  15

Leu Glu Tyr Leu Tyr Ser Gly Cys Arg Leu Ala Ser Leu Arg Pro Glu
            20                  25                  30

Lys Asp Ser Ser Ala Met Ala Val Asp Ala Ile Cys Thr His Arg Pro
        35                  40                  45

Asp Pro Glu Asp Leu Gly Leu Asp Arg Glu Arg Leu Tyr Trp Glu Leu
    50                  55                  60

Ser Asn Leu Thr Asn Gly Ile Gln Glu Leu Gly Pro Tyr Thr Leu Asp
65                  70                  75                  80

Arg Asn Ser Leu Tyr Val Asn Gly Phe Thr His Arg Ser Ser Met Pro
                85                  90                  95

Thr Thr Ser Thr Pro Gly Thr Ser Thr Val Asp Val Gly Thr Ser Gly
            100                 105                 110

Thr Pro Ser Ser Pro Ser Pro Thr Thr Ala Gly Pro Leu Leu Met
        115                 120                 125

Pro Phe Thr Leu Asn Phe Thr Ile Thr Asn Leu Gln Tyr Glu Glu Asp
    130                 135                 140

Met Arg Arg Thr Gly Ser Arg Lys Phe Asn Thr Met Glu Arg Val Leu
145                 150                 155                 160

Gln Gly Pro Leu Ser Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
            180                 185                 190

Ala Thr Gly Met Asp Ala Val Cys Leu Tyr His Pro Asn Pro Lys Arg
        195                 200                 205

Pro Gly Leu Asp Arg Glu Gln Leu Tyr Trp Glu Leu Ser Gln Leu Thr
    210                 215                 220

His Asn Ile Thr Glu Leu Gly Pro Tyr Ser Leu Asp Arg Asp Ser Leu
225                 230                 235                 240

Tyr Val Asn Gly Phe Thr His Gln Asn Ser Val Pro Thr Thr Ser Thr
                245                 250                 255

Pro Gly Thr Ser Thr Val Tyr Trp Ala Thr Gly Thr Pro Ser Ser
            260                 265                 270

Phe Pro Gly His Thr Glu Pro Gly Pro Leu Leu Ile Pro Phe Thr Leu
        275                 280                 285

Asn Phe Thr Ile Thr Asn Leu Gln Tyr Glu Glu Asn Met Gly His Pro
    290                 295                 300

Gly Ser Arg Lys Phe Asn Ile Thr Glu Arg Val Leu Gln Gly Leu Leu
305                 310                 315                 320

Asn Pro Ile Phe Lys Asn Ser Ser Val Gly Pro Leu Tyr Ser Gly Cys
                325                 330                 335

Arg Leu Thr Ser Leu Arg Pro Glu Lys Asp Gly Ala Ala Thr Gly Met
            340                 345                 350

Asp Ala Val Cys Leu Tyr His Pro Asn Pro Lys Arg Pro Gly Leu Asp
        355                 360                 365
```

-continued

```
Arg Glu Gln Leu Tyr Cys Glu Leu Ser Gln Leu Thr His Asn Ile Thr
    370                 375                 380

Glu Leu Gly Pro Tyr Ser Leu Asp Arg Asp Ser Leu Tyr Val Asn Gly
385                 390                 395                 400

Phe Thr His Gln Asn Ser Val Pro Thr Thr Ser Thr Pro Gly Thr Ser
            405                 410                 415

Thr Val Tyr Trp Ala Thr Thr Gly Thr Pro Ser Ser Phe Pro Gly His
        420                 425                 430

Thr Glu Pro Gly Pro Leu Leu Ile Pro Phe Thr Leu Asn Phe Thr Ile
        435                 440                 445

Thr Asn Leu Gln Tyr Glu Glu Asp Met Arg Arg Thr Gly Ser Arg Lys
    450                 455                 460

Phe Asn Thr Met Glu Arg Val Leu Gln Gly Leu Leu Lys Pro Leu Phe
465                 470                 475                 480

Lys Ser Thr Ser Val Gly Pro Leu Tyr Ser Gly Cys Arg Leu Thr Leu
            485                 490                 495

Leu Arg Pro Glu Lys His Gly Ala Ala Thr Gly Val Asp Ala Ile Cys
        500                 505                 510

Thr Leu Arg Leu Asp Pro Thr Gly Pro Gly Leu Asp Arg Glu Arg Leu
    515                 520                 525

Tyr Trp Glu Leu Ser Gln Leu Thr Asn Ser Val Thr Glu Leu Gly Pro
    530                 535                 540

Tyr Thr Leu Asp Arg Asp Ser Leu Tyr Val Asn Gly Phe Thr His Arg
545                 550                 555                 560

Ser Ser Val Pro Thr Thr Ser Ile Pro Gly Thr Ser Ala Val His Leu
            565                 570                 575

Glu Thr Ser Gly Thr Pro Ala Ser Leu Pro Gly His Thr Ala Pro Gly
        580                 585                 590

Pro Leu Leu Val Pro Phe Thr Leu Asn Phe Thr Ile Thr Asn Leu Gln
    595                 600                 605

Tyr Glu Glu Asp Met Arg His Pro Gly Ser Arg Lys Phe Asn Thr Thr
    610                 615                 620

Glu Arg Val Leu Gln Gly Leu Leu Lys Pro Leu Phe Lys Ser Thr Ser
625                 630                 635                 640

Val Gly Pro Leu Tyr Ser Gly Cys Arg Leu Thr Leu Leu Arg Pro Glu
            645                 650                 655

Lys Arg Gly Ala Ala Thr Gly Val Asp Thr Ile Cys Thr His Arg Leu
        660                 665                 670

Asp Pro Leu Asn Pro Gly Leu Asp Arg Glu Gln Leu Tyr Trp Glu Leu
    675                 680                 685

Ser Lys Leu Thr Arg Gly Ile Ile Glu Leu Gly Pro Tyr Leu Leu Asp
    690                 695                 700

Arg Gly Ser Leu Tyr Val Asn Gly Phe Thr His Arg Asn Phe Val Pro
705                 710                 715                 720

Ile Thr Ser Thr Pro Gly Thr Ser Val His Leu Gly Thr Ser Glu
            725                 730                 735

Thr Pro Ser Ser Leu Pro Arg Pro Ile Val Pro Gly Pro Leu Leu Ile
        740                 745                 750

Pro Phe Thr Leu Asn Phe Thr Ile Thr Asn Leu Gln Tyr Glu Glu Asn
    755                 760                 765

Met Gly His Pro Gly Ser Arg Lys Phe Asn Ile Thr Glu Arg Val Leu
    770                 775                 780

Gln Gly Leu Leu Lys Pro Leu Phe Arg Asn Ser Ser Leu Glu Tyr Leu
```

-continued

```
            785                 790                 795                 800
Tyr Ser Gly Cys Arg Leu Ala Ser Leu Arg Pro Glu Lys Asp Ser Ser
                805                 810                 815
Ala Met Ala Val Asp Ala Ile Cys Thr His Arg Pro Asp Pro Glu Asp
            820                 825                 830
Leu Gly Leu Asp Arg Glu Arg Leu Tyr Trp Glu Leu Ser Asn Leu Thr
            835                 840                 845
Asn Gly Ile Gln Glu Leu Gly Pro Tyr Thr Leu Asp Arg Asn Ser Leu
        850                 855                 860
Tyr Val Asn Gly Phe Thr His Arg Ser Ser Met Pro Thr Thr Ser Thr
865                 870                 875                 880
Pro Gly Thr Ser Thr Val Asp Val Gly Thr Ser Gly Thr Pro Ser Ser
                885                 890                 895
Ser Pro Ser Pro Thr Thr Ala Gly Pro Leu Leu Met Pro Phe Thr Leu
            900                 905                 910
Asn Phe Thr Ile Thr Asn Leu Gln Tyr Glu Glu Asp Met Arg Arg Thr
            915                 920                 925
Gly Ser Arg Lys Phe Asn Thr Met Glu Ser Val Leu Gln Gly Leu Leu
        930                 935                 940
Lys Pro Leu Phe Lys Asn Thr Ser Val Gly Pro Leu Tyr Ser Gly Cys
945                 950                 955                 960
Arg Leu Thr Leu Leu Arg Pro Lys Lys Asp Gly Ala Ala Thr Gly Val
                965                 970                 975
Asp Ala Ile Cys Thr His Arg Leu Asp Pro Lys Ser Pro Gly Leu Asn
            980                 985                 990
Arg Glu Gln Leu Tyr Trp Glu Leu  Ser Lys Leu Thr Asn  Asp Ile Glu
        995                 1000                 1005
Glu Val  Gly Pro Tyr Thr Leu  Asp Arg Asn Ser Leu  Tyr Val Asn
    1010                 1015                 1020
Gly Phe  Thr His Arg Ser Phe  Val Ala Pro Thr Ser  Thr Leu Gly
    1025                 1030                 1035
Thr Ser  Thr Val Asp Leu Gly  Thr Ser Gly Thr Pro  Ser Ser Leu
    1040                 1045                 1050
Pro Ser  Pro Thr Thr Gly Val  Pro Leu Leu Ile Pro  Phe Thr Leu
    1055                 1060                 1065
Asn Phe  Thr Ile Thr Asn Leu  Gln Tyr Glu Glu Asn  Met Gly His
    1070                 1075                 1080
Pro Gly  Ser Arg Lys Phe Asn  Ile Met Glu Arg Val  Leu Gln Gly
    1085                 1090                 1095
Leu Leu  Ser Pro Ile Phe Lys  Asn Ser Ser Val Gly  Ser Leu Tyr
    1100                 1105                 1110
Ser Gly  Cys Arg Leu Thr Leu  Leu Arg Pro Glu Lys  Asp Gly Ala
    1115                 1120                 1125
Ala Thr  Arg Val Asp Ala Val  Cys Thr His Arg Pro  Asp Pro Lys
    1130                 1135                 1140
Ser Pro  Gly Leu Asp Arg Glu  Arg Leu Tyr Trp Lys  Leu Ser Gln
    1145                 1150                 1155
Leu Thr  His Gly Ile Ile Glu  Leu Gly Pro Tyr Thr  Leu Asp Arg
    1160                 1165                 1170
His Ser  Phe Tyr Val Asn Gly  Phe Thr His Gln Ser  Ser Met Thr
    1175                 1180                 1185
Thr Thr  Arg Thr Pro Asp Thr  Ser Thr Met His Leu  Ala Thr Ser
    1190                 1195                 1200
```

-continued

```
Arg Thr Pro Ala Ser Leu Ser Gly Pro Thr Thr Ala Ser Pro Leu
    1205                1210                1215

Leu Val Leu Phe Thr Ile Asn Phe Thr Ile Thr Asn Gln Arg Tyr
    1220                1225                1230

Glu Glu Asn Met His His Pro Gly Ser Arg Lys Phe Asn Thr Thr
    1235                1240                1245

Glu Arg Val Leu Gln Gly Leu Leu Arg Pro Val Phe Lys Asn Thr
    1250                1255                1260

Ser Val Gly Pro Leu Tyr Ser Gly Cys Arg Leu Thr Leu Leu Arg
    1265                1270                1275

Pro Lys Lys Asp Gly Ala Ala Thr Lys Val Asp Ala Ile Cys Thr
    1280                1285                1290

Tyr Arg Pro Asp Pro Lys Ser Pro Gly Leu Asp Arg Glu Gln Leu
    1295                1300                1305

Tyr Trp Glu Leu Ser Gln Leu Thr His Ser Ile Thr Glu Leu Gly
    1310                1315                1320

Pro Tyr Thr Gln Asp Arg Asp Ser Leu Tyr Val Asn Gly Phe Thr
    1325                1330                1335

His Arg Ser Ser Val Pro Thr Thr Ser Ile Pro Gly Thr Ser Ala
    1340                1345                1350

Val His Leu Glu Thr Ser Gly Thr Pro Ala Ser Leu Pro Gly Pro
    1355                1360                1365

Ser Ala Ala Ser Pro Leu Leu Val Leu Phe Thr Leu Asn Phe Thr
    1370                1375                1380

Ile Thr Asn Leu Arg Tyr Glu Glu Asn Met Gln His Pro Gly Ser
    1385                1390                1395

Arg Lys Phe Asn Thr Thr Glu Arg Val Leu Gln Gly Leu Leu Arg
    1400                1405                1410

Ser Leu Phe Lys Ser Thr Ser Val Gly Pro Leu Tyr Ser Gly Cys
    1415                1420                1425

Arg Leu Thr Leu Leu Arg Pro Glu Lys Asp Gly Thr Ala Thr Gly
    1430                1435                1440

Val Asp Ala Ile Cys Thr His His Pro Asp Pro Lys Ser Pro Arg
    1445                1450                1455

Leu Asp Arg Glu Gln Leu Tyr Trp Glu Leu Ser Gln Leu Thr His
    1460                1465                1470

Asn Ile Thr Glu Leu Gly His Tyr Ala Leu Asp Asn Asp Ser Leu
    1475                1480                1485

Phe Val Asn Gly Phe Thr His Arg Ser Ser Val Ser Thr Thr Ser
    1490                1495                1500

Thr Pro Gly Thr Pro Thr Val Tyr Leu Gly Ala Ser Lys Thr Pro
    1505                1510                1515

Ala Ser Ile Phe Gly Pro Ser Ala Ala Ser His Leu Leu Ile Leu
    1520                1525                1530

Phe Thr Leu Asn Phe Thr Ile Thr Asn Leu Arg Tyr Glu Glu Asn
    1535                1540                1545

Met Trp Pro Gly Ser Arg Lys Phe Asn Thr Thr Glu Arg Val Leu
    1550                1555                1560

Gln Gly Leu Leu Arg Pro Leu Phe Lys Asn Thr Ser Val Gly Pro
    1565                1570                1575

Leu Tyr Ser Gly Ser Arg Leu Thr Leu Leu Arg Pro Glu Lys Asp
    1580                1585                1590
```

```
Gly Glu Ala Thr Gly Val Asp Ala Ile Cys Thr His Arg Pro Asp
    1595                1600                1605

Pro Thr Gly Pro Gly Leu Asp Arg Glu Gln Leu Tyr Leu Glu Leu
    1610                1615                1620

Ser Gln Leu Thr His Ser Ile Thr Glu Leu Gly Pro Tyr Thr Leu
    1625                1630                1635

Asp Arg Asp Ser Leu Tyr Val Asn Gly Phe Thr His Arg Ser Ser
    1640                1645                1650

Val Pro Thr Thr Ser Thr Gly Val Val Ser Glu Glu Pro Phe Thr
    1655                1660                1665

Leu Asn Phe Thr Ile Asn Asn Leu Arg Tyr Met Ala Asp Met Gly
    1670                1675                1680

Gln Pro Gly Ser Leu Lys Phe Asn Ile Thr Asp Asn Val Met Lys
    1685                1690                1695

His Leu Leu Ser Pro Leu Phe Gln Arg Ser Ser Leu Gly Ala Arg
    1700                1705                1710

Tyr Thr Gly Cys Arg Val Ile Ala Leu Arg Ser Val Lys Asn Gly
    1715                1720                1725

Ala Glu Thr Arg Val Asp Leu Leu Cys Thr Tyr Leu Gln Pro Leu
    1730                1735                1740

Ser Gly Pro Gly Leu Pro Ile Lys Gln Val Phe His Glu Leu Ser
    1745                1750                1755

Gln Gln Thr His Gly Ile Thr Arg Leu Gly Pro Tyr Ser Leu Asp
    1760                1765                1770

Lys Asp Ser Leu Tyr Leu Asn Gly Tyr Asn Glu Pro Gly Leu Asp
    1775                1780                1785

Glu Pro Pro Thr Thr Pro Lys Pro Ala Thr Thr Phe Leu Pro Pro
    1790                1795                1800

Leu Ser Glu Ala Thr Thr Ala Met Gly Tyr His Leu Lys Thr Leu
    1805                1810                1815

Thr Leu Asn Phe Thr Ile Ser Asn Leu Gln Tyr Ser Pro Asp Met
    1820                1825                1830

Gly Lys Gly Ser Ala Thr Phe Asn Ser Thr Glu Gly Val Leu Gln
    1835                1840                1845

His Leu Leu Arg Pro Leu Phe Gln Lys Ser Ser Met Gly Pro Phe
    1850                1855                1860

Tyr Leu Gly Cys Gln Leu Ile Ser Leu Arg Pro Glu Lys Asp Gly
    1865                1870                1875

Ala Ala Thr Gly Val Asp Thr Thr Cys Thr Tyr His Pro Asp Pro
    1880                1885                1890

Val Gly Pro Gly Leu Asp Ile Gln Gln Leu Tyr Trp Glu Leu Ser
    1895                1900                1905

Gln Leu Thr His Gly Val Thr Gln Leu Gly Phe Tyr Val Leu Asp
    1910                1915                1920

Arg Asp Ser Leu Phe Ile Asn Gly Tyr Ala Pro Gln Asn Leu Ser
    1925                1930                1935

Ile Arg Gly Glu Tyr Gln Ile Asn Phe His Ile Val Asn Trp Asn
    1940                1945                1950

Leu Ser Asn Pro Asp Pro Thr Ser Ser Glu Tyr Ile Thr Leu Leu
    1955                1960                1965

Arg Asp Ile Gln Asp Lys Val Thr Thr Leu Tyr Lys Gly Ser Gln
    1970                1975                1980

Leu His Asp Thr Phe Arg Phe Cys Leu Val Thr Asn Leu Thr Met
```

```
                1985                1990                1995

Asp Ser Val Leu Val Thr Val Lys Ala Leu Phe Ser Ser Asn Leu
    2000                2005                2010

Asp Pro Ser Leu Val Glu Gln Val Phe Leu Asp Lys Thr Leu Asn
    2015                2020                2025

Ala Ser Phe His Trp Leu Gly Ser Thr Tyr Gln Leu Val Asp Ile
    2030                2035                2040

His Val Thr Glu Met Glu Ser Ser Val Tyr Gln Pro Thr Ser Ser
    2045                2050                2055

Ser Ser Thr Gln His Phe Tyr Leu Asn Phe Thr Ile Thr Asn Leu
    2060                2065                2070

Pro Tyr Ser Gln Asp Lys Ala Gln Pro Gly Thr Thr Asn Tyr Gln
    2075                2080                2085

Arg Asn Lys Arg Asn Ile Glu Asp Ala Leu Asn Gln Leu Phe Arg
    2090                2095                2100

Asn Ser Ser Ile Lys Ser Tyr Phe Ser Asp Cys Gln Val Ser Thr
    2105                2110                2115

Phe Arg Ser Val Pro Asn Arg His His Thr Gly Val Asp Ser Leu
    2120                2125                2130

Cys Asn Phe Ser Pro Leu Ala Arg Arg Val Asp Arg Val Ala Ile
    2135                2140                2145

Tyr Glu Glu Phe Leu Arg Met Thr Arg Asn Gly Thr Gln Leu Gln
    2150                2155                2160

Asn Phe Thr Leu Asp Arg Ser Ser Val Leu Val Asp Gly Tyr Ser
    2165                2170                2175

Pro Asn Arg Asn Glu Pro Leu Thr Gly Asn Ser Asp Leu Pro Phe
    2180                2185                2190

Trp Ala Val Ile Leu Ile Gly Leu Ala Gly Leu Leu Gly Leu Ile
    2195                2200                2205

Thr Cys Leu Ile Cys Gly Val Leu Val Thr Thr Arg Arg Arg Lys
    2210                2215                2220

Lys Glu Gly Glu Tyr Asn Val Gln Gln Gln Cys Pro Gly Tyr Tyr
    2225                2230                2235

Gln Ser His Leu Asp Leu Glu Asp Leu Gln
    2240                2245

<210> SEQ ID NO 51
<211> LENGTH: 24
<212> TYPE: DNA
<213> ORGANISM: Artificial Sequence
<220> FEATURE:
<223> OTHER INFORMATION: Synthetic Primer

<400> SEQUENCE: 51
cagcagagac cagcacgagt actc                                          24

<210> SEQ ID NO 52
<211> LENGTH: 20
<212> TYPE: DNA
<213> ORGANISM: Artificial Sequence
<220> FEATURE:
<223> OTHER INFORMATION: Synthetic Primer

<400> SEQUENCE: 52
tccactgcca tggctgagct                                               20

<210> SEQ ID NO 53
```

-continued

```
<211> LENGTH: 22
<212> TYPE: DNA
<213> ORGANISM: Artificial Sequence
<220> FEATURE:
<223> OTHER INFORMATION: Synthetic Primer

<400> SEQUENCE: 53
ccagcacagc tcttcccagg ac                                              22

<210> SEQ ID NO 54
<211> LENGTH: 22
<212> TYPE: DNA
<213> ORGANISM: Artificial Sequence
<220> FEATURE:
<223> OTHER INFORMATION: Synthetic Primer

<400> SEQUENCE: 54
ggaatggctg agctgacgtc tg                                              22

<210> SEQ ID NO 55
<211> LENGTH: 21
<212> TYPE: DNA
<213> ORGANISM: Artificial Sequence
<220> FEATURE:
<223> OTHER INFORMATION: Synthetic Primer

<400> SEQUENCE: 55
cttcccagga caacctcaag g                                               21

<210> SEQ ID NO 56
<211> LENGTH: 21
<212> TYPE: DNA
<213> ORGANISM: Artificial Sequence
<220> FEATURE:
<223> OTHER INFORMATION: Synthetic Primer

<400> SEQUENCE: 56
gcaggatgag tgagccacgt g                                               21

<210> SEQ ID NO 57
<211> LENGTH: 22
<212> TYPE: DNA
<213> ORGANISM: Artificial Sequence
<220> FEATURE:
<223> OTHER INFORMATION: Synthetic Primer

<400> SEQUENCE: 57
gtcagatctg gtgacctcac tg                                              22

<210> SEQ ID NO 58
<211> LENGTH: 21
<212> TYPE: DNA
<213> ORGANISM: Artificial Sequence
<220> FEATURE:
<223> OTHER INFORMATION: Synthetic Primer

<400> SEQUENCE: 58
gaggcactgg aaagcccaga g                                               21

<210> SEQ ID NO 59
<211> LENGTH: 25
<212> TYPE: DNA
<213> ORGANISM: Artificial Sequence
<220> FEATURE:
<223> OTHER INFORMATION: Synthetic Primer

<400> SEQUENCE: 59
```

```
ctgatggcat tatggaacac atcac                                         25

<210> SEQ ID NO 60
<211> LENGTH: 22
<212> TYPE: DNA
<213> ORGANISM: Artificial Sequence
<220> FEATURE:
<223> OTHER INFORMATION: Synthetic Primer

<400> SEQUENCE: 60
cccagaacga gagaccagtg ag                                            22

<210> SEQ ID NO 61
<211> LENGTH: 24
<212> TYPE: DNA
<213> ORGANISM: Artificial Sequence
<220> FEATURE:
<223> OTHER INFORMATION: Synthetic Primer

<400> SEQUENCE: 61
gctgatggcg atgaatgaac actg                                          24

<210> SEQ ID NO 62
<211> LENGTH: 22
<212> TYPE: DNA
<213> ORGANISM: Artificial Sequence
<220> FEATURE:
<223> OTHER INFORMATION: Synthetic Primer

<400> SEQUENCE: 62
cccagaacga gagaccagtg ag                                            22

<210> SEQ ID NO 63
<211> LENGTH: 35
<212> TYPE: DNA
<213> ORGANISM: Artificial Sequence
<220> FEATURE:
<223> OTHER INFORMATION: Synthetic Primer

<400> SEQUENCE: 63
cgcggatccg aacactgcgt ttgctggctt tgatg                              35

<210> SEQ ID NO 64
<211> LENGTH: 23
<212> TYPE: DNA
<213> ORGANISM: Artificial Sequence
<220> FEATURE:
<223> OTHER INFORMATION: Synthetic Primer

<400> SEQUENCE: 64
cctctgtgtg ctgcttcatt ggg                                           23

<210> SEQ ID NO 65
<211> LENGTH: 32
<212> TYPE: DNA
<213> ORGANISM: Artificial Sequence
<220> FEATURE:
<223> OTHER INFORMATION: Synthetic Primer

<400> SEQUENCE: 65
accggatcca tgggccacac agagcctggc cc                                 32

<210> SEQ ID NO 66
<211> LENGTH: 29
<212> TYPE: DNA
```

<213> ORGANISM: Artificial Sequence
<220> FEATURE:
<223> OTHER INFORMATION: Synthetic Primer

<400> SEQUENCE: 66

```
tgtaagctta ggcagggagg atggagtcc                                    29
```

<210> SEQ ID NO 67
<211> LENGTH: 507
<212> TYPE: DNA
<213> ORGANISM: Homo sapien

<400> SEQUENCE: 67

```
atgagaggat cgcatcacca tcaccatcac ggatccatgg gccacacaga gcctggccct   60
ctcctgatac cattcacttt caactttacc atcaccaacc tgcattatga ggaaaacatg  120
caacaccctg gttccaggaa gttcaacacc acggagaggg ttctgcaggg tctgctcaag  180
cccttgttca agaacaccag tgttggccct ctgtactctg ctgcagact gaccttgctc   240
agacctgaga agcatgaggc agccactgga gtggacacca tctgtaccca ccgcgttgat  300
cccatcggac ctggactgga cagagagcgg ctatactggg agctgagcca gctgaccaac  360
agcatcacag agctgggacc ctacaccctg acagggaca gtctctatgt caatggcttc   420
aaccctcgga gctctgtgcc aaccaccagc actcctggga cctccacagt gcacctggca  480
acctctggga ctccatcctc cctgcct                                     507
```

<210> SEQ ID NO 68
<211> LENGTH: 169
<212> TYPE: PRT
<213> ORGANISM: Homo sapiens

<400> SEQUENCE: 68

```
Met Arg Gly Ser His His His His His His Gly Ser Met Gly His Thr
1               5                   10                  15
Glu Pro Gly Pro Leu Leu Ile Pro Phe Thr Phe Asn Phe Thr Ile Thr
            20                  25                  30
Asn Leu His Tyr Glu Glu Asn Met Gln His Pro Gly Ser Arg Lys Phe
        35                  40                  45
Asn Thr Thr Glu Arg Val Leu Gln Gly Leu Leu Lys Pro Leu Phe Lys
50                  55                  60
Asn Thr Ser Val Gly Pro Leu Tyr Ser Gly Cys Arg Leu Thr Leu Leu
65                  70                  75                  80
Arg Pro Glu Lys His Glu Ala Ala Thr Gly Val Asp Thr Ile Cys Thr
                85                  90                  95
His Arg Val Asp Pro Ile Gly Pro Gly Leu Asp Arg Glu Arg Leu Tyr
            100                 105                 110
Trp Glu Leu Ser Gln Leu Thr Asn Ser Ile Thr Glu Leu Gly Pro Tyr
        115                 120                 125
Thr Leu Asp Arg Asp Ser Leu Tyr Val Asn Gly Phe Asn Pro Arg Ser
    130                 135                 140
Ser Val Pro Thr Thr Ser Thr Pro Gly Thr Ser Thr Val His Leu Ala
145                 150                 155                 160
Thr Ser Gly Thr Pro Ser Ser Leu Pro
                165
```

<210> SEQ ID NO 69
<211> LENGTH: 909
<212> TYPE: PRT

```
<213> ORGANISM: Homo sapiens
<220> FEATURE:
<221> NAME/KEY: MISC_FEATURE
<222> LOCATION: (1)..(909)
<223> OTHER INFORMATION: Any "X" = any amino acid

<400> SEQUENCE: 69

Glu Arg Val Leu Gln Gly Leu Gly Pro Met Phe Lys Asn Thr Ser
1               5                   10                  15

Val Gly Leu Leu Tyr Ser Gly Cys Arg Leu Thr Leu Leu Arg Pro Lys
            20                  25                  30

Lys Asp Gly Ala Ala Thr Lys Val Asp Ala Ile Cys Thr Tyr Arg Pro
            35                  40                  45

Asp Pro Lys Ser Pro Gly Leu Asp Arg Glu Gln Leu Tyr Trp Glu Leu
    50                  55                  60

Ser Gln Leu Thr His Ser Ile Thr Glu Leu Gly Pro Tyr Thr Leu Asp
65              70                  75                  80

Arg Asp Ser Leu Tyr Val Asn Gly Phe Thr Gln Arg Ser Ser Val Pro
                85                  90                  95

Thr Thr Ser Ile Pro Gly Thr Pro Thr Val Asp Leu Gly Thr Ser Gly
            100                 105                 110

Thr Pro Val Ser Lys Pro Gly Pro Ser Ala Ala Ser Pro Leu Leu Ile
            115                 120                 125

Pro Phe Thr Ile Asn Phe Thr Ile Thr Asn Leu Arg Tyr Glu Glu Asn
    130                 135                 140

Met Gly His Pro Gly Ser Arg Lys Phe Asn Ile Met Glu Arg Val Leu
145             150                 155                 160

Gln Gly Leu Leu Lys Pro Leu Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Gly Val Asp Ala Ile Cys Thr His Arg Leu Asp Pro Lys Ser
            195                 200                 205

Pro Gly Leu Asn Arg Glu Gln Leu Tyr Trp Glu Leu Ser Lys Leu Thr
    210                 215                 220

Asn Asp Ile Glu Glu Leu Gly Pro Tyr Thr Leu Asp Arg Asn Ser Leu
225                 230                 235                 240

Tyr Val Asn Gly Phe Thr His Gln Ser Ser Val Ser Thr Thr Ser Thr
                245                 250                 255

Pro Gly Thr Ser Thr Val Asp Leu Arg Thr Ser Gly Thr Pro Ser Ser
            260                 265                 270

Leu Ser Ser Pro Thr Ile Met Ala Ala Gly Pro Leu Leu Ile Pro Phe
            275                 280                 285

Thr Ile Asn Phe Thr Ile Thr Asn Leu Arg Tyr Glu Glu Asn Met His
    290                 295                 300

His Pro Gly Ser Arg Lys Phe Asn Thr Met Glu Arg Val Leu Gln Gly
305             310                 315                 320

Leu Leu Met Pro Leu Phe Lys Asn Thr Ser Val Ser Ser Leu Tyr Ser
                325                 330                 335

Gly Cys Arg Leu Thr Leu Leu Arg Pro Glu Lys Asp Gly Ala Ala Thr
            340                 345                 350

Arg Val Asp Ala Val Cys Thr His Arg Pro Asp Pro Lys Ser Pro Gly
            355                 360                 365

Leu Asp Arg Glu Arg Leu Tyr Trp Lys Leu Ser Gln Leu Thr His Gly
    370                 375                 380
```

-continued

```
Ile Thr Glu Leu Gly Pro Tyr Thr Leu Asp Arg Asn Ser Leu Tyr Val
385                 390                 395                 400

Asn Gly Phe Thr His Arg Ser Ser Met Pro Thr Thr Ser Thr Pro Gly
                405                 410                 415

Thr Ser Thr Val Asp Val Gly Thr Ser Gly Thr Pro Ser Ser Ser Pro
                420                 425                 430

Ser Pro Thr Thr Ala Gly Pro Leu Leu Met Pro Phe Thr Leu Asn Phe
                435                 440                 445

Thr Ile Thr Asn Leu Gln Tyr Glu Glu Asp Met Arg Arg Thr Gly Ser
            450                 455                 460

Arg Lys Phe Asn Thr Met Glu Arg Val Leu Gln Gly Leu Leu Lys Pro
465                 470                 475                 480

Leu Phe Lys Ser Thr Ser Val Gly Pro Leu Tyr Ser Gly Cys Arg Leu
                485                 490                 495

Thr Leu Leu Arg Pro Glu Lys His Gly Ala Ala Thr Gly Val Asp Ala
                500                 505                 510

Ile Cys Thr Leu Arg Leu Asp Pro Thr Gly Pro Gly Leu Asp Arg Glu
            515                 520                 525

Arg Leu Tyr Trp Glu Leu Ser Gln Leu Thr Asn Ser Val Thr Glu Leu
            530                 535                 540

Gly Pro Tyr Thr Leu Asp Arg Asp Ser Leu Tyr Val Asn Gly Phe Thr
545                 550                 555                 560

His Arg Ser Ser Val Pro Thr Thr Ser Ile Pro Gly Thr Ser Ala Val
                565                 570                 575

His Leu Glu Thr Ser Gly Thr Pro Ala Ser Leu Pro Gly His Thr Ala
                580                 585                 590

Pro Gly Pro Leu Leu Ile Pro Phe Thr Leu Asn Phe Thr Ile Thr Asn
            595                 600                 605

Leu His Tyr Glu Glu Asn Met Gln His Pro Gly Ser Arg Lys Phe Asn
            610                 615                 620

Thr Met Glu Arg Val Leu Gln Gly Cys Leu Val Pro Cys Ser Arg Asn
625                 630                 635                 640

Thr Asn Val Gly Leu Leu Tyr Ser Gly Cys Arg Leu Thr Leu Leu Arg
                645                 650                 655

Xaa Glu Lys Xaa Xaa Ala Ala Thr Xaa Val Asp Xaa Xaa Cys Xaa Xaa
                660                 665                 670

Xaa Xaa Asp Pro Xaa Xaa Pro Gly Leu Asp Arg Glu Xaa Leu Tyr Trp
            675                 680                 685

Glu Leu Ser Xaa Leu Thr Xaa Xaa Ile Xaa Glu Leu Gly Pro Tyr Thr
            690                 695                 700

Leu Asp Arg Asn Ser Leu Tyr Val Asn Gly Phe Thr His Arg Ser Ser
705                 710                 715                 720

Val Ala Pro Thr Ser Thr Pro Gly Thr Ser Thr Val Asp Leu Gly Thr
                725                 730                 735

Ser Gly Thr Pro Ser Ser Leu Pro Ser Pro Thr Thr Val Pro Leu Leu
                740                 745                 750

Val Pro Phe Thr Leu Asn Phe Thr Ile Thr Asn Leu Gln Tyr Gly Glu
                755                 760                 765

Asp Met Arg His Pro Gly Ser Arg Lys Phe Asn Thr Thr Glu Arg Val
            770                 775                 780

Leu Gln Gly Leu Leu Gly Pro Leu Phe Lys Asn Ser Ser Val Gly Pro
785                 790                 795                 800
```

```
Leu Tyr Ser Gly Cys Arg Leu Ile Ser Leu Arg Ser Glu Lys Asp Gly
                805                 810                 815

Ala Ala Thr Gly Val Asp Ala Ile Cys Thr His His Leu Asn Pro Gln
            820                 825                 830

Ser Pro Gly Leu Asp Arg Glu Gln Leu Tyr Trp Gln Leu Ser Gln Val
        835                 840                 845

Thr Asn Gly Ile Lys Glu Leu Gly Pro Tyr Thr Leu Asp Arg Asn Ser
    850                 855                 860

Leu Tyr Val Asn Gly Phe Thr His Arg Ser Ser Gly Leu Thr Thr Ser
865                 870                 875                 880

Thr Pro Trp Thr Ser Thr Val Asp Leu Gly Thr Ser Gly Thr Pro Ser
                885                 890                 895

Pro Val Pro Ser Pro Thr Thr Ala Gly Pro Leu Leu Ile
                900                 905

<210> SEQ ID NO 70
<211> LENGTH: 525
<212> TYPE: PRT
<213> ORGANISM: Homo sapiens

<400> SEQUENCE: 70

Gln Gly Leu Leu Gly Pro Met Phe Lys Asn Thr Ser Val Gly Leu Leu
1               5                   10                  15

Tyr Ser Gly Cys Arg Leu Thr Leu Leu Arg Pro Glu Lys Arg Gly Ala
            20                  25                  30

Ala Thr Gly Val Asp Thr Ile Cys Thr His Arg Leu Asp Pro Leu Asn
        35                  40                  45

Pro Gly Leu Asp Arg Glu Gln Leu Tyr Trp Glu Leu Ser Lys Leu Thr
    50                  55                  60

Arg Gly Ile Ile Glu Leu Gly Pro Tyr Leu Leu Asp Arg Gly Ser Leu
65                  70                  75                  80

Tyr Val Asn Gly Phe Thr His Arg Asn Phe Val Pro Ile Thr Ser Thr
                85                  90                  95

Pro Gly Thr Ser Thr Val His Leu Gly Thr Ser Glu Thr Pro Ser Ser
            100                 105                 110

Leu Pro Arg Pro Ile Val Pro Gly Pro Leu Leu Val Pro Phe Thr Leu
        115                 120                 125

Asn Phe Thr Ile Thr Asn Leu Gln Tyr Glu Glu Ala Met Arg His Pro
    130                 135                 140

Gly Ser Arg Lys Phe Asn Thr Thr Glu Arg Val Leu Gln Gly Leu Leu
145                 150                 155                 160

Arg Pro Leu Phe Lys Asn Thr Ser Val Ser Ser Leu Tyr Ser Gly Cys
                165                 170                 175

Arg Leu Thr Leu Leu Arg Pro Glu Lys Asp Gly Ala Ala Thr Arg Val
            180                 185                 190

Asp Ala Ala Cys Thr Tyr Arg Pro Asp Pro Lys Ser Pro Gly Leu Asp
        195                 200                 205

Arg Glu Gln Leu Tyr Trp Glu Leu Ser Gln Leu Thr His Ser Ile Thr
    210                 215                 220

Glu Leu Gly Pro Tyr Thr Leu Asp Arg Val Ser Leu Tyr Val Asn Gly
225                 230                 235                 240

Phe Asn Pro Arg Ser Ser Val Pro Thr Thr Ser Thr Pro Gly Thr Ser
                245                 250                 255

Thr Val His Leu Ala Thr Ser Gly Thr Pro Ser Ser Leu Pro Gly His
            260                 265                 270
```

```
Thr Ala Pro Val Pro Leu Leu Ile Pro Phe Thr Leu Asn Phe Thr Ile
            275                 280                 285

Thr Asn Leu Gln Tyr Glu Glu Asp Met Arg His Pro Gly Ser Arg Lys
            290                 295                 300

Phe Asn Thr Met Glu Arg Val Leu Gln Gly Leu Leu Arg Pro Leu Phe
305                 310                 315                 320

Lys Asn Thr Ser Ile Gly Pro Leu Tyr Ser Ser Cys Arg Leu Thr Leu
            325                 330                 335

Leu Arg Pro Glu Lys Asp Lys Ala Ala Thr Arg Val Asp Ala Ile Cys
            340                 345                 350

Thr His His Pro Asp Pro Gln Ser Pro Gly Leu Asn Arg Glu Gln Leu
            355                 360                 365

Tyr Trp Glu Leu Ser Gln Leu Thr His Gly Ile Thr Glu Leu Gly Pro
            370                 375                 380

Tyr Thr Leu Asp Arg Asp Ser Leu Tyr Val Asp Gly Phe Thr His Trp
385                 390                 395                 400

Ser Pro Ile Pro Thr Thr Ser Thr Pro Gly Thr Ser Ile Val Asn Leu
            405                 410                 415

Gly Thr Ser Gly Ile Pro Pro Ser Leu Pro Glu Thr Thr Ala Thr Gly
            420                 425                 430

Pro Leu Leu Ile Pro Phe Thr Pro Asn Phe Thr Ile Thr Asn Leu Gln
            435                 440                 445

Tyr Glu Glu Asp Met Arg Arg Thr Gly Ser Arg Lys Phe Asn Thr Met
450                 455                 460

Glu Arg Val Leu Gln Gly Leu Leu Ser Pro Ile Phe Lys Asn Ser Ser
465                 470                 475                 480

Val Gly Pro Leu Tyr Ser Gly Cys Arg Leu Thr Ser Leu Arg Pro Glu
            485                 490                 495

Lys Asp Gly Ala Ala Thr Gly Met Asp Ala Val Cys Leu Tyr His Pro
            500                 505                 510

Asn Pro Lys Arg Pro Gly Leu Asp Arg Glu Gln Leu Tyr
            515                 520                 525

<210> SEQ ID NO 71
<211> LENGTH: 594
<212> TYPE: PRT
<213> ORGANISM: Homo sapiens

<400> SEQUENCE: 71

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
            20                  25                  30

Lys Asp Gly Val Ala Thr Arg Val Asp Ala Ile Cys Thr His Arg Pro
            35                  40                  45

Asp Pro Lys Ile Pro Gly Leu Asp Arg Gln Gln Leu Tyr Trp Glu Leu
        50                  55                  60

Ser Gln Leu Thr His Ser Ile Thr Glu Leu Gly Pro Tyr Thr Leu Asp
65                  70                  75                  80

Arg Asp Ser Leu Tyr Val Asn Gly Phe Thr Gln Arg Ser Ser Val Pro
                85                  90                  95

Thr Thr Ser Thr Pro Gly Thr Phe Thr Val Gln Pro Glu Thr Ser Glu
            100                 105                 110

Thr Pro Ser Ser Leu Pro Gly Pro Thr Ala Thr Gly Pro Val Leu Leu
```

-continued

```
                115                 120                 125
Pro Phe Thr Leu Asn Phe Thr Ile Ile Asn Leu Gln Tyr Glu Glu Asp
        130                 135                 140
Met His Arg Pro Gly Ser Arg Lys Phe Asn Thr Thr Glu Arg Val Leu
145                 150                 155                 160
Gln Gly Leu Leu Met Pro Leu Phe Lys Asn Thr Ser Val Gly Pro Leu
                165                 170                 175
Tyr Ser Gly Cys Arg Leu Thr Leu Leu Arg Pro Glu Lys Gln Glu Ala
                180                 185                 190
Ala Thr Gly Val Asp Thr Ile Cys Thr His Arg Leu Asp Pro Ser Glu
                195                 200                 205
Pro Gly Leu Asp Arg Glu Gln Leu Tyr Trp Glu Leu Ser Gln Leu Thr
        210                 215                 220
Asn Ser Ile Thr Glu Leu Gly Pro Tyr Thr Leu Asp Arg Asp Ser Leu
225                 230                 235                 240
Tyr Val Asn Gly Phe Thr His Ser Gly Val Leu Cys Pro Pro Pro Ser
                245                 250                 255
Ile Leu Gly Ile Phe Thr Val Gln Pro Glu Thr Phe Glu Thr Pro Ser
                260                 265                 270
Ser Leu Pro Gly Pro Thr Ala Thr Gly Pro Val Leu Leu Pro Phe Thr
        275                 280                 285
Leu Asn Phe Thr Ile Ile Asn Leu Gln Tyr Glu Glu Asp Met His Arg
        290                 295                 300
Pro Gly Ser Arg Lys Phe Asn Thr Thr Glu Arg Val Leu Gln Gly Leu
305                 310                 315                 320
Leu Thr Pro Leu Phe Lys Asn Thr Ser Val Gly Pro Leu Tyr Ser Gly
                325                 330                 335
Cys Arg Leu Thr Leu Leu Arg Pro Glu Lys Gln Glu Ala Ala Thr Gly
                340                 345                 350
Val Asp Thr Ile Cys Thr His Arg Val Asp Pro Ile Gly Pro Gly Leu
                355                 360                 365
Asp Arg Glu Arg Leu Tyr Trp Glu Leu Ser Gln Leu Thr Asn Ser Ile
        370                 375                 380
Thr Glu Leu Gly Pro Tyr Thr Leu Asp Arg Asp Ser Leu Tyr Val Asn
385                 390                 395                 400
Gly Phe Asn Pro Trp Ser Ser Val Pro Thr Thr Ser Thr Pro Gly Thr
                405                 410                 415
Ser Thr Val His Leu Ala Thr Ser Gly Thr Pro Ser Ser Leu Pro Gly
                420                 425                 430
His Thr Ala Pro Val Pro Leu Leu Ile Pro Phe Thr Leu Asn Phe Thr
                435                 440                 445
Ile Thr Asn Leu His Tyr Glu Glu Asn Met Gln His Pro Gly Ser Arg
        450                 455                 460
Lys Phe Asn Thr Thr Glu Arg Val Leu Gln Gly Leu Leu Lys Pro Leu
465                 470                 475                 480
Phe Lys Ser Thr Ser Val Gly Pro Leu Tyr Ser Gly Cys Arg Leu Thr
                485                 490                 495
Leu Leu Arg Pro Glu Lys His Gly Ala Ala Thr Gly Val Asp Ala Ile
                500                 505                 510
Cys Thr His Arg Leu Asp Pro Lys Ser Pro Gly Val Asp Arg Glu Gln
                515                 520                 525
Leu Tyr Trp Glu Leu Ser Gln Leu Thr Asn Gly Ile Lys Glu Leu Gly
        530                 535                 540
```

```
Pro Tyr Thr Leu Asp Arg Asn Ser Leu Tyr Val Asn Gly Phe Thr His
545                 550                 555                 560

Trp Ile Pro Val Pro Thr Ser Ser Thr Pro Gly Thr Ser Thr Val Asp
                565                 570                 575

Leu Gly Ser Gly Thr Pro Ser Ser Leu Pro Ser Pro Thr Thr Ala Gly
                580                 585                 590

Pro Leu

<210> SEQ ID NO 72
<211> LENGTH: 424
<212> TYPE: PRT
<213> ORGANISM: Homo sapiens

<400> SEQUENCE: 72

Thr Ser Val Gly Pro Leu Tyr Ser Gly Cys Arg Leu Thr Leu Leu Arg
1               5                   10                  15

Ser Glu Lys Asp Gly Ala Ala Thr Gly Val Asp Ala Ile Tyr Thr His
                20                  25                  30

Arg Leu Asp Pro Lys Ser Pro Gly Val Asp Arg Glu Gln Leu Tyr Trp
            35                  40                  45

Glu Leu Ser Gln Leu Thr Asn Gly Ile Lys Glu Leu Gly Pro Tyr Thr
50                  55                  60

Leu Asp Arg Asn Ser Leu Tyr Val Asn Gly Phe Thr His Gln Thr Ser
65                  70                  75                  80

Ala Pro Asn Thr Ser Thr Pro Gly Thr Ser Thr Val Asp Leu Gly Thr
                85                  90                  95

Ser Gly Thr Pro Ser Ser Leu Pro Ser Pro Thr Ser Ala Gly Pro Leu
            100                 105                 110

Leu Ile Pro Phe Thr Ile Asn Phe Thr Ile Thr Asn Leu Arg Tyr Glu
        115                 120                 125

Glu Asn Met His His Pro Gly Ser Arg Lys Phe Asn Thr Met Glu Arg
130                 135                 140

Val Leu Gln Gly Leu Leu Lys Pro Leu Phe Lys Ser Thr Ser Val Gly
145                 150                 155                 160

Pro Leu Tyr Ser Gly Cys Arg Leu Thr Leu Leu Arg Pro Glu Lys Asp
                165                 170                 175

Gly Val Ala Thr Arg Val Asp Ala Ile Cys Thr His Arg Pro Asp Pro
            180                 185                 190

Lys Ile Pro Gly Leu Asp Arg Gln Gln Leu Tyr Trp Glu Leu Ser Gln
        195                 200                 205

Leu Thr His Ser Ile Thr Glu Leu Gly Pro Tyr Thr Leu Asp Arg Asp
210                 215                 220

Ser Leu Tyr Val Asn Gly Phe Thr Gln Arg Ser Ser Val Pro Thr Thr
225                 230                 235                 240

Ser Thr Pro Gly Thr Phe Thr Val Gln Pro Glu Thr Ser Glu Thr Pro
                245                 250                 255

Ser Ser Leu Pro Gly Pro Thr Ala Thr Gly Pro Val Leu Leu Pro Phe
            260                 265                 270

Thr Leu Asn Phe Thr Ile Ile Asn Leu Gln Tyr Glu Glu Asp Met His
        275                 280                 285

Arg Pro Gly Ser Arg Lys Phe Asn Thr Thr Glu Arg Val Leu Gln Gly
    290                 295                 300

Leu Leu Lys Pro Leu Phe Lys Ser Thr Ser Val Gly Pro Leu Tyr Ser
305                 310                 315                 320
```

-continued

```
Gly Cys Arg Leu Thr Leu Leu Arg Pro Glu Lys His Gly Ala Ala Thr
                325                 330                 335

Gly Val Asp Ala Ile Cys Thr Leu Arg Leu Asp Pro Thr Gly Pro Gly
            340                 345                 350

Leu Asp Arg Glu Arg Leu Tyr Trp Glu Leu Ser Gln Leu Thr Asn Ser
        355                 360                 365

Ile Thr Glu Leu Gly Pro Tyr Thr Leu Asp Arg Asp Ser Leu Tyr Val
    370                 375                 380

Asn Gly Phe Asn Pro Trp Ser Ser Val Pro Thr Thr Ser Thr Pro Gly
385                 390                 395                 400

Thr Ser Thr Val His Leu Ala Thr Ser Gly Thr Pro Ser Ser Leu Pro
                405                 410                 415

Gly His Thr Ala Pro Val Pro Leu
                420

<210> SEQ ID NO 73
<211> LENGTH: 286
<212> TYPE: PRT
<213> ORGANISM: Homo sapiens

<400> SEQUENCE: 73

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
            20                  25                  30

Lys Arg Gly Ala Ala Thr Gly Val Asp Thr Ile Cys Thr His Arg Leu
        35                  40                  45

Asp Pro Leu Asn Pro Gly Leu Asp Arg Glu Gln Leu Tyr Trp Glu Leu
    50                  55                  60

Ser Lys Leu Thr Arg Gly Ile Ile Glu Leu Gly Pro Tyr Leu Leu Asp
65                  70                  75                  80

Arg Asp Ser Leu Tyr Val Asn Gly Phe Thr His Arg Ser Ser Val Pro
                85                  90                  95

Thr Thr Ser Ile Pro Gly Thr Ser Ala Val His Leu Glu Thr Ser Gly
            100                 105                 110

Thr Pro Ala Ser Leu Pro Gly His Thr Ala Pro Gly Pro Leu Leu Val
        115                 120                 125

Pro Phe Thr Leu Asn Phe Thr Ile Thr Asn Leu Gln Tyr Glu Glu Asp
    130                 135                 140

Met Arg His Pro Gly Ser Arg Lys Phe Asn Thr Thr Glu Arg Val Leu
145                 150                 155                 160

Gln Gly Leu Leu Lys Pro Leu Phe Lys Ser Thr Ser Val Gly Pro Leu
                165                 170                 175

Tyr Ser Gly Cys Arg Leu Thr Leu Leu Arg Pro Glu Lys Arg Gly Ala
            180                 185                 190

Ala Thr Gly Val Asp Thr Ile Cys Thr His Arg Leu Asp Pro Leu Asn
        195                 200                 205

Pro Gly Leu Asp Arg Glu Gln Leu Tyr Trp Glu Leu Ser Lys Leu Thr
    210                 215                 220

Arg Gly Ile Ile Glu Leu Gly Pro Tyr Leu Leu Asp Arg Gly Ser Leu
225                 230                 235                 240

Tyr Val Asn Gly Phe Thr His Arg Asn Phe Val Pro Ile Thr Ser Thr
                245                 250                 255

Pro Gly Thr Ser Thr Val His Leu Gly Thr Ser Glu Thr Pro Ser Ser
```

```
                260                 265                 270
Leu Pro Arg Pro Ile Val Pro Gly Pro Leu Leu Ile Pro Phe
            275                 280                 285

<210> SEQ ID NO 74
<211> LENGTH: 286
<212> TYPE: PRT
<213> ORGANISM: Homo sapiens

<400> SEQUENCE: 74

Glu Arg Val Leu Gln Gly Leu Leu Arg Pro Val Phe Lys Asn Thr Ser
1               5                   10                  15

Val Gly Pro Leu Tyr Ser Gly Cys Arg Leu Thr Leu Leu Arg Pro Lys
            20                  25                  30

Lys Asp Gly Ala Ala Thr Lys Val Asp Ala Ile Cys Thr Tyr Arg Pro
        35                  40                  45

Asp Pro Lys Ser Pro Gly Leu Asp Arg Glu Gln Leu Tyr Trp Glu Leu
    50                  55                  60

Ser Gln Leu Thr His Ser Ile Thr Glu Leu Gly Pro Tyr Thr Leu Asp
65                  70                  75                  80

Arg Asp Ser Leu Tyr Val Asn Gly Phe Thr Gln Arg Ser Ser Val Pro
                85                  90                  95

Thr Thr Ser Ile Pro Gly Thr Pro Thr Val Asp Leu Gly Thr Ser Gly
            100                 105                 110

Thr Pro Val Ser Lys Pro Gly Pro Ser Ala Ala Ser Pro Leu Leu Val
        115                 120                 125

Pro Phe Thr Leu Asn Phe Thr Ile Thr Asn Leu Gln Tyr Glu Glu Asp
    130                 135                 140

Met His Arg Pro Gly Ser Arg Lys Phe Asn Ala Thr Glu Arg Val Leu
145                 150                 155                 160

Gln Gly Leu Leu Ser Pro Ile Phe Lys Asn Ser Ser Val Gly Pro Leu
                165                 170                 175

Tyr Ser Gly Cys Arg Leu Thr Ser Leu Arg Pro Glu Lys Asp Gly Ala
            180                 185                 190

Ala Thr Gly Met Asp Ala Val Cys Leu Tyr His Pro Asn Pro Lys Arg
        195                 200                 205

Pro Gly Leu Asp Arg Glu Gln Leu Tyr Trp Glu Leu Ser Gln Leu Thr
    210                 215                 220

His Asn Ile Thr Glu Leu Gly Pro Tyr Ser Leu Asp Arg Asp Ser Leu
225                 230                 235                 240

Tyr Val Asn Gly Phe Thr His Gln Ser Ser Met Thr Thr Thr Arg Thr
                245                 250                 255

Pro Asp Thr Ser Thr Met His Leu Ala Thr Ser Arg Thr Pro Ala Ser
            260                 265                 270

Leu Ser Gly Pro Thr Thr Ala Ser Pro Leu Leu Ile Pro Phe
        275                 280                 285

<210> SEQ ID NO 75
<211> LENGTH: 286
<212> TYPE: PRT
<213> ORGANISM: Homo sapiens

<400> SEQUENCE: 75

Glu Arg Val Leu Gln Gly Leu Leu Lys Pro Leu Phe Lys Ser Thr Ser
1               5                   10                  15

Val Gly Pro Leu Tyr Ser Gly Cys Arg Leu Thr Leu Leu Arg Pro Glu
```

```
                20              25              30
Lys Arg Gly Ala Ala Thr Gly Val Asp Thr Ile Cys Thr His Arg Leu
            35              40              45

Asp Pro Leu Asn Pro Gly Leu Asp Arg Glu Gln Leu Tyr Trp Glu Leu
        50              55              60

Ser Lys Leu Thr Arg Gly Ile Ile Glu Leu Gly Pro Tyr Leu Leu Asp
65              70              75              80

Arg Gly Ser Leu Tyr Val Asn Gly Phe Ser Arg Gln Ser Ser Met Thr
                85              90              95

Thr Thr Arg Thr Pro Asp Thr Ser Thr Met His Leu Ala Thr Ser Arg
            100             105             110

Thr Pro Ala Ser Leu Ser Gly Pro Thr Thr Ala Ser Pro Leu Leu Ile
        115             120             125

Pro Phe Thr Leu Asn Phe Thr Ile Thr Asn Leu Gln Tyr Glu Glu Asn
    130             135             140

Met Gly His Pro Gly Ser Arg Lys Phe Asn Ile Met Glu Arg Val Leu
145             150             155             160

Gln Gly Leu Leu Asn Pro Ile Phe Lys Asn Ser Ser Val Gly Pro Leu
                165             170             175

Tyr Ser Gly Cys Arg Leu Thr Ser Leu Lys Pro Glu Lys Asp Gly Ala
            180             185             190

Ala Thr Gly Met Asp Ala Val Cys Leu Tyr His Pro Asn Pro Lys Arg
        195             200             205

Pro Gly Leu Asp Arg Glu Gln Leu Tyr Trp Glu Leu Ser Gln Leu Thr
    210             215             220

His Gly Ile Lys Glu Leu Gly Pro Tyr Thr Leu Asp Arg Asn Ser Leu
225             230             235             240

Tyr Val Asn Gly Phe Thr His Arg Ser Ser Val Ala Pro Thr Ser Thr
                245             250             255

Pro Gly Thr Ser Thr Val Asp Leu Gly Thr Ser Gly Thr Pro Ser Ser
            260             265             270

Leu Pro Ser Pro Thr Thr Ala Val Pro Leu Leu Ile Pro Phe
        275             280             285

<210> SEQ ID NO 76
<211> LENGTH: 286
<212> TYPE: PRT
<213> ORGANISM: Homo sapiens

<400> SEQUENCE: 76

Glu Arg Val Leu Gln Gly Leu Leu Lys Pro Leu Phe Arg Asn Ser Ser
1               5               10              15

Leu Glu Tyr Leu Tyr Ser Gly Cys Arg Leu Ala Ser Leu Arg Pro Glu
                20              25              30

Lys Asp Ser Ser Ala Met Ala Val Asp Ala Ile Cys Thr His Arg Pro
            35              40              45

Asp Pro Glu Asp Leu Gly Leu Asp Arg Glu Arg Leu Tyr Trp Glu Leu
        50              55              60

Ser Asn Leu Thr Asn Gly Ile Gln Glu Leu Gly Pro Tyr Thr Leu Asp
65              70              75              80

Arg Asn Ser Leu Tyr Val Asn Gly Phe Thr His Arg Ser Ser Gly Leu
                85              90              95

Thr Thr Ser Thr Pro Trp Thr Ser Val Asp Leu Gly Thr Ser Gly Gly
            100             105             110
```

```
Thr Pro Ser Pro Val Pro Ser Pro Thr Thr Ala Gly Pro Leu Leu Ile
        115                 120                 125

Pro Phe Thr Leu Asn Phe Thr Ile Thr Asn Leu Gln Tyr Glu Glu Asn
130                     135                 140

Met Gly His Pro Gly Ser Arg Lys Phe Asn Ile Met Glu Arg Val Leu
145                 150                 155                 160

Gln Gly Leu Leu Met Pro Leu Phe Lys Asn Thr Ser Val Ser Ser Leu
                165                 170                 175

Tyr Ser Gly Cys Arg Leu Thr Leu Leu Arg Pro Glu Lys Asp Gly Ala
            180                 185                 190

Ala Thr Arg Val Asp Ala Val Cys Thr Gln Arg Pro Asp Pro Lys Ser
        195                 200                 205

Pro Gly Leu Asp Arg Glu Arg Leu Tyr Trp Lys Leu Ser Gln Leu Thr
    210                 215                 220

His Gly Ile Thr Glu Leu Gly Pro Tyr Thr Leu Asp Arg His Ser Leu
225                 230                 235                 240

Tyr Val Asn Gly Leu Thr His Gln Ser Ser Met Thr Thr Arg Thr
                245                 250                 255

Pro Asp Thr Ser Thr Met His Leu Ala Thr Ser Arg Thr Pro Ala Ser
                260                 265                 270

Leu Ser Gly Pro Thr Thr Ala Ser Pro Leu Leu Ile Pro Phe
            275                 280                 285
```

<210> SEQ ID NO 77
<211> LENGTH: 288
<212> TYPE: PRT
<213> ORGANISM: Homo sapiens

<400> SEQUENCE: 77

```
Glu Arg Val Leu Gln Gly Leu Leu Ser Pro Ile Ser Lys Asn Ser Ser
1               5                   10                  15

Val Gly Pro Leu Tyr Ser Gly Cys Arg Leu Thr Ser Leu Arg Pro Glu
                20                  25                  30

Lys Asp Gly Ala Ala Thr Gly Met Asp Ala Val Cys Leu Tyr His Pro
            35                  40                  45

Asn Pro Lys Arg Pro Gly Leu Asp Arg Glu Gln Leu Tyr Trp Glu Leu
        50                  55                  60

Ser Gln Leu Thr His Asn Ile Thr Glu Leu Gly Pro Tyr Ser Leu Asp
65                  70                  75                  80

Arg Asp Ser Leu Tyr Val Asn Gly Phe Thr His Gln Asn Ser Val Pro
                85                  90                  95

Thr Thr Ser Thr Pro Gly Thr Ser Thr Val Tyr Trp Ala Thr Thr Gly
                100                 105                 110

Thr Pro Ser Ser Phe Pro Gly His Thr Glu Pro Gly Pro Leu Leu Ile
            115                 120                 125

Pro Phe Thr Val Asn Phe Thr Ile Thr Asn Leu Arg Tyr Glu Glu Asn
        130                 135                 140

Met His His Pro Gly Ser Arg Lys Phe Asn Thr Thr Glu Arg Val Leu
145                 150                 155                 160

Gln Gly Leu Leu Arg Pro Val Phe Lys Asn Thr Ser Val Gly Pro Leu
                165                 170                 175

Tyr Ser Gly Cys Arg Leu Thr Leu Leu Arg Pro Lys Lys Asp Gly Ala
            180                 185                 190

Ala Thr Lys Val Asp Ala Ile Cys Thr Tyr Arg Pro Asp Pro Lys Ser
        195                 200                 205
```

```
Pro Gly Leu Asp Arg Glu Gln Leu Tyr Trp Glu Leu Ser Lys Leu Thr
        210                 215                 220

Asn Asp Ile Glu Glu Leu Gly Pro Tyr Thr Leu Asp Arg Asn Ser Leu
225                 230                 235                 240

Tyr Val Asn Gly Phe Thr His Gln Ser Ser Val Ser Thr Thr Ser Thr
                245                 250                 255

Pro Gly Thr Ser Thr Val Asp Leu Arg Thr Ser Gly Thr Pro Ser Ser
        260                 265                 270

Leu Ser Ser Pro Thr Ile Met Ala Ala Gly Pro Leu Leu Ile Pro Phe
        275                 280                 285
```

<210> SEQ ID NO 78
<211> LENGTH: 597
<212> TYPE: PRT
<213> ORGANISM: Homo sapiens

<400> SEQUENCE: 78

```
Glu Arg Val Leu His Gly Leu Leu Thr Pro Leu Phe Lys Asn Thr Arg
1               5                   10                  15

Val Gly Pro Leu Tyr Ser Gly Cys Arg Leu Thr Leu Leu Arg Pro Glu
            20                  25                  30

Lys Gln Glu Ala Ala Thr Gly Val Asp Thr Ile Cys Thr His Arg Val
        35                  40                  45

Asp Pro Ile Gly Pro Gly Leu Asp Arg Glu Arg Leu Tyr Trp Glu Leu
    50                  55                  60

Ser Gln Leu Thr Asn Ser Ile Thr Glu Leu Gly Pro Tyr Thr Leu Asp
65                  70                  75                  80

Arg Asp Ser Leu Tyr Val Asn Gly Phe Asn Pro Trp Ser Ser Val Pro
                85                  90                  95

Thr Thr Ser Thr Pro Gly Thr Ser Thr Val His Leu Ala Thr Ser Gly
            100                 105                 110

Thr Pro Ser Ser Leu Pro Gly His Thr Ala Pro Val Pro Leu Leu Ile
        115                 120                 125

Pro Phe Thr Leu Asn Phe Thr Ile Thr Asn Leu His Tyr Glu Glu Asn
    130                 135                 140

Met Gln His Pro Gly Ser Arg Lys Phe Asn Thr Thr Glu Arg Val Leu
145                 150                 155                 160

Gln Gly Leu Leu Lys Pro Leu Phe Lys Asn Thr Ser Val Gly Pro Leu
                165                 170                 175

Tyr Ser Gly Cys Arg Leu Thr Leu Phe Lys Pro Glu Lys His Glu Ala
            180                 185                 190

Ala Thr Gly Val Asp Ala Ile Cys Thr Leu Arg Leu Asp Pro Thr Gly
        195                 200                 205

Pro Gly Leu Asp Arg Gln Leu Tyr Trp Glu Leu Ser Gln Leu Thr Asn
    210                 215                 220

Ser Val Thr Glu Leu Gly Pro Tyr Thr Leu Asp Arg Asp Ser Leu Tyr
225                 230                 235                 240

Val Asn Gly Phe Thr His Arg Ser Ser Val Pro Thr Thr Ser Ile Pro
                245                 250                 255

Gly Thr Ser Ala Val His Leu Glu Thr Ser Gly Thr Pro Ala Ser Leu
            260                 265                 270

Pro Gly His Thr Ala Pro Gly Pro Leu Leu Ile Pro Phe Thr Leu Asn
        275                 280                 285

Phe Thr Ile Thr Asn Leu Gln Tyr Glu Glu Asp Met Arg Arg Thr Gly
```

```
                    290                 295                 300
Ser Arg Lys Phe Asn Thr Met Glu Arg Val Leu Gln Gly Leu Leu Lys
305                 310                 315                 320

Pro Leu Phe Lys Ser Thr Ser Val Gly Pro Leu Tyr Ser Gly Cys Arg
                325                 330                 335

Leu Thr Leu Leu Arg Pro Glu Lys Arg Gly Ala Ala Thr Gly Val Asp
                340                 345                 350

Thr Ile Cys Thr His Arg Leu Asp Pro Leu Asn Pro Gly Leu Asp Arg
                355                 360                 365

Glu Gln Leu Tyr Trp Glu Leu Ser Lys Leu Thr Arg Gly Ile Ile Glu
370                 375                 380

Leu Gly Pro Tyr Leu Leu Asp Arg Gly Ser Leu Tyr Val Asn Gly Phe
385                 390                 395                 400

Thr His Arg Asn Phe Val Pro Ile Thr Ser Thr Pro Gly Thr Ser Thr
                405                 410                 415

Val His Leu Gly Thr Ser Glu Thr Pro Ser Ser Leu Pro Arg Pro Ile
                420                 425                 430

Val Pro Gly Pro Leu Leu Ile Pro Phe Thr Ile Asn Phe Thr Ile Thr
                435                 440                 445

Asn Leu Arg Tyr Glu Glu Asn Met His His Pro Gly Ser Arg Lys Phe
450                 455                 460

Asn Ile Met Glu Arg Val Leu Gln Gly Leu Leu Gly Pro Leu Phe Lys
465                 470                 475                 480

Asn Ser Ser Val Gly Pro Leu Tyr Ser Gly Cys Arg Leu Ile Ser Leu
                485                 490                 495

Arg Ser Glu Lys Asp Gly Ala Ala Thr Gly Val Asp Ala Ile Cys Thr
                500                 505                 510

His His Leu Asn Pro Gln Ser Pro Gly Leu Asp Arg Glu Gln Leu Tyr
                515                 520                 525

Trp Gln Leu Ser Gln Met Thr Asn Gly Ile Lys Glu Leu Gly Pro Tyr
                530                 535                 540

Thr Leu Asp Arg Asn Ser Leu Tyr Val Asn Gly Phe Thr His Arg Ser
545                 550                 555                 560

Ser Gly Leu Thr Thr Ser Thr Pro Trp Thr Ser Thr Val Asp Leu Gly
                565                 570                 575

Thr Ser Gly Thr Pro Ser Pro Val Pro Ser Pro Thr Thr Ala Gly Pro
                580                 585                 590

Leu Leu Ile Pro Phe
            595

<210> SEQ ID NO 79
<211> LENGTH: 420
<212> TYPE: PRT
<213> ORGANISM: Homo sapiens

<400> SEQUENCE: 79

Gly Pro Leu Tyr Ser Gly Cys Arg Leu Thr Ser Leu Arg Pro Glu Lys
1               5                   10                  15

Asp Gly Ala Ala Thr Gly Met Asp Ala Val Cys Leu Tyr His Pro Asn
                20                  25                  30

Pro Lys Arg Pro Gly Leu Asp Arg Glu Gln Leu Tyr Trp Glu Leu Ser
                35                  40                  45

Gln Leu Thr His Asn Ile Thr Glu Leu Gly Pro Tyr Ser Leu Asp Arg
            50                  55                  60
```

-continued

```
Asp Ser Leu Tyr Val Asn Gly Phe Thr His Gln Asn Ser Val Pro Thr
 65                  70                  75                  80

Thr Ser Thr Pro Gly Thr Ser Thr Val Tyr Trp Ala Thr Gly Thr
                 85                  90                  95

Pro Ser Ser Phe Pro Gly His Thr Glu Pro Gly Pro Leu Leu Ile Pro
            100                 105                 110

Phe Thr Leu Asn Phe Thr Ile Thr Asn Leu Gln Tyr Glu Glu Asn Met
        115                 120                 125

Gly His Pro Gly Ser Arg Lys Phe Asn Ile Thr Glu Ser Val Leu Gln
    130                 135                 140

Gly Leu Leu Thr Pro Leu Phe Lys Asn Ser Ser Val Gly Pro Leu Tyr
145                 150                 155                 160

Ser Gly Cys Arg Leu Ile Ser Leu Arg Ser Glu Lys Asp Gly Ala Ala
                165                 170                 175

Thr Gly Val Asp Ala Ile Cys Thr His His Leu Asn Pro Gln Ser Pro
            180                 185                 190

Gly Leu Asp Arg Glu Gln Leu Tyr Trp Gln Leu Ser Gln Met Thr Asn
        195                 200                 205

Gly Ile Lys Glu Leu Gly Pro Tyr Thr Leu Asp Arg Asp Ser Leu Tyr
    210                 215                 220

Val Asn Gly Phe Thr His Arg Ser Leu Gly Leu Thr Thr Ser Thr Pro
225                 230                 235                 240

Trp Thr Ser Thr Val Asp Leu Gly Thr Ser Gly Thr Pro Ser Pro Val
                245                 250                 255

Pro Ser Pro Thr Thr Ala Gly Pro Leu Leu Ile Pro Phe Thr Leu Asn
            260                 265                 270

Phe Thr Ile Thr Asn Leu Gln Tyr Glu Glu Asn Met Gly His Pro Gly
        275                 280                 285

Ser Arg Lys Phe Asn Ile Met Glu Arg Val Leu Gln Gly Leu Leu Arg
    290                 295                 300

Pro Val Phe Lys Asn Thr Ser Val Gly Pro Leu Tyr Ser Gly Cys Arg
305                 310                 315                 320

Leu Thr Leu Leu Arg Pro Lys Lys Asp Gly Ala Ala Thr Lys Val Asp
                325                 330                 335

Ala Ile Cys Thr Tyr Arg Pro Asp Pro Lys Ser Pro Gly Leu Asp Arg
            340                 345                 350

Glu Gln Leu Tyr Trp Glu Leu Ser Gln Leu Thr His Ser Ile Thr Glu
        355                 360                 365

Leu Gly Pro Tyr Thr Leu Asp Arg Asp Ser Leu Tyr Val Asn Gly Phe
    370                 375                 380

Thr Gln Arg Ser Ser Val Pro Thr Thr Ser Ile Pro Gly Thr Pro Thr
385                 390                 395                 400

Val Asp Leu Gly Thr Ser Gly Thr Pro Val Ser Lys Pro Gly Pro Ser
                405                 410                 415

Ala Ala Ser Pro
            420

<210> SEQ ID NO 80
<211> LENGTH: 479
<212> TYPE: PRT
<213> ORGANISM: Homo sapiens

<400> SEQUENCE: 80

Gln Leu Tyr Trp Glu Leu Ser Lys Leu Thr Asn Asp Ile Glu Glu Leu
 1               5                  10                  15
```

-continued

```
Gly Pro Tyr Thr Leu Asp Arg Asn Ser Leu Tyr Val Asn Gly Phe Thr
             20                  25                  30
His Gln Ser Ser Val Ser Thr Thr Ser Thr Pro Gly Thr Ser Thr Val
             35                  40                  45
Asp Leu Arg Thr Ser Gly Thr Pro Ser Ser Leu Ser Ser Pro Thr Ile
             50                  55                  60
Met Ala Ala Gly Pro Leu Leu Ile Pro Phe Thr Leu Asn Phe Thr Ile
 65                  70                  75                  80
Thr Asn Leu Gln Tyr Glu Glu Asn Met Gly His Pro Gly Ser Arg Lys
                     85                  90                  95
Phe Asn Ile Met Glu Arg Val Leu Gln Gly Leu Leu Gly Pro Met Phe
                    100                 105                 110
Lys Asn Thr Ser Val Gly Leu Leu Tyr Ser Gly Cys Arg Leu Thr Leu
                    115                 120                 125
Leu Arg Pro Glu Lys Asn Gly Ala Ala Thr Gly Met Asp Ala Ile Cys
            130                 135                 140
Ser His Arg Leu Asp Pro Lys Ser Pro Gly Leu Asn Arg Glu Gln Leu
145                 150                 155                 160
Tyr Trp Glu Leu Ser Gln Leu Thr His Gly Ile Lys Glu Leu Gly Pro
                    165                 170                 175
Tyr Thr Leu Asp Arg Asn Ser Leu Tyr Val Asn Gly Phe Thr His Arg
                180                 185                 190
Ser Ser Val Ala Pro Thr Ser Thr Pro Gly Thr Ser Thr Val Asp Leu
            195                 200                 205
Gly Thr Ser Gly Thr Pro Ser Ser Leu Pro Ser Pro Thr Thr Ala Val
            210                 215                 220
Pro Leu Leu Ile Pro Phe Thr Leu Asn Phe Thr Ile Thr Asn Leu Lys
225                 230                 235                 240
Tyr Glu Glu Asp Met His Cys Pro Gly Ser Arg Lys Phe Asn Thr Thr
                    245                 250                 255
Glu Arg Val Leu Gln Ser Leu Phe Gly Pro Met Phe Lys Asn Thr Ser
            260                 265                 270
Val Gly Pro Leu Tyr Ser Gly Cys Arg Leu Thr Leu Leu Arg Ser Glu
            275                 280                 285
Lys Asp Gly Ala Ala Thr Gly Val Asp Ala Ile Cys Thr His Arg Leu
            290                 295                 300
Asp Pro Lys Ser Leu Gly Val Asp Arg Glu Gln Leu Tyr Trp Glu Leu
305                 310                 315                 320
Ser Gln Leu Thr Asn Gly Ile Lys Glu Leu Gly Pro Tyr Thr Leu Asp
                    325                 330                 335
Arg Asn Ser Leu Tyr Val Asn Gly Phe Thr His Gln Thr Ser Ala Pro
                340                 345                 350
Asn Thr Ser Thr Pro Gly Thr Ser Thr Val Asp Leu Gly Thr Ser Gly
                355                 360                 365
Thr Pro Ser Ser Leu Pro Ser Pro Thr Ser Ala Gly Pro Leu Leu Val
            370                 375                 380
Pro Phe Thr Leu Asn Phe Thr Ile Thr Asn Leu Gln Tyr Glu Glu Asp
385                 390                 395                 400
Met Arg Arg Thr Gly Ser Arg Lys Phe Asn Thr Met Glu Ser Val Leu
                    405                 410                 415
Gln Gly Leu Leu Lys Pro Leu Phe Lys Asn Thr Ser Val Gly Pro Leu
            420                 425                 430
```

|  |  |  |  |  |  |  |  |  |  |
|--|--|--|--|--|--|--|--|--|--|
| Tyr | Ser | Gly | Cys | Arg | Leu | Thr | Leu | Leu | Arg | Pro | Glu | Lys | Asp | Gly | Ala |
|  |  | 435 |  |  |  | 440 |  |  |  |  | 445 |  |  |  |  |

Tyr Ser Gly Cys Arg Leu Thr Leu Leu Arg Pro Glu Lys Asp Gly Ala
    435             440                 445

Ala Thr Gly Val Asp Ala Ile Cys Thr His Arg Leu Asp Pro Lys Ser
    450             455                 460

Pro Gly Leu Asn Arg Glu Gln Leu Tyr Trp Glu Leu Ser Lys Leu
465             470                 475

<210> SEQ ID NO 81
<211> LENGTH: 5465
<212> TYPE: DNA
<213> ORGANISM: Homo sapiens

<400> SEQUENCE: 81

```
cagagagcgt tgagctggga acagtgacaa gtgcttatca agttccttca ctctcaacac      60
ggttgacaag aactgatggc attatggaac acatcacaaa atacccaat gaagcagcac      120
acagaggtac cataagacca gtcaaaggcc ctcagacatc cacttcgcct gccagtccta     180
aaggactaca cacaggaggg acaaaaagaa tggagaccac caccacagct ttgaagacca     240
ccaccacagc tttgaagacc acttccagag ccaccttgac caccagtgtc tatactccca     300
cttgggaac actgactccc tcaatgcat caaggcaaat ggccagcaca atcctcacag       360
aaatgatgat cacaacccca tatgttttcc ctgatgttcc agaaacgaca tcctcattgg     420
ctaccagcct gggagcagaa accagcacag ctcttcccag gacaacccca tctgttctca    480
atagagaatc agagaccaca gcctcactgg tctctcgttc tggggcagag agaagtccgg    540
ttattcaaac tctagatgtt tcttctagtg agccagatac aacagcttca tgggttatcc    600
atcctgcaga gaccatccca actgtttcca agacaacccc caatttttt cacagtgaat     660
tagacactgt atcttccaca gccaccagtc atggggcaga cgtcagctca gccattccaa    720
caaatatctc acctagtgaa ctagatgcac tgaccccact ggtcactatt tcggggacag    780
atactagtac aacattccca acactgacta agtccccaca tgaaacagag acaagaacca    840
catggctcac tcatcctgca gagaccagct caactattcc cagaacaatc cccaattttt    900
ctcatcatga atcagatgcc acaccttcaa tagccaccag tcctggggca gaaaccagtt    960
cagctattcc aattatgact gtctcacctg gtgcagaaga tctggtgacc tcacaggtca   1020
ctagttctgg gacagacaga aatatgacta ttccaacttt gactctttct cctggtgaac   1080
caaagacgat agcctcatta gtcacccatc ctgaagcaca gacaagttcg gccattccaa   1140
cttcaactat ctcgcctgct gtatcacggt tggtgacctc aatggtcacc agtttggcgg   1200
caaagacaag tacaactaat cgagctctga caaactcccc tggtgaacca gctacaacag   1260
tttcattggt cacgcatcct gcacagacca gcccaacagt tccctggaca acttccattt   1320
ttttccatag taaatcagac accacacctt caatgaccac cagtcatggg gcagaatcca   1380
gttcagctgt tccaactcca actgtttcaa ctgaggtacc aggagtagtg accccttgg    1440
tcaccagttc tagggcagtg atcagtacaa ctattccaat tctgactctt tctcctggtg   1500
aaccagagac cacaccttca atggccacca gtcatgggga agaagccagt tctgctattc   1560
caactccaac tgtttcacct ggggtaccag gagtggtgac ctctctggtc actagttcta   1620
gggcagtgac tagtacaact attccaattc tgacttttc tcttggtgaa ccagagacca   1680
caccttcaat ggccaccagt catgggacag aagctggctc agctgttcca actgttttac    1740
ctgaggtacc aggaatggtg acctctctgg ttgctagttc tagggcagta accagtacaa   1800
ctcttccaac tctgactctt tctcctggtg aaccagagac cacaccttca atggccacca   1860
```

```
gtcatggggc agaagccagc tcaactgttc caactgtttc acctgaggta ccaggagtgg    1920
tgacctctct ggtcactagt tctagtggag taaacagtac aagtattcca actctgattc    1980
tttctcctgg tgaactagaa accacacctt caatggccac cagtcatggg gcagaagcca    2040
gctcagctgt tccaactcca actgtttcac ctggggtatc aggagtggtg acccctctgg    2100
tcactagttc cagggcagtg accagtacaa ctattccaat tctaactctt tcttctagtg    2160
agccagagac cacaccttca atggccacca gtcatggggt agaagccagc tcagctgttc    2220
taactgtttc acctgaggta ccaggaatgg tgacctctct ggtcactagt tctagagcag    2280
taaccagtac aactattcca actctgacta tttcttctga tgaaccagag accacaactt    2340
cattggtcac ccattctgag gcaaagatga tttcagccat tccaacttta gctgtctccc    2400
ctactgtaca agggctggtg acttcactgg tcactagttc tgggtcagag accagtgcgt    2460
tttcaaatct aactgttgcc tcaagtcaac cagagaccat agactcatgg gtcgctcatc    2520
ctgggacaga agcaagttct gttgttccaa ctttgactgt ctccactggt gagccgttta    2580
caaatatctc attggtcacc catcctgcag agagtagctc aactcttccc aggacaacct    2640
caaggttttc ccacagtgaa ttagacacta tgccttctac agtcaccagt cctgaggcag    2700
aatccagctc agccatttca actactattt cacctggtat accaggtgtg ctgacatcac    2760
tggtcactag ctctgggaga gacatcagtg caacttttcc aacagtgcct gagtccccac    2820
atgaatcaga ggcaacagcc tcatgggtta ctcatcctgc agtcaccagc acaacagttc    2880
ccaggacaac ccctaattat tctcatagtg aaccagacac cacaccatca atagccacca    2940
gtcctggggc agaagccact tcagattttc caacaataac tgtctcacct gatgtaccag    3000
atatggtaac ctcacaggtc actagttctg ggacagacac cagtataact attccaactc    3060
tgactctttc ttctggtgag ccagagacca caacctcatt tatcacctat tctgagacac    3120
acacaagttc agccattcca actctccctg tctcccctgg tgcatcaaag atgctgacct    3180
cactggtcat cagttctggg acagacagca ctacaacttt cccaacactg acggagaccc    3240
catatgaacc agagacaaca gccatacagc tcattcatcc tgcagagacc aacacaatgg    3300
ttcccaagac aactcccaag ttttcccata gtaagtcaga caccacactc ccagtagcca    3360
tcaccagtcc tgggccagaa gccagttcag ctgtttcaac gacaactatc tcacctgata    3420
tgtcagatct ggtgacctca ctggtcccta gttctgggac agacaccagt acaaccttcc    3480
caacattgag tgagccccca tatgaaccag agactacagt cacgtggctc actcatcctg    3540
cagaaaccag cacaacggtt tctgggacaa ttcccaactt ttcccatagg ggatcagaca    3600
ctgcaccctc aatggtcacc agtcctggag tagacacgag gtcaggtgtt ccaactacaa    3660
ccatcccacc cagtatacca ggggtagtga cctcacaggt cactagttct gcaacagaca    3720
ctagtacagc tattccaact ttgactcctt ctcctggtga accagagacc acagcctcat    3780
cagctaccca tcctgggaca cagactggct tcactgttcc aattcggact gttccctcta    3840
gtgagccaga tacaatggct tcctgggtca ctcatcctcc acagaccagc acacctgttt    3900
ccagaacaac ctccagtttt tcccatagta gtccagatgc cacacctgta atggccacca    3960
gtcctaggac agaagccagt tcagctgtac tgacaacaat ctcacctggt gcaccagaga    4020
tggtgacttc acagatcact agttctgggg cagcaaccag tacaactgtt ccaactttga    4080
ctcattctcc tggtatgcca gagaccacag ccttattgag cacccatccc agaacaggga    4140
caagtaaaac atttcctgct tcaactgtgt ttcctcaagt atcagagacc acagcctcac    4200
tcaccattag acctggtgca gagactagca cagctctccc aactcagaca acatcctctc    4260
```

-continued

```
tcttcaccct acttgtaact ggaaccagca gagttgatct aagtccaact gcttcacctg    4320
gtgtttctgc aaaaacagcc ccactttcca cccatccagg gacagagacc agcacaatga    4380
ttccaacttc aactctttcc cttggtttac tagagactac aggcttactg gccaccagct    4440
cttcagcaga gaccagcacg agtactctaa ctctgactgt ttccctgct gtctctgggc     4500 tttccagtgc ctctataaca actgataagc cccaaactgt gacctcctgg aacacagaaa    4560
cctcaccatc tgtaacttca gttggacccc cagaattttc caggactgtc acaggcacca    4620
ctatgacctt gataccatca gagatgccaa caccacctaa aaccagtcat ggagaaggag    4680
tgagtccaac cactatcttg agaactacaa tggttgaagc cactaattta gctaccacag    4740
gttccagtcc cactgtggcc aagacaacaa ccaccttcaa tacactggct ggaagcctct    4800
ttactcctct gaccacacct gggatgtcca ccttggcctc tgagagtgtg acctcaagaa    4860
caagttataa ccatcggtcc tggatctcca ccaccagcag ttataaccgt cggtactgga    4920 ccctgccac cagcactcca gtgacttcta cattctcccc agggatttcc acatcctcca     4980
tccccagctc cacagcagcc acagtcccat tcatggtgcc attcaccctc aacttcacca    5040
tcaccaacct gcagtacgag gaggacatgc ggcaccctgg ttccaggaag ttcaacgcca    5100
cagagagaga actgcagggt ctgctcaaac ccttgttcag gaatagcagt ctggaatacc    5160
tctattcagg ctgcagacta gcctcactca ggccagagaa ggatagctca gccatggcag    5220
tggatgccat ctgcacacat cgccctgacc ctgaagacct cggactggac agagagcgac    5280
tgtactggga gctgagcaat ctgacaaatg gcatccagga gctgggcccc tacaccctgg    5340
accggaacag tctctatgtc aatggtttca cccatcgaag ctctatgccc accaccagca    5400
ctcctgggac ctccacagtg gatgtgggaa cctcagggac tccatcctcc agccccagcc    5460
ccacg                                                                5465
```

<210> SEQ ID NO 82
<211> LENGTH: 1821
<212> TYPE: PRT
<213> ORGANISM: Homo sapiens

<400> SEQUENCE: 82

```
Glu Ser Val Leu Glu Gly Thr Val Thr Ser Ala Tyr Gln Val Pro Ser
1               5                   10                  15

Leu Ser Thr Arg Leu Thr Arg Thr Asp Gly Ile Met Glu His Ile Thr
            20                  25                  30

Lys Ile Pro Asn Glu Ala Ala His Arg Gly Thr Ile Arg Pro Val Lys
        35                  40                  45

Gly Pro Gln Thr Ser Thr Ser Pro Ala Ser Pro Lys Gly Leu His Thr
    50                  55                  60

Gly Gly Thr Lys Arg Met Glu Thr Thr Thr Ala Leu Lys Thr Thr
65                  70                  75                  80

Thr Thr Ala Leu Lys Thr Thr Ser Arg Ala Thr Leu Thr Thr Ser Val
                85                  90                  95

Tyr Thr Pro Thr Leu Gly Thr Leu Thr Pro Leu Asn Ala Ser Arg Gln
            100                 105                 110

Met Ala Ser Thr Ile Leu Thr Glu Met Met Ile Thr Thr Pro Tyr Val
        115                 120                 125

Phe Pro Asp Val Pro Glu Thr Thr Ser Ser Leu Ala Thr Ser Leu Gly
    130                 135                 140

Ala Glu Thr Ser Thr Ala Leu Pro Arg Thr Thr Pro Ser Val Leu Asn
```

-continued

```
            145                 150                 155                 160
        Arg Glu Ser Glu Thr Thr Ala Ser Leu Val Ser Arg Ser Gly Ala Glu
                        165                 170                 175
        Arg Ser Pro Val Ile Gln Thr Leu Asp Val Ser Ser Ser Glu Pro Asp
                        180                 185                 190
        Thr Thr Ala Ser Trp Val Ile His Pro Ala Glu Thr Ile Pro Thr Val
                        195                 200                 205
        Ser Lys Thr Thr Pro Asn Phe Phe His Ser Glu Leu Asp Thr Val Ser
                210                 215                 220
        Ser Thr Ala Thr Ser His Gly Ala Asp Val Ser Ser Ala Ile Pro Thr
        225                 230                 235                 240
        Asn Ile Ser Pro Ser Glu Leu Asp Ala Leu Thr Pro Leu Val Thr Ile
                        245                 250                 255
        Ser Gly Thr Asp Thr Ser Thr Thr Phe Pro Thr Leu Thr Lys Ser Pro
                        260                 265                 270
        His Glu Thr Glu Thr Arg Thr Thr Trp Leu Thr His Pro Ala Glu Thr
                        275                 280                 285
        Ser Ser Thr Ile Pro Arg Thr Ile Pro Asn Phe Ser His His Glu Ser
                290                 295                 300
        Asp Ala Thr Pro Ser Ile Ala Thr Ser Pro Gly Ala Glu Thr Ser Ser
        305                 310                 315                 320
        Ala Ile Pro Ile Met Thr Val Ser Pro Gly Ala Glu Asp Leu Val Thr
                        325                 330                 335
        Ser Gln Val Thr Ser Ser Gly Thr Asp Arg Asn Met Thr Ile Pro Thr
                        340                 345                 350
        Leu Thr Leu Ser Pro Gly Glu Pro Lys Thr Ile Ala Ser Leu Val Thr
                        355                 360                 365
        His Pro Glu Ala Gln Thr Ser Ser Ala Ile Pro Thr Ser Thr Ile Ser
                370                 375                 380
        Pro Ala Val Ser Arg Leu Val Thr Ser Met Val Thr Ser Leu Ala Ala
        385                 390                 395                 400
        Lys Thr Ser Thr Thr Asn Arg Ala Leu Thr Asn Ser Pro Gly Glu Pro
                        405                 410                 415
        Ala Thr Thr Val Ser Leu Val Thr His Pro Ala Gln Thr Ser Pro Thr
                        420                 425                 430
        Val Pro Trp Thr Thr Ser Ile Phe Phe His Ser Lys Ser Asp Thr Thr
                        435                 440                 445
        Pro Ser Met Thr Thr Ser His Gly Ala Glu Ser Ser Ala Val Pro
                450                 455                 460
        Thr Pro Thr Val Ser Thr Glu Val Pro Gly Val Val Thr Pro Leu Val
        465                 470                 475                 480
        Thr Ser Ser Arg Ala Val Ile Ser Thr Thr Ile Pro Ile Leu Thr Leu
                        485                 490                 495
        Ser Pro Gly Glu Pro Glu Thr Thr Pro Ser Met Ala Thr Ser His Gly
                        500                 505                 510
        Glu Glu Ala Ser Ser Ala Ile Pro Thr Pro Thr Val Ser Pro Gly Val
                        515                 520                 525
        Pro Gly Val Val Thr Ser Leu Val Thr Ser Ser Arg Ala Val Thr Ser
                        530                 535                 540
        Thr Thr Ile Pro Ile Leu Thr Phe Ser Leu Gly Glu Pro Glu Thr Thr
        545                 550                 555                 560
        Pro Ser Met Ala Thr Ser His Gly Thr Glu Ala Gly Ser Ala Val Pro
                        565                 570                 575
```

-continued

```
Thr Val Leu Pro Glu Val Pro Gly Met Val Thr Ser Leu Val Ala Ser
            580                 585                 590

Ser Arg Ala Val Thr Ser Thr Thr Leu Pro Thr Leu Thr Leu Ser Pro
        595                 600                 605

Gly Glu Pro Glu Thr Thr Pro Ser Met Ala Thr Ser His Gly Ala Glu
    610                 615                 620

Ala Ser Ser Thr Val Pro Thr Val Ser Pro Glu Val Pro Gly Val Val
625                 630                 635                 640

Thr Ser Leu Val Thr Ser Ser Gly Val Asn Ser Thr Ser Ile Pro
            645                 650                 655

Thr Leu Ile Leu Ser Pro Gly Glu Leu Glu Thr Thr Pro Ser Met Ala
            660                 665                 670

Thr Ser His Gly Ala Glu Ala Ser Ala Val Pro Thr Pro Thr Val
            675                 680                 685

Ser Pro Gly Val Ser Gly Val Val Thr Pro Leu Val Thr Ser Ser Arg
    690                 695                 700

Ala Val Thr Ser Thr Thr Ile Pro Ile Leu Thr Leu Ser Ser Ser Glu
705                 710                 715                 720

Pro Glu Thr Thr Pro Ser Met Ala Thr Ser His Gly Val Glu Ala Ser
            725                 730                 735

Ser Ala Val Leu Thr Val Ser Pro Glu Val Pro Gly Met Val Thr Ser
            740                 745                 750

Leu Val Thr Ser Ser Arg Ala Val Thr Ser Thr Ile Pro Thr Leu
            755                 760                 765

Thr Ile Ser Ser Asp Glu Pro Glu Thr Thr Thr Ser Leu Val Thr His
    770                 775                 780

Ser Glu Ala Lys Met Ile Ser Ala Ile Pro Thr Leu Ala Val Ser Pro
785                 790                 795                 800

Thr Val Gln Gly Leu Val Thr Ser Leu Val Thr Ser Ser Gly Ser Glu
            805                 810                 815

Thr Ser Ala Phe Ser Asn Leu Thr Val Ala Ser Ser Gln Pro Glu Thr
            820                 825                 830

Ile Asp Ser Trp Val Ala His Pro Gly Thr Glu Ala Ser Ser Val Val
    835                 840                 845

Pro Thr Leu Thr Val Ser Thr Gly Glu Pro Phe Thr Asn Ile Ser Leu
    850                 855                 860

Val Thr His Pro Ala Glu Ser Ser Ser Thr Leu Pro Arg Thr Thr Ser
865                 870                 875                 880

Arg Phe Ser His Ser Glu Leu Asp Thr Met Pro Ser Thr Val Thr Ser
            885                 890                 895

Pro Glu Ala Glu Ser Ser Ser Ala Ile Ser Thr Thr Ile Ser Pro Gly
            900                 905                 910

Ile Pro Gly Val Leu Thr Ser Leu Val Thr Ser Ser Gly Arg Asp Ile
    915                 920                 925

Ser Ala Thr Phe Pro Thr Val Pro Glu Ser Pro His Glu Ser Glu Ala
    930                 935                 940

Thr Ala Ser Trp Val Thr His Pro Ala Val Thr Ser Thr Val Pro
945                 950                 955                 960

Arg Thr Thr Pro Asn Tyr Ser His Ser Glu Pro Asp Thr Thr Pro Ser
            965                 970                 975

Ile Ala Thr Ser Pro Gly Ala Glu Ala Thr Ser Asp Phe Pro Thr Ile
            980                 985                 990
```

-continued

Thr Val Ser Pro Asp Val Pro Asp Met Val Thr Ser Gln Val Thr Ser
         995                 1000                1005

Ser Gly Thr Asp Thr Ser Ile Thr Ile Pro Thr Leu Thr Leu Ser
    1010             1015              1020

Ser Gly Glu Pro Glu Thr Thr Thr Ser Phe Ile Thr Tyr Ser Glu
    1025             1030              1035

Thr His Thr Ser Ser Ala Ile Pro Thr Leu Pro Val Ser Pro Gly
    1040             1045              1050

Ala Ser Lys Met Leu Thr Ser Leu Val Ile Ser Ser Gly Thr Asp
    1055             1060              1065

Ser Thr Thr Thr Phe Pro Thr Leu Thr Glu Thr Pro Tyr Glu Pro
    1070             1075              1080

Glu Thr Thr Ala Ile Gln Leu Ile His Pro Ala Glu Thr Asn Thr
    1085             1090              1095

Met Val Pro Arg Thr Thr Pro Lys Phe Ser His Ser Lys Ser Asp
    1100             1105              1110

Thr Thr Leu Pro Val Ala Ile Thr Ser Pro Gly Pro Glu Ala Ser
    1115             1120              1125

Ser Ala Val Ser Thr Thr Thr Ile Ser Pro Asp Met Ser Asp Leu
    1130             1135              1140

Val Thr Ser Leu Val Pro Ser Ser Gly Thr Asp Thr Ser Thr Thr
    1145             1150              1155

Phe Pro Thr Leu Ser Glu Thr Pro Tyr Glu Pro Glu Thr Thr Ala
    1160             1165              1170

Thr Trp Leu Thr His Pro Ala Glu Thr Ser Thr Thr Val Ser Gly
    1175             1180              1185

Thr Ile Pro Asn Phe Ser His Arg Gly Ser Asp Thr Ala Pro Ser
    1190             1195              1200

Met Val Thr Ser Pro Gly Val Asp Thr Arg Ser Gly Val Pro Thr
    1205             1210              1215

Thr Thr Ile Pro Pro Ser Ile Pro Gly Val Val Thr Ser Gln Val
    1220             1225              1230

Thr Ser Ser Ala Thr Asp Thr Ser Thr Ala Ile Pro Thr Leu Thr
    1235             1240              1245

Pro Ser Pro Gly Glu Pro Glu Thr Thr Ala Ser Ser Ala Thr His
    1250             1255              1260

Pro Gly Thr Gln Thr Gly Phe Thr Val Pro Ile Arg Thr Val Pro
    1265             1270              1275

Ser Ser Glu Pro Asp Thr Met Ala Ser Trp Val Thr His Pro Pro
    1280             1285              1290

Gln Thr Ser Thr Pro Val Ser Arg Thr Thr Ser Ser Phe Ser His
    1295             1300              1305

Ser Ser Pro Asp Ala Thr Pro Val Met Ala Thr Ser Pro Arg Thr
    1310             1315              1320

Glu Ala Ser Ser Ala Val Leu Thr Thr Ile Ser Pro Gly Ala Pro
    1325             1330              1335

Glu Met Val Thr Ser Gln Ile Thr Ser Ser Gly Ala Ala Thr Ser
    1340             1345              1350

Thr Thr Val Pro Thr Leu Thr His Ser Pro Gly Met Pro Glu Thr
    1355             1360              1365

Thr Ala Leu Leu Ser Thr His Pro Arg Thr Glu Thr Ser Lys Thr
    1370             1375              1380

Phe Pro Ala Ser Thr Val Phe Pro Gln Val Ser Glu Thr Thr Ala

-continued

```
            1385                1390                1395
Ser Leu Thr Ile Arg Pro Gly Ala Glu Thr Ser Thr Ala Leu Pro
    1400                1405                1410
Thr Gln Thr Thr Ser Ser Leu Phe Thr Leu Leu Val Thr Gly Thr
    1415                1420                1425
Ser Arg Val Asp Leu Ser Pro Thr Ala Ser Pro Gly Val Ser Ala
    1430                1435                1440
Lys Thr Ala Pro Leu Ser Thr His Pro Gly Thr Glu Thr Ser Thr
    1445                1450                1455
Met Ile Pro Thr Ser Thr Leu Ser Leu Gly Leu Leu Glu Thr Thr
    1460                1465                1470
Gly Leu Leu Ala Thr Ser Ser Ser Ala Glu Thr Ser Thr Ser Thr
    1475                1480                1485
Leu Thr Leu Thr Val Ser Pro Ala Val Ser Gly Leu Ser Ser Ala
    1490                1495                1500
Ser Ile Thr Thr Asp Lys Pro Gln Thr Val Thr Ser Trp Asn Thr
    1505                1510                1515
Glu Thr Ser Pro Ser Val Thr Ser Val Gly Pro Pro Glu Phe Ser
    1520                1525                1530
Arg Thr Val Thr Gly Thr Thr Met Thr Leu Ile Pro Ser Glu Met
    1535                1540                1545
Pro Thr Pro Pro Lys Thr Ser His Gly Glu Gly Val Ser Pro Thr
    1550                1555                1560
Thr Ile Leu Arg Thr Thr Met Val Glu Ala Thr Asn Leu Ala Thr
    1565                1570                1575
Thr Gly Ser Ser Pro Thr Val Ala Lys Thr Thr Thr Thr Phe Asn
    1580                1585                1590
Thr Leu Ala Gly Ser Leu Phe Thr Pro Leu Thr Thr Pro Gly Met
    1595                1600                1605
Ser Thr Leu Ala Ser Glu Ser Val Thr Ser Arg Thr Ser Tyr Asn
    1610                1615                1620
His Arg Ser Trp Ile Ser Thr Thr Ser Ser Tyr Asn Arg Arg Tyr
    1625                1630                1635
Trp Thr Pro Ala Thr Ser Thr Pro Val Thr Ser Thr Phe Ser Pro
    1640                1645                1650
Gly Ile Ser Thr Ser Ser Ile Pro Ser Ser Thr Ala Ala Thr Val
    1655                1660                1665
Pro Phe Met Val Pro Phe Thr Leu Asn Phe Thr Ile Thr Asn Leu
    1670                1675                1680
Gln Tyr Glu Glu Asp Met Arg His Pro Gly Ser Arg Lys Phe Asn
    1685                1690                1695
Ala Thr Glu Arg Glu Leu Gln Gly Leu Leu Lys Pro Leu Phe Arg
    1700                1705                1710
Asn Ser Ser Leu Glu Tyr Leu Tyr Ser Gly Cys Arg Leu Ala Ser
    1715                1720                1725
Leu Arg Pro Glu Lys Asp Ser Ser Ala Met Ala Val Asp Ala Ile
    1730                1735                1740
Cys Thr His Arg Pro Asp Pro Glu Asp Leu Gly Leu Asp Arg Glu
    1745                1750                1755
Arg Leu Tyr Trp Glu Leu Ser Asn Leu Thr Asn Gly Ile Gln Glu
    1760                1765                1770
Leu Gly Pro Tyr Thr Leu Asp Arg Asn Ser Leu Tyr Val Asn Gly
    1775                1780                1785
```

Phe Thr His Arg Ser Ser Met Pro Thr Thr Ser Thr Pro Gly Thr
    1790                1795                1800

Ser Thr Val Asp Val Gly Thr Ser Gly Thr Pro Ser Ser Ser Pro
    1805                1810                1815

Ser Pro Thr
    1820

<210> SEQ ID NO 83
<211> LENGTH: 468
<212> TYPE: DNA
<213> ORGANISM: Homo sapiens

<400> SEQUENCE: 83
gccacagtcc cattcatggt gccattcacc ctcaacttca ccatcaccaa cctgcagtac     60
gaggaggaca tgcggcaccc tggttccagg aagttcaacg ccacagagag agaactgcag    120
ggtctgctca aacccttgtt caggaatagc agtctggaat acctctattc aggctgcaga    180
ctagcctcac tcaggccaga aaggatagc tcagccatgg cagtggatgc catctgcata    240
catcgccctg accctgaaga cctcggactg acagagagc gactgtactg ggagctgagc    300
aatctgacaa atggcatcca ggagctgggc cctacaccc tggaccggaa cagtctctat    360
gtcaatggtt tcacccatcg aagctctatg cccaccacca gcactcctgg gacctccaca    420
gtggatgtgg gaacctcagg gactccatcc tccagcccca gccccacg                 468

<210> SEQ ID NO 84
<211> LENGTH: 474
<212> TYPE: DNA
<213> ORGANISM: Homo sapiens

<400> SEQUENCE: 84
gctgctggcc ctctcctgat gccgttcacc ctcaacttca ccatcaccaa cctgcagtac     60
gaggaggaca tgcgtcgcac tggctccagg aagttcaaca ccatggagag tgtcctgcag    120
ggtctgctca agcccttgtt caagaacacc agtgttggcc ctctgtactc tggctgcaga    180
ttgaccttgc tcaggcccaa gaaagatggg gcagccactg gagtggatgc catctgcacc    240
caccgccttg accccaaaag ccctggactc aacaggagc agctgtactg ggagctaagc    300
aaaactgacc atgacattga gagctgggc cctacaccc tggacaggaa cagtctctat    360
gtcaatggtt tcacccatca gagctctgtg tccaccacca gcactcctgg gacctccaca    420
gtggatctcg gaacctcagg gactccatcc tccctctcca gccccacaat tatg          474

<210> SEQ ID NO 85
<211> LENGTH: 468
<212> TYPE: DNA
<213> ORGANISM: Homo sapiens

<400> SEQUENCE: 85
gctgctggcc ctctcctggt accattcacc ctcaacttca ccatcaccaa cctgcagtat     60
ggggaggaca tgggtcaccc tggctccagg aagttcaaca ccacagagag ggtcctgcag    120
ggtctgcttg gtcccatatt caagaacacc agtgttggcc ctctgtactc tggctgcaga    180
ctgacctctc tcaggtctga aaggatgga gcagccactg gagtggatgc catctgcatc    240
catcatcttg accccaaaag ccctggactc aacagagagc ggctgtactg ggagctgagc    300
caactgacca atggcatcaa agagctgggc cctacaccc tggacaggaa cagtctctat    360
gtcaatggtt tcacccatcg gacctctgtg cccaccacca gcactcctgg gacctccaca    420

```
gtggaccttg gaacctcagg gactccattc tccctcccaa gccccgca         468

<210> SEQ ID NO 86
<211> LENGTH: 465
<212> TYPE: DNA
<213> ORGANISM: Homo sapiens

<400> SEQUENCE: 86
actgctggcc ctctcctggt gctgttcacc ctcaacttca ccatcaccaa cctgaagtat    60
gaggaggaca tgcatcgccc tggctccagg aagttcaaca ccactgagag ggtcctgcag   120
actctgcttg gtcctatgtt caagaacacc agtgttggcc ttctgtactc tggctgcaga   180
ctgaccttgc tcaggtccga aaggatgga gcagccactg gagtggatgc catctgcacc    240
caccgtcttg accccaaaag ccctggactg gacagagagc agctatactg ggagctgagc   300
cagctgacca atggcatcaa agagctgggc cctacacccc tggacaggaa cagtctctat   360
gtcaatggtt tcacccattg gatccctgtg cccaccagca gcactcctgg gacctccaca   420
gtggaccttg ggtcagggac tccatcctcc ctccccagcc ccaca                  465

<210> SEQ ID NO 87
<211> LENGTH: 468
<212> TYPE: DNA
<213> ORGANISM: Homo sapiens

<400> SEQUENCE: 87
gctgctggcc ctctcctggt gccattcacc ctcaacttca ccatcaccaa cctgcagtac    60
gaggaggaca tgcatcaccc aggctccagg aagttcaaca ccacggagcg ggtcctgcag   120
ggtctgcttg gtcccatgtt caagaacacc agtgtcggcc ttctgtactc tggctgcaga   180
ctgaccttgc tcaggtccga aaggatgga gcagccactg gagtggatgc catctgcacc    240
caccgtcttg accccaaaag ccctggagtg gacagggagc agctatactg ggagctgagc   300
cagctgacca atggcatcaa agagctgggt cctacacccc tggacagaaa cagtctctat   360
gtcaatggtt tcacccatca gacctctgcg cccaacacca gcactcctgg gacctccaca   420
gtggaccttg ggacctcagg gactccatcc tccctcccca gccctaca              468

<210> SEQ ID NO 88
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 88
ncnnctgncc ctctcctgnt nccnttcacc ntcaacttna ccatcaccaa cctgcantan    60
gnggannaca tgcnncnccc nggntccagg aagttcaaca ccacngagng ngtnctgcag   120
ggtctgctnn nnccntntt caagaacacc agtgttggcc ctctgtactc tggctgcaga    180
ctgaccttgc tcaggtccga aaggatgga gcagccactg gagtggatgc catctgcacc    240
caccgtcttg accccaaaag ccctggagtg gacagggagc agctatactg ggagctgagc   300
cagctgacca atggcatcaa agagctgggt cctacacccc tggacagaaa cagtctctat   360
gtcaatggtt tcacccatca gacctctgcg cccaacacca gcactcctgg gacctccaca   420
gtggaccttg ggacctcagg gactccatcc tccctcccca gccctaca              468
```

<210> SEQ ID NO 89
<211> LENGTH: 468
<212> TYPE: DNA
<213> ORGANISM: Homo sapiens

<400> SEQUENCE: 89

| | | | | | |
|---|---|---|---|---|---|
| tctgctggcc | ctctcctggt | gccattcacc | ctcaacttca | ccatcaccaa | cctgcagtac | 60 |
| gaggaggaca | tgcatcaccc | aggctccagg | aagttcaaca | ccacggagcg | ggtcctgcag | 120 |
| ggtctgcttg | gtcccatgtt | caagaacacc | agtgtcggcc | ttctgtactc | tggctgcaga | 180 |
| ctgaccttgc | tcaggcctga | gaagaatggg | gcagccactg | gaatggatgc | catctgcagc | 240 |
| caccgtcttg | accccaaaag | ccctggactc | aacagagagc | agctgtactg | ggagctgagc | 300 |
| cagctgaccc | atggcatcaa | agagctgggc | cctacaccc | tggacaggaa | cagtctctat | 360 |
| gtcaatggtt | tcacccatcg | gagctctgtg | gcccccacca | gcactcctgg | acctccaca | 420 |
| gtggaccttg | ggacctcagg | gactccatcc | tccctcccca | gccccaca | | 468 |

<210> SEQ ID NO 90
<211> LENGTH: 468
<212> TYPE: DNA
<213> ORGANISM: Homo sapiens

<400> SEQUENCE: 90

| | | | | | |
|---|---|---|---|---|---|
| acagctgttc | ctctcctggt | gccgttcacc | ctcaacttta | ccatcaccaa | tctgcagtat | 60 |
| ggggaggaca | tgcgtcaccc | tggctccagg | aagttcaaca | ccacagagag | ggtcctgcag | 120 |
| ggtctgcttg | gtcccttgtt | caagaactcc | agtgtcggcc | ctctgtactc | tggctgcaga | 180 |
| ctgatctctc | tcaggtctga | gaaggatggg | gcagccactg | gagtggatgc | catctgcacc | 240 |
| caccaccttta | accctcaaag | ccctggactg | gacagggagc | agctgtactg | gcagctgagc | 300 |
| cagatgacca | atggcatcaa | agagctgggc | cctacaccc | tggaccggaa | cagtctctac | 360 |
| gtcaatggtt | tcacccatcg | gagctctggg | ctcaccacca | gcactccttg | gacttccaca | 420 |
| gttgaccttg | gaacctcagg | gactccatcc | ccgtccccca | gccccaca | | 468 |

<210> SEQ ID NO 91
<211> LENGTH: 468
<212> TYPE: DNA
<213> ORGANISM: Homo sapiens

<400> SEQUENCE: 91

| | | | | | |
|---|---|---|---|---|---|
| actgctggcc | ctctcctggt | gccattcacc | ctcaacttca | ccatcaccaa | cctgcagtat | 60 |
| gaggaggaca | tgcatcgccc | tggatctagg | aagttcaaca | ccacagagag | ggtcctgcag | 120 |
| ggtctgctta | gtcccatttt | caagaactcc | agtgttggcc | ctctgtactc | tggctgcaga | 180 |
| ctgacctctc | tcaggcccga | gaaggatggg | gcagcaactg | gaatggatgc | tgtctgcctc | 240 |
| taccacccta | atcccaaaag | acctggactg | gacagagagc | agctgtactg | ggagctaagc | 300 |
| cagctgaccc | acaacatcac | tgagctgggc | cctacagcc | tggacaggga | cagtctctat | 360 |
| gtcaatggtt | tcacccatca | gaactctgtg | cccaccacca | gtactcctgg | acctccaca | 420 |
| gtgtactggg | caaccactgg | gactccatcc | tccttccccg | gccacaca | | 468 |

<210> SEQ ID NO 92
<211> LENGTH: 468
<212> TYPE: DNA
<213> ORGANISM: Homo sapiens

<400> SEQUENCE: 92

```
gagcctggcc ctctcctgat accattcact ttcaacttta ccatcaccaa cctgcattat     60
gaggaaaaca tgcaacaccc tggttccagg aagttcaaca ccacggagag ggttctgcag    120
ggtctgctca agcccttgtt caagaacacc agtgttggcc ctctgtactc tggctgcaga    180
ctgacctctc tcaggcccga aaggatgggg gcagcaactg aatggatgc tgtctgcctc     240 taccacccta atcccaaaag acctgggctg acagagagc agctgtactg ggagctaagc     300
cagctgaccc acaacatcac tgagctgggc cctacagcc tggacaggga cagtctctat     360
gtcaatggtt tcacccatca gaactctgtg cccaccacca gtactcctgg gacctccaca    420
gtgtactggg caaccactgg gactccatcc tccttcccg gccacaca                  468

<210> SEQ ID NO 93
<211> LENGTH: 468
<212> TYPE: DNA
<213> ORGANISM: Homo sapiens

<400> SEQUENCE: 93
gagcctggcc ctctcctgat accattcact ttcaacttta ccatcaccaa cctgcattat     60
gaggaaaaca tgcaacaccc tggttccagg aagttcaaca ccacggagag ggttctgcag    120
ggtctgctca agcccttgtt caagaacacc agtgttggcc ctctgtactc tggctgcaga    180
ctgaccttgc tcagacctga aagcatgag gcagccactg gagtggacac catctgtacc     240
caccgcgttg atcccatcgg acctggactg acagggagc ggctatactg ggagctgagc     300
cagctgacca acagcattac cgaactggga ccctacaccc tggacaggga cagtctctat    360
gtcaatggct tcaaccctcg gagctctgtg ccaaccacca gcactcctgg gacctccaca    420
gtgcacctgg caacctctgg gactccatcc tccctgcctg gccacaca                 468

<210> SEQ ID NO 94
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 94
gcccctgtcc ctctcttgat accattcacc ctcaacttta ccatcaccaa cctgcattat     60
gaggaaaaca tgcaacaccc tggttccagg aagttcaaca ccacggagag ggttctgcag    120
ggtctgctca agcccttgtt caagaacacc agtgttggcc ctctgtactc tggctgcaga    180
ctgaccttgc tcagacctga aagcatgag gcagccactg gagtggacac catctgtacc     240
caccgcgttg atcccatcgg acctggactg nacagngagc ngctntactg ggagctnagc    300
canctgacca annncatcnn ngagctgggn ccctacaccc tggacaggna cagtctctat    360
gtcaatggtt tcacccatcn ganctctgng cccaccacca gcactcctgg gacctccaca    420
gtgnacntng gnacctcngg gactccatcc tccntcccn gccncaca                  468

<210> SEQ ID NO 95
<211> LENGTH: 468
<212> TYPE: DNA
<213> ORGANISM: Homo sapiens

<400> SEQUENCE: 95
tctgctggcc ctctcctggt gccattcacc ctcaacttca ccatcaccaa cctgcagtac     60
```

```
gaggaggaca tgcatcaccc aggctccagg aagttcaaca ccacggagcg ggtcctgcag      120
ggtctgcttg gtcccatgtt caagaacacc agtgtcggcc ttctgtactc tggctgcaga      180
ctgaccttgc tcaggcctga aagaatgggc cagccactg gaatggatgc catctgcagc       240
caccgtcttg accccaaaag ccctggactc gacagagagc agctgtactg ggagctgagc      300
cagctgaccc atggcatcaa agagctgggc cctacaccc tggacaggaa cagtctctat       360
gtcaatggtt tcacccatcg gagctctgtg ccccccacca gcactcctgg gacctccaca      420
gtggaccttg ggacctcagg gactccatcc tccctcccca gccccaca                   468
```

<210> SEQ ID NO 96
<211> LENGTH: 468
<212> TYPE: DNA
<213> ORGANISM: Homo sapiens

<400> SEQUENCE: 96

```
acagctgttc ctctcctggt gccgttcacc ctcaactta ccatcaccaa tctgcagtat       60
ggggaggaca tgcgtcaccc tggctccagg aagttcaaca ccacagagag ggtcctgcag      120
ggtctgcttg gtcccttgtt caagaactcc agtgtcggcc ctctgtactc tggctgcaga      180
ctgatctctc tcaggtctga aaggatgggc gcagccactg gagtggatgc catctgcacc     240 caccaccta accctcaaag ccctggactg gacaggagc agctgtactg gcagctgagc       300
cagatgacca atggcatcaa agagctgggc cctacaccc tggaccggaa cagtctctac      360
gtcaatggtt tcacccatcg gagctctggg ctcaccacca gcactccttg gacttccaca     420
gttgaccttg gaacctcagg gactccatcc cccgtccca gccccaca                   468
```

<210> SEQ ID NO 97
<211> LENGTH: 468
<212> TYPE: DNA
<213> ORGANISM: Homo sapiens

<400> SEQUENCE: 97

```
actgctggcc ctctcctggt gccattcacc ctaaacttca ccatcaccaa cctgcagtat      60
gaggaggaca tgcatcgccc tggatctagg aagttcaacg ccacagagag ggtcctgcag     120
ggtctgctta gtcccatatt caagaactcc agtgttggcc ctctgtactc tggctgcaga     180
ctgacctctc tcaggcccga aaggatgggc gcagcaactg gaatggatgc tgtctgcctc    240
taccacccta atcccaaaag acctggactg gacagagagc agctgtactg ggagctaagc    300
cagctgaccc acaacatcac tgagctgggc cctacagcc tggacaggga cagtctctat      360
gtcaatggtt tcacccatca gagctctatg acgaccacca gaactcctga tacctccaca    420
atgcacctgg caacctcgag aactccagcc tccctgtctg gacctacg                  468
```

<210> SEQ ID NO 98
<211> LENGTH: 474
<212> TYPE: DNA
<213> ORGANISM: Homo sapiens

<400> SEQUENCE: 98

```
accgccagcc ctctcctggt gctattcaca atcaactgca ccatcaccaa cctgcagtac      60
gaggaggaca tgcgtcgcac tggctccagg aagttcaaca ccatggagag tgtcctgcag     120
ggtctgctca agcccttgtt caagaacacc agtgttggcc ctctgtactc tggctgcaga     180
ttgaccttgc tcaggcccaa gaagatgggc gcagccactg gagtggatgc catctgcacc    240
caccgccttg accccaaaag ccctggactc aacagggagc agctgtactg ggagctaagc    300
```

```
aaactgacca atgacattga agagctgggc ccctacaccc tggacaggaa cagtctctat    360
gtcaatggtt tcacccatca gagctctgtg tccaccacca gcactcctgg gacctccaca    420
gtggatctca gaacctcagg gactccatcc tccctctcca gccccacaat tatg          474
```

<210> SEQ ID NO 99
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 99

```
ncnnctgncc ctctcctgnt nccnttcacc ntcaacttna ccatcaccaa cctgcantan    60
gnggannaca tgcnncnccc nggntccagg aagttcaaca ccacngagag ggtcctacag   120
ggtctgctca ggcccttgtt caagaacacc agtgtcagct ctctgtactc tggttgcaga   180
ctgaccttgc tcaggcctga aaggatgggg gcagccacca gagtggatgc tgcctgcacc   240
taccgccctg atcccaaaag ccctggactg gacagagagc aactatactg ggagctgagc   300
cagctaaccc acagcatcac tgagctggga ccctacaccc tggacagggt cagtctctat   360
gtcaatggct tcaaccctcg gagctctgtg ccaaccacca gcactcctgg gacctccaca   420
gtgcacctgg caacctctgg gactccatcc tccctgcctg gccacaca                468
```

<210> SEQ ID NO 100
<211> LENGTH: 468
<212> TYPE: DNA
<213> ORGANISM: Homo sapiens

<400> SEQUENCE: 100

```
gcccctgtcc ctctcttgat accattcacc ctcaacttta ccatcaccaa cctgcattat    60
gaagaaaaca tgcaacaccc tggttccagg aagttcaaca ccacggagag ggttctgcag   120
ggtctgctca agcccttgtt caagagcacc agcgttggcc ctctgtactc tggctgcaga   180
ctgaccttgc tcagacctga aaacatgggg gcagccactg gagtggacgc catctgcacc   240
ctccgccttg atcccactgg tcctggactg gacagagagc ggctatactg ggagctgagc   300
cagctgacca acagcgttac agagctgggc ccctacaccc tggacaggga cagtctctat   360
gtcaatggct tcacccagcg gagctctgtg ccaaccacca gtattcctgg gacctctgca   420
gtgcacctgg aaacctctgg gactccagcc tccctccctg gccacaca                468
```

<210> SEQ ID NO 101
<211> LENGTH: 468
<212> TYPE: DNA
<213> ORGANISM: Homo sapiens

<400> SEQUENCE: 101

```
gcccctggcc ctctcctggt gccattcacc ctcaacttca ctatcaccaa cctgcagtat    60
gaggtggaca tgcgtcaccc tggttccagg aagttcaaca ccacggagag agtcctgcag   120
ggtctgctca agcccttgtt caagagcacc agtgttggcc ctctgtactc tggctgcaga   180
ctgaccttgc tcaggcctga aaacgtgggg gcagccaccg gcgtggacac catctgcact   240
caccgccttg accctctaaa ccctggactg gacagagagc agctatactg ggagctgagc   300
aaactgaccc gtggcatcat cgagctgggc ccctacctcc tggacagagg cagtctctat   360
```

```
gtcaatggtt tcacccatcg aactttgtg cccatcacca gcactcctgg gacctccaca      420
gtacacctag gaacctctga aactccatcc tccctaccta gacccata                  468
```

<210> SEQ ID NO 102
<211> LENGTH: 468
<212> TYPE: DNA
<213> ORGANISM: Homo sapiens

<400> SEQUENCE: 102

```
gtgcctggcc ctctcctggt gccattcacc ctcaacttca ccatcaccaa cttgcagtat      60
gaggaggcca tgcgacaccc tggctccagg aagttcaata ccacggagag ggtcctacag     120
ggtctgctca ggcccttgtt caagaatacc agtatcggcc ctctgtactc cagctgcaga    180
ctgaccttgc tcaggccaga gaaggacaag gcagccacca gagtggatgc catctgtacc    240
caccaccctg accctcaaag ccctggactg aacagagagc agctgtactg ggagctgagc    300
cagctgaccc acggcatcac tgagctgggc ccctacaccc tggacaggga cagtctctat    360
gtcgatggtt tcactcattg gagccccata ccgaccacca gcactcctgg gacctccata    420
gtgaacctgg gaacctctgg gatcccacct tccctccctg aaaactaca                468
```

<210> SEQ ID NO 103
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 103

```
ncnnctgncc ctctcctgnt nccnttcacc ntcaacttna ccatcaccaa cctgcantan      60
gnggannaca tgcnncnccc nggntccagg aagttcaaca ccacngagag ggttctgcag     120
ggtctgctca aaccccttgtt caggaatagc agtctggaat acctctattc aggctgcaga    180
ctagcctcac tcaggccaga gaaggatagc tcagccatgg cagtggatgc catctgcaca    240
catcgccctg accctgaaga cctcggactg gacagagagc gactgtactg ggagctgagc    300
aatctgacaa atggcatcca ggagctgggc ccctacaccc tggaccggaa cagtctctac    360
gtcaatggtt tcacccatcg gagctctggg ctcaccacca gcactccttg gacttccaca    420
gttgaccttg gaacctcagg gactccatcc cccgtcccca gccccaca                 468
```

<210> SEQ ID NO 104
<211> LENGTH: 468
<212> TYPE: DNA
<213> ORGANISM: Homo sapiens

<400> SEQUENCE: 104

```
actgctggcc ctctcctggt gccattcacc ctcaacttca ccatcaccaa cctgcagtat      60
gaggaggaca tgcatcgccc tggttccagg aggttcaaca ccacggagag ggttctgcag     120
ggtctgctca cgcccttgtt caagaacacc agtgttggcc ctctgtactc tggctgcaga    180
ctgaccttgc tcagacctga gaagcaagag gcagccactg gagtggacac catctgtacc    240
caccgcgttg atcccatcgg acctggactg gacagagagg gctatactg ggagctgagc    300 cagctgacca acagcatcac agagctggga ccctacaccc tggatagga cagtctctat    360 gtcaatggct tcaaccttg gagctctgtg ccaaccacca gcactcctgg gacctccaca    420
gtgcacctgg caacctctgg gactccatcc tccctgcctg gccacaca                 468
```

<210> SEQ ID NO 105
<211> LENGTH: 468
<212> TYPE: DNA
<213> ORGANISM: Homo sapiens

<400> SEQUENCE: 105

```
gcccctgtcc ctctcttgat accattcacc ctcaacttta ccatcaccga cctgcattat      60
gaagaaaaca tgcaacaccc tggttccagg aagttcaaca ccacggagag ggttctgcag     120
ggtctgctca agcccttgtt caagagcacc agcgttggcc ctctgtactc tggctgcaga     180
ctgaccttgc tcagacctga gaaacatggg gcagccactg gagtggacgc catctgcacc     240
ctccgccttg atcccactgg tcctggactg gacagagagc ggctatactg ggagctgagc     300
cagctgacca acagcgttac agagctgggc ccctacaccc tggacaggga cagtctctat     360
gtcaatggct tcacccatcg gagctctgtg ccaaccacca gtattcctgg gacctctgca     420
gtgcacctgg aaacctctgg gactccagcc tccctccctg ccacaca                  468
```

<210> SEQ ID NO 106
<211> LENGTH: 468
<212> TYPE: DNA
<213> ORGANISM: Homo sapiens

<400> SEQUENCE: 106

```
gcccctggcc ctctcctggt gccattcacc ctcaacttca ctatcaccaa cctgcagtat      60
gaggaggaca tgcgtcaccc tggttccagg aagttcagca ccacggagag agtcctgcag     120
ggtctgctca agcccttgtt caagaacacc agtgtcagct ctctgtactc tggttgcaga     180
ctgaccttgc tcaggcctga gaaggatggg gcagccacca gagtggatgc tgtctgcacc     240
catcgtcctg accccaaaag ccctggactg gacagagagc ggctgtactg gaagctgagc     300
cagctgaccc acggcatcac tgagctgggc ccctacaccc tggacaggca cagtctctat     360
gtcaatggtt tcacccatca gagctctatg acgaccacca gaactcctga tacctccaca     420
atgcacctgg caacctcgag aactccagcc tccctgtctg gacctacg                  468
```

<210> SEQ ID NO 107
<211> LENGTH: 468
<212> TYPE: DNA
<213> ORGANISM: Homo sapiens

<400> SEQUENCE: 107

```
accgccagcc ctctcctggt gctattcaca attaacttca ccatcactaa cctgcggtat      60
gaggagaaca tgcatcaccc tggctctaga aagtttaaca ccacggagag agtccttcag     120
ggtctgctca ggcctgtgtt caagaacacc agtgttggcc ctctgtactc tggctgcaga     180
ctgaccacgc tcaggcccaa gaaggatggg gcagccacca agtggatgc catctgcacc     240
taccgccctg atcccaaaag ccctggactg gacagagagc agctatactg ggagctgagc     300
cagctaaccc acagcatcac tgagctgggc ccctacaccc aggacaggga cagtctctat     360
gtcaatggct tcacccatcg gagctctgtg ccaaccacca gtattcctgg gacctctgca     420
gtgcacctgg aaacctctgg gactccagcc tccctccctg ccacaca                  468
```

<210> SEQ ID NO 108
<211> LENGTH: 468
<212> TYPE: DNA
<213> ORGANISM: Homo sapiens

```
<400> SEQUENCE: 108
gcccctggcc ctctcctggt gccattcacc ctcaacttca ctatcaccaa cctgcagtat    60
gaggaggaca tgcgtcaccc tggttccagg aagttcaaca ccacggagag agtcctgcag   120
ggtctgctca agcccttgtt caagagcacc agtgttggcc ctctgtactc tggctgcaga   180
ctgaccttgc tcaggcctga aaaacgtggg gcagccaccg gcgtggacac catctgcact   240
caccgccttg accctctaaa cccaggactg gacagagagc agctatactg ggagctgagc   300
aaactgaccc gtggcatcat cgagctgggc ccctacctcc tggacagagg cagtctctat   360
gtcaatggtt tcacccatcg gacctctgtg cccaccacca gcactcctgg gacctccaca   420
gtggaccttg aacctcagg gactccattc tccctcccaa gccccgca               468

<210> SEQ ID NO 109
<211> LENGTH: 465
<212> TYPE: DNA
<213> ORGANISM: Homo sapiens
<220> FEATURE:
<221> NAME/KEY: misc_feature
<222> LOCATION: (1)..(465)
<223> OTHER INFORMATION: All N's = any nucleotide

<400> SEQUENCE: 109
ncnnctgncc ctctcctgnt nccnttcacc ntcaacttna ccatcaccaa cctgcantan    60
gnggannaca tgcnncnccc nggntccagg aagttcaaca ccacngagag ggtcctgcag   120
actctgcttg gtcctatgtt caagaacacc agtgttggcc ttctgtactc tggctgcaga   180
ctgaccttgc tcaggtccga aaggatgga gcagccactg gagtggatgc catctgcacc   240
caccgtcttg accccaaaag ccctggagtg gacagggagc aactatactg ggagctgagc   300
cagctgacca atggcattaa agaactgggc ccctacaccc tggacaggaa cagtctctat   360
gtcaatgggt tcacccattg gatccctgtg cccaccagca gcactcctgg gacctccaca   420
gtggaccttg ggtcagggac tccatcctcc ctccccagcc ccaca                  465

<210> SEQ ID NO 110
<211> LENGTH: 468
<212> TYPE: DNA
<213> ORGANISM: Homo sapiens

<400> SEQUENCE: 110
actgctggcc ctctcctggt gccgttcacc ctcaacttca ccatcaccaa cctgaagtac    60
gaggaggaca tgcattgccc tggctccagg aagttcaaca ccacagagag agtcctgcag   120
agtctgcttg gtcccatgtt caagaacacc agtgttggcc ctctgtactc tggctgcaga   180
ctgaccttgc tcaggtccga aaggatgga gcagccactg gagtggatgc catctgcacc   240
caccgtcttg accccaaaag ccctggagtg gacagggagc agctatactg ggagctgagc   300
cagctgacca atggcatcaa agagctgggt ccctacaccc tggacagaaa cagtctctat   360
gtcaatggtt tcacccatca gacctctgcg cccaacacca gcactcctgg gacctccaca   420
gtggaccttg ggacctcagg gactccatcc tccctcccca gccctaca               468

<210> SEQ ID NO 111
<211> LENGTH: 465
<212> TYPE: DNA
<213> ORGANISM: Homo sapiens
<220> FEATURE:
<221> NAME/KEY: misc_feature
<222> LOCATION: (1)..(465)
<223> OTHER INFORMATION: All N's = any nucleotide
```

<400> SEQUENCE: 111

```
ncnnctgncc ctctcctgnt nccnttcacc ntcaacttna ccatcaccaa cctgcantan      60
gnggannaca tgcnncnccc nggntccagg aagttcaaca ccacngagng ngtnctgcag     120
ggtctgctnn nnccntntt caagaacncc agtgtnggcc ntctgtactc tggctgcaga      180
ctgacctnnc tcaggncnga gaagnatggn gcagccactg gantggatgc catctgcanc    240
caccnncntn ancccaaaag nctggactg nacagngagc ngctntactg ggagctnagc     300
canctgacca annncatcnn ngagctgggn ccctacaccc tggacaggna cagtctctat    360
gtcaatggtt tcacccattg gatccctgtg cccaccagca gcactcctgg gacctccaca    420
gtggaccttg ggtcagggac tccatcctcc ctccccagcc ccaca                    465
```

<210> SEQ ID NO 112
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 112

```
actgctggcc ctctcctggt gccgttcacc ctcaacttca ccatcaccaa cctgaagtac     60
gaggaggaca tgcattgccc tggctccagg aagttcaaca ccacagagag agtcctgcag    120
agtctgcttg gtcccatgtt caagaacacc agtgttggcc ctctgtactc tggctgcaga    180
ctgacctcgc tcaggtccga gaaggatgga gcagccactg gagtggatgc catctgcacc   240
caccgtgttg accccaaaag ccctggagtg gacaggagc agctatactg ggagctgagc    300
cagctgacca atggcatcaa agagctgggt ccctacaccc tggacagaaa cagtctctat   360
gtcaatggtt tcacccatca gacctctgcg cccaacacca gcactcctgg gacctccaca    420
gtgnacntng gnacctcngg gactccatcc tccntcccn gccncaca                   468
```

<210> SEQ ID NO 113
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 113

```
tctgctggcc ctctcctggt gccattcacc ctcaacttca ccatcaccaa cctgcagtac     60
gaggaggaca tgcatcaccc aggctccagg aagttcaaca ccacggagcg ggtcctgcag    120
ggtctgcttg gtcccatgtt caagaacacc agtgtcggcc ttctgtactc tggctgcaga    180
ctgaccttgc tcaggcctga gaagaatggg gcaaccactg gaatggatgc catctgcacc   240
caccgtcttg accccaaaag ccctggactg nacagngagc ngctntactg ggagctnagc    300
canctgacca annncatcnn ngagctgggn ccctacaccc tggacaggna cagtctctat    360
gtcaatggtt tcacccatcn ganctctgng cccaccacca gcactcctgg gacctccaca    420
gtgnacntng gnacctcngg gactccatcc tccntcccn gccncaca                   468
```

<210> SEQ ID NO 114
<211> LENGTH: 468
<212> TYPE: DNA

<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 114

| | | | | | |
|---|---|---|---|---|---|
| ncnnctgncc | ctctcctgnt | nccnttcacc | ntcaacttna | ccatcaccaa | cctgcantan | 60 |
| gnggannaca | tgcnncnccc | nggntccagg | aagttcaaca | ccacngagag | ggttctgcag | 120 |
| ggtctgctca | aaccctttgt | caggaatagc | agtctggaat | acctctattc | aggctgcaga | 180 |
| ctagcctcac | tcaggccaga | gaaggatagc | tcagccatgg | cagtggatgc | catctgcaca | 240 |
| catcgccctg | accctgaaga | cctcggactg | gacagagagc | gactgtactg | ggagctgagc | 300 |
| aatctgacaa | atggcatcca | ggagctgggc | ccctacaccc | tggaccggaa | cagtctctat | 360 |
| gtcaatggtt | tcacccatcg | aagctctatg | cccaccacca | gcactcctgg | gacctccaca | 420 |
| gtggatgtgg | gaacctcagg | gactccatcc | tccagcccca | gccccacg | | 468 |

<210> SEQ ID NO 115
<211> LENGTH: 468
<212> TYPE: DNA
<213> ORGANISM: Homo sapiens

<400> SEQUENCE: 115

| | | | | | |
|---|---|---|---|---|---|
| actgctggcc | ctctcctgat | accattcacc | ctcaacttca | ccatcaccaa | cctgcagtat | 60 |
| ggggaggaca | tgggtcaccc | tggctccagg | aagttcaaca | ccacagagag | ggtcctgcag | 120 |
| ggtctgcttg | gtcccatatt | caagaacacc | agtgttggcc | ctctgtactc | tggctgcaga | 180 |
| ctgacctctc | tcaggtctga | gaaggatgga | gcagccactg | gagtggatgc | catctgcatc | 240 |
| catcatcttg | accccaaaag | ccctggactc | aacagagagc | ggctgtactg | ggagctgagc | 300 |
| caactgacca | atggcatcaa | agagctgggc | ccctacaccc | tggacaggaa | cagtctctat | 360 |
| gtcaatggtt | tcacccatcg | gacctctgtg | cccaccacca | gcactcctgg | gacctccaca | 420 |
| gtggaccttg | gaacctcagg | gactccattc | tccctcccaa | gccccgca | | 468 |

<210> SEQ ID NO 116
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 116

| | | | | | |
|---|---|---|---|---|---|
| actgctggcc | ctctcctggt | gctgttcacc | ctcaacttca | ccatcaccaa | cctgaagtat | 60 |
| gaggaggaca | tgcatcgccc | tggctccagg | aagttcaaca | ccactgagag | ggtcctgcag | 120 |
| actctgcttg | gtcctatgtt | caagaacacc | agtgttggcc | ttctgtactc | tggctgcaga | 180 |
| ctgaccttgc | tcaggtccga | gaaggatgga | gcagccactg | gagtggatgc | catctgcacc | 240 |
| caccgtcttg | accccaaaag | ccctggactg | nacagngagc | ngctntactg | ggagctnagc | 300 |
| canctgacca | annncatcnn | ngagctgggn | ccctacaccc | tggacaggna | cagtctctat | 360 |
| gtcaatggtt | tcacccatcn | ganctctgng | cccaccacca | gcactcctgg | gacctccaca | 420 |
| gtgnacntng | gnacctcngg | gactccatcc | tccntcnccn | gccncaca | | 468 |

<210> SEQ ID NO 117
<211> LENGTH: 468

```
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 117
ncnnctgncc ctctcctgnt nccnttcacc ntcaacttna ccatcaccaa cctgcantan      60
gnggannaca tgcnncnccc nggntccagg aagttcaaca ccacngagag agtccttcag     120
ggtctgctca ggcctgtgtt caagaacacc agtgttggcc ctctgtactc tggctgcaga    180
ctgaccttgc tcaggcccaa gaaggatggg gcagccacca aagtggatgc catctgcacc    240
taccgccctg atcccaaaag ccctggactg acagagagc agctatactg ggagctgagc     300
cagctaaccc acagcatcac tgagctgggc ccctacaccc aggacaggga cagtctctat    360
gtcaatggct tcacccatcg gagctctgtg ccaaccacca gtattcctgg gacctctgca    420
gtgcacctgg aaaccactgg gactccatcc tccttccccg gccacaca                 468

<210> SEQ ID NO 118
<211> LENGTH: 468
<212> TYPE: DNA
<213> ORGANISM: Homo sapiens

<400> SEQUENCE: 118
gagcctggcc ctctcctgat accattcact ttcaactta ccatcaccaa cctgcgttat      60
gaggaaaaca tgcaacaccc tggttccagg aagttcaaca ccacggagag ggttctgcag    120
ggtctgctca cgcccttgtt caagaacacc agtgttggcc ctctgtactc tggctgcaga    180
ctgaccttgc tcagacctga aagcaggag gcagccactg gagtggacac catctgtacc     240
caccgcgttg atcccatcgg acctggactg acagagagc ggctatactg ggagctgagc     300
cagctgacca acagcatcac agagctggga ccctacaccc tggataggga cagtctctat    360
gtcgatggct tcaacccttg gagctctgtg ccaaccacca gcactcctgg gacctccaca    420
gtgcacctgg caacctctgg gactccatcc cccctgcctg gccacaca                 468

<210> SEQ ID NO 119
<211> LENGTH: 468
<212> TYPE: DNA
<213> ORGANISM: Homo sapiens

<400> SEQUENCE: 119
gcccctgtcc ctctcttgat accattcacc ctcaacttta ccatcaccga cctgcattat      60
gaagaaaaca tgcaacaccc tggttccagg aagttcaaca ccacggagag ggttctgcag    120
ggtctgctca agcccttgtt caagagcacc agcgttggcc ctctgtactc tggctgcaga    180
ctgaccttgc tcagacctga gaaacatggg gcagccactg gagtggacgc catctgcacc    240
ctccgccttg atcccactgg tcctggactg acagagagc ggctatactg ggagctgagc     300
cagctgacca acagcatcac agagctggga ccctacaccc tggataggga cagtctctat    360
gtcaatggct tcaacccttg gagctctgtg ccaaccacca gcactcctgg gacctccaca    420
gtgcacctgg caacctctgg gactccatcc tccctgcctg gccacaca                 468

<210> SEQ ID NO 120
<211> LENGTH: 468
<212> TYPE: DNA
<213> ORGANISM: Homo sapiens
<220> FEATURE:
```

```
<221> NAME/KEY: misc_feature
<222> LOCATION: (1)..(468)
<223> OTHER INFORMATION: All N's = any nucleotide

<400> SEQUENCE: 120
actgctggcc ctctcctggt gccgttcacc ctcaacttca ccatcaccaa cctgaagtac      60
gaggaggaca tgcattgccc tggctccagg aagttcaaca ccacagagag agtcctgcag     120
agtctgcatg gtcccatgtt caagaacacc agtgttggcc ctctgtactc tggctgcaga    180
ctgaccttgc tcaggtccga aaggatgga gcagccactg gagtggatgc catctgcacc     240
caccgtcttg accccaaaag ccctggactg nacagngagc ngctntactg ggagctnagc    300
canctgacca annncatcnn ngagctgggn ccctacaccc tggacaggna cagtctctat    360
gtcaatggtt tcacccatcn ganctctgng cccaccacca gcactcctgg gacctccaca    420
gtgnacntng gnacctcngg gactccatcc tccntcccccn gccncaca              468

<210> SEQ ID NO 121
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 121
ncnnctgncc ctctcctgnt nccnttcacc ntcaacttna ccatcaccaa cctgcantan     60
gnggannaca tgcnncnccc nggntccagg aagttcaaca ccacngagng ngtnctgcag    120
ggtctgctnn nnccntnttt caagaacncc agtgtnggcc ntctgtactc tggctgcaga   180
ctgacctnnc tcaggncnga aagnatggn gcagccactg gantggatgc catctgcanc    240
caccnncntn anccccaaaag ncctggactg nacagngagc ngctntactg ggagctnagc  300
canctgacca acagcatcac agagctggga ccctacaccc tggatagggga cagtctctat  360 gtcaatggtt tcacccatcg aagctctatg cccaccacca gtattcctgg gacctctgca   420
gtgcacctgg aaacctctgg gactccagcc tccctccctg gccacaca               468

<210> SEQ ID NO 122
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 122 gccctggcc ctctcctggt gccattcacc ctcaacttca ctatcaccaa cctgcagtat       60
gaggaggaca tgcgtcaccc tggttccagg aagttcaaca ccacggagag agtcctgcag    120
ggtctgctca agcccttgtt caagagcacc agtgttggcc ctctgtactc tggctgcaga    180
ctgaccttgc tcaggcctga aaaacgtggg gcagccaccg gcgtggacac catctgcact    240
caccgccttg accctctaaa ccctggactg nacagngagc ngctntactg ggagctnagc    300
canctgacca annncatcnn ngagctgggn ccctacaccc tggacaggna cagtctctat    360
gtcaatggtt tcacccatcn ganctctgng cccaccacca gcactcctgg gacctccaca    420
gtgnacntng gnacctcngg gactccatcc tccntcccccn gccncaca              468
```

<210> SEQ ID NO 123
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 123
ncnnctgncc ctctcctgnt nccnttcacc ntcaacttna ccatcaccaa cctgcantan    60
gnggannaca tgcnncnccc nggntccagg aagttcaaca ccacngagng ngtnctgcag   120
ggtctgctnn nnccntntt caagaacncc agtgtnggcc ntctgtactc tggctgcaga   180
ctgacctnnc tcaggncnga gaagnatggn gcagccactg gantgdatgc catctgcanc   240
caccnncntn ancccaaaag ncctggactg nacagngagc ngctntactg ggagctnagc   300
canctgacca annncatcnn ngagctgggn ccctacaccc tggacaggna cagtctctat   360
gtcaatggtt ttcaccctcg gagctctgtg ccaaccacca gcactcctgg gacctccaca   420
gtgcacctgg caacctctgg gactccatcc tccctgcctg gccacaca              468

<210> SEQ ID NO 124
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 124 gccctgtcc ctctcttgat accattcacc ctcaacttta ccatcaccaa cctgcattat    60
gaagaaaaca tgcaacaccc tggttccagg aagttcaaca ccacggagcg ggtcctgcag   120
ggtctgcttg gtcccatgtt caagaacaca agtgtcggcc ttctgtactc tggctgcaga   180
ctgaccttgc tcaggcctga gaagaatggg gcagccactg gaatggatgc catctgcagc   240
caccgtcttg accccaaaag ccctggactg nacagngagc ngctntactg ggagctnagc   300
canctgacca annncatcnn ngagctgggn ccctacaccc tggacaggna cagtctctat   360
gtcaatggtt tcacccatcn ganctctgng ccaccacca gcactcctgg gacctccaca   420
gtgnacntng gnacctcngg gactccatcc tccntcccn gccncaca                468

<210> SEQ ID NO 125
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 125
ncnnctgncc ctctcctgnt nccnttcacc ntcaacttna ccatcaccaa cctgcantan    60
gnggannaca tgcnncnccc nggntccagg aagttcaaca ccacngagng ngtnctgcag   120
ggtctgctnn nnccntntt caagaacncc agtgtnggcc ntctgtactc tggctgcaga   180
ctgacctnnc tcaggncnga gaagnatggn gcagccactg gantggatgc catctgcanc   240
caccnncntn ancccaaaag ncctggactg nacagngagc ngctntactg ggagctnagc   300
canctgacca annncatcnn ngagctgggn ccctacaccc tggacaggna cagtctctat   360

```
gtcaatggtt tcacccatca gaactctgtg cccaccacca gtactcctgg gacctccaca    420
gtgtactggg caaccactgg gactccatcc tccttccccg gccacaca                 468
```

<210> SEQ ID NO 126
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 126

```
gagcctggcc ctctcctgat accattcact ttcaactta ccatcaccaa cctgcattat     60
gaggaaaaca tgcaacaccc tggttccagg aagttcaaca ccacggagag ggttctgcag    120
ggtctgctca cgcccttgtt caagaacacc agtgttggcc ctctgtactc tggctgcaga   180
ctgaccttgc tcagacctga gaagcaggag gcagccactg gagtggacac catctgtacc   240
caccgcgttg atcccatcgg acctggactg nacagngagc ngctntactg ggagctnagc   300
canctgacca annncatcnn ngagctgggn ccctacaccc tggacaggna cagtctctat   360
gtcaatggtt tcacccatcn ganctctgng cccaccacca gcactcctgg gacctccaca   420
gtgnacntng gnacctcngg gactccatcc tccntccccn gccncaca                468
```

<210> SEQ ID NO 127
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 127

```
ncnnctgncc ctctcctgnt nccnttcacc ntcaacttna ccatcaccaa cctgcantan    60
gnggannaca tgcnncnccc nggntccagg aagttcaaca ccacngagng ngtnctgcag   120
ggtctgctnn nnccntnttt caagaacncc agtgtnggcc ntctgtactc tggctgcaga   180
ctgacctnnc tcaggncnga gaagnatggn gcagccactg gantggatgc catctgcanc   240
caccnncntn ancccaaaag ncctggactg nacagngagc ngctntactg ggagctnagc   300
canctgacca annncatcnn ngagctgggn ccctacaccc tggacaggna cagtctctat   360
gtcaatggtt tcacccatcg gagctctgtg ccaaccacca gcagtcctgg gacctccaca   420
gtgcacctgg caacctctgg gactccatcc tccctgcctg gccacaca                468
```

<210> SEQ ID NO 128
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 128

```
gcccctgtcc ctctcttgat accattcacc ctcaactta ccatcaccaa cctgcattat     60
gaagaaaaca tgcaacaccc tggttccagg aagttcaaca ccacggagag ggttctgcag    120
ggtctgctca agcccttgtt caagagcacc agtgttggcc ctctgtactc tggctgcaga   180
ctgaccttgc tcagacctga gaaacatggg gcagccactg gagtggacgc catctgcacc   240
```

```
ctccgccttg atcccactgg tcctggactg nacagngagc ngctntactg ggagctnagc    300
canctgacca annncatcnn ngagctgggn ccctacaccc tggacaggna cagtctctat    360
gtcaatggtt tcacccatcn ganctctgng cccaccacca gcactcctgg gacctccaca   420
gtgnacntng gnacctcngg gactccatcc tccntcccn gccncaca                 468
```

```
<210> SEQ ID NO 129
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 129
ncnnctgncc ctctcctgnt nccnttcacc ntcaacttna ccatcaccaa cctgcantan    60
gnggannaca tgcnncnccc nggntccagg aagttcaaca ccacngagng ngtnctgcag   120
ggtctgctnn nncccntntt caagaacncc agtgtnggcc ntctgtactc tggctgcaga   180
ctgacctnnc tcaggncnga gaagnatggn gcagccactg gantggatgc catctgcanc   240
caccnncntn ancccaaaag ncctggactg nacagngagc ngctntactg ggagctnagc   300
canctgacca annncatcnn ngagctgggn ccctacaccc tggacaggna cagtctctat   360
gtcaatggtt tcacccatcg gacctctgtg cccaccacca gcactcctgg gacctccaca   420
gtgcacctgg caacctctgg gactccatcc tccctgcctg gccacaca                468
```

```
<210> SEQ ID NO 130
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 130
gcccctgtcc ctctcttgat accattcacc ctcaacttta ccatcaccaa cctgcagtat    60
gaggaggaca tgcatcgccc tggatctagg aagttcaaca ccacagagag ggtcctgcag   120
ggtctgctta gtcccatttt caagaactcc agtgttggcc ctctgtactc tggctgcaga   180
ctgacctctc tcaggcccga gaaggatggg gcagcaactg gaatggatgc tgtctgcctc   240
taccacccta atcccaaaag acctggactg nacagngagc ngctntactg ggagctnagc   300
canctgacca annncatcnn ngagctgggn ccctacaccc tggacaggna cagtctctat   360
gtcaatggtt tcacccatcn ganctctgng cccaccacca gcactcctgg gacctccaca   420
gtgnacntng gnacctcngg gactccatcc tccntcccn gccncaca                 468
```

```
<210> SEQ ID NO 131
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 131
ncnnctgncc ctctcctgnt nccnttcacc ntcaacttna ccatcaccaa cctgcantan    60
```

```
gnggannaca tgcnncnccc nggntccagg aagttcaaca ccacngagng ngtnctgcag      120
ggtctgctnn nncccntntt caagaacncc agtgtnggcc ntctgtactc tggctgcaga      180
ctgacctnnc tcaggncnga gaagnatggn gcagccactg gantggatgc catctgcanc      240
caccnncntn ancccaaaag ncctggactg nacagngagc ngctntactg ggagctnagc      300
canctgacca annncatcnn ngagctgggn ccctacaccc tggacaggna cagtctctat      360
gtcaatggtt tcacccattg gagctctggg ctcaccacca gcactccttg gacttccaca      420
gttgaccttg gaacctcagg gactccatcc cccgtcccca gccccaca                   468
```

<210> SEQ ID NO 132
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 132

```
actgctggcc ctctcctggt gccattcacc ctaaacttca ccatcaccaa cctgcagtat      60
gaggaggaca tgcatcgccc tggatctagg aagttcaacg ccacagagag ggtcctgcag      120
ggtctgctta gtcccatatt caagaacacc agtgttggcc ctctgtactc tggctgcaga      180
ctgaccttgc tcagacctga gaagcaggag gcagccactg gagtggacac catctgtacc      240
caccgcgttg atcccatcgg acctggactg nacagngagc ngctntactg ggagctnagc      300
canctgacca annncatcnn ngagctgggn ccctacaccc tggacaggna cagtctctat      360
gtcaatggtt tcacccatcn ganctctgng cccaccacca gcactcctgg gacctccaca      420
gtgnacntng gnacctcngg gactccatcc tccntccccn gccncaca                   468
```

<210> SEQ ID NO 133
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 133

```
ncnnctgncc ctctcctgnt nccnttcacc ntcaacttna ccatcaccaa cctgcantan      60
gnggannaca tgcnncnccc nggntccagg aagttcaaca ccacngagng ngtnctgcag      120
ggtctgctnn nncccntntt caagaacncc agtgtnggcc ntctgtactc tggctgcaga      180
ctgacctnnc tcaggncnga gaagnatggn gcagccactg gantggatgc catctgcanc      240
caccnncntn ancccaaaag ncctggactg nacagngagc ngctntactg ggagctnagc      300
canctgacca annncatcnn ngagctgggn ccctacaccc tggacaggna cagtctctat      360
gtcaatggtt tcacccatcg gagctttggg ctcaccacca gcactccttg gacttccaca      420
gttgaccttg gaacctcagg gactccatcc cccgtcccca gccccaca                   468
```

<210> SEQ ID NO 134
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 134

```
actgctggcc ctctcctggt gccattcacc ctaaacttca ccatcaccaa cctgcagtat      60
gaggaggaca tgcatcgccc tggctccagg aagttcaaca ccacggagag ggtccttcag     120
ggtctgctta cgcccttgtt caggaacacc agtgtcagct ctctgtactc tggttgcaga     180
ctgaccttgc tcaggcctga aaggatggg gcagccacca gagtggatgc tgtctgcacc     240
catcgtcctg accccaaaag ccctggactg nacagngagc ngctntactg ggagctnagc     300
canctgacca annncatcnn ngagctgggn ccctacaccc tggacaggna cagtctctat     360
gtcaatggtt tcacccatcn ganctctgng cccaccacca gcactcctgg gacctccaca     420
gtgnacntng gnacctcngg gactccatcc tccntcccccn gccncaca                 468
```

<210> SEQ ID NO 135
<211> LENGTH: 465
<212> TYPE: DNA
<213> ORGANISM: Homo sapiens
<220> FEATURE:
<221> NAME/KEY: misc_feature
<222> LOCATION: (1)..(465)
<223> OTHER INFORMATION: All N's = any nucleotide

<400> SEQUENCE: 135

```
ncnnctgncc ctctcctgnt nccnttcacc ntcaacttna ccatcaccaa cctgcantan      60
gnggannaca tgcnncnccc nggntccagg aagttcaaca ccacngagng ngtnctgcag     120
ggtctgctnn nncccntntt caagaacncc agtgtnggcc ntctgtactc tggctgcaga     180
ctgacctnnc tcaggncnga gaagnatggn gcagccactg gantggatgc catctgcanc     240
caccnncntn ancccaaaag ncctggactg nacagngagc ngctntactg ggagctnagc     300
canctgacca annncatcnn ngagctgggn ccctacaccc tggacaggna cagtctctat     360
gtcaatggtt tcacccattg gatccctgtg cccaccagca gcactcctgg gacctccaca     420
gtggaccttg ggtcagggac tccatcctcc ctccccagcc ccaca                     465
```

<210> SEQ ID NO 136
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 136

```
actgctggcc ctctcctggt accattcacc ctcaacttca ccatcaccaa cctgcagtat      60
ggggaggaca tgggtcaccc tggctccagg aagttcaaca ccacagagag ggtcctgcag     120
ggtctgcttg gtcccatatt caagaacacc agtgttggcc ctctgtactc tggctgcaga     180
ctgacctctc tcaggtccga aaggatgga gcagccactg gagtggatgc catctgcatc     240
catcatcttg accccaaaag ccctggactg nacagngagc ngctntactg ggagctnagc     300
canctgacca annncatcnn ngagctgggn ccctacaccc tggacaggna cagtctctat     360
gtcaatggtt tcacccatcn ganctctgng cccaccacca gcactcctgg gacctccaca     420
gtgnacntng gnacctcngg gactccatcc tccntcccccn gccncaca                 468
```

<210> SEQ ID NO 137
<211> LENGTH: 468
<212> TYPE: DNA

<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 137

| | | | | | |
|---|---|---|---|---|---|
| ncnnctgncc | ctctcctgnt | nccnttcacc | ntcaacttna | ccatcaccaa | cctgcantan | 60 |
| gnggannaca | tgcnncnccc | nggntccagg | aagttcaaca | ccacngagng | ngtnctgcag | 120 |
| ggtctgctnn | nncccntntt | caagaacncc | agtgtnggcc | ntctgtactc | tggctgcaga | 180 |
| ctgacctnnc | tcaggncnga | gaagnatggn | gcagccactg | gantggatgc | catctgcanc | 240 |
| caccnncntn | ancccaaaag | ncctggactg | nacagngagc | ngctntactg | ggagctnagc | 300 |
| canctgacca | annncatcnn | ngagctgggn | ccctacaccc | tggacaggna | cagtctctat | 360 |
| gtcaatggtt | tcacccatca | gacctttgcg | cccaacacca | gcactcctgg | gacctccaca | 420 |
| gtggaccttg | ggacctcagg | gactccatcc | tccctcccca | gccctaca | | 468 |

<210> SEQ ID NO 138
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 138

| | | | | | |
|---|---|---|---|---|---|
| tctgctggcc | ctctcctggt | gccattcacc | ctcaacttca | ccatcaccaa | cctgcagtac | 60 |
| gaggaggaca | tgcatcaccc | aggctccagg | aagttcaaca | ccacggagcg | ggtcctgcag | 120 |
| ggtctgcttg | gtcccatgtt | caagaacacc | agtgtcggcc | ttctgtactc | tggctgcaga | 180 |
| ctgaccttgc | tcaggcctga | gaagaatggg | gcagccacca | gagtggatgc | tgtctgcacc | 240 |
| catcgtcctg | accccaaaag | ccctggactg | nacagngagc | ngctntactg | ggagctnagc | 300 |
| canctgacca | annncatcnn | ngagctgggn | ccctacaccc | tggacaggna | cagtctctat | 360 |
| gtcaatggtt | tcacccatcn | ganctctgng | cccaccacca | gcactcctgg | gacctccaca | 420 |
| gtgnacntng | gnacctcngg | gactccatcc | tccntccccn | gccncaca | | 468 |

<210> SEQ ID NO 139
<211> LENGTH: 468
<212> TYPE: DNA
<213> ORGANISM: Homo sapiens
<220> FEATURE:
<221> NAME/KEY: misc_feature
<222> LOCATION: (1)..(468)
<223> OTHER INFORMATION: All N's = any nucleotide

<400> SEQUENCE: 139

| | | | | | |
|---|---|---|---|---|---|
| ncnnctgncc | ctctcctgnt | nccnttcacc | ntcaacttna | ccatcaccaa | cctgcantan | 60 |
| gnggannaca | tgcnncnccc | nggntccagg | aagttcaaca | ccacngagag | ggttctgcag | 120 |
| ggtctgctca | agcccttgtt | caagagcacc | agtgttggcc | ctctgtattc | tggctgcaga | 180 |
| ctgaccttgc | tcaggcctga | gaaggacgga | gtagccacca | gagtggacgc | catctgcacc | 240 |
| caccgccctg | accccaaaat | ccctgggcta | gacagacagc | agctatactg | ggagctgagc | 300 |
| cagctgaccc | acagcatcac | tgagctggga | ccctacaccc | tggatgggga | cagtctctat | 360 |
| gtcaatggtt | tcacccagcg | gagctctgtg | cccaccacca | gcactcctgg | gactttcaca | 420 |
| gtacagccgg | aaacctctga | gactccatca | tccctccctg | gccccaca | | 468 |

<210> SEQ ID NO 140
<211> LENGTH: 468
<212> TYPE: DNA
<213> ORGANISM: Homo sapiens

<400> SEQUENCE: 140

| | | | | | |
|---|---|---|---|---|---|
| gccactggcc | ctgtcctgct | gccattcacc | ctcaatttta | ccatcactaa | cctgcagtat | 60 |
| gaggaggaca | tgcatcgccc | tggctccagg | aagttcaaca | ccacggagag | ggtccttcag | 120 |
| ggtctgctta | tgcccttgtt | caagaacacc | agtgtcagct | ctctgtactc | tggttgcaga | 180 |
| ctgaccttgc | tcaggcctga | gaaggatggg | gcagccacca | gagtggatgc | tgtctgcacc | 240 |
| catcgtcctg | accccaaaag | ccctggactg | gacagagagc | ggctgtactg | gaagctgagc | 300 |
| cagctgaccc | acggcatcac | tgagctgggc | ccctacaccc | tggacaggca | cagtctctat | 360 |
| gtcaatggtt | tcacccatca | gagctctatg | acgaccacca | gaactcctga | tacctccaca | 420 |
| atgcacctgg | caacctcgag | aactccagcc | tccctgtctg | gacctacg | | 468 |

<210> SEQ ID NO 141
<211> LENGTH: 468
<212> TYPE: DNA
<213> ORGANISM: Homo sapiens

<400> SEQUENCE: 141

| | | | | | |
|---|---|---|---|---|---|
| accgccagcc | ctctcctggt | gctattcaca | attaacttca | ccatcactaa | cctgcggtat | 60 |
| gaggagaaca | tgcatcaccc | tggctctaga | aagtttaaca | ccacggagag | agtccttcag | 120 |
| ggtctgctca | ggcctgtgtt | caagaacacc | agtgttggcc | ctctgtactc | tggctgcaga | 180 |
| ctgaccttgc | tcaggcccaa | gaaggatggg | gcagccacca | aagtggatgc | catctgcacc | 240 |
| taccgccctg | atcccaaaag | ccctggactg | gacagagagc | agctatactg | ggagctgagc | 300 |
| cagctaaccc | acagcatcac | tgagctgggc | ccctacaccc | tggacaggga | cagtctctat | 360 |
| gtcaatggtt | tcacacagcg | gagctctgtg | cccaccacta | gcattcctgg | gacccccaca | 420 |
| gtggacctgg | gaacatctgg | gactccagtt | tctaaacctg | gtccctcg | | 468 |

<210> SEQ ID NO 142
<211> LENGTH: 468
<212> TYPE: DNA
<213> ORGANISM: Homo sapiens

<400> SEQUENCE: 142

| | | | | | |
|---|---|---|---|---|---|
| gctgccagcc | ctctcctggt | gctattcact | ctcaacttca | ccatcaccaa | cctgcggtat | 60 |
| gaggagaaca | tgcagcaccc | tggctccagg | aagttcaaca | ccacggagag | ggtccttcag | 120 |
| ggcctgctca | ggtccctgtt | caagagcacc | agtgttggcc | ctctgtactc | tggctgcaga | 180 |
| ctgactttgc | tcaggcctga | aaaggatggg | acagccactg | gagtggatgc | catctgcacc | 240 |
| caccaccctg | accccaaaag | ccctaggctg | gacagagagc | agctgtattg | ggagctgagc | 300 |
| cagctgaccc | acaatatcac | tgagctgggc | cactatgccc | tggacaacga | cagcctcttt | 360 |
| gtcaatggtt | tcactcatcg | gagctctgtg | tccaccacca | gcactcctgg | acccccaca | 420 |
| gtgtatctgg | gagcatctaa | gactccagcc | tcgatatttg | gcccttca | | 468 |

<210> SEQ ID NO 143
<211> LENGTH: 399
<212> TYPE: DNA
<213> ORGANISM: Homo sapiens

<400> SEQUENCE: 143

```
gctgccagcc atctcctgat actattcacc ctcaacttca ccatcactaa cctgcggtat      60
gaggagaaca tgtggcctgg ctccaggaag ttcaacacta cagagagggt ccttcagggc     120
ctgctaaggc ccttgttcaa gaacaccagt gttggccctc tgtactctgg ctccaggctg    180
accttgctca ggccagagaa agatgggaa gccaccggag tggatgccat ctgcacccac     240
cgccctgacc ccacaggccc tgggctggac agagagcagc tgtatttgga gctgagccag    300
ctgacccaca gcatcactga gctgggcccc tacacactgg acaggacag tctctatgtc     360 aatggtttca cccatcggag ctctgtaccc accaccagc                            399
```

<210> SEQ ID NO 144
<211> LENGTH: 453
<212> TYPE: DNA
<213> ORGANISM: Homo sapiens

<400> SEQUENCE: 144

```
accggggtgg tcagcgagga gccattcaca ctgaacttca ccatcaacaa cctgcgctac      60
atggcggaca tgggccaacc cggctccctc aagttcaaca tcacagacaa cgtcatgaag     120
cacctgctca gtcctttgtt ccagaggagc agcctgggtg cacggtacac aggctgcagg    180
gtcatcgcac taaggtctgt gaagaacggt gctgagacac gggtggacct cctctgcacc    240
tacctgcagc ccctcagcgg cccaggtctg cctatcaagc aggtgttcca tgagctgagc    300
cagcagaccc atggcatcac ccggctgggc ccctactctc tggacaaaga cagcctctac    360
cttaacggtt acaatgaacc tggtctagat gagcctccta caactcccaa gccagccacc    420
acattcctgc tcctctgtc agaagccaca aca                                   453
```

<210> SEQ ID NO 145
<211> LENGTH: 465
<212> TYPE: DNA
<213> ORGANISM: Homo sapiens

<400> SEQUENCE: 145

```
gccatggggt accacctgaa gaccctcaca ctcaacttca ccatctccaa tctccagtat      60
tcaccagata tgggcaaggg ctcagctaca ttcaactcca ccgagggggt ccttcagcac    120
ctgctcagac ccttgttcca gaagagcagc atgggcccct ctacttggg ttgccaactg     180 atctccctca ggcctgagaa ggatgggca gccactggtg tggacaccac ctgcacctac     240
caccctgacc ctgtgggccc cgggctggac atacagcagc tttactggga gctgagtcag    300
ctgacccatg gtgtcaccca actgggcttc tatgtcctgg acagggatag cctcttcatc    360
aatggctatg caccccagaa tttatcaatc cggggcgagt accagataaa tttccacatt    420
gtcaactgga acctcagtaa tccagacccc acatcctcag agtac                     465
```

<210> SEQ ID NO 146
<211> LENGTH: 9799
<212> TYPE: PRT
<213> ORGANISM: Homo sapiens
<220> FEATURE:
<221> NAME/KEY: MISC_FEATURE
<222> LOCATION: (1)..(9799)
<223> OTHER INFORMATION: Any "X" = any amino acid

<400> SEQUENCE: 146

Ala Thr Val Pro Phe Met Val Pro Phe Thr Leu Asn Phe Thr Ile Thr
1               5                   10                  15

-continued

```
Asn Leu Gln Tyr Glu Glu Asp Met Arg His Pro Gly Ser Arg Lys Phe
         20                  25                  30

Asn Ala Thr Glu Arg Glu Leu Gln Gly Leu Leu Lys Pro Leu Phe Arg
         35                  40                  45

Asn Ser Ser Leu Glu Tyr Leu Tyr Ser Gly Cys Arg Leu Ala Ser Leu
     50                  55                  60

Arg Pro Glu Lys Asp Ser Ser Ala Met Ala Val Asp Ala Ile Cys Thr
 65              70                  75                  80

His Arg Pro Asp Pro Glu Asp Leu Gly Leu Asp Arg Glu Arg Leu Tyr
                 85                  90                  95

Trp Glu Leu Ser Asn Leu Thr Asn Gly Ile Gln Glu Leu Gly Pro Tyr
                100                 105                 110

Thr Leu Asp Arg Asn Ser Leu Tyr Val Asn Gly Phe Thr His Arg Ser
                115                 120                 125

Ser Met Pro Thr Thr Ser Thr Pro Gly Thr Ser Thr Val Asp Val Gly
         130                 135                 140

Thr Ser Gly Thr Pro Ser Ser Pro Ser Pro Thr Ala Ala Gly Pro
145                 150                 155                 160

Leu Leu Met Pro Phe Thr Leu Asn Phe Thr Ile Thr Asn Leu Gln Tyr
                165                 170                 175

Glu Glu Asp Met Arg Arg Thr Gly Ser Arg Lys Phe Asn Thr Met Glu
             180                 185                 190

Ser Val Leu Gln Gly Leu Leu Lys Pro Leu Phe Lys Asn Thr Ser Val
         195                 200                 205

Gly Pro Leu Tyr Ser Gly Cys Arg Leu Thr Leu Leu Arg Pro Glu Lys
     210                 215                 220

Asp Gly Ala Ala Thr Gly Val Asp Ala Ile Cys Thr His Arg Leu Asp
225                 230                 235                 240

Pro Lys Ser Pro Gly Leu Asn Arg Glu Gln Leu Tyr Trp Glu Leu Ser
             245                 250                 255

Lys Leu Thr Asn Asp Ile Glu Glu Leu Gly Pro Tyr Thr Leu Asp Arg
         260                 265                 270

Asn Ser Leu Tyr Val Asn Gly Phe Thr His Gln Ser Ser Val Ser Thr
     275                 280                 285

Thr Ser Thr Pro Gly Thr Ser Thr Val Asp Leu Arg Thr Ser Gly Thr
290                 295                 300

Pro Ser Ser Leu Ser Ser Pro Thr Ile Met Ala Ala Gly Pro Leu Leu
305                 310                 315                 320

Val Pro Phe Thr Leu Asn Phe Thr Ile Thr Asn Leu Gln Tyr Gly Glu
             325                 330                 335

Asp Met Gly His Pro Gly Ser Arg Lys Phe Asn Thr Thr Glu Arg Val
         340                 345                 350

Leu Gln Gly Leu Leu Gly Pro Ile Phe Lys Asn Thr Ser Val Gly Pro
     355                 360                 365

Leu Tyr Ser Gly Cys Arg Leu Thr Ser Leu Arg Ser Glu Lys Asp Gly
     370                 375                 380

Ala Ala Thr Gly Val Asp Ala Ile Cys Ile His His Leu Asp Pro Lys
385                 390                 395                 400

Ser Pro Gly Leu Asn Arg Glu Arg Leu Tyr Trp Glu Leu Ser Gln Leu
             405                 410                 415

Thr Asn Gly Ile Lys Glu Leu Gly Pro Tyr Thr Leu Asp Arg Asn Ser
         420                 425                 430

Leu Tyr Val Asn Gly Phe Thr His Arg Thr Ser Val Pro Thr Ser Ser
```

```
            435                 440                 445
Thr Pro Gly Thr Ser Thr Val Asp Leu Gly Thr Ser Gly Thr Pro Phe
450                 455                 460
Ser Leu Pro Ser Pro Ala Thr Ala Gly Pro Leu Leu Val Leu Phe Thr
465                 470                 475                 480
Leu Asn Phe Thr Ile Thr Asn Leu Lys Tyr Glu Glu Asp Met His Arg
                485                 490                 495
Pro Gly Ser Arg Lys Phe Asn Thr Thr Glu Arg Val Leu Gln Thr Leu
                500                 505                 510
Leu Gly Pro Met Phe Lys Asn Thr Ser Val Gly Leu Leu Tyr Ser Gly
                515                 520                 525
Cys Arg Leu Thr Leu Leu Arg Ser Glu Lys Asp Gly Ala Ala Thr Gly
530                 535                 540
Val Asp Ala Ile Cys Thr His Arg Leu Asp Pro Lys Ser Pro Gly Leu
545                 550                 555                 560
Asp Arg Glu Gln Leu Tyr Trp Glu Leu Ser Gln Leu Thr Asn Gly Ile
                565                 570                 575
Lys Glu Leu Gly Pro Tyr Thr Leu Asp Arg Asn Ser Leu Tyr Val Asn
                580                 585                 590
Gly Phe Thr His Trp Ile Pro Val Pro Thr Ser Ser Thr Pro Gly Thr
                595                 600                 605
Ser Thr Val Asp Leu Gly Ser Gly Thr Pro Ser Ser Leu Pro Ser Pro
610                 615                 620
Thr Ala Gly Pro Leu Leu Val Pro Phe Thr Leu Asn Phe Thr Ile
625                 630                 635                 640
Thr Asn Leu Gln Tyr Glu Glu Asp Met His His Pro Gly Ser Arg Lys
                645                 650                 655
Phe Asn Thr Thr Glu Arg Val Leu Gln Gly Leu Leu Gly Pro Met Phe
                660                 665                 670
Lys Asn Thr Ser Val Gly Leu Leu Tyr Ser Gly Cys Arg Leu Thr Leu
                675                 680                 685
Leu Arg Ser Glu Lys Asp Gly Ala Ala Thr Gly Val Asp Ala Ile Cys
                690                 695                 700
Thr His Arg Leu Asp Pro Lys Ser Pro Gly Val Asp Arg Glu Gln Leu
705                 710                 715                 720
Tyr Trp Glu Leu Ser Gln Leu Thr Asn Gly Ile Lys Glu Leu Gly Pro
                725                 730                 735
Tyr Thr Leu Asp Arg Asn Ser Leu Tyr Val Asn Gly Phe Thr His Gln
                740                 745                 750
Thr Ser Ala Pro Asn Thr Ser Thr Pro Gly Thr Ser Thr Val Asp Leu
                755                 760                 765
Gly Thr Ser Gly Thr Pro Ser Ser Leu Pro Ser Pro Thr Ser Ala Gly
                770                 775                 780
Pro Leu Leu Val Pro Phe Thr Leu Asn Phe Thr Ile Thr Asn Leu Gln
785                 790                 795                 800
Tyr Glu Glu Asp Met Arg His Pro Gly Ser Arg Lys Phe Asn Thr Thr
                805                 810                 815
Glu Arg Val Leu Gln Gly Leu Leu Lys Pro Leu Phe Lys Ser Thr Ser
                820                 825                 830
Val Gly Pro Leu Tyr Ser Gly Cys Arg Leu Thr Leu Leu Arg Ser Glu
                835                 840                 845
Lys Asp Gly Ala Ala Thr Gly Val Asp Ala Ile Cys Thr His Arg Leu
850                 855                 860
```

```
Asp Pro Lys Ser Pro Gly Val Asp Arg Glu Gln Leu Tyr Trp Glu Leu
865                 870                 875                 880

Ser Gln Leu Thr Asn Gly Ile Lys Glu Leu Gly Pro Tyr Thr Leu Asp
                885                 890                 895

Arg Asn Ser Leu Tyr Val Asn Gly Phe Thr His Gln Thr Ser Ala Pro
            900                 905                 910

Asn Thr Ser Thr Pro Gly Thr Ser Thr Val Asp Leu Gly Thr Ser Gly
        915                 920                 925

Thr Pro Ser Ser Leu Pro Ser Pro Thr Ser Ala Gly Pro Leu Leu Val
    930                 935                 940

Pro Phe Thr Leu Asn Phe Thr Ile Thr Asn Leu Gln Tyr Glu Glu Asp
945                 950                 955                 960

Met His His Pro Gly Ser Arg Lys Phe Asn Thr Thr Glu Arg Val Leu
                965                 970                 975

Gln Gly Leu Leu Gly Pro Met Phe Lys Asn Thr Ser Val Gly Leu Leu
            980                 985                 990

Tyr Ser Gly Cys Arg Leu Thr Leu Leu Arg Pro Glu Lys Asn Gly Ala
        995                 1000                1005

Ala Thr Gly Met Asp Ala Ile Cys Ser His Arg Leu Asp Pro Lys
    1010                1015                1020

Ser Pro Gly Leu Asn Arg Glu Gln Leu Tyr Trp Glu Leu Ser Gln
    1025                1030                1035

Leu Thr His Gly Ile Lys Glu Leu Gly Pro Tyr Thr Leu Asp Arg
    1040                1045                1050

Asn Ser Leu Tyr Val Asn Gly Phe Thr His Arg Ser Ser Val Ala
    1055                1060                1065

Pro Thr Ser Thr Pro Gly Thr Ser Thr Val Asp Leu Gly Thr Ser
    1070                1075                1080

Gly Thr Pro Ser Ser Leu Pro Ser Pro Thr Thr Ala Val Pro Leu
    1085                1090                1095

Leu Val Pro Phe Thr Leu Asn Phe Thr Ile Thr Asn Leu Gln Tyr
    1100                1105                1110

Gly Glu Asp Met Arg His Pro Gly Ser Arg Lys Phe Asn Thr Thr
    1115                1120                1125

Glu Arg Val Leu Gln Gly Leu Leu Gly Pro Leu Phe Lys Asn Ser
    1130                1135                1140

Ser Val Gly Pro Leu Tyr Ser Gly Cys Arg Leu Ile Ser Leu Arg
    1145                1150                1155

Ser Glu Lys Asp Gly Ala Ala Thr Gly Val Asp Ala Ile Cys Thr
    1160                1165                1170

His His Leu Asn Pro Gln Ser Pro Gly Leu Asp Arg Glu Gln Leu
    1175                1180                1185

Tyr Trp Gln Leu Ser Gln Met Thr Asn Gly Ile Lys Glu Leu Gly
    1190                1195                1200

Pro Tyr Thr Leu Asp Arg Asn Ser Leu Tyr Val Asn Gly Phe Thr
    1205                1210                1215

His Arg Ser Ser Gly Leu Thr Thr Ser Thr Pro Trp Thr Ser Thr
    1220                1225                1230

Val Asp Leu Gly Thr Ser Gly Thr Pro Ser Pro Val Pro Ser Pro
    1235                1240                1245

Thr Thr Ala Gly Pro Leu Leu Val Pro Phe Thr Leu Asn Phe Thr
    1250                1255                1260
```

```
Ile Thr Asn Leu Gln Tyr Glu Glu Asp Met His Arg Pro Gly Ser
1265                1270                1275

Arg Lys Phe Asn Ala Thr Glu Arg Val Leu Gln Gly Leu Leu Ser
1280                1285                1290

Pro Ile Phe Lys Asn Ser Ser Val Gly Pro Leu Tyr Ser Gly Cys
1295                1300                1305

Arg Leu Thr Ser Leu Arg Pro Glu Lys Asp Gly Ala Ala Thr Gly
1310                1315                1320

Met Asp Ala Val Cys Leu Tyr His Pro Asn Pro Lys Arg Pro Gly
1325                1330                1335

Leu Asp Arg Glu Gln Leu Tyr Trp Glu Leu Ser Gln Leu Thr His
1340                1345                1350

Asn Ile Thr Glu Leu Gly Pro Tyr Ser Leu Asp Arg Asp Ser Leu
1355                1360                1365

Tyr Val Asn Gly Phe Thr His Gln Asn Ser Val Pro Thr Thr Ser
1370                1375                1380

Thr Pro Gly Thr Ser Thr Val Tyr Trp Ala Thr Thr Gly Thr Pro
1385                1390                1395

Ser Ser Phe Pro Gly His Thr Glu Pro Gly Pro Leu Leu Ile Pro
1400                1405                1410

Phe Thr Phe Asn Phe Thr Ile Thr Asn Leu His Tyr Glu Glu Asn
1415                1420                1425

Met Gln His Pro Gly Ser Arg Lys Phe Asn Thr Thr Glu Arg Val
1430                1435                1440

Leu Gln Gly Leu Leu Lys Pro Leu Phe Lys Asn Thr Ser Val Gly
1445                1450                1455

Pro Leu Tyr Ser Gly Cys Arg Leu Thr Ser Leu Arg Pro Glu Lys
1460                1465                1470

Asp Gly Ala Ala Thr Gly Met Asp Ala Val Cys Leu Tyr His Pro
1475                1480                1485

Asn Pro Lys Arg Pro Gly Leu Asp Arg Glu Gln Leu Tyr Cys Glu
1490                1495                1500

Leu Ser Gln Leu Thr His Asn Ile Thr Glu Leu Gly Pro Tyr Ser
1505                1510                1515

Leu Asp Arg Asp Ser Leu Tyr Val Asn Gly Phe Thr His Gln Asn
1520                1525                1530

Ser Val Pro Thr Thr Ser Pro Gly Thr Ser Thr Val Tyr Trp
1535                1540                1545

Ala Thr Thr Gly Thr Pro Ser Ser Phe Pro Gly His Thr Glu Pro
1550                1555                1560

Gly Pro Leu Leu Ile Pro Phe Thr Phe Asn Phe Thr Ile Thr Asn
1565                1570                1575

Leu His Tyr Glu Glu Asn Met Gln His Pro Gly Ser Arg Lys Phe
1580                1585                1590

Asn Thr Thr Glu Arg Val Leu Gln Gly Leu Leu Lys Pro Leu Phe
1595                1600                1605

Lys Asn Thr Ser Val Gly Pro Leu Tyr Ser Gly Cys Arg Leu Thr
1610                1615                1620

Leu Leu Arg Pro Glu Lys His Glu Ala Ala Thr Gly Val Asp Thr
1625                1630                1635

Ile Cys Thr His Arg Val Asp Pro Ile Gly Pro Gly Leu Asp Arg
1640                1645                1650

Glu Arg Leu Tyr Trp Glu Leu Ser Gln Leu Thr Asn Ser Ile Thr
```

-continued

|  | 1655 |  |  | 1660 |  |  | 1665 |  |  |
| --- | --- | --- | --- | --- | --- | --- | --- | --- | --- |
| Glu | Leu | Gly | Pro | Tyr | Thr | Leu | Asp | Arg | Asp | Ser | Leu | Tyr | Val | Asn |
|  | 1670 |  |  |  | 1675 |  |  |  | 1680 |
| Gly | Phe | Asn | Pro | Arg | Ser | Ser | Val | Pro | Thr | Thr | Ser | Thr | Pro | Gly |
|  | 1685 |  |  |  | 1690 |  |  |  | 1695 |
| Thr | Ser | Thr | Val | His | Leu | Ala | Thr | Ser | Gly | Thr | Pro | Ser | Ser | Leu |
|  | 1700 |  |  |  | 1705 |  |  |  | 1710 |
| Pro | Gly | His | Thr | Ala | Pro | Val | Pro | Leu | Leu | Ile | Pro | Phe | Thr | Leu |
|  | 1715 |  |  |  | 1720 |  |  |  | 1725 |
| Asn | Phe | Thr | Ile | Thr | Asn | Leu | His | Tyr | Glu | Glu | Asn | Met | Gln | His |
|  | 1730 |  |  |  | 1735 |  |  |  | 1740 |
| Pro | Gly | Ser | Arg | Lys | Phe | Asn | Thr | Thr | Glu | Arg | Val | Leu | Gln | Gly |
|  | 1745 |  |  |  | 1750 |  |  |  | 1755 |
| Leu | Leu | Lys | Pro | Leu | Phe | Lys | Asn | Thr | Ser | Val | Gly | Pro | Leu | Tyr |
|  | 1760 |  |  |  | 1765 |  |  |  | 1770 |
| Ser | Gly | Cys | Arg | Leu | Thr | Leu | Leu | Arg | Pro | Glu | Lys | His | Glu | Ala |
|  | 1775 |  |  |  | 1780 |  |  |  | 1785 |
| Ala | Thr | Gly | Val | Asp | Thr | Ile | Cys | Thr | His | Arg | Val | Asp | Pro | Ile |
|  | 1790 |  |  |  | 1795 |  |  |  | 1800 |
| Gly | Pro | Gly | Leu | Asp | Arg | Glu | Xaa | Leu | Tyr | Trp | Glu | Leu | Ser | Xaa |
|  | 1805 |  |  |  | 1810 |  |  |  | 1815 |
| Leu | Thr | Xaa | Xaa | Ile | Xaa | Glu | Leu | Gly | Pro | Tyr | Xaa | Leu | Asp | Arg |
|  | 1820 |  |  |  | 1825 |  |  |  | 1830 |
| Xaa | Ser | Leu | Tyr | Val | Asn | Gly | Phe | Xaa | Xaa | Xaa | Xaa | Xaa | Xaa | Xaa |
|  | 1835 |  |  |  | 1840 |  |  |  | 1845 |
| Xaa | Thr | Ser | Thr | Pro | Gly | Thr | Ser | Xaa | Val | Xaa | Leu | Xaa | Thr | Ser |
|  | 1850 |  |  |  | 1855 |  |  |  | 1860 |
| Gly | Thr | Pro | Xaa | Xaa | Xaa | Pro | Xaa | Xaa | Thr | Ser | Ala | Gly | Pro | Leu |
|  | 1865 |  |  |  | 1870 |  |  |  | 1875 |
| Leu | Val | Pro | Phe | Thr | Leu | Asn | Phe | Thr | Ile | Thr | Asn | Leu | Gln | Tyr |
|  | 1880 |  |  |  | 1885 |  |  |  | 1890 |
| Glu | Glu | Asp | Met | His | His | Pro | Gly | Ser | Arg | Lys | Phe | Asn | Thr | Thr |
|  | 1895 |  |  |  | 1900 |  |  |  | 1905 |
| Glu | Arg | Val | Leu | Gln | Gly | Leu | Leu | Gly | Pro | Met | Phe | Lys | Asn | Thr |
|  | 1910 |  |  |  | 1915 |  |  |  | 1920 |
| Ser | Val | Gly | Leu | Leu | Tyr | Ser | Gly | Cys | Arg | Leu | Thr | Leu | Leu | Arg |
|  | 1925 |  |  |  | 1930 |  |  |  | 1935 |
| Pro | Glu | Lys | Asn | Gly | Ala | Ala | Thr | Gly | Met | Asp | Ala | Ile | Cys | Ser |
|  | 1940 |  |  |  | 1945 |  |  |  | 1950 |
| His | Arg | Leu | Asp | Pro | Lys | Ser | Pro | Gly | Leu | Asp | Arg | Glu | Gln | Leu |
|  | 1955 |  |  |  | 1960 |  |  |  | 1965 |
| Tyr | Trp | Glu | Leu | Ser | Gln | Leu | Thr | His | Gly | Ile | Lys | Glu | Leu | Gly |
|  | 1970 |  |  |  | 1975 |  |  |  | 1980 |
| Pro | Tyr | Thr | Leu | Asp | Arg | Asn | Ser | Leu | Tyr | Val | Asn | Gly | Phe | Thr |
|  | 1985 |  |  |  | 1990 |  |  |  | 1995 |
| His | Arg | Ser | Ser | Val | Ala | Pro | Thr | Ser | Thr | Pro | Gly | Thr | Ser | Thr |
|  | 2000 |  |  |  | 2005 |  |  |  | 2010 |
| Val | Asp | Leu | Gly | Thr | Ser | Gly | Thr | Pro | Ser | Ser | Leu | Pro | Ser | Pro |
|  | 2015 |  |  |  | 2020 |  |  |  | 2025 |
| Thr | Thr | Ala | Val | Pro | Leu | Leu | Val | Pro | Phe | Thr | Leu | Asn | Phe | Thr |
|  | 2030 |  |  |  | 2035 |  |  |  | 2040 |
| Ile | Thr | Asn | Leu | Gln | Tyr | Gly | Glu | Asp | Met | Arg | His | Pro | Gly | Ser |
|  | 2045 |  |  |  | 2050 |  |  |  | 2055 |

-continued

```
Arg Lys Phe Asn Thr Thr Glu Arg Val Leu Gln Gly Leu Leu Gly
2060                2065                2070

Pro Leu Phe Lys Asn Ser Ser Val Gly Pro Leu Tyr Ser Gly Cys
2075                2080                2085

Arg Leu Ile Ser Leu Arg Ser Glu Lys Asp Gly Ala Ala Thr Gly
2090                2095                2100

Val Asp Ala Ile Cys Thr His His Leu Asn Pro Gln Ser Pro Gly
2105                2110                2115

Leu Asp Arg Glu Gln Leu Tyr Trp Gln Leu Ser Gln Met Thr Asn
2120                2125                2130

Gly Ile Lys Glu Leu Gly Pro Tyr Thr Leu Asp Arg Asn Ser Leu
2135                2140                2145

Tyr Val Asn Gly Phe Thr His Arg Ser Ser Gly Leu Thr Thr Ser
2150                2155                2160

Thr Pro Trp Thr Ser Thr Val Asp Leu Gly Thr Ser Gly Thr Pro
2165                2170                2175

Ser Pro Val Pro Ser Pro Thr Thr Ala Gly Pro Leu Leu Val Pro
2180                2185                2190

Phe Thr Leu Asn Phe Thr Ile Thr Asn Leu Gln Tyr Glu Glu Asp
2195                2200                2205

Met His Arg Pro Gly Ser Arg Lys Phe Asn Ala Thr Glu Arg Val
2210                2215                2220

Leu Gln Gly Leu Leu Ser Pro Ile Phe Lys Asn Ser Ser Val Gly
2225                2230                2235

Pro Leu Tyr Ser Gly Cys Arg Leu Thr Ser Leu Arg Pro Glu Lys
2240                2245                2250

Asp Gly Ala Ala Thr Gly Met Asp Ala Val Cys Leu Tyr His Pro
2255                2260                2265

Asn Pro Lys Arg Pro Gly Leu Asp Arg Glu Gln Leu Tyr Trp Glu
2270                2275                2280

Leu Ser Gln Leu Thr His Asn Ile Thr Glu Leu Gly Pro Tyr Ser
2285                2290                2295

Leu Asp Arg Asp Ser Leu Tyr Val Asn Gly Phe Thr His Gln Ser
2300                2305                2310

Ser Met Thr Thr Thr Arg Thr Pro Asp Thr Ser Thr Met His Leu
2315                2320                2325

Ala Thr Ser Arg Thr Pro Ala Ser Leu Ser Gly Pro Thr Thr Ala
2330                2335                2340

Ser Pro Leu Leu Val Leu Phe Thr Ile Asn Cys Thr Ile Thr Asn
2345                2350                2355

Leu Gln Tyr Glu Glu Asp Met Arg Arg Thr Gly Ser Arg Lys Phe
2360                2365                2370

Asn Thr Met Glu Ser Val Leu Gln Gly Leu Leu Lys Pro Leu Phe
2375                2380                2385

Lys Asn Thr Ser Val Gly Pro Leu Tyr Ser Gly Cys Arg Leu Thr
2390                2395                2400

Leu Leu Arg Pro Lys Lys Asp Gly Ala Ala Thr Gly Val Asp Ala
2405                2410                2415

Ile Cys Thr His Arg Leu Asp Pro Lys Ser Pro Gly Leu Asn Arg
2420                2425                2430

Glu Gln Leu Tyr Trp Glu Leu Ser Lys Leu Thr Asn Asp Ile Glu
2435                2440                2445
```

-continued

```
Glu Leu Gly Pro Tyr Thr Leu Asp Arg Asn Ser Leu Tyr Val Asn
2450                2455                2460

Gly Phe Thr His Gln Ser Ser Val Ser Thr Ser Thr Pro Gly
2465                2470                2475

Thr Ser Thr Val Asp Leu Arg Thr Ser Gly Thr Pro Ser Ser Leu
2480                2485                2490

Ser Ser Pro Thr Ile Met Xaa Xaa Xaa Pro Leu Leu Xaa Pro Phe
2495                2500                2505

Thr Leu Asn Phe Thr Ile Thr Asn Leu Xaa Tyr Glu Glu Xaa Met
2510                2515                2520

Xaa Xaa Pro Gly Ser Arg Lys Phe Asn Thr Thr Glu Arg Val Leu
2525                2530                2535

Gln Gly Leu Leu Arg Pro Leu Phe Lys Asn Thr Ser Val Ser Ser
2540                2545                2550

Leu Tyr Ser Gly Cys Arg Leu Thr Leu Leu Arg Pro Glu Lys Asp
2555                2560                2565

Gly Ala Ala Thr Arg Val Asp Ala Ala Cys Thr Tyr Arg Pro Asp
2570                2575                2580

Pro Lys Ser Pro Gly Leu Asp Arg Glu Gln Leu Tyr Trp Glu Leu
2585                2590                2595

Ser Gln Leu Thr His Ser Ile Thr Glu Leu Gly Pro Tyr Thr Leu
2600                2605                2610

Asp Arg Val Ser Leu Tyr Val Asn Gly Phe Asn Pro Arg Ser Ser
2615                2620                2625

Val Pro Thr Thr Ser Thr Pro Gly Thr Ser Thr Val His Leu Ala
2630                2635                2640

Thr Ser Gly Thr Pro Ser Ser Leu Pro Gly His Thr Ala Pro Val
2645                2650                2655

Pro Leu Leu Ile Pro Phe Thr Leu Asn Phe Thr Ile Thr Asn Leu
2660                2665                2670

His Tyr Glu Glu Asn Met Gln His Pro Gly Ser Arg Lys Phe Asn
2675                2680                2685

Thr Thr Glu Arg Val Leu Gln Gly Leu Leu Arg Pro Leu Phe Lys
2690                2695                2700

Ser Thr Ser Val Gly Pro Leu Tyr Ser Gly Cys Arg Leu Thr Leu
2705                2710                2715

Leu Arg Pro Glu Lys His Gly Ala Ala Thr Gly Val Asp Ala Ile
2720                2725                2730

Cys Thr Leu Arg Leu Asp Pro Thr Gly Pro Gly Leu Asp Arg Glu
2735                2740                2745

Arg Leu Tyr Trp Glu Leu Ser Gln Leu Thr Asn Ser Val Thr Glu
2750                2755                2760

Leu Gly Pro Tyr Thr Leu Asp Arg Asp Ser Leu Tyr Val Asn Gly
2765                2770                2775

Phe Thr Gln Arg Ser Ser Val Pro Thr Thr Ser Ile Pro Gly Thr
2780                2785                2790

Ser Ala Val His Leu Glu Thr Ser Gly Thr Pro Ala Ser Leu Pro
2795                2800                2805

Gly His Thr Ala Pro Gly Pro Leu Leu Val Pro Phe Thr Leu Asn
2810                2815                2820

Phe Thr Ile Thr Asn Leu Gln Tyr Glu Val Asp Met Arg His Pro
2825                2830                2835

Gly Ser Arg Lys Phe Asn Thr Thr Glu Arg Val Leu Gln Gly Leu
```

-continued

|     |     |     |     |     |     |     |     |     |     |     |     |
|-----|-----|-----|-----|-----|-----|-----|-----|-----|-----|-----|-----|
|     | 2840 |     |     | 2845 |     |     | 2850 |     |     |     |     |
| Leu | Lys | Pro | Leu | Phe | Lys | Ser | Thr | Ser | Val | Gly | Pro | Leu | Tyr | Ser |
|     | 2855 |     |     |     | 2860 |     |     | 2865 |     |     |     |
| Gly | Cys | Arg | Leu | Thr | Leu | Leu | Arg | Pro | Glu | Lys | Arg | Gly | Ala | Ala |
|     | 2870 |     |     |     | 2875 |     |     | 2880 |     |     |     |
| Thr | Gly | Val | Asp | Thr | Ile | Cys | Thr | His | Arg | Leu | Asp | Pro | Leu | Asn |
|     | 2885 |     |     |     | 2890 |     |     | 2895 |     |     |     |
| Pro | Gly | Leu | Asp | Arg | Glu | Gln | Leu | Tyr | Trp | Glu | Leu | Ser | Lys | Leu |
|     | 2900 |     |     |     | 2905 |     |     | 2910 |     |     |     |
| Thr | Arg | Gly | Ile | Ile | Glu | Leu | Gly | Pro | Tyr | Leu | Leu | Asp | Arg | Gly |
|     | 2915 |     |     |     | 2920 |     |     | 2925 |     |     |     |
| Ser | Leu | Tyr | Val | Asn | Gly | Phe | Thr | His | Arg | Asn | Phe | Val | Pro | Ile |
|     | 2930 |     |     |     | 2935 |     |     | 2940 |     |     |     |
| Thr | Ser | Thr | Pro | Gly | Thr | Ser | Thr | Val | His | Leu | Gly | Thr | Ser | Glu |
|     | 2945 |     |     |     | 2950 |     |     | 2955 |     |     |     |
| Thr | Pro | Ser | Ser | Leu | Pro | Arg | Pro | Ile | Val | Pro | Gly | Pro | Leu | Leu |
|     | 2960 |     |     |     | 2965 |     |     | 2970 |     |     |     |
| Val | Pro | Phe | Thr | Leu | Asn | Phe | Thr | Ile | Thr | Asn | Leu | Gln | Tyr | Glu |
|     | 2975 |     |     |     | 2980 |     |     | 2985 |     |     |     |
| Glu | Ala | Met | Arg | His | Pro | Gly | Ser | Arg | Lys | Phe | Asn | Thr | Thr | Glu |
|     | 2990 |     |     |     | 2995 |     |     | 3000 |     |     |     |
| Arg | Val | Leu | Gln | Gly | Leu | Leu | Arg | Pro | Leu | Phe | Lys | Asn | Thr | Ser |
|     | 3005 |     |     |     | 3010 |     |     | 3015 |     |     |     |
| Ile | Gly | Pro | Leu | Tyr | Ser | Ser | Cys | Arg | Leu | Thr | Leu | Leu | Arg | Pro |
|     | 3020 |     |     |     | 3025 |     |     | 3030 |     |     |     |
| Glu | Lys | Asp | Lys | Ala | Ala | Thr | Arg | Val | Asp | Ala | Ile | Cys | Thr | His |
|     | 3035 |     |     |     | 3040 |     |     | 3045 |     |     |     |
| His | Pro | Asp | Pro | Gln | Ser | Pro | Gly | Leu | Asn | Arg | Glu | Gln | Leu | Tyr |
|     | 3050 |     |     |     | 3055 |     |     | 3060 |     |     |     |
| Trp | Glu | Leu | Ser | Gln | Leu | Thr | His | Gly | Ile | Thr | Glu | Leu | Gly | Pro |
|     | 3065 |     |     |     | 3070 |     |     | 3075 |     |     |     |
| Tyr | Thr | Leu | Asp | Arg | Asp | Ser | Leu | Tyr | Val | Asp | Gly | Phe | Thr | His |
|     | 3080 |     |     |     | 3085 |     |     | 3090 |     |     |     |
| Trp | Ser | Pro | Ile | Pro | Thr | Thr | Ser | Thr | Pro | Gly | Thr | Ser | Ile | Val |
|     | 3095 |     |     |     | 3100 |     |     | 3105 |     |     |     |
| Asn | Leu | Gly | Thr | Ser | Gly | Ile | Pro | Pro | Ser | Leu | Pro | Glu | Thr | Thr |
|     | 3110 |     |     |     | 3115 |     |     | 3120 |     |     |     |
| Xaa | Xaa | Xaa | Pro | Leu | Leu | Xaa | Pro | Phe | Thr | Leu | Asn | Phe | Thr | Ile |
|     | 3125 |     |     |     | 3130 |     |     | 3135 |     |     |     |
| Thr | Asn | Leu | Xaa | Tyr | Glu | Glu | Xaa | Met | Xaa | Xaa | Pro | Gly | Ser | Arg |
|     | 3140 |     |     |     | 3145 |     |     | 3150 |     |     |     |
| Lys | Phe | Asn | Thr | Thr | Glu | Arg | Val | Leu | Gln | Gly | Leu | Leu | Lys | Pro |
|     | 3155 |     |     |     | 3160 |     |     | 3165 |     |     |     |
| Leu | Phe | Arg | Asn | Ser | Ser | Leu | Glu | Tyr | Leu | Tyr | Ser | Gly | Cys | Arg |
|     | 3170 |     |     |     | 3175 |     |     | 3180 |     |     |     |
| Leu | Ala | Ser | Leu | Arg | Pro | Glu | Lys | Asp | Ser | Ser | Ala | Met | Ala | Val |
|     | 3185 |     |     |     | 3190 |     |     | 3195 |     |     |     |
| Asp | Ala | Ile | Cys | Thr | His | Arg | Pro | Asp | Pro | Glu | Asp | Leu | Gly | Leu |
|     | 3200 |     |     |     | 3205 |     |     | 3210 |     |     |     |
| Asp | Arg | Glu | Arg | Leu | Tyr | Trp | Glu | Leu | Ser | Asn | Leu | Thr | Asn | Gly |
|     | 3215 |     |     |     | 3220 |     |     | 3225 |     |     |     |
| Ile | Gln | Glu | Leu | Gly | Pro | Tyr | Thr | Leu | Asp | Arg | Asn | Ser | Leu | Tyr |
|     | 3230 |     |     |     | 3235 |     |     | 3240 |     |     |     |

```
Val Asn Gly Phe Thr His Arg Ser Ser Phe Leu Thr Thr Ser Thr
3245                3250                3255

Pro Trp Thr Ser Thr Val Asp Leu Gly Thr Ser Gly Thr Pro Ser
3260                3265                3270

Pro Val Pro Ser Pro Thr Thr Ala Gly Pro Leu Leu Val Pro Phe
3275                3280                3285

Thr Leu Asn Phe Thr Ile Thr Asn Leu Gln Tyr Glu Glu Asp Met
3290                3295                3300

His Arg Pro Gly Ser Arg Arg Phe Asn Thr Thr Glu Arg Val Leu
3305                3310                3315

Gln Gly Leu Leu Thr Pro Leu Phe Lys Asn Thr Ser Val Gly Pro
3320                3325                3330

Leu Tyr Ser Gly Cys Arg Leu Thr Leu Leu Arg Pro Glu Lys Gln
3335                3340                3345

Glu Ala Ala Thr Gly Val Asp Thr Ile Cys Thr His Arg Val Asp
3350                3355                3360

Pro Ile Gly Pro Gly Leu Asp Arg Glu Arg Leu Tyr Trp Glu Leu
3365                3370                3375

Ser Gln Leu Thr Asn Ser Ile Thr Glu Leu Gly Pro Tyr Thr Leu
3380                3385                3390

Asp Arg Asp Ser Leu Tyr Val Asn Gly Phe Asn Pro Trp Ser Ser
3395                3400                3405

Val Pro Thr Thr Ser Thr Pro Gly Thr Ser Thr Val His Leu Ala
3410                3415                3420

Thr Ser Gly Thr Pro Ser Ser Leu Pro Gly His Thr Ala Pro Val
3425                3430                3435

Pro Leu Leu Ile Pro Phe Thr Leu Asn Phe Thr Ile Thr Asp Leu
3440                3445                3450

His Tyr Glu Glu Asn Met Gln His Pro Gly Ser Arg Lys Phe Asn
3455                3460                3465

Thr Thr Glu Arg Val Leu Gln Gly Leu Leu Lys Pro Leu Phe Lys
3470                3475                3480

Ser Thr Ser Val Gly Pro Leu Tyr Ser Gly Cys Arg Leu Thr Leu
3485                3490                3495

Leu Arg Pro Glu Lys His Gly Ala Ala Thr Gly Val Asp Ala Ile
3500                3505                3510

Cys Thr Leu Arg Leu Asp Pro Thr Gly Pro Gly Leu Asp Arg Glu
3515                3520                3525

Arg Leu Tyr Trp Glu Leu Ser Gln Leu Thr Asn Ser Val Thr Glu
3530                3535                3540

Leu Gly Pro Tyr Thr Leu Asp Arg Asp Ser Leu Tyr Val Asn Gly
3545                3550                3555

Phe Thr His Arg Ser Ser Val Pro Thr Thr Ser Ile Pro Gly Thr
3560                3565                3570

Ser Ala Val His Leu Glu Thr Ser Gly Thr Pro Ala Ser Leu Pro
3575                3580                3585

Gly His Thr Ala Pro Gly Pro Leu Leu Val Pro Phe Thr Leu Asn
3590                3595                3600

Phe Thr Ile Thr Asn Leu Gln Tyr Glu Glu Asp Met Arg His Pro
3605                3610                3615

Gly Ser Arg Lys Phe Ser Thr Thr Glu Arg Val Leu Gln Gly Leu
3620                3625                3630
```

-continued

```
Leu Lys Pro Leu Phe Lys Asn Thr Ser Val Ser Leu Tyr Ser
    3635            3640            3645

Gly Cys Arg Leu Thr Leu Leu Arg Pro Glu Lys Asp Gly Ala Ala
    3650            3655            3660

Thr Arg Val Asp Ala Val Cys Thr His Arg Pro Asp Pro Lys Ser
    3665            3670            3675

Pro Gly Leu Asp Arg Glu Arg Leu Tyr Trp Lys Leu Ser Gln Leu
    3680            3685            3690

Thr His Gly Ile Thr Glu Leu Gly Pro Tyr Thr Leu Asp Arg His
    3695            3700            3705

Ser Leu Tyr Val Asn Gly Phe Thr His Gln Ser Ser Met Thr Thr
    3710            3715            3720

Thr Arg Thr Pro Asp Thr Ser Thr Met His Leu Ala Thr Ser Arg
    3725            3730            3735

Thr Pro Ala Ser Leu Ser Gly Pro Thr Thr Ala Ser Pro Leu Leu
    3740            3745            3750

Val Leu Phe Thr Ile Asn Phe Thr Ile Thr Asn Gln Arg Tyr Glu
    3755            3760            3765

Glu Asn Met His His Pro Gly Ser Arg Lys Phe Asn Thr Thr Glu
    3770            3775            3780

Arg Val Leu Gln Gly Leu Leu Arg Pro Val Phe Lys Asn Thr Ser
    3785            3790            3795

Val Gly Pro Leu Tyr Ser Gly Cys Arg Leu Thr Leu Leu Arg Pro
    3800            3805            3810

Lys Lys Asp Gly Ala Ala Thr Lys Val Asp Ala Ile Cys Thr Tyr
    3815            3820            3825

Arg Pro Asp Pro Lys Ser Pro Gly Leu Asp Arg Glu Gln Leu Tyr
    3830            3835            3840

Trp Glu Leu Ser Gln Leu Thr His Ser Ile Thr Glu Leu Gly Pro
    3845            3850            3855

Tyr Thr Gln Asp Arg Asp Ser Leu Tyr Val Asn Gly Phe Thr His
    3860            3865            3870

Arg Ser Ser Val Pro Thr Thr Ser Ile Pro Gly Thr Ser Ala Val
    3875            3880            3885

His Leu Glu Thr Ser Gly Thr Pro Ala Ser Leu Pro Gly His Thr
    3890            3895            3900

Ala Pro Gly Pro Leu Leu Val Pro Phe Thr Leu Asn Phe Thr Ile
    3905            3910            3915

Thr Asn Leu Gln Tyr Glu Glu Asp Met Arg His Pro Gly Ser Arg
    3920            3925            3930

Lys Phe Asn Thr Thr Glu Arg Val Leu Gln Gly Leu Leu Lys Pro
    3935            3940            3945

Leu Phe Lys Ser Thr Ser Val Gly Pro Leu Tyr Ser Gly Cys Arg
    3950            3955            3960

Leu Thr Leu Leu Arg Pro Glu Lys Arg Gly Ala Ala Thr Gly Val
    3965            3970            3975

Asp Thr Ile Cys Thr His Arg Leu Asp Pro Leu Asn Pro Gly Leu
    3980            3985            3990

Asp Arg Glu Gln Leu Tyr Trp Glu Leu Ser Lys Leu Thr Arg Gly
    3995            4000            4005

Ile Ile Glu Leu Gly Pro Tyr Leu Leu Asp Arg Gly Ser Leu Tyr
    4010            4015            4020

Val Asn Gly Phe Thr His Arg Thr Ser Val Pro Thr Thr Ser Thr
```

```
                4025                4030                4035
Pro Gly Thr Ser Thr Val Asp Leu Gly Thr Ser Gly Thr Pro Phe
    4040                4045                4050

Ser Leu Pro Ser Pro Ala Xaa Xaa Xaa Pro Leu Leu Xaa Pro Phe
    4055                4060                4065

Thr Leu Asn Phe Thr Ile Thr Asn Leu Xaa Tyr Glu Glu Xaa Met
    4070                4075                4080

Xaa Xaa Pro Gly Ser Arg Lys Phe Asn Thr Thr Glu Arg Val Leu
    4085                4090                4095

Gln Thr Leu Leu Gly Pro Met Phe Lys Asn Thr Ser Val Gly Leu
    4100                4105                4110

Leu Tyr Ser Gly Cys Arg Leu Thr Leu Leu Arg Ser Glu Lys Asp
    4115                4120                4125

Gly Ala Ala Thr Gly Val Asp Ala Ile Cys Thr His Arg Leu Asp
    4130                4135                4140

Pro Lys Ser Pro Gly Val Asp Arg Glu Gln Leu Tyr Trp Glu Leu
    4145                4150                4155

Ser Gln Leu Thr Asn Gly Ile Lys Glu Leu Gly Pro Tyr Thr Leu
    4160                4165                4170

Asp Arg Asn Ser Leu Tyr Val Asn Gly Phe Thr His Trp Ile Pro
    4175                4180                4185

Val Pro Thr Ser Ser Thr Pro Gly Thr Ser Thr Val Asp Leu Gly
    4190                4195                4200

Ser Gly Thr Pro Ser Leu Pro Ser Ser Pro Thr Thr Ala Gly Pro
    4205                4210                4215

Leu Leu Val Pro Phe Thr Leu Asn Phe Thr Ile Thr Asn Leu Lys
    4220                4225                4230

Tyr Glu Glu Asp Met His Cys Pro Gly Ser Arg Lys Phe Asn Thr
    4235                4240                4245

Thr Glu Arg Val Leu Gln Ser Leu Leu Gly Pro Met Phe Lys Asn
    4250                4255                4260

Thr Ser Val Gly Pro Leu Tyr Ser Gly Cys Arg Leu Thr Leu Leu
    4265                4270                4275

Arg Ser Glu Lys Asp Gly Ala Ala Thr Gly Val Asp Ala Ile Cys
    4280                4285                4290

Thr His Arg Leu Asp Pro Lys Ser Pro Gly Val Asp Arg Glu Gln
    4295                4300                4305

Leu Tyr Trp Glu Leu Ser Gln Leu Thr Asn Gly Ile Lys Glu Leu
    4310                4315                4320

Gly Pro Tyr Thr Leu Asp Arg Asn Ser Leu Tyr Val Asn Gly Phe
    4325                4330                4335

Thr His Gln Thr Ser Ala Pro Asn Thr Ser Thr Pro Gly Thr Ser
    4340                4345                4350

Thr Val Asp Leu Gly Thr Ser Gly Thr Pro Ser Ser Leu Pro Ser
    4355                4360                4365

Pro Thr Xaa Xaa Xaa Pro Leu Leu Xaa Pro Phe Thr Leu Asn Phe
    4370                4375                4380

Thr Ile Thr Asn Leu Xaa Tyr Glu Glu Xaa Met Xaa Xaa Pro Gly
    4385                4390                4395

Ser Arg Lys Phe Asn Thr Thr Glu Arg Val Leu Gln Gly Leu Leu
    4400                4405                4410

Xaa Pro Xaa Phe Lys Xaa Thr Ser Val Gly Xaa Leu Tyr Ser Gly
    4415                4420                4425
```

-continued

```
Cys Arg Leu Thr Leu Leu Arg Xaa Glu Lys Xaa Xaa Ala Ala Thr
    4430                4435                4440

Xaa Val Asp Xaa Xaa Cys Xaa Xaa Xaa Asp Pro Xaa Xaa Pro
    4445            4450                4455

Gly Leu Asp Arg Glu Xaa Leu Tyr Trp Glu Leu Ser Xaa Leu Thr
    4460                4465                4470

Xaa Xaa Ile Xaa Glu Leu Gly Pro Tyr Xaa Leu Asp Arg Xaa Ser
    4475                4480                4485

Leu Tyr Val Asn Gly Phe Thr His Trp Ile Pro Val Pro Thr Ser
    4490                4495                4500

Ser Thr Pro Gly Thr Ser Thr Val Asp Leu Gly Ser Gly Thr Pro
    4505                4510                4515

Ser Ser Leu Pro Ser Pro Thr Thr Ala Gly Pro Leu Leu Val Pro
    4520                4525                4530

Phe Thr Leu Asn Phe Thr Ile Thr Asn Leu Lys Tyr Glu Glu Asp
    4535                4540                4545

Met His Cys Pro Gly Ser Arg Lys Phe Asn Thr Thr Glu Arg Val
    4550                4555                4560

Leu Gln Ser Leu Leu Gly Pro Met Phe Lys Asn Thr Ser Val Gly
    4565                4570                4575

Pro Leu Tyr Ser Gly Cys Arg Leu Thr Ser Leu Arg Ser Glu Lys
    4580                4585                4590

Asp Gly Ala Ala Thr Gly Val Asp Ala Ile Cys Thr His Arg Val
    4595                4600                4605

Asp Pro Lys Ser Pro Gly Val Asp Arg Glu Gln Leu Tyr Trp Glu
    4610                4615                4620

Leu Ser Gln Leu Thr Asn Gly Ile Lys Glu Leu Gly Pro Tyr Thr
    4625                4630                4635

Leu Asp Arg Asn Ser Leu Tyr Val Asn Gly Phe Thr His Gln Thr
    4640                4645                4650

Ser Ala Pro Asn Thr Ser Thr Pro Gly Thr Ser Thr Val Asp Leu
    4655                4660                4665

Gly Thr Ser Gly Thr Pro Ser Ser Leu Pro Ser Pro Thr Ser Ala
    4670                4675                4680

Gly Pro Leu Leu Val Pro Phe Thr Leu Asn Phe Thr Ile Thr Asn
    4685                4690                4695

Leu Gln Tyr Glu Glu Asp Met His His Pro Gly Ser Arg Lys Phe
    4700                4705                4710

Asn Thr Thr Glu Arg Val Leu Gln Gly Leu Leu Gly Pro Met Phe
    4715                4720                4725

Lys Asn Thr Ser Val Gly Leu Leu Tyr Ser Gly Cys Arg Leu Thr
    4730                4735                4740

Leu Leu Arg Pro Glu Lys Asn Gly Ala Ala Thr Gly Met Asp Ala
    4745                4750                4755

Ile Cys Thr His Arg Leu Asp Pro Lys Ser Pro Gly Leu Asp Arg
    4760                4765                4770

Glu Xaa Leu Tyr Trp Glu Leu Ser Xaa Leu Thr Xaa Xaa Ile Xaa
    4775                4780                4785

Glu Leu Gly Pro Tyr Xaa Leu Asp Arg Xaa Ser Leu Tyr Val Asn
    4790                4795                4800

Gly Phe Xaa Xaa Xaa Xaa Xaa Xaa Xaa Xaa Thr Ser Thr Pro Gly
    4805                4810                4815
```

-continued

```
Thr Ser Xaa Val Xaa Leu Xaa Thr Ser Gly Thr Pro Xaa Xaa Xaa
    4820            4825            4830

Pro Xaa Xaa Thr Xaa Xaa Xaa Pro Leu Leu Xaa Pro Phe Thr Leu
    4835            4840            4845

Asn Phe Thr Ile Thr Asn Leu Xaa Tyr Glu Glu Xaa Met Xaa Xaa
    4850            4855            4860

Pro Gly Ser Arg Lys Phe Asn Thr Thr Glu Arg Val Leu Gln Gly
    4865            4870            4875

Leu Leu Lys Pro Leu Phe Arg Asn Ser Ser Leu Glu Tyr Leu Tyr
    4880            4885            4890

Ser Gly Cys Arg Leu Ala Ser Leu Arg Pro Glu Lys Asp Ser Ser
    4895            4900            4905

Ala Met Ala Val Asp Ala Ile Cys Thr His Arg Pro Asp Pro Glu
    4910            4915            4920

Asp Leu Gly Leu Asp Arg Glu Arg Leu Tyr Trp Glu Leu Ser Asn
    4925            4930            4935

Leu Thr Asn Gly Ile Gln Glu Leu Gly Pro Tyr Thr Leu Asp Arg
    4940            4945            4950

Asn Ser Leu Tyr Val Asn Gly Phe Thr His Arg Ser Ser Met Pro
    4955            4960            4965

Thr Thr Ser Thr Pro Gly Thr Ser Thr Val Asp Val Gly Thr Ser
    4970            4975            4980

Gly Thr Pro Ser Ser Ser Pro Ser Pro Thr Thr Ala Gly Pro Leu
    4985            4990            4995

Leu Ile Pro Phe Thr Leu Asn Phe Thr Ile Thr Asn Leu Gln Tyr
    5000            5005            5010

Gly Glu Asp Met Gly His Pro Gly Ser Arg Lys Phe Asn Thr Thr
    5015            5020            5025

Glu Arg Val Leu Gln Gly Leu Leu Gly Pro Ile Phe Lys Asn Thr
    5030            5035            5040

Ser Val Gly Pro Leu Tyr Ser Gly Cys Arg Leu Thr Ser Leu Arg
    5045            5050            5055

Ser Glu Lys Asp Gly Ala Ala Thr Gly Val Asp Ala Ile Cys Ile
    5060            5065            5070

His His Leu Asp Pro Lys Ser Pro Gly Leu Asn Arg Glu Arg Leu
    5075            5080            5085

Tyr Trp Glu Leu Ser Gln Leu Thr Asn Gly Ile Lys Glu Leu Gly
    5090            5095            5100

Pro Tyr Thr Leu Asp Arg Asn Ser Leu Tyr Val Asn Gly Phe Thr
    5105            5110            5115

His Arg Thr Ser Val Pro Thr Thr Ser Thr Pro Gly Thr Ser Thr
    5120            5125            5130

Val Asp Leu Gly Thr Ser Gly Thr Pro Phe Ser Leu Pro Ser Pro
    5135            5140            5145

Ala Thr Ala Gly Pro Leu Leu Val Leu Phe Thr Leu Asn Phe Thr
    5150            5155            5160

Ile Thr Asn Leu Lys Tyr Glu Glu Asp Met His Arg Pro Gly Ser
    5165            5170            5175

Arg Lys Phe Asn Thr Thr Glu Arg Val Leu Gln Thr Leu Leu Gly
    5180            5185            5190

Pro Met Phe Lys Asn Thr Ser Val Gly Leu Leu Tyr Ser Gly Cys
    5195            5200            5205

Arg Leu Thr Leu Leu Arg Ser Glu Lys Asp Gly Ala Ala Thr Gly
```

-continued

```
              5210                5215                5220
Val Asp Ala Ile Cys Thr His Arg Leu Asp Pro Lys Ser Pro Gly
    5225                5230                5235

Leu Asp Arg Glu Xaa Leu Tyr Trp Glu Leu Ser Xaa Leu Thr Xaa
    5240                5245                5250

Xaa Ile Xaa Glu Leu Gly Pro Tyr Xaa Leu Asp Arg Xaa Ser Leu
    5255                5260                5265

Tyr Val Asn Gly Phe Xaa Xaa Xaa Xaa Xaa Xaa Xaa Xaa Thr Ser
    5270                5275                5280

Thr Pro Gly Thr Ser Xaa Val Xaa Leu Xaa Thr Ser Gly Thr Pro
    5285                5290                5295

Xaa Xaa Xaa Pro Xaa Xaa Thr Xaa Xaa Xaa Pro Leu Leu Xaa Pro
    5300                5305                5310

Phe Thr Leu Asn Phe Thr Ile Thr Asn Leu Xaa Tyr Glu Glu Xaa
    5315                5320                5325

Met Xaa Xaa Pro Gly Ser Arg Lys Phe Asn Thr Thr Glu Arg Val
    5330                5335                5340

Leu Gln Gly Leu Leu Arg Pro Val Phe Lys Asn Thr Ser Val Gly
    5345                5350                5355

Pro Leu Tyr Ser Gly Cys Arg Leu Thr Leu Leu Arg Pro Lys Lys
    5360                5365                5370

Asp Gly Ala Ala Thr Lys Val Asp Ala Ile Cys Thr Tyr Arg Pro
    5375                5380                5385

Asp Pro Lys Ser Pro Gly Leu Asp Arg Glu Gln Leu Tyr Trp Glu
    5390                5395                5400

Leu Ser Gln Leu Thr His Ser Ile Thr Glu Leu Gly Pro Tyr Thr
    5405                5410                5415

Gln Asp Arg Asp Ser Leu Tyr Val Asn Gly Phe Thr His Arg Ser
    5420                5425                5430

Ser Val Pro Thr Thr Ser Ile Pro Gly Thr Ser Ala Val His Leu
    5435                5440                5445

Glu Thr Thr Gly Thr Pro Ser Ser Phe Pro Gly His Thr Glu Pro
    5450                5455                5460

Gly Pro Leu Leu Ile Pro Phe Thr Phe Asn Phe Thr Ile Thr Asn
    5465                5470                5475

Leu Arg Tyr Glu Glu Asn Met Gln His Pro Gly Ser Arg Lys Phe
    5480                5485                5490

Asn Thr Thr Glu Arg Val Leu Gln Gly Leu Leu Thr Pro Leu Phe
    5495                5500                5505

Lys Asn Thr Ser Val Gly Pro Leu Tyr Ser Gly Cys Arg Leu Thr
    5510                5515                5520

Leu Leu Arg Pro Glu Lys Gln Glu Ala Ala Thr Gly Val Asp Thr
    5525                5530                5535

Ile Cys Thr His Arg Val Asp Pro Ile Gly Pro Gly Leu Asp Arg
    5540                5545                5550

Glu Arg Leu Tyr Trp Glu Leu Ser Gln Leu Thr Asn Ser Ile Thr
    5555                5560                5565

Glu Leu Gly Pro Tyr Thr Leu Asp Arg Asp Ser Leu Tyr Val Asp
    5570                5575                5580

Gly Phe Asn Pro Trp Ser Ser Val Pro Thr Thr Ser Thr Pro Gly
    5585                5590                5595

Thr Ser Thr Val His Leu Ala Thr Ser Gly Thr Pro Ser Pro Leu
    5600                5605                5610
```

```
Pro Gly His Thr Ala Pro Val Pro Leu Leu Ile Pro Phe Thr Leu
5615                5620                5625

Asn Phe Thr Ile Thr Asp Leu His Tyr Glu Glu Asn Met Gln His
5630                5635                5640

Pro Gly Ser Arg Lys Phe Asn Thr Thr Glu Arg Val Leu Gln Gly
5645                5650                5655

Leu Leu Lys Pro Leu Phe Lys Ser Thr Ser Val Gly Pro Leu Tyr
5660                5665                5670

Ser Gly Cys Arg Leu Thr Leu Leu Arg Pro Glu Lys His Gly Ala
5675                5680                5685

Ala Thr Gly Val Asp Ala Ile Cys Thr Leu Arg Leu Asp Pro Thr
5690                5695                5700

Gly Pro Gly Leu Asp Arg Glu Arg Leu Tyr Trp Glu Leu Ser Gln
5705                5710                5715

Leu Thr Asn Ser Ile Thr Glu Leu Gly Pro Tyr Thr Leu Asp Arg
5720                5725                5730

Asp Ser Leu Tyr Val Asn Gly Phe Asn Pro Trp Ser Ser Val Pro
5735                5740                5745

Thr Thr Ser Thr Pro Gly Thr Ser Thr Val His Leu Ala Thr Ser
5750                5755                5760

Gly Thr Pro Ser Ser Leu Pro Gly His Thr Thr Ala Gly Pro Leu
5765                5770                5775

Leu Val Pro Phe Thr Leu Asn Phe Thr Ile Thr Asn Leu Lys Tyr
5780                5785                5790

Glu Glu Asp Met His Cys Pro Gly Ser Arg Lys Phe Asn Thr Thr
5795                5800                5805

Glu Arg Val Leu Gln Ser Leu His Gly Pro Met Phe Lys Asn Thr
5810                5815                5820

Ser Val Gly Pro Leu Tyr Ser Gly Cys Arg Leu Thr Leu Leu Arg
5825                5830                5835

Ser Glu Lys Asp Gly Ala Ala Thr Gly Val Asp Ala Ile Cys Thr
5840                5845                5850

His Arg Leu Asp Pro Lys Ser Pro Gly Leu Asp Arg Glu Xaa Leu
5855                5860                5865

Tyr Trp Glu Leu Ser Xaa Leu Thr Xaa Xaa Ile Xaa Glu Leu Gly
5870                5875                5880

Pro Tyr Xaa Leu Asp Arg Xaa Ser Leu Tyr Val Asn Gly Phe Xaa
5885                5890                5895

Xaa Xaa Xaa Xaa Xaa Xaa Thr Ser Thr Pro Gly Thr Ser Xaa
5900                5905                5910

Val Xaa Leu Xaa Thr Ser Gly Thr Pro Xaa Xaa Xaa Pro Xaa Xaa
5915                5920                5925

Thr Xaa Xaa Xaa Pro Leu Leu Xaa Pro Phe Thr Leu Asn Phe Thr
5930                5935                5940

Ile Thr Asn Leu Xaa Tyr Glu Glu Xaa Met Xaa Xaa Pro Gly Ser
5945                5950                5955

Arg Lys Phe Asn Thr Thr Glu Arg Val Leu Gln Gly Leu Leu Xaa
5960                5965                5970

Pro Xaa Phe Lys Xaa Thr Ser Val Gly Xaa Leu Tyr Ser Gly Cys
5975                5980                5985

Arg Leu Thr Leu Leu Arg Xaa Glu Lys Xaa Xaa Ala Ala Thr Xaa
5990                5995                6000
```

-continued

```
Val Asp Xaa Xaa Cys Xaa Xaa Xaa Xaa Asp Pro Xaa Xaa Pro Gly
    6005              6010                  6015

Leu Asp Arg Glu Xaa Leu Tyr Trp Glu Leu Ser Xaa Leu Thr Asn
    6020              6025                  6030

Ser Ile Thr Glu Leu Gly Pro Tyr Thr Leu Asp Arg Asp Ser Leu
    6035              6040                  6045

Tyr Val Asn Gly Phe Thr His Arg Ser Ser Met Pro Thr Thr Ser
    6050              6055                  6060

Ile Pro Gly Thr Ser Ala Val His Leu Glu Thr Ser Gly Thr Pro
    6065              6070                  6075

Ala Ser Leu Pro Gly His Thr Ala Pro Gly Pro Leu Leu Val Pro
    6080              6085                  6090

Phe Thr Leu Asn Phe Thr Ile Thr Asn Leu Gln Tyr Glu Glu Asp
    6095              6100                  6105

Met Arg His Pro Gly Ser Arg Lys Phe Asn Thr Thr Glu Arg Val
    6110              6115                  6120

Leu Gln Gly Leu Leu Lys Pro Leu Phe Lys Ser Thr Ser Val Gly
    6125              6130                  6135

Pro Leu Tyr Ser Gly Cys Arg Leu Thr Leu Leu Arg Pro Glu Lys
    6140              6145                  6150

Arg Gly Ala Ala Thr Gly Val Asp Thr Ile Cys Thr His Arg Leu
    6155              6160                  6165

Asp Pro Leu Asn Pro Gly Leu Asp Arg Glu Xaa Leu Tyr Trp Glu
    6170              6175                  6180

Leu Ser Xaa Leu Thr Xaa Xaa Ile Xaa Glu Leu Gly Pro Tyr Xaa
    6185              6190                  6195

Leu Asp Arg Xaa Ser Leu Tyr Val Asn Gly Phe Xaa Xaa Xaa Xaa
    6200              6205                  6210

Xaa Xaa Xaa Xaa Thr Ser Thr Pro Gly Thr Ser Xaa Val Xaa Leu
    6215              6220                  6225

Xaa Thr Ser Gly Thr Pro Xaa Xaa Xaa Pro Xaa Xaa Thr Xaa Xaa
    6230              6235                  6240

Xaa Pro Leu Leu Xaa Pro Phe Thr Leu Asn Phe Thr Ile Thr Asn
    6245              6250                  6255

Leu Xaa Tyr Glu Glu Xaa Met Xaa Xaa Pro Gly Ser Arg Lys Phe
    6260              6265                  6270

Asn Thr Thr Glu Arg Val Leu Gln Gly Leu Leu Xaa Pro Xaa Phe
    6275              6280                  6285

Lys Xaa Thr Ser Val Gly Xaa Leu Tyr Ser Gly Cys Arg Leu Thr
    6290              6295                  6300

Leu Leu Arg Xaa Glu Lys Xaa Xaa Ala Ala Thr Xaa Val Asp Xaa
    6305              6310                  6315

Xaa Cys Xaa Xaa Xaa Xaa Asp Pro Xaa Xaa Pro Gly Leu Asp Arg
    6320              6325                  6330

Glu Xaa Leu Tyr Trp Glu Leu Ser Xaa Leu Thr Xaa Xaa Ile Xaa
    6335              6340                  6345

Glu Leu Gly Pro Tyr Xaa Leu Asp Arg Xaa Ser Leu Tyr Val Asn
    6350              6355                  6360

Gly Phe His Pro Arg Ser Ser Val Pro Thr Thr Ser Thr Pro Gly
    6365              6370                  6375

Thr Ser Thr Val His Leu Ala Thr Ser Gly Thr Pro Ser Ser Leu
    6380              6385                  6390

Pro Gly His Thr Ala Pro Val Pro Leu Leu Ile Pro Phe Thr Leu
```

-continued

```
                    6395                6400                6405
Asn Phe Thr Ile Thr Asn Leu His Tyr Glu Glu Asn Met Gln His
        6410                6415                6420
Pro Gly Ser Arg Lys Phe Asn Thr Thr Glu Arg Val Leu Gln Gly
        6425                6430                6435
Leu Leu Gly Pro Met Phe Lys Asn Thr Ser Val Gly Leu Leu Tyr
        6440                6445                6450
Ser Gly Cys Arg Leu Thr Leu Leu Arg Pro Glu Lys Asn Gly Ala
        6455                6460                6465
Ala Thr Gly Met Asp Ala Ile Cys Ser His Arg Leu Asp Pro Lys
        6470                6475                6480
Ser Pro Gly Leu Asp Arg Glu Xaa Leu Tyr Trp Glu Leu Ser Xaa
        6485                6490                6495
Leu Thr Xaa Xaa Ile Xaa Glu Leu Gly Pro Tyr Xaa Leu Asp Arg
        6500                6505                6510
Xaa Ser Leu Tyr Val Asn Gly Phe Xaa Xaa Xaa Xaa Xaa Xaa Xaa
        6515                6520                6525
Xaa Thr Ser Thr Pro Gly Thr Ser Xaa Val Xaa Leu Xaa Thr Ser
        6530                6535                6540
Gly Thr Pro Xaa Xaa Xaa Pro Xaa Xaa Thr Xaa Xaa Xaa Pro Leu
        6545                6550                6555
Leu Xaa Pro Phe Thr Leu Asn Phe Thr Ile Thr Asn Leu Xaa Tyr
        6560                6565                6570
Glu Glu Xaa Met Xaa Xaa Pro Gly Ser Arg Lys Phe Asn Thr Thr
        6575                6580                6585
Glu Arg Val Leu Gln Gly Leu Leu Xaa Pro Xaa Phe Lys Xaa Thr
        6590                6595                6600
Ser Val Gly Xaa Leu Tyr Ser Gly Cys Arg Leu Thr Leu Leu Arg
        6605                6610                6615
Xaa Glu Lys Xaa Xaa Ala Ala Thr Xaa Val Asp Xaa Xaa Cys Xaa
        6620                6625                6630
Xaa Xaa Xaa Asp Pro Xaa Xaa Pro Gly Leu Asp Arg Glu Xaa Leu
        6635                6640                6645
Tyr Trp Glu Leu Ser Xaa Leu Thr Xaa Xaa Ile Xaa Glu Leu Gly
        6650                6655                6660
Pro Tyr Xaa Leu Asp Arg Xaa Ser Leu Tyr Val Asn Gly Phe Thr
        6665                6670                6675
His Gln Asn Ser Val Pro Thr Thr Ser Thr Pro Gly Thr Ser Thr
        6680                6685                6690
Val Tyr Trp Ala Thr Thr Gly Thr Pro Ser Ser Phe Pro Gly His
        6695                6700                6705
Thr Glu Pro Gly Pro Leu Leu Ile Pro Phe Thr Phe Asn Phe Thr
        6710                6715                6720
Ile Thr Asn Leu His Tyr Glu Glu Asn Met Gln His Pro Gly Ser
        6725                6730                6735
Arg Lys Phe Asn Thr Thr Glu Arg Val Leu Gln Gly Leu Leu Thr
        6740                6745                6750
Pro Leu Phe Lys Asn Thr Ser Val Gly Pro Leu Tyr Ser Gly Cys
        6755                6760                6765
Arg Leu Thr Leu Leu Arg Pro Glu Lys Gln Glu Ala Ala Thr Gly
        6770                6775                6780
Val Asp Thr Ile Cys Thr His Arg Val Asp Pro Ile Gly Pro Gly
        6785                6790                6795
```

-continued

```
Leu Asp Arg Glu Xaa Leu Tyr Trp Glu Leu Ser Xaa Leu Thr Xaa
6800                 6805                 6810

Xaa Ile Xaa Glu Leu Gly Pro Tyr Xaa Leu Asp Arg Xaa Ser Leu
6815                 6820                 6825

Tyr Val Asn Gly Phe Xaa Xaa Xaa Xaa Xaa Xaa Xaa Xaa Thr Ser
6830                 6835                 6840

Thr Pro Gly Thr Ser Xaa Val Xaa Leu Xaa Thr Ser Gly Thr Pro
6845                 6850                 6855

Xaa Xaa Xaa Pro Xaa Xaa Thr Xaa Xaa Xaa Pro Leu Leu Xaa Pro
6860                 6865                 6870

Phe Thr Leu Asn Phe Thr Ile Thr Asn Leu Xaa Tyr Glu Glu Xaa
6875                 6880                 6885

Met Xaa Xaa Pro Gly Ser Arg Lys Phe Asn Thr Thr Glu Arg Val
6890                 6895                 6900

Leu Gln Gly Leu Leu Xaa Pro Xaa Phe Lys Xaa Thr Ser Val Gly
6905                 6910                 6915

Xaa Leu Tyr Ser Gly Cys Arg Leu Thr Leu Leu Arg Xaa Glu Lys
6920                 6925                 6930

Xaa Xaa Ala Ala Thr Xaa Val Asp Xaa Xaa Cys Xaa Xaa Xaa Xaa
6935                 6940                 6945

Asp Pro Xaa Xaa Pro Gly Leu Asp Arg Glu Xaa Leu Tyr Trp Glu
6950                 6955                 6960

Leu Ser Xaa Leu Thr Xaa Xaa Ile Xaa Glu Leu Gly Pro Tyr Xaa
6965                 6970                 6975

Leu Asp Arg Xaa Ser Leu Tyr Val Asn Gly Phe Thr His Arg Ser
6980                 6985                 6990

Ser Val Pro Thr Thr Ser Ser Pro Gly Thr Ser Thr Val His Leu
6995                 7000                 7005

Ala Thr Ser Gly Thr Pro Ser Ser Leu Pro Gly His Thr Ala Pro
7010                 7015                 7020

Val Pro Leu Leu Ile Pro Phe Thr Leu Asn Phe Thr Ile Thr Asn
7025                 7030                 7035

Leu His Tyr Glu Glu Asn Met Gln His Pro Gly Ser Arg Lys Phe
7040                 7045                 7050

Asn Thr Thr Glu Arg Val Leu Gln Gly Leu Leu Lys Pro Leu Phe
7055                 7060                 7065

Lys Ser Thr Ser Val Gly Pro Leu Tyr Ser Gly Cys Arg Leu Thr
7070                 7075                 7080

Leu Leu Arg Pro Glu Lys His Gly Ala Ala Thr Gly Val Asp Ala
7085                 7090                 7095

Ile Cys Thr Leu Arg Leu Asp Pro Thr Gly Pro Gly Leu Asp Arg
7100                 7105                 7110

Glu Xaa Leu Tyr Trp Glu Leu Ser Xaa Leu Thr Xaa Xaa Ile Xaa
7115                 7120                 7125

Glu Leu Gly Pro Tyr Xaa Leu Asp Arg Xaa Ser Leu Tyr Val Asn
7130                 7135                 7140

Gly Phe Xaa Xaa Xaa Xaa Xaa Xaa Xaa Xaa Thr Ser Thr Pro Gly
7145                 7150                 7155

Thr Ser Xaa Val Xaa Leu Xaa Thr Ser Gly Thr Pro Xaa Xaa Xaa
7160                 7165                 7170

Pro Xaa Xaa Thr Xaa Xaa Xaa Pro Leu Leu Xaa Pro Phe Thr Leu
7175                 7180                 7185
```

-continued

```
Asn Phe Thr Ile Thr Asn Leu Xaa Tyr Glu Glu Xaa Met Xaa Xaa
        7190                7195                7200

Pro Gly Ser Arg Lys Phe Asn Thr Thr Glu Arg Val Leu Gln Gly
        7205                7210                7215

Leu Leu Xaa Pro Xaa Phe Lys Xaa Thr Ser Val Gly Xaa Leu Tyr
        7220                7225                7230

Ser Gly Cys Arg Leu Thr Leu Leu Arg Xaa Glu Lys Xaa Xaa Ala
        7235                7240                7245

Ala Thr Xaa Val Asp Xaa Xaa Cys Xaa Xaa Xaa Asp Pro Xaa
        7250                7255                7260

Xaa Pro Gly Leu Asp Arg Glu Xaa Leu Tyr Trp Glu Leu Ser Xaa
        7265                7270                7275

Leu Thr Xaa Xaa Ile Xaa Glu Leu Gly Pro Tyr Xaa Leu Asp Arg
        7280                7285                7290

Xaa Ser Leu Tyr Val Asn Gly Phe Thr His Arg Thr Ser Val Pro
        7295                7300                7305

Thr Thr Ser Thr Pro Gly Thr Ser Thr Val His Leu Ala Thr Ser
        7310                7315                7320

Gly Thr Pro Ser Ser Leu Pro Gly His Thr Ala Pro Val Pro Leu
        7325                7330                7335

Leu Ile Pro Phe Thr Leu Asn Phe Thr Ile Thr Asn Leu Gln Tyr
        7340                7345                7350

Glu Glu Asp Met His Arg Pro Gly Ser Arg Lys Phe Asn Thr Thr
        7355                7360                7365

Glu Arg Val Leu Gln Gly Leu Leu Ser Pro Ile Phe Lys Asn Ser
        7370                7375                7380

Ser Val Gly Pro Leu Tyr Ser Gly Cys Arg Leu Thr Ser Leu Arg
        7385                7390                7395

Pro Glu Lys Asp Gly Ala Ala Thr Gly Met Asp Ala Val Cys Leu
        7400                7405                7410

Tyr His Pro Asn Pro Lys Arg Pro Gly Leu Asp Arg Glu Gln Leu
        7415                7420                7425

Tyr Cys Glu Leu Ser Gln Leu Thr His Asn Ile Thr Glu Leu Gly
        7430                7435                7440

Pro Tyr Ser Leu Asp Arg Asp Ser Leu Tyr Val Asn Gly Phe Thr
        7445                7450                7455

His Gln Asn Ser Val Pro Thr Thr Ser Thr Pro Gly Thr Ser Thr
        7460                7465                7470

Val Tyr Trp Ala Thr Thr Gly Thr Pro Ser Ser Phe Pro Gly His
        7475                7480                7485

Thr Xaa Xaa Xaa Pro Leu Leu Xaa Pro Phe Thr Leu Asn Phe Thr
        7490                7495                7500

Ile Thr Asn Leu Xaa Tyr Glu Glu Xaa Met Xaa Xaa Pro Gly Ser
        7505                7510                7515

Arg Lys Phe Asn Thr Thr Glu Arg Val Leu Gln Gly Leu Leu Xaa
        7520                7525                7530

Pro Xaa Phe Lys Xaa Thr Ser Val Gly Xaa Leu Tyr Ser Gly Cys
        7535                7540                7545

Arg Leu Thr Leu Leu Arg Xaa Glu Lys Xaa Xaa Ala Ala Thr Xaa
        7550                7555                7560

Val Asp Xaa Xaa Cys Xaa Xaa Xaa Asp Pro Xaa Xaa Pro Gly
        7565                7570                7575

Leu Asp Arg Glu Xaa Leu Tyr Trp Glu Leu Ser Xaa Leu Thr Xaa
```

-continued

```
            7580                7585                7590
Xaa Ile Xaa Glu Leu Gly Pro Tyr Xaa Leu Asp Arg Xaa Ser Leu
    7595                7600                7605
Tyr Val Asn Gly Phe Thr His Trp Ser Ser Gly Leu Thr Thr Ser
    7610                7615                7620
Thr Pro Trp Thr Ser Thr Val Asp Leu Gly Thr Ser Gly Thr Pro
    7625                7630                7635
Ser Pro Val Pro Ser Pro Thr Thr Ala Gly Pro Leu Leu Val Pro
    7640                7645                7650
Phe Thr Leu Asn Phe Thr Ile Thr Asn Leu Gln Tyr Glu Glu Asp
    7655                7660                7665
Met His Arg Pro Gly Ser Arg Lys Phe Asn Ala Thr Glu Arg Val
    7670                7675                7680
Leu Gln Gly Leu Leu Ser Pro Ile Phe Lys Asn Thr Ser Val Gly
    7685                7690                7695
Pro Leu Tyr Ser Gly Cys Arg Leu Thr Leu Leu Arg Pro Glu Lys
    7700                7705                7710
Gln Glu Ala Ala Thr Gly Val Asp Thr Ile Cys Thr His Arg Val
    7715                7720                7725
Asp Pro Ile Gly Pro Gly Leu Asp Arg Glu Xaa Leu Tyr Trp Glu
    7730                7735                7740
Leu Ser Xaa Leu Thr Xaa Xaa Ile Xaa Glu Leu Gly Pro Tyr Xaa
    7745                7750                7755
Leu Asp Arg Xaa Ser Leu Tyr Val Asn Gly Phe Xaa Xaa Xaa Xaa
    7760                7765                7770
Xaa Xaa Xaa Xaa Thr Ser Thr Pro Gly Thr Ser Xaa Val Xaa Leu
    7775                7780                7785
Xaa Thr Ser Gly Thr Pro Xaa Xaa Xaa Pro Xaa Xaa Thr Xaa Xaa
    7790                7795                7800
Xaa Pro Leu Leu Xaa Pro Phe Thr Leu Asn Phe Thr Ile Thr Asn
    7805                7810                7815
Leu Xaa Tyr Glu Glu Xaa Met Xaa Xaa Pro Gly Ser Arg Lys Phe
    7820                7825                7830
Asn Thr Thr Glu Arg Val Leu Gln Gly Leu Leu Xaa Pro Xaa Phe
    7835                7840                7845
Lys Xaa Thr Ser Val Gly Xaa Leu Tyr Ser Gly Cys Arg Leu Thr
    7850                7855                7860
Leu Leu Arg Xaa Glu Lys Xaa Xaa Ala Ala Thr Xaa Val Asp Xaa
    7865                7870                7875
Xaa Cys Xaa Xaa Xaa Xaa Asp Pro Xaa Xaa Pro Gly Leu Asp Arg
    7880                7885                7890
Glu Xaa Leu Tyr Trp Glu Leu Ser Xaa Leu Thr Xaa Xaa Ile Xaa
    7895                7900                7905
Glu Leu Gly Pro Tyr Xaa Leu Asp Arg Xaa Ser Leu Tyr Val Asn
    7910                7915                7920
Gly Phe Thr His Arg Ser Phe Gly Leu Thr Thr Ser Thr Pro Trp
    7925                7930                7935
Thr Ser Thr Val Asp Leu Gly Thr Ser Gly Thr Pro Ser Pro Val
    7940                7945                7950
Pro Ser Pro Thr Thr Ala Gly Pro Leu Leu Val Pro Phe Thr Leu
    7955                7960                7965
Asn Phe Thr Ile Thr Asn Leu Gln Tyr Glu Glu Asp Met His Arg
    7970                7975                7980
```

-continued

```
Pro Gly Ser Arg Lys Phe Asn Thr Thr Glu Arg Val Leu Gln Gly
    7985                7990                7995

Leu Leu Thr Pro Leu Phe Arg Asn Thr Ser Val Ser Ser Leu Tyr
    8000                8005                8010

Ser Gly Cys Arg Leu Thr Leu Leu Arg Pro Glu Lys Asp Gly Ala
    8015                8020                8025

Ala Thr Arg Val Asp Ala Val Cys Thr His Arg Pro Asp Pro Lys
    8030                8035                8040

Ser Pro Gly Leu Asp Arg Glu Xaa Leu Tyr Trp Glu Leu Ser Xaa
    8045                8050                8055

Leu Thr Xaa Xaa Ile Xaa Glu Leu Gly Pro Tyr Xaa Leu Asp Arg
    8060                8065                8070

Xaa Ser Leu Tyr Val Asn Gly Phe Xaa Xaa Xaa Xaa Xaa Xaa
    8075                8080                8085

Xaa Thr Ser Thr Pro Gly Thr Ser Xaa Val Xaa Leu Xaa Thr Ser
    8090                8095                8100

Gly Thr Pro Xaa Xaa Xaa Pro Xaa Xaa Thr Xaa Xaa Xaa Pro Leu
    8105                8110                8115

Leu Xaa Pro Phe Thr Leu Asn Phe Thr Ile Thr Asn Leu Xaa Tyr
    8120                8125                8130

Glu Glu Xaa Met Xaa Xaa Pro Gly Ser Arg Lys Phe Asn Thr Thr
    8135                8140                8145

Glu Arg Val Leu Gln Gly Leu Leu Xaa Pro Xaa Phe Lys Xaa Thr
    8150                8155                8160

Ser Val Gly Xaa Leu Tyr Ser Gly Cys Arg Leu Thr Leu Leu Arg
    8165                8170                8175

Xaa Glu Lys Xaa Xaa Ala Ala Thr Xaa Val Asp Xaa Xaa Cys Xaa
    8180                8185                8190

Xaa Xaa Xaa Asp Pro Xaa Xaa Pro Gly Leu Asp Arg Glu Xaa Leu
    8195                8200                8205

Tyr Trp Glu Leu Ser Xaa Leu Thr Xaa Xaa Ile Xaa Glu Leu Gly
    8210                8215                8220

Pro Tyr Xaa Leu Asp Arg Xaa Ser Leu Tyr Val Asn Gly Phe Thr
    8225                8230                8235

His Trp Ile Pro Val Pro Thr Ser Ser Thr Pro Gly Thr Ser Thr
    8240                8245                8250

Val Asp Leu Gly Ser Gly Thr Pro Ser Ser Leu Pro Ser Pro Thr
    8255                8260                8265

Thr Ala Gly Pro Leu Leu Val Pro Phe Thr Leu Asn Phe Thr Ile
    8270                8275                8280

Thr Asn Leu Gln Tyr Gly Glu Asp Met Gly His Pro Gly Ser Arg
    8285                8290                8295

Lys Phe Asn Thr Thr Glu Arg Val Leu Gln Gly Leu Leu Gly Pro
    8300                8305                8310

Ile Phe Lys Asn Thr Ser Val Gly Pro Leu Tyr Ser Gly Cys Arg
    8315                8320                8325

Leu Thr Ser Leu Arg Ser Glu Lys Asp Gly Ala Ala Thr Gly Val
    8330                8335                8340

Asp Ala Ile Cys Ile His His Leu Asp Pro Lys Ser Pro Gly Leu
    8345                8350                8355

Asp Arg Glu Xaa Leu Tyr Trp Glu Leu Ser Xaa Leu Thr Xaa Xaa
    8360                8365                8370
```

-continued

Ile Xaa Glu Leu Gly Pro Tyr Xaa Leu Asp Arg Xaa Ser Leu Tyr
8375            8380            8385

Val Asn Gly Phe Xaa Xaa Xaa Xaa Xaa Xaa Xaa Thr Ser Thr
8390            8395            8400

Pro Gly Thr Ser Xaa Val Xaa Leu Xaa Thr Ser Gly Thr Pro Xaa
8405            8410            8415

Xaa Xaa Pro Xaa Xaa Thr Xaa Xaa Xaa Pro Leu Leu Xaa Pro Phe
8420            8425            8430

Thr Leu Asn Phe Thr Ile Thr Asn Leu Xaa Tyr Glu Glu Xaa Met
8435            8440            8445

Xaa Xaa Pro Gly Ser Arg Lys Phe Asn Thr Thr Glu Arg Val Leu
8450            8455            8460

Gln Gly Leu Leu Xaa Pro Xaa Phe Lys Xaa Thr Ser Val Gly Xaa
8465            8470            8475

Leu Tyr Ser Gly Cys Arg Leu Thr Leu Leu Arg Xaa Glu Lys Xaa
8480            8485            8490

Xaa Ala Ala Thr Xaa Val Asp Xaa Xaa Cys Xaa Xaa Xaa Xaa Asp
8495            8500            8505

Pro Xaa Xaa Pro Gly Leu Asp Arg Glu Xaa Leu Tyr Trp Glu Leu
8510            8515            8520

Ser Xaa Leu Thr Xaa Xaa Ile Xaa Glu Leu Gly Pro Tyr Xaa Leu
8525            8530            8535

Asp Arg Xaa Ser Leu Tyr Val Asn Gly Phe Thr His Gln Thr Phe
8540            8545            8550

Ala Pro Asn Thr Ser Thr Pro Gly Thr Ser Thr Val Asp Leu Gly
8555            8560            8565

Thr Ser Gly Thr Pro Ser Ser Leu Pro Ser Pro Thr Ser Ala Gly
8570            8575            8580

Pro Leu Leu Val Pro Phe Thr Leu Asn Phe Thr Ile Thr Asn Leu
8585            8590            8595

Gln Tyr Glu Glu Asp Met His His Pro Gly Ser Arg Lys Phe Asn
8600            8605            8610

Thr Thr Glu Arg Val Leu Gln Gly Leu Leu Gly Pro Met Phe Lys
8615            8620            8625

Asn Thr Ser Val Gly Leu Leu Tyr Ser Gly Cys Arg Leu Thr Leu
8630            8635            8640

Leu Arg Pro Glu Lys Asn Gly Ala Ala Thr Arg Val Asp Ala Val
8645            8650            8655

Cys Thr His Arg Pro Asp Pro Lys Ser Pro Gly Leu Asp Arg Glu
8660            8665            8670

Xaa Leu Tyr Trp Glu Leu Ser Xaa Leu Thr Xaa Xaa Ile Xaa Glu
8675            8680            8685

Leu Gly Pro Tyr Xaa Leu Asp Arg Xaa Ser Leu Tyr Val Asn Gly
8690            8695            8700

Phe Xaa Xaa Xaa Xaa Xaa Xaa Xaa Thr Ser Thr Pro Gly Thr
8705            8710            8715

Ser Xaa Val Xaa Leu Xaa Thr Ser Gly Thr Pro Xaa Xaa Xaa Pro
8720            8725            8730

Xaa Xaa Thr Xaa Xaa Xaa Pro Leu Leu Xaa Pro Phe Thr Leu Asn
8735            8740            8745

Phe Thr Ile Thr Asn Leu Xaa Tyr Glu Glu Xaa Met Xaa Xaa Pro
8750            8755            8760

Gly Ser Arg Lys Phe Asn Thr Thr Glu Arg Val Leu Gln Gly Leu

-continued

| | | | |
|---|---|---|---|
| 8765 | 8770 | 8775 | |

Leu Lys Pro Leu Phe Lys Ser Thr Ser Val Gly Pro Leu Tyr Ser
   8780                8785                8790

Gly Cys Arg Leu Thr Leu Leu Arg Pro Glu Lys Asp Gly Val Ala
   8795                8800                8805

Thr Arg Val Asp Ala Ile Cys Thr His Arg Pro Asp Pro Lys Ile
   8810                8815                8820

Pro Gly Leu Asp Arg Gln Gln Leu Tyr Trp Glu Leu Ser Gln Leu
   8825                8830                8835

Thr His Ser Ile Thr Glu Leu Gly Pro Tyr Thr Leu Asp Arg Asp
   8840                8845                8850

Ser Leu Tyr Val Asn Gly Phe Thr Gln Arg Ser Ser Val Pro Thr
   8855                8860                8865

Thr Ser Thr Pro Gly Thr Phe Thr Val Gln Pro Glu Thr Ser Glu
   8870                8875                8880

Thr Pro Ser Ser Leu Pro Gly Pro Thr Ala Thr Gly Pro Val Leu
   8885                8890                8895

Leu Pro Phe Thr Leu Asn Phe Thr Ile Thr Asn Leu Gln Tyr Glu
   8900                8905                8910

Glu Asp Met His Arg Pro Gly Ser Arg Lys Phe Asn Thr Thr Glu
   8915                8920                8925

Arg Val Leu Gln Gly Leu Leu Met Pro Leu Phe Lys Asn Thr Ser
   8930                8935                8940

Val Ser Ser Leu Tyr Ser Gly Cys Arg Leu Thr Leu Leu Arg Pro
   8945                8950                8955

Glu Lys Asp Gly Ala Ala Thr Arg Val Asp Ala Val Cys Thr His
   8960                8965                8970

Arg Pro Asp Pro Lys Ser Pro Gly Leu Asp Arg Glu Arg Leu Tyr
   8975                8980                8985

Trp Lys Leu Ser Gln Leu Thr His Gly Ile Thr Glu Leu Gly Pro
   8990                8995                9000

Tyr Thr Leu Asp Arg His Ser Leu Tyr Val Asn Gly Phe Thr His
   9005                9010                9015

Gln Ser Ser Met Thr Thr Thr Arg Thr Pro Asp Thr Ser Thr Met
   9020                9025                9030

His Leu Ala Thr Ser Arg Thr Pro Ala Ser Leu Ser Gly Pro Thr
   9035                9040                9045

Thr Ala Ser Pro Leu Leu Val Leu Phe Thr Ile Asn Phe Thr Ile
   9050                9055                9060

Thr Asn Leu Arg Tyr Glu Glu Asn Met His His Pro Gly Ser Arg
   9065                9070                9075

Lys Phe Asn Thr Thr Glu Arg Val Leu Gln Gly Leu Leu Arg Pro
   9080                9085                9090

Val Phe Lys Asn Thr Ser Val Gly Pro Leu Tyr Ser Gly Cys Arg
   9095                9100                9105

Leu Thr Leu Leu Arg Pro Lys Lys Asp Gly Ala Ala Thr Lys Val
   9110                9115                9120

Asp Ala Ile Cys Thr Tyr Arg Pro Asp Pro Lys Ser Pro Gly Leu
   9125                9130                9135

Asp Arg Glu Gln Leu Tyr Trp Glu Leu Ser Gln Leu Thr His Ser
   9140                9145                9150

Ile Thr Glu Leu Gly Pro Tyr Thr Gln Asp Arg Asp Ser Leu Tyr
   9155                9160                9165

-continued

```
Asn Val Gly Phe Thr Gln Arg Ser Ser Val Pro Thr Thr Ser Val
    9170                9175                9180
Pro Gly Thr Pro Thr Val Asp Leu Gly Thr Ser Gly Thr Pro Val
    9185                9190                9195
Ser Lys Pro Gly Pro Ser Ala Ala Ser Pro Leu Leu Val Leu Phe
    9200                9205                9210
Thr Leu Asn Gly Thr Ile Thr Asn Leu Arg Tyr Glu Glu Asn Met
    9215                9220                9225
Gln His Pro Gly Ser Arg Lys Phe Asn Thr Thr Glu Arg Val Leu
    9230                9235                9240
Gln Gly Leu Leu Arg Ser Leu Phe Lys Ser Thr Ser Val Gly Pro
    9245                9250                9255
Leu Tyr Ser Gly Cys Arg Leu Thr Leu Leu Arg Pro Glu Lys Asp
    9260                9265                9270
Gly Thr Ala Thr Gly Val Asp Ala Ile Cys Thr His His Pro Asp
    9275                9280                9285
Pro Lys Ser Pro Arg Leu Asp Arg Glu Gln Leu Tyr Trp Glu Leu
    9290                9295                9300
Ser Gln Leu Thr His Asn Ile Thr Glu Leu Gly His Tyr Ala Leu
    9305                9310                9315
Asp Asn Asp Ser Leu Phe Val Asn Gly Phe Thr His Arg Ser Ser
    9320                9325                9330
Val Ser Thr Thr Ser Thr Pro Gly Thr Pro Thr Val Tyr Leu Gly
    9335                9340                9345
Ala Ser Lys Thr Pro Ala Ser Ile Phe Gly Pro Ser Ala Ala Ser
    9350                9355                9360
His Leu Leu Ile Leu Phe Thr Leu Asn Phe Thr Ile Thr Asn Leu
    9365                9370                9375
Arg Tyr Glu Glu Asn Met Trp Pro Gly Ser Arg Lys Phe Asn Thr
    9380                9385                9390
Thr Glu Arg Val Leu Gln Gly Leu Leu Arg Pro Leu Phe Lys Asn
    9395                9400                9405
Thr Ser Val Gly Pro Leu Tyr Ser Gly Ser Arg Leu Thr Leu Leu
    9410                9415                9420
Arg Pro Glu Lys Asp Gly Glu Ala Thr Gly Val Asp Ala Ile Cys
    9425                9430                9435
Thr His Arg Pro Asp Pro Thr Gly Pro Gly Leu Asp Arg Glu Gln
    9440                9445                9450
Leu Tyr Leu Glu Leu Ser Gln Leu Thr His Ser Ile Thr Glu Leu
    9455                9460                9465
Gly Pro Tyr Thr Leu Asp Arg Asp Ser Leu Tyr Val Asn Gly Phe
    9470                9475                9480
Thr His Arg Ser Ser Val Pro Thr Thr Ser Thr Gly Val Val Ser
    9485                9490                9495
Glu Glu Pro Phe Thr Leu Asn Phe Thr Ile Asn Asn Leu Arg Tyr
    9500                9505                9510
Met Ala Asp Met Gly Gln Pro Gly Ser Leu Lys Phe Asn Ile Thr
    9515                9520                9525
Asp Asn Val Met Lys His Leu Leu Ser Pro Leu Phe Gln Arg Ser
    9530                9535                9540
Ser Leu Gly Ala Arg Tyr Thr Gly Cys Arg Val Ile Ala Leu Arg
    9545                9550                9555
```

```
Ser Val Lys Asn Gly Ala Glu Thr Arg Val Asp Leu Leu Cys Thr
    9560            9565            9570

Tyr Leu Gln Pro Leu Ser Gly Pro Gly Leu Pro Ile Lys Gln Val
    9575            9580            9585

Phe His Glu Leu Ser Gln Gln Thr His Gly Ile Thr Arg Leu Gly
    9590            9595            9600

Pro Tyr Ser Leu Asp Lys Asp Ser Leu Tyr Leu Asn Gly Tyr Asn
    9605            9610            9615

Glu Pro Gly Leu Asp Glu Pro Thr Thr Pro Lys Pro Ala Thr
    9620            9625            9630

Thr Phe Leu Pro Pro Leu Ser Glu Ala Thr Thr Ala Met Gly Tyr
    9635            9640            9645

His Leu Lys Thr Leu Thr Leu Asn Phe Thr Ile Ser Asn Leu Gln
    9650            9655            9660

Tyr Ser Pro Asp Met Gly Lys Gly Ser Ala Thr Phe Asn Ser Thr
    9665            9670            9675

Glu Gly Val Leu Gln His Leu Leu Arg Pro Leu Phe Gln Lys Ser
    9680            9685            9690

Ser Met Gly Pro Phe Tyr Leu Gly Cys Gln Leu Ile Ser Leu Arg
    9695            9700            9705

Pro Glu Lys Asp Gly Ala Ala Thr Gly Val Asp Thr Thr Cys Thr
    9710            9715            9720

Tyr His Pro Asp Pro Val Gly Pro Gly Leu Asp Ile Gln Gln Leu
    9725            9730            9735

Tyr Trp Glu Leu Ser Gln Leu Thr His Gly Val Thr Gln Leu Gly
    9740            9745            9750

Phe Tyr Val Leu Asp Arg Asp Ser Leu Phe Ile Asn Gly Tyr Ala
    9755            9760            9765

Pro Gln Asn Leu Ser Ile Arg Gly Glu Tyr Gln Ile Asn Phe His
    9770            9775            9780

Ile Val Asn Trp Asn Leu Ser Asn Pro Asp Pro Thr Ser Ser Glu
    9785            9790            9795

Tyr
```

<210> SEQ ID NO 147
<211> LENGTH: 1422
<212> TYPE: DNA
<213> ORGANISM: Homo sapiens

<400> SEQUENCE: 147

```
gccatgggt accacctgaa gaccctcaca ctcaacttca ccatctccaa tctccagtat     60
tcaccagata tgggcaaggg ctcagctaca ttcaactcca ccgagggggt ccttcagcac    120
ctgctcagac ccttgttcca gaagagcagc atgggcccct tctacttggg ttgccaactg    180
atctccctca ggcctgagaa ggatggggca gccactggtg tggacaccac ctgcacctac    240
caccctgacc ctgtgggccc cgggctggac atacagcagc tttactggga gctgagtcag    300
ctgacccatg gtgtcaccca actgggcttc tatgtcctgg acaggatag cctcttcatc    360
aatggctatg cacccagaa tttatcaatc cggggcgagt accagataaa tttccacatt    420
gtcaactgga acctcagtaa tccagacccc catcctcag agtacatcac cctgctgagg    480
gacatccagg acaaggtcac cacactctac aaaggcagtc aactacatga cacattccgc    540
ttctgcctgg tcaccaactt gacgatggac tccgtgttgg tcactgtcaa ggcattgttc    600
tcctccaatt tggaccccag cctggtggag caagtctttc tagataagac cctgaatgcc    660
```

-continued

```
tcattccatt ggctgggctc cacctaccag ttggtggaca tccatgtgac agaaatggag    720
tcatcagttt atcaaccaac aagcagctcc agcacccagc acttctacct gaatttcacc    780
atcaccaacc taccatattc ccaggacaaa gcccagccag gcaccaccaa ttaccagagg    840
aacaaaagga atattgagga tgcgctcaac caactcttcc gaaacagcag catcaagagt    900 tattttctg  actgtcaagt ttcaacattc aggtctgtcc caacaggca  ccacccggg     960 gtggactccc tgtgtaactt ctcgccactg gctcggagag tagacagagt tgccatctat   1020
gaggaatttc tgcggatgac ccggaatggt acccagctgc agaacttcac cctggacagg   1080
agcagtgtcc ttgtggatgg gtattctccc aacagaaatg agcccttaac tgggaattct   1140
gaccttccct tctgggctgt catcctcatc ggcttggcag gactcctggg actcatcaca   1200
tgcctgatct gcggtgtcct ggtgaccacc cgccggcgga agaaggaagg agaatacaac   1260
gtccagcaac agtgcccagg ctactaccag tcacacctag acctggagga tctgcaatga   1320
ctggaacttg ccggtgcctg gggtgccttt cccccagcca gggtccaaag aagcttggct   1380
ggggcagaaa taaccatat  tggtcggaaa aaaaaaaaa  aa                      1422
```

<210> SEQ ID NO 148
<211> LENGTH: 439
<212> TYPE: PRT
<213> ORGANISM: Homo sapiens

<400> SEQUENCE: 148

```
Ala Met Gly Tyr His Leu Lys Thr Leu Thr Leu Asn Phe Thr Ile Ser
1               5                   10                  15

Asn Leu Gln Tyr Ser Pro Asp Met Gly Lys Gly Ser Ala Thr Phe Asn
            20                  25                  30

Ser Thr Glu Gly Val Leu Gln His Leu Leu Arg Pro Leu Phe Gln Lys
        35                  40                  45

Ser Ser Met Gly Pro Phe Tyr Leu Gly Cys Gln Leu Ile Ser Leu Arg
    50                  55                  60

Pro Glu Lys Asp Gly Ala Ala Thr Gly Val Asp Thr Thr Cys Thr Tyr
65                  70                  75                  80

His Pro Asp Pro Val Gly Pro Gly Leu Asp Ile Gln Gln Leu Tyr Trp
                85                  90                  95

Glu Leu Ser Gln Leu Thr His Gly Val Thr Gln Leu Gly Phe Tyr Val
            100                 105                 110

Leu Asp Arg Asp Ser Leu Phe Ile Asn Gly Tyr Ala Pro Gln Asn Leu
        115                 120                 125

Ser Ile Arg Gly Glu Tyr Gln Ile Asn Phe His Ile Val Asn Trp Asn
    130                 135                 140

Leu Ser Asn Pro Asp Pro Thr Ser Ser Glu Tyr Ile Thr Leu Leu Arg
145                 150                 155                 160

Asp Ile Gln Asp Lys Val Thr Thr Leu Tyr Lys Gly Ser Gln Leu His
                165                 170                 175

Asp Thr Phe Arg Phe Cys Leu Val Thr Asn Leu Thr Met Asp Ser Val
            180                 185                 190

Leu Val Thr Val Lys Ala Leu Phe Ser Ser Asn Leu Asp Pro Ser Leu
        195                 200                 205

Val Glu Gln Val Phe Leu Asp Lys Thr Leu Asn Ala Ser Phe His Trp
    210                 215                 220

Leu Gly Ser Thr Tyr Gln Leu Val Asp Ile His Val Thr Glu Met Glu
225                 230                 235                 240
```

-continued

```
Ser Ser Val Tyr Gln Pro Thr Ser Ser Ser Thr Gln His Phe Tyr
            245                 250                 255

Leu Asn Phe Thr Ile Thr Asn Leu Pro Tyr Ser Gln Asp Lys Ala Gln
            260                 265                 270

Pro Gly Thr Thr Asn Tyr Gln Arg Asn Lys Arg Asn Ile Glu Asp Ala
            275                 280                 285

Leu Asn Gln Leu Phe Arg Asn Ser Ser Ile Lys Ser Tyr Phe Ser Asp
        290                 295                 300

Cys Gln Val Ser Thr Phe Arg Ser Val Pro Asn Arg His His Thr Gly
305                 310                 315                 320

Val Asp Ser Leu Cys Asn Phe Ser Pro Leu Ala Arg Val Asp Arg
            325                 330                 335

Val Ala Ile Tyr Glu Glu Phe Leu Arg Met Thr Arg Asn Gly Thr Gln
            340                 345                 350

Leu Gln Asn Phe Thr Leu Asp Arg Ser Ser Val Leu Val Asp Gly Tyr
            355                 360                 365

Ser Pro Asn Arg Asn Glu Pro Leu Thr Gly Asn Ser Asp Leu Pro Phe
        370                 375                 380

Trp Ala Val Ile Leu Ile Gly Leu Ala Gly Leu Leu Gly Leu Ile Thr
385                 390                 395                 400

Cys Leu Ile Cys Gly Val Leu Val Thr Thr Arg Arg Arg Lys Lys Glu
                405                 410                 415

Gly Glu Tyr Asn Val Gln Gln Gln Cys Pro Gly Tyr Tyr Gln Ser His
            420                 425                 430

Leu Asp Leu Glu Asp Leu Gln
            435

<210> SEQ ID NO 149
<211> LENGTH: 1799
<212> TYPE: PRT
<213> ORGANISM: Homo sapiens

<400> SEQUENCE: 149

Arg Thr Asp Gly Ile Met Glu His Ile Thr Lys Ile Pro Asn Glu Ala
1               5                   10                  15

Ala His Arg Gly Thr Ile Arg Pro Val Lys Gly Pro Gln Thr Ser Thr
            20                  25                  30

Ser Pro Ala Ser Pro Lys Gly Leu His Thr Gly Gly Thr Lys Arg Met
        35                  40                  45

Glu Thr Thr Thr Thr Ala Leu Lys Thr Thr Thr Ala Leu Lys Thr
    50                  55                  60

Thr Ser Arg Ala Thr Leu Thr Thr Ser Val Tyr Thr Pro Thr Leu Gly
65                  70                  75                  80

Thr Leu Thr Pro Leu Asn Ala Ser Arg Gln Met Ala Ser Thr Ile Leu
                85                  90                  95

Thr Glu Met Met Ile Thr Thr Pro Tyr Val Phe Pro Asp Val Pro Glu
            100                 105                 110

Thr Thr Ser Ser Leu Ala Thr Ser Leu Gly Ala Glu Thr Ser Thr Ala
        115                 120                 125

Leu Pro Arg Thr Thr Pro Ser Val Leu Asn Arg Glu Ser Glu Thr Thr
    130                 135                 140

Ala Ser Leu Val Ser Arg Ser Gly Ala Glu Arg Ser Pro Val Ile Gln
145                 150                 155                 160

Thr Leu Asp Val Ser Ser Ser Glu Pro Asp Thr Thr Ala Ser Trp Val
```

```
                165                 170                 175
Ile His Pro Ala Glu Thr Ile Pro Thr Val Ser Lys Thr Thr Pro Asn
            180                 185                 190

Phe Phe His Ser Glu Leu Asp Thr Val Ser Ser Thr Ala Thr Ser His
            195                 200                 205

Gly Ala Asp Val Ser Ser Ala Ile Pro Thr Asn Ile Ser Pro Ser Glu
            210                 215                 220

Leu Asp Ala Leu Thr Pro Leu Val Thr Ile Ser Gly Thr Asp Thr Ser
225                 230                 235                 240

Thr Thr Phe Pro Thr Leu Thr Lys Ser Pro His Glu Thr Glu Thr Arg
                245                 250                 255

Thr Thr Trp Leu Thr His Pro Ala Glu Thr Ser Ser Thr Ile Pro Arg
                260                 265                 270

Thr Ile Pro Asn Phe Ser His His Glu Ser Asp Ala Thr Pro Ser Ile
                275                 280                 285

Ala Thr Ser Pro Gly Ala Glu Thr Ser Ser Ala Ile Pro Ile Met Thr
            290                 295                 300

Val Ser Pro Gly Ala Glu Asp Leu Val Thr Ser Gln Val Thr Ser Ser
305                 310                 315                 320

Gly Thr Asp Arg Asn Met Thr Ile Pro Thr Leu Thr Leu Ser Pro Gly
                325                 330                 335

Glu Pro Lys Thr Ile Ala Ser Leu Val Thr His Pro Glu Ala Gln Thr
                340                 345                 350

Ser Ser Ala Ile Pro Thr Ser Thr Ile Ser Pro Ala Val Ser Arg Leu
            355                 360                 365

Val Thr Ser Met Val Thr Ser Leu Ala Ala Lys Thr Ser Thr Thr Asn
370                 375                 380

Arg Ala Leu Thr Asn Ser Pro Gly Glu Pro Ala Thr Thr Val Ser Leu
385                 390                 395                 400

Val Thr His Pro Ala Gln Thr Ser Pro Thr Val Pro Trp Thr Thr Ser
                405                 410                 415

Ile Phe Phe His Ser Lys Ser Asp Thr Thr Pro Ser Met Thr Thr Ser
                420                 425                 430

His Gly Ala Glu Ser Ser Ala Val Pro Thr Pro Thr Val Ser Thr
            435                 440                 445

Glu Val Pro Gly Val Val Thr Pro Leu Val Thr Ser Ser Arg Ala Val
            450                 455                 460

Ile Ser Thr Thr Ile Pro Ile Leu Thr Leu Ser Pro Gly Glu Pro Glu
465                 470                 475                 480

Thr Thr Pro Ser Met Ala Thr Ser His Gly Glu Glu Ala Ser Ser Ala
                485                 490                 495

Ile Pro Thr Pro Thr Val Ser Pro Gly Val Pro Gly Val Val Thr Ser
                500                 505                 510

Leu Val Thr Ser Ser Arg Ala Val Thr Ser Thr Ile Pro Ile Leu
            515                 520                 525

Thr Phe Ser Leu Gly Glu Pro Glu Thr Thr Pro Ser Met Ala Thr Ser
            530                 535                 540

His Gly Thr Glu Ala Gly Ser Ala Val Pro Thr Val Leu Pro Glu Val
545                 550                 555                 560

Pro Gly Met Val Thr Ser Leu Val Ala Ser Ser Arg Ala Val Thr Ser
                565                 570                 575

Thr Thr Leu Pro Thr Leu Thr Leu Ser Pro Gly Glu Pro Glu Thr Thr
            580                 585                 590
```

-continued

```
Pro Ser Met Ala Thr Ser His Gly Ala Glu Ala Ser Ser Thr Val Pro
        595                 600                 605

Thr Val Ser Pro Glu Val Pro Gly Val Val Thr Ser Leu Val Thr Ser
        610                 615                 620

Ser Ser Gly Val Asn Ser Thr Ser Ile Pro Thr Leu Ile Leu Ser Pro
625                 630                 635                 640

Gly Glu Leu Glu Thr Thr Pro Ser Met Ala Thr Ser His Gly Ala Glu
                645                 650                 655

Ala Ser Ser Ala Val Pro Thr Pro Thr Val Ser Pro Gly Val Ser Gly
                660                 665                 670

Val Val Thr Pro Leu Val Thr Ser Ser Arg Ala Val Thr Ser Thr Thr
                675                 680                 685

Ile Pro Ile Leu Thr Leu Ser Ser Glu Pro Glu Thr Thr Pro Ser
        690                 695                 700

Met Ala Thr Ser His Gly Val Glu Ala Ser Ser Ala Val Leu Thr Val
705                 710                 715                 720

Ser Pro Glu Val Pro Gly Met Val Thr Ser Leu Val Thr Ser Ser Arg
                725                 730                 735

Ala Val Thr Ser Thr Thr Ile Pro Thr Leu Thr Ile Ser Ser Asp Glu
                740                 745                 750

Pro Glu Thr Thr Thr Ser Leu Val Thr His Ser Glu Ala Lys Met Ile
        755                 760                 765

Ser Ala Ile Pro Thr Leu Ala Val Ser Pro Thr Val Gln Gly Leu Val
        770                 775                 780

Thr Ser Leu Val Thr Ser Ser Gly Ser Glu Thr Ser Ala Phe Ser Asn
785                 790                 795                 800

Leu Thr Val Ala Ser Ser Gln Pro Glu Thr Ile Asp Ser Trp Val Ala
                805                 810                 815

His Pro Gly Thr Glu Ala Ser Ser Val Val Pro Thr Leu Thr Val Ser
                820                 825                 830

Thr Gly Glu Pro Phe Thr Asn Ile Ser Leu Val Thr His Pro Ala Glu
        835                 840                 845

Ser Ser Ser Thr Leu Pro Arg Thr Thr Ser Arg Phe Ser His Ser Glu
850                 855                 860

Leu Asp Thr Met Pro Ser Thr Val Thr Ser Pro Glu Ala Glu Ser Ser
865                 870                 875                 880

Ser Ala Ile Ser Thr Thr Ile Ser Pro Gly Ile Pro Gly Val Leu Thr
                885                 890                 895

Ser Leu Val Thr Ser Ser Gly Arg Asp Ile Ser Ala Thr Phe Pro Thr
                900                 905                 910

Val Pro Glu Ser Pro His Glu Ser Glu Ala Thr Ala Ser Trp Val Thr
                915                 920                 925

His Pro Ala Val Thr Ser Thr Val Pro Arg Thr Thr Pro Asn Tyr
        930                 935                 940

Ser His Ser Glu Pro Asp Thr Thr Pro Ser Ile Ala Thr Ser Pro Gly
945                 950                 955                 960

Ala Glu Ala Thr Ser Asp Phe Pro Thr Ile Thr Val Ser Pro Asp Val
                965                 970                 975

Pro Asp Met Val Thr Ser Gln Val Thr Ser Ser Gly Thr Asp Thr Ser
                980                 985                 990

Ile Thr Ile Pro Thr Leu Thr Leu  Ser Ser Gly Glu Pro  Glu Thr Thr
        995                 1000                1005
```

-continued

```
Thr Ser Phe Ile Thr Tyr Ser Glu Thr His Ser Ser Ala Ile
1010             1015             1020

Pro Thr Leu Pro Val Ser Pro Gly Ala Ser Lys Met Leu Thr Ser
1025             1030             1035

Leu Val Ile Ser Ser Gly Thr Asp Ser Thr Thr Phe Pro Thr
1040             1045             1050

Leu Thr Glu Thr Pro Tyr Glu Pro Glu Thr Thr Ala Ile Gln Leu
1055             1060             1065

Ile His Pro Ala Glu Thr Asn Thr Met Val Pro Arg Thr Thr Pro
1070             1075             1080

Lys Phe Ser His Ser Lys Ser Asp Thr Thr Leu Pro Val Ala Ile
1085             1090             1095

Thr Ser Pro Gly Pro Glu Ala Ser Ser Ala Val Ser Thr Thr Thr
1100             1105             1110

Ile Ser Pro Asp Met Ser Asp Leu Val Thr Ser Leu Val Pro Ser
1115             1120             1125

Ser Gly Thr Asp Thr Ser Thr Thr Phe Pro Thr Leu Ser Glu Thr
1130             1135             1140

Pro Tyr Glu Pro Glu Thr Thr Ala Thr Trp Leu Thr His Pro Ala
1145             1150             1155

Glu Thr Ser Thr Thr Val Ser Gly Thr Ile Pro Asn Phe Ser His
1160             1165             1170

Arg Gly Ser Asp Thr Ala Pro Ser Met Val Thr Ser Pro Gly Val
1175             1180             1185

Asp Thr Arg Ser Gly Val Pro Thr Thr Thr Ile Pro Pro Ser Ile
1190             1195             1200

Pro Gly Val Val Thr Ser Gln Val Thr Ser Ser Ala Thr Asp Thr
1205             1210             1215

Ser Thr Ala Ile Pro Thr Leu Thr Pro Ser Pro Gly Glu Pro Glu
1220             1225             1230

Thr Thr Ala Ser Ser Ala Thr His Pro Gly Thr Gln Thr Gly Phe
1235             1240             1245

Thr Val Pro Ile Arg Thr Val Pro Ser Ser Glu Pro Asp Thr Met
1250             1255             1260

Ala Ser Trp Val Thr His Pro Pro Gln Thr Ser Thr Pro Val Ser
1265             1270             1275

Arg Thr Thr Ser Ser Phe Ser His Ser Ser Pro Asp Ala Thr Pro
1280             1285             1290

Val Met Ala Thr Ser Pro Arg Thr Glu Ala Ser Ser Ala Val Leu
1295             1300             1305

Thr Thr Ile Ser Pro Gly Ala Pro Glu Met Val Thr Ser Gln Ile
1310             1315             1320

Thr Ser Ser Gly Ala Ala Thr Ser Thr Thr Val Pro Thr Leu Thr
1325             1330             1335

His Ser Pro Gly Met Pro Glu Thr Thr Ala Leu Leu Ser Thr His
1340             1345             1350

Pro Arg Thr Glu Thr Ser Lys Thr Phe Pro Ala Ser Thr Val Phe
1355             1360             1365

Pro Gln Val Ser Glu Thr Thr Ala Ser Leu Thr Ile Arg Pro Gly
1370             1375             1380

Ala Glu Thr Ser Thr Ala Leu Pro Thr Gln Thr Thr Ser Ser Leu
1385             1390             1395

Phe Thr Leu Leu Val Thr Gly Thr Ser Arg Val Asp Leu Ser Pro
```

```
                1400                1405                1410
Thr Ala Ser Pro Gly Val Ser Ala Lys Thr Ala Pro Leu Ser Thr
    1415                1420                1425

His Pro Gly Thr Glu Thr Ser Thr Met Ile Pro Thr Ser Thr Leu
    1430                1435                1440

Ser Leu Gly Leu Leu Glu Thr Thr Gly Leu Leu Ala Thr Ser Ser
    1445                1450                1455

Ser Ala Glu Thr Ser Thr Ser Thr Leu Thr Leu Thr Val Ser Pro
    1460                1465                1470

Ala Val Ser Gly Leu Ser Ser Ala Ser Ile Thr Thr Asp Lys Pro
    1475                1480                1485

Gln Thr Val Thr Ser Trp Asn Thr Glu Thr Ser Pro Ser Val Thr
    1490                1495                1500

Ser Val Gly Pro Pro Glu Phe Ser Arg Thr Val Thr Gly Thr Thr
    1505                1510                1515

Met Thr Leu Ile Pro Ser Glu Met Pro Thr Pro Pro Lys Thr Ser
    1520                1525                1530

His Gly Glu Gly Val Ser Pro Thr Thr Ile Leu Arg Thr Thr Met
    1535                1540                1545

Val Glu Ala Thr Asn Leu Ala Thr Thr Gly Ser Ser Pro Thr Val
    1550                1555                1560

Ala Lys Thr Thr Thr Thr Phe Asn Thr Leu Ala Gly Ser Leu Phe
    1565                1570                1575

Thr Pro Leu Thr Thr Pro Gly Met Ser Thr Leu Ala Ser Glu Ser
    1580                1585                1590

Val Thr Ser Arg Thr Ser Tyr Asn His Arg Ser Trp Ile Ser Thr
    1595                1600                1605

Thr Ser Ser Tyr Asn Arg Arg Tyr Trp Thr Pro Ala Thr Ser Thr
    1610                1615                1620

Pro Val Thr Ser Thr Phe Ser Pro Gly Ile Ser Thr Ser Ser Ile
    1625                1630                1635

Pro Ser Ser Thr Ala Ala Thr Val Pro Phe Met Val Pro Phe Thr
    1640                1645                1650

Leu Asn Phe Thr Ile Thr Asn Leu Gln Tyr Glu Glu Asp Met Arg
    1655                1660                1665

His Pro Gly Ser Arg Lys Phe Asn Ala Thr Glu Arg Glu Leu Gln
    1670                1675                1680

Gly Leu Leu Lys Pro Leu Phe Arg Asn Ser Ser Leu Glu Tyr Leu
    1685                1690                1695

Tyr Ser Gly Cys Arg Leu Ala Ser Leu Arg Pro Glu Lys Asp Ser
    1700                1705                1710

Ser Ala Met Ala Val Asp Ala Ile Cys Thr His Arg Pro Asp Pro
    1715                1720                1725

Glu Asp Leu Gly Leu Asp Arg Glu Arg Leu Tyr Trp Glu Leu Ser
    1730                1735                1740

Asn Leu Thr Asn Gly Ile Gln Glu Leu Gly Pro Tyr Thr Leu Asp
    1745                1750                1755

Arg Asn Ser Leu Tyr Val Asn Gly Phe Thr His Arg Ser Ser Met
    1760                1765                1770

Pro Thr Thr Ser Thr Pro Gly Thr Ser Thr Val Asp Val Gly Thr
    1775                1780                1785

Ser Gly Thr Pro Ser Ser Ser Pro Ser Pro Thr
    1790                1795
```

<210> SEQ ID NO 150
<211> LENGTH: 156
<212> TYPE: PRT
<213> ORGANISM: Homo sapiens

<400> SEQUENCE: 150

```
Glu Pro Gly Pro Leu Leu Ile Pro Phe Thr Phe Asn Phe Thr Ile Thr
1               5                   10                  15

Asn Leu His Tyr Glu Glu Asn Met Gln His Pro Gly Ser Arg Lys Phe
            20                  25                  30

Asn Thr Thr Glu Arg Val Leu Gln Gly Leu Leu Lys Pro Leu Phe Lys
        35                  40                  45

Asn Thr Ser Val Gly Pro Leu Tyr Ser Gly Cys Arg Leu Thr Leu Leu
    50                  55                  60

Arg Pro Glu Lys His Glu Ala Ala Thr Gly Val Asp Thr Ile Cys Thr
65                  70                  75                  80

His Arg Val Asp Pro Ile Gly Pro Gly Leu Asp Arg Glu Arg Leu Tyr
                85                  90                  95

Trp Glu Leu Ser Gln Leu Thr Asn Ser Ile Thr Glu Leu Gly Pro Tyr
            100                 105                 110

Thr Leu Asp Arg Asp Ser Leu Tyr Val Asn Gly Phe Asn Pro Arg Ser
        115                 120                 125

Ser Val Pro Thr Thr Ser Thr Pro Gly Thr Ser Thr Val His Leu Ala
    130                 135                 140

Thr Ser Gly Thr Pro Ser Ser Leu Pro Lys Leu Thr
145                 150                 155
```

<210> SEQ ID NO 151
<211> LENGTH: 507
<212> TYPE: DNA
<213> ORGANISM: Homo sapiens
<220> FEATURE:
<221> NAME/KEY: CDS
<222> LOCATION: (1)..(507)
<223> OTHER INFORMATION:

<400> SEQUENCE: 151

```
atg aga gga tcg cat cac cat cac cat cac gga tcc atg ggc cac aca       48
Met Arg Gly Ser His His His His His His Gly Ser Met Gly His Thr
1               5                   10                  15 gag cct ggc cct ctc ctg ata cca ttc act ttc aac ttt acc atc acc       96
Glu Pro Gly Pro Leu Leu Ile Pro Phe Thr Phe Asn Phe Thr Ile Thr
            20                  25                  30 aac ctg cat tat gag gaa aac atg caa cac cct ggt tcc agg aag ttc      144
Asn Leu His Tyr Glu Glu Asn Met Gln His Pro Gly Ser Arg Lys Phe
        35                  40                  45 aac acc acg gag agg gtt ctg cag ggt ctg ctc aag ccc ttg ttc aag      192
Asn Thr Thr Glu Arg Val Leu Gln Gly Leu Leu Lys Pro Leu Phe Lys
    50                  55                  60 aac acc agt gtt ggc cct ctg tac tct ggc tgc aga ctg acc ttg ctc      240
Asn Thr Ser Val Gly Pro Leu Tyr Ser Gly Cys Arg Leu Thr Leu Leu
65                  70                  75                  80 aga cct gag aag cat gag gca gcc act gga gtg gac acc atc tgt acc      288
Arg Pro Glu Lys His Glu Ala Ala Thr Gly Val Asp Thr Ile Cys Thr
                85                  90                  95 cac cgc gtt gat ccc atc gga cct gga ctg gac aga gag cgg cta tac      336
His Arg Val Asp Pro Ile Gly Pro Gly Leu Asp Arg Glu Arg Leu Tyr
            100                 105                 110
```

```
tgg gag ctg agc cag ctg acc aac agc atc aca gag ctg gga ccc tac    384
Trp Glu Leu Ser Gln Leu Thr Asn Ser Ile Thr Glu Leu Gly Pro Tyr
            115                 120                 125 acc ctg gac agg gac agt ctc tat gtc aat ggc ttc aac cct cgg agc    432
Thr Leu Asp Arg Asp Ser Leu Tyr Val Asn Gly Phe Asn Pro Arg Ser
130                 135                 140 tct gtg cca acc acc agc act cct ggg acc tcc aca gtg cac ctg gca    480
Ser Val Pro Thr Thr Ser Thr Pro Gly Thr Ser Thr Val His Leu Ala
145                 150                 155                 160 acc tct ggg act cca tcc tcc ctg cct                                507
Thr Ser Gly Thr Pro Ser Ser Leu Pro
                165
```

<210> SEQ ID NO 152
<211> LENGTH: 169
<212> TYPE: PRT
<213> ORGANISM: Homo sapiens

<400> SEQUENCE: 152

```
Met Arg Gly Ser His His His His His Gly Ser Met Gly His Thr
1               5                   10                  15

Glu Pro Gly Pro Leu Leu Ile Pro Phe Thr Phe Asn Phe Thr Ile Thr
            20                  25                  30

Asn Leu His Tyr Glu Glu Asn Met Gln His Pro Gly Ser Arg Lys Phe
        35                  40                  45

Asn Thr Thr Glu Arg Val Leu Gln Gly Leu Leu Lys Pro Leu Phe Lys
    50                  55                  60

Asn Thr Ser Val Gly Pro Leu Tyr Ser Gly Cys Arg Leu Thr Leu Leu
65                  70                  75                  80

Arg Pro Glu Lys His Glu Ala Ala Thr Gly Val Asp Thr Ile Cys Thr
                85                  90                  95

His Arg Val Asp Pro Ile Gly Pro Gly Leu Asp Arg Glu Arg Leu Tyr
            100                 105                 110

Trp Glu Leu Ser Gln Leu Thr Asn Ser Ile Thr Glu Leu Gly Pro Tyr
        115                 120                 125

Thr Leu Asp Arg Asp Ser Leu Tyr Val Asn Gly Phe Asn Pro Arg Ser
    130                 135                 140

Ser Val Pro Thr Thr Ser Thr Pro Gly Thr Ser Thr Val His Leu Ala
145                 150                 155                 160

Thr Ser Gly Thr Pro Ser Ser Leu Pro
                165
```

<210> SEQ ID NO 153
<211> LENGTH: 507
<212> TYPE: DNA
<213> ORGANISM: Homo sapiens

<400> SEQUENCE: 153

```
aggcagggag gatggagtcc cagaggttgc caggtgcact gtggaggtcc caggagtgct      60
ggtggttggc acagagctcc gagggttgaa gccattgaca tagagactgt ccctgtccag     120
ggtgtagggt cccagctctg tgatgctgtt ggtcagctgg ctcagctccc agtatagccg     180
ctctctgtcc agtccaggtc cgatgggatc aacgcggtgg gtacagatgg tgtccactcc     240
agtggctgcc tcatgcttct caggtctgag caaggtcagt ctgcagccag agtacagagg     300
gccaacactg gtgttcttga caagggctt gagcagaccc tgcagaaccc tctccgtggt     360
gttgaacttc ctggaaccag ggtgttgcat gttttcctca taatgcaggt tggtgatggt     420
```

-continued

```
aaagttgaaa gtgaatggta tcaggagagg gccaggctct gtgtggccca tggatccgtg      480
atggtgatgg tgatgcgatc ctctcat                                          507
```

<210> SEQ ID NO 154
<211> LENGTH: 9
<212> TYPE: PRT
<213> ORGANISM: Homo sapiens

<400> SEQUENCE: 154

Arg Leu Tyr Trp Glu Leu Ser Gln Leu
1               5

<210> SEQ ID NO 155
<211> LENGTH: 9
<212> TYPE: PRT
<213> ORGANISM: Homo sapiens

<400> SEQUENCE: 155

Thr Leu Asp Arg Asp Ser Leu Tyr Val
1               5

<210> SEQ ID NO 156
<211> LENGTH: 9
<212> TYPE: PRT
<213> ORGANISM: Homo sapiens

<400> SEQUENCE: 156

Val Leu Gln Gly Leu Leu Lys Pro Leu
1               5

<210> SEQ ID NO 157
<211> LENGTH: 9
<212> TYPE: PRT
<213> ORGANISM: Homo sapiens

<400> SEQUENCE: 157

Gln Leu Thr Asn Ser Ile Thr Glu Leu
1               5

<210> SEQ ID NO 158
<211> LENGTH: 780
<212> TYPE: PRT
<213> ORGANISM: Homo sapiens

<400> SEQUENCE: 158

Ala Thr Val Pro Phe Met Val Pro Phe Thr Leu Asn Phe Thr Ile Thr
1               5                   10                  15

Asn Leu Gln Tyr Glu Glu Asp Met Arg His Pro Gly Ser Arg Lys Phe
                20                  25                  30

Asn Ala Thr Glu Arg Glu Leu Gln Gly Leu Leu Lys Pro Leu Phe Arg
            35                  40                  45

Asn Ser Ser Leu Glu Tyr Leu Tyr Ser Gly Cys Arg Leu Ala Ser Leu
        50                  55                  60

Arg Pro Glu Lys Asp Ser Ser Ala Met Ala Val Asp Ala Ile Cys Thr
65                  70                  75                  80

His Arg Pro Asp Pro Glu Asp Leu Gly Leu Asp Arg Glu Arg Leu Tyr
                85                  90                  95

Trp Glu Leu Ser Asn Leu Thr Asn Gly Ile Gln Glu Leu Gly Pro Tyr
                100                 105                 110

Thr Leu Asp Arg Asn Ser Leu Tyr Val Asn Gly Phe Thr His Arg Ser
            115                 120                 125

```
Ser Met Pro Thr Thr Ser Thr Pro Gly Thr Ser Thr Val Asp Val Gly
    130                 135                 140

Thr Ser Gly Thr Pro Ser Ser Pro Ser Pro Thr Ala Ala Gly Pro
145                 150                 155                 160

Leu Leu Met Pro Phe Thr Leu Asn Phe Thr Ile Thr Asn Leu Gln Tyr
                165                 170                 175

Glu Glu Asp Met Arg Arg Thr Gly Ser Arg Lys Phe Asn Thr Met Glu
            180                 185                 190

Ser Val Leu Gln Gly Leu Leu Lys Pro Leu Phe Lys Asn Thr Ser Val
        195                 200                 205

Gly Pro Leu Tyr Ser Gly Cys Arg Leu Thr Leu Arg Pro Glu Lys
    210                 215                 220

Asp Gly Ala Ala Thr Gly Val Asp Ala Ile Cys Thr His Arg Leu Asp
225                 230                 235                 240

Pro Lys Ser Pro Gly Leu Asn Arg Glu Gln Leu Tyr Trp Glu Leu Ser
                245                 250                 255

Lys Leu Thr Asn Asp Ile Glu Glu Leu Gly Pro Tyr Thr Leu Asp Arg
            260                 265                 270

Asn Ser Leu Tyr Val Asn Gly Phe Thr His Gln Ser Ser Val Ser Thr
        275                 280                 285

Thr Ser Thr Pro Gly Thr Ser Thr Val Asp Leu Arg Thr Ser Gly Thr
    290                 295                 300

Pro Ser Ser Leu Ser Ser Pro Thr Ile Met Ala Gly Pro Leu Leu Val
305                 310                 315                 320

Pro Phe Thr Leu Asn Phe Thr Ile Thr Asn Leu Gln Tyr Gly Glu Asp
                325                 330                 335

Met Gly His Pro Gly Ser Arg Lys Phe Asn Thr Thr Glu Arg Val Leu
            340                 345                 350

Gln Gly Leu Leu Gly Pro Ile Phe Lys Asn Thr Ser Val Gly Pro Leu
        355                 360                 365

Tyr Ser Gly Cys Arg Leu Thr Ser Leu Arg Ser Glu Lys Asp Gly Ala
    370                 375                 380

Ala Thr Gly Val Asp Ala Ile Cys Ile His His Leu Asp Pro Lys Ser
385                 390                 395                 400

Pro Gly Leu Asn Arg Glu Arg Leu Tyr Trp Glu Leu Ser Gln Leu Thr
                405                 410                 415

Asn Gly Ile Lys Glu Leu Gly Pro Tyr Thr Leu Asp Arg Asn Ser Leu
            420                 425                 430

Tyr Val Asn Gly Phe Thr His Arg Thr Ser Val Pro Thr Ser Ser Thr
        435                 440                 445

Pro Gly Thr Ser Thr Val Asp Leu Gly Thr Ser Gly Thr Pro Phe Ser
    450                 455                 460

Leu Pro Ser Pro Ala Thr Ala Gly Pro Leu Leu Val Leu Phe Thr Leu
465                 470                 475                 480

Asn Phe Thr Ile Thr Asn Leu Lys Tyr Glu Glu Asp Met His Arg Pro
                485                 490                 495

Gly Ser Arg Lys Phe Asn Thr Thr Glu Arg Val Leu Gln Thr Leu Leu
            500                 505                 510

Gly Pro Met Phe Lys Asn Thr Ser Val Gly Leu Leu Tyr Ser Gly Cys
        515                 520                 525

Arg Leu Thr Leu Leu Arg Ser Glu Lys Asp Gly Ala Ala Thr Gly Val
530                 535                 540
```

-continued

```
Asp Ala Ile Cys Thr His Arg Leu Asp Pro Lys Ser Pro Gly Leu Asp
545                 550                 555                 560

Arg Glu Gln Leu Tyr Trp Glu Leu Ser Gln Leu Thr Asn Gly Ile Lys
                565                 570                 575

Glu Leu Gly Pro Tyr Thr Leu Asp Arg Asn Ser Leu Tyr Val Asn Gly
            580                 585                 590

Phe Thr His Trp Ile Pro Val Pro Thr Ser Ser Thr Pro Gly Thr Ser
        595                 600                 605

Thr Val Asp Leu Gly Ser Gly Thr Pro Ser Ser Leu Pro Ser Pro Thr
    610                 615                 620

Ala Ala Gly Pro Leu Leu Val Pro Phe Thr Leu Asn Phe Thr Ile Thr
625                 630                 635                 640

Asn Leu Gln Tyr Glu Glu Asp Met His His Pro Gly Ser Arg Lys Phe
                645                 650                 655

Asn Thr Thr Glu Arg Val Leu Gln Gly Leu Leu Gly Pro Met Phe Lys
            660                 665                 670

Asn Thr Ser Val Gly Leu Leu Tyr Ser Gly Cys Arg Leu Thr Leu Leu
        675                 680                 685

Arg Ser Glu Lys Asp Gly Ala Ala Thr Gly Val Asp Ala Ile Cys Thr
    690                 695                 700

His Arg Leu Asp Pro Lys Ser Pro Gly Val Asp Arg Glu Gln Leu Tyr
705                 710                 715                 720

Trp Glu Leu Ser Gln Leu Thr Asn Gly Ile Lys Glu Leu Gly Pro Tyr
                725                 730                 735

Thr Leu Asp Arg Asn Ser Leu Tyr Val Asn Gly Phe Thr His Gln Thr
            740                 745                 750

Ser Ala Pro Asn Thr Ser Thr Pro Gly Thr Ser Thr Val Asp Leu Gly
        755                 760                 765

Thr Ser Gly Thr Pro Ser Ser Leu Pro Ser Pro Thr
    770                 775                 780

<210> SEQ ID NO 159
<211> LENGTH: 780
<212> TYPE: PRT
<213> ORGANISM: Homo sapiens

<400> SEQUENCE: 159

Ser Ala Gly Pro Leu Leu Val Pro Phe Thr Leu Asn Phe Thr Ile Thr
1               5                   10                  15

Asn Leu Gln Tyr Glu Glu Asp Met His His Pro Gly Ser Arg Lys Phe
                20                  25                  30

Asn Thr Thr Glu Arg Val Leu Gln Gly Leu Leu Gly Pro Met Phe Lys
            35                  40                  45

Asn Thr Ser Val Gly Leu Leu Tyr Ser Gly Cys Arg Leu Thr Leu Leu
        50                  55                  60

Arg Pro Glu Lys Asn Gly Ala Ala Thr Gly Met Asp Ala Ile Cys Ser
65                  70                  75                  80

His Arg Leu Asp Pro Lys Ser Pro Gly Leu Asn Arg Glu Gln Leu Tyr
                85                  90                  95

Trp Glu Leu Ser Gln Leu Thr His Gly Ile Lys Glu Leu Gly Pro Tyr
            100                 105                 110

Thr Leu Asp Arg Asn Ser Leu Tyr Val Asn Gly Phe Thr His Arg Ser
        115                 120                 125

Ser Val Ala Pro Thr Ser Thr Pro Gly Thr Ser Thr Val Asp Leu Gly
    130                 135                 140
```

-continued

```
Thr Ser Gly Thr Pro Ser Ser Leu Pro Ser Pro Thr Thr Ala Val Pro
145                 150                 155                 160

Leu Leu Val Pro Phe Thr Leu Asn Phe Thr Ile Thr Asn Leu Gln Tyr
                165                 170                 175

Gly Glu Asp Met Arg His Pro Gly Ser Arg Lys Phe Asn Thr Thr Glu
            180                 185                 190

Arg Val Leu Gln Gly Leu Leu Gly Pro Leu Phe Lys Asn Ser Ser Val
        195                 200                 205

Gly Pro Leu Tyr Ser Gly Cys Arg Leu Ile Ser Leu Arg Ser Glu Lys
    210                 215                 220

Asp Gly Ala Ala Thr Gly Val Asp Ala Ile Cys Thr His His Leu Asn
225                 230                 235                 240

Pro Gln Ser Pro Gly Leu Asp Arg Glu Gln Leu Tyr Trp Gln Leu Ser
                245                 250                 255

Gln Met Thr Asn Gly Ile Lys Glu Leu Gly Pro Tyr Thr Leu Asp Arg
            260                 265                 270

Asn Ser Leu Tyr Val Asn Gly Phe Thr His Arg Ser Ser Gly Leu Thr
        275                 280                 285

Thr Ser Thr Pro Trp Thr Ser Thr Val Asp Leu Gly Thr Ser Gly Thr
    290                 295                 300

Pro Ser Pro Val Pro Ser Pro Thr Thr Ala Gly Pro Leu Leu Val Pro
305                 310                 315                 320

Phe Thr Leu Asn Phe Thr Ile Thr Asn Leu Gln Tyr Glu Glu Asp Met
                325                 330                 335

His Arg Pro Gly Ser Arg Lys Phe Asn Ala Thr Glu Arg Val Leu Gln
            340                 345                 350

Gly Leu Leu Ser Pro Ile Phe Lys Asn Ser Ser Val Gly Pro Leu Tyr
        355                 360                 365

Ser Gly Cys Arg Leu Thr Ser Leu Arg Pro Glu Lys Asp Gly Ala Ala
    370                 375                 380

Thr Gly Met Asp Ala Val Cys Leu Tyr His Pro Asn Pro Lys Arg Pro
385                 390                 395                 400

Gly Leu Asp Arg Glu Gln Leu Tyr Trp Glu Leu Ser Gln Leu Thr His
                405                 410                 415

Asn Ile Thr Glu Leu Gly Pro Tyr Ser Leu Asp Arg Asp Ser Leu Tyr
            420                 425                 430

Val Asn Gly Phe Thr His Gln Asn Ser Val Pro Thr Thr Ser Thr Pro
        435                 440                 445

Gly Thr Ser Thr Val Tyr Trp Ala Thr Thr Gly Thr Pro Ser Ser Phe
    450                 455                 460

Pro Gly His Thr Glu Pro Gly Pro Leu Leu Ile Pro Phe Thr Phe Asn
465                 470                 475                 480

Phe Thr Ile Thr Asn Leu His Tyr Glu Glu Asn Met Gln His Pro Gly
                485                 490                 495

Ser Arg Lys Phe Asn Thr Thr Glu Arg Val Leu Gln Gly Leu Leu Lys
            500                 505                 510

Pro Leu Phe Lys Asn Thr Ser Val Gly Pro Leu Tyr Ser Gly Cys Arg
        515                 520                 525

Leu Thr Ser Leu Arg Pro Glu Lys Asp Gly Ala Ala Thr Gly Met Asp
    530                 535                 540

Ala Val Cys Leu Tyr His Pro Asn Pro Lys Arg Pro Gly Leu Asp Arg
545                 550                 555                 560
```

```
Glu Gln Leu Tyr Cys Glu Leu Ser Gln Leu Thr His Asn Ile Thr Glu
                565                 570                 575

Leu Gly Pro Tyr Ser Leu Asp Arg Asp Ser Leu Tyr Val Asn Gly Phe
                580                 585                 590

Thr His Gln Asn Ser Val Pro Thr Thr Ser Thr Pro Gly Thr Ser Thr
            595                 600                 605

Val Tyr Trp Ala Thr Thr Gly Thr Pro Ser Ser Phe Pro Gly His Thr
        610                 615                 620

Glu Pro Gly Pro Leu Leu Ile Pro Phe Thr Phe Asn Phe Thr Ile Thr
625                 630                 635                 640

Asn Leu His Tyr Glu Glu Asn Met Gln His Pro Gly Ser Arg Lys Phe
                645                 650                 655

Asn Thr Thr Glu Arg Val Leu Gln Gly Leu Leu Lys Pro Leu Phe Lys
                660                 665                 670

Asn Thr Ser Val Gly Pro Leu Tyr Ser Gly Cys Arg Leu Thr Leu Leu
            675                 680                 685

Arg Pro Glu Lys His Glu Ala Ala Thr Gly Val Asp Thr Ile Cys Thr
690                 695                 700

His Arg Val Asp Pro Ile Gly Pro Gly Leu Asp Arg Glu Arg Leu Tyr
705                 710                 715                 720

Trp Glu Leu Ser Gln Leu Thr Asn Ser Ile Thr Glu Leu Gly Pro Tyr
                725                 730                 735

Thr Leu Asp Arg Asp Ser Leu Tyr Val Asn Gly Phe Asn Pro Arg Ser
            740                 745                 750

Ser Val Pro Thr Thr Ser Thr Pro Gly Thr Ser Thr Val His Leu Ala
        755                 760                 765

Thr Ser Gly Thr Pro Ser Ser Leu Pro Gly His Thr
770                 775                 780

<210> SEQ ID NO 160
<211> LENGTH: 624
<212> TYPE: PRT
<213> ORGANISM: Homo sapiens

<400> SEQUENCE: 160

Thr Ala Gly Pro Leu Leu Val Pro Phe Thr Leu Asn Phe Thr Ile Thr
1               5                   10                  15

Asn Leu Gln Tyr Glu Glu Asp Met His Arg Pro Gly Ser Arg Arg Phe
                20                  25                  30

Asn Thr Thr Glu Arg Val Leu Gln Gly Leu Leu Thr Pro Leu Phe Lys
            35                  40                  45

Asn Thr Ser Val Gly Pro Leu Tyr Ser Gly Cys Arg Leu Thr Leu Leu
        50                  55                  60

Arg Pro Glu Lys Gln Glu Ala Ala Thr Gly Val Asp Thr Ile Cys Thr
65                  70                  75                  80

His Arg Val Asp Pro Ile Gly Pro Gly Leu Asp Arg Glu Arg Leu Tyr
                85                  90                  95

Trp Glu Leu Ser Gln Leu Thr Asn Ser Ile Thr Glu Leu Gly Pro Tyr
                100                 105                 110

Thr Leu Asp Arg Asp Ser Leu Tyr Val Asn Gly Phe Asn Pro Trp Ser
            115                 120                 125

Ser Val Pro Thr Thr Ser Thr Pro Gly Thr Ser Thr Val His Leu Ala
        130                 135                 140

Thr Ser Gly Thr Pro Ser Ser Leu Pro Gly His Thr Ala Pro Val Pro
145                 150                 155                 160
```

```
Leu Leu Ile Pro Phe Thr Leu Asn Phe Thr Ile Thr Asp Leu His Tyr
            165                 170                 175

Glu Glu Asn Met Gln His Pro Gly Ser Arg Lys Phe Asn Thr Thr Glu
        180                 185                 190

Arg Val Leu Gln Gly Leu Leu Lys Pro Leu Phe Lys Ser Thr Ser Val
            195                 200                 205

Gly Pro Leu Tyr Ser Gly Cys Arg Leu Thr Leu Arg Pro Glu Lys
    210                 215                 220

His Gly Ala Ala Thr Gly Val Asp Ala Ile Cys Thr Leu Arg Leu Asp
225                 230                 235                 240

Pro Thr Gly Pro Gly Leu Asp Arg Glu Arg Leu Tyr Trp Glu Leu Ser
                245                 250                 255

Gln Leu Thr Asn Ser Val Thr Glu Leu Gly Pro Tyr Thr Leu Asp Arg
            260                 265                 270

Asp Ser Leu Tyr Val Asn Gly Phe Thr His Arg Ser Ser Val Pro Thr
        275                 280                 285

Thr Ser Ile Pro Gly Thr Ser Ala Val His Leu Glu Thr Ser Gly Thr
290                 295                 300

Pro Ala Ser Leu Pro Gly His Thr Ala Pro Gly Pro Leu Leu Val Pro
305                 310                 315                 320

Phe Thr Leu Asn Phe Thr Ile Thr Asn Leu Gln Tyr Glu Glu Asp Met
                325                 330                 335

Arg His Pro Gly Ser Arg Lys Phe Ser Thr Thr Glu Arg Val Leu Gln
                340                 345                 350

Gly Leu Leu Lys Pro Leu Phe Lys Asn Thr Ser Val Ser Ser Leu Tyr
            355                 360                 365

Ser Gly Cys Arg Leu Thr Leu Leu Arg Pro Glu Lys Asp Gly Ala Ala
        370                 375                 380

Thr Arg Val Asp Ala Val Cys Thr His Arg Pro Asp Pro Lys Ser Pro
385                 390                 395                 400

Gly Leu Asp Arg Glu Arg Leu Tyr Trp Lys Leu Ser Gln Leu Thr His
                405                 410                 415

Gly Ile Thr Glu Leu Gly Pro Tyr Thr Leu Asp Arg His Ser Leu Tyr
            420                 425                 430

Val Asn Gly Phe Thr His Gln Ser Ser Met Thr Thr Thr Arg Thr Pro
            435                 440                 445

Asp Thr Ser Thr Met His Leu Ala Thr Ser Arg Thr Pro Ala Ser Leu
        450                 455                 460

Ser Gly Pro Thr Thr Ala Ser Pro Leu Leu Val Leu Phe Thr Ile Asn
465                 470                 475                 480

Phe Thr Ile Thr Asn Gln Arg Tyr Glu Glu Asn Met His His Pro Gly
                485                 490                 495

Ser Arg Lys Phe Asn Thr Thr Glu Arg Val Leu Gln Gly Leu Leu Arg
            500                 505                 510

Pro Val Phe Lys Asn Thr Ser Val Gly Pro Leu Tyr Ser Gly Cys Arg
            515                 520                 525

Leu Thr Leu Leu Arg Pro Lys Lys Asp Gly Ala Ala Thr Lys Val Asp
        530                 535                 540

Ala Ile Cys Thr Tyr Arg Pro Asp Pro Lys Ser Pro Gly Leu Asp Arg
545                 550                 555                 560

Glu Gln Leu Tyr Trp Glu Leu Ser Gln Leu Thr His Ser Ile Thr Glu
                565                 570                 575
```

```
Leu Gly Pro Tyr Thr Gln Asp Arg Asp Ser Leu Tyr Val Asn Gly Phe
            580                 585                 590

Thr His Arg Ser Ser Val Pro Thr Thr Ser Ile Pro Gly Thr Ser Ala
        595                 600                 605

Val His Leu Glu Thr Ser Gly Thr Pro Ala Ser Leu Pro Gly His Thr
    610                 615                 620
```

<210> SEQ ID NO 161
<211> LENGTH: 468
<212> TYPE: PRT
<213> ORGANISM: Homo sapiens

<400> SEQUENCE: 161

```
Ala Thr Gly Pro Val Leu Leu Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Thr Glu Arg Val Leu Gln Gly Leu Leu Met Pro Leu Phe Lys
        35                  40                  45

Asn Thr Ser Val Ser Ser Leu Tyr Ser Gly Cys Arg Leu Thr Leu Leu
    50                  55                  60

Arg Pro Glu Lys Asp Gly Ala Ala Thr Arg Val Asp Ala Val Cys Thr
65                  70                  75                  80

His Arg Pro Asp Pro Lys Ser Pro Gly Leu Asp Arg Glu Arg Leu Tyr
                85                  90                  95

Trp Lys Leu Ser Gln Leu Thr His Gly Ile Thr Glu Leu Gly Pro Tyr
            100                 105                 110

Thr Leu Asp Arg His Ser Leu Tyr Val Asn Gly Phe Thr His Gln Ser
        115                 120                 125

Ser Met Thr Thr Thr Arg Thr Pro Asp Thr Ser Thr Met His Leu Ala
    130                 135                 140

Thr Ser Arg Thr Pro Ala Ser Leu Ser Gly Pro Thr Thr Ala Ser Pro
145                 150                 155                 160

Leu Leu Val Leu Phe Thr Ile Asn Phe Thr Ile Thr Asn Leu Arg Tyr
                165                 170                 175

Glu Glu Asn Met His His Pro Gly Ser Arg Lys Phe Asn Thr Thr Glu
            180                 185                 190

Arg Val Leu Gln Gly Leu Leu Arg Pro Val Phe Lys Asn Thr Ser Val
        195                 200                 205

Gly Pro Leu Tyr Ser Gly Cys Arg Leu Thr Leu Leu Arg Pro Lys Lys
    210                 215                 220

Asp Gly Ala Ala Thr Lys Val Asp Ala Ile Cys Thr Tyr Arg Pro Asp
225                 230                 235                 240

Pro Lys Ser Pro Gly Leu Asp Arg Glu Gln Leu Tyr Trp Glu Leu Ser
                245                 250                 255

Gln Leu Thr His Ser Ile Thr Glu Leu Gly Pro Tyr Thr Gln Asp Arg
            260                 265                 270

Asp Ser Leu Tyr Asn Val Gly Phe Thr Gln Arg Ser Ser Val Pro Thr
        275                 280                 285

Thr Ser Val Pro Gly Thr Pro Thr Val Asp Leu Gly Thr Ser Gly Thr
    290                 295                 300

Pro Val Ser Lys Pro Gly Pro Ser Ala Ala Ser Pro Leu Leu Val Leu
305                 310                 315                 320

Phe Thr Leu Asn Gly Thr Ile Thr Asn Leu Arg Tyr Glu Glu Asn Met
                325                 330                 335
```

```
Gln His Pro Gly Ser Arg Lys Phe Asn Thr Thr Glu Arg Val Leu Gln
            340                 345                 350

Gly Leu Leu Arg Ser Leu Phe Lys Ser Thr Ser Val Gly Pro Leu Tyr
            355                 360                 365

Ser Gly Cys Arg Leu Thr Leu Leu Arg Pro Glu Lys Asp Gly Thr Ala
            370                 375                 380

Thr Gly Val Asp Ala Ile Cys Thr His His Pro Asp Pro Lys Ser Pro
385                 390                 395                 400

Arg Leu Asp Arg Glu Gln Leu Tyr Trp Glu Leu Ser Gln Leu Thr His
                405                 410                 415

Asn Ile Thr Glu Leu Gly His Tyr Ala Leu Asp Asn Asp Ser Leu Phe
            420                 425                 430

Val Asn Gly Phe Thr His Arg Ser Val Ser Thr Thr Ser Thr Pro
            435                 440                 445

Gly Thr Pro Thr Val Tyr Leu Gly Ala Ser Lys Thr Pro Ala Ser Ile
            450                 455                 460

Phe Gly Pro Ser
465

<210> SEQ ID NO 162
<211> LENGTH: 11721
<212> TYPE: PRT
<213> ORGANISM: Homo sapiens
<220> FEATURE:
<221> NAME/KEY: MISC_FEATURE
<222> LOCATION: (1)..(11721)
<223> OTHER INFORMATION: Any "X" = any amino acid

<400> SEQUENCE: 162

Met Glu His Ile Thr Lys Ile Pro Asn Glu Ala Ala His Arg Gly Thr
1               5                   10                  15

Ile Arg Pro Val Lys Gly Pro Gln Thr Ser Thr Ser Pro Ala Ser Pro
            20                  25                  30

Lys Gly Leu His Thr Gly Gly Thr Lys Arg Met Glu Thr Thr Thr Thr
            35                  40                  45

Ala Leu Lys Thr Thr Thr Thr Ala Leu Lys Thr Thr Ser Arg Ala Thr
        50                  55                  60

Leu Thr Thr Ser Val Tyr Thr Pro Thr Leu Gly Thr Leu Thr Pro Leu
65                  70                  75                  80

Asn Ala Ser Arg Gln Met Ala Ser Thr Ile Leu Thr Glu Met Met Ile
                85                  90                  95

Thr Thr Pro Tyr Val Phe Pro Asp Val Pro Glu Thr Thr Ser Ser Leu
            100                 105                 110

Ala Thr Ser Leu Gly Ala Glu Thr Ser Thr Ala Leu Pro Arg Thr Thr
            115                 120                 125

Pro Ser Val Leu Asn Arg Glu Ser Glu Thr Thr Ala Ser Leu Val Ser
        130                 135                 140

Arg Ser Gly Ala Glu Arg Ser Pro Val Ile Gln Thr Leu Asp Val Ser
145                 150                 155                 160

Ser Ser Glu Pro Asp Thr Thr Ala Ser Trp Val Ile His Pro Ala Glu
                165                 170                 175

Thr Ile Pro Thr Val Ser Lys Thr Thr Pro Asn Phe Phe His Ser Glu
            180                 185                 190

Leu Asp Thr Val Ser Ser Thr Ala Thr Ser His Gly Ala Asp Val Ser
            195                 200                 205
```

-continued

```
Ser Ala Ile Pro Thr Asn Ile Ser Pro Ser Glu Leu Asp Ala Leu Thr
    210                 215                 220
Pro Leu Val Thr Ile Ser Gly Thr Asp Thr Ser Thr Thr Phe Pro Thr
225                 230                 235                 240
Leu Thr Lys Ser Pro His Glu Thr Glu Thr Arg Thr Thr Trp Leu Thr
                245                 250                 255
His Pro Ala Glu Thr Ser Ser Thr Ile Pro Arg Thr Ile Pro Asn Phe
            260                 265                 270
Ser His His Glu Ser Asp Ala Thr Pro Ser Ile Ala Thr Ser Pro Gly
        275                 280                 285
Ala Glu Thr Ser Ser Ala Ile Pro Ile Met Thr Val Ser Pro Gly Ala
    290                 295                 300
Glu Asp Leu Val Thr Ser Gln Val Thr Ser Ser Gly Thr Asp Arg Asn
305                 310                 315                 320
Met Thr Ile Pro Thr Leu Thr Leu Ser Pro Gly Glu Pro Lys Thr Ile
                325                 330                 335
Ala Ser Leu Val Thr His Pro Glu Ala Gln Thr Ser Ser Ala Ile Pro
            340                 345                 350
Thr Ser Thr Ile Ser Pro Ala Val Ser Arg Leu Val Thr Ser Met Val
        355                 360                 365
Thr Ser Leu Ala Ala Lys Thr Ser Thr Asn Arg Ala Leu Thr Asn
    370                 375                 380
Ser Pro Gly Glu Pro Ala Thr Val Ser Leu Val Thr His Pro Ala
385                 390                 395                 400
Gln Thr Ser Pro Thr Val Pro Trp Thr Thr Ser Ile Phe Phe His Ser
                405                 410                 415
Lys Ser Asp Thr Thr Pro Ser Met Thr Thr Ser His Gly Ala Glu Ser
            420                 425                 430
Ser Ser Ala Val Pro Thr Pro Thr Val Ser Thr Glu Val Pro Gly Val
        435                 440                 445
Val Thr Pro Leu Val Thr Ser Ser Arg Ala Val Ile Ser Thr Thr Ile
    450                 455                 460
Pro Ile Leu Thr Leu Ser Pro Gly Glu Pro Thr Thr Pro Ser Met
465                 470                 475                 480
Ala Thr Ser His Gly Glu Glu Ala Ser Ser Ala Ile Pro Thr Pro Thr
                485                 490                 495
Val Ser Pro Gly Val Pro Gly Val Val Thr Ser Leu Val Thr Ser Ser
            500                 505                 510
Arg Ala Val Thr Ser Thr Thr Ile Pro Ile Leu Thr Phe Ser Leu Gly
        515                 520                 525
Glu Pro Glu Thr Thr Pro Ser Met Ala Thr Ser His Gly Thr Glu Ala
    530                 535                 540
Gly Ser Ala Val Pro Thr Val Leu Pro Glu Val Pro Gly Met Val Thr
545                 550                 555                 560
Ser Leu Val Ala Ser Ser Arg Ala Val Thr Ser Thr Leu Pro Thr
                565                 570                 575
Leu Thr Leu Ser Pro Gly Glu Pro Thr Thr Pro Ser Met Ala Thr
            580                 585                 590
Ser His Gly Ala Glu Ala Ser Ser Thr Val Pro Thr Val Ser Pro Glu
        595                 600                 605
Val Pro Gly Val Val Thr Ser Leu Val Thr Ser Ser Ser Gly Val Asn
    610                 615                 620
Ser Thr Ser Ile Pro Thr Leu Ile Leu Ser Pro Gly Glu Leu Glu Thr
```

-continued

```
              625                 630                 635                 640
Thr Pro Ser Met Ala Thr Ser His Gly Ala Glu Ala Ser Ser Ala Val
                    645                 650                 655
Pro Thr Pro Thr Val Ser Pro Gly Val Ser Gly Val Val Thr Pro Leu
                660                 665                 670
Val Thr Ser Ser Arg Ala Val Thr Ser Thr Ile Pro Ile Leu Thr
            675                 680                 685
Leu Ser Ser Ser Glu Pro Glu Thr Thr Pro Ser Met Ala Thr Ser His
        690                 695                 700
Gly Val Glu Ala Ser Ser Ala Val Leu Thr Val Ser Pro Glu Val Pro
705                 710                 715                 720
Gly Met Val Thr Ser Leu Val Thr Ser Ser Arg Ala Val Thr Ser Thr
                    725                 730                 735
Thr Ile Pro Thr Leu Thr Ile Ser Ser Asp Glu Pro Glu Thr Thr Thr
                740                 745                 750
Ser Leu Val Thr His Ser Glu Ala Lys Met Ile Ser Ala Ile Pro Thr
            755                 760                 765
Leu Ala Val Ser Pro Thr Val Gln Gly Leu Val Thr Ser Leu Val Thr
        770                 775                 780
Ser Ser Gly Ser Glu Thr Ser Ala Phe Ser Asn Leu Thr Val Ala Ser
785                 790                 795                 800
Ser Gln Pro Glu Thr Ile Asp Ser Trp Val Ala His Pro Gly Thr Glu
                    805                 810                 815
Ala Ser Ser Val Val Pro Thr Leu Thr Val Ser Thr Gly Glu Pro Phe
                820                 825                 830
Thr Asn Ile Ser Leu Val Thr His Pro Ala Glu Ser Ser Ser Thr Leu
            835                 840                 845
Pro Arg Thr Thr Ser Arg Phe Ser His Ser Glu Leu Asp Thr Met Pro
        850                 855                 860
Ser Thr Val Thr Ser Pro Glu Ala Glu Ser Ser Ser Ala Ile Ser Thr
865                 870                 875                 880
Thr Ile Ser Pro Gly Ile Pro Gly Val Leu Thr Ser Leu Val Thr Ser
                    885                 890                 895
Ser Gly Arg Asp Ile Ser Ala Thr Phe Pro Thr Val Pro Glu Ser Pro
                900                 905                 910
His Glu Ser Glu Ala Thr Ala Ser Trp Val Thr His Pro Ala Val Thr
            915                 920                 925
Ser Thr Thr Val Pro Arg Thr Thr Pro Asn Tyr Ser His Ser Glu Pro
        930                 935                 940
Asp Thr Thr Pro Ser Ile Ala Thr Ser Pro Gly Ala Glu Ala Thr Ser
945                 950                 955                 960
Asp Phe Pro Thr Ile Thr Val Ser Pro Asp Val Pro Asp Met Val Thr
                    965                 970                 975
Ser Gln Val Thr Ser Ser Gly Thr Asp Thr Ser Ile Thr Ile Pro Thr
                980                 985                 990
Leu Thr Leu Ser Ser Gly Glu Pro Glu Thr Thr Thr Ser  Phe Ile Thr
            995                 1000                1005
Tyr Ser  Glu Thr His Thr Ser   Ser Ala Ile Pro Thr  Leu Pro Val
        1010                1015                1020
Ser Pro Gly Ala Ser Lys Met  Leu Thr Ser Leu Val  Ile Ser Ser
    1025                1030                1035
Gly Thr  Asp Ser Thr Thr Thr  Phe Pro Thr Leu Thr  Glu Thr Pro
        1040                1045                1050
```

-continued

```
Tyr Glu Pro Glu Thr Thr Ala Ile Gln Leu Ile His Pro Ala Glu
    1055            1060            1065

Thr Asn Thr Met Val Pro Arg Thr Thr Pro Lys Phe Ser His Ser
    1070            1075            1080

Lys Ser Asp Thr Thr Leu Pro Val Ala Ile Thr Ser Pro Gly Pro
    1085            1090            1095

Glu Ala Ser Ser Ala Val Ser Thr Thr Thr Ile Ser Pro Asp Met
    1100            1105            1110

Ser Asp Leu Val Thr Ser Leu Val Pro Ser Ser Gly Thr Asp Thr
    1115            1120            1125

Ser Thr Thr Phe Pro Thr Leu Ser Glu Thr Pro Tyr Glu Pro Glu
    1130            1135            1140

Thr Thr Ala Thr Trp Leu Thr His Pro Ala Glu Thr Ser Thr Thr
    1145            1150            1155

Val Ser Gly Thr Ile Pro Asn Phe Ser His Arg Gly Ser Asp Thr
    1160            1165            1170

Ala Pro Ser Met Val Thr Ser Pro Gly Val Asp Thr Arg Ser Gly
    1175            1180            1185

Val Pro Thr Thr Thr Ile Pro Pro Ser Ile Pro Gly Val Val Thr
    1190            1195            1200

Ser Gln Val Thr Ser Ser Ala Thr Asp Thr Ser Thr Ala Ile Pro
    1205            1210            1215

Thr Leu Thr Pro Ser Pro Gly Glu Pro Glu Thr Thr Ala Ser Ser
    1220            1225            1230

Ala Thr His Pro Gly Thr Gln Thr Gly Phe Thr Val Pro Ile Arg
    1235            1240            1245

Thr Val Pro Ser Ser Glu Pro Asp Thr Met Ala Ser Trp Val Thr
    1250            1255            1260

His Pro Pro Gln Thr Ser Thr Pro Val Ser Arg Thr Thr Ser Ser
    1265            1270            1275

Phe Ser His Ser Ser Pro Asp Ala Thr Pro Val Met Ala Thr Ser
    1280            1285            1290

Pro Arg Thr Glu Ala Ser Ser Ala Val Leu Thr Thr Ile Ser Pro
    1295            1300            1305

Gly Ala Pro Glu Met Val Thr Ser Gln Ile Thr Ser Ser Gly Ala
    1310            1315            1320

Ala Thr Ser Thr Thr Val Pro Thr Leu Thr His Ser Pro Gly Met
    1325            1330            1335

Pro Glu Thr Thr Ala Leu Leu Ser Thr His Pro Arg Thr Glu Thr
    1340            1345            1350

Ser Lys Thr Phe Pro Ala Ser Thr Val Phe Pro Gln Val Ser Glu
    1355            1360            1365

Thr Thr Ala Ser Leu Thr Ile Arg Pro Gly Ala Glu Thr Ser Thr
    1370            1375            1380

Ala Leu Pro Thr Gln Thr Thr Ser Ser Leu Phe Thr Leu Leu Val
    1385            1390            1395

Thr Gly Thr Ser Arg Val Asp Leu Ser Pro Thr Ala Ser Pro Gly
    1400            1405            1410

Val Ser Ala Lys Thr Ala Pro Leu Ser Thr His Pro Gly Thr Glu
    1415            1420            1425

Thr Ser Thr Met Ile Pro Thr Ser Thr Leu Ser Leu Gly Leu Leu
    1430            1435            1440
```

-continued

| | | | | | | | | | | | |
|---|---|---|---|---|---|---|---|---|---|---|---|
|Glu|Thr|Thr|Gly|Leu|Leu|Ala|Thr|Ser|Ser|Ala|Glu Thr Ser|
| |1445| | | |1450| | | |1455| | |
|Thr|Ser|Thr|Leu|Thr|Leu|Thr|Val|Ser|Pro|Ala|Val Ser Gly Leu|
| |1460| | | |1465| | | |1470| | |
|Ser|Ser|Ala|Ser|Ile|Thr|Thr|Asp|Lys|Pro|Gln|Thr Val Thr Ser|
| |1475| | | |1480| | | |1485| | |
|Trp|Asn|Thr|Glu|Thr|Ser|Pro|Ser|Val|Thr|Ser|Val Gly Pro Pro|
| |1490| | | |1495| | | |1500| | |
|Glu|Phe|Ser|Arg|Thr|Val|Thr|Gly|Thr|Thr|Met|Thr Leu Ile Pro|
| |1505| | | |1510| | | |1515| | |
|Ser|Glu|Met|Pro|Thr|Pro|Pro|Lys|Thr|Ser|His|Gly Glu Gly Val|
| |1520| | | |1525| | | |1530| | |
|Ser|Pro|Thr|Thr|Ile|Leu|Arg|Thr|Thr|Met|Val|Glu Ala Thr Asn|
| |1535| | | |1540| | | |1545| | |
|Leu|Ala|Thr|Thr|Gly|Ser|Ser|Pro|Thr|Val|Ala|Lys Thr Thr Thr|
| |1550| | | |1555| | | |1560| | |
|Thr|Phe|Asn|Thr|Leu|Ala|Gly|Ser|Leu|Phe|Thr|Pro Leu Thr Thr|
| |1565| | | |1570| | | |1575| | |
|Pro|Gly|Met|Ser|Thr|Leu|Ala|Ser|Glu|Ser|Val|Thr Ser Arg Thr|
| |1580| | | |1585| | | |1590| | |
|Ser|Tyr|Asn|His|Arg|Ser|Trp|Ile|Ser|Thr|Thr|Ser Ser Tyr Asn|
| |1595| | | |1600| | | |1605| | |
|Arg|Arg|Tyr|Trp|Thr|Pro|Ala|Thr|Ser|Thr|Pro|Val Thr Ser Thr|
| |1610| | | |1615| | | |1620| | |
|Phe|Ser|Pro|Gly|Ile|Ser|Thr|Ser|Ser|Ile|Pro|Ser Ser Thr Ala|
| |1625| | | |1630| | | |1635| | |
|Ala|Thr|Val|Pro|Phe|Met|Val|Pro|Phe|Thr|Leu|Asn Phe Thr Ile|
| |1640| | | |1645| | | |1650| | |
|Thr|Asn|Leu|Gln|Tyr|Glu|Glu|Asp|Met|Arg|His|Pro Gly Ser Arg|
| |1655| | | |1660| | | |1665| | |
|Lys|Phe|Asn|Ala|Thr|Glu|Arg|Glu|Leu|Gln|Gly|Leu Leu Lys Pro|
| |1670| | | |1675| | | |1680| | |
|Leu|Phe|Arg|Asn|Ser|Ser|Leu|Glu|Tyr|Leu|Tyr|Ser Gly Cys Arg|
| |1685| | | |1690| | | |1695| | |
|Leu|Ala|Ser|Leu|Arg|Pro|Glu|Lys|Asp|Ser|Ser|Ala Met Ala Val|
| |1700| | | |1705| | | |1710| | |
|Asp|Ala|Ile|Cys|Thr|His|Arg|Pro|Asp|Pro|Glu|Asp Leu Gly Leu|
| |1715| | | |1720| | | |1725| | |
|Asp|Arg|Glu|Arg|Leu|Tyr|Trp|Glu|Leu|Ser|Asn|Leu Thr Asn Gly|
| |1730| | | |1735| | | |1740| | |
|Ile|Gln|Glu|Leu|Gly|Pro|Tyr|Thr|Leu|Asp|Arg|Asn Ser Leu Tyr|
| |1745| | | |1750| | | |1755| | |
|Val|Asn|Gly|Phe|Thr|His|Arg|Ser|Ser|Met|Pro|Thr Thr Ser Thr|
| |1760| | | |1765| | | |1770| | |
|Pro|Gly|Thr|Ser|Thr|Val|Asp|Val|Gly|Thr|Ser|Gly Thr Pro Ser|
| |1775| | | |1780| | | |1785| | |
|Ser|Ser|Pro|Ser|Pro|Thr|Ala|Ala|Gly|Pro|Leu|Leu Met Pro Phe|
| |1790| | | |1795| | | |1800| | |
|Thr|Leu|Asn|Phe|Thr|Ile|Thr|Asn|Leu|Gln|Tyr|Glu Glu Asp Met|
| |1805| | | |1810| | | |1815| | |
|Arg|Arg|Thr|Gly|Ser|Arg|Lys|Phe|Asn|Thr|Met|Glu Ser Val Leu|
| |1820| | | |1825| | | |1830| | |
|Gln|Gly|Leu|Leu|Lys|Pro|Leu|Phe|Lys|Asn|Thr|Ser Val Gly Pro|

-continued

```
            1835                1840                1845

Leu Tyr Ser Gly Cys Arg Leu Thr Leu Arg Pro Glu Lys Asp
            1850                1855                1860

Gly Ala Ala Thr Gly Val Asp Ala Ile Cys Thr His Arg Leu Asp
            1865                1870                1875

Pro Lys Ser Pro Gly Leu Asn Arg Glu Gln Leu Tyr Trp Glu Leu
            1880                1885                1890

Ser Lys Leu Thr Asn Asp Ile Glu Glu Leu Gly Pro Tyr Thr Leu
            1895                1900                1905

Asp Arg Asn Ser Leu Tyr Val Asn Gly Phe Thr His Gln Ser Ser
            1910                1915                1920

Val Ser Thr Thr Ser Thr Pro Gly Thr Ser Thr Val Asp Leu Arg
            1925                1930                1935

Thr Ser Gly Thr Pro Ser Ser Leu Ser Ser Pro Thr Ile Met Ala
            1940                1945                1950

Ala Gly Pro Leu Leu Val Pro Phe Thr Leu Asn Phe Thr Ile Thr
            1955                1960                1965

Asn Leu Gln Tyr Gly Glu Asp Met Gly His Pro Gly Ser Arg Lys
            1970                1975                1980

Phe Asn Thr Thr Glu Arg Val Leu Gln Gly Leu Leu Gly Pro Ile
            1985                1990                1995

Phe Lys Asn Thr Ser Val Gly Pro Leu Tyr Ser Gly Cys Arg Leu
            2000                2005                2010

Thr Ser Leu Arg Ser Glu Lys Asp Gly Ala Ala Thr Gly Val Asp
            2015                2020                2025

Ala Ile Cys Ile His His Leu Asp Pro Lys Ser Pro Gly Leu Asn
            2030                2035                2040

Arg Glu Arg Leu Tyr Trp Glu Leu Ser Gln Leu Thr Asn Gly Ile
            2045                2050                2055

Lys Glu Leu Gly Pro Tyr Thr Leu Asp Arg Asn Ser Leu Tyr Val
            2060                2065                2070

Asn Gly Phe Thr His Arg Thr Ser Val Pro Thr Ser Ser Thr Pro
            2075                2080                2085

Gly Thr Ser Thr Val Asp Leu Gly Thr Ser Gly Thr Pro Phe Ser
            2090                2095                2100

Leu Pro Ser Pro Ala Thr Ala Gly Pro Leu Leu Val Leu Phe Thr
            2105                2110                2115

Leu Asn Phe Thr Ile Thr Asn Leu Lys Tyr Glu Glu Asp Met His
            2120                2125                2130

Arg Pro Gly Ser Arg Lys Phe Asn Thr Thr Glu Arg Val Leu Gln
            2135                2140                2145

Thr Leu Leu Gly Pro Met Phe Lys Asn Thr Ser Val Gly Leu Leu
            2150                2155                2160

Tyr Ser Gly Cys Arg Leu Thr Leu Leu Arg Ser Glu Lys Asp Gly
            2165                2170                2175

Ala Ala Thr Gly Val Asp Ala Ile Cys Thr His Arg Leu Asp Pro
            2180                2185                2190

Lys Ser Pro Gly Leu Asp Arg Glu Gln Leu Tyr Trp Glu Leu Ser
            2195                2200                2205

Gln Leu Thr Asn Gly Ile Lys Glu Leu Gly Pro Tyr Thr Leu Asp
            2210                2215                2220

Arg Asn Ser Leu Tyr Val Asn Gly Phe Thr His Trp Ile Pro Val
            2225                2230                2235
```

-continued

```
Pro Thr Ser Ser Thr Pro Gly Thr Ser Thr Val Asp Leu Gly Ser
    2240                2245                2250

Gly Thr Pro Ser Ser Leu Pro Ser Pro Thr Ala Ala Gly Pro Leu
    2255                2260                2265

Leu Val Pro Phe Thr Leu Asn Phe Thr Ile Thr Asn Leu Gln Tyr
    2270                2275                2280

Glu Glu Asp Met His His Pro Gly Ser Arg Lys Phe Asn Thr Thr
    2285                2290                2295

Glu Arg Val Leu Gln Gly Leu Leu Gly Pro Met Phe Lys Asn Thr
    2300                2305                2310

Ser Val Gly Leu Leu Tyr Ser Gly Cys Arg Leu Thr Leu Leu Arg
    2315                2320                2325

Ser Glu Lys Asp Gly Ala Ala Thr Gly Val Asp Ala Ile Cys Thr
    2330                2335                2340

His Arg Leu Asp Pro Lys Ser Pro Gly Val Asp Arg Glu Gln Leu
    2345                2350                2355

Tyr Trp Glu Leu Ser Gln Leu Thr Asn Gly Ile Lys Glu Leu Gly
    2360                2365                2370

Pro Tyr Thr Leu Asp Arg Asn Ser Leu Tyr Val Asn Gly Phe Thr
    2375                2380                2385

His Gln Thr Ser Ala Pro Asn Thr Ser Thr Pro Gly Thr Ser Thr
    2390                2395                2400

Val Asp Leu Gly Thr Ser Gly Thr Pro Ser Ser Leu Pro Ser Pro
    2405                2410                2415

Thr Ser Ala Gly Pro Leu Leu Val Pro Phe Thr Leu Asn Phe Thr
    2420                2425                2430

Ile Thr Asn Leu Gln Tyr Glu Glu Asp Met Arg His Pro Gly Ser
    2435                2440                2445

Arg Lys Phe Asn Thr Thr Glu Arg Val Leu Gln Gly Leu Leu Lys
    2450                2455                2460

Pro Leu Phe Lys Ser Thr Ser Val Gly Pro Leu Tyr Ser Gly Cys
    2465                2470                2475

Arg Leu Thr Leu Leu Arg Ser Glu Lys Asp Gly Ala Ala Thr Gly
    2480                2485                2490

Val Asp Ala Ile Cys Thr His Arg Leu Asp Pro Lys Ser Pro Gly
    2495                2500                2505

Val Asp Arg Glu Gln Leu Tyr Trp Glu Leu Ser Gln Leu Thr Asn
    2510                2515                2520

Gly Ile Lys Glu Leu Gly Pro Tyr Thr Leu Asp Arg Asn Ser Leu
    2525                2530                2535

Tyr Val Asn Gly Phe Thr His Gln Thr Ser Ala Pro Asn Thr Ser
    2540                2545                2550

Thr Pro Gly Thr Ser Thr Val Asp Leu Gly Thr Ser Gly Thr Pro
    2555                2560                2565

Ser Ser Leu Pro Ser Pro Thr Ser Ala Gly Pro Leu Leu Val Pro
    2570                2575                2580

Phe Thr Leu Asn Phe Thr Ile Thr Asn Leu Gln Tyr Glu Glu Asp
    2585                2590                2595

Met His His Pro Gly Ser Arg Lys Phe Asn Thr Thr Glu Arg Val
    2600                2605                2610

Leu Gln Gly Leu Leu Gly Pro Met Phe Lys Asn Thr Ser Val Gly
    2615                2620                2625
```

-continued

```
Leu Leu Tyr Ser Gly Cys Arg Leu Thr Leu Arg Pro Glu Lys
    2630                2635            2640

Asn Gly Ala Ala Thr Gly Met Asp Ala Ile Cys Ser His Arg Leu
    2645                2650            2655

Asp Pro Lys Ser Pro Gly Leu Asn Arg Glu Gln Leu Tyr Trp Glu
    2660                2665            2670

Leu Ser Gln Leu Thr His Gly Ile Lys Glu Leu Gly Pro Tyr Thr
    2675                2680            2685

Leu Asp Arg Asn Ser Leu Tyr Val Asn Gly Phe Thr His Arg Ser
    2690                2695            2700

Ser Val Ala Pro Thr Ser Thr Pro Gly Thr Ser Thr Val Asp Leu
    2705                2710            2715

Gly Thr Ser Gly Thr Pro Ser Ser Leu Pro Ser Pro Thr Thr Ala
    2720                2725            2730

Val Pro Leu Leu Val Pro Phe Thr Leu Asn Phe Thr Ile Thr Asn
    2735                2740            2745

Leu Gln Tyr Gly Glu Asp Met Arg His Pro Gly Ser Arg Lys Phe
    2750                2755            2760

Asn Thr Thr Glu Arg Val Leu Gln Gly Leu Leu Gly Pro Leu Phe
    2765                2770            2775

Lys Asn Ser Ser Val Gly Pro Leu Tyr Ser Gly Cys Arg Leu Ile
    2780                2785            2790

Ser Leu Arg Ser Glu Lys Asp Gly Ala Ala Thr Gly Val Asp Ala
    2795                2800            2805

Ile Cys Thr His His Leu Asn Pro Gln Ser Pro Gly Leu Asp Arg
    2810                2815            2820

Glu Gln Leu Tyr Trp Gln Leu Ser Gln Met Thr Asn Gly Ile Lys
    2825                2830            2835

Glu Leu Gly Pro Tyr Thr Leu Asp Arg Asn Ser Leu Tyr Val Asn
    2840                2845            2850

Gly Phe Thr His Arg Ser Ser Gly Leu Thr Thr Ser Thr Pro Trp
    2855                2860            2865

Thr Ser Thr Val Asp Leu Gly Thr Ser Gly Thr Pro Ser Pro Val
    2870                2875            2880

Pro Ser Pro Thr Thr Ala Gly Pro Leu Leu Val Pro Phe Thr Leu
    2885                2890            2895

Asn Phe Thr Ile Thr Asn Leu Gln Tyr Glu Glu Asp Met His Arg
    2900                2905            2910

Pro Gly Ser Arg Lys Phe Asn Ala Thr Glu Arg Val Leu Gln Gly
    2915                2920            2925

Leu Leu Ser Pro Ile Phe Lys Asn Ser Ser Val Gly Pro Leu Tyr
    2930                2935            2940

Ser Gly Cys Arg Leu Thr Ser Leu Arg Pro Glu Lys Asp Gly Ala
    2945                2950            2955

Ala Thr Gly Met Asp Ala Val Cys Leu Tyr His Pro Asn Pro Lys
    2960                2965            2970

Arg Pro Gly Leu Asp Arg Glu Gln Leu Tyr Trp Glu Leu Ser Gln
    2975                2980            2985

Leu Thr His Asn Ile Thr Glu Leu Gly Pro Tyr Ser Leu Asp Arg
    2990                2995            3000

Asp Ser Leu Tyr Val Asn Gly Phe Thr His Gln Asn Ser Val Pro
    3005                3010            3015

Thr Thr Ser Thr Pro Gly Thr Ser Thr Val Tyr Trp Ala Thr Thr
```

-continued

```
            3020                3025                 3030
Gly Thr Pro Ser Ser Phe Pro Gly His Thr Glu Pro Gly Pro Leu
            3035                3040                3045
Leu Ile Pro Phe Thr Phe Asn Phe Thr Ile Thr Asn Leu His Tyr
            3050                3055                3060
Glu Glu Asn Met Gln His Pro Gly Ser Arg Lys Phe Asn Thr Thr
            3065                3070                3075
Glu Arg Val Leu Gln Gly Leu Leu Lys Pro Leu Phe Lys Asn Thr
            3080                3085                3090
Ser Val Gly Pro Leu Tyr Ser Gly Cys Arg Leu Thr Ser Leu Arg
            3095                3100                3105
Pro Glu Lys Asp Gly Ala Ala Thr Gly Met Asp Ala Val Cys Leu
            3110                3115                3120
Tyr His Pro Asn Pro Lys Arg Pro Gly Leu Asp Arg Glu Gln Leu
            3125                3130                3135
Tyr Cys Glu Leu Ser Gln Leu Thr His Asn Ile Thr Glu Leu Gly
            3140                3145                3150
Pro Tyr Ser Leu Asp Arg Asp Ser Leu Tyr Val Asn Gly Phe Thr
            3155                3160                3165
His Gln Asn Ser Val Pro Thr Thr Ser Thr Pro Gly Thr Ser Thr
            3170                3175                3180
Val Tyr Trp Ala Thr Thr Gly Thr Pro Ser Ser Phe Pro Gly His
            3185                3190                3195
Thr Glu Pro Gly Pro Leu Leu Ile Pro Phe Thr Phe Asn Phe Thr
            3200                3205                3210
Ile Thr Asn Leu His Tyr Glu Glu Asn Met Gln His Pro Gly Ser
            3215                3220                3225
Arg Lys Phe Asn Thr Thr Glu Arg Val Leu Gln Gly Leu Leu Lys
            3230                3235                3240
Pro Leu Phe Lys Asn Thr Ser Val Gly Pro Leu Tyr Ser Gly Cys
            3245                3250                3255
Arg Leu Thr Leu Leu Arg Pro Glu Lys His Glu Ala Ala Thr Gly
            3260                3265                3270
Val Asp Thr Ile Cys Thr His Arg Val Asp Pro Ile Gly Pro Gly
            3275                3280                3285
Leu Asp Arg Glu Arg Leu Tyr Trp Glu Leu Ser Gln Leu Thr Asn
            3290                3295                3300
Ser Ile Thr Glu Leu Gly Pro Tyr Thr Leu Asp Arg Asp Ser Leu
            3305                3310                3315
Tyr Val Asn Gly Phe Asn Pro Arg Ser Ser Val Pro Thr Thr Ser
            3320                3325                3330
Thr Pro Gly Thr Ser Thr Val His Leu Ala Thr Ser Gly Thr Pro
            3335                3340                3345
Ser Ser Leu Pro Gly His Thr Ala Pro Val Pro Leu Leu Ile Pro
            3350                3355                3360
Phe Thr Leu Asn Phe Thr Ile Thr Asn Leu His Tyr Glu Glu Asn
            3365                3370                3375
Met Gln His Pro Gly Ser Arg Lys Phe Asn Thr Thr Glu Arg Val
            3380                3385                3390
Leu Gln Gly Leu Leu Lys Pro Leu Phe Lys Asn Thr Ser Val Gly
            3395                3400                3405
Pro Leu Tyr Ser Gly Cys Arg Leu Thr Leu Leu Arg Pro Glu Lys
            3410                3415                3420
```

-continued

```
His Glu Ala Ala Thr Gly Val Asp Thr Ile Cys Thr His Arg Val
3425                3430                3435

Asp Pro Ile Gly Pro Gly Leu Asp Arg Glu Xaa Leu Tyr Trp Glu
3440                3445                3450

Leu Ser Xaa Leu Thr Xaa Xaa Ile Xaa Glu Leu Gly Pro Tyr Xaa
3455                3460                3465

Leu Asp Arg Xaa Ser Leu Tyr Val Asn Gly Phe Xaa Xaa Xaa Xaa
3470                3475                3480

Xaa Xaa Xaa Xaa Thr Ser Thr Pro Gly Thr Ser Xaa Val Xaa Leu
3485                3490                3495

Xaa Thr Ser Gly Thr Pro Xaa Xaa Xaa Pro Xaa Xaa Thr Ser Ala
3500                3505                3510

Gly Pro Leu Leu Val Pro Phe Thr Leu Asn Phe Thr Ile Thr Asn
3515                3520                3525

Leu Gln Tyr Glu Glu Asp Met His His Pro Gly Ser Arg Lys Phe
3530                3535                3540

Asn Thr Thr Glu Arg Val Leu Gln Gly Leu Leu Gly Pro Met Phe
3545                3550                3555

Lys Asn Thr Ser Val Gly Leu Leu Tyr Ser Gly Cys Arg Leu Thr
3560                3565                3570

Leu Leu Arg Pro Glu Lys Asn Gly Ala Ala Thr Gly Met Asp Ala
3575                3580                3585

Ile Cys Ser His Arg Leu Asp Pro Lys Ser Pro Gly Leu Asp Arg
3590                3595                3600

Glu Gln Leu Tyr Trp Glu Leu Ser Gln Leu Thr His Gly Ile Lys
3605                3610                3615

Glu Leu Gly Pro Tyr Thr Leu Asp Arg Asn Ser Leu Tyr Val Asn
3620                3625                3630

Gly Phe Thr His Arg Ser Ser Val Ala Pro Thr Ser Thr Pro Gly
3635                3640                3645

Thr Ser Thr Val Asp Leu Gly Thr Ser Gly Thr Pro Ser Ser Leu
3650                3655                3660

Pro Ser Pro Thr Thr Ala Val Pro Leu Leu Val Pro Phe Thr Leu
3665                3670                3675

Asn Phe Thr Ile Thr Asn Leu Gln Tyr Gly Glu Asp Met Arg His
3680                3685                3690

Pro Gly Ser Arg Lys Phe Asn Thr Thr Glu Arg Val Leu Gln Gly
3695                3700                3705

Leu Leu Gly Pro Leu Phe Lys Asn Ser Ser Val Gly Pro Leu Tyr
3710                3715                3720

Ser Gly Cys Arg Leu Ile Ser Leu Arg Ser Glu Lys Asp Gly Ala
3725                3730                3735

Ala Thr Gly Val Asp Ala Ile Cys Thr His His Leu Asn Pro Gln
3740                3745                3750

Ser Pro Gly Leu Asp Arg Glu Gln Leu Tyr Trp Gln Leu Ser Gln
3755                3760                3765

Met Thr Asn Gly Ile Lys Glu Leu Gly Pro Tyr Thr Leu Asp Arg
3770                3775                3780

Asn Ser Leu Tyr Val Asn Gly Phe Thr His Arg Ser Ser Gly Leu
3785                3790                3795

Thr Thr Ser Thr Pro Trp Thr Ser Thr Val Asp Leu Gly Thr Ser
3800                3805                3810
```

-continued

| | | | | | | | | | | |
|---|---|---|---|---|---|---|---|---|---|---|
| Gly | Thr | Pro | Ser | Pro | Val | Pro | Ser | Pro | Thr | Ala | Gly | Pro | Leu |
| | 3815 | | | | 3820 | | | | 3825 | | | | |
| Leu | Val | Pro | Phe | Thr | Leu | Asn | Phe | Thr | Ile | Thr | Asn | Leu | Gln | Tyr |
| | 3830 | | | | 3835 | | | | 3840 | | | | |
| Glu | Glu | Asp | Met | His | Arg | Pro | Gly | Ser | Arg | Lys | Phe | Asn | Ala | Thr |
| | 3845 | | | | 3850 | | | | 3855 | | | | |
| Glu | Arg | Val | Leu | Gln | Gly | Leu | Leu | Ser | Pro | Ile | Phe | Lys | Asn | Ser |
| | 3860 | | | | 3865 | | | | 3870 | | | | |
| Ser | Val | Gly | Pro | Leu | Tyr | Ser | Gly | Cys | Arg | Leu | Thr | Ser | Leu | Arg |
| | 3875 | | | | 3880 | | | | 3885 | | | | |
| Pro | Glu | Lys | Asp | Gly | Ala | Ala | Thr | Gly | Met | Asp | Ala | Val | Cys | Leu |
| | 3890 | | | | 3895 | | | | 3900 | | | | |
| Tyr | His | Pro | Asn | Pro | Lys | Arg | Pro | Gly | Leu | Asp | Arg | Glu | Gln | Leu |
| | 3905 | | | | 3910 | | | | 3915 | | | | |
| Tyr | Trp | Glu | Leu | Ser | Gln | Leu | Thr | His | Asn | Ile | Thr | Glu | Leu | Gly |
| | 3920 | | | | 3925 | | | | 3930 | | | | |
| Pro | Tyr | Ser | Leu | Asp | Arg | Asp | Ser | Leu | Tyr | Val | Asn | Gly | Phe | Thr |
| | 3935 | | | | 3940 | | | | 3945 | | | | |
| His | Gln | Ser | Ser | Met | Thr | Thr | Thr | Arg | Thr | Pro | Asp | Thr | Ser | Thr |
| | 3950 | | | | 3955 | | | | 3960 | | | | |
| Met | His | Leu | Ala | Thr | Ser | Arg | Thr | Pro | Ala | Ser | Leu | Ser | Gly | Pro |
| | 3965 | | | | 3970 | | | | 3975 | | | | |
| Thr | Thr | Ala | Ser | Pro | Leu | Leu | Val | Leu | Phe | Thr | Ile | Asn | Cys | Thr |
| | 3980 | | | | 3985 | | | | 3990 | | | | |
| Ile | Thr | Asn | Leu | Gln | Tyr | Glu | Glu | Asp | Met | Arg | Arg | Thr | Gly | Ser |
| | 3995 | | | | 4000 | | | | 4005 | | | | |
| Arg | Lys | Phe | Asn | Thr | Met | Glu | Ser | Val | Leu | Gln | Gly | Leu | Leu | Lys |
| | 4010 | | | | 4015 | | | | 4020 | | | | |
| Pro | Leu | Phe | Lys | Asn | Thr | Ser | Val | Gly | Pro | Leu | Tyr | Ser | Gly | Cys |
| | 4025 | | | | 4030 | | | | 4035 | | | | |
| Arg | Leu | Thr | Leu | Leu | Arg | Pro | Lys | Lys | Asp | Gly | Ala | Ala | Thr | Gly |
| | 4040 | | | | 4045 | | | | 4050 | | | | |
| Val | Asp | Ala | Ile | Cys | Thr | His | Arg | Leu | Asp | Pro | Lys | Ser | Pro | Gly |
| | 4055 | | | | 4060 | | | | 4065 | | | | |
| Leu | Asn | Arg | Glu | Gln | Leu | Tyr | Trp | Glu | Leu | Ser | Lys | Leu | Thr | Asn |
| | 4070 | | | | 4075 | | | | 4080 | | | | |
| Asp | Ile | Glu | Glu | Leu | Gly | Pro | Tyr | Thr | Leu | Asp | Arg | Asn | Ser | Leu |
| | 4085 | | | | 4090 | | | | 4095 | | | | |
| Tyr | Val | Asn | Gly | Phe | Thr | His | Gln | Ser | Ser | Val | Ser | Thr | Thr | Ser |
| | 4100 | | | | 4105 | | | | 4110 | | | | |
| Thr | Pro | Gly | Thr | Ser | Thr | Val | Asp | Leu | Arg | Thr | Ser | Gly | Thr | Pro |
| | 4115 | | | | 4120 | | | | 4125 | | | | |
| Ser | Ser | Leu | Ser | Ser | Pro | Thr | Ile | Met | Xaa | Xaa | Xaa | Pro | Leu | Leu |
| | 4130 | | | | 4135 | | | | 4140 | | | | |
| Xaa | Pro | Phe | Thr | Leu | Asn | Phe | Thr | Ile | Thr | Asn | Leu | Xaa | Tyr | Glu |
| | 4145 | | | | 4150 | | | | 4155 | | | | |
| Glu | Xaa | Met | Xaa | Xaa | Pro | Gly | Ser | Arg | Lys | Phe | Asn | Thr | Thr | Glu |
| | 4160 | | | | 4165 | | | | 4170 | | | | |
| Arg | Val | Leu | Gln | Gly | Leu | Leu | Arg | Pro | Leu | Phe | Lys | Asn | Thr | Ser |
| | 4175 | | | | 4180 | | | | 4185 | | | | |
| Val | Ser | Ser | Leu | Tyr | Ser | Gly | Cys | Arg | Leu | Thr | Leu | Leu | Arg | Pro |
| | 4190 | | | | 4195 | | | | 4200 | | | | |
| Glu | Lys | Asp | Gly | Ala | Ala | Thr | Arg | Val | Asp | Ala | Ala | Cys | Thr | Tyr |

-continued

```
              4205                  4210                  4215

Arg Pro Asp Pro Lys Ser Pro Gly Leu Asp Arg Glu Gln Leu Tyr
    4220                  4225                  4230

Trp Glu Leu Ser Gln Leu Thr His Ser Ile Thr Glu Leu Gly Pro
    4235                  4240                  4245

Tyr Thr Leu Asp Arg Val Ser Leu Tyr Val Asn Gly Phe Asn Pro
    4250                  4255                  4260

Arg Ser Ser Val Pro Thr Thr Ser Thr Pro Gly Thr Ser Thr Val
    4265                  4270                  4275

His Leu Ala Thr Ser Gly Thr Pro Ser Ser Leu Pro Gly His Thr
    4280                  4285                  4290

Xaa Xaa Xaa Pro Leu Leu Xaa Pro Phe Thr Leu Asn Phe Thr Ile
    4295                  4300                  4305

Thr Asn Leu Xaa Tyr Glu Glu Xaa Met Xaa Xaa Pro Gly Ser Arg
    4310                  4315                  4320

Lys Phe Asn Thr Thr Glu Arg Val Leu Gln Gly Leu Leu Lys Pro
    4325                  4330                  4335

Leu Phe Arg Asn Ser Ser Leu Glu Tyr Leu Tyr Ser Gly Cys Arg
    4340                  4345                  4350

Leu Ala Ser Leu Arg Pro Glu Lys Asp Ser Ser Ala Met Ala Val
    4355                  4360                  4365

Asp Ala Ile Cys Thr His Arg Pro Asp Pro Glu Asp Leu Gly Leu
    4370                  4375                  4380

Asp Arg Glu Arg Leu Tyr Trp Glu Leu Ser Asn Leu Thr Asn Gly
    4385                  4390                  4395

Ile Gln Glu Leu Gly Pro Tyr Thr Leu Asp Arg Asn Ser Leu Tyr
    4400                  4405                  4410

Val Asn Gly Phe Thr His Arg Ser Ser Phe Leu Thr Thr Ser Thr
    4415                  4420                  4425

Pro Trp Thr Ser Thr Val Asp Leu Gly Thr Ser Gly Thr Pro Ser
    4430                  4435                  4440

Pro Val Pro Ser Pro Thr Thr Ala Gly Pro Leu Leu Val Pro Phe
    4445                  4450                  4455

Thr Leu Asn Phe Thr Ile Thr Asn Leu Gln Tyr Glu Glu Asp Met
    4460                  4465                  4470

His Arg Pro Gly Ser Arg Arg Phe Asn Thr Thr Glu Arg Val Leu
    4475                  4480                  4485

Gln Gly Leu Leu Thr Pro Leu Phe Lys Asn Thr Ser Val Gly Pro
    4490                  4495                  4500

Leu Tyr Ser Gly Cys Arg Leu Thr Leu Leu Arg Pro Glu Lys Gln
    4505                  4510                  4515

Glu Ala Ala Thr Gly Val Asp Thr Ile Cys Thr His Arg Val Asp
    4520                  4525                  4530

Pro Ile Gly Pro Gly Leu Asp Arg Glu Arg Leu Tyr Trp Glu Leu
    4535                  4540                  4545

Ser Gln Leu Thr Asn Ser Ile Thr Glu Leu Gly Pro Tyr Thr Leu
    4550                  4555                  4560

Asp Arg Asp Ser Leu Tyr Val Asn Gly Phe Asn Pro Trp Ser Ser
    4565                  4570                  4575

Val Pro Thr Thr Ser Thr Pro Gly Thr Ser Thr Val His Leu Ala
    4580                  4585                  4590

Thr Ser Gly Thr Pro Ser Ser Leu Pro Gly His Thr Ala Pro Val
    4595                  4600                  4605
```

-continued

```
Pro Leu Leu Ile Pro Phe Thr Leu Asn Phe Thr Ile Thr Asp Leu
    4610            4615            4620

His Tyr Glu Glu Asn Met Gln His Pro Gly Ser Arg Lys Phe Asn
    4625            4630            4635

Thr Thr Glu Arg Val Leu Gln Gly Leu Leu Lys Pro Leu Phe Lys
    4640            4645            4650

Ser Thr Ser Val Gly Pro Leu Tyr Ser Gly Cys Arg Leu Thr Leu
    4655            4660            4665

Leu Arg Pro Glu Lys His Gly Ala Ala Thr Gly Val Asp Ala Ile
    4670            4675            4680

Cys Thr Leu Arg Leu Asp Pro Thr Gly Pro Gly Leu Asp Arg Glu
    4685            4690            4695

Arg Leu Tyr Trp Glu Leu Ser Gln Leu Thr Asn Ser Val Thr Glu
    4700            4705            4710

Leu Gly Pro Tyr Thr Leu Asp Arg Asp Ser Leu Tyr Val Asn Gly
    4715            4720            4725

Phe Thr His Arg Ser Ser Val Pro Thr Thr Ser Ile Pro Gly Thr
    4730            4735            4740

Ser Ala Val His Leu Glu Thr Ser Gly Thr Pro Ala Ser Leu Pro
    4745            4750            4755

Gly His Thr Ala Pro Gly Pro Leu Leu Val Pro Phe Thr Leu Asn
    4760            4765            4770

Phe Thr Ile Thr Asn Leu Gln Tyr Glu Glu Asp Met Arg His Pro
    4775            4780            4785

Gly Ser Arg Lys Phe Ser Thr Thr Glu Arg Val Leu Gln Gly Leu
    4790            4795            4800

Leu Lys Pro Leu Phe Lys Asn Thr Ser Val Ser Ser Leu Tyr Ser
    4805            4810            4815

Gly Cys Arg Leu Thr Leu Leu Arg Pro Glu Lys Asp Gly Ala Ala
    4820            4825            4830

Thr Arg Val Asp Ala Val Cys Thr His Arg Pro Asp Pro Lys Ser
    4835            4840            4845

Pro Gly Leu Asp Arg Glu Arg Leu Tyr Trp Lys Leu Ser Gln Leu
    4850            4855            4860

Thr His Gly Ile Thr Glu Leu Gly Pro Tyr Thr Leu Asp Arg His
    4865            4870            4875

Ser Leu Tyr Val Asn Gly Phe Thr His Gln Ser Ser Met Thr Thr
    4880            4885            4890

Thr Arg Thr Pro Asp Thr Ser Thr Met His Leu Ala Thr Ser Arg
    4895            4900            4905

Thr Pro Ala Ser Leu Ser Gly Pro Thr Thr Ala Ser Pro Leu Leu
    4910            4915            4920

Val Leu Phe Thr Ile Asn Phe Thr Ile Thr Asn Gln Arg Tyr Glu
    4925            4930            4935

Glu Asn Met His His Pro Gly Ser Arg Lys Phe Asn Thr Thr Glu
    4940            4945            4950

Arg Val Leu Gln Gly Leu Leu Arg Pro Val Phe Lys Asn Thr Ser
    4955            4960            4965

Val Gly Pro Leu Tyr Ser Gly Cys Arg Leu Thr Leu Leu Arg Pro
    4970            4975            4980

Lys Lys Asp Gly Ala Ala Thr Lys Val Asp Ala Ile Cys Thr Tyr
    4985            4990            4995
```

-continued

```
Arg Pro Asp Pro Lys Ser Pro Gly Leu Asp Arg Glu Gln Leu Tyr
    5000                5005                5010

Trp Glu Leu Ser Gln Leu Thr His Ser Ile Thr Glu Leu Gly Pro
    5015                5020                5025

Tyr Thr Gln Asp Arg Asp Ser Leu Tyr Val Asn Gly Phe Thr His
    5030                5035                5040

Arg Ser Ser Val Pro Thr Thr Ser Ile Pro Gly Thr Ser Ala Val
    5045                5050                5055

His Leu Glu Thr Ser Gly Thr Pro Ala Ser Leu Pro Gly His Thr
    5060                5065                5070

Ala Pro Gly Pro Leu Leu Val Pro Phe Thr Leu Asn Phe Thr Ile
    5075                5080                5085

Thr Asn Leu Gln Tyr Glu Glu Asp Met Arg His Pro Gly Ser Arg
    5090                5095                5100

Lys Phe Asn Thr Thr Glu Arg Val Leu Gln Gly Leu Leu Lys Pro
    5105                5110                5115

Leu Phe Lys Ser Thr Ser Val Gly Pro Leu Tyr Ser Gly Cys Arg
    5120                5125                5130

Leu Thr Leu Leu Arg Pro Glu Lys Arg Gly Ala Ala Thr Gly Val
    5135                5140                5145

Asp Thr Ile Cys Thr His Arg Leu Asp Pro Leu Asn Pro Gly Leu
    5150                5155                5160

Asp Arg Glu Gln Leu Tyr Trp Glu Leu Ser Lys Leu Thr Arg Gly
    5165                5170                5175

Ile Ile Glu Leu Gly Pro Tyr Leu Leu Asp Arg Gly Ser Leu Tyr
    5180                5185                5190

Val Asn Gly Phe Thr His Arg Thr Ser Val Pro Thr Thr Ser Thr
    5195                5200                5205

Pro Gly Thr Ser Thr Val Asp Leu Gly Thr Ser Gly Thr Pro Phe
    5210                5215                5220

Ser Leu Pro Ser Pro Ala Xaa Xaa Xaa Pro Leu Leu Xaa Pro Phe
    5225                5230                5235

Thr Leu Asn Phe Thr Ile Thr Asn Leu Xaa Tyr Glu Glu Xaa Met
    5240                5245                5250

Xaa Xaa Pro Gly Ser Arg Lys Phe Asn Thr Thr Glu Arg Val Leu
    5255                5260                5265

Gln Thr Leu Leu Gly Pro Met Phe Lys Asn Thr Ser Val Gly Leu
    5270                5275                5280

Leu Tyr Ser Gly Cys Arg Leu Thr Leu Leu Arg Ser Glu Lys Asp
    5285                5290                5295

Gly Ala Ala Thr Gly Val Asp Ala Ile Cys Thr His Arg Leu Asp
    5300                5305                5310

Pro Lys Ser Pro Gly Val Asp Arg Glu Gln Leu Tyr Trp Glu Leu
    5315                5320                5325

Ser Gln Leu Thr Asn Gly Ile Lys Glu Leu Gly Pro Tyr Thr Leu
    5330                5335                5340

Asp Arg Asn Ser Leu Tyr Val Asn Gly Phe Thr His Trp Ile Pro
    5345                5350                5355

Val Pro Thr Ser Ser Thr Pro Gly Thr Ser Thr Val Asp Leu Gly
    5360                5365                5370

Ser Gly Thr Pro Ser Leu Pro Ser Ser Pro Thr Ala Gly Pro
    5375                5380                5385

Leu Leu Val Pro Phe Thr Leu Asn Phe Thr Ile Thr Asn Leu Lys
```

-continued

```
              5390                5395                5400
Tyr Glu Glu Asp Met His Cys Pro Gly Ser Arg Lys Phe Asn Thr
5405                5410                5415
Thr Glu Arg Val Leu Gln Ser Leu Leu Gly Pro Met Phe Lys Asn
5420                5425                5430
Thr Ser Val Gly Pro Leu Tyr Ser Gly Cys Arg Leu Thr Leu Leu
5435                5440                5445
Arg Ser Glu Lys Asp Gly Ala Ala Thr Gly Val Asp Ala Ile Cys
5450                5455                5460
Thr His Arg Leu Asp Pro Lys Ser Pro Gly Val Asp Arg Glu Gln
5465                5470                5475
Leu Tyr Trp Glu Leu Ser Gln Leu Thr Asn Gly Ile Lys Glu Leu
5480                5485                5490
Gly Pro Tyr Thr Leu Asp Arg Asn Ser Leu Tyr Val Asn Gly Phe
5495                5500                5505
Thr His Gln Thr Ser Ala Pro Asn Thr Ser Thr Pro Gly Thr Ser
5510                5515                5520
Thr Val Asp Leu Gly Thr Ser Gly Thr Pro Ser Ser Leu Pro Ser
5525                5530                5535
Pro Thr Xaa Xaa Xaa Pro Leu Leu Xaa Pro Phe Thr Leu Asn Phe
5540                5545                5550
Thr Ile Thr Asn Leu Xaa Tyr Glu Glu Xaa Met Xaa Xaa Pro Gly
5555                5560                5565
Ser Arg Lys Phe Asn Thr Thr Glu Arg Val Leu Gln Gly Leu Leu
5570                5575                5580
Xaa Pro Xaa Phe Lys Xaa Thr Ser Val Gly Xaa Leu Tyr Ser Gly
5585                5590                5595
Cys Arg Leu Thr Leu Leu Arg Xaa Glu Lys Xaa Xaa Ala Ala Thr
5600                5605                5610
Xaa Val Asp Xaa Xaa Cys Xaa Xaa Xaa Xaa Asp Pro Xaa Xaa Pro
5615                5620                5625
Gly Leu Asp Arg Glu Xaa Leu Tyr Trp Glu Leu Ser Xaa Leu Thr
5630                5635                5640
Xaa Xaa Ile Xaa Glu Leu Gly Pro Tyr Xaa Leu Asp Arg Xaa Ser
5645                5650                5655
Leu Tyr Val Asn Gly Phe Thr His Trp Ile Pro Val Pro Thr Ser
5660                5665                5670
Ser Thr Pro Gly Thr Ser Thr Val Asp Leu Gly Ser Gly Thr Pro
5675                5680                5685
Ser Ser Leu Pro Ser Pro Thr Ala Gly Pro Leu Leu Val Pro
5690                5695                5700
Phe Thr Leu Asn Phe Thr Ile Thr Asn Leu Lys Tyr Glu Glu Asp
5705                5710                5715
Met His Cys Pro Gly Ser Arg Lys Phe Asn Thr Thr Glu Arg Val
5720                5725                5730
Leu Gln Ser Leu Leu Gly Pro Met Phe Lys Asn Thr Ser Val Gly
5735                5740                5745
Pro Leu Tyr Ser Gly Cys Arg Leu Thr Ser Leu Arg Ser Glu Lys
5750                5755                5760
Asp Gly Ala Ala Thr Gly Val Asp Ala Ile Cys Thr His Arg Val
5765                5770                5775
Asp Pro Lys Ser Pro Gly Val Asp Arg Glu Gln Leu Tyr Trp Glu
5780                5785                5790
```

-continued

```
Leu Ser Gln Leu Thr Asn Gly Ile Lys Glu Leu Gly Pro Tyr Thr
        5795                5800                5805

Leu Asp Arg Asn Ser Leu Tyr Val Asn Gly Phe Thr His Gln Thr
    5810                5815                5820

Ser Ala Pro Asn Thr Ser Thr Pro Gly Thr Ser Thr Val Asp Leu
5825                5830                5835

Gly Thr Ser Gly Thr Pro Ser Ser Leu Pro Ser Pro Thr Ser Ala
5840                5845                5850

Gly Pro Leu Leu Val Pro Phe Thr Leu Asn Phe Thr Ile Thr Asn
5855                5860                5865

Leu Gln Tyr Glu Glu Asp Met His His Pro Gly Ser Arg Lys Phe
5870                5875                5880

Asn Thr Thr Glu Arg Val Leu Gln Gly Leu Leu Gly Pro Met Phe
5885                5890                5895

Lys Asn Thr Ser Val Gly Leu Leu Tyr Ser Gly Cys Arg Leu Thr
5900                5905                5910

Leu Leu Arg Pro Glu Lys Asn Gly Ala Ala Thr Gly Met Asp Ala
5915                5920                5925

Ile Cys Thr His Arg Leu Asp Pro Lys Ser Pro Gly Leu Asp Arg
5930                5935                5940

Glu Xaa Leu Tyr Trp Glu Leu Ser Xaa Leu Thr Xaa Xaa Ile Xaa
5945                5950                5955

Glu Leu Gly Pro Tyr Xaa Leu Asp Arg Xaa Ser Leu Tyr Val Asn
5960                5965                5970

Gly Phe Xaa Xaa Xaa Xaa Xaa Xaa Xaa Xaa Thr Ser Thr Pro Gly
5975                5980                5985

Thr Ser Xaa Val Xaa Leu Xaa Thr Ser Gly Thr Pro Xaa Xaa Xaa
5990                5995                6000

Pro Xaa Xaa Thr Xaa Xaa Xaa Pro Leu Leu Xaa Pro Phe Thr Leu
6005                6010                6015

Asn Phe Thr Ile Thr Asn Leu Xaa Tyr Glu Glu Xaa Met Xaa Xaa
6020                6025                6030

Pro Gly Ser Arg Lys Phe Asn Thr Thr Glu Arg Val Leu Gln Gly
6035                6040                6045

Leu Leu Lys Pro Leu Phe Arg Asn Ser Ser Leu Glu Tyr Leu Tyr
6050                6055                6060

Ser Gly Cys Arg Leu Ala Ser Leu Arg Pro Glu Lys Asp Ser Ser
6065                6070                6075

Ala Met Ala Val Asp Ala Ile Cys Thr His Arg Pro Asp Pro Glu
6080                6085                6090

Asp Leu Gly Leu Asp Arg Glu Arg Leu Tyr Trp Glu Leu Ser Asn
6095                6100                6105

Leu Thr Asn Gly Ile Gln Glu Leu Gly Pro Tyr Thr Leu Asp Arg
6110                6115                6120

Asn Ser Leu Tyr Val Asn Gly Phe Thr His Arg Ser Ser Met Pro
6125                6130                6135

Thr Thr Ser Thr Pro Gly Thr Ser Thr Val Asp Val Gly Thr Ser
6140                6145                6150

Gly Thr Pro Ser Ser Ser Pro Ser Pro Thr Thr Ala Gly Pro Leu
6155                6160                6165

Leu Ile Pro Phe Thr Leu Asn Phe Thr Ile Thr Asn Leu Gln Tyr
6170                6175                6180
```

-continued

| | | | | | | | | | | | |
|---|---|---|---|---|---|---|---|---|---|---|---|
|Gly|Glu|Asp|Met|Gly|His|Pro|Gly|Ser|Arg|Lys|Phe|Asn|Thr|Thr|
| |6185| | | |6190| | | |6195| | | | | |
|Glu|Arg|Val|Leu|Gln|Gly|Leu|Leu|Gly|Pro|Ile|Phe|Lys|Asn|Thr|
| |6200| | | |6205| | | |6210| | | | | |
|Ser|Val|Gly|Pro|Leu|Tyr|Ser|Gly|Cys|Arg|Leu|Thr|Ser|Leu|Arg|
| |6215| | | |6220| | | |6225| | | | | |
|Ser|Glu|Lys|Asp|Gly|Ala|Ala|Thr|Gly|Val|Asp|Ala|Ile|Cys|Ile|
| |6230| | | |6235| | | |6240| | | | | |
|His|His|Leu|Asp|Pro|Lys|Ser|Pro|Gly|Leu|Asn|Arg|Glu|Arg|Leu|
| |6245| | | |6250| | | |6255| | | | | |
|Tyr|Trp|Glu|Leu|Ser|Gln|Leu|Thr|Asn|Gly|Ile|Lys|Glu|Leu|Gly|
| |6260| | | |6265| | | |6270| | | | | |
|Pro|Tyr|Thr|Leu|Asp|Arg|Asn|Ser|Leu|Tyr|Val|Asn|Gly|Phe|Thr|
| |6275| | | |6280| | | |6285| | | | | |
|His|Arg|Thr|Ser|Val|Pro|Thr|Thr|Ser|Thr|Pro|Gly|Thr|Ser|Thr|
| |6290| | | |6295| | | |6300| | | | | |
|Val|Asp|Leu|Gly|Thr|Ser|Gly|Thr|Pro|Phe|Ser|Leu|Pro|Ser|Pro|
| |6305| | | |6310| | | |6315| | | | | |
|Ala|Thr|Ala|Gly|Pro|Leu|Leu|Val|Leu|Phe|Thr|Leu|Asn|Phe|Thr|
| |6320| | | |6325| | | |6330| | | | | |
|Ile|Thr|Asn|Leu|Lys|Tyr|Glu|Glu|Asp|Met|His|Arg|Pro|Gly|Ser|
| |6335| | | |6340| | | |6345| | | | | |
|Arg|Lys|Phe|Asn|Thr|Thr|Glu|Arg|Val|Leu|Gln|Thr|Leu|Leu|Gly|
| |6350| | | |6355| | | |6360| | | | | |
|Pro|Met|Phe|Lys|Asn|Thr|Ser|Val|Gly|Leu|Leu|Tyr|Ser|Gly|Cys|
| |6365| | | |6370| | | |6375| | | | | |
|Arg|Leu|Thr|Leu|Leu|Arg|Ser|Glu|Lys|Asp|Gly|Ala|Ala|Thr|Gly|
| |6380| | | |6385| | | |6390| | | | | |
|Val|Asp|Ala|Ile|Cys|Thr|His|Arg|Leu|Asp|Pro|Lys|Ser|Pro|Gly|
| |6395| | | |6400| | | |6405| | | | | |
|Leu|Asp|Arg|Glu|Xaa|Leu|Tyr|Trp|Glu|Leu|Ser|Xaa|Leu|Thr|Xaa|
| |6410| | | |6415| | | |6420| | | | | |
|Xaa|Ile|Xaa|Glu|Leu|Gly|Pro|Tyr|Xaa|Leu|Asp|Arg|Xaa|Ser|Leu|
| |6425| | | |6430| | | |6435| | | | | |
|Tyr|Val|Asn|Gly|Phe|Xaa|Xaa|Xaa|Xaa|Xaa|Xaa|Xaa|Xaa|Thr|Ser|
| |6440| | | |6445| | | |6450| | | | | |
|Thr|Pro|Gly|Thr|Ser|Xaa|Val|Xaa|Leu|Xaa|Thr|Ser|Gly|Thr|Pro|
| |6455| | | |6460| | | |6465| | | | | |
|Xaa|Xaa|Xaa|Pro|Xaa|Xaa|Thr|Xaa|Xaa|Xaa|Pro|Leu|Leu|Xaa|Pro|
| |6470| | | |6475| | | |6480| | | | | |
|Phe|Thr|Leu|Asn|Phe|Thr|Ile|Thr|Asn|Leu|Xaa|Tyr|Glu|Glu|Xaa|
| |6485| | | |6490| | | |6495| | | | | |
|Met|Xaa|Xaa|Pro|Gly|Ser|Arg|Lys|Phe|Asn|Thr|Thr|Glu|Arg|Val|
| |6500| | | |6505| | | |6510| | | | | |
|Leu|Gln|Gly|Leu|Leu|Arg|Pro|Val|Phe|Lys|Asn|Thr|Ser|Val|Gly|
| |6515| | | |6520| | | |6525| | | | | |
|Pro|Leu|Tyr|Ser|Gly|Cys|Arg|Leu|Thr|Leu|Leu|Arg|Pro|Lys|Lys|
| |6530| | | |6535| | | |6540| | | | | |
|Asp|Gly|Ala|Ala|Thr|Lys|Val|Asp|Ala|Ile|Cys|Thr|Tyr|Arg|Pro|
| |6545| | | |6550| | | |6555| | | | | |
|Asp|Pro|Lys|Ser|Pro|Gly|Leu|Asp|Arg|Glu|Gln|Leu|Tyr|Trp|Glu|
| |6560| | | |6565| | | |6570| | | | | |
|Leu|Ser|Gln|Leu|Thr|His|Ser|Ile|Thr|Glu|Leu|Gly|Pro|Tyr|Thr|

-continued

|  | 6575 |  |  |  | 6580 |  |  |  | 6585 |  |  |
| --- | --- | --- | --- | --- | --- | --- | --- | --- | --- | --- | --- |
| Gln | Asp | Arg | Asp | Ser | Leu | Tyr | Val | Asn | Gly | Phe | Thr | His | Arg | Ser |
|  | 6590 |  |  |  | 6595 |  |  |  | 6600 |  |  |
| Ser | Val | Pro | Thr | Thr | Ser | Ile | Pro | Gly | Thr | Ser | Ala | Val | His | Leu |
|  | 6605 |  |  |  | 6610 |  |  |  | 6615 |  |  |
| Glu | Thr | Thr | Gly | Thr | Pro | Ser | Ser | Phe | Pro | Gly | His | Thr | Glu | Pro |
|  | 6620 |  |  |  | 6625 |  |  |  | 6630 |  |  |
| Gly | Pro | Leu | Leu | Ile | Pro | Phe | Thr | Phe | Asn | Phe | Thr | Ile | Thr | Asn |
|  | 6635 |  |  |  | 6640 |  |  |  | 6645 |  |  |
| Leu | Arg | Tyr | Glu | Glu | Asn | Met | Gln | His | Pro | Gly | Ser | Arg | Lys | Phe |
|  | 6650 |  |  |  | 6655 |  |  |  | 6660 |  |  |
| Asn | Thr | Thr | Glu | Arg | Val | Leu | Gln | Gly | Leu | Leu | Thr | Pro | Leu | Phe |
|  | 6665 |  |  |  | 6670 |  |  |  | 6675 |  |  |
| Lys | Asn | Thr | Ser | Val | Gly | Pro | Leu | Tyr | Ser | Gly | Cys | Arg | Leu | Thr |
|  | 6680 |  |  |  | 6685 |  |  |  | 6690 |  |  |
| Leu | Leu | Arg | Pro | Glu | Lys | Gln | Glu | Ala | Ala | Thr | Gly | Val | Asp | Thr |
|  | 6695 |  |  |  | 6700 |  |  |  | 6705 |  |  |
| Ile | Cys | Thr | His | Arg | Val | Asp | Pro | Ile | Gly | Pro | Gly | Leu | Asp | Arg |
|  | 6710 |  |  |  | 6715 |  |  |  | 6720 |  |  |
| Glu | Arg | Leu | Tyr | Trp | Glu | Leu | Ser | Gln | Leu | Thr | Asn | Ser | Ile | Thr |
|  | 6725 |  |  |  | 6730 |  |  |  | 6735 |  |  |
| Glu | Leu | Gly | Pro | Tyr | Thr | Leu | Asp | Arg | Asp | Ser | Leu | Tyr | Val | Asp |
|  | 6740 |  |  |  | 6745 |  |  |  | 6750 |  |  |
| Gly | Phe | Asn | Pro | Trp | Ser | Ser | Val | Pro | Thr | Thr | Ser | Thr | Pro | Gly |
|  | 6755 |  |  |  | 6760 |  |  |  | 6765 |  |  |
| Thr | Ser | Thr | Val | His | Leu | Ala | Thr | Ser | Gly | Thr | Pro | Ser | Pro | Leu |
|  | 6770 |  |  |  | 6775 |  |  |  | 6780 |  |  |
| Pro | Gly | His | Thr | Ala | Pro | Val | Pro | Leu | Leu | Ile | Pro | Phe | Thr | Leu |
|  | 6785 |  |  |  | 6790 |  |  |  | 6795 |  |  |
| Asn | Phe | Thr | Ile | Thr | Asp | Leu | His | Tyr | Glu | Glu | Asn | Met | Gln | His |
|  | 6800 |  |  |  | 6805 |  |  |  | 6810 |  |  |
| Pro | Gly | Ser | Arg | Lys | Phe | Asn | Thr | Thr | Glu | Arg | Val | Leu | Gln | Gly |
|  | 6815 |  |  |  | 6820 |  |  |  | 6825 |  |  |
| Leu | Leu | Lys | Pro | Leu | Phe | Lys | Ser | Thr | Ser | Val | Gly | Pro | Leu | Tyr |
|  | 6830 |  |  |  | 6835 |  |  |  | 6840 |  |  |
| Ser | Gly | Cys | Arg | Leu | Thr | Leu | Leu | Arg | Pro | Glu | Lys | His | Gly | Ala |
|  | 6845 |  |  |  | 6850 |  |  |  | 6855 |  |  |
| Ala | Thr | Gly | Val | Asp | Ala | Ile | Cys | Thr | Leu | Arg | Leu | Asp | Pro | Thr |
|  | 6860 |  |  |  | 6865 |  |  |  | 6870 |  |  |
| Gly | Pro | Gly | Leu | Asp | Arg | Glu | Arg | Leu | Tyr | Trp | Glu | Leu | Ser | Gln |
|  | 6875 |  |  |  | 6880 |  |  |  | 6885 |  |  |
| Leu | Thr | Asn | Ser | Ile | Thr | Glu | Leu | Gly | Pro | Tyr | Thr | Leu | Asp | Arg |
|  | 6890 |  |  |  | 6895 |  |  |  | 6900 |  |  |
| Asp | Ser | Leu | Tyr | Val | Asn | Gly | Phe | Asn | Pro | Trp | Ser | Ser | Val | Pro |
|  | 6905 |  |  |  | 6910 |  |  |  | 6915 |  |  |
| Thr | Thr | Ser | Thr | Pro | Gly | Thr | Ser | Thr | Val | His | Leu | Ala | Thr | Ser |
|  | 6920 |  |  |  | 6925 |  |  |  | 6930 |  |  |
| Gly | Thr | Pro | Ser | Ser | Leu | Pro | Gly | His | Thr | Thr | Ala | Gly | Pro | Leu |
|  | 6935 |  |  |  | 6940 |  |  |  | 6945 |  |  |
| Leu | Val | Pro | Phe | Thr | Leu | Asn | Phe | Thr | Ile | Thr | Asn | Leu | Lys | Tyr |
|  | 6950 |  |  |  | 6955 |  |  |  | 6960 |  |  |
| Glu | Glu | Asp | Met | His | Cys | Pro | Gly | Ser | Arg | Lys | Phe | Asn | Thr | Thr |
|  | 6965 |  |  |  | 6970 |  |  |  | 6975 |  |  |

-continued

```
Glu Arg Val Leu Gln Ser Leu His Gly Pro Met Phe Lys Asn Thr
    6980                6985                6990

Ser Val Gly Pro Leu Tyr Ser Gly Cys Arg Leu Thr Leu Leu Arg
    6995                7000                7005

Ser Glu Lys Asp Gly Ala Ala Thr Gly Val Asp Ala Ile Cys Thr
    7010                7015                7020

His Arg Leu Asp Pro Lys Ser Pro Gly Leu Asp Arg Glu Xaa Leu
    7025                7030                7035

Tyr Trp Glu Leu Ser Xaa Leu Thr Xaa Xaa Ile Xaa Glu Leu Gly
    7040                7045                7050

Pro Tyr Xaa Leu Asp Arg Xaa Ser Leu Tyr Val Asn Gly Phe Xaa
    7055                7060                7065

Xaa Xaa Xaa Xaa Xaa Xaa Thr Ser Thr Pro Gly Thr Ser Xaa
    7070                7075                7080

Val Xaa Leu Xaa Thr Ser Gly Thr Pro Xaa Xaa Xaa Pro Xaa Xaa
    7085                7090                7095

Thr Xaa Xaa Xaa Pro Leu Leu Xaa Pro Phe Thr Leu Asn Phe Thr
    7100                7105                7110

Ile Thr Asn Leu Xaa Tyr Glu Glu Xaa Met Xaa Xaa Pro Gly Ser
    7115                7120                7125

Arg Lys Phe Asn Thr Thr Glu Arg Val Leu Gln Gly Leu Leu Xaa
    7130                7135                7140

Pro Xaa Phe Lys Xaa Thr Ser Val Gly Xaa Leu Tyr Ser Gly Cys
    7145                7150                7155

Arg Leu Thr Leu Leu Arg Xaa Glu Lys Xaa Xaa Ala Ala Thr Xaa
    7160                7165                7170

Val Asp Xaa Xaa Cys Xaa Xaa Xaa Xaa Asp Pro Xaa Xaa Pro Gly
    7175                7180                7185

Leu Asp Arg Glu Xaa Leu Tyr Trp Glu Leu Ser Xaa Leu Thr Asn
    7190                7195                7200

Ser Ile Thr Glu Leu Gly Pro Tyr Thr Leu Asp Arg Asp Ser Leu
    7205                7210                7215

Tyr Val Asn Gly Phe Thr His Arg Ser Ser Met Pro Thr Thr Ser
    7220                7225                7230

Ile Pro Gly Thr Ser Ala Val His Leu Glu Thr Ser Gly Thr Pro
    7235                7240                7245

Ala Ser Leu Pro Gly His Thr Ala Pro Gly Pro Leu Leu Val Pro
    7250                7255                7260

Phe Thr Leu Asn Phe Thr Ile Thr Asn Leu Gln Tyr Glu Glu Asp
    7265                7270                7275

Met Arg His Pro Gly Ser Arg Lys Phe Asn Thr Thr Glu Arg Val
    7280                7285                7290

Leu Gln Gly Leu Leu Lys Pro Leu Phe Lys Ser Thr Ser Val Gly
    7295                7300                7305

Pro Leu Tyr Ser Gly Cys Arg Leu Thr Leu Leu Arg Pro Glu Lys
    7310                7315                7320

Arg Gly Ala Ala Thr Gly Val Asp Thr Ile Cys Thr His Arg Leu
    7325                7330                7335

Asp Pro Leu Asn Pro Gly Leu Asp Arg Glu Xaa Leu Tyr Trp Glu
    7340                7345                7350

Leu Ser Xaa Leu Thr Xaa Xaa Ile Xaa Glu Leu Gly Pro Tyr Xaa
    7355                7360                7365
```

-continued

```
Leu Asp Arg Xaa Ser Leu Tyr Val Asn Gly Phe Xaa Xaa Xaa Xaa
        7370                7375                7380

Xaa Xaa Xaa Xaa Thr Ser Thr Pro Gly Thr Ser Xaa Val Xaa Leu
        7385                7390                7395

Xaa Thr Ser Gly Thr Pro Xaa Xaa Xaa Pro Xaa Xaa Thr Xaa Xaa
        7400                7405                7410

Xaa Pro Leu Leu Xaa Pro Phe Thr Leu Asn Phe Thr Ile Thr Asn
        7415                7420                7425

Leu Xaa Tyr Glu Glu Xaa Met Xaa Xaa Pro Gly Ser Arg Lys Phe
        7430                7435                7440

Asn Thr Thr Glu Arg Val Leu Gln Gly Leu Leu Xaa Pro Xaa Phe
        7445                7450                7455

Lys Xaa Thr Ser Val Gly Xaa Leu Tyr Ser Gly Cys Arg Leu Thr
        7460                7465                7470

Leu Leu Arg Xaa Glu Lys Xaa Xaa Ala Ala Thr Xaa Val Asp Xaa
        7475                7480                7485

Xaa Cys Xaa Xaa Xaa Xaa Asp Pro Xaa Xaa Pro Gly Leu Asp Arg
        7490                7495                7500

Glu Xaa Leu Tyr Trp Glu Leu Ser Xaa Leu Thr Xaa Xaa Ile Xaa
        7505                7510                7515

Glu Leu Gly Pro Tyr Xaa Leu Asp Arg Xaa Ser Leu Tyr Val Asn
        7520                7525                7530

Gly Phe His Pro Arg Ser Ser Val Pro Thr Thr Ser Thr Pro Gly
        7535                7540                7545

Thr Ser Thr Val His Leu Ala Thr Ser Gly Thr Pro Ser Ser Leu
        7550                7555                7560

Pro Gly His Thr Ala Pro Val Pro Leu Leu Ile Pro Phe Thr Leu
        7565                7570                7575

Asn Phe Thr Ile Thr Asn Leu His Tyr Glu Glu Asn Met Gln His
        7580                7585                7590

Pro Gly Ser Arg Lys Phe Asn Thr Thr Glu Arg Val Leu Gln Gly
        7595                7600                7605

Leu Leu Gly Pro Met Phe Lys Asn Thr Ser Val Gly Leu Leu Tyr
        7610                7615                7620

Ser Gly Cys Arg Leu Thr Leu Leu Arg Pro Glu Lys Asn Gly Ala
        7625                7630                7635

Ala Thr Gly Met Asp Ala Ile Cys Ser His Arg Leu Asp Pro Lys
        7640                7645                7650

Ser Pro Gly Leu Asp Arg Glu Xaa Leu Tyr Trp Glu Leu Ser Xaa
        7655                7660                7665

Leu Thr Xaa Xaa Ile Xaa Glu Leu Gly Pro Tyr Xaa Leu Asp Arg
        7670                7675                7680

Xaa Ser Leu Tyr Val Asn Gly Phe Xaa Xaa Xaa Xaa Xaa Xaa Xaa
        7685                7690                7695

Xaa Thr Ser Thr Pro Gly Thr Ser Xaa Val Xaa Leu Xaa Thr Ser
        7700                7705                7710

Gly Thr Pro Xaa Xaa Xaa Pro Xaa Xaa Thr Xaa Xaa Xaa Pro Leu
        7715                7720                7725

Leu Xaa Pro Phe Thr Leu Asn Phe Thr Ile Thr Asn Leu Xaa Tyr
        7730                7735                7740

Glu Glu Xaa Met Xaa Xaa Pro Gly Ser Arg Lys Phe Asn Thr Thr
        7745                7750                7755

Glu Arg Val Leu Gln Gly Leu Leu Xaa Pro Xaa Phe Lys Xaa Thr
```

-continued

```
              7760                7765                 7770
Ser  Val  Gly  Xaa  Leu  Tyr  Ser  Gly  Cys  Arg  Leu  Thr  Leu  Leu  Arg
              7775                7780                 7785

Xaa  Glu  Lys  Xaa  Xaa  Ala  Ala  Thr  Xaa  Val  Asp  Xaa  Xaa  Cys  Xaa
              7790                7795                 7800

Xaa  Xaa  Xaa  Asp  Pro  Xaa  Xaa  Pro  Gly  Leu  Asp  Arg  Glu  Xaa  Leu
              7805                7810                 7815

Tyr  Trp  Glu  Leu  Ser  Xaa  Leu  Thr  Xaa  Xaa  Ile  Xaa  Glu  Leu  Gly
              7820                7825                 7830

Pro  Tyr  Xaa  Leu  Asp  Arg  Xaa  Ser  Leu  Tyr  Val  Asn  Gly  Phe  Thr
              7835                7840                 7845

His  Gln  Asn  Ser  Val  Pro  Thr  Thr  Ser  Thr  Pro  Gly  Thr  Ser  Thr
              7850                7855                 7860

Val  Tyr  Trp  Ala  Thr  Thr  Gly  Thr  Pro  Ser  Ser  Phe  Pro  Gly  His
              7865                7870                 7875

Thr  Glu  Pro  Gly  Pro  Leu  Leu  Ile  Pro  Phe  Thr  Phe  Asn  Phe  Thr
              7880                7885                 7890

Ile  Thr  Asn  Leu  His  Tyr  Glu  Glu  Asn  Met  Gln  His  Pro  Gly  Ser
              7895                7900                 7905

Arg  Lys  Phe  Asn  Thr  Thr  Glu  Arg  Val  Leu  Gln  Gly  Leu  Leu  Thr
              7910                7915                 7920

Pro  Leu  Phe  Lys  Asn  Thr  Ser  Val  Gly  Pro  Leu  Tyr  Ser  Gly  Cys
              7925                7930                 7935

Arg  Leu  Thr  Leu  Leu  Arg  Pro  Glu  Lys  Gln  Glu  Ala  Ala  Thr  Gly
              7940                7945                 7950

Val  Asp  Thr  Ile  Cys  Thr  His  Arg  Val  Asp  Pro  Ile  Gly  Pro  Gly
              7955                7960                 7965

Leu  Asp  Arg  Glu  Xaa  Leu  Tyr  Trp  Glu  Leu  Ser  Xaa  Leu  Thr  Xaa
              7970                7975                 7980

Xaa  Ile  Xaa  Glu  Leu  Gly  Pro  Tyr  Xaa  Leu  Asp  Arg  Xaa  Ser  Leu
              7985                7990                 7995

Tyr  Val  Asn  Gly  Phe  Xaa  Xaa  Xaa  Xaa  Xaa  Xaa  Xaa  Xaa  Thr  Ser
              8000                8005                 8010

Thr  Pro  Gly  Thr  Ser  Xaa  Val  Xaa  Leu  Xaa  Thr  Ser  Gly  Thr  Pro
              8015                8020                 8025

Xaa  Xaa  Xaa  Pro  Xaa  Xaa  Thr  Xaa  Xaa  Xaa  Pro  Leu  Leu  Xaa  Pro
              8030                8035                 8040

Phe  Thr  Leu  Asn  Phe  Thr  Ile  Thr  Asn  Leu  Xaa  Tyr  Glu  Glu  Xaa
              8045                8050                 8055

Met  Xaa  Xaa  Pro  Gly  Ser  Arg  Lys  Phe  Asn  Thr  Thr  Glu  Arg  Val
              8060                8065                 8070

Leu  Gln  Gly  Leu  Leu  Xaa  Pro  Xaa  Phe  Lys  Xaa  Thr  Ser  Val  Gly
              8075                8080                 8085

Xaa  Leu  Tyr  Ser  Gly  Cys  Arg  Leu  Thr  Leu  Leu  Arg  Xaa  Glu  Lys
              8090                8095                 8100

Xaa  Xaa  Ala  Ala  Thr  Xaa  Val  Asp  Xaa  Xaa  Cys  Xaa  Xaa  Xaa  Xaa
              8105                8110                 8115

Asp  Pro  Xaa  Xaa  Pro  Gly  Leu  Asp  Arg  Glu  Xaa  Leu  Tyr  Trp  Glu
              8120                8125                 8130

Leu  Ser  Xaa  Leu  Thr  Xaa  Xaa  Ile  Xaa  Glu  Leu  Gly  Pro  Tyr  Xaa
              8135                8140                 8145

Leu  Asp  Arg  Xaa  Ser  Leu  Tyr  Val  Asn  Gly  Phe  Thr  His  Arg  Ser
              8150                8155                 8160
```

-continued

```
Ser Val Pro Thr Thr Ser Ser Pro Gly Thr Ser Thr Val His Leu
    8165                8170                8175
Ala Thr Ser Gly Thr Pro Ser Ser Leu Pro Gly His Thr Ala Pro
    8180                8185                8190
Val Pro Leu Leu Ile Pro Phe Thr Leu Asn Phe Thr Ile Thr Asn
    8195                8200                8205
Leu His Tyr Glu Glu Asn Met Gln His Pro Gly Ser Arg Lys Phe
    8210                8215                8220
Asn Thr Thr Glu Arg Val Leu Gln Gly Leu Leu Lys Pro Leu Phe
    8225                8230                8235
Lys Ser Thr Ser Val Gly Pro Leu Tyr Ser Gly Cys Arg Leu Thr
    8240                8245                8250
Leu Leu Arg Pro Glu Lys His Gly Ala Ala Thr Gly Val Asp Ala
    8255                8260                8265
Ile Cys Thr Leu Arg Leu Asp Pro Thr Gly Pro Gly Leu Asp Arg
    8270                8275                8280
Glu Xaa Leu Tyr Trp Glu Leu Ser Xaa Leu Thr Xaa Xaa Ile Xaa
    8285                8290                8295
Glu Leu Gly Pro Tyr Xaa Leu Asp Arg Xaa Ser Leu Tyr Val Asn
    8300                8305                8310
Gly Phe Xaa Xaa Xaa Xaa Xaa Xaa Xaa Thr Ser Thr Pro Gly
    8315                8320                8325
Thr Ser Xaa Val Xaa Leu Xaa Thr Ser Gly Thr Pro Xaa Xaa Xaa
    8330                8335                8340
Pro Xaa Xaa Thr Xaa Xaa Xaa Pro Leu Leu Xaa Pro Phe Thr Leu
    8345                8350                8355
Asn Phe Thr Ile Thr Asn Leu Xaa Tyr Glu Glu Xaa Met Xaa Xaa
    8360                8365                8370
Pro Gly Ser Arg Lys Phe Asn Thr Thr Glu Arg Val Leu Gln Gly
    8375                8380                8385
Leu Leu Xaa Pro Xaa Phe Lys Xaa Thr Ser Val Gly Xaa Leu Tyr
    8390                8395                8400
Ser Gly Cys Arg Leu Thr Leu Arg Xaa Glu Lys Xaa Xaa Ala
    8405                8410                8415
Ala Thr Xaa Val Asp Xaa Xaa Cys Xaa Xaa Xaa Xaa Asp Pro Xaa
    8420                8425                8430
Xaa Pro Gly Leu Asp Arg Glu Xaa Leu Tyr Trp Glu Leu Ser Xaa
    8435                8440                8445
Leu Thr Xaa Xaa Ile Xaa Glu Leu Gly Pro Tyr Xaa Leu Asp Arg
    8450                8455                8460
Xaa Ser Leu Tyr Val Asn Gly Phe Thr His Arg Thr Ser Val Pro
    8465                8470                8475
Thr Thr Ser Thr Pro Gly Thr Ser Thr Val His Leu Ala Thr Ser
    8480                8485                8490
Gly Thr Pro Ser Ser Leu Pro Gly His Thr Ala Pro Val Pro Leu
    8495                8500                8505
Leu Ile Pro Phe Thr Leu Asn Phe Thr Ile Thr Asn Leu Gln Tyr
    8510                8515                8520
Glu Glu Asp Met His Arg Pro Gly Ser Arg Lys Phe Asn Thr Thr
    8525                8530                8535
Glu Arg Val Leu Gln Gly Leu Leu Ser Pro Ile Phe Lys Asn Ser
    8540                8545                8550
```

-continued

Ser Val Gly Pro Leu Tyr Ser Gly Cys Arg Leu Thr Ser Leu Arg
    8555                8560            8565

Pro Glu Lys Asp Gly Ala Ala Thr Gly Met Asp Ala Val Cys Leu
    8570                8575            8580

Tyr His Pro Asn Pro Lys Arg Pro Gly Leu Asp Arg Glu Gln Leu
    8585                8590            8595

Tyr Cys Glu Leu Ser Gln Leu Thr His Asn Ile Thr Glu Leu Gly
    8600                8605            8610

Pro Tyr Ser Leu Asp Arg Asp Ser Leu Tyr Val Asn Gly Phe Thr
    8615                8620            8625

His Gln Asn Ser Val Pro Thr Thr Ser Thr Pro Gly Thr Ser Thr
    8630                8635            8640

Val Tyr Trp Ala Thr Thr Gly Thr Pro Ser Ser Phe Pro Gly His
    8645                8650            8655

Thr Xaa Xaa Xaa Pro Leu Leu Xaa Pro Phe Thr Leu Asn Phe Thr
    8660                8665            8670

Ile Thr Asn Leu Xaa Tyr Glu Glu Xaa Met Xaa Xaa Pro Gly Ser
    8675                8680            8685

Arg Lys Phe Asn Thr Thr Glu Arg Val Leu Gln Gly Leu Leu Xaa
    8690                8695            8700

Pro Xaa Phe Lys Xaa Thr Ser Val Gly Xaa Leu Tyr Ser Gly Cys
    8705                8710            8715

Arg Leu Thr Leu Leu Arg Xaa Glu Lys Xaa Xaa Ala Ala Thr Xaa
    8720                8725            8730

Val Asp Xaa Xaa Cys Xaa Xaa Xaa Xaa Asp Pro Xaa Xaa Pro Gly
    8735                8740            8745

Leu Asp Arg Glu Xaa Leu Tyr Trp Glu Leu Ser Xaa Leu Thr Xaa
    8750                8755            8760

Xaa Ile Xaa Glu Leu Gly Pro Tyr Xaa Leu Asp Arg Xaa Ser Leu
    8765                8770            8775

Tyr Val Asn Gly Phe Thr His Trp Ser Ser Gly Leu Thr Thr Ser
    8780                8785            8790

Thr Pro Trp Thr Ser Thr Val Asp Leu Gly Thr Ser Gly Thr Pro
    8795                8800            8805

Ser Pro Val Pro Ser Pro Thr Thr Ala Gly Pro Leu Leu Val Pro
    8810                8815            8820

Phe Thr Leu Asn Phe Thr Ile Thr Asn Leu Gln Tyr Glu Glu Asp
    8825                8830            8835

Met His Arg Pro Gly Ser Arg Lys Phe Asn Ala Thr Glu Arg Val
    8840                8845            8850

Leu Gln Gly Leu Leu Ser Pro Ile Phe Lys Asn Thr Ser Val Gly
    8855                8860            8865

Pro Leu Tyr Ser Gly Cys Arg Leu Thr Leu Leu Arg Pro Glu Lys
    8870                8875            8880

Gln Glu Ala Ala Thr Gly Val Asp Thr Ile Cys Thr His Arg Val
    8885                8890            8895

Asp Pro Ile Gly Pro Gly Leu Asp Arg Glu Xaa Leu Tyr Trp Glu
    8900                8905            8910

Leu Ser Xaa Leu Thr Xaa Xaa Ile Xaa Glu Leu Gly Pro Tyr Xaa
    8915                8920            8925

Leu Asp Arg Xaa Ser Leu Tyr Val Asn Gly Phe Xaa Xaa Xaa Xaa
    8930                8935            8940

Xaa Xaa Xaa Xaa Thr Ser Thr Pro Gly Thr Ser Xaa Val Xaa Leu

```
                 8945               8950                8955
Xaa Thr Ser Gly Thr Pro Xaa Xaa Pro Xaa Xaa Thr Xaa Xaa
                 8960               8965                8970

Xaa Pro Leu Leu Xaa Pro Phe Thr Leu Asn Phe Thr Ile Thr Asn
                 8975               8980                8985

Leu Xaa Tyr Glu Glu Xaa Met Xaa Xaa Pro Gly Ser Arg Lys Phe
                 8990               8995                9000

Asn Thr Thr Glu Arg Val Leu Gln Gly Leu Leu Xaa Pro Xaa Phe
                 9005               9010                9015

Lys Xaa Thr Ser Val Gly Xaa Leu Tyr Ser Gly Cys Arg Leu Thr
                 9020               9025                9030

Leu Leu Arg Xaa Glu Lys Xaa Xaa Ala Ala Thr Xaa Val Asp Xaa
                 9035               9040                9045

Xaa Cys Xaa Xaa Xaa Xaa Asp Pro Xaa Xaa Pro Gly Leu Asp Arg
                 9050               9055                9060

Glu Xaa Leu Tyr Trp Glu Leu Ser Xaa Leu Thr Xaa Xaa Ile Xaa
                 9065               9070                9075

Glu Leu Gly Pro Tyr Xaa Leu Asp Arg Xaa Ser Leu Tyr Val Asn
                 9080               9085                9090

Gly Phe Thr His Arg Ser Phe Gly Leu Thr Thr Ser Thr Pro Trp
                 9095               9100                9105

Thr Ser Thr Val Asp Leu Gly Thr Ser Gly Thr Pro Ser Pro Val
                 9110               9115                9120

Pro Ser Pro Thr Thr Ala Gly Pro Leu Leu Val Pro Phe Thr Leu
                 9125               9130                9135

Asn Phe Thr Ile Thr Asn Leu Gln Tyr Glu Glu Asp Met His Arg
                 9140               9145                9150

Pro Gly Ser Arg Lys Phe Asn Thr Thr Glu Arg Val Leu Gln Gly
                 9155               9160                9165

Leu Leu Thr Pro Leu Phe Arg Asn Thr Ser Val Ser Ser Leu Tyr
                 9170               9175                9180

Ser Gly Cys Arg Leu Thr Leu Leu Arg Pro Glu Lys Asp Gly Ala
                 9185               9190                9195

Ala Thr Arg Val Asp Ala Val Cys Thr His Arg Pro Asp Pro Lys
                 9200               9205                9210

Ser Pro Gly Leu Asp Arg Glu Xaa Leu Tyr Trp Glu Leu Ser Xaa
                 9215               9220                9225

Leu Thr Xaa Xaa Ile Xaa Glu Leu Gly Pro Tyr Xaa Leu Asp Arg
                 9230               9235                9240

Xaa Ser Leu Tyr Val Asn Gly Phe Xaa Xaa Xaa Xaa Xaa Xaa Xaa
                 9245               9250                9255

Xaa Thr Ser Thr Pro Gly Thr Ser Xaa Val Xaa Leu Xaa Thr Ser
                 9260               9265                9270

Gly Thr Pro Xaa Xaa Xaa Pro Xaa Xaa Thr Xaa Xaa Xaa Pro Leu
                 9275               9280                9285

Leu Xaa Pro Phe Thr Leu Asn Phe Thr Ile Thr Asn Leu Xaa Tyr
                 9290               9295                9300

Glu Glu Xaa Met Xaa Xaa Pro Gly Ser Arg Lys Phe Asn Thr Thr
                 9305               9310                9315

Glu Arg Val Leu Gln Gly Leu Leu Xaa Pro Xaa Phe Lys Xaa Thr
                 9320               9325                9330

Ser Val Gly Xaa Leu Tyr Ser Gly Cys Arg Leu Thr Leu Leu Arg
                 9335               9340                9345
```

-continued

```
Xaa Glu Lys Xaa Xaa Ala Ala Thr Xaa Val Asp Xaa Xaa Cys Xaa
    9350              9355                9360

Xaa Xaa Xaa Asp Pro Xaa Xaa Pro Gly Leu Asp Arg Glu Xaa Leu
    9365              9370                9375

Tyr Trp Glu Leu Ser Xaa Leu Thr Xaa Xaa Ile Xaa Glu Leu Gly
    9380              9385                9390

Pro Tyr Xaa Leu Asp Arg Xaa Ser Leu Tyr Val Asn Gly Phe Thr
    9395              9400                9405

His Trp Ile Pro Val Pro Thr Ser Ser Thr Pro Gly Thr Ser Thr
    9410              9415                9420

Val Asp Leu Gly Ser Gly Thr Pro Ser Ser Leu Pro Ser Pro Thr
    9425              9430                9435

Thr Ala Gly Pro Leu Leu Val Pro Phe Thr Leu Asn Phe Thr Ile
    9440              9445                9450

Thr Asn Leu Gln Tyr Gly Glu Asp Met Gly His Pro Gly Ser Arg
    9455              9460                9465

Lys Phe Asn Thr Thr Glu Arg Val Leu Gln Gly Leu Leu Gly Pro
    9470              9475                9480

Ile Phe Lys Asn Thr Ser Val Gly Pro Leu Tyr Ser Gly Cys Arg
    9485              9490                9495

Leu Thr Ser Leu Arg Ser Glu Lys Asp Gly Ala Ala Thr Gly Val
    9500              9505                9510

Asp Ala Ile Cys Ile His His Leu Asp Pro Lys Ser Pro Gly Leu
    9515              9520                9525

Asp Arg Glu Xaa Leu Tyr Trp Glu Leu Ser Xaa Leu Thr Xaa Xaa
    9530              9535                9540

Ile Xaa Glu Leu Gly Pro Tyr Xaa Leu Asp Arg Xaa Ser Leu Tyr
    9545              9550                9555

Val Asn Gly Phe Xaa Xaa Xaa Xaa Xaa Xaa Xaa Thr Ser Thr
    9560              9565                9570

Pro Gly Thr Ser Xaa Val Xaa Leu Xaa Thr Ser Gly Thr Pro Xaa
    9575              9580                9585

Xaa Xaa Pro Xaa Xaa Thr Xaa Xaa Xaa Pro Leu Leu Xaa Pro Phe
    9590              9595                9600

Thr Leu Asn Phe Thr Ile Thr Asn Leu Xaa Tyr Glu Glu Xaa Met
    9605              9610                9615

Xaa Xaa Pro Gly Ser Arg Lys Phe Asn Thr Thr Glu Arg Val Leu
    9620              9625                9630

Gln Gly Leu Leu Xaa Pro Xaa Phe Lys Xaa Thr Ser Val Gly Xaa
    9635              9640                9645

Leu Tyr Ser Gly Cys Arg Leu Thr Leu Leu Arg Xaa Glu Lys Xaa
    9650              9655                9660

Xaa Ala Ala Thr Xaa Val Asp Xaa Xaa Cys Xaa Xaa Xaa Xaa Asp
    9665              9670                9675

Pro Xaa Xaa Pro Gly Leu Asp Arg Glu Xaa Leu Tyr Trp Glu Leu
    9680              9685                9690

Ser Xaa Leu Thr Xaa Xaa Ile Xaa Glu Leu Gly Pro Tyr Xaa Leu
    9695              9700                9705

Asp Arg Xaa Ser Leu Tyr Val Asn Gly Phe Thr His Gln Thr Phe
    9710              9715                9720

Ala Pro Asn Thr Ser Thr Pro Gly Thr Ser Thr Val Asp Leu Gly
    9725              9730                9735
```

```
Thr  Ser  Gly  Thr  Pro  Ser  Ser  Leu  Pro  Ser  Pro  Thr  Ser  Ala  Gly
     9740                9745                9750

Pro  Leu  Leu  Val  Pro  Phe  Thr  Leu  Asn  Phe  Thr  Ile  Thr  Asn  Leu
     9755                9760                9765

Gln  Tyr  Glu  Glu  Asp  Met  His  His  Pro  Gly  Ser  Arg  Lys  Phe  Asn
     9770                9775                9780

Thr  Thr  Glu  Arg  Val  Leu  Gln  Gly  Leu  Leu  Gly  Pro  Met  Phe  Lys
     9785                9790                9795

Asn  Thr  Ser  Val  Gly  Leu  Leu  Tyr  Ser  Gly  Cys  Arg  Leu  Thr  Leu
     9800                9805                9810

Leu  Arg  Pro  Glu  Lys  Asn  Gly  Ala  Ala  Thr  Arg  Val  Asp  Ala  Val
     9815                9820                9825

Cys  Thr  His  Arg  Pro  Asp  Pro  Lys  Ser  Pro  Gly  Leu  Asp  Arg  Glu
     9830                9835                9840

Xaa  Leu  Tyr  Trp  Glu  Leu  Ser  Xaa  Leu  Thr  Xaa  Xaa  Ile  Xaa  Glu
     9845                9850                9855

Leu  Gly  Pro  Tyr  Xaa  Leu  Asp  Arg  Xaa  Ser  Leu  Tyr  Val  Asn  Gly
     9860                9865                9870

Phe  Xaa  Xaa  Xaa  Xaa  Xaa  Xaa  Xaa  Thr  Ser  Thr  Pro  Gly  Thr
     9875                9880                9885

Ser  Xaa  Val  Xaa  Leu  Xaa  Thr  Ser  Gly  Thr  Pro  Xaa  Xaa  Xaa  Pro
     9890                9895                9900

Xaa  Xaa  Thr  Ala  Pro  Val  Pro  Leu  Leu  Ile  Pro  Phe  Thr  Leu  Asn
     9905                9910                9915

Phe  Thr  Ile  Thr  Asn  Leu  His  Tyr  Glu  Glu  Asn  Met  Gln  His  Pro
     9920                9925                9930

Gly  Ser  Arg  Lys  Phe  Asn  Thr  Thr  Glu  Arg  Val  Leu  Gln  Gly  Leu
     9935                9940                9945

Leu  Arg  Pro  Leu  Phe  Lys  Ser  Thr  Ser  Val  Gly  Pro  Leu  Tyr  Ser
     9950                9955                9960

Gly  Cys  Arg  Leu  Thr  Leu  Leu  Arg  Pro  Glu  Lys  His  Gly  Ala  Ala
     9965                9970                9975

Thr  Gly  Val  Asp  Ala  Ile  Cys  Thr  Leu  Arg  Leu  Asp  Pro  Thr  Gly
     9980                9985                9990

Pro  Gly  Leu  Asp  Arg  Glu  Arg  Leu  Tyr  Trp  Glu  Leu  Ser  Gln  Leu
     9995                10000               10005

Thr  Asn  Ser  Val  Thr  Glu  Leu  Gly  Pro  Tyr  Thr  Leu  Asp  Arg  Asp
     10010               10015               10020

Ser  Leu  Tyr  Val  Asn  Gly  Phe  Thr  Gln  Arg  Ser  Ser  Val  Pro  Thr
     10025               10030               10035

Thr  Ser  Ile  Pro  Gly  Thr  Ser  Ala  Val  His  Leu  Glu  Thr  Ser  Gly
     10040               10045               10050

Thr  Pro  Ala  Ser  Leu  Pro  Gly  His  Thr  Ala  Pro  Gly  Pro  Leu  Leu
     10055               10060               10065

Val  Pro  Phe  Thr  Leu  Asn  Phe  Thr  Ile  Thr  Asn  Leu  Gln  Tyr  Glu
     10070               10075               10080

Val  Asp  Met  Arg  His  Pro  Gly  Ser  Arg  Lys  Phe  Asn  Thr  Thr  Glu
     10085               10090               10095

Arg  Val  Leu  Gln  Gly  Leu  Leu  Lys  Pro  Leu  Phe  Lys  Ser  Thr  Ser
     10100               10105               10110

Val  Gly  Pro  Leu  Tyr  Ser  Gly  Cys  Arg  Leu  Thr  Leu  Leu  Arg  Pro
     10115               10120               10125

Glu  Lys  Arg  Gly  Ala  Ala  Thr  Gly  Val  Asp  Thr  Ile  Cys  Thr  His
```

-continued

|     |     |     |     |     |     |     |     |     |     |     |     |
|---|---|---|---|---|---|---|---|---|---|---|---|
| | 10130 | | | | 10135 | | | | 10140 | | |
| Arg | Leu | Asp | Pro | Leu | Asn | Pro | Gly | Leu | Asp | Arg | Glu | Gln | Leu | Tyr |
| 10145 | | | | | 10150 | | | | | 10155 | | | | |
| Trp | Glu | Leu | Ser | Lys | Leu | Thr | Arg | Gly | Ile | Ile | Glu | Leu | Gly | Pro |
| 10160 | | | | | 10165 | | | | | 10170 | | | | |
| Tyr | Leu | Leu | Asp | Arg | Gly | Ser | Leu | Tyr | Val | Asn | Gly | Phe | Thr | His |
| 10175 | | | | | 10180 | | | | | 10185 | | | | |
| Arg | Asn | Phe | Val | Pro | Ile | Thr | Ser | Thr | Pro | Gly | Thr | Ser | Thr | Val |
| 10190 | | | | | 10195 | | | | | 10200 | | | | |
| His | Leu | Gly | Thr | Ser | Glu | Thr | Pro | Ser | Ser | Leu | Pro | Arg | Pro | Ile |
| 10205 | | | | | 10210 | | | | | 10215 | | | | |
| Val | Pro | Gly | Pro | Leu | Leu | Val | Pro | Phe | Thr | Leu | Asn | Phe | Thr | Ile |
| 10220 | | | | | 10225 | | | | | 10230 | | | | |
| Thr | Asn | Leu | Gln | Tyr | Glu | Glu | Ala | Met | Arg | His | Pro | Gly | Ser | Arg |
| 10235 | | | | | 10240 | | | | | 10245 | | | | |
| Lys | Phe | Asn | Thr | Thr | Glu | Arg | Val | Leu | Gln | Gly | Leu | Leu | Arg | Pro |
| 10250 | | | | | 10255 | | | | | 10260 | | | | |
| Leu | Phe | Lys | Asn | Thr | Ser | Ile | Gly | Pro | Leu | Tyr | Ser | Ser | Cys | Arg |
| 10265 | | | | | 10270 | | | | | 10275 | | | | |
| Leu | Thr | Leu | Leu | Arg | Pro | Glu | Lys | Asp | Lys | Ala | Ala | Thr | Arg | Val |
| 10280 | | | | | 10285 | | | | | 10290 | | | | |
| Asp | Ala | Ile | Cys | Thr | His | His | Pro | Asp | Pro | Gln | Ser | Pro | Gly | Leu |
| 10295 | | | | | 10300 | | | | | 10305 | | | | |
| Asn | Arg | Glu | Gln | Leu | Tyr | Trp | Glu | Leu | Ser | Gln | Leu | Thr | His | Gly |
| 10310 | | | | | 10315 | | | | | 10320 | | | | |
| Ile | Thr | Glu | Leu | Gly | Pro | Tyr | Thr | Leu | Asp | Arg | Asp | Ser | Leu | Tyr |
| 10325 | | | | | 10330 | | | | | 10335 | | | | |
| Val | Asp | Gly | Phe | Thr | His | Trp | Ser | Pro | Ile | Pro | Thr | Thr | Ser | Thr |
| 10340 | | | | | 10345 | | | | | 10350 | | | | |
| Pro | Gly | Thr | Ser | Ile | Val | Asn | Leu | Gly | Thr | Ser | Gly | Ile | Pro | Pro |
| 10355 | | | | | 10360 | | | | | 10365 | | | | |
| Ser | Leu | Pro | Glu | Thr | Thr | Xaa | Xaa | Xaa | Pro | Leu | Leu | Xaa | Pro | Phe |
| 10370 | | | | | 10375 | | | | | 10380 | | | | |
| Thr | Leu | Asn | Phe | Thr | Ile | Thr | Asn | Leu | Xaa | Tyr | Glu | Glu | Xaa | Met |
| 10385 | | | | | 10390 | | | | | 10395 | | | | |
| Xaa | Xaa | Pro | Gly | Ser | Arg | Lys | Phe | Asn | Thr | Thr | Glu | Arg | Val | Leu |
| 10400 | | | | | 10405 | | | | | 10410 | | | | |
| Gln | Gly | Leu | Leu | Lys | Pro | Leu | Phe | Lys | Ser | Thr | Ser | Val | Gly | Pro |
| 10415 | | | | | 10420 | | | | | 10425 | | | | |
| Leu | Tyr | Ser | Gly | Cys | Arg | Leu | Thr | Leu | Leu | Arg | Pro | Glu | Lys | Asp |
| 10430 | | | | | 10435 | | | | | 10440 | | | | |
| Gly | Val | Ala | Thr | Arg | Val | Asp | Ala | Ile | Cys | Thr | His | Arg | Pro | Asp |
| 10445 | | | | | 10450 | | | | | 10455 | | | | |
| Pro | Lys | Ile | Pro | Gly | Leu | Asp | Arg | Gln | Gln | Leu | Tyr | Trp | Glu | Leu |
| 10460 | | | | | 10465 | | | | | 10470 | | | | |
| Ser | Gln | Leu | Thr | His | Ser | Ile | Thr | Glu | Leu | Gly | Pro | Tyr | Thr | Leu |
| 10475 | | | | | 10480 | | | | | 10485 | | | | |
| Asp | Arg | Asp | Ser | Leu | Tyr | Val | Asn | Gly | Phe | Thr | Gln | Arg | Ser | Ser |
| 10490 | | | | | 10495 | | | | | 10500 | | | | |
| Val | Pro | Thr | Thr | Ser | Thr | Pro | Gly | Thr | Phe | Thr | Val | Gln | Pro | Glu |
| 10505 | | | | | 10510 | | | | | 10515 | | | | |
| Thr | Ser | Glu | Thr | Pro | Ser | Ser | Leu | Pro | Gly | Pro | Thr | Ala | Thr | Gly |
| 10520 | | | | | 10525 | | | | | 10530 | | | | |

-continued

| | | | | | | | | | | |
|---|---|---|---|---|---|---|---|---|---|---|
| Pro | Val 10535 | Leu | Leu | Pro | Phe 10540 | Thr | Leu | Asn | Phe 10545 | Thr | Ile | Thr | Asn | Leu |
| Gln | Tyr 10550 | Glu | Glu | Asp | Met 10555 | His | Arg | Pro | Gly 10560 | Ser | Arg | Lys | Phe | Asn |
| Thr | Thr 10565 | Glu | Arg | Val | Leu 10570 | Gln | Gly | Leu | Leu 10575 | Met | Pro | Leu | Phe | Lys |
| Asn | Thr 10580 | Ser | Val | Ser | Ser 10585 | Leu | Tyr | Ser | Gly 10590 | Cys | Arg | Leu | Thr | Leu |
| Leu | Arg 10595 | Pro | Glu | Lys | Asp 10600 | Gly | Ala | Ala | Thr 10605 | Arg | Val | Asp | Ala | Val |
| Cys | Thr 10610 | His | Arg | Pro | Asp 10615 | Pro | Lys | Ser | Pro 10620 | Gly | Leu | Asp | Arg | Glu |
| Arg | Leu 10625 | Tyr | Trp | Lys | Leu 10630 | Ser | Gln | Leu | Thr 10635 | His | Gly | Ile | Thr | Glu |
| Leu | Gly 10640 | Pro | Tyr | Thr | Leu 10645 | Asp | Arg | His | Ser 10650 | Leu | Tyr | Val | Asn | Gly |
| Phe | Thr 10655 | His | Gln | Ser | Ser 10660 | Met | Thr | Thr | Thr 10665 | Arg | Thr | Pro | Asp | Thr |
| Ser | Thr 10670 | Met | His | Leu | Ala 10675 | Thr | Ser | Arg | Thr 10680 | Pro | Ala | Ser | Leu | Ser |
| Gly | Pro 10685 | Thr | Thr | Ala | Ser 10690 | Pro | Leu | Leu | Val 10695 | Leu | Phe | Thr | Ile | Asn |
| Phe | Thr 10700 | Ile | Thr | Asn | Leu 10705 | Arg | Tyr | Glu | Glu 10710 | Asn | Met | His | His | Pro |
| Gly | Ser 10715 | Arg | Lys | Phe | Asn 10720 | Thr | Thr | Glu | Arg 10725 | Val | Leu | Gln | Gly | Leu |
| Leu | Arg 10730 | Pro | Val | Phe | Lys 10735 | Asn | Thr | Ser | Val 10740 | Gly | Pro | Leu | Tyr | Ser |
| Gly | Cys 10745 | Arg | Leu | Thr | Leu 10750 | Leu | Arg | Pro | Lys 10755 | Lys | Asp | Gly | Ala | Ala |
| Thr | Lys 10760 | Val | Asp | Ala | Ile 10765 | Cys | Thr | Tyr | Arg 10770 | Pro | Asp | Pro | Lys | Ser |
| Pro | Gly 10775 | Leu | Asp | Arg | Glu 10780 | Gln | Leu | Tyr | Trp 10785 | Glu | Leu | Ser | Gln | Leu |
| Thr | His 10790 | Ser | Ile | Thr | Glu 10795 | Leu | Gly | Pro | Tyr 10800 | Thr | Gln | Asp | Arg | Asp |
| Ser | Leu 10805 | Tyr | Asn | Val | Gly 10810 | Phe | Thr | Gln | Arg 10815 | Ser | Val | Pro | Thr |
| Thr | Ser 10820 | Val | Pro | Gly | Thr 10825 | Pro | Thr | Val | Asp 10830 | Leu | Gly | Thr | Ser | Gly |
| Thr | Pro 10835 | Val | Ser | Lys | Pro 10840 | Gly | Pro | Ser | Ala 10845 | Ala | Ser | Pro | Leu | Leu |
| Val | Leu 10850 | Phe | Thr | Leu | Asn 10855 | Gly | Thr | Ile | Thr 10860 | Asn | Leu | Arg | Tyr | Glu |
| Glu | Asn 10865 | Met | Gln | His | Pro 10870 | Gly | Ser | Arg | Lys 10875 | Phe | Asn | Thr | Thr | Glu |
| Arg | Val 10880 | Leu | Gln | Gly | Leu 10885 | Leu | Arg | Ser | Leu 10890 | Phe | Lys | Ser | Thr | Ser |
| Val | Gly 10895 | Pro | Leu | Tyr | Ser 10900 | Gly | Cys | Arg | Leu 10905 | Thr | Leu | Leu | Arg | Pro |
| Glu | Lys 10910 | Asp | Gly | Thr | Ala 10915 | Thr | Gly | Val | Asp 10920 | Ala | Ile | Cys | Thr | His |

```
His Pro  Asp Pro Lys Ser Pro  Arg Leu Asp Arg Glu  Gln Leu Tyr
    10925            10930             10935

Trp Glu  Leu Ser Gln Leu Thr  His Asn Ile Thr Glu  Leu Gly His
    10940            10945             10950

Tyr Ala  Leu Asp Asn Asp Ser  Leu Phe Val Asn Gly  Phe Thr His
    10955            10960             10965

Arg Ser  Ser Val Ser Thr Thr  Ser Thr Pro Gly Thr  Pro Thr Val
    10970            10975             10980

Tyr Leu  Gly Ala Ser Lys Thr  Pro Ala Ser Ile Phe  Gly Pro Ser
    10985            10990             10995

Ala Ala  Ser His Leu Leu Ile  Leu Phe Thr Leu Asn  Phe Thr Ile
    11000            11005             11010

Thr Asn  Leu Arg Tyr Glu Glu  Asn Met Trp Pro Gly  Ser Arg Lys
    11015            11020             11025

Phe Asn  Thr Thr Glu Arg Val  Leu Gln Gly Leu Leu  Arg Pro Leu
    11030            11035             11040

Phe Lys  Asn Thr Ser Val Gly  Pro Leu Tyr Ser Gly  Ser Arg Leu
    11045            11050             11055

Thr Leu  Leu Arg Pro Glu Lys  Asp Gly Glu Ala Thr  Gly Val Asp
    11060            11065             11070

Ala Ile  Cys Thr His Arg Pro  Asp Pro Thr Gly Pro  Gly Leu Asp
    11075            11080             11085

Arg Glu  Gln Leu Tyr Leu Glu  Leu Ser Gln Leu Thr  His Ser Ile
    11090            11095             11100

Thr Glu  Leu Gly Pro Tyr Thr  Leu Asp Arg Asp Ser  Leu Tyr Val
    11105            11110             11115

Asn Gly  Phe Thr His Arg Ser  Ser Val Pro Thr Thr  Ser Thr Gly
    11120            11125             11130

Val Val  Ser Glu Glu Pro Phe  Thr Leu Asn Phe Thr  Ile Asn Asn
    11135            11140             11145

Leu Arg  Tyr Met Ala Asp Met  Gly Gln Pro Gly Ser  Leu Lys Phe
    11150            11155             11160

Asn Ile  Thr Asp Asn Val Met  Lys His Leu Leu Ser  Pro Leu Phe
    11165            11170             11175

Gln Arg  Ser Ser Leu Gly Ala  Arg Tyr Thr Gly Cys  Arg Val Ile
    11180            11185             11190

Ala Leu  Arg Ser Val Lys Asn  Gly Ala Glu Thr Arg  Val Asp Leu
    11195            11200             11205

Leu Cys  Thr Tyr Leu Gln Pro  Leu Ser Gly Pro Gly  Leu Pro Ile
    11210            11215             11220

Lys Gln  Val Phe His Glu Leu  Ser Gln Gln Thr His  Gly Ile Thr
    11225            11230             11235

Arg Leu  Gly Pro Tyr Ser Leu  Asp Lys Asp Ser Leu  Tyr Leu Asn
    11240            11245             11250

Gly Tyr  Asn Glu Pro Gly Leu  Asp Glu Pro Pro Thr  Thr Pro Lys
    11255            11260             11265

Pro Ala  Thr Thr Phe Leu Pro  Pro Leu Ser Glu Ala  Thr Thr Ala
    11270            11275             11280

Met Gly  Tyr His Leu Lys Thr  Leu Thr Leu Asn Phe  Thr Ile Ser
    11285            11290             11295

Asn Leu  Gln Tyr Ser Pro Asp  Met Gly Lys Gly Ser  Ala Thr Phe
    11300            11305             11310

Asn Ser  Thr Glu Gly Val Leu  Gln His Leu Leu Arg  Pro Leu Phe
```

-continued

```
               11315                11320                     11325
Gln  Lys  Ser  Ser  Met  Gly  Pro  Phe  Tyr  Leu  Gly  Cys  Gln  Leu  Ile
     11330               11335                     11340

Ser  Leu  Arg  Pro  Glu  Lys  Asp  Gly  Ala  Ala  Thr  Gly  Val  Asp  Thr
     11345               11350                     11355

Thr  Cys  Thr  Tyr  His  Pro  Asp  Pro  Val  Gly  Pro  Gly  Leu  Asp  Ile
     11360               11365                     11370

Gln  Gln  Leu  Tyr  Trp  Glu  Leu  Ser  Gln  Leu  Thr  His  Gly  Val  Thr
     11375               11380                     11385

Gln  Leu  Gly  Phe  Tyr  Val  Leu  Asp  Arg  Asp  Ser  Leu  Phe  Ile  Asn
     11390               11395                     11400

Gly  Tyr  Ala  Pro  Gln  Asn  Leu  Ser  Ile  Arg  Gly  Glu  Tyr  Gln  Ile
     11405               11410                     11415

Asn  Phe  His  Ile  Val  Asn  Trp  Asn  Leu  Ser  Asn  Pro  Asp  Pro  Thr
     11420               11425                     11430

Ser  Ser  Glu  Tyr  Ile  Thr  Leu  Leu  Arg  Asp  Ile  Gln  Asp  Lys  Val
     11435               11440                     11445

Thr  Thr  Leu  Tyr  Lys  Gly  Ser  Gln  Leu  His  Asp  Thr  Phe  Arg  Phe
     11450               11455                     11460

Cys  Leu  Val  Thr  Asn  Leu  Thr  Met  Asp  Ser  Val  Leu  Val  Thr  Val
     11465               11470                     11475

Lys  Ala  Leu  Phe  Ser  Ser  Asn  Leu  Asp  Pro  Ser  Leu  Val  Glu  Gln
     11480               11485                     11490

Val  Phe  Leu  Asp  Lys  Thr  Leu  Asn  Ala  Ser  Phe  His  Trp  Leu  Gly
     11495               11500                     11505

Ser  Thr  Tyr  Gln  Leu  Val  Asp  Ile  His  Val  Thr  Glu  Met  Glu  Ser
     11510               11515                     11520

Ser  Val  Tyr  Gln  Pro  Thr  Ser  Ser  Ser  Ser  Thr  Gln  His  Phe  Tyr
     11525               11530                     11535

Leu  Asn  Phe  Thr  Ile  Thr  Asn  Leu  Pro  Tyr  Ser  Gln  Asp  Lys  Ala
     11540               11545                     11550

Gln  Pro  Gly  Thr  Thr  Asn  Tyr  Gln  Arg  Asn  Lys  Arg  Asn  Ile  Glu
     11555               11560                     11565

Asp  Ala  Leu  Asn  Gln  Leu  Phe  Arg  Asn  Ser  Ser  Ile  Lys  Ser  Tyr
     11570               11575                     11580

Phe  Ser  Asp  Cys  Gln  Val  Ser  Thr  Phe  Arg  Ser  Val  Pro  Asn  Arg
     11585               11590                     11595

His  His  Thr  Gly  Val  Asp  Ser  Leu  Cys  Asn  Phe  Ser  Pro  Leu  Ala
     11600               11605                     11610

Arg  Arg  Val  Asp  Arg  Val  Ala  Ile  Tyr  Glu  Glu  Phe  Leu  Arg  Met
     11615               11620                     11625

Thr  Arg  Asn  Gly  Thr  Gln  Leu  Gln  Asn  Phe  Thr  Leu  Asp  Arg  Ser
     11630               11635                     11640

Ser  Val  Leu  Val  Asp  Gly  Tyr  Ser  Pro  Asn  Arg  Asn  Glu  Pro  Leu
     11645               11650                     11655

Thr  Gly  Asn  Ser  Asp  Leu  Pro  Phe  Trp  Ala  Val  Ile  Leu  Ile  Gly
     11660               11665                     11670

Leu  Ala  Gly  Leu  Leu  Gly  Leu  Ile  Thr  Cys  Leu  Ile  Cys  Gly  Val
     11675               11680                     11685

Leu  Val  Thr  Thr  Arg  Arg  Arg  Lys  Lys  Glu  Gly  Glu  Tyr  Asn  Val
     11690               11695                     11700

Gln  Gln  Gln  Cys  Pro  Gly  Tyr  Tyr  Gln  Ser  His  Leu  Asp  Leu  Glu
     11705               11710                     11715
```

Asp Leu Gln
   117  20

<210> SEQ ID NO 163
<211> LENGTH: 156
<212> TYPE: PRT
<213> ORGANISM: Homo sapiens

<400> SEQUENCE: 163

Thr Ala Gly Pro Leu Val Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Ala Thr Glu Arg Val Leu Gln Gly Leu Leu Ser Pro Ile Phe Lys
        35                  40                  45

Asn Ser Ser Val Gly Pro Leu Tyr Ser Gly Cys Arg Leu Thr Ser Leu
    50                  55                  60

Arg Pro Glu Lys Asp Gly Ala Ala Thr Gly Met Asp Ala Val Cys Leu
65                  70                  75                  80

Tyr His Pro Asn Pro Lys Arg Pro Gly Leu Asp Arg Glu Gln Leu Tyr
                85                  90                  95

Trp Glu Leu Ser Gln Leu Thr His Asn Ile Thr Glu Leu Gly Pro Tyr
            100                 105                 110

Ser Leu Asp Arg Asp Ser Leu Tyr Val Asn Gly Phe Thr His Gln Asn
        115                 120                 125

Ser Val Pro Thr Thr Ser Thr Pro Gly Thr Ser Thr Val Tyr Trp Ala
    130                 135                 140

Thr Thr Gly Thr Pro Ser Ser Phe Pro Gly His Thr
145                 150                 155

<210> SEQ ID NO 164
<211> LENGTH: 42
<212> TYPE: PRT
<213> ORGANISM: Homo sapiens

<400> SEQUENCE: 164

Ala Thr Val Pro Phe Met Val Pro Phe Thr Leu Asn Phe Thr Ile Thr
1               5                   10                  15

Asn Leu Gln Tyr Glu Glu Asp Met Arg His Pro Gly Ser Arg Lys Phe
            20                  25                  30

Asn Ala Thr Glu Arg Glu Leu Gln Gly Leu
        35                  40

<210> SEQ ID NO 165
<211> LENGTH: 42
<212> TYPE: PRT
<213> ORGANISM: Homo sapiens

<400> SEQUENCE: 165

Thr Ala Val Pro Leu Leu Val Pro Phe Thr Leu Asn Phe Thr Ile Thr
1               5                   10                  15

Asn Leu Gln Tyr Gly Glu Asp Met Arg His Pro Gly Ser Arg Lys Phe
            20                  25                  30

Asn Thr Thr Glu Arg Val Leu Gln Gly Leu
        35                  40

<210> SEQ ID NO 166
<211> LENGTH: 42

-continued

<212> TYPE: PRT
<213> ORGANISM: Homo sapiens

<400> SEQUENCE: 166

Val Pro Gly Pro Leu Leu Val Pro Phe Thr Leu Asn Phe Thr Ile Thr
1               5                   10                  15

Asn Leu Gln Tyr Glu Glu Ala Met Arg His Pro Gly Ser Arg Lys Phe
            20                  25                  30

Asn Thr Thr Glu Arg Val Leu Gln Gly Leu
        35                  40

<210> SEQ ID NO 167
<211> LENGTH: 42
<212> TYPE: PRT
<213> ORGANISM: Homo sapiens

<400> SEQUENCE: 167

Ala Pro Gly Pro Leu Leu Val Pro Phe Thr Leu Asn Phe Thr Ile Thr
1               5                   10                  15

Asn Leu Gln Tyr Glu Glu Asp Met Arg His Pro Gly Ser Arg Lys Phe
            20                  25                  30

Ser Thr Thr Glu Arg Val Leu Gln Gly Leu
        35                  40

<210> SEQ ID NO 168
<211> LENGTH: 42
<212> TYPE: PRT
<213> ORGANISM: Homo sapiens

<400> SEQUENCE: 168

Ala Pro Gly Pro Leu Leu Val Pro Phe Thr Leu Asn Phe Thr Ile Thr
1               5                   10                  15

Asn Leu Gln Tyr Glu Glu Asp Met Arg His Pro Gly Ser Arg Lys Phe
            20                  25                  30

Asn Thr Thr Glu Arg Val Leu Gln Gly Leu
        35                  40

<210> SEQ ID NO 169
<211> LENGTH: 42
<212> TYPE: PRT
<213> ORGANISM: Homo sapiens

<400> SEQUENCE: 169

Ala Pro Gly Pro Leu Leu Val Pro Phe Thr Leu Asn Phe Thr Ile Thr
1               5                   10                  15

Asn Leu Gln Tyr Glu Val Asp Met Arg His Pro Gly Ser Arg Lys Phe
            20                  25                  30

Asn Thr Thr Glu Arg Val Leu Gln Gly Leu
        35                  40

<210> SEQ ID NO 170
<211> LENGTH: 42
<212> TYPE: PRT
<213> ORGANISM: Homo sapiens

<400> SEQUENCE: 170

Ser Ala Gly Pro Leu Leu Val Pro Phe Thr Leu Asn Phe Thr Ile Thr
1               5                   10                  15

Asn Leu Gln Tyr Glu Glu Asp Met Arg His Pro Gly Ser Arg Lys Phe
            20                  25                  30

-continued

Asn Thr Thr Glu Arg Val Leu Gln Gly Leu
        35                  40

<210> SEQ ID NO 171
<211> LENGTH: 42
<212> TYPE: PRT
<213> ORGANISM: Homo sapiens

<400> SEQUENCE: 171

Ala Ala Gly Pro Leu Leu Met Pro Phe Thr Leu Asn Phe Thr Ile Thr
1               5                   10                  15

Asn Leu Gln Tyr Glu Glu Asp Met Arg Arg Thr Gly Ser Arg Lys Phe
            20                  25                  30

Asn Thr Met Glu Ser Val Leu Gln Gly Leu
        35                  40

<210> SEQ ID NO 172
<211> LENGTH: 42
<212> TYPE: PRT
<213> ORGANISM: Homo sapiens

<400> SEQUENCE: 172

Thr Ala Ser Pro Leu Leu Val Leu Phe Thr Ile Asn Cys Thr Ile Thr
1               5                   10                  15

Asn Leu Gln Tyr Glu Glu Asp Met Arg Arg Thr Gly Ser Arg Lys Phe
            20                  25                  30

Asn Thr Met Glu Ser Val Leu Gln Gly Leu
        35                  40

<210> SEQ ID NO 173
<211> LENGTH: 42
<212> TYPE: PRT
<213> ORGANISM: Homo sapiens

<400> SEQUENCE: 173

Ala Ala Gly Pro Leu Leu Val Pro Phe Thr Leu Asn Phe Thr Ile Thr
1               5                   10                  15

Asn Leu Gln Tyr Gly Glu Asp Met Gly His Pro Gly Ser Arg Lys Phe
            20                  25                  30

Asn Thr Thr Glu Arg Val Leu Gln Gly Leu
        35                  40

<210> SEQ ID NO 174
<211> LENGTH: 42
<212> TYPE: PRT
<213> ORGANISM: Homo sapiens

<400> SEQUENCE: 174

Thr Ala Gly Pro Leu Leu Ile Pro Phe Thr Leu Asn Phe Thr Ile Thr
1               5                   10                  15

Asn Leu Gln Tyr Gly Glu Asp Met Gly His Pro Gly Ser Arg Lys Phe
            20                  25                  30

Asn Thr Thr Glu Arg Val Leu Gln Gly Leu
        35                  40

<210> SEQ ID NO 175
<211> LENGTH: 42
<212> TYPE: PRT
<213> ORGANISM: Homo sapiens

<400> SEQUENCE: 175

```
Thr Ala Gly Pro Leu Leu Val Pro Phe Thr Leu Asn Phe Thr Ile Thr
1               5                   10                  15

Asn Leu Gln Tyr Gly Glu Asp Met Gly His Pro Gly Ser Arg Lys Phe
            20                  25                  30

Asn Thr Thr Glu Arg Val Leu Gln Gly Leu
            35                  40
```

<210> SEQ ID NO 176
<211> LENGTH: 42
<212> TYPE: PRT
<213> ORGANISM: Homo sapiens

<400> SEQUENCE: 176

```
Thr Ala Gly Pro Leu Leu Val Leu Phe Thr Leu Asn Phe Thr Ile Thr
1               5                   10                  15

Asn Leu Lys Tyr Glu Glu Asp Met His Arg Pro Gly Ser Arg Lys Phe
            20                  25                  30

Asn Thr Thr Glu Arg Val Leu Gln Thr Leu
            35                  40
```

<210> SEQ ID NO 177
<211> LENGTH: 42
<212> TYPE: PRT
<213> ORGANISM: Homo sapiens

<400> SEQUENCE: 177

```
Thr Ala Gly Pro Leu Leu Val Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Ala Thr Glu Arg Val Leu Gln Gly Leu
            35                  40
```

<210> SEQ ID NO 178
<211> LENGTH: 42
<212> TYPE: PRT
<213> ORGANISM: Homo sapiens

<400> SEQUENCE: 178

```
Thr Ala Gly Pro Leu Leu Val Pro Phe Thr Leu Asn Phe Thr Ile Thr
1               5                   10                  15

Asn Leu Gln Tyr Glu Glu Asp Met His Arg Pro Gly Ser Arg Arg Phe
            20                  25                  30

Asn Thr Thr Glu Arg Val Leu Gln Gly Leu
            35                  40
```

<210> SEQ ID NO 179
<211> LENGTH: 42
<212> TYPE: PRT
<213> ORGANISM: Homo sapiens

<400> SEQUENCE: 179

```
Thr Ala Gly Pro Leu Leu Val Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Thr Thr Glu Arg Val Leu Gln Gly Leu
            35                  40
```

<210> SEQ ID NO 180

```
<211> LENGTH: 42
<212> TYPE: PRT
<213> ORGANISM: Homo sapiens

<400> SEQUENCE: 180

Ala Pro Val Pro Leu Leu Ile Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Thr Thr Glu Arg Val Leu Gln Gly Leu
        35                  40

<210> SEQ ID NO 181
<211> LENGTH: 42
<212> TYPE: PRT
<213> ORGANISM: Homo sapiens

<400> SEQUENCE: 181

Ala Thr Gly Pro Val Leu Leu Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Thr Thr Glu Arg Val Leu Gln Gly Leu
        35                  40

<210> SEQ ID NO 182
<211> LENGTH: 42
<212> TYPE: PRT
<213> ORGANISM: Homo sapiens

<400> SEQUENCE: 182

Ala Ala Gly Pro Leu Leu Val Pro Phe Thr Leu Asn Phe Thr Ile Thr
1               5                   10                  15

Asn Leu Gln Tyr Glu Glu Asp Met His His Pro Gly Ser Arg Lys Phe
            20                  25                  30

Asn Thr Thr Glu Arg Val Leu Gln Gly Leu
        35                  40

<210> SEQ ID NO 183
<211> LENGTH: 42
<212> TYPE: PRT
<213> ORGANISM: Homo sapiens

<400> SEQUENCE: 183

Ser Ala Gly Pro Leu Leu Val Pro Phe Thr Leu Asn Phe Thr Ile Thr
1               5                   10                  15

Asn Leu Gln Tyr Glu Glu Asp Met His His Pro Gly Ser Arg Lys Phe
            20                  25                  30

Asn Thr Thr Glu Arg Val Leu Gln Gly Leu
        35                  40

<210> SEQ ID NO 184
<211> LENGTH: 42
<212> TYPE: PRT
<213> ORGANISM: Homo sapiens

<400> SEQUENCE: 184

Thr Ala Ser Pro Leu Leu Val Leu Phe Thr Ile Asn Phe Thr Ile Thr
1               5                   10                  15

Asn Gln Arg Tyr Glu Glu Asn Met His His Pro Gly Ser Arg Lys Phe
            20                  25                  30
```

Asn Thr Thr Glu Arg Val Leu Gln Gly Leu
        35                  40

<210> SEQ ID NO 185
<211> LENGTH: 42
<212> TYPE: PRT
<213> ORGANISM: Homo sapiens

<400> SEQUENCE: 185

Thr Ala Ser Pro Leu Leu Val Leu Phe Thr Ile Asn Phe Thr Ile Thr
1               5                   10                  15

Asn Leu Arg Tyr Glu Glu Asn Met His His Pro Gly Ser Arg Lys Phe
            20                  25                  30

Asn Thr Thr Glu Arg Val Leu Gln Gly Leu
        35                  40

<210> SEQ ID NO 186
<211> LENGTH: 42
<212> TYPE: PRT
<213> ORGANISM: Homo sapiens

<400> SEQUENCE: 186

Glu Pro Gly Pro Leu Leu Ile Pro Phe Thr Phe Asn Phe Thr Ile Thr
1               5                   10                  15

Asn Leu His Tyr Glu Glu Asn Met Gln His Pro Gly Ser Arg Lys Phe
            20                  25                  30

Asn Thr Thr Glu Arg Val Leu Gln Gly Leu
        35                  40

<210> SEQ ID NO 187
<211> LENGTH: 42
<212> TYPE: PRT
<213> ORGANISM: Homo sapiens

<400> SEQUENCE: 187

Glu Pro Gly Pro Leu Leu Ile Pro Phe Thr Phe Asn Phe Thr Ile Thr
1               5                   10                  15

Asn Leu Arg Tyr Glu Glu Asn Met Gln His Pro Gly Ser Arg Lys Phe
            20                  25                  30

Asn Thr Thr Glu Arg Val Leu Gln Gly Leu
        35                  40

<210> SEQ ID NO 188
<211> LENGTH: 42
<212> TYPE: PRT
<213> ORGANISM: Homo sapiens

<400> SEQUENCE: 188

Ala Pro Val Pro Leu Leu Ile Pro Phe Thr Leu Asn Phe Thr Ile Thr
1               5                   10                  15

Asn Leu His Tyr Glu Glu Asn Met Gln His Pro Gly Ser Arg Lys Phe
            20                  25                  30

Asn Thr Thr Glu Arg Val Leu Gln Gly Leu
        35                  40

<210> SEQ ID NO 189
<211> LENGTH: 42
<212> TYPE: PRT
<213> ORGANISM: Homo sapiens

<400> SEQUENCE: 189

-continued

Ala Pro Val Pro Leu Ile Pro Phe Thr Leu Asn Phe Thr Ile Thr
1               5                   10                  15

Asp Leu His Tyr Glu Glu Asn Met Gln His Pro Gly Ser Arg Lys Phe
            20                  25                  30

Asn Thr Thr Glu Arg Val Leu Gln Gly Leu
        35                  40

<210> SEQ ID NO 190
<211> LENGTH: 42
<212> TYPE: PRT
<213> ORGANISM: Homo sapiens

<400> SEQUENCE: 190

Ala Ala Ser Pro Leu Leu Val Leu Phe Thr Leu Asn Gly Thr Ile Thr
1               5                   10                  15

Asn Leu Arg Tyr Glu Glu Asn Met Gln His Pro Gly Ser Arg Lys Phe
            20                  25                  30

Asn Thr Thr Glu Arg Val Leu Gln Gly Leu
        35                  40

<210> SEQ ID NO 191
<211> LENGTH: 42
<212> TYPE: PRT
<213> ORGANISM: Homo sapiens

<400> SEQUENCE: 191

Thr Ala Gly Pro Leu Leu Val Pro Phe Thr Leu Asn Phe Thr Ile Thr
1               5                   10                  15

Asn Leu Lys Tyr Glu Glu Asp Met His Cys Pro Gly Ser Arg Lys Phe
            20                  25                  30

Asn Thr Thr Glu Arg Val Leu Gln Ser Leu
        35                  40

<210> SEQ ID NO 192
<211> LENGTH: 41
<212> TYPE: PRT
<213> ORGANISM: Homo sapiens

<400> SEQUENCE: 192

Ala Ala Ser His Leu Leu Ile Leu Phe Thr Leu Asn Phe Thr Ile Thr
1               5                   10                  15

Asn Leu Arg Tyr Glu Glu Asn Met Trp Pro Gly Ser Arg Lys Phe Asn
            20                  25                  30

Thr Thr Glu Arg Val Leu Gln Gly Leu
        35                  40

<210> SEQ ID NO 193
<211> LENGTH: 42
<212> TYPE: PRT
<213> ORGANISM: Homo sapiens

<400> SEQUENCE: 193

Thr Gly Val Val Ser Glu Glu Pro Phe Thr Leu Asn Phe Thr Ile Asn
1               5                   10                  15

Asn Leu Arg Tyr Met Ala Asp Met Gly Gln Pro Gly Ser Leu Lys Phe
            20                  25                  30

Asn Ile Thr Asp Asn Val Met Lys His Leu
        35                  40

```
<210> SEQ ID NO 194
<211> LENGTH: 42
<212> TYPE: PRT
<213> ORGANISM: Homo sapiens

<400> SEQUENCE: 194

Ala Met Gly Tyr His Leu Lys Thr Leu Thr Leu Asn Phe Thr Ile Ser
1               5                   10                  15

Asn Leu Gln Tyr Ser Pro Asp Met Gly Lys Gly Ser Ala Thr Phe Asn
            20                  25                  30

Ser Thr Glu Gly Val Leu Gln His Leu Leu
        35                  40

<210> SEQ ID NO 195
<211> LENGTH: 23
<212> TYPE: PRT
<213> ORGANISM: Homo sapiens

<400> SEQUENCE: 195

Leu Lys Pro Leu Phe Arg Asn Ser Ser Leu Glu Tyr Leu Tyr Ser Gly
1               5                   10                  15

Cys Arg Leu Ala Ser Leu Arg
            20

<210> SEQ ID NO 196
<211> LENGTH: 23
<212> TYPE: PRT
<213> ORGANISM: Homo sapiens

<400> SEQUENCE: 196

Leu Lys Pro Leu Phe Lys Asn Thr Ser Val Ser Ser Leu Tyr Ser Gly
1               5                   10                  15

Cys Arg Leu Thr Leu Leu Arg
            20

<210> SEQ ID NO 197
<211> LENGTH: 23
<212> TYPE: PRT
<213> ORGANISM: Homo sapiens

<400> SEQUENCE: 197

Leu Lys Pro Leu Phe Lys Asn Thr Ser Val Gly Pro Leu Tyr Ser Gly
1               5                   10                  15

Cys Arg Leu Thr Leu Leu Arg
            20

<210> SEQ ID NO 198
<211> LENGTH: 23
<212> TYPE: PRT
<213> ORGANISM: Homo sapiens

<400> SEQUENCE: 198

Leu Lys Pro Leu Phe Lys Ser Thr Ser Val Gly Pro Leu Tyr Ser Gly
1               5                   10                  15

Cys Arg Leu Thr Leu Leu Arg
            20

<210> SEQ ID NO 199
<211> LENGTH: 23
<212> TYPE: PRT
<213> ORGANISM: Homo sapiens

<400> SEQUENCE: 199
```

-continued

Leu Lys Pro Leu Phe Lys Ser Thr Ser Val Gly Pro Leu Tyr Ser Ser
1               5                   10                  15

Cys Arg Leu Thr Leu Leu Arg
            20

<210> SEQ ID NO 200
<211> LENGTH: 23
<212> TYPE: PRT
<213> ORGANISM: Homo sapiens

<400> SEQUENCE: 200

Leu Lys Pro Leu Phe Lys Asn Thr Ser Val Gly Pro Leu Tyr Ser Gly
1               5                   10                  15

Cys Arg Leu Thr Ser Leu Arg
            20

<210> SEQ ID NO 201
<211> LENGTH: 23
<212> TYPE: PRT
<213> ORGANISM: Homo sapiens

<400> SEQUENCE: 201

Leu Gly Pro Ile Phe Lys Asn Thr Ser Val Gly Pro Leu Tyr Ser Gly
1               5                   10                  15

Cys Arg Leu Thr Ser Leu Arg
            20

<210> SEQ ID NO 202
<211> LENGTH: 23
<212> TYPE: PRT
<213> ORGANISM: Homo sapiens

<400> SEQUENCE: 202

Leu Gly Pro Met Phe Lys Asn Thr Ser Val Gly Leu Leu Tyr Ser Gly
1               5                   10                  15

Cys Arg Leu Thr Leu Leu Arg
            20

<210> SEQ ID NO 203
<211> LENGTH: 23
<212> TYPE: PRT
<213> ORGANISM: Homo sapiens

<400> SEQUENCE: 203

Leu Gly Pro Met Phe Lys Asn Thr Ser Val Gly Pro Leu Tyr Ser Gly
1               5                   10                  15

Cys Arg Leu Thr Leu Leu Arg
            20

<210> SEQ ID NO 204
<211> LENGTH: 23
<212> TYPE: PRT
<213> ORGANISM: Homo sapiens

<400> SEQUENCE: 204

Leu Gly Pro Met Phe Lys Asn Thr Ser Val Gly Pro Leu Tyr Ser Gly
1               5                   10                  15

Cys Arg Leu Thr Ser Leu Arg
            20

<210> SEQ ID NO 205

```
<211> LENGTH: 23
<212> TYPE: PRT
<213> ORGANISM: Homo sapiens

<400> SEQUENCE: 205

Leu Gly Pro Leu Phe Lys Asn Ser Ser Val Gly Pro Leu Tyr Ser Gly
1               5                   10                  15

Cys Arg Leu Ile Ser Leu Arg
            20

<210> SEQ ID NO 206
<211> LENGTH: 23
<212> TYPE: PRT
<213> ORGANISM: Homo sapiens

<400> SEQUENCE: 206

Leu Gly Pro Leu Phe Lys Asn Ser Ser Val Asp Pro Leu Tyr Ser Gly
1               5                   10                  15

Cys Arg Leu Thr Ser Leu Arg
            20

<210> SEQ ID NO 207
<211> LENGTH: 23
<212> TYPE: PRT
<213> ORGANISM: Homo sapiens

<400> SEQUENCE: 207

Leu Ser Pro Ile Phe Lys Asn Ser Ser Val Gly Pro Leu Tyr Ser Gly
1               5                   10                  15

Cys Arg Leu Thr Ser Leu Arg
            20

<210> SEQ ID NO 208
<211> LENGTH: 23
<212> TYPE: PRT
<213> ORGANISM: Homo sapiens

<400> SEQUENCE: 208

Leu Ser Pro Ile Phe Lys Asn Thr Ser Val Gly Pro Leu Tyr Ser Gly
1               5                   10                  15

Cys Arg Leu Thr Leu Leu Arg
            20

<210> SEQ ID NO 209
<211> LENGTH: 23
<212> TYPE: PRT
<213> ORGANISM: Homo sapiens

<400> SEQUENCE: 209

Leu Ser Pro Leu Phe Gln Arg Ser Ser Leu Gly Ala Arg Tyr Thr Gly
1               5                   10                  15

Cys Arg Val Ile Ala Leu Arg
            20

<210> SEQ ID NO 210
<211> LENGTH: 23
<212> TYPE: PRT
<213> ORGANISM: Homo sapiens

<400> SEQUENCE: 210

Leu Arg Pro Leu Phe Lys Asn Thr Ser Val Ser Ser Leu Tyr Ser Gly
1               5                   10                  15
```

```
Cys Arg Leu Thr Leu Leu Arg
            20

<210> SEQ ID NO 211
<211> LENGTH: 23
<212> TYPE: PRT
<213> ORGANISM: Homo sapiens

<400> SEQUENCE: 211

Leu Arg Pro Leu Phe Lys Asn Thr Ser Val Gly Pro Leu Tyr Ser Gly
1               5                   10                  15

Ser Arg Leu Thr Leu Leu Arg
            20

<210> SEQ ID NO 212
<211> LENGTH: 23
<212> TYPE: PRT
<213> ORGANISM: Homo sapiens

<400> SEQUENCE: 212

Leu Arg Pro Leu Phe Lys Asn Thr Ser Ile Gly Pro Leu Tyr Ser Ser
1               5                   10                  15

Cys Arg Leu Thr Leu Leu Arg
            20

<210> SEQ ID NO 213
<211> LENGTH: 23
<212> TYPE: PRT
<213> ORGANISM: Homo sapiens

<400> SEQUENCE: 213

Leu Arg Pro Leu Phe Lys Ser Thr Ser Val Gly Pro Leu Tyr Ser Gly
1               5                   10                  15

Cys Arg Leu Thr Leu Leu Arg
            20

<210> SEQ ID NO 214
<211> LENGTH: 23
<212> TYPE: PRT
<213> ORGANISM: Homo sapiens

<400> SEQUENCE: 214

Leu Arg Pro Val Phe Lys Asn Thr Ser Val Gly Leu Leu Tyr Ser Gly
1               5                   10                  15

Cys Arg Leu Thr Leu Leu Arg
            20

<210> SEQ ID NO 215
<211> LENGTH: 23
<212> TYPE: PRT
<213> ORGANISM: Homo sapiens

<400> SEQUENCE: 215

Leu Arg Pro Val Phe Lys Asn Thr Ser Val Gly Pro Leu Tyr Ser Gly
1               5                   10                  15

Cys Arg Leu Thr Leu Leu Arg
            20

<210> SEQ ID NO 216
<211> LENGTH: 23
<212> TYPE: PRT
<213> ORGANISM: Homo sapiens
```

-continued

```
<400> SEQUENCE: 216

Leu Arg Ser Leu Phe Lys Ser Thr Ser Val Gly Pro Leu Tyr Ser Gly
1               5                   10                  15

Cys Arg Leu Thr Leu Leu Arg
            20

<210> SEQ ID NO 217
<211> LENGTH: 23
<212> TYPE: PRT
<213> ORGANISM: Homo sapiens

<400> SEQUENCE: 217

Leu Arg Ser Leu Phe Lys Ser Thr Ser Val Gly Pro Leu Tyr Ser Gly
1               5                   10                  15

Cys Arg Leu Thr Ser Leu Arg
            20

<210> SEQ ID NO 218
<211> LENGTH: 23
<212> TYPE: PRT
<213> ORGANISM: Homo sapiens

<400> SEQUENCE: 218

Leu Thr Pro Leu Phe Lys Asn Thr Ser Val Gly Pro Leu Tyr Ser Gly
1               5                   10                  15

Cys Arg Leu Thr Leu Leu Arg
            20

<210> SEQ ID NO 219
<211> LENGTH: 23
<212> TYPE: PRT
<213> ORGANISM: Homo sapiens

<400> SEQUENCE: 219

Leu Thr Pro Leu Phe Arg Asn Thr Ser Val Ser Ser Leu Tyr Ser Gly
1               5                   10                  15

Cys Arg Leu Thr Leu Leu Arg
            20

<210> SEQ ID NO 220
<211> LENGTH: 23
<212> TYPE: PRT
<213> ORGANISM: Homo sapiens

<400> SEQUENCE: 220

Leu Met Pro Leu Phe Lys Asn Thr Ser Val Ser Ser Leu Tyr Ser Gly
1               5                   10                  15

Cys Arg Leu Thr Leu Leu Arg
            20

<210> SEQ ID NO 221
<211> LENGTH: 22
<212> TYPE: PRT
<213> ORGANISM: Homo sapiens

<400> SEQUENCE: 221

Arg Pro Leu Phe Gln Lys Ser Ser Met Gly Pro Phe Tyr Leu Gly Cys
1               5                   10                  15

Gln Leu Ile Ser Leu Arg
            20
```

-continued

<210> SEQ ID NO 222
<211> LENGTH: 58
<212> TYPE: PRT
<213> ORGANISM: Homo sapiens

<400> SEQUENCE: 222

Pro Glu Lys Asp Ser Ser Ala Met Ala Val Asp Ala Ile Cys Thr His
1               5                   10                  15

Arg Pro Asp Pro Glu Asp Leu Gly Leu Asp Arg Glu Arg Leu Tyr Trp
            20                  25                  30

Glu Leu Ser Asn Leu Thr Asn Gly Ile Gln Glu Leu Gly Pro Tyr Thr
        35                  40                  45

Leu Asp Arg Asn Ser Leu Tyr Val Asn Gly
    50                  55

<210> SEQ ID NO 223
<211> LENGTH: 58
<212> TYPE: PRT
<213> ORGANISM: Homo sapiens

<400> SEQUENCE: 223

Pro Glu Lys Asp Gly Ala Ala Thr Gly Val Asp Ala Ile Cys Thr His
1               5                   10                  15

Arg Leu Asp Pro Lys Ser Pro Gly Leu Asn Arg Glu Gln Leu Tyr Trp
            20                  25                  30

Glu Leu Ser Lys Leu Thr Asn Asp Ile Glu Glu Leu Gly Pro Tyr Thr
        35                  40                  45

Leu Asp Arg Asn Ser Leu Tyr Val Asn Gly
    50                  55

<210> SEQ ID NO 224
<211> LENGTH: 58
<212> TYPE: PRT
<213> ORGANISM: Homo sapiens

<400> SEQUENCE: 224

Pro Lys Lys Asp Gly Ala Ala Thr Gly Val Asp Ala Ile Cys Thr His
1               5                   10                  15

Arg Leu Asp Pro Lys Ser Pro Gly Leu Asn Arg Glu Gln Leu Tyr Trp
            20                  25                  30

Glu Leu Ser Lys Leu Thr Asn Asp Ile Glu Glu Leu Gly Pro Tyr Thr
        35                  40                  45

Leu Asp Arg Asn Ser Leu Tyr Val Asn Gly
    50                  55

<210> SEQ ID NO 225
<211> LENGTH: 58
<212> TYPE: PRT
<213> ORGANISM: Homo sapiens

<400> SEQUENCE: 225

Pro Glu Lys Asp Gly Thr Ala Thr Gly Val Asp Ala Ile Cys Thr His
1               5                   10                  15

His Pro Asp Pro Lys Ser Pro Arg Leu Asp Arg Glu Gln Leu Tyr Trp
            20                  25                  30

Glu Leu Ser Gln Leu Thr His Asn Ile Thr Glu Leu Gly His Tyr Ala
        35                  40                  45

Leu Asp Asn Asp Ser Leu Phe Val Asn Gly
    50                  55

```
<210> SEQ ID NO 226
<211> LENGTH: 58
<212> TYPE: PRT
<213> ORGANISM: Homo sapiens

<400> SEQUENCE: 226

Pro Glu Lys Asp Gly Glu Ala Thr Gly Val Asp Ala Ile Cys Thr His
1               5                   10                  15

Arg Pro Asp Pro Thr Gly Pro Gly Leu Asp Arg Glu Gln Leu Tyr Leu
            20                  25                  30

Glu Leu Ser Gln Leu Thr His Ser Ile Thr Glu Leu Gly Pro Tyr Thr
        35                  40                  45

Leu Asp Arg Asp Ser Leu Tyr Val Asn Gly
    50                  55

<210> SEQ ID NO 227
<211> LENGTH: 58
<212> TYPE: PRT
<213> ORGANISM: Homo sapiens

<400> SEQUENCE: 227

Pro Glu Lys Asp Gly Ala Ala Thr Gly Met Asp Ala Val Cys Leu Tyr
1               5                   10                  15

His Pro Asn Pro Lys Arg Pro Gly Leu Asp Arg Glu Gln Leu Tyr Trp
            20                  25                  30

Glu Leu Ser Gln Leu Thr His Asn Ile Thr Glu Leu Gly Pro Tyr Ser
        35                  40                  45

Leu Asp Arg Asp Ser Leu Tyr Val Asn Gly
    50                  55

<210> SEQ ID NO 228
<211> LENGTH: 58
<212> TYPE: PRT
<213> ORGANISM: Homo sapiens

<400> SEQUENCE: 228

Pro Glu Lys Asp Gly Ala Ala Thr Gly Met Asp Ala Val Cys Leu Tyr
1               5                   10                  15

His Pro Asn Pro Lys Arg Pro Gly Leu Asp Arg Glu Gln Leu Tyr Cys
            20                  25                  30

Glu Leu Ser Gln Leu Thr His Asn Ile Thr Glu Leu Gly Pro Tyr Ser
        35                  40                  45

Leu Asp Arg Asp Ser Leu Tyr Val Asn Gly
    50                  55

<210> SEQ ID NO 229
<211> LENGTH: 58
<212> TYPE: PRT
<213> ORGANISM: Homo sapiens

<400> SEQUENCE: 229

Pro Glu Lys Asp Gly Ala Ala Thr Arg Val Asp Ala Ala Cys Thr Tyr
1               5                   10                  15

Arg Pro Asp Pro Lys Ser Pro Gly Leu Asp Arg Glu Gln Leu Tyr Trp
            20                  25                  30

Glu Leu Ser Gln Leu Thr His Ser Ile Thr Glu Leu Gly Pro Tyr Thr
        35                  40                  45

Leu Asp Arg Val Ser Leu Tyr Val Asn Gly
    50                  55
```

<210> SEQ ID NO 230
<211> LENGTH: 58
<212> TYPE: PRT
<213> ORGANISM: Homo sapiens

<400> SEQUENCE: 230

Pro Lys Lys Asp Gly Ala Ala Thr Lys Val Asp Ala Ile Cys Thr Tyr
1               5                   10                  15

Arg Pro Asp Pro Lys Ser Pro Gly Leu Asp Arg Glu Gln Leu Tyr Trp
                20                  25                  30

Glu Leu Ser Gln Leu Thr His Ser Ile Thr Glu Leu Gly Pro Tyr Thr
            35                  40                  45

Gln Asp Arg Asp Ser Leu Tyr Val Asn Gly
        50                  55

<210> SEQ ID NO 231
<211> LENGTH: 58
<212> TYPE: PRT
<213> ORGANISM: Homo sapiens

<400> SEQUENCE: 231

Pro Lys Lys Asp Gly Ala Ala Thr Lys Val Asp Ala Ile Cys Thr Tyr
1               5                   10                  15

Arg Pro Asp Pro Lys Ser Pro Gly Leu Asp Arg Glu Gln Leu Tyr Trp
                20                  25                  30

Glu Leu Ser Gln Leu Thr His Ser Ile Thr Glu Leu Gly Pro Tyr Thr
            35                  40                  45

Gln Asp Arg Asp Ser Leu Tyr Asn Val Gly
        50                  55

<210> SEQ ID NO 232
<211> LENGTH: 58
<212> TYPE: PRT
<213> ORGANISM: Homo sapiens

<400> SEQUENCE: 232

Pro Glu Lys Asp Gly Ala Ala Thr Arg Val Asp Ala Val Cys Thr His
1               5                   10                  15

Arg Pro Asp Pro Lys Ser Pro Gly Leu Asp Arg Glu Arg Leu Tyr Trp
                20                  25                  30

Lys Leu Ser Gln Leu Thr His Gly Ile Thr Glu Leu Gly Pro Tyr Thr
            35                  40                  45

Leu Asp Arg His Ser Leu Tyr Val Asn Gly
        50                  55

<210> SEQ ID NO 233
<211> LENGTH: 58
<212> TYPE: PRT
<213> ORGANISM: Homo sapiens

<400> SEQUENCE: 233

Pro Glu Lys Asp Gly Val Ala Thr Arg Val Asp Ala Ile Cys Thr His
1               5                   10                  15

Arg Pro Asp Pro Lys Ile Pro Gly Leu Asp Arg Gln Gln Leu Tyr Trp
                20                  25                  30

Glu Leu Ser Gln Leu Thr His Ser Ile Thr Glu Leu Gly Pro Tyr Thr
            35                  40                  45

Leu Asp Arg Asp Ser Leu Tyr Val Asn Gly

```
                    50                  55

<210> SEQ ID NO 234
<211> LENGTH: 58
<212> TYPE: PRT
<213> ORGANISM: Homo sapiens

<400> SEQUENCE: 234

Ser Glu Lys Asp Gly Ala Ala Thr Gly Val Asp Ala Ile Cys Ile His
1               5                   10                  15

His Leu Asp Pro Lys Ser Pro Gly Leu Asn Arg Glu Arg Leu Tyr Trp
            20                  25                  30

Glu Leu Ser Gln Leu Thr Asn Gly Ile Lys Glu Leu Gly Pro Tyr Thr
        35                  40                  45

Leu Asp Arg Asn Ser Leu Tyr Val Asn Gly
    50                  55

<210> SEQ ID NO 235
<211> LENGTH: 58
<212> TYPE: PRT
<213> ORGANISM: Homo sapiens

<400> SEQUENCE: 235

Ser Glu Lys Asp Gly Ala Ala Thr Gly Val Asp Ala Ile Cys Thr His
1               5                   10                  15

Arg Leu Asp Pro Lys Ser Pro Gly Leu Asp Arg Glu Gln Leu Tyr Trp
            20                  25                  30

Glu Leu Ser Gln Leu Thr Asn Gly Ile Lys Glu Leu Gly Pro Tyr Thr
        35                  40                  45

Leu Asp Arg Asn Ser Leu Tyr Val Asn Gly
    50                  55

<210> SEQ ID NO 236
<211> LENGTH: 58
<212> TYPE: PRT
<213> ORGANISM: Homo sapiens

<400> SEQUENCE: 236

Ser Glu Lys Asp Gly Ala Ala Thr Gly Val Asp Ala Ile Cys Thr His
1               5                   10                  15

Arg Leu Asp Pro Lys Ser Pro Gly Val Asp Arg Glu Gln Leu Tyr Trp
            20                  25                  30

Glu Leu Ser Gln Leu Thr Asn Gly Ile Lys Glu Leu Gly Pro Tyr Thr
        35                  40                  45

Leu Asp Arg Asn Ser Leu Tyr Val Asn Gly
    50                  55

<210> SEQ ID NO 237
<211> LENGTH: 58
<212> TYPE: PRT
<213> ORGANISM: Homo sapiens

<400> SEQUENCE: 237

Ser Glu Lys Asp Gly Ala Ala Thr Gly Val Asp Ala Ile Cys Thr His
1               5                   10                  15

Arg Val Asp Pro Lys Ser Pro Gly Val Asp Arg Glu Gln Leu Tyr Trp
            20                  25                  30

Glu Leu Ser Gln Leu Thr Asn Gly Ile Lys Glu Leu Gly Pro Tyr Thr
        35                  40                  45
```

```
Leu Asp Arg Asn Ser Leu Tyr Val Asn Gly
         50                  55
```

<210> SEQ ID NO 238
<211> LENGTH: 58
<212> TYPE: PRT
<213> ORGANISM: Homo sapiens

<400> SEQUENCE: 238

```
Ser Glu Lys Asp Gly Ala Ala Thr Gly Val Asp Ala Ile Cys Thr His
 1               5                  10                  15

His Leu Asn Pro Gln Ser Pro Gly Leu Asp Arg Glu Gln Leu Tyr Trp
            20                  25                  30

Gln Leu Ser Gln Met Thr Asn Gly Ile Lys Glu Leu Gly Pro Tyr Thr
        35                  40                  45

Leu Asp Arg Asn Ser Leu Tyr Val Asn Gly
         50                  55
```

<210> SEQ ID NO 239
<211> LENGTH: 58
<212> TYPE: PRT
<213> ORGANISM: Homo sapiens

<400> SEQUENCE: 239

```
Pro Glu Lys Arg Gly Ala Ala Thr Gly Val Asp Thr Ile Cys Thr His
 1               5                  10                  15

Arg Leu Asp Pro Leu Asn Pro Gly Leu Asp Arg Glu Gln Leu Tyr Trp
            20                  25                  30

Glu Leu Ser Lys Leu Thr Arg Gly Ile Ile Glu Leu Gly Pro Tyr Leu
        35                  40                  45

Leu Asp Arg Gly Ser Leu Tyr Val Asn Gly
         50                  55
```

<210> SEQ ID NO 240
<211> LENGTH: 58
<212> TYPE: PRT
<213> ORGANISM: Homo sapiens

<400> SEQUENCE: 240

```
Pro Glu Lys Asn Gly Ala Ala Thr Gly Met Asp Ala Ile Cys Ser His
 1               5                  10                  15

Arg Leu Asp Pro Lys Ser Pro Gly Leu Asn Arg Glu Gln Leu Tyr Trp
            20                  25                  30

Glu Leu Ser Gln Leu Thr His Gly Ile Lys Glu Leu Gly Pro Tyr Thr
        35                  40                  45

Leu Asp Arg Asn Ser Leu Tyr Val Asn Gly
         50                  55
```

<210> SEQ ID NO 241
<211> LENGTH: 58
<212> TYPE: PRT
<213> ORGANISM: Homo sapiens

<400> SEQUENCE: 241

```
Pro Glu Lys Asn Gly Ala Ala Thr Gly Met Asp Ala Ile Cys Ser His
 1               5                  10                  15

Arg Leu Asp Pro Lys Ser Pro Gly Leu Asp Arg Glu Gln Leu Tyr Trp
            20                  25                  30

Glu Leu Ser Gln Leu Thr His Gly Ile Lys Glu Leu Gly Pro Tyr Thr
        35                  40                  45
```

Leu Asp Arg Asn Ser Leu Tyr Val Asn Gly
    50                  55

<210> SEQ ID NO 242
<211> LENGTH: 58
<212> TYPE: PRT
<213> ORGANISM: Homo sapiens

<400> SEQUENCE: 242

Pro Glu Lys His Gly Ala Ala Thr Gly Val Asp Ala Ile Cys Thr Leu
1               5                   10                  15

Arg Leu Asp Pro Thr Gly Pro Gly Leu Asp Arg Glu Arg Leu Tyr Trp
            20                  25                  30

Glu Leu Ser Gln Leu Thr Asn Ser Val Thr Glu Leu Gly Pro Tyr Thr
        35                  40                  45

Leu Asp Arg Asp Ser Leu Tyr Val Asn Gly
    50                  55

<210> SEQ ID NO 243
<211> LENGTH: 58
<212> TYPE: PRT
<213> ORGANISM: Homo sapiens

<400> SEQUENCE: 243

Pro Glu Lys His Gly Ala Ala Thr Gly Val Asp Ala Ile Cys Thr Leu
1               5                   10                  15

Arg Leu Asp Pro Thr Gly Pro Gly Leu Asp Arg Glu Arg Leu Tyr Trp
            20                  25                  30

Glu Leu Ser Gln Leu Thr Asn Ser Ile Thr Glu Leu Gly Pro Tyr Thr
        35                  40                  45

Leu Asp Arg Asp Ser Leu Tyr Val Asn Gly
    50                  55

<210> SEQ ID NO 244
<211> LENGTH: 58
<212> TYPE: PRT
<213> ORGANISM: Homo sapiens

<400> SEQUENCE: 244

Pro Glu Lys His Glu Ala Ala Thr Gly Val Asp Thr Ile Cys Thr His
1               5                   10                  15

Arg Val Asp Pro Ile Gly Pro Gly Leu Asp Arg Glu Arg Leu Tyr Trp
            20                  25                  30

Glu Leu Ser Gln Leu Thr Asn Ser Ile Thr Glu Leu Gly Pro Tyr Thr
        35                  40                  45

Leu Asp Arg Asp Ser Leu Tyr Val Asn Gly
    50                  55

<210> SEQ ID NO 245
<211> LENGTH: 58
<212> TYPE: PRT
<213> ORGANISM: Homo sapiens

<400> SEQUENCE: 245

Pro Glu Lys Gln Glu Ala Ala Thr Gly Val Asp Thr Ile Cys Thr His
1               5                   10                  15

Arg Val Asp Pro Ile Gly Pro Gly Leu Asp Arg Glu Arg Leu Tyr Trp
            20                  25                  30

Glu Leu Ser Gln Leu Thr Asn Ser Ile Thr Glu Leu Gly Pro Tyr Thr

```
                35                  40                  45

Leu Asp Arg Asp Ser Leu Tyr Val Asn Gly
    50                  55

<210> SEQ ID NO 246
<211> LENGTH: 58
<212> TYPE: PRT
<213> ORGANISM: Homo sapiens

<400> SEQUENCE: 246

Pro Glu Lys Gln Glu Ala Ala Thr Gly Val Asp Thr Ile Cys Thr His
1               5                   10                  15

Arg Val Asp Pro Ile Gly Pro Gly Leu Asp Arg Glu Arg Leu Tyr Trp
            20                  25                  30

Glu Leu Ser Gln Leu Thr Asn Ser Ile Thr Glu Leu Gly Pro Tyr Thr
        35                  40                  45

Leu Asp Arg Asp Ser Leu Tyr Val Asp Gly
    50                  55

<210> SEQ ID NO 247
<211> LENGTH: 58
<212> TYPE: PRT
<213> ORGANISM: Homo sapiens

<400> SEQUENCE: 247

Pro Glu Lys Asp Lys Ala Ala Thr Arg Val Asp Ala Ile Cys Thr His
1               5                   10                  15

His Pro Asp Pro Gln Ser Pro Gly Leu Asn Arg Glu Gln Leu Tyr Trp
            20                  25                  30

Glu Leu Ser Gln Leu Thr His Gly Ile Thr Glu Leu Gly Pro Tyr Thr
        35                  40                  45

Leu Asp Arg Asp Ser Leu Tyr Val Asp Gly
    50                  55

<210> SEQ ID NO 248
<211> LENGTH: 58
<212> TYPE: PRT
<213> ORGANISM: Homo sapiens

<400> SEQUENCE: 248

Ser Val Lys Asn Gly Ala Glu Thr Arg Val Asp Leu Leu Cys Thr Tyr
1               5                   10                  15

Leu Gln Pro Leu Ser Gly Pro Gly Leu Pro Ile Lys Gln Val Phe His
            20                  25                  30

Glu Leu Ser Gln Gln Thr His Gly Ile Thr Arg Leu Gly Pro Tyr Ser
        35                  40                  45

Leu Asp Lys Asp Ser Leu Tyr Leu Asn Gly
    50                  55

<210> SEQ ID NO 249
<211> LENGTH: 58
<212> TYPE: PRT
<213> ORGANISM: Homo sapiens

<400> SEQUENCE: 249

Pro Glu Lys Asp Gly Ala Ala Thr Gly Val Asp Thr Thr Cys Thr Tyr
1               5                   10                  15

His Pro Asp Pro Val Gly Pro Gly Leu Asp Ile Gln Gln Leu Tyr Trp
            20                  25                  30
```

-continued

```
Glu Leu Ser Gln Leu Thr His Gly Val Thr Gln Leu Gly Phe Tyr Val
        35                  40                  45
Leu Asp Arg Asp Ser Leu Phe Ile Asn Gly
    50                  55

<210> SEQ ID NO 250
<211> LENGTH: 12
<212> TYPE: PRT
<213> ORGANISM: Homo sapiens

<400> SEQUENCE: 250

Phe Thr His Arg Ser Ser Met Pro Thr Thr Ser Thr
1               5                   10

<210> SEQ ID NO 251
<211> LENGTH: 12
<212> TYPE: PRT
<213> ORGANISM: Homo sapiens

<400> SEQUENCE: 251

Phe Thr His Arg Ser Ser Met Pro Thr Thr Ser Ile
1               5                   10

<210> SEQ ID NO 252
<211> LENGTH: 12
<212> TYPE: PRT
<213> ORGANISM: Homo sapiens

<400> SEQUENCE: 252

Phe Thr His Arg Thr Ser Val Pro Thr Ser Ser Thr
1               5                   10

<210> SEQ ID NO 253
<211> LENGTH: 12
<212> TYPE: PRT
<213> ORGANISM: Homo sapiens

<400> SEQUENCE: 253

Phe Thr His Arg Thr Ser Val Pro Thr Thr Ser Thr
1               5                   10

<210> SEQ ID NO 254
<211> LENGTH: 12
<212> TYPE: PRT
<213> ORGANISM: Homo sapiens

<400> SEQUENCE: 254

Phe Thr His Arg Ser Ser Val Pro Thr Thr Ser Ser
1               5                   10

<210> SEQ ID NO 255
<211> LENGTH: 12
<212> TYPE: PRT
<213> ORGANISM: Homo sapiens

<400> SEQUENCE: 255

Phe Thr His Arg Ser Ser Val Ser Thr Thr Ser Thr
1               5                   10

<210> SEQ ID NO 256
<211> LENGTH: 12
<212> TYPE: PRT
<213> ORGANISM: Homo sapiens

<400> SEQUENCE: 256
```

Phe Thr His Arg Ser Ser Val Ala Pro Thr Ser Thr
1               5                   10

<210> SEQ ID NO 257
<211> LENGTH: 12
<212> TYPE: PRT
<213> ORGANISM: Homo sapiens

<400> SEQUENCE: 257

Phe Thr His Arg Ser Ser Gly Leu Thr Thr Ser Thr
1               5                   10

<210> SEQ ID NO 258
<211> LENGTH: 12
<212> TYPE: PRT
<213> ORGANISM: Homo sapiens

<400> SEQUENCE: 258

Phe Thr His Arg Ser Phe Gly Leu Thr Thr Ser Thr
1               5                   10

<210> SEQ ID NO 259
<211> LENGTH: 12
<212> TYPE: PRT
<213> ORGANISM: Homo sapiens

<400> SEQUENCE: 259

Phe Thr His Arg Ser Ser Phe Leu Thr Thr Ser Thr
1               5                   10

<210> SEQ ID NO 260
<211> LENGTH: 12
<212> TYPE: PRT
<213> ORGANISM: Homo sapiens

<400> SEQUENCE: 260

Phe Thr His Arg Asn Phe Val Pro Ile Thr Ser Thr
1               5                   10

<210> SEQ ID NO 261
<211> LENGTH: 12
<212> TYPE: PRT
<213> ORGANISM: Homo sapiens

<400> SEQUENCE: 261

Phe Thr His Arg Ser Ser Val Pro Thr Thr Ser Ile
1               5                   10

<210> SEQ ID NO 262
<211> LENGTH: 12
<212> TYPE: PRT
<213> ORGANISM: Homo sapiens

<400> SEQUENCE: 262

Phe Thr His Gln Ser Ser Val Ser Thr Thr Ser Thr
1               5                   10

<210> SEQ ID NO 263
<211> LENGTH: 12
<212> TYPE: PRT
<213> ORGANISM: Homo sapiens

<400> SEQUENCE: 263

Phe Thr His Gln Thr Ser Ala Pro Asn Thr Ser Thr

-continued

```
  1               5                  10
```

<210> SEQ ID NO 264
<211> LENGTH: 12
<212> TYPE: PRT
<213> ORGANISM: Homo sapiens

<400> SEQUENCE: 264

```
Phe Thr His Gln Thr Phe Ala Pro Asn Thr Ser Thr
  1               5                  10
```

<210> SEQ ID NO 265
<211> LENGTH: 12
<212> TYPE: PRT
<213> ORGANISM: Homo sapiens

<400> SEQUENCE: 265

```
Phe Thr His Gln Asn Ser Val Pro Thr Thr Ser Thr
  1               5                  10
```

<210> SEQ ID NO 266
<211> LENGTH: 12
<212> TYPE: PRT
<213> ORGANISM: Homo sapiens

<400> SEQUENCE: 266

```
Phe Thr His Gln Ser Ser Met Thr Thr Thr Arg Thr
  1               5                  10
```

<210> SEQ ID NO 267
<211> LENGTH: 12
<212> TYPE: PRT
<213> ORGANISM: Homo sapiens

<400> SEQUENCE: 267

```
Phe Thr His Trp Ile Pro Val Pro Thr Ser Ser Thr
  1               5                  10
```

<210> SEQ ID NO 268
<211> LENGTH: 12
<212> TYPE: PRT
<213> ORGANISM: Homo sapiens

<400> SEQUENCE: 268

```
Phe Thr His Trp Ser Pro Ile Pro Thr Thr Ser Thr
  1               5                  10
```

<210> SEQ ID NO 269
<211> LENGTH: 12
<212> TYPE: PRT
<213> ORGANISM: Homo sapiens

<400> SEQUENCE: 269

```
Phe Thr His Trp Ser Ser Gly Leu Thr Thr Ser Thr
  1               5                  10
```

<210> SEQ ID NO 270
<211> LENGTH: 12
<212> TYPE: PRT
<213> ORGANISM: Homo sapiens

<400> SEQUENCE: 270

```
Phe His Pro Arg Ser Ser Val Pro Thr Thr Ser Thr
  1               5                  10
```

```
<210> SEQ ID NO 271
<211> LENGTH: 12
<212> TYPE: PRT
<213> ORGANISM: Homo sapiens

<400> SEQUENCE: 271

Phe Asn Pro Arg Ser Ser Val Pro Thr Thr Ser Thr
1               5                   10

<210> SEQ ID NO 272
<211> LENGTH: 12
<212> TYPE: PRT
<213> ORGANISM: Homo sapiens

<400> SEQUENCE: 272

Phe Asn Pro Trp Ser Ser Val Pro Thr Thr Ser Thr
1               5                   10

<210> SEQ ID NO 273
<211> LENGTH: 12
<212> TYPE: PRT
<213> ORGANISM: Homo sapiens

<400> SEQUENCE: 273

Phe Thr Gln Arg Ser Ser Val Pro Thr Thr Ser Ile
1               5                   10

<210> SEQ ID NO 274
<211> LENGTH: 12
<212> TYPE: PRT
<213> ORGANISM: Homo sapiens

<400> SEQUENCE: 274

Phe Thr Gln Arg Ser Ser Val Pro Thr Thr Ser Thr
1               5                   10

<210> SEQ ID NO 275
<211> LENGTH: 12
<212> TYPE: PRT
<213> ORGANISM: Homo sapiens

<400> SEQUENCE: 275

Phe Thr Gln Arg Ser Ser Val Pro Thr Thr Ser Val
1               5                   10

<210> SEQ ID NO 276
<211> LENGTH: 12
<212> TYPE: PRT
<213> ORGANISM: Homo sapiens

<400> SEQUENCE: 276

Tyr Asn Glu Pro Gly Leu Asp Glu Pro Pro Thr Thr
1               5                   10

<210> SEQ ID NO 277
<211> LENGTH: 12
<212> TYPE: PRT
<213> ORGANISM: Homo sapiens

<400> SEQUENCE: 277

Tyr Ala Pro Gln Asn Leu Ser Ile Arg Gly Glu Tyr
1               5                   10

<210> SEQ ID NO 278
```

<211> LENGTH: 21
<212> TYPE: PRT
<213> ORGANISM: Homo sapiens

<400> SEQUENCE: 278

Pro Gly Thr Ser Thr Val Asp Val Gly Thr Ser Gly Thr Pro Ser Ser
1               5                   10                  15

Ser Pro Ser Pro Thr
            20

<210> SEQ ID NO 279
<211> LENGTH: 23
<212> TYPE: PRT
<213> ORGANISM: Homo sapiens

<400> SEQUENCE: 279

Pro Gly Thr Ser Thr Val Asp Leu Arg Thr Ser Gly Thr Pro Ser Ser
1               5                   10                  15

Leu Ser Ser Pro Thr Ile Met
            20

<210> SEQ ID NO 280
<211> LENGTH: 21
<212> TYPE: PRT
<213> ORGANISM: Homo sapiens

<400> SEQUENCE: 280

Pro Gly Thr Ser Thr Val Asp Leu Gly Thr Ser Gly Thr Pro Phe Ser
1               5                   10                  15

Leu Pro Ser Pro Ala
            20

<210> SEQ ID NO 281
<211> LENGTH: 20
<212> TYPE: PRT
<213> ORGANISM: Homo sapiens

<400> SEQUENCE: 281

Pro Gly Thr Ser Thr Val Asp Leu Gly Ser Gly Thr Pro Ser Ser Leu
1               5                   10                  15

Pro Ser Pro Thr
            20

<210> SEQ ID NO 282
<211> LENGTH: 20
<212> TYPE: PRT
<213> ORGANISM: Homo sapiens

<400> SEQUENCE: 282

Pro Gly Thr Ser Thr Val Asp Leu Gly Ser Gly Thr Pro Ser Leu Pro
1               5                   10                  15

Ser Ser Pro Thr
            20

<210> SEQ ID NO 283
<211> LENGTH: 21
<212> TYPE: PRT
<213> ORGANISM: Homo sapiens

<400> SEQUENCE: 283

Pro Gly Thr Ser Thr Val Asp Leu Gly Thr Ser Gly Thr Pro Ser Ser
1               5                   10                  15

-continued

Leu Pro Ser Pro Thr
            20

<210> SEQ ID NO 284
<211> LENGTH: 21
<212> TYPE: PRT
<213> ORGANISM: Homo sapiens

<400> SEQUENCE: 284

Pro Gly Thr Pro Thr Val Asp Leu Gly Thr Ser Gly Thr Pro Val Ser
1               5                   10                  15

Lys Pro Gly Pro Ser
            20

<210> SEQ ID NO 285
<211> LENGTH: 21
<212> TYPE: PRT
<213> ORGANISM: Homo sapiens

<400> SEQUENCE: 285

Pro Trp Thr Ser Thr Val Asp Leu Gly Thr Ser Gly Thr Pro Ser Pro
1               5                   10                  15

Val Pro Ser Pro Thr
            20

<210> SEQ ID NO 286
<211> LENGTH: 21
<212> TYPE: PRT
<213> ORGANISM: Homo sapiens

<400> SEQUENCE: 286

Pro Gly Thr Ser Thr Val Tyr Trp Ala Thr Thr Gly Thr Pro Ser Ser
1               5                   10                  15

Phe Pro Gly His Thr
            20

<210> SEQ ID NO 287
<211> LENGTH: 21
<212> TYPE: PRT
<213> ORGANISM: Homo sapiens

<400> SEQUENCE: 287

Pro Gly Thr Ser Thr Val His Leu Ala Thr Ser Gly Thr Pro Ser Ser
1               5                   10                  15

Leu Pro Gly His Thr
            20

<210> SEQ ID NO 288
<211> LENGTH: 21
<212> TYPE: PRT
<213> ORGANISM: Homo sapiens

<400> SEQUENCE: 288

Pro Gly Thr Ser Thr Val His Leu Ala Thr Ser Gly Thr Pro Ser Pro
1               5                   10                  15

Leu Pro Gly His Thr
            20

<210> SEQ ID NO 289
<211> LENGTH: 21
<212> TYPE: PRT
<213> ORGANISM: Homo sapiens

```
<400> SEQUENCE: 289

Pro Asp Thr Ser Thr Met His Leu Ala Thr Ser Arg Thr Pro Ala Ser
1               5                   10                  15

Leu Ser Gly Pro Thr
            20

<210> SEQ ID NO 290
<211> LENGTH: 21
<212> TYPE: PRT
<213> ORGANISM: Homo sapiens

<400> SEQUENCE: 290

Pro Gly Thr Ser Ala Val His Leu Glu Thr Ser Gly Thr Pro Ala Ser
1               5                   10                  15

Leu Pro Gly His Thr
            20

<210> SEQ ID NO 291
<211> LENGTH: 21
<212> TYPE: PRT
<213> ORGANISM: Homo sapiens

<400> SEQUENCE: 291

Pro Gly Thr Ser Ala Val His Leu Glu Thr Thr Gly Thr Pro Ser Ser
1               5                   10                  15

Phe Pro Gly His Thr
            20

<210> SEQ ID NO 292
<211> LENGTH: 21
<212> TYPE: PRT
<213> ORGANISM: Homo sapiens

<400> SEQUENCE: 292

Pro Gly Thr Ser Thr Val His Leu Gly Thr Ser Glu Thr Pro Ser Ser
1               5                   10                  15

Leu Pro Arg Pro Ile
            20

<210> SEQ ID NO 293
<211> LENGTH: 21
<212> TYPE: PRT
<213> ORGANISM: Homo sapiens

<400> SEQUENCE: 293

Pro Gly Thr Ser Ile Val Asn Leu Gly Thr Ser Gly Ile Pro Pro Ser
1               5                   10                  15

Leu Pro Glu Thr Thr
            20

<210> SEQ ID NO 294
<211> LENGTH: 21
<212> TYPE: PRT
<213> ORGANISM: Homo sapiens

<400> SEQUENCE: 294

Pro Gly Thr Phe Thr Val Gln Pro Glu Thr Ser Glu Thr Pro Ser Ser
1               5                   10                  15

Leu Pro Gly Pro Thr
            20
```

```
<210> SEQ ID NO 295
<211> LENGTH: 21
<212> TYPE: PRT
<213> ORGANISM: Homo sapiens

<400> SEQUENCE: 295

Pro Gly Thr Pro Thr Val Asp Leu Gly Thr Ser Gly Thr Pro Val Ser
1               5                   10                  15

Lys Pro Gly Pro Ser
            20

<210> SEQ ID NO 296
<211> LENGTH: 21
<212> TYPE: PRT
<213> ORGANISM: Homo sapiens

<400> SEQUENCE: 296

Pro Gly Thr Pro Thr Val Tyr Leu Gly Ala Ser Lys Thr Pro Ala Ser
1               5                   10                  15

Ile Phe Gly Pro Ser
            20

<210> SEQ ID NO 297
<211> LENGTH: 16
<212> TYPE: PRT
<213> ORGANISM: Homo sapiens

<400> SEQUENCE: 297

Pro Lys Pro Ala Thr Thr Phe Leu Pro Pro Leu Ser Glu Ala Thr Thr
1               5                   10                  15

<210> SEQ ID NO 298
<211> LENGTH: 21
<212> TYPE: PRT
<213> ORGANISM: Homo sapiens

<400> SEQUENCE: 298

Gln Ile Asn Phe His Ile Val Asn Trp Asn Leu Ser Asn Pro Asp Pro
1               5                   10                  15

Thr Ser Ser Glu Tyr
            20

<210> SEQ ID NO 299
<211> LENGTH: 1794
<212> TYPE: PRT
<213> ORGANISM: Homo sapiens

<400> SEQUENCE: 299

Met Glu His Ile Thr Lys Ile Pro Asn Glu Ala Ala His Arg Gly Thr
1               5                   10                  15

Ile Arg Pro Val Lys Gly Pro Gln Thr Ser Thr Ser Pro Ala Ser Pro
            20                  25                  30

Lys Gly Leu His Thr Gly Gly Thr Lys Arg Met Glu Thr Thr Thr Thr
        35                  40                  45

Ala Leu Lys Thr Thr Thr Thr Ala Leu Lys Thr Thr Ser Arg Ala Thr
    50                  55                  60

Leu Thr Thr Ser Val Tyr Thr Pro Thr Leu Gly Thr Leu Thr Pro Leu
65                  70                  75                  80

Asn Ala Ser Arg Gln Met Ala Ser Thr Ile Leu Thr Glu Met Met Ile
                85                  90                  95

Thr Thr Pro Tyr Val Phe Pro Asp Val Pro Glu Thr Thr Ser Ser Leu
```

-continued

```
                100                 105                 110
Ala Thr Ser Leu Gly Ala Glu Thr Ser Thr Ala Leu Pro Arg Thr Thr
            115                 120                 125
Pro Ser Val Leu Asn Arg Glu Ser Glu Thr Thr Ala Ser Leu Val Ser
            130                 135                 140
Arg Ser Gly Ala Glu Arg Ser Pro Val Ile Gln Thr Leu Asp Val Ser
145                 150                 155                 160
Ser Ser Glu Pro Asp Thr Thr Ala Ser Trp Val Ile His Pro Ala Glu
                165                 170                 175
Thr Ile Pro Thr Val Ser Lys Thr Thr Pro Asn Phe Phe His Ser Glu
            180                 185                 190
Leu Asp Thr Val Ser Ser Thr Ala Thr Ser His Gly Ala Asp Val Ser
            195                 200                 205
Ser Ala Ile Pro Thr Asn Ile Ser Pro Ser Glu Leu Asp Ala Leu Thr
            210                 215                 220
Pro Leu Val Thr Ile Ser Gly Thr Asp Thr Ser Thr Phe Pro Thr
225                 230                 235                 240
Leu Thr Lys Ser Pro His Glu Thr Glu Thr Arg Thr Thr Trp Leu Thr
                245                 250                 255
His Pro Ala Glu Thr Ser Ser Thr Ile Pro Arg Thr Ile Pro Asn Phe
            260                 265                 270
Ser His His Glu Ser Asp Ala Thr Pro Ser Ile Ala Thr Ser Pro Gly
            275                 280                 285
Ala Glu Thr Ser Ser Ala Ile Pro Ile Met Thr Val Ser Pro Gly Ala
            290                 295                 300
Glu Asp Leu Val Thr Ser Gln Val Thr Ser Ser Gly Thr Asp Arg Asn
305                 310                 315                 320
Met Thr Ile Pro Thr Leu Thr Leu Ser Pro Gly Glu Pro Lys Thr Ile
                325                 330                 335
Ala Ser Leu Val Thr His Pro Glu Ala Gln Thr Ser Ser Ala Ile Pro
            340                 345                 350
Thr Ser Thr Ile Ser Pro Ala Val Ser Arg Leu Val Thr Ser Met Val
            355                 360                 365
Thr Ser Leu Ala Ala Lys Thr Ser Thr Thr Asn Arg Ala Leu Thr Asn
            370                 375                 380
Ser Pro Gly Glu Pro Ala Thr Thr Val Ser Leu Val Thr His Pro Ala
385                 390                 395                 400
Gln Thr Ser Pro Thr Val Pro Trp Thr Thr Ser Ile Phe Phe His Ser
                405                 410                 415
Lys Ser Asp Thr Thr Pro Ser Met Thr Thr Ser His Gly Ala Glu Ser
            420                 425                 430
Ser Ser Ala Val Pro Thr Pro Thr Val Ser Thr Glu Val Pro Gly Val
            435                 440                 445
Val Thr Pro Leu Val Thr Ser Ser Arg Ala Val Ile Ser Thr Thr Ile
            450                 455                 460
Pro Ile Leu Thr Leu Ser Pro Gly Glu Pro Glu Thr Thr Pro Ser Met
465                 470                 475                 480
Ala Thr Ser His Gly Glu Glu Ala Ser Ser Ala Ile Pro Thr Pro Thr
                485                 490                 495
Val Ser Pro Gly Val Pro Gly Val Val Thr Ser Leu Val Thr Ser Ser
            500                 505                 510
Arg Ala Val Thr Ser Thr Thr Ile Pro Ile Leu Thr Phe Ser Leu Gly
            515                 520                 525
```

-continued

```
Glu Pro Glu Thr Thr Pro Ser Met Ala Thr Ser His Gly Thr Glu Ala
        530                 535                 540

Gly Ser Ala Val Pro Thr Val Leu Pro Glu Val Pro Gly Met Val Thr
545                 550                 555                 560

Ser Leu Val Ala Ser Ser Arg Ala Val Thr Ser Thr Thr Leu Pro Thr
                565                 570                 575

Leu Thr Leu Ser Pro Gly Glu Pro Glu Thr Thr Pro Ser Met Ala Thr
                580                 585                 590

Ser His Gly Ala Glu Ala Ser Ser Thr Val Pro Thr Val Ser Pro Glu
        595                 600                 605

Val Pro Gly Val Val Thr Ser Leu Val Thr Ser Ser Ser Gly Val Asn
    610                 615                 620

Ser Thr Ser Ile Pro Thr Leu Ile Leu Ser Pro Gly Glu Leu Glu Thr
625                 630                 635                 640

Thr Pro Ser Met Ala Thr Ser His Gly Ala Glu Ala Ser Ser Ala Val
                645                 650                 655

Pro Thr Pro Thr Val Ser Pro Gly Val Ser Gly Val Val Thr Pro Leu
                660                 665                 670

Val Thr Ser Ser Arg Ala Val Thr Ser Thr Thr Ile Pro Ile Leu Thr
            675                 680                 685

Leu Ser Ser Ser Glu Pro Glu Thr Thr Pro Ser Met Ala Thr Ser His
        690                 695                 700

Gly Val Glu Ala Ser Ser Ala Val Leu Thr Val Ser Pro Glu Val Pro
705                 710                 715                 720

Gly Met Val Thr Ser Leu Val Thr Ser Ser Arg Ala Val Thr Ser Thr
                725                 730                 735

Thr Ile Pro Thr Leu Thr Ile Ser Ser Asp Glu Pro Glu Thr Thr Thr
                740                 745                 750

Ser Leu Val Thr His Ser Glu Ala Lys Met Ile Ser Ala Ile Pro Thr
            755                 760                 765

Leu Ala Val Ser Pro Thr Val Gln Gly Leu Val Thr Ser Leu Val Thr
770                 775                 780

Ser Ser Gly Ser Glu Thr Ser Ala Phe Ser Asn Leu Thr Val Ala Ser
785                 790                 795                 800

Ser Gln Pro Glu Thr Ile Asp Ser Trp Val Ala His Pro Gly Thr Glu
                805                 810                 815

Ala Ser Ser Val Val Pro Thr Leu Thr Val Ser Thr Gly Glu Pro Phe
                820                 825                 830

Thr Asn Ile Ser Leu Val Thr His Pro Ala Glu Ser Ser Ser Thr Leu
                835                 840                 845

Pro Arg Thr Thr Ser Arg Phe Ser His Ser Glu Leu Asp Thr Met Pro
        850                 855                 860

Ser Thr Val Thr Ser Pro Glu Ala Glu Ser Ser Ser Ala Ile Ser Thr
865                 870                 875                 880

Thr Ile Ser Pro Gly Ile Pro Gly Val Leu Thr Ser Leu Val Thr Ser
                885                 890                 895

Ser Gly Arg Asp Ile Ser Ala Thr Phe Pro Thr Val Pro Glu Ser Pro
            900                 905                 910

His Glu Ser Glu Ala Thr Ala Ser Trp Val Thr His Pro Ala Val Thr
        915                 920                 925

Ser Thr Thr Val Pro Arg Thr Thr Pro Asn Tyr Ser His Ser Glu Pro
    930                 935                 940
```

-continued

```
Asp Thr Thr Pro Ser Ile Ala Thr Ser Pro Gly Ala Glu Ala Thr Ser
945                 950                 955                 960

Asp Phe Pro Thr Ile Thr Val Ser Pro Asp Val Pro Asp Met Val Thr
                965                 970                 975

Ser Gln Val Thr Ser Ser Gly Thr Asp Thr Ser Ile Thr Ile Pro Thr
            980                 985                 990

Leu Thr Leu Ser Ser Gly Glu Pro Glu Thr Thr Thr Ser Phe Ile Thr
        995                1000                1005

Tyr Ser Glu Thr His Thr Ser Ser Ala Ile Pro Thr Leu Pro Val
    1010                1015                1020

Ser Pro Gly Ala Ser Lys Met Leu Thr Ser Leu Val Ile Ser Ser
    1025                1030                1035

Gly Thr Asp Ser Thr Thr Thr Phe Pro Thr Leu Thr Glu Thr Pro
    1040                1045                1050

Tyr Glu Pro Glu Thr Thr Ala Ile Gln Leu Ile His Pro Ala Glu
    1055                1060                1065

Thr Asn Thr Met Val Pro Arg Thr Thr Pro Lys Phe Ser His Ser
    1070                1075                1080

Lys Ser Asp Thr Thr Leu Pro Val Ala Ile Thr Ser Pro Gly Pro
    1085                1090                1095

Glu Ala Ser Ser Ala Val Ser Thr Thr Thr Ile Ser Pro Asp Met
    1100                1105                1110

Ser Asp Leu Val Thr Ser Leu Val Pro Ser Ser Gly Thr Asp Thr
    1115                1120                1125

Ser Thr Thr Phe Pro Thr Leu Ser Glu Thr Pro Tyr Glu Pro Glu
    1130                1135                1140

Thr Thr Ala Thr Trp Leu Thr His Pro Ala Glu Thr Ser Thr Thr
    1145                1150                1155

Val Ser Gly Thr Ile Pro Asn Phe Ser His Arg Gly Ser Asp Thr
    1160                1165                1170

Ala Pro Ser Met Val Thr Ser Pro Gly Val Asp Thr Arg Ser Gly
    1175                1180                1185

Val Pro Thr Thr Thr Ile Pro Pro Ser Ile Pro Gly Val Val Thr
    1190                1195                1200

Ser Gln Val Thr Ser Ser Ala Thr Asp Thr Ser Thr Ala Ile Pro
    1205                1210                1215

Thr Leu Thr Pro Ser Pro Gly Glu Pro Glu Thr Thr Ala Ser Ser
    1220                1225                1230

Ala Thr His Pro Gly Thr Gln Thr Gly Phe Thr Val Pro Ile Arg
    1235                1240                1245

Thr Val Pro Ser Ser Glu Pro Asp Thr Met Ala Ser Trp Val Thr
    1250                1255                1260

His Pro Pro Gln Thr Ser Thr Pro Val Ser Arg Thr Thr Ser Ser
    1265                1270                1275

Phe Ser His Ser Ser Pro Asp Ala Thr Pro Val Met Ala Thr Ser
    1280                1285                1290

Pro Arg Thr Glu Ala Ser Ser Ala Val Leu Thr Thr Ile Ser Pro
    1295                1300                1305

Gly Ala Pro Glu Met Val Ser Gln Ile Thr Ser Ser Gly Ala
    1310                1315                1320

Ala Thr Ser Thr Thr Val Pro Thr Leu Thr His Ser Pro Gly Met
    1325                1330                1335

Pro Glu Thr Thr Ala Leu Leu Ser Thr His Pro Arg Thr Glu Thr
```

-continued

```
            1340                1345                1350
Ser Lys Thr Phe Pro Ala Ser Thr Val Phe Pro Gln Val Ser Glu
    1355                1360                1365

Thr Thr Ala Ser Leu Thr Ile Arg Pro Gly Ala Glu Thr Ser Thr
    1370                1375                1380

Ala Leu Pro Thr Gln Thr Thr Ser Ser Leu Phe Thr Leu Leu Val
    1385                1390                1395

Thr Gly Thr Ser Arg Val Asp Leu Ser Pro Thr Ala Ser Pro Gly
    1400                1405                1410

Val Ser Ala Lys Thr Ala Pro Leu Ser Thr His Pro Gly Thr Glu
    1415                1420                1425

Thr Ser Thr Met Ile Pro Thr Ser Thr Leu Ser Leu Gly Leu Leu
    1430                1435                1440

Glu Thr Thr Gly Leu Leu Ala Thr Ser Ser Ala Glu Thr Ser
    1445                1450                1455

Thr Ser Thr Leu Thr Leu Thr Val Ser Pro Ala Val Ser Gly Leu
    1460                1465                1470

Ser Ser Ala Ser Ile Thr Thr Asp Lys Pro Gln Thr Val Thr Ser
    1475                1480                1485

Trp Asn Thr Glu Thr Ser Pro Ser Val Thr Ser Val Gly Pro Pro
    1490                1495                1500

Glu Phe Ser Arg Thr Val Thr Gly Thr Thr Met Thr Leu Ile Pro
    1505                1510                1515

Ser Glu Met Pro Thr Pro Pro Lys Thr Ser His Gly Glu Gly Val
    1520                1525                1530

Ser Pro Thr Thr Ile Leu Arg Thr Thr Met Val Glu Ala Thr Asn
    1535                1540                1545

Leu Ala Thr Thr Gly Ser Ser Pro Thr Val Ala Lys Thr Thr Thr
    1550                1555                1560

Thr Phe Asn Thr Leu Ala Gly Ser Leu Phe Thr Pro Leu Thr Thr
    1565                1570                1575

Pro Gly Met Ser Thr Leu Ala Ser Glu Ser Val Thr Ser Arg Thr
    1580                1585                1590

Ser Tyr Asn His Arg Ser Trp Ile Ser Thr Thr Ser Ser Tyr Asn
    1595                1600                1605

Arg Arg Tyr Trp Thr Pro Ala Thr Ser Thr Pro Val Thr Ser Thr
    1610                1615                1620

Phe Ser Pro Gly Ile Ser Thr Ser Ser Ile Pro Ser Ser Thr Ala
    1625                1630                1635

Ala Thr Val Pro Phe Met Val Pro Phe Thr Leu Asn Phe Thr Ile
    1640                1645                1650

Thr Asn Leu Gln Tyr Glu Glu Asp Met Arg His Pro Gly Ser Arg
    1655                1660                1665

Lys Phe Asn Ala Thr Glu Arg Glu Leu Gln Gly Leu Leu Lys Pro
    1670                1675                1680

Leu Phe Arg Asn Ser Ser Leu Glu Tyr Leu Tyr Ser Gly Cys Arg
    1685                1690                1695

Leu Ala Ser Leu Arg Pro Glu Lys Asp Ser Ser Ala Met Ala Val
    1700                1705                1710

Asp Ala Ile Cys Thr His Arg Pro Asp Pro Glu Asp Leu Gly Leu
    1715                1720                1725

Asp Arg Glu Arg Leu Tyr Trp Glu Leu Ser Asn Leu Thr Asn Gly
    1730                1735                1740
```

```
Ile Gln Glu Leu Gly Pro Tyr Thr Leu Asp Arg Asn Ser Leu Tyr
    1745                1750                1755

Val Asn Gly Phe Thr His Arg Ser Ser Met Pro Thr Thr Ser Thr
    1760                1765                1770

Pro Gly Thr Ser Thr Val Asp Val Gly Thr Ser Gly Thr Pro Ser
    1775                1780                1785

Ser Ser Pro Ser Pro Thr
    1790

<210> SEQ ID NO 300
<211> LENGTH: 284
<212> TYPE: PRT
<213> ORGANISM: Homo sapiens

<400> SEQUENCE: 300

Ile Thr Leu Leu Arg Asp Ile Gln Asp Lys Val Thr Thr Leu Tyr Lys
1               5                   10                  15

Gly Ser Gln Leu His Asp Thr Phe Arg Phe Cys Leu Val Thr Asn Leu
                20                  25                  30

Thr Met Asp Ser Val Leu Val Thr Val Lys Ala Leu Phe Ser Ser Asn
        35                  40                  45

Leu Asp Pro Ser Leu Val Glu Gln Val Phe Leu Asp Lys Thr Leu Asn
    50                  55                  60

Ala Ser Phe His Trp Leu Gly Ser Thr Tyr Gln Leu Val Asp Ile His
65                  70                  75                  80

Val Thr Glu Met Glu Ser Ser Val Tyr Gln Pro Thr Ser Ser Ser Ser
                85                  90                  95

Thr Gln His Phe Tyr Leu Asn Phe Thr Ile Thr Asn Leu Pro Tyr Ser
                100                 105                 110

Gln Asp Lys Ala Gln Pro Gly Thr Thr Asn Tyr Gln Arg Asn Lys Arg
            115                 120                 125

Asn Ile Glu Asp Ala Leu Asn Gln Leu Phe Arg Asn Ser Ser Ile Lys
    130                 135                 140

Ser Tyr Phe Ser Asp Cys Gln Val Ser Thr Phe Arg Ser Val Pro Asn
145                 150                 155                 160

Arg His His Thr Gly Val Asp Ser Leu Cys Asn Phe Ser Pro Leu Ala
                165                 170                 175

Arg Arg Val Asp Arg Val Ala Ile Tyr Glu Glu Phe Leu Arg Met Thr
            180                 185                 190

Arg Asn Gly Thr Gln Leu Gln Asn Phe Thr Leu Asp Arg Ser Ser Val
        195                 200                 205

Leu Val Asp Gly Tyr Ser Pro Asn Arg Asn Glu Pro Leu Thr Gly Asn
    210                 215                 220

Ser Asp Leu Pro Phe Trp Ala Val Ile Leu Ile Gly Leu Ala Gly Leu
225                 230                 235                 240

Leu Gly Leu Ile Thr Cys Leu Ile Cys Gly Val Leu Val Thr Thr Arg
                245                 250                 255

Arg Arg Lys Lys Glu Gly Glu Tyr Asn Val Gln Gln Cys Pro Gly
            260                 265                 270

Tyr Tyr Gln Ser His Leu Asp Leu Glu Asp Leu Gln
            275                 280

<210> SEQ ID NO 301
<211> LENGTH: 24
<212> TYPE: DNA
```

```
<213> ORGANISM: Artificial Sequence
<220> FEATURE:
<223> OTHER INFORMATION: Synthetic primer

<400> SEQUENCE: 301
gtctctatgt caatggtttc accc                                              24

<210> SEQ ID NO 302
<211> LENGTH: 21
<212> TYPE: DNA
<213> ORGANISM: Artificial Sequence
<220> FEATURE:
<223> OTHER INFORMATION: Synthetic primer

<400> SEQUENCE: 302
tagctgctct ctgtccagtc c                                                 21

<210> SEQ ID NO 303
<211> LENGTH: 22
<212> TYPE: DNA
<213> ORGANISM: Artificial Sequence
<220> FEATURE:
<223> OTHER INFORMATION: Synthetic primer

<400> SEQUENCE: 303
ggacaaggtc accacactct ac                                                22

<210> SEQ ID NO 304
<211> LENGTH: 24
<212> TYPE: DNA
<213> ORGANISM: Artificial Sequence
<220> FEATURE:
<223> OTHER INFORMATION: Synthetic primer

<400> SEQUENCE: 304
gcagatcctc caggtctagg tgtg                                              24

<210> SEQ ID NO 305
<211> LENGTH: 24
<212> TYPE: DNA
<213> ORGANISM: Artificial Sequence
<220> FEATURE:
<223> OTHER INFORMATION: Synthetic primer

<400> SEQUENCE: 305
gtctctatgt caatggtttc accc                                              24

<210> SEQ ID NO 306
<211> LENGTH: 21
<212> TYPE: DNA
<213> ORGANISM: Artificial Sequence
<220> FEATURE:
<223> OTHER INFORMATION: Synthetic primer

<400> SEQUENCE: 306
tagctgctct ctgtccagtc c                                                 21

<210> SEQ ID NO 307
<211> LENGTH: 468
<212> TYPE: DNA
<213> ORGANISM: Homo sapiens

<400> SEQUENCE: 307
actgctggcc ctctcctggt gccattcacc ctcaacttca ccatcaccaa cctgcagtat       60
gaggaggaca tgcatcgccc tggatctagg aagttcaaca ccacagagag ggtcctgcag      120
```

```
ggtctgctta gtcccatatt caagaacacc agtgttggcc ctctgtactc tggctgcaga      180
ctgacctctc tcaggtctga gaaggatgga gcagccactg gagtggatgc catctgcatc      240
catcatcttg accccaaaag ccctggactc aacagagagc ggctgtactg ggagctgagc      300
cgactgacca atggcatcaa agagctgggc ccctacaccc tggacaggaa cagtctctat      360
gtcaatggtt tcacccatcg gacctctgtg cccaccacca gcactcctgg gacctccaca      420
gtggaccttg gaacctcagg gactccattc tccctcccaa gccccgca                   468
```

<210> SEQ ID NO 308
<211> LENGTH: 156
<212> TYPE: PRT
<213> ORGANISM: Homo sapiens

<400> SEQUENCE: 308

```
Thr Ala Gly Pro Leu Leu Val Pro Phe Thr Leu Asn Phe Thr Ile Thr
1               5                   10                  15

Asn Leu Gln Tyr Glu Glu Asp Met His Arg Pro Gly Ser Arg Lys Phe
            20                  25                  30

Asn Thr Thr Glu Arg Val Leu Gln Gly Leu Leu Ser Pro Ile Phe Lys
        35                  40                  45

Asn Thr Ser Val Gly Pro Leu Tyr Ser Gly Cys Arg Leu Thr Ser Leu
    50                  55                  60

Arg Ser Glu Lys Asp Gly Ala Ala Thr Gly Val Asp Ala Ile Cys Ile
65                  70                  75                  80

His His Leu Asp Pro Lys Ser Pro Gly Leu Asn Arg Glu Arg Leu Tyr
                85                  90                  95

Trp Glu Leu Ser Arg Leu Thr Asn Gly Ile Lys Glu Leu Gly Pro Tyr
            100                 105                 110

Thr Leu Asp Arg Asn Ser Leu Tyr Val Asn Gly Phe Thr His Arg Thr
        115                 120                 125

Ser Val Pro Thr Thr Ser Thr Pro Gly Thr Ser Thr Val Asp Leu Gly
    130                 135                 140

Thr Ser Gly Thr Pro Phe Ser Leu Pro Ser Pro Ala
145                 150                 155
```

REPEAT SEQUENCES OF THE CA125 GENE AND THEIR USE FOR DIAGNOSTIC AND THERAPEUTIC INTERVENTIONS

CROSS REFERENCE TO RELATED APPLICATIONS

This application claims the benefit of U.S. Provisional Application Ser. No. 60/284,175 filed Apr. 17, 2001 and U.S. Provisional Application Ser. No. 60/299,380 filed Jun. 19, 2001, which are incorporated by reference in their entirety.

BACKGROUND OF THE INVENTION

The present invention relates generally to the cloning, identification, and expression of multiple repeat sequences of the CA125 gene in vitro and, more specifically, to the use of recombinant CA125 with epitope binding sites for diagnostic and therapeutic purposes.

CA125 is an antigenic determinant located on the surface of ovarian carcinoma cells with essentially no expression in normal adult ovarian tissue. Elevated in the sera of patients with ovarian adenocarcinoma, CA125 has played a critical role for more than 15 years in the management of these patients relative to their response to therapy and also as an indicator of recurrent disease.

It is well established that CA125 is not uniquely expressed in ovarian carcinoma, but is also found in both normal secretory tissues and other carcinomas (i.e., pancreas, liver, colon) [Hardardottir H et al., Distribution of CA125 in embryonic tissue and adult derivatives of the fetal periderm, *Am J Obstet. Gynecol.* 163;6(1):1925-1931 (1990); Zurawski V R et al., Tissue distribution and characteristics of the CA125 antigen, *Cancer Rev.* 11-12:102-108 (1988); and O'Brien T J et al., CA125 antigen in human amniotic fluid and fetal membranes, *Am J Obstet Gynecol.* 155:50-55, (1986); Nap M et al., Immunohistochemical characterization of 22 monoclonal antibodies against the CA125 antigen: 2nd report from the ISOBM TD-1 workshop, Tumor Biology 17:325-332 (1996)]. Notwithstanding, CA125 correlates directly with the disease status of affected patients (i.e., progression, regression, and no change), and has become the "gold standard" for monitoring patients with ovarian carcinoma [Bast R C et al, A radioimmunoassay using a monoclonal antibody to monitor the course of epithelial ovarian cancer, *N Engl J Med.* 309:883-887 (1983); and Bon G C et al., Serum tumor marker immunoassays in gynecologic oncology: Establishment of reference values, *Am J Obstet. Gynecol.* 174:107-114 (1996)]. CA125 is especially useful in post-menopausal patients where endometrial tissue has become atrophic and, as a result, is not a major source of normal circulating CA125.

During the mid 1980's, the inventor of the present invention and others developed M11, a monoclonal antibody to CA125. M11 binds to a dominant epitope on the repeat structure of the CA125 molecule [O'Brien T J et al., New monoclonal antibodies identify the glycoprotein carrying the CA125 epitope, *Am J Obstet Gynecol* 165:1857-64(1991)]. More recently, the inventor and others developed a purification and stabilization scheme for CA125, which allows for the accumulation of highly purified high molecular weight CA125 [O'Brien T J et al., More than 15 years of CA125: What is known about the antigen, its structure and its function, *Int J Biological Markers* 13(4): 188-195 (1998)].

Considerable progress has been made over the years to further characterize the CA125 molecule, its structure and its function. The CA125 molecule is a high molecular weight glycoprotein with a predominance of O-linked sugar side chains. The native molecule exists as a very large complex (~2-5 million daltons). The complex appears to be composed of an epitope containing CA125 molecule and binding proteins which carry no CA125 epitopes. The CA125 molecule is heterogenous in both size and charge, most likely due to continuous deglycosylation of the side chains during its life-span in bodily fluids. The core CA125 subunit is in excess of 200,000 daltons, and retains the capacity to bind both OC125 and M11 class antibodies. While the glycoprotein has been described biochemically and metabolically by the inventor of the present invention and others, no one has yet cloned the CA125 gene, which would provide the basis for understanding its structure and its physiologic role in both normal and malignant tissues.

Despite the advances in detection and quantitation of serum tumor markers like CA125, the majority of ovarian cancer patients are still diagnosed at an advanced stage of the disease—Stage III or IV. Further, the management of patients' responses to treatment and the detection of disease recurrence remain major problems. There, thus, remains a need to significantly improve and standardize current CA125 assay systems. Further, the development of an early indicator of risk of ovarian cancer will provide a useful tool for early diagnosis and improved prognosis.

SUMMARY OF THE INVENTION

The CA125 gene has been cloned and multiple repeat sequences as well as the carboxy terminus have been identified. CA125 requires a transcript of more than 35,000 bases and occupies approximately 150,000 bp on chromosome 19q 13.2. The CA125 molecule comprises three major domains: an extracellular amino terminal domain (Domain 1); a large multiple repeat domain (Domain 2); and a carboxy terminal domain (Domain 3) which includes a transmembrane anchor with a short cytoplasmic domain. The amino terminal domain is assembled by combining five genomic exons, four very short amino terminal sequences and one extraordinarily large exon. This domain is dominated by its capacity for O-glycosylation and its resultant richness in serine and threonine residues.

The extracellular repeat domain, which characterizes the CA125 molecule, also represents a major portion of the CA125 molecular structure. It is downstream from the amino terminal domain and presents itself in a much different manner to its extracellular matrix neighbors. These repeats are characterized by many features including a highly-conserved nature and a uniformity in exon structure. But most consistently, a cysteine enclosed sequence may form a cysteine loop. Domain 2 comprises 156 amino acid repeat units of the CA125 molecule. The repeat domain constitutes the largest proportion of the CA125 molecule. The repeat units also include the epitopes now well-described and classified for both the major class of CA125 antibodies of the OC125 group and the M11 group. More than 60 repeat units have been identified, sequenced, and contiguously placed in the CA125 domain structure. The repeat sequences demonstrated 70-85% homology to each other. The existence of the repeat sequences was confirmed by expression of the recombinant protein in *E. coli* where both OC125/M11 class antibodies were found to bind to sites on the CA125 repeat.

The CA125 molecule is anchored at its carboxy terminal through a transmembrane domain and a short cytoplasmic tail. The carboxy terminal also contains a proteolytic cleavage site approximately 50 amino acids upstream from the transmembrane domain, which allows for proteolytic cleavage and release of the CA125 molecule.

The identification and sequencing of multiple repeat domains of the CA125 antigen provides potentially new clinical and therapeutic applications for detecting, monitoring and treating patients with ovarian cancer and other carcinomas where CA125 is expressed. For example, the ability to express repeat domains of CA125 with the appropriate epitopes would provide a much needed standard reagent for research and clinical applications. Current assays for CA125 utilize as standards either CA125 produced from cultured cell lines or from patient ascites fluid. Neither source is defined with regard to the quality or purity of the CA125 molecule. The present invention overcomes the disadvantages of current assays by providing multiple repeat domains of CA125 with epitope binding sites. At least one or more of any of the more than 60 repeats shown in Table 16 can be used as a "gold standard" for testing the presence of CA125. Furthermore, new and more specific assays may be developed utilizing recombinant products for antibody production.

Perhaps even more significantly, the multiple repeat domains of CA125 or other domains could also be used for the development of a potential vaccine for patients with ovarian cancer. In order to induce cellular and humoral immunity in humans to CA125, murine antibodies specific for CA125 were utilized in anticipation of patient production of anti-ideotypic antibodies, thus indirectly allowing the induction of an immune response to the CA125 molecule. With the availability of recombinant CA125, especially domains which encompass epitope binding sites for known murine antibodies, it will be feasible to more directly stimulate patients' immune systems to CA125 and, as a result, extend the life of ovarian carcinoma patients.

The recombinant CA125 of the present invention may also be used to develop therapeutic targets. Molecules like CA125, which are expressed on the surface of tumor cells, provide potential targets for immune stimulation, drug delivery, biological modifier delivery or any agent which can be specifically delivered to ultimately kill the tumor cells. Humanized or human antibodies to CA125 epitopes could be used to deliver all drug or toxic agents including radioactive agents to mediate direct killing of tumor cells. Natural ligands having a natural binding affinity for domains on the CA125 molecule could also be utilized to deliver therapeutic agents to tumor cells.

CA125 expression may further provide a survival or metastatic advantage to ovarian tumor cells. Antisense oligonucleotides derived from the CA125 repeat sequences could be used to down-regulate the expression of CA125. Further, antisense therapy could be used in association with a tumor cell delivery system of the type described above.

Recombinant domains of the CA125 molecule also have the potential to identify small molecules, which bind to individual domains of the CA125 molecule. These small molecules could also be used as delivery agents or as biological modifiers.

In one aspect of the present invention, a CA125 molecule is disclosed comprising: (a) an extracellular amino terminal domain, comprising 5 genomic exons, wherein exon 1 comprises amino acids #1-33 of SEQ ID NO: 299, exon 2 comprises amino acids #34-1593 of SEQ ID NO: 299, exon 3 comprises amino acids #1594-1605 of SEQ ID NO: 299, exon 4 comprises amino acids #1606-1617 of SEQ ID NO: 299, and exon 5 comprises amino acids #1618-1637 of SEQ ID NO: 299; (b) a multiple repeat domain, wherein each repeat unit comprises 5 genomic exons, wherein exon 1 comprises amino acids #1-42 in any of SEQ ID NOS: 164 through 194; exon 2 comprises amino acids #43-65 in any of SEQ ID NOS: 195 through 221; exon 3 comprises amino acids #66-123 in any of SEQ ID NOS: 222 through 249; exon 4 comprises amino acids #124-135 in any of SEQ ID NOS: 250 through 277; and exon 5 comprises amino acids #136-156 in any of SEQ ID NOS: 278 through 298; and (c) a carboxy terminal domain comprising a transmembrane anchor with a short cytoplasmic domain, and further comprising 9 genomic exons, wherein exon 1 comprises amino acids #1-11 of SEQ ID NO: 300; exon 2 comprises amino acids #12-33 of SEQ ID NO: 300; exon 3 comprises amino acids #34-82 of SEQ ID NO: 300; exon 4 comprises amino acids #83-133 of SEQ ID NO: 300; exon 5 comprises amino acids #134-156 of SEQ ID NO: 300; exon 6 comprises amino acids #157-212 of SEQ ID NO: 300; exon 7 comprises amino acids #213-225 of SEQ ID NO: 300; exon 8 comprises amino acids #226-253 of SEQ ID NO: 300; and exon 9 comprises amino acids #254-284 of SEQ ID NO: 300.

In another aspect of the present invention, the N-glycosylation sites of the amino terminal domain marked (x) in FIG. 8B are encoded at positions #81, #271, #320, #624, #795, #834, #938, and #1,165 in SEQ ID NO: 299.

In another aspect of the present invention, the serine and threonine O-glycosylation pattern for the amino terminal domain is marked (o) in SEQ ID NO: 299 in FIG. 8B.

In another aspect of the present invention, exon 1 in the repeat domain comprises at least 31 different copies; exon 2 comprises at least 27 different copies; exon 3 comprises at least 28 different copies; exon 4 comprises at least 28 different copies, and exon 5 comprises at least 21 different copies.

In another aspect of the present invention, the repeat domain comprises 156 amino acid repeat units which comprise epitope binding sites. The epitope binding sites are located in the C-enclosure at amino acids #59-79 (marked C-C) in SEQ ID NO: 150 in FIG. 5.

In another aspect, the 156 amino acid repeat unit comprises O-glycosylation sites at positions #128, #129, #132, #133, #134, #135, #139, #145, #146, #148, #150, #151, and #156, in SEQ ID NO: 150 in FIG. 5C. The 156 amino acid repeat unit further comprises N-glycosylation sites at positions #33 and #49 in SEQ ID NO: 150 in FIG. 5C. The repeat unit also includes at least one conserved methionine (designated M) at position #24 in SEQ ID NO: 150 in FIG. 5C.

In yet another aspect, the transmembrane domain of the carboxy terminal domain is located at positions #230-252 (underlined) in SEQ ID NO: 300 of FIG. 9B. The cytoplasmic domain of the carboxy terminal domain comprises a highly basic sequence adjacent to the transmembrane at positions #256-260 in SEQ ID NO: 300 of FIG. 9B, serine and threonine phosporylation sites at positions #254, #255, and #276 in SEQ ID NO: 300 in FIG. 9B, and tyrosine phosphorylation sites at positions #264, #273, and #274 in SEQ ID NO: 300 of FIG. 9B.

In another aspect of the present invention, an isolated nucleic acid of the CA125 gene is disclosed, which comprises a nucleotide sequence selected from the group consisting of: (a) the nucleotide sequences set forth in SEQ ID NOS: 49, 67, 81, 83-145, 147, 150, and 152; (b) a nucleotide sequence having at least 70% sequence identity to any one of the sequences in (a); (c) a degenerate variant of any one of (a) to (b); and (d) a fragment of any one of (a) to (c).

In another aspect of the present invention, an isolated nucleic acid of the CA125 gene, comprising a sequence that encodes a polypeptide with the amino acid sequence selected from the group consisting of: (a) the amino acid sequences set forth in SEQ ID NOS: 11-47, 50-80, 82, 146, 148, 149, 151, and 153-158; (b) an amino acid sequence having at least 50% sequence identity to any one of the sequences in (a); (c) a conservative variant of any one of (a) to (b); and (d) a fragment of any one of (a) to (c).

In yet another aspect, a vector comprising the nucleic acid of the CA125 gene is disclosed. The vector may be a cloning vector, a shuttle vector, or an expression vector. A cultured cell comprising the vector is also disclosed.

In yet another aspect, a method of expressing CA125 antigen in a cell is disclosed, comprising the steps of: (a) providing at least one nucleic acid comprising a nucleotide sequence selected from the group consisting of: (i) the nucleotide sequences set forth in SEQ ID NOS: 49, 67, 81, 83-145, 147, 150, and 152; (ii) a nucleotide sequence having at least 70% sequence identity to any one of the sequences in (i); (iii) a degenerate variant of any one of (i) to (ii); and (iv) a fragment of any one of (i) to (iii); (b) providing cells comprising an mRNA encoding the CA125 antigen; and (c) introducing the nucleic acid into the cells, wherein the CA125 antigen is expressed in the cells.

In yet another aspect, a purified polypeptide of the CA125 gene, comprising an amino acid sequence selected from the group consisting of: (a) the amino acid sequences set forth in SEQ ID NOS: 11-48, 50, 68-80, 82, 146, 148, 149, 150, 151, and 153-158; (b) an amino acid sequence having at least 50% sequence identity to any one of the sequences in (a); (c) a conservative variant of any one of (a) to (b); and (d) a fragment of any one of (a) to (c).

In another aspect, a purified antibody that selectively binds to an epitope in the receptor-binding domain of CA125 protein, wherein the epitope is within the amino acid sequence selected from the group consisting of: (a) the amino acid sequences set forth in SEQ ID NOS: 11-48, 50, 68-80, 146, 151, and 153-158; (b) an amino acid sequence having at least 50% sequence identity to any one of the sequences in (a); (c) a conservative variant of any one of (a) to (b); and (d) a fragment of any one of (a) to (c).

A diagnostic for detecting and monitoring the presence of CA125 antigen is also disclosed, which comprises recombinant CA125 comprising at least one repeat unit of the CA125 repeat domain including epitope binding sites selected from the group consisting of amino acid sequences set forth in SEQ ID NOS: 11-48, 50, 68-80, 82, 146, 150, 151, 153-161, and 162 (amino acids #1,643-11,438).

A therapeutic vaccine to treat mammals with elevated CA125 antigen levels or at risk of developing a disease or disease recurrence associated with elevated CA125 antigen levels is also disclosed. The vaccine comprises recombinant CA125 repeat domains including epitope binding sites, wherein the repeat domains are selected from the group of amino acid sequences consisting of SEQ ID NOS: 11-48, 50, 68-80, 82, 146, 148, 149, 150, 151, 153-161, and 162 (amino acids #1,643-11,438), and amino acids #175-284 of SEQ ID NO: 300. Mammals include animals and humans.

In another aspect of the present invention, an antisense oligonucleotide is disclosed that inhibits the expression of CA125 encloded by: (a) the nucleotide sequences set forth in SEQ ID NOS: 49, 67, 81, 83-145, 147, 150, and 152; (b) a nucleotide sequence having at least 70% sequence identity to any one of the sequences in (a); (c) a degenerate variant of any one of (a) to (b); and (d) a fragment of any one of (a) to (c).

The preceeding and further aspects of the present invention will be apparent to those of ordinary skill in the art from the following description of the presently preferred embodiments of the invention, such description being merely illustrative of the present invention.

BRIEF DESCRIPTION OF THE DRAWINGS

FIG. 7B represents the genomic structure and exon configuration of a 156 amino acid repeat sequence of CA125 (SEQ ID NO: 163), which comprises a standard repeat unit.

FIG. 7C lists the individual known sequences for each exon, which have been determined as follows: Exon 1—SEQ ID NOS: 164-194; Exon 2—SEQ ID NOS: 195-221; Exon 3—SEQ ID NOS: 222-249; Exon 4–SEQ ID NOS: 250-277; and Exon 5- SEQ ID NOS: 278-298.

FIG. 8B illustrates the amino acid composition of the amino terminal domain (SEQ ID NO: 299) with each potential O-glycosylation site marked with a superscript (o) and N-glycosylation sites marked with a superscript (x). T-TALK sequences are underlined.

FIG. 9B illustrates the amino acid composition of the carboxy terminal domain (SEQ ID NO: 300) including the exon boundaries, O-glycosylation sites (o), and N-glycosylation sites (x). The proposed transmembrane domain is underlined.

DETAILED DESCRIPTION OF THE INVENTION

Figure 1:
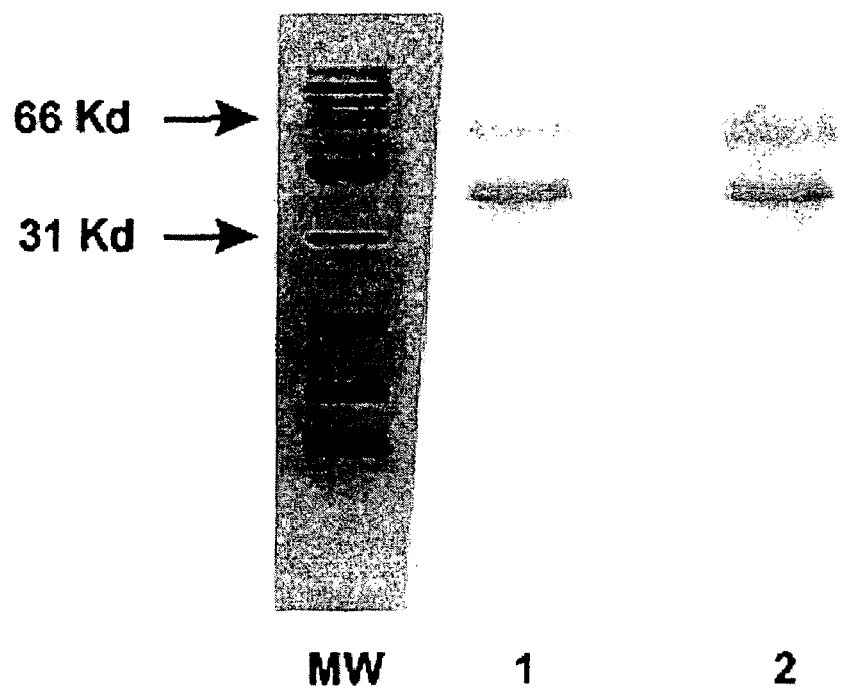
FIG. 1 illustrates the cyanogen bromide digested products of CA125 on Western blot probed with M11 and OC125 antibodies. Table 1 shows the amino acid sequence derived from the amino terminal end of the 40 kDa cyanogen bromide peptide along with internal sequences obtained after protease digestion of the 40 kDa fragment (SEQ ID NOS: 1-4). SEQ ID NO: 1 is the amino terminal sequence derived of the 40 kDa peptide and SEQ ID NOS: 2, 3, and 4 reflect internal amino acid sequences derived from peptides after protease digestion of the 40 kDa fragment. Table 1 further provides a translation of the EST (BE005912) with homologous sequences (SEQ ID NOS: 5 and 6) either boxed or underlined. Protease cleavage sites are indicated by arrows.

In accordance with the present invention, conventional molecular biology, microbiology, and recombinant DNA techniques may be used that will be apparent to those skilled in the relevant art. Such techniques are explained fully in the literature (see, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshhey, ed. (1986)); "Immobilized Cells And Enzymes" (IRL Press, (1986)); and B. Perbal, "A Practical Guide To Molecular Cloning" (1984)).

Therefore, if appearing herein, the following terms shall have the definitions set out below.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

As used herein, the term "gene" shall mean a region of DNA encoding a polypeptide chain.

"Messenger RNA" or "mRNA" shall mean an RNA molecule that encodes for one or more polypeptides.

"DNA polymerase" shall mean an enzyme which catalyzes the polymerization of deoxyribonucleotide triphosphates to make DNA chains using a DNA template.

"Reverse transcriptase" shall mean an enzyme which catalyzes the polymerization of deoxy- or ribonucleotide triphosphates to make DNA or RNA chains using an RNA or DNA template.

"Complementary DNA" or "cDNA" shall mean the DNA molecule synthesized by polymerization of deoxyribonucleotides by an enzyme with reverse transcriptase activity.

An "isolated nucleic acid" is a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein.

"Oligonucleotide", as used herein in referring to probes or primers of the present invention, is defined as a molecule comprised of two or more deoxy- or ribonucleotides, preferably more than ten. Its exact size will depend upon many factors which, in turn, depend upon the ultimate function and use of the oligonucleotide.

"DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have non naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species which include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

"Primer" shall refer to an oligonucleotide, whether occurring naturally or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used. For example, for diagnostic applications, depending on the complexity of the target sequence, the oligonucleotide primer typically contains 10-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the term "hybridization" refers generally to a technique wherein denatured RNA or DNA is combined with complementary nucleic acid sequence which is either free in solution or bound to a solid phase. As recognized by one skilled in the art, complete complementarity between the two nucleic acid sequences is not a pre-requisite for hybridization to occur. The technique is ubiquitous in molecular genetics and its use centers around the identification of particular DNA or RNA sequences within complex mixtures of nucleic acids.

As used herein, "restriction endonucleases" and "restriction enzymes" shall refer to bacterial enzymes which cut double-stranded DNA at or near a specific nucleotide sequence.

"Purified polypeptide" refers to any peptide generated from CA125 either by proteolytic cleavage or chemical cleavage.

"Degenerate variant" refers to any amino acid variation in the repeat sequence, which fulfills the homology exon structure and conserved sequences and is recognized by the M11, OC125 and ISOBM series of antibodies.

"Fragment" refers to any part of the CA125 molecule identified in a purification scheme.

"Conservative variant antibody" shall mean any antibody that fulfills the criteria of M11, OC125 or any of the ISOBM antibody series.

Materials and Methods

A. Tissue collection, RNA Isolation and cDNA Synthesis

Both normal and ovarian tumor tissues were utilized for cDNA preparation. Tissues were routinely collected and stored at −80° C. according to a tissue collection protocol.

Total RNA isolation was performed according to the manufacturer's instructions using the TriZol Reagent purchased from GibcoBRL (Catalog #15596-018). In some instances, mRNA was isolated using oligo dT affinity chromatography. The amount of RNA recovered was quantitated by UV spectrophotometry. First strand complementary DNA (cDNA) was synthesized using 5.0 μg of RNA and random hexamer primers according to the manufacturer's protocol utilizing a first strand synthesis kit obtained from Clontech (Catalog #K1402-1). The purity of the cDNA was evaluated by PCR using primers specific for the 13-tubulin gene. These primers span an intron such that the PCR products generated from pure cDNA can be distinguished from cDNA contaminated with genomic DNA.

B. Identification and Ordering of CA125 Repeat Units

It has been demonstrated that the 2-5 million dalton CA125 glycoprotein (with repeat domains) can be chemically segmented into glycopeptide fragments using cyanogen bromide. As shown in FIG. 1, several of these fragments, in particular the 40 kDa and 60 kDa fragments, still bind to the to the two classical antibody groups defined by OC 125 and M11.

To convert CA125 into a consistent glycopeptide, the CA125 parent molecule was processed by cyanogen bromide digestion. This cleavage process resulted in two main fractions on commassie blue staining following polyacrylamide gel electrophoresis. An approximately 60 kDa band and a more dominant 40 kDa band were identified as shown in FIG. 1. When a Western blot of these bands was probed with either OC125 or M11 antibodies (both of which define the CA125 molecule), these bands bound both antibodies. The 40 kDa band was significantly more prominent than the 60 kDa band. These data thus established the likelihood of these bands (most especially the 40 kDa band) as being an authentic cleavage peptide of the CA125 molecule, which retained the identifying characteristic of OC125 and M11 binding.

The 40 kDa and 60 kDa bands were excised from PVDF blots and submitted to amino terminal and internal peptide amino acid sequencing as described and practiced by Harvard Sequencing, (Harvard Microchemistry Facility and The Biological Laboratories, 16 Divinity Avenue, Cambridge, Mass. 02138). Sequencing was successful only for the 40 kDa band where both amino terminal sequences and some internal sequences were obtained as shown in Table 1 at SEQ ID NOS: 1-4. The 40 kDa fragment of the CA125 protein was found to have homology to two translated EST sequences (GenBank Accession Nos. BE005912 and AA640762). Visual examination of these translated sequences revealed similar amino acid regions, indicating a possible repetitive domain. The nucleotide and amino acid sequences for EST Genbank Accession No. BE005912 (corresponding to SEQ ID NO: 5 and SEQ ID NO: 6, respectively) are illustrated in Table 1. Common sequences are boxed or underlined.

In an attempt to identify other individual members of this proposed repeat family, two oligonucleotide primers were synthesized based upon regions of homology in these EST sequences. Shown in Table 2A, the primer sequences correspond to SEQ ID NOS: 7 and 8 (sense primers) and SEQ ID NOS: 9 and 10 (antisense primers). Repeat sequences were amplified in accordance with the methods disclosed in the following references: Shigemasa K et al., p21: A monitor of p53 dysfunction in ovarian neoplasia, *Int. J Gynecol. Cancer* 7:296-303 (1997) and Shigemasa K et al., p16 Overexpression: A potential early indicator of transformation in ovarian carcinoma, *J Soc. Gynecol. Invest.* 4:95-102 (1997). Ovarian tumor cDNA obtained from a tumor cDNA bank was used.

Amplification was accomplished in a Thermal Cycler (Perkin-Elmer Cetus). The reaction mixture consisted of 1U Taq DNA Polymerase in storage buffer A (Promega), 1× Thermophilic DNA Polymerase 10× Mg free buffer (Promega), 300 mM dNTPs, 2.5 mM MgCl2, and 0.25 mM each of the sense and antisense primers for the target gene. A 20 µl reaction included 1 µl of cDNA synthesized from 50 ng of mRNA from serous tumor mRNA as the template. PCR reactions required an initial denaturation step at 94° C./1.5 min. followed by 35 cycles of 94° C./0.5 min., 48° C./0.5 min., 72° C./0.5 min. with a final extension at 72° C./7 min. Three bands were initially identified (>>400 bp, >>800 bp, and >>1200 bp) and isolated. After size analysis by agarose gel electrophoresis, these bands as well as any other products of interest were then ligated into a T-vector plasmid (Promega) and transformed into competent DH5α strain of *E. coli* cells. After growth on selective media, individual colonies were cultured overnight at 37° C., and plasmid DNA was extracted using the QIAprep Spin Miniprep kit (Qiagen). Positive clones were identified by restriction digests using Apa I and Sac I. Inserts were sequenced using an ABI automatic sequencer, Model 377, T7 primers, and a Big Dye Terminator Cycle Sequencing Kit (Applied Biosystems).

Obtained sequences were analyzed using the Pileup program of the Wisconsin Genetic's Computer Group (GCG). Repeat units were ordered using primers designed against two highly conserved regions within the nucleotide sequence of these identified repeat units. Shown in Table 2B, the sense and antisense primers (5'-GTCTCTATGT-CAATGGTTTCACCC-3'/5'-TAGCTGCTCTCTGTC-CAGTCC-3' SEQ ID NOS: 301 and 302, respectively) faced away from one another within any one repeat creating an overlap sequence, thus enabling amplification across the junction of any two repeat units. PCR reactions, cloning, sequencing, and analysis were performed as described above.

C. Identification and Assembly of the CA125 Amino Terminal Domain

In search of open reading frames containing sequences in addition to CA125 repeat units, database searches were performed using the BLAST program available at the National Center for Biotechnology Information (www.ncbi.nlm.nih.gov/). Using a repeat unit as the query sequence, cosmid AC008734 was identified as having multiple repeat sequences throughout the unordered (35) contiguous pieces of DNA, also known as contigs. One of these contigs, #32, was found to have exons 1 and 2 of a repeat region at its 3' end. Contig#32 was also found to contain a large open reading frame (ORF) upstream of the repeat sequence. PCR was again used to verify the existence of this ORF and confirm its connection to the repeat sequence. The specific primers recognized the 3' end of this ORF (5'-CAGCAGAGACCAGCACGAGTACTC-3')(SEQ ID NO: 51) and sequence within the repeat (5'-TCCACTGCCATG-GCTGAGCT-3')(SEQ ID NO: 52). The remainder of the amino-terminal domain was assembled from this contig in a similar manner. With each PCR confirmation, a new primer (see Table 10A) was designed against the assembled sequence and used in combination with a primer designed against another upstream potential ORF (Set 1: 5'-CCAG-CACAGCTCTTCCCAGGAC-3'/5'-GGAATGGCT-GAGCTGACGTCTG-3'(SEQ ID NO: 53 and SEQ ID NO: 54); Set 2: 5'-CTTCCCAGGACAACCTCAAGG-3'/5'-GCAGGATGAGTGAGCCACGTG-3'(SEQ ID NO: 55 and SEQ ID NO: 56); Set 3: 5'-GTCAGATCTGGTGACCT-CACTG-3'/5'-GAGGCACTGGAAAGCCCAGAG-3') (SEQ ID NO: 57 and SEQ ID NO: 58). Potential adjoining sequence (contig #7 containing EST AU133673) was also identified using contig #32 sequence as query sequence in database searches. Confirmation primers were designed and used in a typical manner (5'-CTGATGGCATTATGGAA-CACATCAC-3'/5'-CCCAGAACGAGAGACCAGTGAG-3')(SEQ ID NO: 59 and SEQ ID NO: 60).

In order to identify the 5' end of the CA125 sequence, 5' Rapid Amplification of cDNA Ends (FirstChoice™ RLM-RACE Kit, Ambion) was performed using tumor cDNA. The primary PCR reaction used a sense primer supplied by Ambion (5'-GCTGATGGCGATGAATGAACACTG-3') (SEQ ID NO: 61) and an anti-sense primer specific to confirmed contig #32 sequence (5'-CCCAGAAC-GAGAGACCAGTGAG-3')(SEQ ID NO: 62). The secondary PCR was then performed using nested primers, sense from Ambion (5'-CGCGGATCCGAACACT-GCGTTTGCTGGCTTTGATG-3') (SEQ ID NO: 63) and the anti-sense was specific to confirmed contig #7 sequence (5'-CCTCTGTGTGCTGCTTCATTGGG-3')(SEQ ID NO: 64). The RACE PCR product (a band of approximately 300 bp) was cloned and sequenced as previously described.

D. Identification and Assembly of the CA125 Carboxy Terminal Domain

Database searches using confirmed repeat units as query also identified a cDNA sequence (GenBank AK024365) containing other repeat units, but also a potential carboxy terminal sequence. The contiguous nature of this sequence with assembled CA125 was confirmed using PCR (5'-GGACAAGGTCACCACACTCTAC-3'/5'-GCAGATC-CTCCAGGTCTAGGTGTG-3'), (SEQ ID NO: 303 and SEQ ID NO: 304, respectively) as well as contig and EST analysis.

E. Expression of 6xHis-tagged CA125 repeat in *E. coli*

The open reading frame of a CA125 repeat shown in Table 11 was amplified by PCR with the sense primer (5'-ACCGGATCCATGGGCCACACAGAGCCTGGCCC-3') (SEQ ID NO: 65) the antisense primer (5'-TGTAAGCT-TAGGCAGGGAGGATGGAGTCC-3') (SEQ ID NO: 66) PCR was performed in a reaction mixture consisting of ovarian tumor cDNA derived from 50 ng of mRNA, 5 pmol each of sense and antisense primers for the CA125 repeat, 0.2 mmol of dNTPs, and 0.625 U of Taq polymerase in 1×buffer in a final volume of 25 ml. This mixture was subjected to 1 minute of denaturation at 95° C. followed by 30 cycles of PCR consisting of the following: denaturation for 30 seconds at 95° C., 30 seconds of annealing at 62° C., and 1 minute of extension at 72° C. with an additional 7 minutes of extension on the last cycle. The product was electrophoresed through a 2% agarose gel for separation. The PCR product was purified and digested with the restriction enzymes Bam HI and Hind III. This digested PCR product was then ligated into the expression vector pQE-30, which had also been digested with Bam HI and Hind III. This clone would allow for expression of recombinant 6×His-tagged CA125 repeat. Transformed *E. coli* (JM109) were grown to an OD600 of 1.5-2.0 at 37° C. and then induced with IPTG (0.1 mM) for 4-6 hours at 25° C. to produce recombinant protein. Whole *E. coli* lysate was electrophoresed through a 12% SDS polyacrylamide gel and Coomassie stained to detect highly expressed proteins.

F. Western Blot Analysis

Proteins were separated on a 12% SDS-PAGE gel and electroblotted at 100V for 40 minutes at 4° C. to nitrocellulose membrane. Blots were blocked overnight in phosphate-buffered saline (PBS) pH 7.3 containing 5% non-fat milk. CA125 antibodies M11, OC125, or ISOBM 9.2 were incubated with the membrane at a dilution of 5 µg/ml in 5% milk/PBS-T (PBS plus 0.1% TX-100) and incubated for 2 hours at room temperature. The blot was washed for 30 minutes with several changes of PBS and incubated with a 1:10,000 dilution of horseradish peroxidase (HRP) conjugated goat anti-mouse IgG antibody (Bio-Rad) for 1 hour at room temperature. Blots were washed for 30 minutes with several changes of PBS and incubated with a chemiluminescent substrate (ECL from Amersham Pharmacia Biotech) before a 10-second exposure to X-ray film for visualization.

Figure 4:
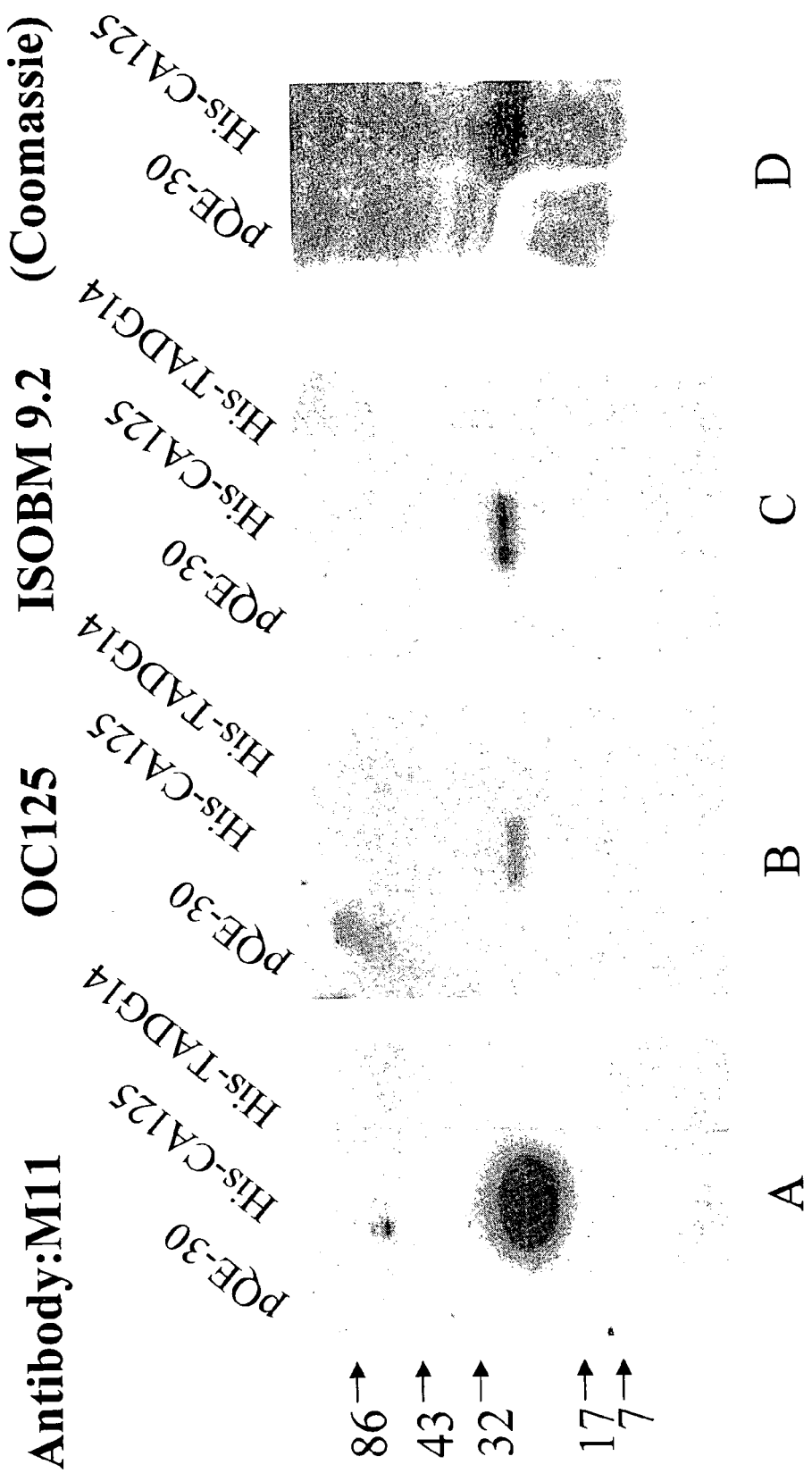
FIG. 4 illustrates three Western immunoblot patterns: Panel A=probed with M11, Panel B=probed with OC125 and Panel C=probed with antibody ISOBM 9.2. Each panel represents *E. coli* extracts as follows: lane 1=*E. coli* extract from bacteria with the plasmid PQE-30 only. Lane 2=*E. coli* extract from bacteria with the plasmid PQE-30 which includes the CA125 repeat unit. Lane 3=*E. coli* extract from bacteria with the plasmid PQE-30 which includes the TADG-14 protease unrelated to CA125. Panel D shows a Coomassie blue stain of a PAGE gel of *E. coli* extract derived from either PQE-30 alone or from bacteria infected with PQE-30-CA125 repeat (recombinant CA125 repeat).

FIG. 4 illustrates three Western immunoblot patterns of the recombinant CA125 repeat purified from *E. coli* lysate (lane 2) compared to *E. coli* lysate with no recombinant protein (lane 1-negative control) and a recombinant protein TADG-14 which is unrelated to CA125 (lane 3). As shown, the M11 antibody, the OC125 antibody and the antibody ISOBM 9.2 (an OC125-like antibody) all recognized the CA125 recombinant repeat (lane 2), but did not recognize either the *E. coli* lysate (lane 1) or the unrelated TADG-14 recombinant (lane 3). These data confirm that the recombinant repeat encodes both independent epitopes for CA125, the OC125 epitope and the M11 epitope.

G. Northern Blot Analysis

Total RNA samples (approximately 10 µg) were separated by electrophoresis through a 6.3% formaldehyde, 1.2% agarose gel in 0.02 M MOPS, 0.05 M sodium acetate (pH 7.0), and 0.001 M EDTA. The RNAs were then blotted to Hybond-N (Amersham) by capillary action in 20×SSPE and fixed to the membrane by baking for 2 hours at 80° C. A PCR product representing one 400 bp repeat of the CA125 molecule was radiolabelled using the Prime-a-Gene Labeling System available from Promega (cat. #U1100). The blot was probed and stripped according to the ExpressHyb Hybridization Solution protocol available from Clontech (Catalog #8015-1).

Results

In 1997, a system was described by a co-inventor of the present invention and others for purification of CA125 primarily from patient ascites fluid, which when followed by cyanogen bromide digestion, resulted in peptide fragments of CA125 of 60 kDa and 40 kDa [O'Brien T J et al., More than 15 years of CA125: What is known about the antigen, its structure and its function, *Int J Biological Markers* 13(4)188-195 (1998)]. Both fragments were identifiable by commassie blue staining on polyacrylamide gels and by Western blot. Both fragments were shown to bind both OC125 and M11 antibodies, indicating both major classes of epitopes were preserved in the released peptides (FIG. 1).

Figure 2:
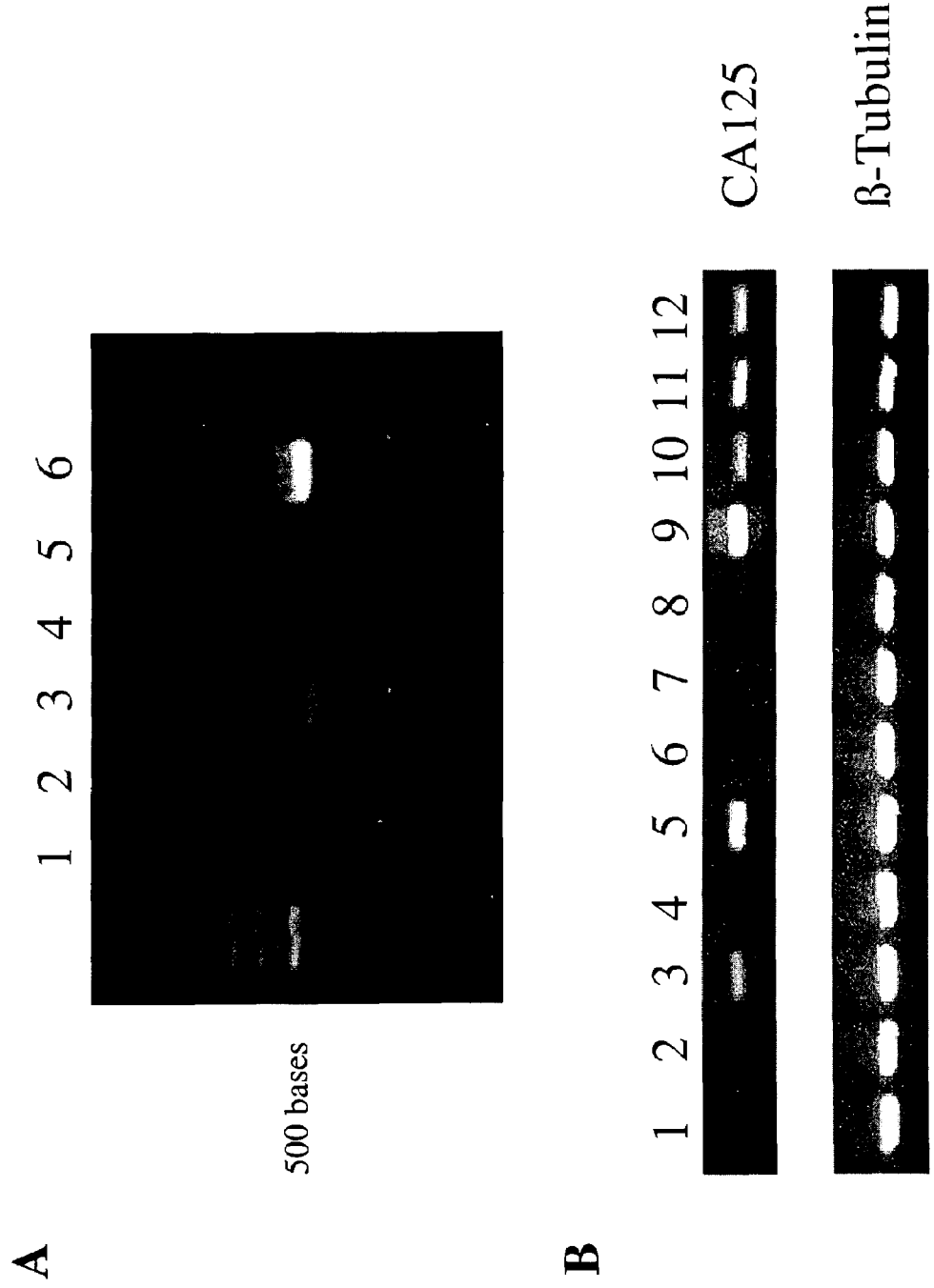
FIG. 2A illustrates PCR amplification of products generated from primers utilizing the EST sequence referred to in FIG. 1, the amino acid sequence obtained from the 40 kDa fragment and EST sequence AA#640762. Lane 1-2: normal; 3: serous ovarian carcinoma; 4: serous ovarian carcinoma; 5: mucinous ovarian carcinoma; 6: β-tubulin control. The anticipated size band 400 b is present in lane 3 and less abundantly in lane 4.
FIG. 2B illustrates the RT-PCR that was performed to determine the presence or absence of CA125 transcripts in primary culture cells of ovarian tumors. This expression was compared to tubulin expression as an internal control. Lanes 1, 3, 5, 7, and 9 represent the primary ovarian tumor cell lines. Lanes 2, 4, 6, and 8 represent peripheral blood mononuclear cell lines derived from the corresponding patients in lanes 1, 3, 5, and 7. Lane 10 represents fibroblasts from the patient tumor in lane 9. Lanes 11 and 12 are CaOV3 and a primary tumor specimen, respectively.

Protein sequencing of the 40 kDa band yielded both amino terminal sequences and some internal sequences generated by protease digestion (Table 1—SEQ ID NOS: 1-4). Insufficient yields of the 60 kDa band resulted in unreliable sequence information. Unfortunately, efforts to amplify PCR products utilizing redundant primers designed to these sequences were not successful. In mid 2000, an EST (#BE005912) was entered into the GCG database, which contained homology to the 40 kDa band sequence as shown in Table 1 (SEQ ID NOS: 5 and 6). The translation of this EST indicated good homology to the amino terminal sequence of the 40 kDa repeat (e.g. residues 2-12 of SEQ ID NO:6) with only one amino acid difference (i.e. an asparagine is present instead of phenylalanine in the EST sequence). Also, some of the internal sequences are partially conserved (e.g. SEQ ID NO: 2 and to a lesser extent, SEQ ID NO: 3 and SEQ ID NO: 4). More importantly, all the internal sequences are preceded by a basic amino acid (Table 1, indicated by arrows) appropriate for proteolysis by the trypsin used to create the internal peptides from the 40 kDa cyanogen bromide repeat. Utilizing the combined sequences, those obtained by amino acid sequencing and those identified in the EST (#BE005912) and a second EST (#AA640762) identified in the database, sense primers were created as follows: 5'-GGA GAG GGT TCT GCA GGG TC-3' (SEQ ID NO: 7) representing amino acids ERVLQG (SEQ ID NO: 8) and anti-sense primer, 5' GTG AAT GGT ATC AGG AGA GG-3' (SEQ ID NO: 9) representing PLLIPF (SEQ ID NO: 10). Using PCR, the presence of transcripts was confirmed representing these sequences in ovarian tumors and their absence in normal ovary and either very low levels or no detectable levels in a mucinous tumor (FIG. 2A). The existence of transcripts was further confirmed in cDNA derived from multiple primary ovarian carcinoma cell lines and the absence of transcripts in matched lymphocyte cultures from the same patient (FIG. 2B).

After cloning and sequencing of the amplified 400 base pair PCR products, a series of sequences were identified, which had high homology to each other but which were clearly distinct repeat entities (FIG. 3) (SEQ ID NOS: 158 through 161).

Examples of each category of repeats were sequenced, and the results are shown in Tables 3, 4, and 5. The sequences represent amplification and sequence data of PCR products obtained using oligonucleotide primers derived from an EST (Genbank Accession No. BE005912). Table 3 illustrates the amino acid sequence for a 400 bp repeat in the CA125 molecule, which is identified as SEQ ID NO: 11 through SEQ ID NO: 21. Table 4 illustrates the amino acid sequence for a 800 bp repeat in the CA125 molecule, which corresponds to SEQ ID NO: 22 through SEQ ID NO: 35. Table 5 illustrates the amino acid sequence for a 1200 bp repeat in the CA125 molecule, which is identified as SEQ ID NO: 36 through SEQ ID NO: 46. Assembly of these repeat sequences (which showed 75-80% homology to each other as determined by GCG Software (GCG—Genetics Computer Group) using the Pileup application) utilizing PCR amplification and sequencing of overlapping sequences allowed for the construction of a 9 repeat structure. The amino acid sequence for the 9 repeat is shown in Table 6 as SEQ ID NO: 47. The individual C-enclosures are highlighted in the table.

Using the assembled repeat sequence in Table 6 to search genebank databases, a cDNA sequence referred to as Genbank Accession No. AK024365 (entered on Sep. 29, 2000) was discovered. Table 7 shows the amino acid sequence for AK024365, which corresponds to SEQ ID NO: 48. AK024365 was found to overlap with two repeats of the assembled repeat sequence shown in Table 6. Individual C-enclosures are highlighted in Table 7.

Figure 6:
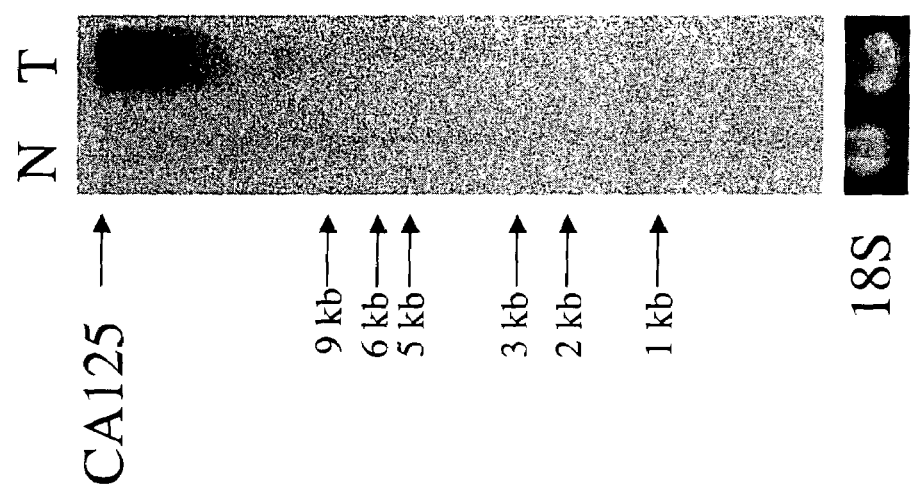
FIG. 6 illustrates a Northern blot analysis of RNA derived from either normal ovary (N) or ovarian carcinoma (T) probed with a $p^{32}$ cDNA repeat sequence of CA125. Total RNA samples (10 μg) were size separated by electrophoresis on a formaldehyde 1.2% agarose gel. After blotting to Hybond N, the lanes were probed with $p^{32}$ radiolabelled 400 bp repeat (see FIG. 2). Lane 1 represents RNA from normal ovarian tissue, and lane 2 represents RNA from serous ovarian tumor tissue.

The cDNA for AK024365 allowed alignment of four additional repeats as well as a downstream carboxy terminus sequence of the CA125 gene. Table 8 illustrates the complete DNA sequence of 13 repeats contiguous with the carboxy terminus of the CA125 molecule, which corresponds to SEQ ID NO: 49. Table 9 illustrates the complete amino acid sequence of the 13 repeats and the carboxy terminus of the CA125 molecule, which corresponds to SEQ ID NO: 50. The carboxy terminus domain was further confirmed by the existence of two EST's (Genbank Accession Nos. AW150602 and A1923224) in the genebank database, both of which confirmed the stop-codon indicated (TGA) as well as the poly A signal sequence (AATAA) and the poly A tail (see Table 9). The presence of these repeats has been confirmed in serous ovarian tumors and their absence in normal ovarian tissue and mucinous tumors as expected (see FIG. 2A). Also, the transcripts for these repeats have been shown to be present in tumor cell lines derived from ovarian tumors, but not in normal lymphocyte cell lines (FIG. 2B). Moreover, Northern blot analysis of mRNA derived from normal or ovarian carcinoma and probed with a $p^{32}$ labeled CA125 repeat sequence (as shown in FIG. 6) confirmed the presence of an RNA transcript in excess of 20 kb in ovarian tumor extracts (see FIG. 2B).

Figure 3:
FIG. 3 illustrates repeat sequences determined by sequencing cloned cDNA from the 400 b band in FIG. 2B. Placing of repeat sequences in a contiguous fashion was accomplished by PCR amplification and sequencing of overlap areas between two repeat sequences. A sample of the complete repeat sequences is shown in SEQ ID NOS: 158, 159, 160, and 161, which was obtained in this manner and placed next to each other based on overlap sequences. The complete list of repeat sequences that was obtained is shown in Table 21 (SEQ ID NO: 162).

To date, 45 repeat sequences have been identified with high homology to each other. To order these repeat units, overlapping sequences were amplified using a sense primer (5' GTC TCT ATG TCA ATG GTT TCA CCC-3') (SEQ ID NO: 305) from an upstream repeat and an antisense primer from a downstream repeat sequence (antisense 5' TAG CTG CTC TCT GTC CAG TCC-3') (SEQ ID NO: 306). Attempts have been made to place these repeats in a contiguous fashion as shown in FIG. 3. There is some potential redundancy. Further, there is evidence from overlapping sequences that some repeats exist in more than one location in the sequence giving a total of more than 60 repeats in the CA125 molecule (see Table 21 SEQ ID NO: 162).

Final confirmation of the relationship of the putative CA125 repeat domain to the known CA125 molecule was achieved by expressing a recombinant repeat domain in E. coli. In FIG. 4, expression of a recombinant CA125 repeat domain is shown in lane 2 compared to the vector alone in lane 1, Panel D. A series of Western blots representing E. coli extracts of vector alone in lane 1; CA125 recombinant protein lane in 2 and recombinant TADG-14 (an unrelated recombinant protease), lane 3, were probed with the CA125 antibodies M11, Panel A; OC125, Panel B; and ISOBM 9.2, Panel C. In all cases, CA125 antibodies recognized only the recombinant CA125 antigen (lane 2 of each panel).

Figure 5:
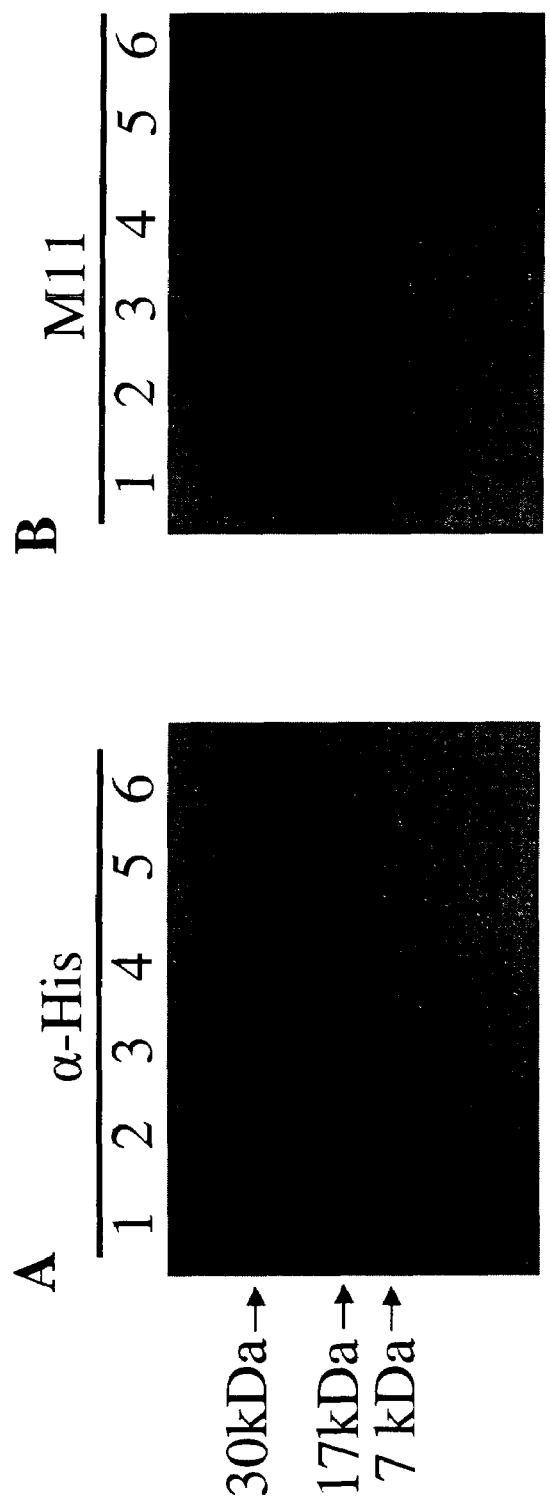
FIG. 5 represents Western blots of the CA125 repeat sequence that were generated to determine the position of the M11 epitope within the recombinant CA125 repeat. The expressed protein was bound to Ni-NTA agarose beads. The protein was left undigested or digested with Asp-N or Lys-C. The protein remaining bound to the beads was loaded into lanes 1, 2, or 3 corresponding to undigested, Asp-N digested and Lys-C digested, respectively. The supernatants from the digestions were loaded in lanes 4, 5, and 6 corresponding to undigested, Asp-N digested and Lys-C digested, respectively. The blots were probed with either anti-His tag antibody (A) or M11 antibody (B). Panel C shows a typical repeat sequence corresponding to SEQ ID NO: 150 with each exon defined by arrows. All proteolytic aspartic acid and lysine sites are marked with overhead arrow or dashes. In the lower panel, the O-glycosylation sites in exons 4 and 5 are marked with O, the N-glycosylation sites are marked with X plus the amino acid number in the repeat (#12, 33, and 49) the conserved methionine is designated with M plus the amino acid number (M#24), and the cysteine enclosure which is also present in all repeats and encompasses 19 amino acids between the cysteines is marked with C—C (amino acids #59-79). The epitopes for M11 and OC125 are located in the latter part of the C-enclosure or downstream from the C-enclosure.

To further characterize the epitope location of the CA125 antibodies, recombinant CA125 repeat was digested with the endoprotease Lys-C and separately with the protease Asp-N. In both cases, epitope recognition was destroyed. As shown in FIG. 5, the initial cleavage site for ASP-N is at amino acid #76 (indicated by arrow in FIG. 5C). This sequence (amino acids #1-76), a 17 kDa band, was detected with anti-histidine antibodies (FIG. 5A,Lane 3) and found to have no capacity to bind CA125 antibodies (FIG. 5B, Lane 3). The upper bands in FIGS. 5A and 5B represent the undigested remaining portion of the CA125 recombinant repeat. From these data, one can reasonably conclude that epitopes are either located at the site of cleavage and are destroyed by Asp-N or are downstream from this site and also destroyed by cleavage. Likewise, cleavage with Lys-C would result in a peptide, which includes amino acids #68-154 (FIG. 5C) and again, no antibody binding was detected. In view of the foregoing, it seems likely that epitope binding resides in the cysteine loop region containing a possible disulfide bridge (amino acids #59-79). Final confirmation of epitope sites are being examined by mutating individual amino acids.

To determine transcript size of the CA125 molecule, Northern blot analysis was performed on mRNA extracts from both normal and tumor tissues. In agreement with the notion that CA125 may be represented by an unusually large transcript due to its known mega dalton size in tumor sera, ascites fluid, and peritoneal fluid [Nustad K et al., CA125—epitopes and molecular size, *Int. J of Biolog. Markers,* 13(4)196-199 (1998)], a transcript was discovered which barely entered the gel from the holding well (FIG. 6). CA125 mRNA was only present in the tumor RNA sample and while a precise designation of its true size remains difficult due to the lack of appropriate standards, its unusually large size would accommodate a protein core structure in excess of 11,000 amino acids.

Evidence demonstrates that the repeat domain of the CA125 molecule encompasses a minimum of 45 different 156 amino acid repeat units and possibly greater than 60 repeats, as individual repeats occur more than once in the sequence. This finding may well account for the extraordinary size of the observed transcript. The amino acid composition of the repeat units (FIGS. 7A, 7C, Table 21) indicates that the sequence is rich in serine, threonine, and proline typical of the high STP repeat regions of the mucin genes [Gum Jr., J R, Mucin genes and the proteins they encode: Structure, diversity and regulation, *Am J Respir. Cell Mol. Biol.* 7:557-564 (1992)]. Results suggest that the downstream end of the repeat is heavily glycosylated.

Figure 7A:
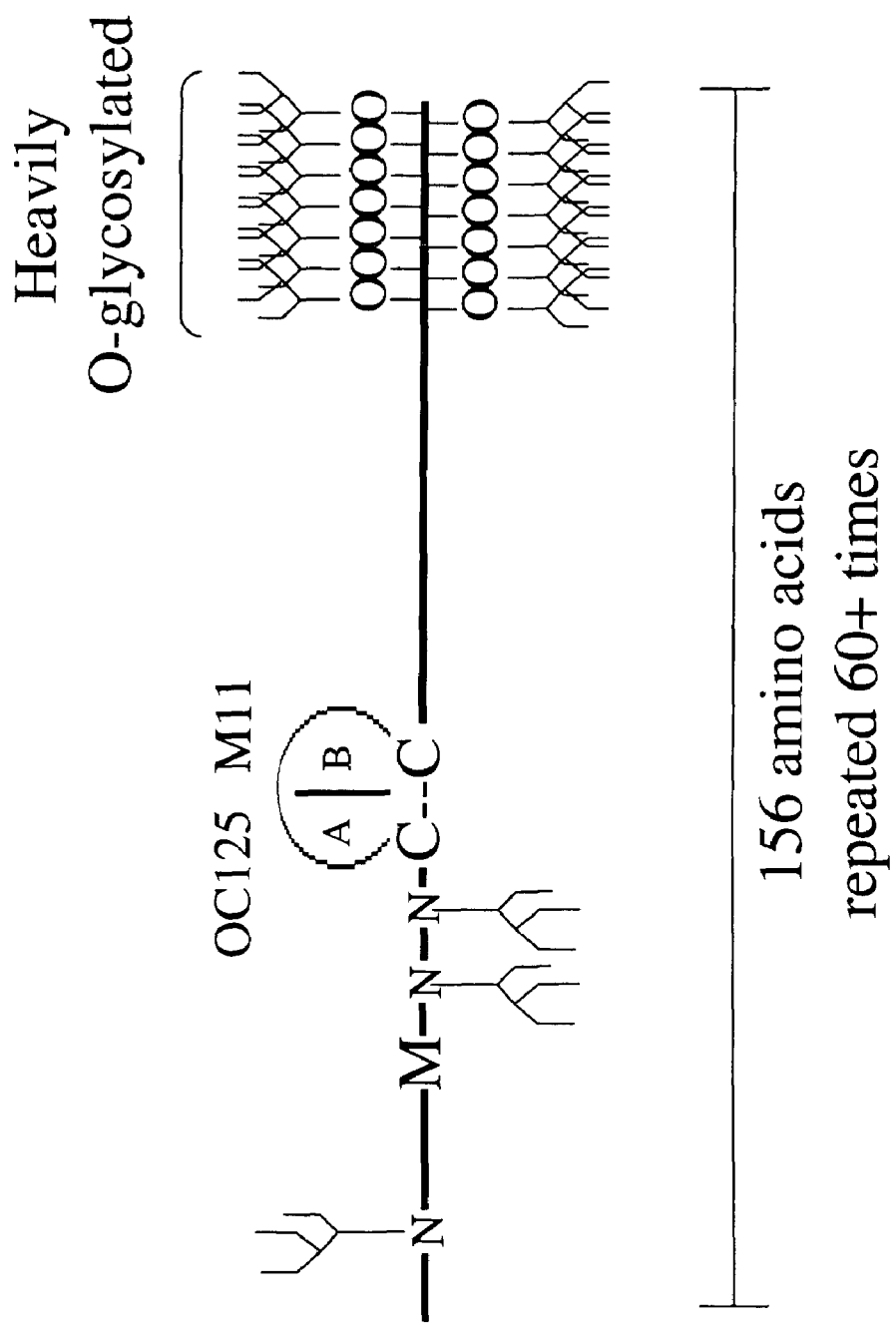
FIG. 7A is a schematic diagram of a typical repeat unit for CA125 showing the N-glycosylation sites at the amino end and the totally conserved methionine (M). Also shown is the proposed cysteine enclosed loop with antibody binding sites for OC125 and M11. Also noted are the highly O-glycosylated residues at the carboxy end of the repeat.

Also noteworthy is a totally conserved methionine at position 24 of the repeat (FIGS. 7A, 7C). It is this methionine which allowed cyanogen bromide digestion of the CA125 molecule, resulting in the 40 kDa glycopeptide that was identified with OC125 and M11 antibodies in Western blots of the CNBr digested peptides. These data predict that the epitopes for the CA125 antibodies are located in the repeat sequence. By production of a recombinant product representing the repeat sequence, results have confirmed this to be true. A potential disulfide bond is noted, which would encompass a C-enclosure comprising 19 amino acids enclosed by two cysteines at positions #59 and #79. The cysteines are totally conserved, which suggest a biological role for the resulting putative C-enclosure in each repeat. As mentioned above, it is likely that the OC125 and M11epitopes are located in the C-enclosure, indicating its relative availability for immune detection. This is probably due to the C-enclosure structure and the paucity of glycosylation in the immediate surrounding areas. Domain searches also suggest some homology in the repeat domain to an SEA domain commonly found in the mucin genes [Williams S J et al., MUC13, a novel human cell surface mucin expressed by epithelial and hemopoietic cells, *J of Biol. Chem* 276(21)18327-18336 (2001)] beginning at amino acid #1 and ending at #131 of each repeat. No biological function has been described for this domain.

Based on homology of the repeat sequences to chromosome 19q 13.2 (cosmid #AC008734) and confirmed by genomic amplification, it has been established that each repeat is comprised of 5 exons (covering approximately 1900 bases of genomic DNA): exon 1 comprises 42 amino acids (#1-42); exon 2 comprises 23 amino acids (#43-65); exon 3 comprises 58 amino acids (#66-123); exon 4 comprises 12 amino acids (#124-135); and exon 5 comprises 21amino acids (#136-156) (see FIG. 7B). Homology pile-ups of individual exons have also been completed (see FIG. 7C), which indicates that exon 1 has a minimum of 3 different copies of the exon; exon 2 has 27 copies; exon 3 has 28 copies, exon 4 has 28 copies and exon 5 has 21 copies. If all exons were only found in a single configuration relative to each other, one could determine that a minimum number of repeats of 31 were present in the CA125 molecule. Using the exon 2 pile-up data as an example, it has been established as mentioned above that there are 27 individual exon 2 sequences. Using exon 2, which was sequenced fully in both the repeat units and the overlaps, results established that a minimum of 45 repeat units are present when exon 2 is combined with unique other exon combinations. However, based on overlap sequence information, 60+ repeat units are likely present in the CA125 molecule (Table 21). This larger number of repeat units can be accounted for by the presence of the same repeat unit occurring in more than one location.

Currently, the repetitive units of the repeat domain of the CA125 molecule constitute the majority of its extracellular molecular structure. These sequences have been presented in a tandem fashion based on overlap sequencing data. Some sequences may be incorrectly placed and some repeat units may not as yet be identified (Table 21). More recently, an additional repeat was identified in CA125 as shown in Tables 22 and 23 (SEQ. ID NOS: 307 and 308). The exact position has not yet been identified. Also, there is a potential that alternate splicing and/or mutation could account for some of the repeat variants that are listed. Studies are being conducted to compare both normal tissue derived CA125 repeats to individual tumor derived CA125 repeats to determine if such variation is present. Currently, the known exon configurations would easily accommodate the greater than 60 repeat units as projected. It is, therefore, unlikely that alternate splicing is a major contributor to the repetitive sequences in CA125. It should also be noted that the genomic database for chromosome 19q 13.2 only includes about 10 repeat units, thus indicating a discrepancy between the data of the present invention (more than 60 repeats) and the genomic database. A recent evaluation of the methods used for selection and assembly for genomic sequence [Marshall E, DNA Sequencing: Genome teams adjust to shotgun marriage, *Science* 292:1982-1983 (2001)] reports that "more research is needed on repeat blocks of almost identical DNA sequence which are more common in the human genome. Existing assembly programs can't handle them well and often delete them." The CA125 repeat units located on chromosome 19 may well be victims of deletion in the genomic database, thus accounting for most CA125 repeat units absent from the current databases.

A. Sequence Confirmation and Assembly of the Amino Terminal Domain (Domain 1) of the CA125 Molecule As previously mentioned, homology for repeat sequences was found in the chromosome 19 cosmid AC008734 of the GCG database. This cosmid at the time consisted of 35 unordered contigs. After searching the cosmid for repeat sequences, contig #32 was found to have exons 1 and 2 of a repeat unit at its 3' end. Contig #32 also had a large open reading frame upstream from the two repeat units, which suggested that this contig contained sequences consistent with the amino terminal end of the CA125 molecule. A sense primer was synthesized to the upstream non-repeat part of contig #32 coupled with a specific primer from within the repeat region (see Methods). PCR amplification of ovarian tumor cDNA confirmed the contiguous positioning of these two domains.

The PCR reaction yielded a band of approximately 980 bp. The band was sequenced and found to connect the upstream open reading frame to the repeat region of CA125. From these data, more primer sets (see Methods) were synthesized and used in PCR reactions to piece together the entire open reading frame contained in contig #32. To find the 5' most end of the sequence, an EST (AU133673) was discovered, which linked contig #32 to contig #7 of the same cosmid. Specific primers were synthesized, (5'-CTGATG-GCATTATGGAACACATCAC-3' (SEQ ID NO: 59) and 5'-CCCAGAACGAGAGACCAGTGAG-3' (SEQ ID NO: 60)), to the EST and contig #32. A PCR reaction was performed to confirm that part of the EST sequence was in fact contiguous with contig #32. Confirmation of this contiguous 5' prime sequencing strategy using overlapping sequences allowed the assembly of the 5' region (Domain 1) (FIG. 8A). 5' RACE PCR was performed on tumor cDNA to confirm the amino terminal sequence to CA125. The test confirmed the presence of contig #7 sequence at the amino terminal end of CA125.

Figure 8A:
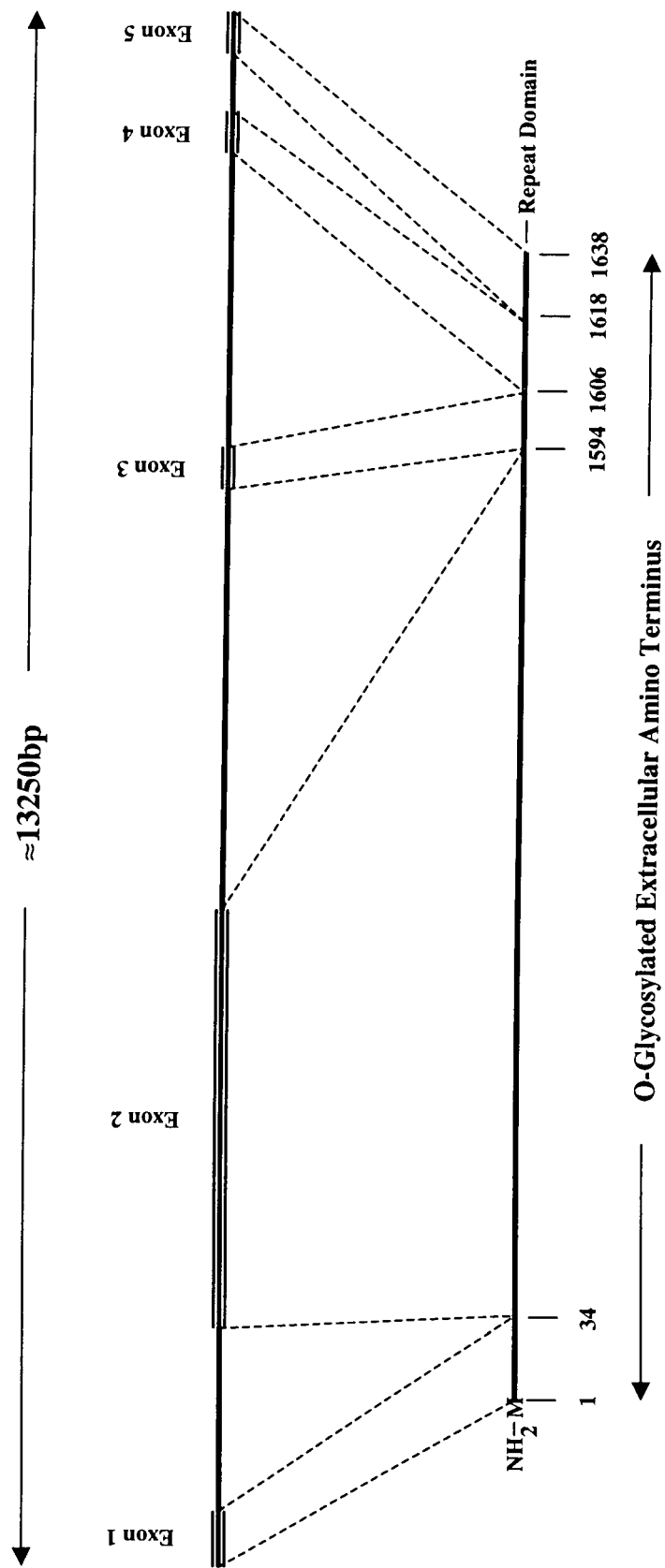
FIG. 8A shows the genomic structure of the amino terminal end of the CA125 gene. It also indicates the amino composition of each exon in the extracellular domain.

The amino terminal domain comprises five genomic exons covering approximately 13,250 bp. Exon 1, a small exon, (amino acids #1-33) is derived from contig #7 (FIG. 8A). The remaining exons are all derived from contig #32: Exon 2 (amino acids #34-1593), an extraordinarily large exon, Exon 3 (amino acids #1594-1605), Exon 4 (amino acids #1606-1617) and Exon 5 (amino acids #1618-1637) (see FIG. 8A).

Potential N-glycosylation sites marked (x) are encoded at positions #81, #271, #320, #624, #795, #834, #938, and #1,165 (see FIG. 8B). O-glycosylation sites are extraordinarily abundant and essentially cover the amino terminal domain (FIG. 8B). As shown by the O-glycosylation pattern, Domain 1 is highly enriched in both threonine and serine (FIG. 8B).

B. Sequence Confirmation and Assembly of the CA125 Carboxy Terminal End (Domain 3)

Figure 9A:
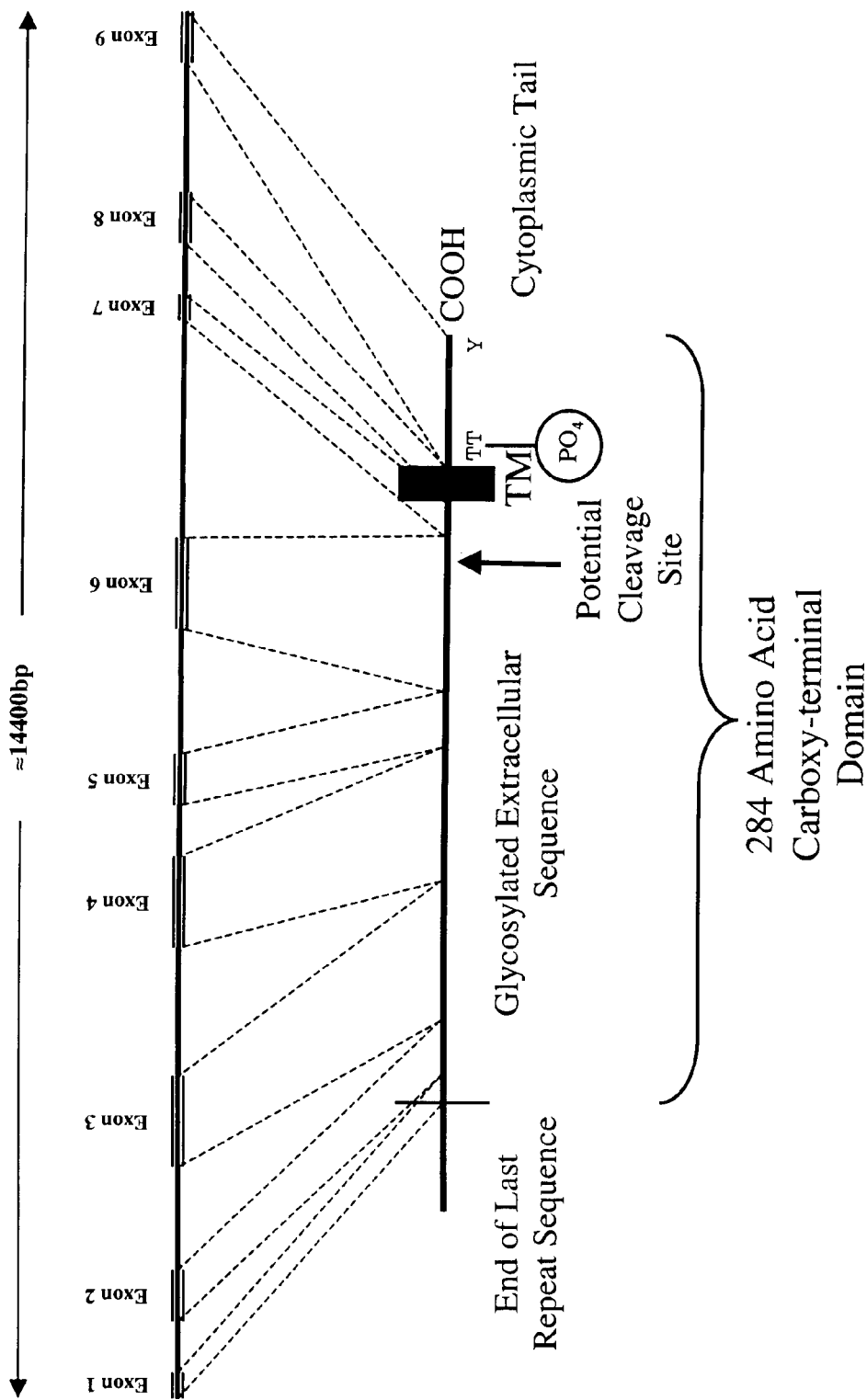
FIG. 9A illustrates the genomic exon structure of the carboxy-terminal domain of the CA125 gene. It includes a diagram showing the extracellular portion, the potential cleavage site, the transmembrane domain and the cytoplasmic tail.

A search of Genbank using the repeat sequences described above uncovered a cDNA sequence referred to as Genbank accession number AK024365. This sequence was found to have 2 repeat sequences, which overlapped 2 known repeat sequences of a series of 6 repeats. As a result, the cDNA allowed the alignment of all six carboxy terminal repeats along with a unique carboxy terminal sequence. The carboxy terminus was further confirmed by the existence of two other ESTs (Genbank accession numbers AW150602 and A1923224), both of which confirmed a stop codon as well as a poly-A signal sequence and a poly-A tail (see GCG database #AF414442). The sequence of the carboxy terminal domain was confirmed using primers designed to sequence just downstream of the repeat domain (sense primer 5' GGA CAA GGT CAC CAC ACT CTA C-3') (SEQ ID NO: 303) and an antisense primer (5'-GCA GAT CCT CCA GGT CTA GGT GTG-3') (SEQ ID NO: 304) designed to carboxy terminus (FIG. 9A).

The carboxy terminal domain covers more than 14,000 genomic bp. By ligation, this domain comprises nine exons as shown in FIG. 9A. The carboxy-terminus is defined by a 284 amino acid sequence downstream from the repeat domains (see FIG. 9B). Both N-glycosylation sites marked (x) (#31, #64, #103, #140, #194, #200) and a small number of O-glycosylation sites marked (o) are predicted for the carboxy end of the molecule (FIGS. 9A, 9B). Of special note is a putative transmembrane domain at positions #230-#252 followed by a cytoplasmic domain, which is characterized by a highly basic sequence adjacent to the membrane (#256-#260) as well as several potential S/T phosphorylation sites (#254, #255, #276) and tyrosine phosphorylation sites (at #264, #273, #274) (FIGS. 9A, 9B).

Figure 10:
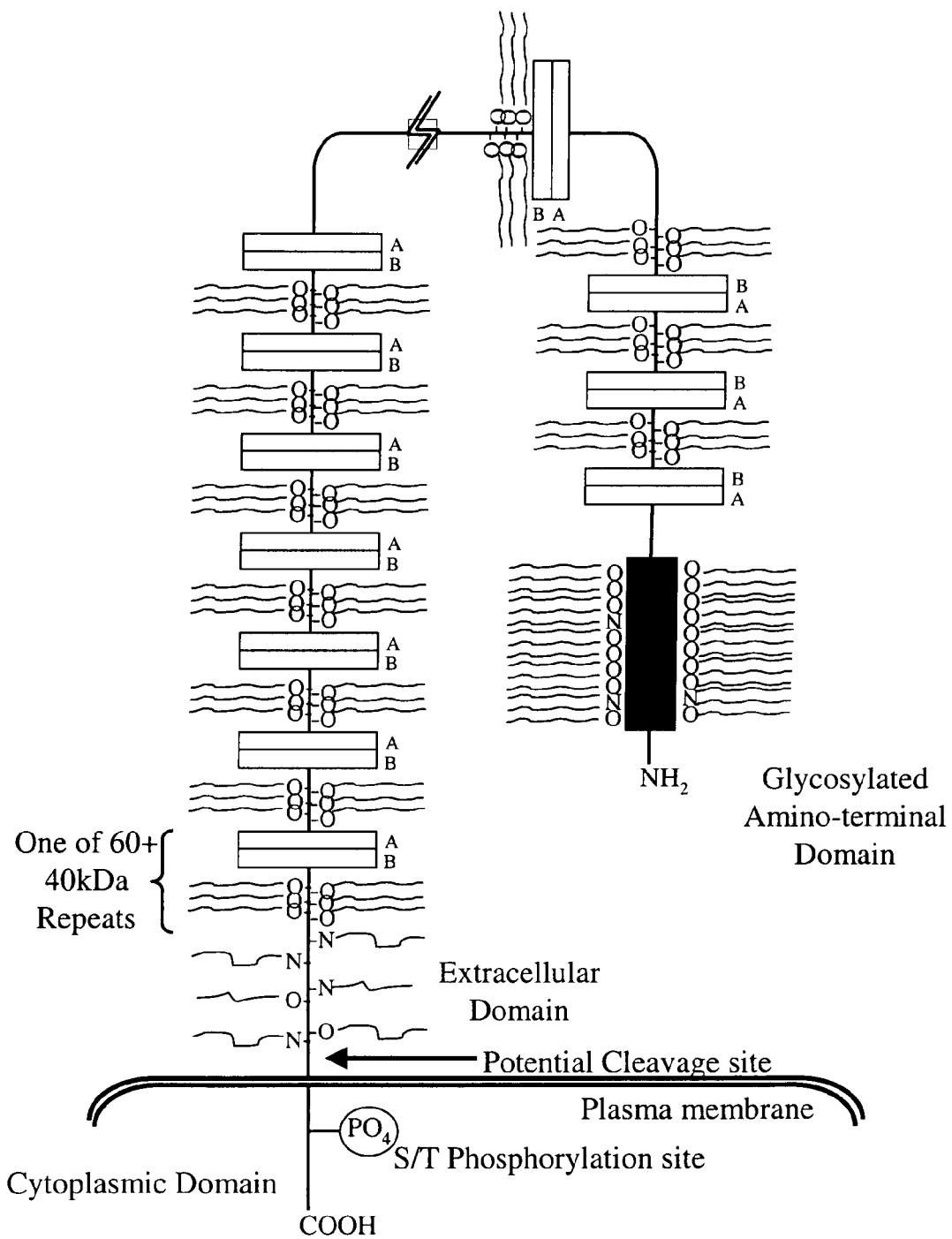
FIG. 10 illustrates the proposed structure of the CA125 molecule based on the open reading frame sequence described herein. As shown, the molecule is dominated by a major repeat domain in the extracellular space along with a highly glycosylated amino terminal repeat. The molecule is anchored by a transmembrane domain and also includes a cytoplasmic tail with potential for phosphorylation.

Assembly of the CA125 molecule as validated by PCR amplification of overlap sequence provides a picture of the whole molecule (see FIG. 10 and Table 21). The complete nucleotide sequence is available in Genebank, Accession #AF414442 and the amino acid sequence as currently aligned is shown in Table 21.

Discussion

The CA125 molecule comprises three major domains; an extracellular amino terminal domain (Domain 1), a large multiple repeat domain (Domain 2) and a carboxy terminal domain (Domain 3), which includes a transmembrane anchor with a short cytoplasmic domain (FIG. 10). The amino terminal domain is assembled by combining five genomic exons, four very short amino terminal sequences and one extraordinarily large exon, which often typifies mucin extracellular glycosylated domains [Desseyn J L et al., Human mucin gene MUC5B, the 10.7-kb large central exon encodes various alternate subdomains resulting in a super-repeat. Structural evidence for a 11 p 15.5 gene family, *J. Biol. Chem.* 272(6):3168-3178 (1997)]. This domain is dominated by its capacity for O-glycosylation and its resultant richness in serine and threonine residues. Overall, the potential for O-glycosylation essentially covers this domain and, as such, may allow the carbohydrate superstructure to influence ECM interaction at this end of the CA125 molecule (FIG. 8). There is one short area (amino acids #74-120) where little or no glycosylation is predicted, which could allow for protein-protein interaction in the extracellular matrix.

Efforts to purify CA125 over the years were obviously complicated by the presence of this amino terminal domain, which is unlikely to have any epitope sites recognized by the OC125 or M11 class antibodies. As the CA125 molecule is degraded in vivo, it is likely that this highly glycosylated amino terminal end will be found associated with varying numbers of repeat units. This could very well account for both the charge and size heterogeneity of the CA125 molecule so often identified from serum and ascites fluid. Also of note are two T-TALK sequences at amino acids #45-58 (underlined in FIG. 8B), which are unique to the CA125 molecule.

The extracellular repeat domain, which characterizes the CA125 molecule, also represents a major portion of the molecular structure. It is downstream from the amino terminal domain and presents itself in a much different manner to its extracellular matrix neighbors. These repeats are characterized by many features including a highly-conserved nature (FIG. 3) and a uniformity in exon structure (FIG. 7). But most consistently, a cysteine enclosed sequence may form a cysteine loop (Table 21). This structure may provide extraordinary potential for interaction with neighboring matrix molecules. Domain 2 encompasses the 156 amino acid repeat units of the CA125 molecule. The repeat domain constitutes the largest proportion of the CA125 molecule (Table 21 and FIG. 10). Because it has been known for more than 15 years that antibodies bind in a multivalent fashion to CA125, it has been predicted that the CA125 molecule would include multiple repeat domains capable of binding the OC125 and M11 class of sentinel antibodies which define this molecule [O'Brien et al., New monoclonal antibodies identify the glycoprotein carrying the CA125 epitope, *Am J Obstet Gynecol.* 165:1857-1964 (1991); Nustad K et al., Specificity and affinity of 26 monoclonal antibodies against the CA125 antigen: First report from the ISOBM TD-1 workshop, *Tumor Biology* 17:196-219 (1996); and Bast R C et al., A radioimmunoassay using a monoclonal antibody to monitor the course of epithelial ovarian cancer, *N. Engl. J. Med.* 309:883-887 (1983)]. In the present invention, more than 60 repeat units have been identified, which are in tandem array in the extracellular portion of the CA125 molecule. Individual repeat units have been confirmed by sequencing and further identified by PCR amplification of the overlapping repeat sequences. Results confirm the contiguous placement of most repeats relative to its neighbor (Table 21).

Initial evidence suggests that this area is a potential site for antibody binding and also for ligand binding. The highly conserved methionine and several highly conserved sequences within the repeat domain also suggests a functional capacity for these repeat units. The extensive glycosylation of exons 4 & 5 of the repeat unit and the N-glycosylation potential in exon 1 and the 5' end of exon 2 might further point to a functional capacity for the latter part of exon 2 and exon 3 which includes the C-enclosure (see FIG. 7). It should be apparent that the C-enclosure might be a prime target for protease activity and such cleavage may well explain the difficulty experienced by many investigators in obtaining an undigested CA125 parent molecule. Such activity might explain the diffuse pattern of antibody binding and the loss of antibody binding for molecules of less than 200,000 kDa. Proteolysis would destroy the epitopes and, therefore, only multiple repeats could be identified by blotting with CA125 antibodies. The repeat unit organization also suggests the potential for a multivalent interaction with extracellular entities.

The carboxy terminal domain of the CA125 molecule comprises an extracellular domain, which does not have any homology to other known domains. It encodes a typical transmembrane domain and a short cytoplasmic tail. It also contains a proteolytic cleavage site approximately 50 amino acids upstream from the transmembrane domain. This would allow for proteolytic cleavage and release of the CA125 molecule (FIG. 9). As indicated by Fendrick, et al. [CA125 phosphorylation is associated with its secretion from the WISH human amnion cell line, *Tumor Biology* 18:278-289 (1997)], release of the CA125 molecule is preceded by phosphorylation and sustained by inhibitors of phosphatases, especially inhibition of phosphatase 2B. The cytoplasmic tail which contains S/T phosphorylation sites next to the transmembrane domain and tyrosine phosphorylation sites downstream from there could accommodate such phosphorylation. A very distinguishable positively charged sequence is present upstream from the tyrosine, suggesting a signal transduction system involving negatively charged phosphate groups and positively charged lysine and arginine groups.

These features of the CA125 molecule suggest a signal transduction pathway involvement in the biological function of CA125 [Fendrick J L et al., CA125 phosphorylation is associated with its secretion from the WISH human amnion cell line, *Tumor Biology* 18:278-289 (1997); and Konish I et al, Epidermal growth factor enhances secretion of the ovarian tumor-associated cancer antigen CA125 from the human amnion WISH cell line, *J Soc. Gynecol. Invest.* 1:89-96 (1994)]. It also reinforces the prediction of phosphorylation prior to CA125 release from the membrane surface as previously proposed [Fendrick J L et al., CA125 phosphorylation is associated with its secretion from the WISH human amnion cell line, *Tumor Biology* 18:278-289 (1997); and Konish I et al., Epidermal growth factor enhances secretion of the ovarian tumor-associated cancer antigen CA125 from the human amnion WISH cell line, *J Soc. GynecoL Invest.* 1:89-96 (1994)]. Furthermore, a putative proteolytic cleavage site on the extra-cellular side of the transmembrane domain is present at position #176-181.

How well does the CA125 structure described in the present invention compare to the previously known CA125 structure? O'Brien et al. reported that a number of questions needed to be addressed: 1) the multivalent nature of the molecule; 2) the heterogeneity of CA125; 3) the carbohydrate composition; 4) the secretory or membrane bound nature of the CA125 molecule; 5) the function of the CA125 molecule; and 6) the elusive CA125 gene [More than 15 years of CA125: What is known about the antigen, its structure and its function, *Int J Biological Markers* 13(4) 188-195 (1998)]. Several of these questions have been addressed in the present invention including, of course, the gene and its protein core product. Perhaps, most interestingly is the question of whether an individual large transcript accounted for the whole CA125 molecule, or a number of smaller transcripts which represented subunits that specifically associated to produce the CA125 molecule. From the results produced by way of the present invention, it is now apparent that the transcript of CA125 is large—similar to some of the mucin gene transcripts e.g. MUC 5B [see Verma M et al., Mucin genes: Structure, expression and regulation, *Glycoconjugate J.* 11:172-179 (1994); and Gendler S J et al., Epithelial mucin genes, *Annu. Rev. Physiol.* 57:607-634 (1995)]. The protein core extracellular domains all have a high capacity for O-glycosylation and, therefore, probably accounts for the heterogeneity of charge and size encountered in the isolation of CA125. The data also confirm the O-glycosylation inhibition data, indicating CA125 to be rich in O-glycosylation [Lloyd K O et al., Synthesis and secretion of the ovarian cancer antigen CA125 by the human cancer cell line NIH: OVCAR-3, *Tumor Biology* 22, 77-82 (2001); Lloyd K O et al., Isolation and characterization of ovarian cancer antigen CA125 using a new monoclonal antibody (VK-8): Identification as a mucin-type molecule, *Int. J. Cancer,* 71:842-850 (1997); and Fendrick J L et al., Characterization of CA125 synthesized by the human epithelial amnion WISH cell line, *Tumor Biology* 14:310-318 (1993)].

The repeat domain which includes more than 60 repeat units accounts for the multivalent nature of the epitopes present, as each repeat unit likely contains epitope binding sites for both OC125-like antibodies and M11-like antibodies. The presence of a transmembrane domain and cleavage site confirms the membrane association of CA125, and reinforces the data which indicates a dependence of CA125 release on proteolysis. Also, the release of CA125 from the cell surface may well depend on cytoplasmic phosphorylation and be the result of EGF signaling [Nustad K et al., Specificity and affinity of 26 monoclonal antibodies against the CA125 antigen: First report from the ISOBM TD-1 workshop, *Tumor Biology* 17:196-219 (1996)]. As for the question of inherent capacity of CA125 for proteolytic activity, this does not appear to be the case. However, it is likely that the associated proteins isolated along with CA125 (e.g. the 50 kDa protein which has no antibody binding ability) may have proteolytic activity. In any case, proteolysis of an extracellular cleavage site is the most likely mechanism of CA125 release. Such cleavage would be responsive to cytoplasmic signaling and mediated by an associated extracellular protease activity.

In summary, the large number of tandem repeats of the CA125 molecule, which dominate its molecular structure and contain the likely epitope binding sites of the CA125 molecule, was unexpected. Also, one cannot as yet account for the proteolytic activity, which has plagued the isolation and characterization of this molecule for many years. While no protease domain per se is constituitively part of the CA125 molecule, there is a high likelihood of a direct association by an extracellular protease with the ligand binding domains of the CA125 molecule. Finally, what is the role of the dominant repeat domain of this extracellular structure? Based on the expression data of CA125 on epithelial surfaces and in glandular ducts, it is reasonable to conclude that the unique structure of these repeat units with their cysteine loops plays a role both as glandular anti-invasive molecules (bacterial entrapment) and/or a role in anti-adhesion (maintaining patency) between epithelial surfaces and in ductal linings.

Recently, Yin and Lloyd described the partial cloning of the CA125 antigen using a completely different approach to that described in the present invention [Yin T W T et al., Molecular cloning of the CA125 ovarian cancer antigen. Identification as a new mucin (MUC16), *J Biol. Chem.* 276:27371-27375 (2001)]. Utilizing a polyclonal antibody to CA125 to screen an expression library of the ovarian tumor cell line OVCAR-3, these researchers identified a 5965 bp clone containing a stop codon and a poly A tail, which included nine partially conserved tandem repeats followed by a potential transmembrane region with a cytoplasmic tail. The 5965 bp sequence is almost completely homologous to the carboxy terminus region shown in Table 21. Although differing in a few bases, the sequences are homologous. As mentioned above, the cytoplasmic tail has the potential for phosphorylation and a transmembrane domain would anchor this part of the CA125 molecule to the surface of the epithelial or tumor cell. In the extracellular matrix, a relatively short transition domain connects the transmembrane anchor to a series of tandem repeats—in the case of Yin and Lloyd, nine.

By contrast, the major extracellular part of the molecule of the present invention as shown is upstream from the sequence described by Yin and includes a large series of tandem repeats. These results, of course, provide a different picture of the CA125 molecule, which suggest that CA125 is dominated by the series of extracellular repeats. Also included is a major amino terminal domain (~1638 amino acids) for the CA125 molecule, which it is believed accounts for a great deal of the O-glycosylation known to be an important structural component of CA125.

In conclusion, a CA125 molecule is disclosed which requires a transcript of more than 35,000 bases and occupies approximately 150,000 bp on chromosome 19q 13.2. It is dominated by a large series of extracellular repeat units (156 amino acids), which offer the potential for molecular interactions especially through a highly conserved unique cysteine loop. The repeat units also include the epitopes now well-described and classified for both the major class of CA125 antibodies (i.e., the OC125 and the M11 groups). The CA125 molecule is anchored at its carboxy terminal through a transmembrane domain and a short cytoplasmic tail. CA125 also contains a highly glycosylated amino terminal domain, which includes a large extracellular exon typical of some mucins. Given the massive repeat domain presence of both epithelial surfaces and ovarian tumor cell surfaces, it might be anticipated that CA125 may play a major role in determining the extracellular environment surrounding epithelial and tumor cells.

Advantages and Uses of the CA125 Recombinant Products

1) Current assays to CA125 utilize as standards either CA125 produced from cultured cell lines or from patient ascites fluid. Neither source is defined with regard to the quality or purity of the CA125 molecule. Therefore arbitrary units are used to describe patient levels of CA125. Because cut-off values are important in the treatment of patients with elevated CA125 and because many different assay systems are used clinically to measure CA125, it is relevant and indeed necessary to define a standard for all CA125 assays. Recombinant CA125 containing epitope binding sites could fulfill this need for standardization. Furthermore, new and more specific assays may be developed utilizing recombinant products for antibody production.

2) Vaccines: Adequate data now exists [see Wagner U et al., Immunological consolidation of ovarian carcinoma recurrences with monoclonal anti-idiotype antibody ACA125: Immune responses and survival in palliative treatment, *Clin. Cancer Res.* 7:1112-1115 (2001)], which suggest and support the idea that CA125 could be used as a therapeutic vaccine to treat patients with ovarian carcinoma. Heretofore, in order to induce cellular and humoral immunity in humans to CA125, murine antibodies specific for CA125 were utilized in anticipation of patient production of anti-ideotypic antibodies, thus indirectly allowing the induction of an immune response to the CA125 molecule. With the availability of recombinant CA125, especially domains which encompass epitope binding sites for known murine antibodies and domains directly anchoring CA125 on the tumor cell, it will be feasible to more directly stimulate patients' immune systems to CA125 and as a result, extend the life of ovarian carcinoma patients as demonstrated by Wagner et al.

Several approaches can be utilized to achieve such a therapeutic response in the immune system by: 1) directly immunizing the patient with recombinant antigen containing the CA125 epitopes or other domains; 2) harvesting dendritic cells from the patient; 3) expanding these cells in in vitro culture; 4) activating the dendritic cells with the recombinant CA125 epitope domain or other domains or with peptides derived from these domains [see Santin A D et al., Induction of ovarian tumor-specific CD8+cytotoxic T lymphocytes by acid-eluted peptide-pulsed autologous dendritic cells, *Obstetrics & Gynecology* 96(3):422-430 (2000)]; and then 5) returning these immune stem cells to the patient to achieve an immune response to CA125. This procedure can also be accomplished using specific peptides which are compatible with histocompatibility antigens of the patient. Such peptides compatible with the HLA-A2 binding motifs common in the population are indicated in FIG. 12.

3) Therapeutic Targets: Molecules, which are expressed on the surface of tumor cells as CA125 is, offer potential targets for immune stimulation, drug delivery, biological modifier delivery or any agent which can be specifically delivered to ultimately kill the tumor cells. CA125 offers such potential as a target: 1) Antibodies to CA125 epitopes or newly described potential epitopes: Most especially humanized or human antibodies to CA125 which could directly activate the patients' immune system to attack and kill tumor cells. Antibodies could be used to deliver all drug or toxic agents including radioactive agents to mediate direct killing of tumor cells. 2) Natural ligands: Under normal circumstances, molecules are bound to the CA125 molecule e.g. a 50 k dalton protein which does not contain CA125 epitopes co-purifies with CA125. Such a molecule, which might have a natural binding affinity for domains on the CA125 molecule, could also be utilized to deliver therapeutic agents to tumor cells.

4) Anti-sense therapy: CA125 expression may provide a survival or metastatic advantage to ovarian tumor cells as such antisense oligonucleotide derived from the CA125 sequence could be used to down-regulate the expression of CA125. Antisense therapy could be used in association with a tumor cell delivery system such as described above.

5) Small Molecules: Recombinant domains of CA125 also offer the potential to identify small molecules which bind to individual domains of the molecule. Small molecules either from combinatorial chemical libraries or small peptides can also be used as delivery agents or as biological modifiers.

All references referred to herein are hereby incorporated by reference in their entirety.

It should be understood that various changes and modifications to the presently preferred embodiments described herein will be apparent to those skilled in the art. Such changes and modifications can be made without departing from the spirit and scope of the present invention and without diminishing its attendant advantages.

TABLE 1

Comparison of the Amino Acid Terminal Sequences and Several Internal Sequences for the 40 kD Band for CA125 glycoprotein (SEQ ID NO: 1 through SEQ ID NO: 4) to the Nucleotide and Amino Acid Sequences for EST Genbank Accession No. AA640762 (SEQ ID NO: 5 and SEQ ID NO: 6, respectively)

40 kDa Nterm - QHPGSRKFKTTEG　　　　(SEQ ID NO: 1)

Peak 68 - FLTVERVLQGL　　　　(SEQ ID NO: 2)

TABLE 1-continued

Comparison of the Amino Acid Terminal Sequences and Several Internal Sequences
for the 40 kD Band for CA125 glycoprotein (SEQ ID NO: 1 through SEQ ID NO: 4) to
the Nucleotide and Amino Acid Sequences for EST Genbank Accession No. AA640762
(SEQ ID NO: 5 and SEQ ID NO: 6, respectively)

Peak 65 - DTYVGPLY          (SEQ ID NO: 3)

Peak 30 - DGAANGVD          (SEQ ID NO: 4)

(SEQ ID NO: 5 and SEQ ID NO: 6)

```
  1 CGTCGACCTGGCTCTAGAAAGTTTAACACCACGGAGAGAGTCCTTCAGGGTCTGCTCAGG
     R  R    P  G  S  R  K  F  N  T  T  E   R  V  L  Q  G  L  L  R

61 CCTGTGTTCAAGAACACCAGTGTTGGCCCTCTGTACTCTGGCTGCAGACTGACCTTGCTC
     P  V  F  K  N  T  S  V  G  P  L  Y  S  G  C  R  L  T  L  L

121 AGGCCCAAGAAGGATGGGGCAGCCACCAAAGTGGATGCCATCTGCACCTACCGCCCTGAT
     R  P  K  K  D  G  A  A  T  K  V  D  A  I  C  T  Y  R  P  D

181 CCCAAAAGCCCTGGACTGGACAGAGAGCAGCTATACTGGGAGCTGAGCCAGGGTGATGCA
     P  K  S  P  G  L  D  R  E  Q  L  Y  W  E  L  S  Q  G  D  A
```

TABLE 2A

Nucleotide and Amino Acid Sequences for Sense Primer 5' 3' (SEQ ID NO:7 and SEQ ID NO:8 respectively) and Antisense Primer 5' 3' (SEQ ID NO:9 and SEQ ID NO:10 respectively) based upon Regions of Homology for EST Genbank Accession Nos. BE005912 and AA640762)

| | |
|---|---|
| GGA GAG GGT TCT GCA GGG TC | (SEQ ID NO:7) |
| E   R   V   L   Q   G | (SEQ ID NO:8) |
| GTG AAT GGT ATC AGG AGA GG | (SEQ ID NO:9) |
| P   L   L   I   P   F | (SEQ ID NO:10) |

TABLE 2B

Sense and Anti-Sense Primers Used for Ordering Repeat Units (SEQ ID NO:301 and SEQ ID NO:302, respectively)

| | |
|---|---|
| 5'-GTCTCTATGTCAATGGTTTCACCC-3' | (SEQ ID NO:301) |
| 5'-TAGCTGCTCTCTGTCCAGTCC-3' | (SEQ ID NO:302) |

TABLE 3

Amino Acid Sequence for a 400 bp Repeat in the CA125 Molecule
(SEQ ID NO:11 thru SEQ ID NO:21)

```
           1                                                  50
12 ERVLQGLLRS LFKSTSVGPL YSGCRLTLLR PEKDGTATGV DAICTHHPDP  (SEQ ID NO:11)

34 ERVLQGLLMP LFKNTSVSSL YSGCRLTLLR PEKDGAATRA DAVCTHRPDP  (SEQ ID NO:12)

32 ERVLQGLLGP IFKNTSVGPL YSGCRLTSLR SEKDGAATGV DAICIHRLDP  (SEQ ID NO:13)

46 ERVLQGLLGP MFKNTSVGLL YSGCRLTLLR PEKNGAATGM DAICSHRLDP  (SEQ ID NO:14)

33 ERVLQGLLGP LFKNSSVGPL YSGCRLISLR SEKDGAATGV DAICTHHLNP  (SEQ ID NO:15)
```

TABLE 3-continued

Amino Acid Sequence for a 400 bp Repeat in the CA125 Molecule
(SEQ ID NO:11 thru SEQ ID NO:21)

```
 15 ERVLQGLLRP LFKSTSAGPL YSGCRLTLLR PEKHGAATGV DAICTLRLDP  (SEQ ID NO:16)

35 ERVLQGLLKP LFKSTSVGPL YSGCRLTLLR PEKRGAATGV DTICTHRLDP  (SEQ ID NO:17)

111 ERVLQGLLTP LFKNTSVGPL YSGCRLTLLR PEKQEAATGV DTICTHRVDP  (SEQ ID NO:18)

42 ERVLQGLLKP LFKKTSVGPL YSGCRLTLLR PEKHEAATGV DTICTHRLDP  (SEQ ID NO:19)

116 ERVLQGLLSP LFKNSSVGPL YSGCRLTSLR PEKDGAATGM DAVCLYHPNP  (SEQ ID NO:20)

23 ERVLQGLLRP LFKNTSIGPL YSSCRLTLLR PEKDKAATRV DAICTHHPDP  (SEQ ID NO:21)

51                                                100
 12 KSPRLDREQL YWELSQLTHN ITELGPYALD NDSLFVNGFT HRSSVSTTST

34 KSPGLDRERL YWKLSQLTHG ITELGPYTLD RHSLYVNGFT HQSSMTTTRT

32 KSPGLNREQL YWELSKLTND IEELGPYTLD RNSLYVNGFT HQSSVSTTST

46 KSPGLNREQL YWELSQLTHG IKELGPYTLD RNSLYVNGFT HRSSVAPTST

33 QSPGLDRFQL YWQLSQMTNG IKELGPYTLD RNSLYVNGFT HRSSGLTTST

15 TGPGLDRERL YWELSQLTNS VTELGPYTLD RDSLYVNGFT HRSSVPTTSI

35 LNPGLDREQL YWELSKLTRG IIELGPYTLD RDSLYVNGFT HRSSVPTTSI

111 IGPGLDRERL YWELSQLTNS ITELGPYTLD RDSLYVDGFN PWSSVPTTST

42 LNPGLDREQL YWELSKLTRG IIELGPYLLD RGSLYVNGFT HRNFVPITST

116 KRPGLDREQL YWELSQLTHN ITELGPYSLD RDSLYVNGFT HQNSVPTTST

23 QSPGLNREQL YWELSQLTHG ITELGPYTLD RDSLYVDGFT HWSPIPTTST 101                                                150
 12 PGTPTVYLGA SKTPASIFGP S..AASPLLI PFT~~~~~~~ ~~~~~~~~~~

34 PDTSTMHLAT SRTPASLSGP T..TASPLLI PF~~~~~~~~ ~~~~~~~~~~

32 PGTSTVDLRT SGTPSSLSSP TIMAAGPLLI PF~~~~~~~~ ~~~~~~~~~~

46 PGTSTVDLGT SGTPSSLPSP T..TAVPLLT PF~~~~~~~~ ~~~~~~~~~~

33 PWTSTVDIGT SGTPSPVPSP T..TAGPFLI PF~~~~~~~~ ~~~~~~~~~~

15 PGTSAVHLET SGTPASLPGH T..APGPLLI PF~~~~~~~~ ~~~~~~~~~~

35 PGTSAVHLET SGTPASLPGH I..VPGPLLI PF~~~~~~~~ ~~~~~~~~~~

111 PGTSTVHLAT SGTPSPLPGH T..APVPLLI PFT~~~~~~~ ~~~~~~~~~~

42 PGTSTVHLGT SETPSSLPRP I..VPGPLLV PFT~~~~~~~ ~~~~~~~~~~

116 PGTSTVYWAT TGTPSSEPGH T..EPGPLLI PF~~~~~~~~ ~~~~~~~~~~

23 PGTSIVNLGT SGIPPSLPET T..ATGFLLI PFT~~~~~~~ ~~~~~~~~~~

151            170
 12 ~~~~~~~~~~ ~~~~~~~~~~

34 ~~~~~~~~~~ ~~~~~~~~~~

32 ~~~~~~~~~~ ~~~~~~~~~~

46 ~~~~~~~~~~ ~~~~~~~~~~

33 ~~~~~~~~~~ ~~~~~~~~~~

15 ~~~~~~~~~~ ~~~~~~~~~~

35 ~~~~~~~~~~ ~~~~~~~~~~

111 ~~~~~~~~~~ ~~~~~~~~~~

42 ~~~~~~~~~~ ~~~~~~~~~~
```

TABLE 3-continued

Amino Acid Sequence for a 400 bp Repeat in the CA125 Molecule
(SEQ ID NO:11 thru SEQ ID NO:21)

116~~~~~~~~~ ~~~~~~~~~

23~~~~~~~~~ ~~~~~~~~~

TABLE 4

Amino Acid Sequence for a 800 bp Repeat in the CA125 Molecule
(SEQ ID NO:22 thru SEQ ID NO:35)

```
        1                                               50
 79 ERVLQGLLKP LFPNSSLEYL YSGCRLASLR PEKDSSAMAV DAICTHRPDP  (SEQ ID NO:22)

811 ERVLQGLLKP LFRNSSLEYL YSGCRLASLR PEKDSSAMAV DAICTHRPDP  (SEQ ID NO:23)

21 ERVLQGLLKP LFKSTSVGPL YSGCRLTLLR PEKRGAATGV DTICTHRLDP  (SEQ ID NO:24)

89 ERVLQGLLKP LFKSTSVGPL YSGCRLTLLR FEKRGAATGV DTICTHRLDP  (SEQ ID NO:25)

85 ERVLQGLLKP LFKSTSVGPL YSGCRLTLLR PEKRGAATGV DTICTHRLDP  (SEQ ID NO:26)

712 ERVLQGLLKP LFKSTSVGPL YSGCRLTLLR PEKRGAATGV DTICTHRLDP  (SEQ ID NO:27)

86 ERVLQGLLKP LFKSTSVGPL Y8GCRLTLLR PEKHGAATGV DAICTLRLDP  (SEQ ID NO:28)

87 ERVLQGLLTP LFKNTSVGPL YSGCRLTLLR PEKQEAATGV DTICTHRVDP  (SEQ ID NO:29)

810 ERVLQGLLRP LFKNTSIGFL YSSCRLTLLR PEKDKAATRV DAICTHHPDP  (SEQ ID NO:30)

83 ERVLQGLLRP VFKNTSVGPL YSGCRLTLLR PKKDGAATKV DAICTYRPDP  (SEQ ID NO:31)

81 ERVLQGLLGP MFKNTSVGLL YSGCRLTLLR PKKDGAATKV DAICTYRPDP  (SEQ ID NO:32)

44 ERVLQGLLKP LFKSTSVGPL YSGCRLTLLR PEKDGAATGM DAVCLYHPNP  (SEQ ID NO:33)

812 ERVLQGLLSP ISKNSSVGPL YSGCRLTSLR PEKDGAATGM DAVCLYHPNP  (SEQ ID NO:34)

76 ERVLQGLLSP IFKNSSVGSL YSGCRLTLLR PEKDGAATRV DAVCTHRPDP  (SEQ ID NO:35)

51                                              100
 79 EDLGLDRERL YWELSNLTNG IQELGPYTLD RNSLYVNGFT HRSSMPTTST

811 EDLGLDRERL YWELSNLTNG IQELGPYTLD RNSLYVNGFT HRSSGLTTST

21 LNPGLDREQL YWELSKLTRG IIELGPYLLD RGSLYVNGFT HRTSVPTTST

89 LNPGLDREQL YWELSKLTRG IIELGPYLLD RGSLYVNGFT HRNFVPITST

85 LNPGLDREQL YWELSKLTRG IIELGPYLLD RGSLYVNGFS RQSSMTTTRT

712 LNPGLDREQL YWELSKLTRG IIELGPYLLD RDSLYVNGFT HRSSVFTTSI

86 TGPGLDRERL YWELSQLTNS VTELGPYLLD RDSLYVNGFT HRS8VPTTSI

87 TGPGLDRERL YWELSQLTNS ITELGPYTLD RDSLYVNGFN PWSSVPTTST

810 QSPGLNREQL YWELSQLTHG ITELGPYTLD RDSLYVDGFT HWSPIPTTST

83 KSPGLDREQL YWELSQLTHS ITELGPYTLD RDSLYVNGFT QRSSVPTTSI

81 KSPGLDREQL YWELSQLTHS ITELGPYTLD RDSLYVNGFT QRSSVPTTSI

44 KRPGLDREQL YCELSQLTHD ITELGPYSLD RDSLYVNGFT HQNSVPTTST

812 KRPGLDREQL YWELSQLTHN ITELGPYSLD RDSLYVNGFT HQNSVPTTST

76 KSPGLDRERL YWKLSQLTHG ITELGPYTLD RHSLYVNGFT HQSSMTTTRT 101                                              150
 79 PGTSTVDVGT SGTPSSSPSP TTAGPLLMPF TLNFTITNLQ YEEDMRRTGS

811 PWTSTVDLGT SGTPSPVPSP TTAGPLLIPF TLNFTITNLQ YEBNMGHPGS

21 PGTSTVDLGT SGTPFSLPSP ATAGPLLVLF TLNFTITNLK YEEDMHRPGS
```

TABLE 4-continued

Amino Acid Sequence for a 800 bp Repeat in the CA125 Molecule
(SEQ ID NO:22 thru SEQ ID NO:35)

```
 89 PGTSTVHLGT SETPSSLPRP IVPGPLLIPF TINFTITNLR YEENMHHPGS

85 PDTSTMHLAT SRTPASLSGP TTASPLLIPF TLNFTITNLQ YEENMGHPGS

712 PGTSAVHLET FGTPASLHGH TAPGPVLVPF TLNFTITNLQ YEEDMRHPGS

86 PGTSAVHLET SGTPASLPGH TAPGPLLVPF TLNFTITNLQ YEEDMRHPGS

87 PGTSTVHLAT SGTPSSLPGH TAPVPLLIPF TLNFTITNLH YEENMQHPGS

810 PGTSIVNLGT SGIPPSLPET TATGPLLIPF TPNFTITNLQ YEEDMRRTGS

83 PGTPTVDLGT SGTPVSKPGP SAASPLLVPF TLNFTTTNLQ YEEDMHRPGS

81 PGTPTVDLGT SGTPVSKPGP SAASPLLIPF TTNFTITNLR YEENMGHPGS

44 PGTSTVYWAT TGTPSSFPGH TEPGPLLIPF TFNFTITNLH YEENMQHPGS

812 PGTSTVYWAT TGTPSSFPGH TEPGPLLIPF TVNFTITNLR YEENMHHPGS

76 PDTSTMHLAT SRTPASLSGP TTASPLLVLF TTNFTITNQR YEENMHHPGS 151                                                  200
 79 RKFNTMERVL QGLLSPIFKN SSVGPLYSGC RLTSLRPEKD GAATGMDAVC

811 RKFNIMERVL QGLLMPLFKN TSVSSLYSGC RLTLLRPEKD GAATRVDAVC

21 RKFNTTERVL QTLLGPMFKN TSVGLLYSGC RLTLLRSEKD CAATGVDAIC

89 RKFNIMERVL QGLLGPLFKN SSVGPLYSGC RLTSLRSEKD GAATGVDAIC

85 RKFNIMERVL QGLLNPIFKN SSVGPLYSGC RLTSLKPEKD GAATGMDAVC

712 RKFNTTERVL QGLLKPLFKS TSVGPLYSGC RLTLLRPEKR GAATGVDTIC

86 RKFNTTERVL QGLLKPLFKS TSVGPLYSGC RLTLLRPEKR GAATGVDTIC

87 RKFNTTERVL QGLLKPLFKS TSVGPLYSGC RLTLLRPEKH GAATGVDAIC

810 RKFNTMERVL QGLLSPIFKN SSVGPLYSGC RLTSLRPEKD GAATGMDAVC

83 RKFNATERVL QGLLSPIFKU SSVGPLYSGC RLTSLRPEKD GAATGMDAVC

81 RKFNIMERVL QGLLKPLFKN TSVGPLYSGC RLTLLRPKKD GAATGVDAIC

44 RKFNTTERVL QGLLKPLFKN TSVGPLYSGC RLTLLRPEKH EAATGVDTIC

812 RKFNTTERVL QGLLRPVFKN TSVGPLYSGC RLTLLRPKKD GAATKVDAIC

76 RKFNTTERVL QGLLRPVFKN TSVGPLYSGC RLTLLRPKKD GAATKVDATC 201                                                  250
 79 LYHPNPKRPG LDREQLYWEL SQLTHNTTEL GPYSLDRDSL YVNGFTHQN8

811 TQRPDPKSPG LDRERLYWKL SQLTEGITEL GPYTLDRMSL YVNGLTHQSS

21 THRLDPKSPG VDREQLYWEL SQLTNGIKEL GPYTLDRNSL YVNGFTHWIP

89 THHLNPQSPG LDREQLYWQL SQMTNGIKEL GFYTLDRNSL YVNGFTHRSS

85 LYHPNPKRPG LDREQLYWEL SQLTHGIKEL GPYTLDRNSL YVNGFTHRSS

712 THRLDPLNPG LDREQLYWEL SKLTRGIIEL GPYLLDRGSL YVNGFTHRNF

86 THRLDPLNPG LDREQLYWEL SKLTRGIIEL GPYLLDRGSL YVNGPTHPNF

87 TERLDPKSPG VDREQLYWEL SQLTNGIKEL GPYTLDRNSL YVNGFTHWIP

810 LYHPNPKRPG LDREQLY~~~ ~~~~~~~~~~ ~~~~~~~~~~ ~~~~~~~~~~

83 LYHPNPKRPG LDREQLYWEL SQLTHNITEL GPYSLDRDSL YVNGFTHQSS

81 THRLDPKSPG LNREQLYWEL SKLTNDIEEL GPYTLDRNSL YVNGFTHQSS

44 THRVDPIGPG LDRERLYWEL SQLTNSIHEL GPYTLDRDSL YVNGFNPRSS
```

TABLE 4-continued

Amino Acid Sequence for a 800 bp Repeat in the CA125 Molecule
(SEQ ID NO:22 thru SEQ ID NO:35)

```
812 TYRPDPKSPG LDREQLYWEL SKLTNDTEEL GPYTLDRNSL YVNGFTHQSS

76 TYRPDPKSFG LDREQLYWEL SQLTHSITEL GPYTQDRDSL YVNGFTHRSS 251                                      288
 79 VPTTSTPGTS TVYWATTGTP SSFPGHT..E PGPL~~~~

811 MTTTRTPDTS TMHLATSRTP ASLSGPT..T A8PLLIPF

21 ~~~~~~~~~~ ~~~~~~~~~~ ~~~~~~~~~~ ~~~~~~~~

89 GLTTSTPWTS TVDLGTSGTP SPVPSPT..T AGPTLLIFF

85 VAPTSTPGTS TVDLGTSGTP SSLPSPT..T AVPLLIPF

712 VPITSTPGTS TVHLGTSETP SSLFRPI..V PGPLLIPF

86 VPITSTPGTS TVELGTSETP SSLPRPI..V PGPLLIPF

87 VPTSSTPGTS TVDLG.SGTP SSLPSPT..T AGPL~~~~

810 ~~~~~~~~~~ ~~~~~~~~~~ ~~~~~~~~~~ ~~~~~~~~

83 MTTTRTPDTS TMHLATSRTP ASLSGPT..T ASPLLIPF

81 VSTTSTFGTS TVDLRTSGTP SSLSSPTIMA AGPLLIPF

44 VPTTSTPGTS TVHLATSGTP SSLPGHT..A PVPLLI~~

812 VSTTSTPGTS TVDLRTSGTP SSLSSPTIMA AGPLLIPF

76 VPTTSIPGTS AVHLETSGTP ASLP~~~~~ ~~~~~~~~
```

TABLE 5

Amino Acid Sequence for a 1200 bp Repeat in the CA125 Molecule
(SEQ ID NO:36 thru SEQ ID NO:46)

```
      1                                              50
910 ERVLQGLLGP MFKNTSVGLL YSGCRLTLLR PEKRGAATGV DTICTHRLDP  (SEQ ID NO:36)

99 ERVLHGLLTP LFKNTRVGPL YSGCRLTLLR PEKQEAATGV DTTCTHRVDP  (SEQ ID NO:37)

112 ~~~~~~~~~~ ~~~~~~GPL YSGCRLTSLR PEKDGAATGM DAVCLYHPNP   (SEQ ID NO:38)

95 ERVLQGPLSP IFKNSSVGPL YSGCRLTSLR PEKDGAATGM DAVCLYHPNP  (SEQ ID NO:39)

71 ~~~~~~~~~~ ~~~~TSVGPL YSGCRLTLLR SEKDGAATGV DAIYTHRLDP  (SEQ ID NO:40)

78 ~~~~~~~~~~ ~~~~~~~~~~ ~~~~~~TLLR PKKDGVATGV DAICTHRLDP  (SEQ ID NO:41)

115 ERVLQGLLKP LFKSTSVGPL YSGCRLTLLR PEKDGVATRV DAICTHRPDP  (SEQ ID NO:42)

91 ERVLQGLLKP LFRNSSLEYL YSGCRLASLR PEKDSSAMAV DAICTHRPDP  (SEQ ID NO:43)

92 ERVLQGLLKP LFKSTSVGPL YSGCRLTLLR PEKRGAATGV DTICTHRLDP  (SEQ ID NO:44)

113 ERVLQGLLGP MFKNTSVGLL YSGCRLTLLR PEKNGAATGM DATCSHRLDP  (SEQ ID NO:45)

711 ERVLQGLLKP LFKSTSVGPL YSGCRLTLLR PEKHGAATGV DAICTLRLDF  (SEQ ID NO:46)

51                                             100
910 LNPGLDREQL YWELSKLTRG ITELGPYLLD RGSLYVNGFT HRNFVPITST

99 IGPGLDRERL YWELSQLTNS ITELGPYTLD RDSLYVNGFN PWSSVPTTST

112 KRPGLDREQL YWELSQLTHN ITELGPYSLD RDSLYVNGFT HQNSVPTTST

95 KRPGLDREQL YWELSQLTHN ITELGPYSLD RDSLYVNGFT HQNSVPTTST

71 KSFGVDREQL YWELSQLTNG IKELGPYTLD RNSLYVNGFT HQTSAPNTST

78 KSPGLNREQL YWELSKLTND IEELGPYTLD RNSLYVNGFT HQSSVSTTST
```

TABLE 5-continued

Amino Acid Sequence for a 1200 bp Repeat in the CA125 Molecule
(SEQ ID NO:36 thru SEQ ID NO:46)

```
115 KIPGLDRQQL YWELSQLTHS ITELGPYTLD RDSLYVNGFT QRSSVPTTST

91 EDLGLDRERL YWELSNLTNG IQELGPYTLD RNSLYVNGFT HRSSMPTTST

92 LNPGLDREQL YWELSKLTRG IIELGPYLLD RGSLYVNGFT HRNFVPITST

113 KSPGLNRBQL YWELSQLTHG IKELGFYTLD RNSLYVNGFT HRSSVAPTST

711 TGPGLDRERL YWELSQLTNS VTELGPYTLD RDSLYVNGFT HRSSVPTTSI
        101                                              150
910 PGTSTVHLGT SETPSSLPRP IV..PGPLLV PFTLNFTITN LQYEEAMRHP

99 PGTSTVHLAT SGTPSSLFGH TA..PVPLLI PFTLNFTITN LHYEENMQHP

112 PGTSTVYWAT TGTPSSFFGH T..EPGFLLI PFTLNFTITN LQYEENMGHP

95 PGTSTVYWAT TGTPSSFPGH T..EPGPLLI PFTLNFTITN LQYEENMGHP

71 PGTSTVDLGT SGTPSSLPSP T..SAGPLLI PFTINFTITN LRYEENMHHP

78 PGTSTVDLRT SGTPSSLSSP TIMAAGPLLI PFTINFTITN LRYEENMHHP

115 PGTFTVQPET SETPSSLPGP T..ATGPVLL PFTLNFTIIN LQYEEDMHRP

91 PGTSTVDVGT SGTPSSSPSP T..TAGFLLM PFTLNFTITN LQYEEDMRRT

92 PGTSTVHLGT SETPSSLPRP TV..PGPLLI PFTLNFTITN LQYEENMGHP

113 PGTSTVDLGT SGTPSSLPSP T..TAVPLLI PFTLNFTITN LKYEEDMHCP

711 PGTSAVHLET SGTPASLPGH T..APGPLLI PFTLNFTITN LHYEENMQHP
        151                                              200
910 GSRKFNTTER VLQGLLRPLF KNTSVSSLYS GCRLTLLRPE KDGAATRVDA

99 GSRKFNTTER VLQGLLKPLF KNTSVGPLYS GCRLTLFKPE KHEAATGVDA

112 GSRKFNITES VLQGLLTPLF KNSSVGPLYS GCRLISLRSE KDGAATGVDA

95 GSRKFNITER VLQGLLNPIF KNSSVGPLYS GCRLTSLRPE KDGAATGMDA

71 GSRKFNTMER VLQGLLKPLF KSTSVGPLYS GCRLTLLRPE KDGVATRVDA

78 GSRKFNTMER VLQGLLMPLF KNTSVSSLYS GCRLTLLRPE KDGAATRVDA

115 GSRKFNTTER VLQGLLMPLF KNTSVGPLYS GCRLTLLRPE KQEAATGVDT

91 GSRKFNTMES VLQGLLKPLF KNTSVGPLYS GCRLTLLRPK KDGAATGVDA

92 GSRKFNITER VLQGLLKPLF RNSSLEYLYS GCRLTSLRPE KDSSTMAVDA

113 GSRKFNTTER VLQSLFGPMF KNTSVGPLYS GCRLTLFRSE KDGAATGVDA

711 GSRKFNTMER VLQGCLVPCS RNTNVGLLYS GCRLTLLXXX XXXXXXXXX
        201                                              250
910 ACTYRPDPKS PGLDREQLYW ELSQLTHSIT ELGPYTLDRV SLYVNGFNPR

99 ICTLRLDPTG PGLDRERLYW ELSQLTNSVT ELGPYTLDRD SLYVNGFTHR

112 ICTHHLNPQS PGLDREQLYW QLSQMTNGTK ELGPYTLDRD SLYVNGFTHR

95 VCLYHPNPKR PGLDREQLYC ELSQLTHNIT ELGPYSLDRD SLYVNGFTHQ

71 ICTHRPDPKI PGLDRQQLYW ELSQLTHSTT ELGPYTLDRD SLYVNGFTQR

78 VCTHRPDPKS PGLDRERLYW KLSQLTHGIT ELGPYTLDRN SLYVNGFTHR

115 ICTHRLDPSE PGLDREQLYW ELSQLTNSTT ELGPYTLDRD SLYVNGFTHS

91 ICTHRLDPKS PGLNREQLYW ELSKLTNDIE EVGPYTLDRN SLYVNGFTHR

92 ICTHRPDPED LGLDRERLYW ELSNLTNGTQ ELGFYTLDRN SLYVNGFTHR
```

TABLE 5-continued

Amino Acid Sequence for a 1200 bp Repeat in the CA125 Molecule
(SEQ ID NO:36 thru SEQ ID NO:46)

```
113 ICTHRLDPKS PGVDREQLYW ELSQLTNGIK ELGPYTLDRN SLYVNGFTHQ

711 XXXXXXXXXX XXXXXXXXXX XXXXXXXXXX XXGPYTLDRN SLYVNGFTHR 251                                              300
910 SSV.PTTSTP GTSTVHLATS GTPSSLPGHT APVPLLIPFT LNFTITNLQY

99 SSV.PTTSIP GTSAVHLETS GTPASLPGHT APGPLLIPFT LNFTITNLQY

112 SL.GLTTSTP WTSTVDLGTS GTPSPVPSPT TAGPLLTPFT LNFTITNLQY

95 NS.VPTTSTP GTSTVYWATT GTPSSFPGHT EPGPLLIPFT LNFTITNLQY

71 SSV.PTTSTP GTFTVQPETS ETPSSLPGPT ATGPVLLPFT LNFTIINLQY

78 SSM.PTTSTP GTSTVDVGTS GTPSSSPSPT TAGPLLMFFT LNFTITNLQY

115 GVLCPPPSIL GIFTVQPETF ETPSSLPGPT ATGPVLLPFT LNFTIINLQY

91 SFVAP.TSTL GTSTVDLGTS GTPSSLPSPT TGVPLLIPFT LNFTITNLQY

92 SFM.PTTSTL GTSTVDVGTS GTPSSSPSPT TAGPLLMPFT LNFTITNLQY

113 TS.APNTSTP GTSTVDLGTS GTPSSLPSPT SAGPLLVPFT LNFTITNLQY

711 SSVAP.TSTP GTSTVDLGTS GTPSSLPSPT TV.PLLVPFT LNFTITNLQY 301                                              350
910 EEDMRHPGSR KFNTMERVLQ GLLRPLFKNT SIGFLYSSCR LTLLRPEKDK

99 EEDMRRTGSR KFNTMERVLQ GLLKPLFKST SVGPLYSGCR LTLLRPEKRG

112 EENMGHPGSR KFNIMERVLQ GLLRPVFKNT SVGPLYSGCR LTLLRPKKDG

95 EEDMRRTGSR KFNTMERVLQ GLLKPLFKST SVGPLYSGCR LTLLRPEKHG

71 EEDMHRPGSR KFNTTERVLQ GLLKPLFKST SVGPLYSGCR LTLLRPEKHG

78 EEDMRRTGSR KFNTMERVLQ GLLKPLFKST SVGFLYSGCR LTLLRPEKHG

115 EEDMHRPGSR KFNTTERVLQ GLLMPLFKNT SVGPLYSGCR LTLLRPEKQE

91 EENMGHPGSR KFNTMERVLQ GLLMPLFKNT SVSSLYSGCR LTLLRPEKDG

92 EEDMRRTGSR KFNTMESVLQ GLLKPLFKNT SVGPLYSGCR LTLLRPKKDG

113 EEDMRRTGSR KFNTMESVLQ GLLKPLFKNT SVGPLYSGCR LTLLRPEKDG

711 GEDMRHPGSR KFNTTERVLQ GLLGPLFKNS SVGPLYSGCR LISLRSEKDG 351                                              400
910 AATRVDAICT HHPDPQSPGL NREQLYWELS QLTHGITEL~ ~~~~~~~~~~

99 AATGVDTICT HRLDPLNPGL DREQLYWELS KLTRGIIELG PYLLDRGSLY

112 AATKVDAICT YRPDPKSPGL DREQLYWELS QLTHSITELG PYTLDRDSLY

95 AATGVDAICT LRLDPTGPGL DRERLYWELS QLTNSVTELG PYTLDRDSLY

71 AATGVDAICT LRLDPTGPGL DRERLYWELS QLTNSTTELG PYTLDRDSLY

78 AATGVDAICT LRLDPTGFGL DRERLYWELS QLTNSVTELG PYTLDRDSLY

115 AATGVDTICT HRVDPIGPGL DRERLYWELS QLTNSITELG PYTLDRDSLY

91 AATRVVAVCT HRPDPKSPGL DRERLYWKLS QLTHGITELG PYTLDRHSLY

92 AATGVDAICT HRLDPKSPGL NREQLYWELS KLTNDIEELG PYTLDRNSLY

113 AATGVDATCT HRLDPKSPGL NREQLYWELS KL~~~~~~~~ ~~~~~~~~~~

711 AATGVDAICT HHLNPQSPGL DREQLYWQLS QVTNGIKELG PYTLDRNSLY
```

TABLE 5-continued

Amino Acid Sequence for a 1200 bp Repeat in the CA125 Molecule
(SEQ ID NO:36 thru SEQ ID NO:46)

```
       401                                              447
910~~~~~~~~~~ ~~~~~~~~~~ ~~~~~~~~~~ ~~~~~~~~~~ ~~~~~~~

99VNGFTHRNFV PITSTPGTST VHLGTSEIHP SLPRPI..VP GPL~~~~

112VNGFTQRSSV PTTSIPGTPT VDLGTSGTPV SKPGPS..AA SP~~~~~

95VNGFTHRSSV PTTSIPGTSA VMLETSGTPA SLPGHT..AP GPLL~~~

71VNGFNPWSSV PTTSTPGTST VHLATSGTPS SLPGHT..AP VPL~~~~

78VNGFTHRSSV PTTSIPGTSA VHLETSGTPA SLPGHT..AP GPLLIPF

115VNGFNPWSSV PTTSTPGTST VHLATSGTPS SLPGHT..AP VPLLIPF

91VNGFTHQSSM TTTRTPDTST MHLATSRTPA SLSGPT..TA SPLLIPF

92VWGFTHQSSV STTSTPGTST VDPRTSGTPS SLSSPTIMAA GPLLI~~

113~~~~~~~~~~ ~~~~~~~~~~ ~~~~~~~~~~ ~~~~~~~~~~ ~~~~~~~

711VNGFTHRSSG LTTSTPWTST VDLGTSGTPS PVPSPT..TA GPLLI~~
```

TABLE 6

Amino Acid Sequence for a 9 Repeat Structure in the CA125 Molecule (SEQ ID NO:47)

```
ERVLQGLLKP LFRNSSLEYL YSGCRLASLR PEKDSSAMAV
DAICTHRPDP EDLGLDRERL YWELSNLTNG IQELGPYTLD
RNSLYVNGFT HRSSMPTTST PGTSTVDVGT SGTPSSSPSP
TTAGPLLMPF TLNFTITNLQ YEEDMRRTGS RKFNTMERVL
QGPLSPIFKN SSVGPLYSGC RLTSLRPEKD GAATGM DAV
CLYHPNPKRP GLDREQLYWE LSQLTHNITE LGPYSLDRDS
LYVNGFTHQN SVPTTSTPGT STVYWATTGT PSSFPGHTEP
GPLLIPFTLN FTITNLQYEE NMGHPGSRKF NITERVLQGL
LNPIFKNSSV GPLYSGCRLT SLRPEKDGAA TGMDAVCLYH
PNPKRPGLDR EQLYCELSQL THNITELGPY SLDRDSLYVN
GFTHQNSVPT TSTPGTSTVY WATTGTPSSF PGHTEPGPLL
IPFTLNFTIT NLQYEEDMRR TGSRKFNTME RVLQGLLKPL
FKSTSVGPLY SGCRLTLLRP EKHGAATGVD AICTLRLDPT
GPGLDRERLY WELSQLTNSV TELGPYTLDR DSLYVNGFTH
RSSVPTTSIP GTSAVHLETS GTPASLPGHT APGPLLVPFT
LNFTITNLQY EEDMRHPGSR KFNTTERVLQ GLLKPLFKST
SVGPLYSGCR LTLLRPEKRG AATGVDTICT HRLDPLNPGL
DREQLYWELS KLTRGIIELG PYLLDRGSLY VNGFTHRNFV
PITSTPGTST VHLGTSETPS SLPRPIVPGP LLIPFTLNFT
ITNLQYEENM GHPGSRKFNT TERVLQGLLK PLFRNSSLEY
LYSGCRLASL RPEKDSSAMA VDAICTHRPD PEDLGLDRER
LYWELSNLTN GIQELGPYTL DRNSLYVNGF THRSSMPTTS

TPGTSTVDVG TSGTPSSSPS PTTAGPLLMP FTLNFTTTNL
QYEEDMRRTG SRKFNTMESV LQGLLKPLFK NTSVGPLYSG
CRLTLLRPKK DGAATGVDAT CTHRLDPKSP GLNREQLYWE
LSKLTNDTEE VGPYTLDRNS LYVNGFTHRS FVAPTSTLGT
STVDLGTSGT FSSLPSPTTG VPLLIPFTLN FTITNLQYEE
NMGHPGSRKF NIMERVLQGL LSPIFKNSSV GSLYSGCRLT
LLRPEKDGAA TRVDAVCTHR PDPKSPGLDR ERLYWKLSQL
THGIIELGPY TLDRHSFYVN GFTHQSSMTT TRTPDTSTMH
LATSRTPASL SGPTTASPLL WLFTINFTIT NQRYEENMHH
PGSRKFNTTE RVLQGLLRPV FKNTSVGPLY SGCRLTLLRP
KKDGAATKVD AICTYRPDPK SPGLDREQLY WELSQLTHSI
TELGPYTQDR DSLYVNGFTH RSSVPTTSIP GTSAVHLETS
GTPASLP
```

TABLE 7 cDNA Genbank Accession #AX024365 Encompasses Repeat Sequences (Repeats 1 & 2) Homologous to Two Repeats Shown in Table 6

(SEQ ID NO: 48)

```
MPLFKNTSVS SLYSGCRLTL LRPEKDGAAT RVDAVCTHRP
DPKSPGLDRE RLYWKLSQLT HGIIELGPYT LDRHSFYVNG
FTHQSSMTTT RTPDTSTMHL ATSRTPASLS GPTTASPLLV
LFTINFTITN QRYEENMHHP GSRKFNTTER VLQGLLRPVF
KNTSVGPLYS GCRLTLLRPK KDGAATKVDA ICTYRPDPKS
```

TABLE 7-continued cDNA Genbank Accession #AX024365 Encompasses Repeat Sequences (Repeats 1 & 2) Homologous to Two Repeats Shown in Table 6

PGLDREQLYW ELSQLTHSIT ELGPYTQDRD SLYVNGFTHR

SSVPTTSIPG TSAVHLETSG TPASLPGPSA ASPLLVLFTL

NFTITNLRYE ENMQHPGSRK FNTTERVLQG LLRSLFKSTS

VGPLYSGCRL TLLRPEKDGT ATGVDATCTH HPDPKSPRLD

REQLYWELSQ LTHNITELGH YALDNDSLFV NGFTHRSSVS

TTSTPGTPTV YLGASKTPAS IFGPSAASHL LILFTLNFTI

TNLRYEENMW PGSRKPNTTE RVLQGLLRPL FKNTSVGPLY

SGSRLTLLRP EKDGEATGVD AICTHRPDPT GPGLDREQLY

LELSQLTHSI TELGPYTLDR DSLYVNGFTH RSSVPTTSTG

VVSEEPFTLN FTINNLRYMA DMGQPGSLKF NITDNVMKHL

LSPLFQRSSL GARYTGCRVI ALRSVKNGAE TRVDLLCTYL

QPLSGPGLPT KQVFHELSQQ THGITRLGPY SLDKDSLYLN

TABLE 7-continued cDNA Genbank Accession #AX024365 Encompasses Repeat Sequences (Repeats 1 & 2) Homologous to Two Repeats Shown in Table 6

GYNEPGLDEP PTTPKPATTF LPPLSEATTA MGYHLKTLTL

NFTISNLQYS PDMGKGSATF NSTEGVLQHL LRPLFQKSSM

GPFYLGCQLI SLRPEKDGAA TGVDTTCTYH PDPVGPGLDI

QQLYWELSQL THGVTQLGFY VLDRDSLFIN GYAPQNLSIR

GEYQINFHIV NWNLSNPDPT SSEYITLLRD IQDKVTTLYK

GSQLHDTFRF CLVTNLTMDS VLVTVKALFS SNLDPSLVEQ

VFLDKTLNAS FHWLGSTYQL VDIHVTEMES SVYQPTSSSS

TQHFYLNFTI TNLPYSQDKA QPGTTNYQRN KRNIEDALNQ

LFPNSSIKSY FSDCQVSTFR SVPNRHHTGV DSLCNFSPLA

RRVDRVAIYE EFLRMTRNGT QLQNFTLDRS SVLVDGYSPN

RNEPLTGNSD LPFWAVILIG LAGLLGLTTC LICGVLVTTR

RRKKEGEYNV QQQCPGYYQS HLDLEDLQ

TABLE 8

Complete DNA Sequence for 13 Repeats including the Carboxy Terminus of CA12S

| | |
|---|---|
| 1 | GAGAGGGTTC TGCAGGGTCT GCTCAAACCC TTGTTCAGGA ATAGCAGTCT (SEQ ID NO:49) |
| 51 | GGAATACCTC TATTCAGGCT GCAGACTAGC CTCACTCAGG CCAGAGAAGG |
| 101 | ATAGCTCAGC CATGGCAGTG GATGCCATCT GCACACATCG CCCTGACCCT |
| 151 | GAAGACCTCG GACTGGACAG AGAGCGACTG TACTGGGAGC TGAGCAATCT |
| 201 | GACAAATGGC ATCCAGGAGC TGGGCCCCTA CACCCTGGAC CGGAACAGTC |
| 251 | TCTATGTCAA TGGTTTCACC CATCGAAGCT CTATGCCCAC CACCAGCACT |
| 301 | CCTGGGACCT CCACAGTGGA TGTGGGAACC TCAGGGACTC CATCCTCCAG |
| 351 | CCCCAGCCCC ACGACTGCTG GCCCTCTCCT GATGCCGTTC ACCCTCAACT |
| 401 | TCACCATCAC CAACCTGCAG TACGAGGAGG ACATGCGTCG CACTGGCTCC |
| 451 | AGGAAGTTCA ACACCATGGA GAGGGTTCTG CAGGGTCCGC TTAGTCCCAT |
| 501 | ATTCAAGAAC TCCAGTGTTG GCCCTCTGTA CTCTGGCTGC AGACTGACCT |
| 551 | CTCTCAGGCC CGAGAAGGAT GGGGCAGCAA CTGGAATGGA TCCTGTCTGC |
| 601 | CTCTACCACC CTAATCCCAA AGACCTGGGC TGGACAGAG AGCAGCTGTA |
| 651 | CTGGGAGCTA AGCCAGCTGA CCCACAACAT CACTGAGCTG GCCCCTACA |
| 701 | GCCTGGACAG GGACAGTCTC TATGTCAATG GTTTCACCCA TCAGAACTCT |
| 751 | GTGCCCACCA CCAGTACTCC TGGGACCTCC ACAGTGTACT GGGCAACCAC |
| 801 | TCGCACTCCA TCCTCCTTCC CCGGCCACAC AGAGCCTGGC CCTCTCCTGA |
| 851 | TACCATTGAC GCTCAACTTC ACCATCACTA ACCTACAGTA TGAGGAGAAC |

TABLE 8-continued

Complete DNA Sequence for 13 Repeats including the Carboxy Terminus of CA12S

```
 901 ATGGGTCACC CTGGCTCCAG GAAGTTCAAC ATCACGGAGA GGGTTCTGCA
 951 GGGTCTGCTT AATCCCATTT TCAAGAACTC CAGTGTTGGC CCTCTGTACT
1001 CTGGCTGCAG ACTGACCTCT CTCAGGCCCG AGAAGGATGG GGCAGCAACT
1051 GGAATGGATG CTGTCTGCCT CTACCACCCT AATCCCAAAA GACCTGGGCT
1101 GGACAGAGAG CAGCTGTACT GCGAGCTAAG CCAGCTGACC CACAACATCA
1151 CTGAGCTGGG CCCCTACAGC TTGGACAGGG ACAGTCTTTA TGTCAATGGT
1201 TTCACCCATC AGAACTCTGT GCCCACCACC AGTACTCCTG GACCTCCAC
1251 AGTGTACTGG GCAACCACTG GGACTCCATC CTCCTTCCCC GGCCACACAG
1301 AGCCTGGCCC TCTCCTGATA CCATTCACCC TCAACTTCAC CATCACCAAC
1351 CTGCAGTACG AGGAGGACAT GCGTCGCACT GGCTCCAGGA AGTTCAACAC
1401 CATGGAGAGG GTTCTGCAGG GTCTGCTCAA GCCCTTGTTC AAGAGCACCA
1451 GCGTTGGCCC TCTGTACTCT GGCTGCAGAC TGACCTTGCT CAGACCTGAG
1501 AAACATGGGG CAGCCACTGG AGTGGACGCC ATCTGCACCC TCCGCCTTGA
1551 TCCCACTGGT CCTGGACTGG ACAGAGAGCG GCTATACTGG GAGCTGAGCC
1601 AGCTGACCAA CAGCGTTACA GAGCTGGGCC CCTACACCCT GGACAGGGAC
1651 AGTCTCTATG TCAATGGCTT CACCCATCGG AGCTCTGTGC CAACCACCAG
1701 TATTCCTGGG ACCTCTGCAG TGCACCTGGA AACCTCTGGG ACTCCAGCCT
1751 CCCTCCCTGG CCACACAGCC CCTGGCCCTC TCCTGGTGCC ATTCACCCTC
1801 AACTTCACTA TCACCAACCT GCAGTATGAG GAGGACATGC GTCACCCTGG
1851 TTCCAGGAAG TTCAACACCA CGGAGAGAGT CCTGCAGGGT CTGCTCAAGC
1901 CCTTGTTCAA GAGCACCAGT GTTGGCCCTC TGTACTCTGG CTGCAGACTG
1951 ACCTTGCTCA GGCCTGAAAA ACGTGGGGCA GCCACCGGCG TGGACACCAT
2001 CTGCACTCAC CGCCTTGACC CTCTAAACCC TGGACTGGAC AGAGAGCAGC
2051 TATACTGGGA GCTGAGCAAA CTGACCCGTG GCATCATCGA GCTGGGCCCC
2101 TACCTCCTGG ACAGAGGCAG TCTCTATGTC AATGGTTTCA CCCATCGGAA
2151 CTTTGTGCCC ATCACCAGCA CTCCTGGGAC CTCCACAGTA CACCTAGGAA
2201 CCTCTGAAAC TCCATCCTCC CTACCTAGAC CCATAGTGCC TGGCCCTCTC
2251 CTGATACCAT TCACACTCAA CTTCACCATC ACTAACCTAC AGTATGAGGA
2301 GAACATGGGT CACCCTGGCT CCAGGAAGTT CAACATCACG GAGAGGGTTC
2351 TGCAGGGTCT GCTCAAACCC TTGTTCAGGA ATAGCAGTCT GGAATACCTC
2401 TATTCAGGCT GCAGACTAAC CTCACTCAGG CCAGAGAAGG ATAGCTCAAC
2451 CATGGCAGTG GATGCCATCT GCACACATCG CCCTGACCCT GAAGACCTCG
2501 GACTGGACAG AGAGCGACTG TACTGGGAGC TGAGCAATCT GACAAATGGC
2551 ATCCAGGAGC TGGGCCCCTA CACCCTGGAC CGGAACAGTC TCTATGTCAA
2601 TGGTTTCACC CATCGAAGCT CTATGCCCAC CACCAGCACT CCTGGGACCT
2651 CCACAGTGGA TGTGGGAACC TCAGGGACTC CATCCTCCAG CCCCAGCCCC
2701 ACGACTGCTG GCCCTCTCCT GATGCCGTTC ACCCTCAACT TCACCATCAC
2751 CAACCTGCAG TACGAGGAGG ACATGCGTCG CACTGGCTCC AGGAAGTTCA
```

TABLE 8-continued

Complete DNA Sequence for 13 Repeats including the Carboxy Terminus of CA12S

```
2801 ACACCATGGA GAGTGTCCTG CAGGGTCTGC TCAAGCCCTT GTTCAAGAAC

2851 ACCAGTGTTG GCCCTCTGTA CTCTGGCTGC AGATTGACCT TGCTCAGGCC

2901 CAAGAAAGAT GGGGCAGCCA CTGGAGTGGA TGCCATCTGC ACCCACCGCC

2951 TTGACCCCAA AAGCCCTGGA CTCAACAGGG AGCAGCTGTA CTGGGAGTTA

3001 AGCAAACTGA CCAATGACAT TGAAGAGGTG GGCCCCTACA CCTTGGACAG

3051 GAACAGTCTC TATGTCAATG GTTTCACCCA TCGGAGCTTT GTGGCCCCCA

3101 CCAGCACTCT TGGGACCTCC ACAGTGGACC TTGGGACCTC AGGGACTCCA

3151 TCCTCCCTCC CCAGCCCCAC AACAGGTGTT CCTCTCCTGA TACCATTCAC

3201 ACTCAACTTC ACCATCACTA ACCTACAGTA TGAGGAGAAC ATGGGTCACC

3251 CTGGCTCCAG GAAGTTCAAC ATCATGGAGA GGGTTCTGCA GGGTCTGCTT

3301 ATGCCCTTGT TCAAGAACAC CAGTGTCAGC TCTCTGTACT CTGGTTGCAG

3351 ACTGACCTTG CTCACCCCTG AGAAGGATGG GGCAGCCACC AGAGTGGTTG

3401 CTGTCTGCAC CCATCGTCCT GACCCCAAAA GCCCTGGACT GGACAGAGAG

3451 CGGCTGTACT GGAAGCTGAG CCAGCTGACC ACGGCATCA CTGAGCTGGG

3501 CCCCTACACC CTGGACAGGC ACAGTCTCTA TGTCAATGGT TTCACCCATC

3551 AGAGCTCTAT GACGACCACC AGAACTCCTG ATACCTCCAC AATGCACCTG

3601 GCAACCTCGA GAACTCCAGC CTCCCTGTCT GGACCTACGA CCGCCAGCCC

3651 TCTCCTGATA CCATTCACAA TTAACTTCAC CATCACTAAC CTGCGGTATG

3701 AGGAGAACAT GCATCACCCT GGCTCTAGAA AGTTTAACAC CACGGAGAGA

3751 GTCCTTCAGG GTCTGCTCAG GCCTGTGTTC AAGAACACCA GTGTTGGCCC

3801 TCTGTACTCT GGCTGCAGAC TGACCTTGCT CAGGCCCAAG AAGGATGGGG

3851 CAGCCACCAA AGTGGATGCC ATCTGCACCT ACCGCCCTGA TCCCAAAAGC

3901 CCTGGACTGG ACAGAGACCA GCTATACTGG GAGCTGAGCC AGCTAACCCA

3951 CAGCATCACT GAGCTGGGCC CCTACACCCT GGACAGGGAC AGTCTCTATG

4001 TCAATGGTTT CACACAGCGG AGCTCTGTGC CACCACTAG CATTCCTGGG

4051 ACCCCCACAG TGGACCTGGG AACATCTGGG ACTCCAGTTT CTAAACCTGG

4101 TCCCTCGGCT GCCAGCCCTC TCCTGGTGCT ATTCACTCTC AACTTCACCA

4151 TCACCAACCT GCGGTATGAG GAGAACATGC AGCACCCTGG CTCCAGGAAG

4201 TTCAACACCA CGGAGAGGGT CCTTCAGGGC CTGCTCAGGT CCCTGTTCAA

4251 GAGCACCAGT GTTGGCCCTC TGTACTCTGG CTGCAGACTG ACTTTGCTCA

4301 GGCCTGAAAA GGATGGGACA GCCACTGGAG TGGATGCCAT CTGCACCCAC

4351 CACCCTGACC CCAAAAGCCC TAGGCTGGAC AGAGAGCAGC TGTATTGGGA

4401 GCTGAGCCAG CTGACCCACA ATATCACTGA GCTGGGCCAC TATGCCCTGG

4451 ACAACGACAG CCTCTTTGTC AATGGTTTCA CTCATCGGAG CTCTGTGTCC

4501 ACCACCAGCA CTCCTGGGAC CCCCACAGTG TATCTGGGAG CATCTAAGAC

4551 TCCAGCCTCG ATATTTGGCC CTTCAGCTGC CAGCCATCTC CTGATACTAT

4601 TCACCCTCAA CTTCACCATC ACTAACCTGC GGTATGAGGA GAACATGTGG

4651 CCTGGCTCCA GGAAGTTCAA CACTACAGAG AGGGTCCTTC AGGGCCTGCT
```

TABLE 8-continued

Complete DNA Sequence for 13 Repeats including the Carboxy Terminus of CA12S

```
4701 AAGGCCCTTG TTCAAGAACA CCAGTGTTGG CCCTCTGTAC TCTGGCTCCA
4751 GGCTGACCTT GCTCAGGCCA GAGAAAGATG GGGAAGCCAC CGGAGTGGAT
4801 GCCATCTGCA CCCACCGCCC TGACCCCACA GGCCCTGGGC TGGACAGAGA
4851 GCAGCTGTAT TTGGAGCTGA GCCAGCTGAC CCACAGCATC ACTGAGCTGG
4901 GCCCCTACAC ACTGGACAGG GACAGTCTCT ATGTCAATGG TTTCACCCAT
4951 CGGAGCTCTG TACCCACCAC CAGCACCGGG GTGGTCAGCG AGGAGCCATT
5001 CACACTGAAC TTCACCATCA ACAACCTGCG CTACATGGCG GACATGGGCC
5051 AACCCGGCTC CCTCAAGTTC AACATCACAG ACAACGTCAT GAAGCACCTG
5101 CTCAGTCCTT TGTTCCAGAG GAGCAGCCTG GGTGCACGGT ACACAGGCTG
5151 CAGGGTCATC GCACTAAGGT CTGTGAAGAA CGGTGCTGAG ACACGGGTGG
5201 ACCTCCTCTG CACCTACCTG CAGCCCCTCA GCGGCCCAGG TCTGCCTATC
5251 AAGCAGGTGT TCCATGAGCT GAGCCAGCAG ACCCATGGCA TCACCCGGCT
5301 GGGCCCCTAC TCTCTGGACA AAGACAGCCT CTACCTTAAC GGTTACAATG
5351 AACCTGGTCT AGATGAGCCT CCTACAACTC CCAAGCCAGC CACCCACATTC
5401 CTGCCTCCTC TGTCAGAAGC CACAACAGCC ATGGGGTACC ACCTGAAGAC
5451 CCTCACACTC AACTTCACCA TCTCCAATCT CCAGTATTCA CCAGATATGG
5501 GCAAGGGCTC AGCTACATTC AACTCCACCG AGGGGGTCCT TCAGCACCTG
5551 CTCAGACCCT TGTTCCAGAA GAGCAGCATG GGCCCCTTCT ACTTGGGTTG
5601 CCAACTGATC TCCCTCAGGC CTGAGAAGGA TGGGGCAGCC ACTGGTGTGG
5651 ACACCACCTG CACCTACCAC CCTGACCCTG TGGGCCCCGG GCTGGACATA
5701 CAGCAGCTTT ACTGGGAGCT GAGTCAGCTG ACCCATGGTG TCACCCAACT
5751 GGGCTTCTAT GTCCTGGACA GGGATAGCCT CTTCATCAAT GGCTATGCAC
5801 CCCAGAATTT ATCAATCCGG GGCGAGTACC AGATAAATTT CCACATTGTC
5851 AACTGGAACC TCAGTAATCC AGACCCCACA TCCTCAGAGT ACATCACCCT
5901 GCTGAGGGAC ATCCAGGACA AGGTCACCAC ACTCTACAAA GGCAGTCAAC
5951 TACATGACAC ATTCCGCTTC TGCCTGGTCA CCAACTTGAC GATGGACTCC
6001 GTGTTGGTCA CTGTCAAGGC ATTGTTCTCC TCCAATTTGG ACCCCAGCCT
6051 GGTGGAGCAA GTCTTTCTAG ATAAGACCCT GAATGCCTCA TTCCATTGGC
6101 TGGGCTCCAC CTACCAGTTG GTGGACATCC ATGTGACAGA AATGGAGTCA
6151 TCAGTTTATC AACCAACAAG CAGCTCCAGC ACCCAGCACT TCTACCCGAA
6201 TTTCACCATC ACCAACCTAC CATATTCCCA GGACAAAGCC CAGCCAGGCA
6251 CCACCAATTA CCAGAGGAAC AAAAGGAATA TTGAGGATGC GCTCAACCAA
6301 CTCTTCCGAA ACAGCAGCAT CAAGAGTTAT TTTTCTGACT GTCAAGTTTC
6351 AACATTCAGG TCTGTCCCCA ACAGGCACCA CACCGGGGTG GACTCCCTGT
6401 GTAACTTCTC GCCACTGGCT CGGAGAGTAG ACAGAGTTGC CATCTATGAG
6451 GAATTTCTGC GGATGACCCG GAATGGTACC CAGCTGCAGA ACTTCACCCT
6501 GGACAGGAGC AGTGTCCTTG TGGATGGGTA TTCTCCCAAC AGAAATGAGC
6551 CCTTAACTGG GPATTCTGAC CTTCCCTTCT GGGCTGTCAT CTTCATCGGC
```

TABLE 8-continued

Complete DNA Sequence for 13 Repeats including the Carboxy Terminus of CA12S

```
6601 TTGGCAGGAC TCCTGGGACT CATCACATGC CTGATCTGCG GTGTCCTGGT

6651 GACCACCCGC CGGCGGAAGA AGGAAGGAGA ATACAACGTC CAGCAACAGT

6701 GCCCAGGCTA CTACCAGTCA CACCTAGACC TGGAGGATCT GCAATGACTG

6751 GAACTTGCCG GTGCCTGGGG TGCCTTTCCC CCAGCCAGGG TCCAAAGAAG

6801 CTTGGCTGGG GCAGAAATAA ACCATATTGG TCG
```

TABLE 9

Complete Amino Acid Sequence for 13 Repeats Contiguous with the Carboxy Terminus of CA125

1
ERVLQGLLKP LFRNSSLEYL YSGCRLASLR PEKDSSAMAV DAICTHRPDP (SEQ ID NO:50)

EDLGLDRERL YWELSNLTNG IQELGPYTLD RNSLYVNGFT HRSSMPTTST

PGTSTVDVGT SGTPSSSPSP TTAGPLLMPF TLNFTITNLQ YEEDMRRTGS

2
RKFNTMERVL QGPLSPIFKN SSVGPLYSGC RLTSLRPEKD GAATGMDAVC

LYHPNPKRPG LDREQLYWEL SQLTHNITEL GPYSLDRDSL YVNGFTHQNS

VPTTSTPGTS TVYWATTGTP SSFPGHTEPG PLLIPPTLNF TTTNLQYEEN

3
MGHPGSRKFN ITERVLLQGLL NPIFKNSSVG PLYSGCRLTS LRPEKDGAAT

GMDAVCLYHP NPKRPGLDRE QLYCELSQLT HNITELGPYS LDRDSLYVNG

FTHQNSVPTT STPGTSTVYW ATTGTPSSFP GHTEPGPLLI PFTLNFTITN

4
LQYEEDMRRT GSRKFNTMER VLQCLLKPLF KSTSVGPLYS GCRLTLLRPE

KHGAATGVDA ICTLRLDPTG PGLDRERLYW ELSQLTNSVT ELGPYTLDRD

SLYVNGFTHR SSVPTTSIPG TSAVHLETSG TPASLPGHTA PGPLLVPFTL

NFTITNLQYE EDMRHPGSRK FNTTERVLQG LLKPTLFKSTS VGPLYSGCRL

5
TLLRPEKRGA ATGVDTICTH RLDPLNPGLD REQLYWELSK LTRGIIELGP

YLLDRGSLYV NGFTHRNFVP TTSTPGTSTV HLGTSETPSS LPRPIVPGPL

LIPFTLNFTI TNLQYEENMG HPGSRKFNIT ERVLQGLLKP LFRNSSLEYL

6
YSGCRLASLR PEKDSSAMAV DAICTHRPDF EDLGLDRERL YWELSNLTNG

IQELGPYTLD RNSLYVNGFT HRSSMPTTST PGTSTVDVGT SGTPSSSPSP

TTAGPLLMPF TLNFTITNLQ YEEDMRRTGS RKFNTMESVL QGLLKPLFKN

7
TSVGPLYSGC RLTLLRPKKD GAATGVDATC THRLDPKSPG LNREQLYWEL

SKLTNDIEEV GPYTLDRNSL YVNGFTHRSF VAPTSTLGTS TVDLGTSGTP

SSLPSPTTGV PLLIPFTLNF TITNLQYEEN MGHPGSRKFN IMERVLQGLL

8
SPIFKNSSVG SLYSGCRLTL LRPEKDGAAT RVDAVCTHRP DPKSPGLDRE

RLYWKLSQLT HGIIELGPYT LDRHSFYVNG FTHQSSMTTT RTPDTSTMHL

ATSRTPASLS GPTTASPLLV LFTTNFTITN QRYEENMHHP GSRKFNTTER

TABLE 9-continued

Complete Amino Acid Sequence for 13 Repeats Contiguous with the Carboxy Terminus of CA125

```
                                              9
VLQGLLRPVF KHTSVGPLYS GCRLTLLRPK KDGAATKVDA ICTYRPDPKS

PGLDREQLYW ELSQLTHSIT ELGPYTQDRD SLYVNGFTHR SSVPTTSIPG

TSAVHLETSG TPASLPGPSA ASPLLVLFTL NFTITNLRYE ENMQHPGSRK
                                             10
FNTTERVLQG LLRSLFKSTS VGPLYSGCRL TLLRPEKDGT ATGVDAICTH

HPDPKSPRLD REQLYWELSQ LTHNITELGH YALDNDSLFV NGFTHRSSVS

TTSTPGTPTV YLGASKTPAS IFGPSAASHL LILFTLNFTI TNLRYEENMW
                                             11
PGSRKFNTTE RVLQGLLRPL FKNTSVGPLY SGSRLTLLRP EKDGEATGVD

AICTHRPDPT GPGLDREQLY LELSQLTHSI TELGPYTLDR DSLYVNGFTH

RSSVPTTSTG VVSEEPFTLN FTINNLRYMA DMGQPGSLKF NTTDNVMKHL
                                             12
LSPLFQRSSL GARYTGCRVI ALRSVKtLGAE TRVDLLCTYL QPLSGPGLPI

KQVFHELSQQ THGTTRLGPY SLDKDSLYLN GYNEPGLDEP PTTPKPATTF

LPPLSEATTA MGYHLKTLTL NFTTSNLQYS PDMGKGSATF NSTEGVLQHL
                                             13
LRPLFQKSSM GPFYLGCQLI SLRPEKDGAA TGVDTTCTYH PDPVGPGLDI

QQLYWELSQL THGVTQLGFY VLDRDSLFIN GYAPQNLSIR GEYQINFHIV

NWNLSNPDPT SSEYITLLRD IQDKVTTLYK GSQLHDTFRF CLVTNLTMDS

VLVTVKALFS SNLDPSLVEQ VFLDKTLNAS FHWLGSTYQL VDIHVTEMES

SVYQPTSSSS TQHFYLNFTI TNLPYSQDKA QPGTTNYQRN KRNIEDALNQ

LFRNSSIKSY FSDCQVSTFR SVPNRHHTGV DSLCNFSPLA RRVDRVAIYE

EFLRMTRNGT QLQNFTLDRS SVLVDGYSPN RNEPLTGNSD LPFWAVILIG

LAGLLGLITC LICGVLVTTR RRKKEGEYNV QQQCPGYYQS HLDLEDLQ
```

TABLE 10A

5' Primer Sequence for End of the Open Reading Frame for Contig #32 of Chromosome 19 Cosmid AC008734 (SEQ ID NO: 51), Primer Sequence from within the Repeat Region (SEQ ID NO: 52, 3 Primer Sets Synthesized to Piece Together Entire Open Reading Frame in Contig #32 (SEQ ID NOS: 53 thru 58), Primers to Cosmid No. AC008734 for Contig #32 (SEQ ID NOS: 59 and 60), Sense Primer Sequence (supplied by Ambion) (SEQ ID NO: 61), Anti-Sense Primer Sequence for CA125 (SEQ ID NO: 62), and 5'Sense Primer Sequence (from Ambion) (SEQ ID NO: 63) and Anti-Sense Primer Specific to CA125 (SEQ ID NO: 64)

(SEQ ID NO:51)
(5'-CAGCAGAGACCAGCACGAGTACTC-3')

(SEQ ID NO:52)
(5'-TCCACTGCCATGGCTGAGCT-3')

Primer Sets (Set 1)  5'-CCAGCACAGCTCTTCCCAGGAC-3'  (SEQ ID NO:53)

5'-GGAATGGCTGAGCTGACGTCTG-3'  (SEQ ID NO:54)

TABLE 10A-continued

5' Primer Sequence for End of the Open Reading Frame for Contig #32 of Chromosome 19 Cosmid AC008734 (SEQ ID NO: 51), Primer Sequence from within the Repeat Region (SEQ ID NO: 52, 3 Primer Sets Synthesized to Piece Together Entire Open Reading Frame in Contig #32 (SEQ ID NOS: 53 thru 58), Primers to Cosmid No. AC008734 for Contig #32 (SEQ ID NOS: 59 and 60), Sense Primer Sequence (supplied by Ambion) (SEQ ID NO: 61), Anti-Sense Primer Sequence for CA125 (SEQ ID NO: 62), and 5'Sense Primer Sequence (from Ambion) (SEQ ID NO: 63) and Anti-Sense Primer Specific to CA125 (SEQ ID NO: 64)

(Set 2)  5'-CTTCCCAGGACAACCTCAAGG-3'            (SEQ ID NO:55)

5'-GCAGGATGAGTGAGCCACGTG-3'            (SEQ ID NO:56)

(Set 3)  5'-GTCAGATCTGGTGACCTCACTG-3'           (SEQ ID NO:57)

5'-GAGGCACTGGAAAGCCCAGAG-3'            (SEQ ID NO:58)

5'-CTGATGGCATTATGGAACACATCAC-3'        (SEQ ID NO:59)

5'-CCCAGAACGAGAGACCAGTGAG-3'           (SEQ ID NO:60)

5'-GCTGATGGCGATGAATGAACACTG-3'         (SEQ ID NO:61)

5'-CCCAGAACGAGAGACCAGTGAG-3'           (SEQ ID NO:62)

5'-CGCGGATCCGAACACTGCGTTTGCTGGCTTTGATG-3'   (SEQ ID NO:63)

5'-CCTCTGTGTGCTGCTTCATTGGG-3'          (SEQ ID NO:64)

TABLE 10B

Sense and Anti-Sense Primers Used to Order the CA125 Carboxy Terminal Domain (SEQ. ID NO: 303 and SEQ ID NO: 304, respectively)

5'-GGACAAGGTCACCACACTCTAC-3'     (SEQ ID NO:303)

5'-GCAGATCCTCCAGGTCTAGGTGTG-3'   (SEQ ID NO:304)

TABLE 10C

Sense and Anti-Sense Primers Used to Amplify Overlapping Sequences in the Repeat Domain (SEQ ID NO: 305 and SEQ ID NO: 306, respectively)

5' GTC TCT ATG TCA ATG GTT TCA CCC-3'   (SEQ ID NO:305)

5'-TAG CTG CTC TCT GTC CAG TCC-3'       (SEQ ID NO:306)

TABLE 11

5' Sense Primer 1 Sequence and 3' Antisense Primer 2 (SEQ ID NO: 65 and SEQ ID NO: 66, respectively), and Nucleotide and Amino Acid Sequences of the CA125 Repeat Expressed in *E. coli* (SEQ ID NO: 67 and SEQ ID NO: 68, respectively)

5'-ACCGGATCCATGGGCCACACAGAGCCTGGCCC-3'   (SEQ ID NO:65)

5'-TGTAAGCTTAGGCAGGGAGGATGGAGTCC-3'      (SEQ ID NO:66)

```
  1 ATGAGAGGAT CGCATCACCA TCACCATCAC GGATCCATGG GCCACACAGA   (SEQ ID NO:67)
                                                ↑
 51 GCCTGGCCCT CTCCTGATAC CATTCACTTT CAACTTTACC ATCACCAACC

101 TGCATTATGA GGAAAACATG CAACACCCTG GTTCCAGGAA GTTCAACACC

151 ACGGAGAGGG TTCTGCAGGG TCTGCTCAAG CCCTTGTTCA AGAACACCAG

201 TGTTGGCCCT CTGTACTCTG GCTGCAGACT GACCTTGCTC AGACCTGAGA

251 AGCATGAGGC AGCCACTGGA GTGGACACCA TCTGTACCCA CCGCGTTGAT

301 CCCATCGGAC CTGGACTGGA CAGAGAGCGG CTATACTGGG AGCTGAGCCA

351 GCTGACCAAC AGCATCACAG AGCTGGGACC CTACACCCTG GACAGGGACA

401 GTCTCTATGT CAATGGCTTC AACCCTCGGA GCTCTGTGCC AACCACCAGC
```

TABLE 11-continued

5' Sense Primer 1 Sequence and 3' Antisense Primer 2
(SEQ ID NO: 65 and SEQ ID NO: 66, respectively), and
Nucleotide and Amino Acid Sequences of the CA125 Repeat Expressed in *E. coli* (SEQ ID NO: 67 and SEQ ID NO: 68, respectively)

451 ACTCCTGGGA CCTCCACAGT GCACCTGGCA ACCTCTGGGA CTCCATCCTC

501 CCTGCCT

M R G S H H H H H H G S M G H T E P G L L L I P F T F N F (SEQ ID NO:68)

T I T N L H Y E E N M Q H P G S R K F N T T E R V L Q G L

L K P L F K N T S V G P L Y S G C R L T L L R P E K H E A

A T G V D T I C T H R V D P I G P G L D R E R L Y W E L S

Q L T N S I T E L G P Y T L D R D S L Y V N G F N P R S S

V P T T S T P G T S T V H L A T S G T P S S L P

TABLE 12

Additional Multiple Repeat Amino Acid Sequences
(SEQ ID NO:69 thru SEQ ID NO:80)

ERVLQGLLGP MFKNTSVGLL YSGCRLTLLR PKKDGAATKV DAICTYRPDP (SEQ ID NO:69)

KSPGLDREQL YWELSQLTHS ITELGPYTLD RDSLYVNGFT QRSSVPTTSI

PGTPTVDLGT SGTPVSKPGP SAASPLLIPF TINFTITNLR YEENMGHPGS

RKFNIMERVL QGLLKPLFKN TSVGPLYSGC RLTLLRPKKD GAATGVDAIC

THRLDPKSPG LNREQLYWEL SKLTNDIEEL GPYTLDRNSL YVNGFTHQSS

VSTTSTPGTS TVDLRTSGTP SSLSSPTIMA AGPLLIPFTI NFTITNLRYE

ENMHHPGSRK FNTMERVLQG LLMPLFKNTS VSSLYSGCRL TLLRPEKDGA

ATRVDAVCTH RPDPKSPGLD RERLYWKLSQ LTHGITELGP YTLDRNSLYV

NGFTHRSSMP TTSTPGTSTV DVGTSGTPSS SPSPTTAGPL LMPFTLNFTI

TNLQYEEDMR RTGSRKFNTM ERVLQGLLKP LFKSTSVGPL YSGCRLTLLR

PEKHGAATGV DAICTLRLDP TGPGLDRERL YWELSQLTNS VTELGPYTLD

RDSLYVNGFT HRSSVPTTSI PGTSAVHLET SGTPASLPGH TAPGPLLIPF

TLNFTITNLH YEENMQHPGS RKFNTMERVL QGCLVPCSRN TNVGLLYSGC

RLTLLRXEKX XAATXVDXXC XXXXDPXXPG LDREXLYWEL SXLTXXIXEL

GPYTLDRNSL YVNGFTHRSS VAPTSTPGTS TVDLGTSGTP SSLPSPTTVP

LLVPFTLNFT ITNLQYGEDM RHPGSRKFNT TERVLQGLLG PLFKNSSVGP

LYSGCRLISL RSEKDGAATG VDAICTHHLN PQSPGLDREQ LYWQLSQVTN

GIKELGPYTL DRNSLYVNGF THRSSGLTTS TPWTSTVDLG TSGTPSPVPS

PTTAGPLLI

QGLLGPMFKN TSVGLLYSGC RLTLLRPEKR GAATGVDTIC THRLDPLNPG (SEQ ID NO:70)

LDREQLYWEL SKLTRGIIEL GPYLLDRGSL YVNGFTHRNF VPITSTPGTS

TVHLGTSETP SSLPRPIVPG PLLVPFTLNF TITNLQYEEA MRHPGSRKFN

TTERVLQGLL RPLFKNTSVS SLYSGCRLTL LRPEKDGAAT RVDAACTYRP

DPKSPGLDRE QLYWELSQLT HSITELGPYT LDRVSLYVNG FNPRSSVPTT

STPGTSTVHL ATSGTPSSLP GHTAPVPLLI PFTLNFTITN LQYEEDMRHP

TABLE 12-continued

Additional Multiple Repeat Amino Acid Sequences
(SEQ ID NO:69 thru SEQ ID NO:80)

GSRKFNTMER VLQGLLRPLF KNTSIGPLYS <u>SCRLTLLRPE KDKAATRVDA</u>

<u>IC</u>THHPDPQS PGLNREQLYW ELSQLTHGIT ELGPYTLDRD SLYVDGFTHW

SPIPTTSTPG TSIVNLGTSG IPPSLPETTA TGPLLIPFTP NFTITNLQYE

EDMRRTGSRK FNTMERVLQG LLSPIFKNSS VGPLYSG<u>CRL TSLRPEKDGA</u>

<u>ATGMDAVC</u>LY HPNPKRPGLD REQLY

ERVLQGLLKP LFKSTSVGPL YSG<u>CRLTLLR PEKDGVATRV DAIC</u>THRPDP (SEQ ID NO:71)

KIPGLDRQQL YWELSQLTHS ITELGPYTLD RDSLYVNGFT QRSSVPTTST

PGTFTVQPET SETPSSLPGP TATGPVLLPF TLNFTIINLQ YEEDMHRPGS

RKFNTTERVL QGLLMPLFKN TSVGPLYSG<u>C RLTLLRPEKQ EAATGVDTIC</u>

THRLDPSEPG LDREQLYWEL SQLTNSITEL GPYTLDRDSL YVNGFTHSGV

LCPPPSILGI FTVQPETFET PSSLPGPTAT GPVLLPFTLN FTIINLQYEE

DMHRPGSRKF NTTERVLQGL TPLFKNTSV GPLYSG<u>CRLT LLRPEKQEAA</u>

<u>TGVDTIC</u>THR VDPIGPGLDR ERLYWELSQL TNSITELGPY TLDRDSLYVN

GFNPWSSVPT TSTPGTSTVH LATSGTPSSL PGHTAPVPLL IPFTLNFTIT

NLHYEENMQH PGSRKFNTTE RVLQGLLKPL FKSTSVGPLY SG<u>CRLTLLRP</u>

<u>EKHGAATGVD AIC</u>THRLDPK SPGVDREQLY WELSQLTNGI KELGPYTLDR

NSLYVNGFTH WIPVPTSSTP GTSTVDLGSG TPSSLPSPTT AGPL

TSVGPLYSG<u>C RLTLLRSEKD GAATGVDAIY</u> THRLDPKSPG VDREQLYWEL (SEQ ID NO:72)

SQLTNGIKEL GPYTLDRNSL YVNGFTHQTS APNTSTPGTS TVDLGTSGTP

SSLPSPTSAG PLLIPFTINF TTTNLRYEEN MHHPGSRKFN TMERVLQGLL

KPLFKSTSVG PLYSG<u>CRLTL LRPEKDGVAT RVDAIC</u>THRP DPKIPGLDRQ

QLYWELSQLT HSITELGPYT LDRDSLYVNG FTQRSSVPTT STPGTFTVQP

ETSETPSSLP GPTATGPVLL PFTLNFTIIN LQYEEDMHRP GSRKFNTTER

VLQGLLKPLF KSTSVGPLYS G<u>CRLTLLRPE KHGAATGVDA IC</u>TLRLDPTG

PGLDRERLYW ELSQLTNSIT ELGPYTLDRD SLYVNGFNPW SSVPTTSTPG

TSTVHLATSG TPSSLPGHTA PVPL

ERVLQGLLKP LFKSTSVGPL YSG<u>CRLTLLR PEKRGAATGV DTIC</u>THRLDP (SEQ ID NO:73)

LNPGLDREQL YWELSKLTRG IIELGPYLLD RDSLYVNGFT HRSSVPTTSI

PGTSAVHLET SGTPASLPGH TAPGPLLVPF TLNFTITNLQ YEEDMRHPGS

RKFNTTERVL QGLLKPLFKS TSVGPLYSG<u>C RLTLLRPEKR GAATGVDTIC</u>

THRLDPLNPG LDREQLYWEL SKLTRGIIEL GPYLLDRGSL YVNGFTHRNF

VPITSTPGTS TVHLGTSETP SSLPRPTVPG PLLIPF

ERVLQGLLRP VFKNTSVGPL YSG<u>CRLTLLR PKKDGAATKV DAIC</u>YRPDP (SEQ ID NO:74)

KSPGLDREQL YWELSQLTHS ITELGPYTLD RDSLYVNGFT QRSSVPTTSI

PGTPTVDLGT SGTPVSKPGP SAASPLLVFF TLNFTITNLQ YEEDMHRPGS

RKFNATERVL QGLLSPIFKN SSVGPLYSG<u>C RLTSLRPEKD GAATGMDAVC</u>

LYHPNPKRPG LDREQLYWEL SQLTHNITEL GPYSLDRDSL YVNGFTHQSS

MTTTRTPDTS TMHLATSRTP ASLSGPTTAS PLLIPF

TABLE 12-continued

Additional Multiple Repeat Amino Acid Sequences
(SEQ ID NO:69 thru SEQ ID NO:80)

ERVLQGLLKP LFKSTSVGPL YSG<u>CRLTLLR PEKRGAATGV DTIC</u>THRLDP (SEQ ID NO:75)

LNPGLDREQL YWELSKLTRG IIELGPYLLD RGSLYVNGFS RQSSMTTTRT

PDTSTMHLAT SRTPASLSGP TTASPLLIPF TLNFTITNLQ YEENMGHPGS

RKFNIMERVL QGLLNPIFKN SSVGPLYS<u>GC RLTSLKPEKD GAATGMDAVC</u>

LYHPNPKRPG LDREQLYWEL SQLTHGIKEL GPYTLDPNSL YVNGFTHRSS

VAPTSTPGTS TVDLGTSGTP SSLPSPTTAV PLLTPF

ERVLQGLLKP LFRNSSLEYL YSG<u>CRLASLR PEKDSSAMAV DAIC</u>THRPDP (SEQ ID NO:76)

EDLGLDRERL YWELSNLTNG IQELGPYTLD RNSLYVNGFT HRSSGLTTST

PWTSTVDLGT SGTPSPVPSP TTAGPLLIPF TLNFTITNLQ YEENMGHPGS

RKFNIMERVL QGLLMPLFKN TSVSSLYS<u>GC RLTLLRPEKD GAATRVDAVC</u>

TQRPDPKSPG LDRERLYWKL SQLTHGITEL GPYTLDRHSL YVNGLTHQSS

MTTTRTPDTS TMHLATSRTP ASLSGPTTAS PLLIPF

ERVLQGLLSP ISKNSSVGPL YSG<u>CRLTSLR PEKDGAATGM DAVC</u>LYHPNP (SEQ ID NO:77)

KRPGLDREQL YWELSQLTHN ITELGPYSLD RDSLYVNGFT HQNSVPTTST

PGTSTVYWAT TGTPSSFPGH TEPGPLLIPF TVNFTITNLR YEENMHHPGS

RKFNTTERVL QGLLRPVFKN TSVGPLYSG<u>C RLTLLRPKKD GAATKVDATC</u>

TYRPDPKSPG LDREQLYWEL SKLTNDIEEL GPYTLDRNSL YVNGFTHQSS

VSTTSTPGTS TVDLRTSGTP SSLSSPTIMA AGPLLIPF

ERVLHGLLTP LFKNTRVGPL YSG<u>CRLTLLR PEKQEAATGV DTIC</u>THRVDP (SEQ ID NO:78)

IGPGLDRERL YWELSQLTNS ITELGPYTLD RDSLYVNGFN PWSSVPTTST

PGTSTVHLAT SGTPSSLPGH TAPVPLLIPF TLNFTITNLH YEENMQHPGS

RKFNTTERVL QGLLKPLFKN TSVGPLYSG<u>C RLTLFKPEKH EAATGVDAIC</u>

TLRLDPTGPG LDRQLYWELS QLTNSVTELG PYTLDRDSLY VNGFTHRSSV

PTTSIPGTSA VHLETSGTPA SLPGHTAPGP LLIPFTLNFT ITNLQYEEDM

RRTGSRKFNT MERVLQGLLK PLFKSTSVGP LYSG<u>CRLTLL RPEKRGAATG</u>

<u>VDTIC</u>THRLD PLNPGLDREQ LYWELSKLTR GIIELGPYLL DRGSLYVNGF

THRNFVPITS TPGTSTVHLG TSETPSSLPR PIVPGPLLIP FTINFTITNL

RYEENMHHPG SRKFNIMERV LQGLLGPLFK NSSVGPLYSG <u>CRLISLRSEK</u>

<u>DGAATGVDAIC</u>THHLNPQSP GLDREQLYWQ LSQMTNGIKE LGPYTLDRNS

LYVNGFTHRS SGLTTSTPWT STVDLGTSGT PSPVPSPTTA GPLLILPF

GPLYSG<u>CRLT SLRPEKDGAA TGMDAVC</u>LYH PNPKRPGLDR EQLYWELSQL (SEQ ID NO:79)

THNITELGPY SLDRDSLYVN GFTHQNSVPT TSTPGTSTVY WATTGTPSSF

PGHTEPGPLL IPFTLNFTIT NLQYEENMOH PGSRKFNITE SVLQGLLTPL

FKNSSVGPLY SG<u>CRLISLRS EKDGAATGVD AIC</u>THHLNPQ SPGLDREQLY

WQLSQMTNGI KELGPYTLDR DSLYVNGFTH RSLGLTTSTP WTSTVDLGTS

GTPSPVPSPT TAGPLLIPFT LNFTITNLQY EENMGHPGSR KFNIMERVLQ

GLLRPVFKNT SVGPLYSG<u>CR LTLLRPKKDG AATKVDAICT</u> YRPDPKSPGL

TABLE 12-continued

Additional Multiple Repeat Amino Acid Sequences
(SEQ ID NO:69 thru SEQ ID NO:80)

DREQLYWELS QLTHSITELG PYTLDRDSLY VNGFTQRSSV PTTSIPGTPT

VDLGTSGTPV SKPGPSAASP

QLYWELSKLT NDIEELGPYT LDRNSLYVNG FTHQSSVSTT STPGTSTVDL (SEQ ID NO:80)

RTSGTPSSLS SPTIMAAGPL LIPFTLNFTI TNLQYEENMG HPGSRKFNJM

ERVLQGLLGP MFKNTSVGLL YSG<u>CRLTLLR PEKNGAATGM DAIC</u>SHRLDP

KSPGLNREQL YWELSQLTHG IKELGPYTLD RNSLYVNGFT HRSSVAPTST

PGTSTVDLGT SGTPSSLPSP TTAVPLLIPF TLNFTITNLK YEEDMHCPGS

RKFNTTERVL QSLFGPMFKN TSVGPLYSG<u>C RLTLLRSEKD GAATGVDAIC</u>

THRLDPKSLG VDREQLYWEL SQLTNGIKEL GPYTLDRNSL YVNGFTHQTS

APNTSTPGTS TVDLGTSGTP SSLPSPTSAG FLLVPFTLNF TITNLQYEED

MRRTGSRKFN TMESVLQGLL KPLFKNTSVG PLYSG<u>CRLTL LRPEKDGAAT</u>

<u>GVDAIC</u>THRL DPKSPGLNRE QLYWELSKL

TABLE 13

Amino Terminal Nucleotide Sequence

```
   1 CAGAGAGCGT TGAGCTGGGA ACAGTGACAA GTGCTTATCA AGTTCCTTCA (SEQ ID NO:81)
  51 CTCTCAACAC GGTTGACAAG AACTGATGGC ATTATGGAAC ACATCACAAA
 101 AATACCCAAT GAAGCAGCAC ACAGAGGTAC CATAAGACCA GTCAAAGGCC
 151 CTCAGACATC CACTTCGCCT GCCAGTCCTA AAGGACTACA CACAGGAGGG
 201 ACAAAAAGAA TCGAGACCAC CACCACAGCT TTGAAGACCA CCACCACAGC
 251 TTTGAACACC ACTTCCAGAG CCACCTTGAC CACCAGTGTC TATACTCCCA
 301 CTTTGGGAAC ACTGACTCCC CTCAATGCAT CAAGGCAAAT GGCCAGCACA
 351 ATCCTCACAG AAATGATGAT CACAACCCCA TATGTTTTCC CTGATGTTCC
 401 AGAAACGACA TCCTCATTGG CTACCAGCCT GGGAGCAGAA ACCAGCACAG
 451 CTCTTCCCAG GACAACCCCA TCTGTTCTCA ATAGAGAATC AGAGACCACA
 501 GCCTCACTGG TCTCTCGTTC TGGGGCAGAG AGAAGTCCGG TTATTCAAAC
 551 TCTAGATGTT TCTTCTAGTG AGCCAGATAC AACAGCTTCA TGGGTTATCC
 601 ATCCTGCAGA GACCATCCCA ACTGTTTCCA AGACAACCCC CAATTTTTTC
 651 CACAGTGAAT TAGACACTGT ATCTTCCACA GCCACCAGTC ATGGGGCAGA
 701 CGTCAGCTCA GCCATTCCAA CAAATATCTC ACCTAGTGAA CTAGATGCAC
 751 TGACCCCACT GGTCACTATT TCGGGGACAG ATACTAGTAC AACATTCCCA
 801 ACACTGACTA AGTCCCCACA TGAAACAGAG ACAAGAACCA CATGGCTCAC
 851 TCATCCTGCA GAGACCAGCT CAACTATTCC CAGAACAATC CCCAATTTTT
 901 CTCATCATGA ATCAGATGCC ACACCTTCAA TAGCCACCAG TCCTGGGGCA
 951 GAAACCAGTT CAGCTATTCC AATTATGACT GTCTCACCTG GTGCAGAAGA
1001 TCTGGTGACC TCACAGGTCA CTAGTTCTGG GACAGACAGA AATATGACTA
1051 TTCCAACTTT GACTCTTTCT CCTGGTGAAC CAAAGACGAT AGCCTCATTA
1101 GTCACCCATC CTGAAGCACA GACAAGTTCG GCCATTCCAA CTTCAACTAT
```

TABLE 13-continued

Amino Terminal Nucleotide Sequence

```
1151 CTCGCCTGCT GTATCACGGT TGGTGACCTC AATGGTCACC AGTTTGGCGG
1201 CAAAGACAAG TACAACTAAT CGAGCTCTGA CAAACTCCCC TGGTGAACCA
1251 GCTACAACAG TTTCATTGGT CACGCATCCT GCACAGACCA GCCCAACAGT
1301 TCCCTGGACA ACTTCCATTT TTTTCCATAG TAAATCAGAC ACCACACCTT
1351 CAATGACCAC CAGTCATGGG GCAGAATCCA GTTCAGCTGT TCCAACTCCA
1401 ACTGTTTCAA CTGAGGTACC AGGAGTAGTG ACCCCTTTGG TCACCAGTTC
1451 TAGGGCAGTG ATCAGTACAA CTATTCCAAT TCTGACTCTT TCTCCTGGTG
1501 AACCAGAGAC CACACCTTCA ATGGCCACCA GTCATGGGGA AGAAGCCAGT
1551 TCTGCTATTC CAACTCCAAC TGTTTCACCT GGGGTACCAG GAGTGGTGAC
1601 CTCTCTGGTC ACTAGTTCTA GGGCAGTGAC TAGTACAACT ATTCCAATTC
1651 TGACTTTTTC TCTTGGTGAA COAGAGACCA CACCTTCAAT GGCCACCAGT
1701 CATGGGACAG AAGCTGGCTC AGCTGTTCCA ACTGTTTTAC CTGAGGTACC
1751 AGGAATGGTG ACCTCTCTGG TTGCTAGTTC TAGGGCAGTA ACCAGTACAA
1801 CTCTTCCAAC TCTGACTCTT TCTCCTGGTG AACCAGAGAC CACACCTTCA
1851 ATGGCCACCA GTCATGGGGC AGAAGCCAGC TCAACTGTTC CAACTGTTTC
1901 ACCTGAGGTA CCAGGAGTGG TGACCTCTCT GGTCACTAGT TCTAGTGGAG
1951 TAAACAGTAC AAGTATTCCA ACTCTGATTC TTTCTCCTGG TGAACTAGAA
2001 ACCACACCTT CAATGGCCAC CAGTCATGGG GCAGAAGCCA GCTCAGCTGT
2051 TCCAACTCCA ACTGTTTCAC TGGGGTATC AGGAGTGGTG ACCCCTCTGG
2101 TCACTAGTTC CAGGGCAGTG ACCAGTACAA CTATTCCAAT TCTAACTCTT
2151 TCTTCTAGTG AGCCAGAGAC CACACCTTCA ATGGCCACCA GTCATGGGGT
2201 AGAAGCCAGC TCAGCTGTTC TAACTGTTTC ACCTGAGGTA CCAGGAATGG
2251 TGACCTCTCT GGTCACTAGT TCTAGAGCAG TAACCAGTAC AACTATTCCA
2301 ACTCTGACTA TTTCTTCTGA TGAACCAGAG ACCACAACTT CATTGGTCAC
2351 CCATTCTGAG GCAAAGATGA TTTCAGCCAT TCCAACTTTA GCTGTCTCCC
2401 CTACTGTACA AGGGCTGGTG ACTTCACTGG TCACTAGTTC TGGGTCAGAG
2451 ACCAGTGCGT TTTCAAATCT AACTGTTGCC TCAAGTCAAC CAGAGACCAT
2501 AGACTCATGG GTCGCTCATC CTGGGACAGA AGCAAGTTCT GTTGTTCCAA
2551 CTTTGACTGT CTCCACTGGT GAGCCGTTTA CAAATATCTC ATTGGTCACC
2601 CATCCTGCAG AGAGTAGCTC AACTCTTCCC AGGACAACCT CAAGGTTTTC
2651 CCACAGTGAA TTAGACACTA TGCCTTCTAC AGTCACCAGT CCTGAGGCAG
2701 AATCCAGCTC AGCCATTTCA ACTACTATTT CACCTGGTAT ACCAGGTGTG
2751 CTGACATCAC TGGTCACTAG CTCTGGGAGA GACATCAGTG CAACTTTTCC
2801 AACAGTGCCT GAGTCCCCAC ATGAATCAGA GGCAACAGCC TCATGGGTTA
2851 CTCATCCTGC AGTCACCAGC ACAACAGTTC CCAGGACAAC CCCTAATTAT
2901 TCTCATAGTG AACCAGACAC CACACCATCA ATAGCCACCA GTCCTGGGGC
2951 AGAAGCCACT TCAGATTTTC CAACAATAAC TGTCTCACCT GATGTACCAG
3001 ATATGGTAAC CTCACAGGTC ACTAGTTCTG GGACAGACAC CAGTATAACT
3051 ATTCCAACTC TGACTCTTTC TTCTGGTGAG OCAGAGACCA CAACCTCATT
```

TABLE 13-continued

Amino Terminal Nucleotide Sequence

```
3101 TATCACCTAT TCTGAGACAC ACACAAGTTC AGCCATTCCA ACTCTCCCTG
3151 TCTCCCCTGG TGCATCAAAG ATGCTGACCT CACTGGTCAT CAGTTCTGGG
3201 ACAGACAGCA CTACAACTTT CCCAACACTG ACGGAGACCC CATATGAAOC
3251 AGAGACAACA GCCATACAGC TCATTCATCC TGCAGAGACC AACACAATGG
3301 TTCCCAAGAC AACTCCCAAG TTTTCCCATA GTAAGTCAGA CACCACACTC
3351 CCAGTAGCCA TCACCAGTCC TGGGCCAGAA GCCAGTTCAG CTGTTTCAAC
3401 GACAACTATC TCACCTGATA TGTCAGATCT GGTGACCTCA CTGGTCCCTA
3451 GTTCTGGGAC AGACACCAGT ACAACCTTCC CAACATTGAG TGAGACCCCA
3501 TATGAACCAG AGACTACAGT CACGTGGCTC ACTCATCCTG CAGAAACCAG
3551 CACAACGGTT TCTGGGACAA TTCCCAACTT TTCCCATAGG GGATCAGACA
3601 CTGCACCCTC AATGGTCACC AGTCCTGGAG TAGACACGAG GTCAGGTGTT
3651 CCAACTACAA CCATCCCACC CAGTATACCA GGGGTAGTGA CCTCACAGGT
3701 CACTAGTTCT GCAACAGACA CTAGTACAGC TATTCCAACT TTGACTCCTT
3751 CTCCTGGTGA ACCAGAGACC ACAGCCTCAT CAGCTACCCA TCCTGGGACA
3801 CAGACTGGCT TCACTGTTCC AATTCGGACT GTTCCCTCTA GTGAGCCAGA
3851 TACAATGGCT TCCTGGGTCA CTCATCCTCC ACAGACCAGC ACACCTGTTT
3901 CCAGAACAAC CTCCAGTTTT TCCCATAGTA GTCCAGATGC CACACCTGTA
3951 ATGGCCACCA GTCCTAGGAC AGAAGCCAGT TCAGCTGTAC TGACAACAAT
4001 CTCACCTGGT GCACCAGAGA TGGTGACTTC ACAGATCACT AGTTCTGGGG
4051 CAGCAACCAG TACAACTGTT CCAACTTTGA CTCATTCTCC TGGTATGCCA
4101 GAGACCACAG CCTTATTGAG CACCCATCCC AGAACAGGGA CAAGTAAAAC
4151 ATTTCCTGCT TCAACTGTGT TTCCTCAAGT ATCAGAGACC ACAGCCTCAC
4201 TCACCATTAG ACCTGGTGCA GAGACTAGCA CAGCTCTCCC AACTCAGACA
4251 ACATCCTCTC TCTTCACCCT ACTTGTAACT GGAACCAGCA GAGTTGATCT
4301 AAGTCCAACT GCTTCACCTG GTGTTTCTGC AAAAACAGCC CCACTTTCCA
4351 CCCATCCAGG GACAGAGACO AGCACAATGA TTCCAACTTC AACTCTTTCC
4401 CTTGGTTTAC TAGAGACTAC AGGCTTACTG CCACCAGCT CTTCAGCAGA
4451 GACCAGCACG AGTACTCTAA CTCTGACTGT TTCCCCTGCT GTCTCTGGGC
4501 TTTCCAGTGC CTCTATAACA ACTGATAAGC CCCAAACTGT GACCTCCTGG
4551 AACACAGAAA CCTCACCATC TGTAACTTCA GTTGGACCCC CAGAATTTTC
4601 CAGGACTGTC ACAGGCACCA CTATGACCTT GATACCATCA GAGATGCCAA
4651 CACCACCTAA AACCAGTCAT GGAGAAGGAG TGAGTCCAAC CACTATCTTG
4701 AGAACTACAA TGGTTGAAGC CACTAATTTA GCTACCACAG GTTCCAGTCC
4751 CACTGTGGCC AAGACAACAA CCACCTTCAA TACACTGGCT GGAAGCCTCT
4801 TTACTCCTCT GACCACACCT GGGATGTCCA CCTTGGCCTC TGAGAGTGTG
4851 ACCTCAAGAA CAAGTTATAA CCATCGGTCC TGGATCTCCA CCACCAGCAG
4901 TTATAACCGT CGGTACTGGA CCCCTGCCAC CAGCACTCCA GTGACTTCTA
4951 CATTCTCCCC AGGGATTTCC ACATCCTCCA TCCCCAGCTC CACAGCAGCC
5001 ACAGTCCCAT TCATGGTGCC ATTCACCCTC AACTTCACCA TCACCAACCT
```

TABLE 13-continued

Amino Terminal Nucleotide Sequence

5051 GCAGTACGAG GAGGACATGC GGCACCCTGG TTCCAGGAAG TTCAACGCCA

5101 CAGAGAGAGA ACTGCAGGGT CTGCTCAAAC CCTTGTTCAG GAATAGCAGT

5151 CTGCAATACC TCTATTCAGG CTGCAGACTA GCCTCACTCA GGCCAGAGAA

5201 GGATAGCTCA GCCATGGCAG TGGATGCCAT CTGCACACAT CGCCCTGACC

5251 CTGAAGACCT CGGACTGGAC AGAGAGCGAC TGTACTGGGA GCTGAGCAAT

5301 CTGACAAATG GCATCCAGGA GCTGGGCCCC TACACCCTGG ACCGGAACAG

5351 TCTCTATGTC AATGGTTTCA CCCATCGAAG CTCTATGCCC ACCACCAGCA

5401 CTCCTGGGAC CTCCACAGTG GATGTGGGAA CCTCAGGGAC TCCATCCTCC

5451 AGCCCCAGCC CCACG

TABLE 14

Amino Terminal Protein Sequence

1 ESVLEGTVTS AYQVPSLSTR LTRTDGIMEH ITKIPNEAAH RGTIRPVKGP (SEQ ID NO:82)

51 QTSTSPASPK GLHTGGTKRM ETTTTALKTT TTALKTTSRA TLTTSVYTPT

101 LGTLTPLNAS RQMASTILTE MMITTPYVFP DVPETTSSLA TSLGAETSTA

151 LPRTTPSVLN RESETTASLV SRSGAERSPV IQTLDVSSSE PDTTASWVIH

201 PAETIPTVSK TTPNFFHSEL DTVSSTATSH GADVSSAIPT NISPSELDAL

251 TPLVTISGTD TSTTFPTLTK SPHETETRTT WLTHPAETSS TIPRTIPNFS

301 HHESDATPSI ATSPGAETSS AIPIMTVSPG AEDLVTSQVT SSGTDRNMTI

351 PTLTLSPGEP KTIASLVTHP EAQTSSAIPT STISPAVSRL VTSMVTSLAA

401 KTSTTNRALT NSPGEPATTV SLVTHPAQTS PTVPWTTSIF FHSKSDTTPS

451 MTTSHGAESS SAVPTPTVST EVPGVVTPLV TSSRAVISTT IPILTLSPGE

501 PETTPSMATS HGEEASSAIP TPTVSPGVPG VVTSLVTSSR AVTSTTIPIL

551 TPSLGEPETT PSMATSHGTE AGSAVPTVLP EVPGMVTSLV ASSRAVTSTT

601 LPTLTLSPGE PETTPSMATS HGAEASSTVP TVSPEVPGVV TSLVTSSSGV

651 NSTSIPTLIL SPGELETTPS MATSHGAEAS SAVPTPTVSP GVSGVVTPLV

701 TSSPAVTSTT IPILTLSSSE PETTPSMATS HGVEASSAVL TVSPEVPGMV

751 TSLVTSSRAV TSTTIPTLTI SSDEPETTTS LVTHSEAKMI SAIPTLAVSP

801 TVQGLVTSLV TSSGSETSAF SNLTVASSQP ETIDSWVAHP GTEASSVVPT

851 LTVSTGEPFT NISLVTHPAE SSSTLPRTTS RFSHSELDTM PSTVTSPEAE

901 SSSAISTTIS PGIPGVLTSL VTSSGRDISA TFPTVPESPH ESEATASWVT

951 HPAVTSTTVP RTTPNYSHSE PDTTPSIATS PGAEATSDFP TITVSPDVPD

1001 MVTSQVTSSG TDTSITIPTL TLSSGEPETT TSFITYSETH TSSAIPTLPV

1051 SPGASKMLTS LVISSGTDST TTFPTLTETP YEPETTAIQL IHPAETNTMV

1101 PRTTPKFSHS KSDTTLPVAI TSRGPEASSA VSTTTISRDM SDLVTSLVPS

1151 SGTDTSTTFP TLSETPYEPE TTATWLTHPA ETSTTVSGTI PNFSHRGSDT

1201 APSMVTSPGV DTRSGVPTTT IPPSIPGVVT SQVTSSATDT STAIPTLTPS

1251 PGEPETTASS ATHPGTQTGF TVPIRTVPSS EPDTMASWVT HPPQTSTPVS

TABLE 14-continued

Amino Terminal Protein Sequence

```
1301 RTTSSFSHSS PDATPVMATS PRTEASSAVL TTISPGAPEM VTSQITSSGA

1351 ATSTTVPTLT HSPGMPETTA LLSTHPRTET SKTFPASTVF PQVSETTASL

1401 TIRPGAETST ALPTQTTSSL FTLLVTGTSR VDLSPTASPG VSAKTAPLST

1451 HPGTETSTMI PTSTLSLGLL ETTGLLATSS SAETSTSTLT LTVSPAVSGL

1501 SSASITTDKP QTVTSWNTET SPSVTSVGPP EFSRTVTGTT MTLIPSEMPT

1551 PPKTSHGEGV SPTTILRTTM VEATNLATTG SSPTVAKTTT TFNTLAGSLF

1601 TPLTTPGMST LASESVTSRT SYNHRSWIST TSSYNRRYWT PATSTPVTST

1651 FSPGISTSSI PSSTAATVPF MVPFTLNFTI TNLQYEEDMR HPGSRKFNAT

1701 ERELQGLLKP LFRNSSLEYL YSGCRLASLR PEKDSSAMAV DATCTHRPDP

1751 EDLGLDRERL YWELSNLTNG IQELGPYTLD RNSLYVNGFT HRSSMPTTST

1801 PGTSTVDVGT SGTPSSSPSP T
```

TABLE 15

CA125 Repeat Nucleotide Sequence
(SEQ ID NO:83 thru SEQ ID NO:145)

```
  1 GCCACAGTCC CATTCATGGT GCCATTCACC CTCAACTTCA CCATCACCAA (SEQ ID NO:83)

51 CCTGCAGTAC GAGGAGGACA TGCGGCACCC TGGTTCCAGG AAGTTCAACG

101 CCACAGAGAG AGAACTGCAG GGTCTGCTCA AACCCTTGTT CAGGAATAGC

151 AGTCTGGAAT ACCTCTATTC AGGCTGCAGA CTAGCCTCAC TCAGGCCAGA

201 GAAGGATAGC TCAGCCATGG CAGTGGATGC CATCTGCATA CATCGCCCTG

251 ACCCTGAAGA CCTCGGACTG GACAGAGAGC GACTGTACTG GGAGCTGAGC

301 AATCTGACAA ATGGCATCCA GGAGCTGGGC CCCTACACCC TGGACCGGAA

351 CAGTCTCTAT GTCAATGGTT TCACCCATCG AAGCTCTATG CCCACCACCA

401 GCACTCCTGG GACCTCCACA GTGGATGTGG GAACCTCAGG GACTCCATCC

451 TCCAGCCCCA GCCCCACG

1 GCTGCTGGCC CTCTCCTGAT GCCGTTCACC CTCAACTTCA CCATCACCAA (SEQ ID NO:84)

51 CCTGCAGTAC GAGGAGGACA TGCGTCGCAC TGGCTCCAGG AAGTTCAACA

101 CCATGGAGAG TGTCCTGCAG GGTCTGCTCA AGCCCTTGTT CAAGAACACC

151 AGTGTTGGCC CTCTGTACTC TGGCTGCAGA TTGACCTTGC TCAGGCCCAA

201 GAAAGATGGG GCAGCCACTG GAGTGGATGC CATCTGCACC CACCGCCTTG

251 ACCCCAAAAG CCCTGGACTC AACAGGGAGC AGCTGTACTG GGAGCTAAGC

301 AAACTGACCA ATGACATTGA AGAGCTGGGC CCCTACACCC TGGACAGGAA

351 CAGTCTCTAT GTCAATGGTT TCACCCATCA GAGCTCTGTG CCACCACCA

401 GCACTCCTGG GACCTCCACA GTGGATCTCA GAACCTCAGG GACTCCATCC

451 TCCCTCTCCA GCCCCACAAT TATG

1 GCTGCTGGCC CTCTCCTGGT ACCATTCACC CTCAACTTCA CCATCACCAA (SEQ ID NO:85)

51 CCTGCAGTAT GGGGAGGACA TGGGTCACCC TGGCTCCAGG AAGTTCAACA

101 CCACAGAGAG GGTCCTGCAG GGTCTGCTTG GTCCCATATT CAAGAACACC

151 AGTGTTGGCC CTCTGTACTC TGGCTGCAGA CTGACCTCTC TCAGGTCTGA
```

TABLE 15-continued

CA125 Repeat Nucleotide Sequence
(SEQ ID NO:83 thru SEQ ID NO:145)

201 CAAGGATGGA GCAGCCACTG GAGTGGATGC CATCTGCATC CATCATCTTG

251 ACCCCAAAAG CCCTGGACTC AACAGAGAGC GGCTGTACTG GGAGCTGAGC

301 CAACTGACCA ATGGCATCAA AGAGCTGGGC CCCTACACCC TGGACAGGAA

351 CAGTCTCTAT GTCAATGGTT TCACCCATCG ACCTCTGTG CCCACCACCA

401 GCACTCCTGG GACCTCCACA GTGGACCTTG GAACCCTCAGG GACTCCATTC

451 TCCCTCCCAA GCCCCGCA

1 ACTGCTGGCC CTCTCCTGGT GCTGTTCACC CTCAACTTCA CCATCACCAA (SEQ ID NO:86)

51 CCTGAAGTAT GAGGAGGACA TGCATCGCCC TGGCTCCAGG AAGTTCAACA

101 CCACTGAGAG GGTCCTGCAG ACTCTGCTTG GTCCTATGTT CAAGAACACC

151 AGTGTTGGCC TTCTGTACTC TGGCTGCAGA CTGACCTTGC TCAGGTCCGA

201 GAAGGATGGA GCAGCCACTG GAGTGGATGC CATCTGCACC CACCGTCTTG

251 ACCCCAAAAG CCCTGGACTG GACAGAGAGC AGCTATACTG GGAGCTGAGC

301 CAGCTGACCA ATGGCATCAA AGAGCTGGGC CCCTACACCC TGGACAGGAA

351 CAGTCTCTAT GTCAATGGTT TCACCCATTG GATCCCTGTG CCCACCAGCA

401 GCACTCCTGG GACCTCCACA GTGGACCTTG GGTCACCGAC TCCATCCTCC

451 CTCCCCAGCC CCACA

1 GCTGCTGGCC CTCTCCTGGT GCCATTCACC CTCAACTTCA CCATCACCAA (SEQ ID NO:87)

51 CCTGCAGTAC GAGGAGGACA TGCATCACCC AGGCTCCAGG AAGTTCAACA

101 CCACGGAGCG GGTCCTGCAG GGTCTGCTTG GTCCCATGTT CAAGAACACC

151 AGTGTCGGCC TTCTGTACTC TGGCTGCAGA CTGACCTTGC TCAGGTCCGA

201 GAAGGATGGA GCAGCCACTG GAGTGGATGC CATCTGCACC CACCGTCTTG

251 ACCCCAAAAG CCCTGGAGTG GACAGGGAGC AGCTATACTG GGAGCTGAGC

301 CAGCTGACCA ATGGCATCAA AGAGCTGGGT CCCTACACCC TGGACAGAAA

351 CAGTCTCTAT GTCAATGGTT TCACCCATCA GACCTCTGCG CCCAACACCA

401 GCACTCCTGG GACCTCCACA GTGGACCTTG GGACCTCAGG GACTCCATCC

451 TCCCTCCCCA GCCCTACA

1 NCNNCTGNCC CTCTCCTGNT NCCNTTCACC NTCAACTTNA CCATCACCAA (SEQ ID NO:88)

51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACACC

151 AGTGTTGGCC CTCTGTACTC TGGCTGCAGA CTGACCTTGC TCAGGTCCGA

201 GAAGGATGGA GCAGCCACTG GAGTGGATGC CATCTGCACC CACCGTCTTG

251 ACCCCAAAAG CCCTGGAGTG GACAGGGAGC AGCTATACTG GGAGCTGAGC

301 CAGCTGACCA ATGGCATCAA AGAGCTGGGT CCCTACACCC TGGACAGAAA

351 CAGTCTCTAT GTCAATGGTT TCACCCATCA GACCTCTGCG CCCAA(ACCA

401 GCACTCCTGG GACCTCCACA GTGGACCTTG GGACCTCAGG GACTCCATCC

451 TCCCTCCCCA GCCCTACA

1 TCTGCTGGCC CTCTCCTGGT GCCATTCACC CTCAACTTCA CCATCACCAA (SEQ ID NO:89)

51 CCTGCAGTAC GAGGAGGACA TGCATCACCC AGGCTCCAGG AAGTTCAACA

TABLE 15-continued

CA125 Repeat Nucleotide Sequence
(SEQ ID NO:83 thru SEQ ID NO:145)

```
101 CCACGGAGCG GGTCCTGCAG GGTCTGCTTG GTCCCATGTT CAAGAACACC

151 AGTGTCGGCC TTCTGTACTC TGGCTGCAGA CTGACCTTGC TCAGGCCTGA

201 GAAGAATGGG GCAGCCACTG GAATGGATGC CATCTGCAGC CACCGTCTTG

251 ACCCCAAAAG CCCTGGACTC AACAGAGAGC AGCTGTACTG GGAGCTGAGC

301 CAGCTGACCC ATGGCATCAA AGAGCTGGGC CCTACACCC TGGACAGGAA

351 CAGTCTCTAT GTCAATGGTT TCACCCATCG GAGCTCTGTG GCCCCCACCA

401 GCACTCCTGG GACCTCCACA GTGGACCTTG GGACCTCAGG GACTCCATCC

451 TCCCTCCCCA GCCCCACA

1 ACAGCTGTTC CTCTCCTGGT GCCGTTCACC CTCAACTTTA CCATCACCAA (SEQ ID NO:90)

51 TCTGCAGTAT GGGGAGGACA TGCGTCACCC TGGCTCCAGG AAGTTCAACA

101 CCACAGAGAG GGTCCTGCAG GGTCTGCTTG GTCCCTTGTT CAAGAACTCC

151 AGTGTCGGCC CTCTGTACTC TGGCTGCAGA CTGATCTCTC TCAGGTCTGA

201 GAAGGATGGG GCAGCCACTG GAGTGGATGC CATCTGCACC CACCACCTTA

251 ACCCTCAAAG CCCTGGACTG GACAGGGAGC AGCTGTACTG GCAGCTGAGC

301 CAGATGACCA ATGGCATCAA AGAGCTGGGC CCTACACCC TGGACCGGAA

351 CAGTCTCTAC GTCAATGGTT TCACCCATCG GAGCTCTGGG CTCACCACCA

401 GCACTCCTTG GACTTCCACA GTTGACCTTG GAACCTCAGG GACTCCATCC

451 CCCGTCCCCA GCCCCACA

1 ACTGCTGGCC CTCTCCTGGT GCCATTCACC CTCAACTTCA CCATCACCAA (SEQ ID NO:91)

51 CCTGCAGTAT GAGGAGGACA TGCATCGCCC TGGATCTAGG AAGTTCAACA

101 CCACAGAGAG GGTCCTGCAG GGTCTGCTTA GTCCCATTTT CAAGAACTCC

151 AGTGTTGGCC CTCTGTACTC TGGCTGCAGA CTGACCTCTC TCAGGCCCGA

201 GAAGGATGGG GCAGCAACTG GAATGGATGC TGTCTGCCTC TACCACCCTA

251 ATCCCAAAAG ACCTGGACTG GACAGAGAGC AGCTGTACTG GGAGCTAAGC

301 CAGCTGACCC ACAACATCAC TGAGCTGGGC CCTACAGCC TGGACAGGGA

351 CAGTCTCTAT GTCAATGGTT TCACCCATCA GAACTCTGTG CCCACCACCA

401 GTACTCCTGG GACCTCCACA GTGTACTGGG CAACCACTGG GACTCCATCC

451 TCCTTCCCCG GCCACACA

1 GAGCCTGGCC CTCTCCTGAT ACCATTCACT TTCAACTTTA CCATCACCAA (SEQ ID NO:92)

51 CCTGCATTAT GAGGAAAACA TGCAACACCC TGGTTCCAGG AAGTTCAACA

101 CCACGGAGAG GGTTCTGCAG GGTCTGCTCA AGCCCTTGTT CAAGAACACC

151 AGTGTTGGCC CTCTGTACTC TGGCTGCAGA CTGACCTCTC TCAGGCCCGA

201 GAAGGATGGG GCAGCAACTG GAATGGATGC TGTCTGCCTC TACCACCCTA

251 ATCCCAAAAG ACCTGGGCTG GACAGAGAGC AGCTGTACTG GGAGCTAAGC

301 CAGCTGACCC ACAACATCAC TGAGCTGGGC CCTACAGCC TGGACAGGGA

351 CAGTCTCTAT GTCAATGGTT TCACCCATCA GAACTCTGTG CCCACCACCA

401 GTACTCCTGG GACCTCCACA GTGTACTGGG CAACCACTGG GACTCCATCC

451 TCCTTCCCCG GCCACACA
```

TABLE 15-continued

CA125 Repeat Nucleotide Sequence
(SEQ ID NO:83 thru SEQ ID NO:145)

```
  1 GAGCCTGGCC CTCTCCTGAT ACCATTCACT TTCAACTTTA CCATCACCAA   (SEQ ID NO:93)
 51 CCTGCATTAT GAGGAAAACA TGCAACACCC TGGTTCCAGG AAGTTCAACA
101 CCACGGAGAG GGTTCTGCAG GGTCTGCTCA AGCCCTTGTT CAAGAACACC
151 AGTGTTGGCC CTCTGTACTC TGGCTGCAGA CTGACCTTGC TCAGACCTGA
201 GAAGCATGAG GCAGCCACTG GAGTGGACAC CATCTGTACC CACCGCGTTG
251 ATCCCATCGG ACCTGGACTG GACAGGGAGC GGCTATACTG GGAGCTGAGC
301 CAGCTGACCA ACAGCATTAC CGAACTGGGA CCCTACACCC TGGACAGGGA
351 CAGTCTCTAT GTCAATGGCT TCAACCCTCG GAGCTCTGTG CCAACCACCA
401 GCACTCCTGG GACCTCCACA GTGCACCTGG CAACCTCTGG GACTCCATCC
451 TCCCTGCCTG GCCACACA

1 GCCCCTGTCC CTCTCTTGAT ACCATTCACC CTCAACTTTA CCATCACCAA   (SEQ ID NO:94)
 51 CCTGCATTAT GAGGAAAACA TGCAACACCC TGGTTCCAGG AAGTTCAACA
101 CCACGGAGAG GGTTCTGCAG GGTCTGCTCA AGCCCTTGTT CAAGAACACC
151 AGTGTTGGCC CTCTGTACTC TGGCTGCAGA CTGACCTTGC TCAGACCTGA
201 GAAGCATGAG GCAGCCACTG GAGTGGACAC CATCTGTACC CACCGCGTTG
251 ATCCCATCGG ACCTGCACTG NACAGNGAGC NGCTNTACTG GGAGCTNAGC
301 CANCTGACCA ANNNCATCNN NGAGCTGGGN CCCTACACCC TGGACAGGNA
351 CAGTCTCTAT GTCAATGGTT TCACCCATCN GANCTCTGNG CCCACCACCA
401 GCACTCCTGG GACCTCCACA GTGNACNTNG GNACCTCNGG GACTCCATCC
451 TCCNTCCCCN GCCNCACA

1 TCTGCTGGCC CTCTCCTGGT GCCATTCACC CTCAACTTCA CCATCACCAA   (SEQ ID NO:95)
 51 CCTGCAGTAC GAGGAGGACA TGCATCACCC AGGCTCCAGG AAGTTCAACA
101 CCACGGAGCG GGTCCTGCAG GGTCTGCTTG GTCCCATGTT CAAGAACACC
151 AGTGTCGGCC TTCTGTACTC TGGCTGCAGA CTGACCTTGC TCAGGCCTGA
201 GAAGAATGGG GCAGCCACTG GAATGGATGC CATCTGCAGC CACCGTCTTG
251 ACCCCAAAAG CCCTGGACTC GACAGAGAGC AGCTGTACTG GGAGCTGAGC
301 CAGCTGACCC ATGGCATCAA AGAGCTGGGC CCCTACACCC TGGACAGGAA
351 CAGTCTCTAT GTCAATGGTT TCACCCATCG GAGCTCTGTG GCCCCCACCA
401 GCACTCCTGG GACCTCCACA GTGGACCTTG GGACCTCAGG GACTCCATCC
451 TCCCTCCCCA GCCCCACA

1 ACAGCTGTTC CTCTCCTGGT GCCGTTCACC CTCAACTTTA CCATCACCAA   (SEQ ID NO:96)
 51 TCTGCAGTAT GGGGAGGACA TGCGTCACCC TGGCTCCAGG AAGTTCAACA
101 CCACAGAGAG GGTCCTGCAG GGTCTGCTTG GTCCCTTGTT CAAGAACTCC
151 AGTGTCGGCC CTCTGTACTC TGGCTGCAGA CTGATCTCTC TCAGGTCTGA
201 GAAGGATGGG GCAGCCACTG GAGTGGATGC CATCTGCACC CACCACCTTA
251 ACCCTCAAAG CCCTGGACTG GACAGGGAGC AGCTGTACTG GCAGCTGAGC
301 CAGATGACCA ATGGCATCAA AGAGCTGGGC CCCTACACCC TGGACCGGAA
351 CAGTCTCTAC GTCAATGGTT TCACCCATCG GAGCTCTGGG CTCACCACCA
```

TABLE 15-continued

CA125 Repeat Nucleotide Sequence
(SEQ ID NO:83 thru SEQ ID NO:145)

```
401 GCACTCCTTG GACTTCCACA GTTGACCTTG GAACCTCAGG GACTCCATCC
451 CCCGTCCCCA GCCCCACA
  1 ACTGCTGGCC CTCTCCTGGT GCCATTCACC CTAAACTTCA CCATCACCAA  (SEQ ID NO:97)
 51 CCTGCAGTAT GAGGAGGACA TGCATCGCCC TGGATCTAGG AAGTTCAACG
101 CCACAGAGAG GGTCCTGCAG GGTCTGCTTA GTCCCATATT CAAGAACTCC
151 AGTGTTGGCC CTCTGTACTC TGGCTGCAGA CTGACCTCTC TCAGGCCCGA
201 GAAGGATGGG GCAGCAACTG GAATGGATGC TGTCTGCCTC TACCACCCTA
251 ATCCCAAAAG ACCTGGACTG GACAGAGAGC AGCTGTACTG GGAGCTAAGC
301 CAGCTGACCC ACAACATCAC TGAGCTGGGC CCTACAGCC TGGACAGGGA
351 CAGTCTCTAT GTCAATGGTT TCACCCATCA GAGCTCTATG ACGACCACCA
401 GAACTCCTGA TACCTCCACA ATGCACCTGG CAACCTCCAG AACTCCAGCC
451 TCCCTGTCTG GACCTACG
  1 ACCGCCAGCC CTCTCCTGGT GCTATTCACA ATCAACTGCA CCATCACCAA  (SEQ ID NO:98)
 51 CCTGCAGTAC GAGGAGGACA TGCGTCGCAC TGGCTCCAGG AAGTTCAACA
101 CCATGGAGAG TGTCCTGCAG GGTCTGCTCA AGCCCTTGTT CAAGAACACC
151 AGTGTTGGCC CTCTGTACTC TGGCTGCAGA TTGACCTTGC TCAGGCCCAA
201 GAAAGATGGG GCAGCCACTG GAGTGGATGC CATCTGCACC CACCGCCTTG
251 ACCCCAAAAG CCCTGGACTC AACAGGGAGC AGCTGTACTG GGAGCTAAGC
301 AAACTGACCA ATGACATTGA AGAGCTGGGC CCTACACCC TGGACAGGAA
351 CAGTCTCTAT GTCAATGGTT TCACCCATCA GAGCTCTGTG TCCACCACCA
401 GCACTCCTGG GACCTCCACA GTGGATCTCA GAACCTCAGG GACTCCATCC
451 TCCCTCTCCA GCCCCACAAT TATG
  1 NCNNCTGNCC CTCTCCTGNT NCCNTTCACC NTCAACTTNA CCATCACCAA  (SEQ ID NO:99)
 51 CCTGCANTAN GNGGANNACA TGCNNCNCCC NGGNTCCAGG AAGTTCAACA
101 CCACNGAGAG GGTCCTACAG GGTCTGCTCA GGCCCTTGTT CAAGAACACC
151 AGTGTCAGCT CTCTGTACTC TGGTTGCAGA CTGACCTTGC TCAGGCCTGA
201 GAAGGATGGG GCAGCCACCA GAGTGGATGC TGCCTGCACC TACCGCCCTG
251 ATCCCAAAAG CCCTGGACTG GACAGAGAGC AACTATACTG GGAGCTGAGC
301 CAGCTAACCC ACAGCATCAC TGAGCTGGGA CCCTACACCC TGGACAGGGT
351 CAGTCTCTAT GTCAATGGCT TCAACCCTCG GAGCTCTGTG CCAACCACCA
401 GCACTCCTGG GACCTCCACA GTGCACCTGG CAACCTCTGG GACTCCATCC
451 TCCCTGCCTG GCCACACA
  1 GCCCCTGTCC CTCTCTTGAT ACCATTCACC CTCAACTTTA CCATCACCAA  (SEQ ID NO:100)
 51 CCTGCATTAT GAAGAAAACA TGCAACACCC TGGTTCCAGG AAGTTCAACA
101 CCACGGAGAG GGTTCTGCAG GGTCTGCTCA AGCCCTTGTT CAAGAGCACC
151 AGCGTTGGCC CTCTGTACTC TGGCTGCAGA CTGACCTTGC TCAGACCTGA
201 GAAACATGGG GCAGCCACTG GAGTGGACGC CATCTGCACC CTCCGCCTTG
251 ATCCCACTGG TCCTGGACTG GACAGAGAGC GGCTATACTG GGAGCTGACC
```

TABLE 15-continued

CA125 Repeat Nucleotide Sequence
(SEQ ID NO:83 thru SEQ ID NO:145)

```
301 CAGCTGACCA ACAGCGTTAC AGAGCTGGGC CCCTACACCC TGGACAGGGA
351 CAGTCTCTAT GTCAATGGCT TCACCCAGCG GAGCTCTGTG CCAACCACCA
401 GTATTCCTGG GACCTCTGCA GTGCACCTGG AAACCTCTGG GACTCCAGCC
451 TCCCTCCCTG GCCACACA

1 GCCCCTGGCC CTCTCCTGGT GCCATTCACC CTCAACTTCA CTATCACCAA  (SEQ ID NO:101)
 51 CCTGCAGTAT GAGGTGGACA TGCGTCACCC TGGTTCCAGG AACTTCAACA
101 CCACGGAGAG AGTCCTGCAG GGTCTGCTCA AGCCCTTGTT CAAGAGCACC
151 AGTGTTGGCC CTCTGTACTC TGGCTGCAGA CTGACCTTGC TCAGGCCTGA
201 AAAACGTGGG GCAGCCACCG GCGTGGACAC CATCTGCACT CACCGCCTTG
251 ACCCTCTAAA CCCTGGACTG GACAGAGAGC AGCTATACTG GCAGCTGAGC
301 AAACTGACCC GTGGCATCAT CGAGCTGGGC CCTACCTCC TCCACAGAGG
351 CAGTCTCTAT GTCAATGGTT TCACCCATCG GAACTTTGTG CCCATCACCA
401 GCACTCCTGG GACCTCCACA GTACACCTAG GAACCTCTGA AACTCCATCC
451 TCCCTACCTA GACCCATA

1 GTGCCTGGCC CTCTCCTGGT GCCATTCACC CTCAACTTCA CCATCACCAA  (SEQ ID NO:102)
 51 CTTGCAGTAT GAGGAGGCCA TGCGACACCC TGGCTCCAGG AAGTTCAATA
101 CCACGGAGAG GGTCCTACAG GGTCTGCTCA GGCCCTTGTT CAAGAATACC
151 AGTATCGGCC CTCTGTACTC CAGCTGCAGA CTGACCTTGC TCAGGCCAGA
201 GAAGGACAAG GCAGCCACCA GAGTGGATGC CATCTGTACC CACCACCCTG
251 ACCCTCAAAG CCCTGGACTG AACAGAQAGC AGCTGTACTG GGAGCTGAGC
301 CAGCTGACCC ACGGCATCAC TGAGCTGGGC CCTACACCC TGGACAGGGA
351 CAGTCTCTAT GTCGATGGTT TCACTCATTG GAGCCCCATA CCGACCACCA
401 GCACTCCTGG GACCTCCATA GTGAACCTGG GAACCTCTGG GATCCCACCT
451 TCCCTCCCTG AAACTACA

1 NCNNCTGNCC CTCTCCTGNT NCCNTTCACC NTCAACTTNA CCATCACCAA  (SEQ ID NO:103)
 51 CCTGCANTAN GNGGANNACA TGCNNCNCCC NGCNTCCAGG AAGTTCAACA
101 CCACNGAGAG GGTTCTGCAG GGTCTGCTCA AACCCTTGTT CAGGAATAGC
151 AGTCTGGAAT ACCTCTATTC AGGCTGCAGA CTAGCCTCAC TCAGGCCAGA
201 GAAGGATAGC TCAGCCATGG CAGTGGATGC CATCTGCACA CATCGCCCTG
251 ACCCTGAAGA CCTCGGACTG GACAGAGAGC GACTGTACTG GGAGCTGAGC
301 AATCTGACAA ATGGCATCCA GGAGCTGGGC CCTACACCC TGGACCGGAA
351 CAGTCTCTAC GTCAATGGTT TCACCCATCG GAGCTCTGGG CTCACCACCA
401 GCACTCCTTG GACTTCCACA GTTGACCTTG GAACCTCAGG GACTCCATCC
451 CCCGTCCCCA GCCCCACA

1 ACTGCTGGCC CTCTCCTGGT GCCATTCACC CTCAACTTCA CCATCACCAA  (SEQ ID NO:104)
 51 CCTGCAGTAT GAGGAGGACA TGCATCGCCC TGGTTCCAGG AGGTTCAACA
101 CCACGGAGAG GGTTCTGCAG GGTCTGCTCA CGCCCTTGTT CAAGAACACC
151 AGTGTTGGCC CTCTGTACTC TGGCTGCAGA CTGACCTTGC TCAGACCTGA
```

TABLE 15-continued

CA125 Repeat Nucleotide Sequence
(SEQ ID NO:83 thru SEQ ID NO:145)

```
201 GAAGCAAGAG GCAGCCACTG GAGTGGACAC CATCTGTACC CACCGCGTTG
251 ATCCCATCGG ACCTGGACTG GACAGAGAGC GGCTATACTG GGAGCTGAGC
301 CAGCTGACCA ACAGCATCAC AGAGCTGGGA CCCTACACCC TGGATAGGGA
351 CAGTCTCTAT GTCAATGGCT TCAACCCTTG GAGCTCTGTG CCAACCACCA
401 GCACTCCTGG GACCTCCACA GTGCACCTGG CAACCTCTGG GACTCCATCC
451 TCCCTGCCTG GCCACACA
  1 GCCCCTGTCC CTCTCTTGAT ACCATTCACC CTCAACTTTA CCATCACCGA (SEQ ID NO:105)
 51 CCTGCATTAT GAAGAAAACA TGCAACACCC TGGTTCCAGG AAGTTCAACA
101 CCACGGAGAG GGTTCTGCAG GGTCTGCTCA AGCCCTTGTT CAAGAGCACC
151 AGCGTTGGCC CTCTGTACTC TGGCTGCAGA CTGACCTTGC TCAGACCTGA
201 GAAACATGGG GCAGCCACTG GAGTGGACGC CATCTGCACC CTCCGCCTTG
251 ATCCCACTGG TCCTGGACTG GACAGAGAGC GGCTATACTG GGAGCTGAGC
301 CAGCTGACCA ACAGCGTTAC AGAGCTGGGC CCCTACACCC TGGACAGGGA
351 CAGTCTCTAT GTCAATGGCT TCACCCATCG GAGCTCTGTG CCAACCACCA
401 GTATTCCTGG GACCTCTGCA GTGCACCTGG AAACCTCTGG GACTCCAGCC
451 TCCCTCCCTG GCCACACA
  1 GCCCCTGGCC CTCTCCTGGT GCCATTCACC CTCAACTTCA CTATCACCAA (SEQ ID NO:106)
 51 CCTGCAGTAT GAGGAGGACA TGCGTCACCC TGGTTCCAGG AAGTTCAGCA
101 CCACGGAGAG AGTCCTGCAG GGTCTGCTCA AGCCCTTGTT CAAGAACACC
151 AGTGTCAGCT CTCTGTACTC TGGTTGCAGA CTGACCTTGC TCAGGCCTGA
201 GAAGGATGGG GCAGCCACCA GAGTGGATGC TGTCTGCACC CATCGTCCTG
251 ACCCCAAAAG CCCTGGACTG GACAGAGAGC GGCTGTACTG GAAGCTGAGC
301 CAGCTGACCC ACGGCATCAC TGAGCTGGGC CCCTACACCC TGGACAGGCA
351 CAGTCTCTAT GTCAATGGTT TCACCCATCA GAGCTCTATG ACGACCACCA
401 GAACTCCTGA TACCTCCACA ATGCACCTGG CAACCTCGAG AACTCCAGCC
451 TCCCTGTCTG GACCTACG
  1 ACCGCCAGCC CTCTCCTGGT GCTATTCACA ATTAACTTCA CCATCACTAA (SEQ ID NO:107)
 51 CCTGCGGTAT GAGGAGAACA TGCATCACCC TGGCTCTAGA AAGTTTAACA
101 CCACGGAGAG AGTCCTTCAG GGTCTGCTCA GGCCTGTGTT CAAGAACACC
151 AGTGTTGGCC CTCTGTACTC TGGCTGCAGA CTGACCACGC TCAGGCCCAA
201 GAAGGATGGG GCAGCCACCA AAGTGGATGC CATCTGCACC TACCGCCCTG
251 ATCCCAAAAG CCCTGGACTG GACAGAGAGC AGCTATACTG GGAGCTGAGC
301 CAGCTAACCC ACAGCATCAC TGAGCTGGGC CCCTACACCC AGGACAGGGA
351 CAGTCTCTAT GTCAATGGCT TCACCCATCG GAGCTCTGTG CCAACCACCA
401 GTATTCCTGG GACCTCTGCA GTGCACCTGG AAACCTCTGG GACTCCAGCC
451 TCCCTCCCTG GCCACACA
  1 GCCCCTGGCC CTCTCCTGGT GCCATTCACC CTCAACTTCA CTATCACCAA (SEQ ID NO:108)
 51 CCTGCAGTAT GAGGAGGACA TGCGTCACCC TGGTTCCAGG AAGTTCAACA
```

TABLE 15-continued

CA125 Repeat Nucleotide Sequence
(SEQ ID NO:83 thru SEQ ID NO:145)

101 CCACGGAGAG AGTCCTGCAG GGTCTGCTCA AGCCCTTGTT CAAGAGCACC

151 AGTGTTGGCC CTCTGTACTC TGGCTGCAGA CTGACCTTGC TCAGGCCTGA

201 AAAACGTGGG GCAGCCACCG GCGTGGACAC CATCTGCACT CACCGCCTTG

251 ACCCTCTAAA CCCAGGACTG GACAGAGAGC AGCTATACTG GGAGCTGAGC

301 AAACTGACCC GTGGCATCAT CGAGCTGGGC CCTACCTCC TGGACAGAGG

351 CAGTCTCTAT GTCAATGGTT TCACCCATCG GACCTCTGTG CCCACCACCA

401 GCACTCCTGG GACCTCCACA GTGGACCTTG GAACCTCAGG GACTCCATTC

451 TCCCTCCCAA GCCCCGCA

1 NCNNCTGNCC CTCTCCTGNT NCCNTTCACC NTCAACTTNA CCATCACCAA (SEQ ID NO:109)

51 CCTGCANTAN GNGGANNACA TGCNNCNCCC NGGNTCCAGG AAGTTCAACA

101 CCACNGAGAG GGTCCTGCAG ACTCTGCTTG GTCCTATGTT CAAGAACACC

151 AGTGTTGGCC TTCTGTACTC TGGCTGCAGA CTGACCTTGC TCAGGTCCGA

201 GAAGGATGGA GCAGCCACTG GAGTGGATGC CATCTGCACC CACCGTCTTG

251 ACCCCAAAAG CCCTGGAGTG GACAGGGAGC AACTATACTG GGAGCTGAGC

301 CAGCTGACCA ATGGCATTAA AGAACTGGGC CCTACACCC TGGACAGGAA

351 CAGTCTCTAT GTCAATGGGT TCACCCATTG GATCCCTGTG CCCACCAGCA

401 GCACTCCTGG GACCTCCACA GTGGACCTTG GGTCAGGGAC TCCATCCTCC

451 CTCCCCAGCC CCACA

1 ACTGCTGGCC CTCTCCTGGT GCCGTTCACC CTCAACTTCA CCATCACCAA (SEQ ID NO:110)

51 CCTGAAGTAC GAGGAGGACA TGCATTGCCC TGGCTCCAGG AAGTTCAACA

101 CCACAGAGAG AGTCCTGCAG AGTCTGCTTG GTCCCATGTT CAAGAACACC

151 AGTGTTGGCC CTCTGTACTC TGGCTGCAGA CTGACCTTGC TCAGGTCCGA

201 GAAGGATGGA GCAGCCACTG GAGTGGATGC CATCTGCACC CACCGTCTTG

251 ACCCCAAAAG CCCTGGAGTG GACAGGGAGC AGCTATACTG GGAGCTGAGC

301 CAGCTGACCA ATGGCATCAA AGAGCTGGGT CCCTACACCC TGGACAGAAA

351 CAGTCTCTAT GTCAATGGTT TCACCCATCA GACCTCTGCG CCCAACACCA

401 GCACTCCTGG GACCTCCACA GTGGACCTTG GGACCTCAGG GACTCCATCC

451 TCCCTCCCCA GCCCTACA

1 NCNNCTGNCC CTCTCCTGNT NCCNTTCACC NTCAACTTNA CCATCACCAA (SEQ ID NO:111)

51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACNCC

151 AGTGTNGGCC NTCTGTACTC TGGCTGCAGA CTGACCTTNC TCAGGNCNGA

201 GAAGNATGGN GCAGCCACTG GANTGGATGC CATCTGCANC CACCNNCNTN

251 ANCCCAAAAG NCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATTG GATCCCTGTG CCCACCAGCA

401 GCACTCCTGG GACCTCCACA GTGGACCTTG GGTCAGGGAC TCCATCCTCC

451 CTCCCCAGCC CCACA

TABLE 15-continued

CA125 Repeat Nucleotide Sequence
(SEQ ID NO:83 thru SEQ ID NO:145)

```
  1 ACTGCTGGCC CTCTCCTGGT GCCGTTCACC CTCAACTTCA CCATCACCAA (SEQ ID NO:112)
 51 CCTGAAGTAC GAGGAGGACA TGCATTGCCC TGGCTCCAGG AAGTTCAACA
101 CCACAGAGAG AGTCCTGCAG AGTCTGCTTG GTCCCATGTT CAAGAACACC
151 AGTGTTGGCC CTCTGTACTC TGGCTGCAGA CTGACCTCGC TCAGGTCCGA
201 GAAGGATGGA GCAGCCACTG GAGTGGATGC CATCTGCACC CACCGTGTTG
251 ACCCCAAAAG CCCTGGAGTG GACAGGGAGC AGCTATACTG GGAGCTGAGC
301 CAGCTGACCA ATGGCATCAA AGAGCTGGGT CCCTACACCC TGGACAGAAA
351 CAGTCTCTAT GTCAATGGTT TCACCCATCA GACCTCTGCG CCCAACACCA
401 GCACTCCTGG GACCTCCACA GTGNACNTNG GNACCTCNGG GACTCCATCC
451 TCCNTCCCCN GCCNCACA
```

```
  1 TCTGCTGGCC CTCTCCTGGT GCCATTCACC CTCAACTTCA CCATCACCAA (SEQ ID NO:113)
 51 CCTGCAGTAC GAGGAGGACA TGCATCACCC AGGCTCCAGG AAGTTCAACA
101 CCACGGAGCG GGTCCTGCAG GGTCTGCTTG GTCCCATGTT CAAGAACACC
151 AGTGTCGGCC TTCTGTACTC TGGCTGCAGA CTGACCTTGC TCAGGCCTGA
201 GAAGAATGGG GCAACCACTG GAATGGATGC CATCTGCACC CACCGTCTTG
251 ACCCCAAAAG CCCTGGACTG NACAGNGAGC NGCTNTACTG GGAGCTNAGC
301 CANCTGACCA ANNNCATCNK NGAGCTGGGN CCCTACACCC TGGACAGGNA
351 CAGTCTCTAT GTCAATGGTT TCACCCATCN GANCTCTGNG CCCACCACCA
401 GCACTCCTGG GACCTCCACA GTGNACNTNG GNACCTCNGG GACTCCATCC
451 TCCNTCCCCN GCCNCACA
```

```
  1 NCNNCTGNCC CTCTCCTGNT NCCNTTCACC NTCAACTTNA CCATCACCAA (SEQ ID NO:114)
 51 CCTGCANTAN GNGGANNACA TGCNNCNCCC NGGNTCCAGG AAGTTCAACA
101 CCACNGAGAG GGTTCTGCAG GGTCTGCTCA AACCCTTGTT CAGGAATAGC
151 AGTCTGGAAT ACCTCTATTC AGGCTGCAGA CTAGCCTCAC TCAGGCCAGA
201 GAAGGATAGC TCAGCCATGG CAGTGGATGC CATCTGCACA CATCGCCCTG
251 ACCCTGAAGA CCTCGGACTG GACAGAGAGO GACTGTACTG GGAGCTGAGC
301 AATCTGACAA ATGGCATCCA GGAGCTGGGC CCCTACACCC TGGACCGGAA
351 CAGTCTCTAT GTCAATGGTT TCACCCATCG AAGCTCTATG CCCACCACCA
401 GCACTCCTGG GACCTCCACA GTGGATGTGG GAACCTCAGG GACTCCATCC
451 TCCAGCCCCA GCCCCACG
```

```
  1 ACTGCTGGCC CTCTCCTGAT ACCATTCACC CTCAACTTCA CCATCACCAA (SEQ ID NO:115)
 51 CCTGCAGTAT GGGGAGGACA TGGGTCACCC TGGCTCCAGG AAGTTCAACA
101 CCACAGAGAG GGTCCTGCAG GGTCTGCTTG GTCCCATATT CAAGAACACC
151 AGTGTTGGCC CTCTGTACTC TGGCTGCAGA CTGACCTCTC TCAGGTCTGA
201 GAAGGATGGA GCAGCCACTG GAGTGGATGC CATCTGCATC CATCATCTTG
251 ACCCCAAAAG CCCTGGACTC AACAGAGAGC GGCTGTACTG GGAGCTGAGC
301 CAACTGACCA ATGGCATCAA AGAGCTGGGC CCCTACACCC TGGACAGGAA
351 CAGTCTCTAT GTCAATGGTT TCACCCATCG GACCTCTGTG COCACCACCA
```

TABLE 15-continued

CA125 Repeat Nucleotide Sequence
(SEQ ID NO:83 thru SEQ ID NO:145)

```
401 GCACTCCTGG GACCTCCACA GTGGACCTTG GAACCTCAGG GACTCCATTC

451 TCCCTCCCAA GCCCCGCA

1 ACTGCTGGCC CTCTCCTGGT GCTGTTCACC CTCAACTTCA CCATCACCAA (SEQ ID NO:116)

51 CCTGAAGTAT GAGGAGGACA TGCATCGCCC TGGCTCCAGG AAGTTCAACA

101 CCACTGAGAG GGTCCTGCAG ACTCTGCTTG GTCCTATGTT CAAGAACACC

151 AGTGTTGGCC TTCTGTACTC TGGCTGCAGA CTGACCTTGC TCAGGTCCGA

201 GAAGGATGGA GCAGCCACTG GAGTGGATGC CATCTGCACC CACCGTCTTG

251 ACCCCAAAAG CCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA (SEQ ID NO:117)

51 CCTGCANTAN GNGGANNACA TGCNNCNCCC NGGNTCCAGG AAGTTCAACA

101 CCACNGAGAG AGTCCTTCAG GGTCTGCTCA GGCCTGTGTT CAAGAACACC

151 AGTGTTGGCC CTCTGTACTC TGGCTGCAGA CTGACCTTGC TCAGGCCCAA

201 GAAGGATGGG GCAGCCACCA AGTGGATGC CATCTGCACC TACCGCCCTG

251 ATCCCAAAAG CCCTGGACTG GACAGAGAGC AGCTATACTG GGAGCTGAGC

301 CAGCTAACCC ACAGCATCAC TGAGCTGGGC CCCTACACCC AGGACAGGGA

351 CAGTCTCTAT GTCAATGGCT TCACCCATCG GAGCTCTGTG CCAACCACCA

401 GTATTCCTGG GACCTCTGCA GTGCACCTGG AAACCACTGG GACTCCATCC

451 TCCTTCCCCG GCCACACA

1 GAGCCTGGCC CTCTCCTGAT ACCATTOACT TTCAACTTTA CCATCACCAA (SEQ ID NO:118)

51 CCTGCGTTAT GAGGAAAACA TGCAACACCC TGGTTCCAGG AAGTTCAACA

101 CCACGGAGAG GGTTCTGCAG GGTCTGCTCA CGCCCTTGTT CAAGAACACC

151 AGTGTTGGCC CTCTGTACTC TGGCTGCAGA CTGACCTTGC TCAGACCTGA

201 CAAGCAGGAG GCAGCCACTG GAGTGGACAC CATCTGTACC CACCGCGTTG

251 ATCCCATCGG ACCTGGACTG GACAGAGAGC GGCTATACTG GGAGCTGAGC

301 CAGCTGACCA ACAGCATCAC AGAGCTGGGA CCCTACACCC TGGATAGGGA

351 CAGTCTCTAT GTCGATGGCT TCAACCCTTG GAGCTCTGTG CCAACCACCA

401 GCACTCCTGG GACCTCCACA GTGCACCTGG CAACCTCTGG GACTCCATCC

451 CCCCTGCCTG OCCACACA

1 GCCCCTGTCC CTCTCTTGAT ACCATTCACC CTCAACTTTA CCATCACCGA (SEQ ID NO:119)

51 CCTGCATTAT GAAGAAAACA TGCAACACCC TGGTTCCAGG AAGTTCAACA

101 CCACGGAGAG GGTTCTGCAG GGTCTGCTCA AGCCCTTGTT CAAGAGCACC

151 AGCGTTGGCC CTCTGTACTC TGGCTGCAGA CTGACCTTGC TCAGACCTGA
201 GAAACATGGG GCAGCCACTG GAGTGGACGC CATCTGCACC CTCCGCCTTG
251 ATCCCACTGG TCCTGGACTG GACAGAGAGC GGCTATACTG GGAGCTGAGC
301 CAGCTGACCA ACAGCATCAC AGAGCTGGGA CCCTACACCC TGGATAGGGA
351 CAGTCTCTAT GTCAATGGCT TCAACCCTTG GAGCTCTGTG CCAACCACCA
```

TABLE 15-continued

CA125 Repeat Nucleotide Sequence
(SEQ ID NO:83 thru SEQ ID NO:145)

```
401 GCACTCCTGG GACCTCCACA GTGCACCTGG CAACCTCTGG GACTCCATCC
451 TCCCTGCCTG GCCACACA

1 ACTGCTGGCC CTCTCCTGGT GCCGTTCACC CTCAACTTCA CCATCACCAA (SEQ ID NO:120)
 51 CCTGAAGTAC GAGGAGGACA TGCATTGCCC TGGCTCCAGG AAGTTCAACA
101 CCACAGAGAG AGTCCTGCAG AGTCTGCATG GTCCCATGTT CAAGAACACC
151 AGTGTTGGCC CTCTGTACTC TGGCTGCAGA CTGACCTTGC TCAGGTCCGA
201 GAAGGATGGA GCAGCCACTG GAGTGGATGC CATCTGCACC CACCGTCTTG
251 ACCCCAAAAG CCCTGGACTG NACAGNGAGC NGCTNTACTG GGAGCTNAGC
301 CANCTGACCA ANNNCATCNN NGAGCTGGGN CCCTACACCC TGGACAGGNA
351 CAGTCTCTAT GTCAATGGTT TCACCCATCN GANCTCTGNG CCCACCACCA
401 GCACTCCTGG GACCTCCACA GTGNACNTNG GNACCTCNGG GACTCCATCC
451 TCCNTCCCCN GCCNCACA

1 NCNNCTGNCC CTCTCCTGNT NCCNTTCACC NTCAACTTNA CCATCACCAA (SEQ ID NO:121)
 51 CCTGCANTAN GNGGANNACA TGCNNCNCCC NGGNTCCAGG AAGTTCAACA
101 CCACNGAGNG NGTNCTGCAG GGTCTGCTNN NNCCCNTNTT CAAGAACNCC
151 AGTGTNGGCC NTCTGTACTC TGGCTGCAGA CTGACCTNNC TCAGGNCNGA
201 GAAGNATGGN GCAGCCACTG GANTGGATGC CATCTGCANC CACCNNCNTN
251 ANCCCAAAAG NCCTGGACTG NACAGNGAGC NGCTNTACTG GGAGCTNAGC
301 CANCTGACCA ACAGCATCAC AGAGCTGGGA CCCTACACCC TGGATAGGGA
351 CAGTCTCTAT GTCAATGGTT TCACCCATCG AAGCTCTATG CCCACCACCA
401 GTATTCCTGG GACCTCTGCA GTGCACCTGG AAACCTCTGG GACTCCAGCC
451 TCCCTCCCTG GCCACACA

1 GCCCCTGGCC CTCTCCTGGT GCCATTCACC CTCAACTTCA CTATCACCAA (SEQ ID NO:122)
 51 CCTGCAGTAT GAGGAGGACA TGCGTCACCC TGGTTCCAGG AAGTTCAACA
101 CCACGGAGAG AGTCCTGCAG GGTCTGCTCA AGCCCTTGTT CAAGAGCACC
151 AGTGTTGGCC CTCTGTACTC TGGCTGCAGA CTGACCTTGC TCAGGCCTGA
201 AAAACGTGGG GCAGCCACCG GCGTGGACAC CATCTGCACT CACCGCCTTG
251 ACCCTCTAAA CCCTGGACTG NACAGNGAGC NGCTNTACTG GGAGCTNAGC
301 CANCTOACCA ANNNCATCNN NGAGCTGGGN CCCTACACCC TGGACAGGNA
351 CAGTCTCTAT GTCAATGGTT TCACCCATCN GANCTCTGNG CCCACCACCA
401 GCACTCCTGG GACCTCCACA GTGNACNTNG GNACCTCNGG GACTCCATCC
451 TCCNTCCCCN GCCNCACA

1 NCNNCTGNCC CTCTCCTGNT NCCNTTCACC NTCAACTTNA CCATCACCAA (SEQ ID NO:123)
 51 CCTGCANTAN GNGGANNACA TGCNNCNCCC NGGNTCCAGG AAGTTCAACA
101 CCACNGAGNG NGTNCTGCAG GGTCTGCTNN NNCCCNTNTT CAAGAACNCC
151 AGTGTNGGCC NTCTGTACTC TGGCTGCAGA CTGACCTNNC TCAGGNCNGA
201 GAAGNATGGN GCAGCCACTG GANTGGATGC CATCTGCANC CACCNNCNTN
251 ANCCCAAAAG NCCTGGACTG NACAGNGAGC NGCTNTACTG GGAGCTNAGC
301 CANCTGACCA ANNNCATCNN NGAGCTGGGN CCCTACACCC TGGACAGGNA
```

TABLE 15-continued

CA125 Repeat Nucleotide Sequence
(SEQ ID NO:83 thru SEQ ID NO:145)

```
351 CAGTCTCTAT GTCAATGGTT TTCACCCTCG GAGCTCTGTG CCAACCACCA

401 GCACTCCTGG GACCTCCACA GTGCACCTGG CAACCTCTGG GACTCCATCC

451 TCCCTGCCTG GCCACACA

1 GCCCCTGTCC CTCTCTTGAT ACCATTCACC CTCAACTTTA CCATCACCAA  (SEQ ID NO:124)

51 CCTGCATTAT GAAGAAAACA TGCAACACCC TGGTTCCAGG AAGTTCAACA

101 CCACGGAGCG GGTCCTGCAG GGTCTGCTTG GTCCCATGTT CAAGAACACA

151 AGTGTCGGCC TTCTGTACTC TGGCTGCAGA CTGACCTTGC TCAGGCCTGA

201 GAAGAATGGG GCAGCCACTG GAATGGATGC CATCTGCAGC CACCGTCTTG

251 ACCCCAAAAG CCCTGGACTG NACAGNGAGC NGCTNTACTG GGAGCTNAGC

301 CANCTGACCA ANNNCATCNN NCAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA  (SEQ ID NO:125)

51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACNCC

151 AGTGTNGGCC NTCTGTACTC TGGCTGCAGA CTGACCTNNC TCAGGNCNGA

201 GAAGNATGGN GCAGCCACTG GANTGGATGC CATCTGCMJC CACCNNCNTN

251 ANCCCAAAAG NCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCA GAACTCTGTG CCCACCACCA

401 GTACTCCTGG GACCTCCACA GTGTACTGGG CAACCACTGG GACTCCATCC

451 TCCTTCCCCG GCCACACA

1 GAGCCTGGCC CTCTCCTGAT ACCATTOACT TTCAACTTTA CCATCACCAA  (SEQ ID NO:126)

51 CCTGCATTAT GAGGAAAACA TGCAACACCC TGGTTCCAGG AAGTTCAACA

101 CCACGGAGAG GGTTCTGCAG GGTCTGCTCA CGCCCTTGTT CAAGAACACC

151 AGTGTTGGCC CTCTGTACTC TGGCTGCAGA CTCACCTTGC TCAGACCTGA

201 GAAGCAGGAG GCAGCCACTG GAGTGGACAC CATCTGTACC CACCGCGTTG

251 ATCCCATCGG ACCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA  (SEQ ID NO:127)

51 CCTGCANTAN GNGGANNACA TGCNKCNCCC NGGNTCCAGG AAGTTCAACA
101 CCACNGAGNG NGTNCTGCAG GGTCTGCTNN NNCCCNTNTT CAAGAACNCC

151 AGTGTNGGCC NTCTGTACTC TGGCTGCAGA CTGACCTNNC TCAGGNCNGA

201 GAAGNATGGN GCAGCCACTG GANTGGATGC CATCTGCANC CACCNNCNTN

251 ANCCCAAAAG NCCTGGACTG NACAGNGAGC NGCTNTACTG GGAGCTNAGC
```

TABLE 15-continued

CA125 Repeat Nucleotide Sequence
(SEQ ID NO:83 thru SEQ ID NO:145)

```
301 CANCTGACCA ANNNCATCNN NGAGCTGGGN CCCTACACCC TGGACAGGNA

351 CAGTCTCTAT GTCAATGGTT TCACCCATCG GAGCTCTGTG CCAACCACCA

401 GCAGTCCTGG GACCTCCACA GTGCACCTGG CAACCTCTGG GACTCCATCC

451 TCCCTGCCTG GCCACACA

1 GCCCCTGTCC CTCTCTTGAT ACCATTCACC CTCAACTTTA CCATCACCAA (SEQ ID NO:128)

51 CCTGCATTAT GAAGAAAACA TGCAACACCC TGGTTCCAGG AAGTTCAACA

101 CCACGGAGAG GGTTCTGCAG GGTCTGCTCA AGCCCTTGTT CAAGAGCACC

151 AGTGTTGGCC CTCTQTACTC TGGCTGCAGA CTGACCTTGC TCAGACCTGA

201 GAAACATGGG GCAGCCACTG GAGTGGACGC CATCTGCACC CTCCGCCTTG

251 ATCCCACTGG TCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA (SEQ ID NO:129)

51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACNCC

151 AGTGTNGGCC NTCTGTACTC TGGCTGCAGA CTGACCTNNC TCAGGNCNGA

201 GAAGNATGGN GCAGCCACTG GANTGGATGC CATCTGCANC CACCNNCNTN

251 ANCCCAAAAG NCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCG GACCTCTGTG CCCACCACCA

401 GCACTCCTGG GACCTCCACA GTGCACCTGG CAACCTCTGG GACTCCATCC

451 TCCCTGCCTG GCCACACA

1 GCCCCTGTCC CTCTCTTGAT ACCATTCACC CTCAACTTTA CCATCACCAA (SEQ ID NO:130)

51 CCTGCAGTAT GAGGAGGACA TGCATCGCCC TGGATCTAGG AAGTTCAACA

101 CCACAGAGAG GGTCCTGCAG GGTCTGCTTA GTCCCATTTT CAAGAACTCC

151 AGTGTTGGCC CTCTGTACTC TGGCTGCAGA CTGACCTCTC TCAGGCCCGA

201 GAAGGATGGG GCAGCAACTG GAATGGATGC TGTCTGCCTC TACCACCCTA

251 ATCCCAAAAG ACCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA (SEQ ID NO:131)
 51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACNCC

151 AGTGTNGGCC NTCTGTACTC TGGCTGCAGA CTGACCTNNC TCAGGNCNGA

201 GAAGNATGGN GCAGCCACTG GANTGGATGC CATCTGCANC CACCNNCNTN
```

TABLE 15-continued

CA125 Repeat Nucleotide Sequence
(SEQ ID NO:83 thru SEQ ID NO:145)

```
251 ANCCCAAAAG NCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATTG GAGCTCTGGG CTCACCACCA

401 GCACTCCTTG GACTTCCACA GTTGACCTTG GAACCTCAGG GACTCCATCC

451 CCCGTCCCCA GCCCCACA

1 ACTGCTGGCC CTCTCCTGGT GCCATTCACC CTAAACTTCA CCATCACCAA (SEQ ID NO:132)

51 CCTGCAGTAT GAGGAGGACA TGCATCGCCC TGGATCTAGG AAGTTCAACG

101 CCACAGAGAG GGTCCTGCAG GGTCTGCTTA GTCCCATATT CAAGAACACC

151 AGTGTTGGCC CTCTGTACTC TGGCTGCAGA CTGACCTTGC TCAGACCTGA

201 GAAGCAGGAG GCAGCCACTG GAGTGGACAC CATCTGTACC CACCGCGTTG

251 ATCCCATCGG ACCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA (SEQ ID NO:133)

51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACNCC

151 AGTGTNGGCC NTCTGTACTC TGGCTGCAGA CTGACCTNNC TCAGGNCNGA

201 GAAGNATGGN GCAGCCACTG GANTGGATGC CATCTGCANC CACCNNCNTN

251 ANCCCAAAAG NCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCG GAGCTTTGGG CTCACCACCA

401 GCACTCCTTG GACTTCCACA GTTGACCTTG GAACCTCAGG GACTCCATCC

451 CCCGTCCCCA GCCCCACA

1 ACTGCTGGCC CTCTCCTGGT GCCATTCACC CTAAACTTCA CCATCACCAA (SEQ ID NO:134)

51 CCTGCAGTAT GAGGAGGACA TGCATCGCCC TGGCTCCAGG AAGTTCAACA

101 CCACGGAGAG GGTCCTTCAG GGTCTGCTTA CGCCCTTGTT CAGGAACACC

151 AGTGTCAGCT CTCTGTACTC TGGTTGCAGA CTGACCTTGC TCAGGCCTGA

201 GAAGGATGGG GCAGCCACCA GAGTGGATGC TGTCTGCACC CATCGTCCTG

251 ACCCCAAAAG CCCTGGACTG NACAGNGAGC NGCTNTACTG GGAGCTNAGC

301 CANCTGACCA ANNNCATCNN NGAGCTGGGN CCCTACACCC TGGACAGGNA

351 CAGTCTCTAT GTCAATGGTT TCACCCATCN GANCTCTGNG CCCACCACCA

401 GCACTCCTGG GACCTCCACA GTGNACNTNG GNACCTCNGG GACTCCATCC

451 TCCNTCCCCN GCCNCACA

1 NCNNCTGNCC CTCTCCTGNT NCCNTTCACC NTCAACTTNA CCATCACCAA (SEQ ID NO:135)

51 CCTGCANTAN GNGGANNACA TGCNNCNCCC NGGNTCCAGG AAGTTCAACA

101 CCACNGAGNG NGTNCTGCAG GGTCTGCTNN NNCCCNTNTT CAAGAACNCC
```

TABLE 15-continued

CA125 Repeat Nucleotide Sequence
(SEQ ID NO:83 thru SEQ ID NO:145)

```
151 AGTGTNGGCC NTCTGTACTC TGGCTGCAGA CTGACCTNNC TCAGGNCNGA
201 GAAGNATGGN GCAGCCACTG GANTGGATGC CATCTGCANC CACCNNCNTN
251 ANCCCAAAAG NCCTGGACTG NACAGNGAGC NGCTNTACTG GGAGCTNAGC
301 CANCTGACCA ANNNCATCNN NGAGCTGGGN CCCTACACCC TGGACAGGNA
351 CAGTCTCTAT GTCAATGGTT TCACCCATTG GATCCCTGTG CCCACCAGCA
401 GCACTCCTGG GACCTCCACA GTGGACCTTG GGTCAGGGAC TCCATCCTCC
451 CTCCCCAGCC CCACA
  1 ACTGCTGGCC CTCTCCTGGT ACCATTCACC CTCAACTTCA CCATCACCAA (SEQ ID NO:136)
 51 CCTGCAGTAT GGGGAGGACA TGGGTCACCC TGGCTCCAGG AAGTTCAACA
101 CCACAGAGAG GGTCCTGCAG GGTCTGCTTG GTCCCATATT CAAGAACACC
151 AGTGTTGGCC CTCTGTACTC TGGCTGCAGA CTGACCTCTC TCAGGTCCGA
201 GAAGGATGGA GCAGCCACTG GAGTGGATGC CATCTGCATC CATCATCTTG
251 ACCCCAAAAG CCCTGGACTG NACAGNGAGC NGCTNTACTG GGAGCTNAGC
301 CANCTGACCA ANNNCATCNN NGAGCTGGGN CCCTACACCC TGGACAGGNA
351 CAGTCTCTAT GTCAATGGTT TCACCCATCN GANCTCTGNG CCCACCACCA
401 GCACTCCTGG GACCTCCACA GTGNACNTNG GNACCTCNGG GACTCCATCC
451 TCCNTCCCCN GCCNCACA
  1 NCNNCTGNCC CTCTCCTGNT NCCNTTCACC NTCAACTTNA CCATCACCAA (SEQ ID NO:137)
 51 CCTGCANTAN GNGGANNACA TGCNNCNCCC NGGNTCCAGG AAGTTCAACA
101 CCACNGAGNG NCTNCTGCAG GGTCTGCTNN NNCCCNTNTT CAAGAACNCC
151 AGTGTNGGCC NTCTGTACTC TGGCTGCAGA CTGACCTNNC TCAGGNCNGA
201 GAAGNATGGN GCAGCCACTG GANTGGATGC CATCTGCANC CACCNNCNTN
251 ANCCCAAAAG NCCTGGACTG NACAGNGAGC NGCTNTACTG GGAGCTNAGC
301 CANCTGACCA ANNNCATCNN NGAGCTGGGN CCCTACACCC TGGACAGGNA
351 CAGTCTCTAT GTCAATGGTT TCACCCATCA GACCTTTGCG CCCAACACCA
401 GCACTCCTGG GACCTCCACA GTGGACCTTG GGACCTCAGG GACTCCATCC
451 TCCCTCCCC AGCCCTACA
  1 TCTGCTGGCC CTCTCCTGGT GCCATTCACC CTCAACTTCA CCATCACCAA (SEQ ID NO:138)
 51 CCTGCAGTAC GAGGAGGACA TGCATCACCC AGGCTCCAGG AAGTTCAACA
101 CCACGGAGCG GGTCCTGCAG GGTCTGCTTG GTCCCATGTT CAAGAACACC
151 AGTGTCGGCC TTCTGTACTC TGGCTGCAGA CTGACCTTGC TCAGGCCTGA
201 GAAGAATGGG GCAGCCACCA GAGTGGATGC TGTCTGCACC CATCGTCCTG
251 ACCCCAAAAG CCCTGGACTG NACAGNGAGC NGCTNTACTG GGAGCTNAGC
301 CANCTGACCA ANNNCATCNN NGAGCTGGGN CCCTACACCC TGGACAGGNA
351 CAGTCTCTAT GTCAATGGTT TCACCCATCN GANCTCTGNG CCCACCACCA
401 GCACTCCTGG GACCTCCACA GTGNACNTNG GNACCTCNGG GACTCCATCC
451 TCCNTCCCCN GCCNCACA
```

TABLE 15-continued

CA125 Repeat Nucleotide Sequence
(SEQ ID NO:83 thru SEQ ID NO:145)

```
  1 NCNNCTGNCC CTCTCCTGNT NCCNTTCACC NTCAACTTNA CCATCACCAA (SEQ ID NO:139)
 51 CCTGCANTAN GNGGANNACA TGCNNCNCCC NGGNTCCAGG AAGTTCAACA
101 CCACNGAGAG GGTTCTGCAG GGTCTGCTCA AGCCCTTGTT CAAGAGCACC
151 AGTGTTGGCC CTCTGTATTC TGGCTGCAGA CTGACCTTGC TCAGGCCTGA
201 GAAGGACGGA GTAGCCACCA GAGTGGACGC CATCTGCACC CACCGCCCTG
251 ACCCCAAAAT CCCTGGGCTA GACAGACAGC AGCTATACTG GGAGCTGAGC
301 CAGCTGACCC ACAGCATCAC TGAGCTGGGA CCCTACACCC TGGATAGGGA
351 CAGTCTCTAT GTCAATGGTT TCACCCAGCG GAGCTCTGTG CCCACCACCA
401 GCACTCCTGG GACTTTCACA GTACAGCCGG AAACCTCTGA GACTCCATCA
451 TCCCTCCCTG GCCCCACA
  1 GCCACTGGCC CTGTCCTGCT GCCATTCACC CTCAATTTTA CCATCACTAA (SEQ ID NO:140)
 51 CCTGCAGTAT GAGGAGGACA TGCATCGCCC TGGCTCCAGG AAGTTCAACA
101 CCACGGAGAG GGTCCTTCAG GGTCTGCTTA TGCCCTTGTT CAAGAACACC
151 AGTGTCAGCT CTCTGTACTC TGGTTGCAGA CTGACCTTGC TCAGGCCTGA
201 GAAGGATGGG GCAGCCACCA GAGTGGATGC TGTCTGCACC CATCGTCCTG
251 ACCCCAAAAG CCCTGGACTG GACAGAGAGC GGCTGTACTG GAAGCTGAGC
301 CAGCTGACCC ACGGCATCAC TGAGCTGGGC CCCTACACCC TGGACAGGCA
351 CAGTCTCTAT GTCAATGGTT TCACCCATCA GAGCTCTATG ACGACCACCA
401 GAACTCCTGA TACCTCCACA ATGCACCTGG CAACCTCGAG AACTCCAGCC
451 TCCCTGTCTG GACCTACG
  1 ACCGCCAGCC CTCTCCTGGT GCTATTCACA ATTAACTTCA CCATCACTAA (SEQ ID NO:141)
 51 CCTGCGGTAT GAGGAGAACA TGCATCACCC TGGCTCTAGA AAGTTTAACA
101 CCACGGAGAG AGTCCTTCAG GGTCTGCTCA GGCCTGTGTT CAAGAACACC
151 AGTGTTGGCC CTCTGTACTC TGGCTGCAGA CTGACCTTGC TCAOGCCCAA
201 GAAGGATGGG GCAGCCACCA AAGTGGATGC CATCTGCACC TACCGCCCTG
251 ATCCCAAAAG CCCTGGACTG GACAGAGAGC AGCTATACTG GGAGCTGAGC
301 CAGCTAACCC ACAGCATCAC TGAGCTGGGC CCCTACACCC TGGACAGGGA
351 CAGTCTCTAT GTCAATGGTT TCACACAGCG GAGCTCTGTG CCCACCACTA
401 GCATTCCTGG GACCCCCACA GTGGACCTGG AACATCTGG GACTCCAGTT
451 TCTAAACCTG GTCCCTCG
  1 GCTGCCAGCC CTCTCCTGGT GCTATTCACT CTCAACTTCA CCATCACCAA (SEQ ID NO:142)
 51 CCTGCGGTAT GAGGAGAACA TGCAGCACCC TGGCTCCAGG AAGTTCAACA
101 CCACGGAGAG GGTCCTTCAG GGCCTGCTCA GGTCCCTGTT CAAGAGCACC
151 AGTGTTGGCC CTCTGTACTC TGGCTGCAGA CTGACTTTGC TCAGGCCTGA
201 AAAGGATGGG ACAGCCACTG GAGTGGATGC CATCTGCACC CACCACCCTG
251 ACCCCAAAAG CCCTAGGCTG GACAGAGAGC AGCTGTATTG GGAGCTGAGC
301 CAGCTGACCC ACAATATCAC TGAGCTGGGC CACTATGCCC TGGACAACGA
351 CAGCCTCTTT GTCAATGGTT TCACTCATCG GAGCTCTGTG TCCACCACCA
```

TABLE 15-continued

CA125 Repeat Nucleotide Sequence
(SEQ ID NO:83 thru SEQ ID NO:145)

```
401 GCACTCCTGG GACCCCCACA GTGTATCTGG GAGCATCTAA GACTCCAGCC

451 TCGATATTTG GCCCTTCA

1 GCTGCCAGCC ATCTCCTGAT ACTATTCACC CTCAACTTCA CCATCACTAA   (SEQ ID NO:143)

51 CCTGCGGTAT GAGGAGAACA TGTGGCCTGG CTCCAGGAAG TTCAACACTA

101 CAGAGAGGGT CCTTCAGGGC CTGCTAAGGC CCTTGTTCAA GAACACCAGT

151 GTTGGCCCTC TGTACTCTGG CTCCAGGCTG ACCTTGCTCA GGCCAGAGAA

201 AGATGGGGAA GCCACCGGAG TGGATGCCAT CTGCACCCAC CGCCCTGACC

251 CCACAGGCCC TGGGCTGGAC AGAGAGCAGC TGTATTTGGA GCTGAGCCAG

301 CTGACCCACA GCATCACTGA GCTGGGCCCC TACACACTGG ACAGGACAG

351 TCTCTATGTC AATGGTTTCA CCCATCGGAG CTCTGTACCC ACCACCAGC

1 ACCGGGGTGG TCAGCGAGGA GCCATTCACA CTGAACTTCA CCATCAACAA   (SEQ ID NO:144)

51 CCTGCGCTAC ATGGCGGACA TGGGCCAACC CGGCTCCCTC AAGTTCAACA

101 TCACAGACAA CGTCATGAAG CACCTGCTCA GTCCTTTGTT CCAGAGGAGC

151 AGCCTGGGTG CACGGTACAC AGGCTGCAGG GTCATCGCAC TAAGGTCTGT

201 GAAGAACGGT GCTGAGACAC GGGTGGACCT CCTCTGCACC TACCTGCAGC

251 CCCTCAGCGG CCCAGGTCTG CCTATCAAGC AGGTGTTCCA TGAGCTGAGC

301 CAGCAGACCC ATGGCATCAC CCGGCTGGGC CCCTACTCTC TGGACAAAGA

351 CAGCCTCTAC CTTAACGGTT ACAATGAACC TGGTCTAGAT GAGCCTCCTA

401 CAACTCCCAA GCCAGCCACC ACATTCCTGC CTCCTCTGTC AGAAGCCACA

451 ACA

1 GCCATGGGGT ACCACCTGAA CACCCTCACA CTCAACTTCA CCATCTCCAA   (SEQ ID NO:145)

51 TCTCCAGTAT TCACCAGATA TGGGCAAGGG CTCAGCTACA TTCAACTCCA

101 CCGAGGGGGT CCTTCAGCAC CTGCTCAGAC CCTTGTTCCA GAAGAGCAGC

151 ATGGGCCCCT TCTACTTGGG TTGCCAACTG ATCTCCCTCA GGCCTGAGAA

201 GGATGGGGCA GCCACTGGTG TGACACCAC CTGCACCTAC CACCCTGACC

251 CTGTGGGCCC CGGGCTGGAC ATACAGCAGC TTTACTGGGA GCTGAGTCAG

301 CTGACCCATG GTGTCACCCA ACTGGGCTTC TATGTCCTGG ACAGGGATAG

351 CCTCTTCATC AATGGCTATG CACCCAGAA TTTATCAATC CGGCGCGAGT

401 ACCAGATAAA TTTCCACATT GTCAACTGGA ACCTCAGTAA TCCAGACCCC

451 ACATCCTCAG AGTAC
```

TABLE 16

CA125 Repeat Domains (SEQ ID NO: 146)
ATVPFMVPFTLNFTITNLQYEEDMRHPGSRKFNATERELQGLLKPLFRNSSLEYLYSG<u>CRLASLRPEKDSSAMAVDAIC</u>THRPDPEDLGLDRERLYWELSNLT
                                      NGIQELGPYTLDRNSLYVNGFTHRSSMPTTSTPGTSTVDVGTSGTPSSSPSPT AAGPLLMPFTLNFTITNLQYEEDMRRTGSRKFNTMESVLQGLLKPLFKNTSVGPLYSG<u>CRLTLLRPEKDGAATGVDAIC</u>THRLDPKSPGLNREQLYWELSKLT
                                      NDIEELGPYTLDRNSLYVNGFTHQSSVSTTSTPGTSTVDLRTSGTPSSLSSPTIM AAGPLLVPFTLNFTITNLQYGEDMGHPGSRKFNTTERVLQGLLGPIFKNTSVGPLYSG<u>CRLTSLRSEKDGAATGVDAIC</u>IHHLDPKSPGLNRERLYWELSQLT
                                      NGIKELGPYTLDRNSLYVNGFTHRTSVPTSSTPGTSTVDLGTSGTPFSLPSPA

TABLE 16-continued

CA125 Repeat Domains

```
TAGPLLVLFTLNFTITNLKYEEDMHRPGSRKFNTTERVLQTLLGPMFKNTSVGLLYSGCRLTLLRSEKDGAATGVDAICTHRLDPKSPGLDREQLYWELSQLT
                                                         NGIKELGPYTLDRNSLYVNGFTHWIPVPTSSTPGTSTVDLG.SGTPSSLPSPT

AAGPLLVPFTLNFTITNLQYEEDMHHPGSRKFNTTERVLQGLLGPMFKNTSVGLLYSGCRLTLLRSEKDGAATGVDAICTHRLDPKSPGVDREQLYWELSQLT
                                                         NGIKELGPYTLDRNSLYVNGFTHQTSAPNTSTPGTSTVDLGTSGTPSSLPSPT

SAGPLLVPFTLNFTITNLQYEEDMRHPGSRKFNTTERVLQGLLKPLFKSTSVGPLYSGCRLTLLRSEKDGAATGVDAICTHRLDPKSPGVDREQLYWELSQLT
                                                         NGIKELGPYTLDRNSLYVNGFTHQTSAPNTSTPGTSTVDLGTSGTPSSLPSPT

SAGPLLVPFTLNFTITNLQYEEDMHHPGSRKFNTTERVLQGLLGPMFKNTSVGLLYSGCRLTLLRPEKNGAATGMDAICSHRLDPKSPGLNREQLYWELSQLT
                                                         HGIKELGPYTLDRNSLYVNGFTHRSSVAPTSTPGTSTVDLGTSGTPSSLPSPT

TAVPLLVPFTLNFTITNLQYGEDMRHPGSRKFNTTERVLQGLLGPLFKNSSVGPLYSGCRLISLRSEKDGAATGVDAICTHHLNPQSPGLDREQLYWQLSQMT
                                                         NGIKELGPYTLDRNSLYVNGFTHRSSGLTTSTPWTSTVDLGTSGTPSPVPSPT

TAGPLLVPFTLNFTITNLQYEEDMHRPGSRKFNATERVLQGLLSPIFKNSSVGPLYSGCRLTSLRPEKDGAATGMDAVCLYHPNPKRPGLDREQLYWELSQLT
                                                         HNITELGPYSLDRDSLYVNGFTHQNSVPTTSTPGTSTVYWATTGTPSSFPGHT

EPGPLLIPFTFNFTITNLHYEENMQHPGSRKFNTTERVLQGLLKPLFKNTSVGPLYSGCRLTSLRPEKDGAATGMDAVCLYHPNPKRPGLDREQLYCELSQLT
                                                         HNITELGPYSLDRDSLYVNGFTHQNSVPTTSTPGTSTVYWATTGTPSSFPGHT

EPGPLLIPFTFNFTITNLHYEENMQHPGSRKFNTTERVLQGLLKPLFKNTSVGPLYSGCRLTLLRPEKHEAATGVDTICTHRVDPIGPGLDRERLYWELSQLT
                                                         NSITELGPYTLDRDSLYVNGFNPRSSVPTTSTPGTSTVHLATSGTPSSLPGHT

APVPLLIPFTLNFTITNLHYEENMQHPGSRKFNTTERVLQGLLKPLFKNTSVGPLYSGCRLTLLRPEKHEAATGVDTICTHRVDPIGPGLDREXLYWELSXLT
                                                         XXIXELGPYXLDRXSLYVNGFXXXXXXXXTSTPGTSXVXLXTSGTPXXXPXXT

SAGPLLVPFTLNFTITNLQYEEDMHHPGSRKFNTTERVLQGLLGPMFKNTSVGLLYSGCRLTLLRPEKNGAATGMDAICSHRLDPKSPGLDREQLYWELSQLT
                                                         HGIKELGPYTLDRNSLYVNGFTHRSSVAPTSTPGTSTVDLGTSGTPSSLPSPT

TAVPLLVPFTLNFTITNLQYGEDMRHPGSRKFNTTERVLQGLLGPLFKNSSVGPLYSGCRLISLRSEKDGAATGVDAICTHHLNPQSPGLDREQLYWQLSQMT
                                                         NGIKELGPYTLDRNSLYVNGFTHRSSGLTTSTPWTSTVDLGTSGTPSPVPSPT

TAGPLLVPFTLNFTITNLQYEEDMHRPGSRKFNATERVLQGLLSPIFKNSSVGPLYSGCRLTSLRPEKDGAATGMDAVCLYHPNPKRPGLDREQLYWELSQLT
                                                         HNITELGPYSLDRDSLYVNGFTHQSSMTTTRTPDTSTMHLATSRTPASLSGPT

TASPLLVLFTINCTITNLQYEEDMRRTGSRKFNTMESVLQGLLKPLFKNTSVGPLYSGCRLTLLRPKKDGAATGVDAICTHRLDPKSPGLNREQLYWELSKLT
                                                         NDIEELGPYTLDRNSLYVNGFTHQSSVSTTSTPGTSTVDLRTSGTPSSLSSPTIM

XXXPLLXPFTLNFTITNLXYEEXMXXPGSRKFNTTERVLQGLLRPLFKNTSVSSLYSGCRLTLLRPEKDGAATRVDAACTYRPDPKSPGLDREQLYWELSQLT
                                                         HSITELGPYTLDRVSLYVNGFNPRSSVPTTSTPGTSTVHLATSGTPSSLPGHT

APVPLLIPFTLNFTITNLHYEENMQHPGSRKFNTTERVLQGLLRPLFKSTSVGPLYSGCRLTLLRPEKHGAATGVDAICTLRLDPTGPGLDRERLYWELSQLT
                                                         NSVTELGPYTLDRDSLYVNGFTQRSSVPTTSIPGTSAVHLETSGTPASLPGHT

APGPLLVPFTLNFTITNLQYEVDMRHPGSRKFNTTERVLQGLLKPLFKSTSVGPLYSGCRLTLLRPEKRGAATGVDTICTHRLDPLNPGLDREQLYWELSKLT
                                                         RGIIELGPYLLDRGSLYVNGFTHRNFVPITSTPGTSTVHLGTSETPSSLPRPI

VPGPLLVPFTLNFTITNLQYEEAMRHPGSRKFNTTERVLQGLLRPLFKNTSIGPLYSSCRLTLLRPEKDKAATRVDAICTHHPDPQSPGLNREQLYWELSKLT
                                                         HGITELGPYTLDRDSLYVDGFTHWSPIPTTSTPGTSIVNLGTSGIPPSLPETT

XXXPLLXPFTLNFTITNLXYEEXMXXPGSRKFNTTERVLQGLLKPLFRNSSLEYLYSGCRLASLRPEKDSSAMAVDAICTHRPDPEDLGLDRERLYWELSNLT
                                                         NGIQELGPYTLDRNSLYVNGFTHRSSFLTTSTPWTSTVDLGTSGTPSPVPSPT

TAGPLLVPFTLNFTITNLQYEEDMHRPGSRRFNTTERVLQGLLTPLFKNTSVGPLYSGCRLTLLRPEKQEAATGVDTICTHRVDPIGPGLDRERLYWELSQLT
                                                         NSITELGPYTLDRDSLYVNGFNPWSSVPTTSTPGTSTVHLATSGTPSSLPGHT

APVPLLIPFTLNFTITDLHYEENMQHPGSRKFNTTERVLQGLLKPLFKSTSVGPLYSGCRLTLLRPEKHGAATGVDAICTLRLDPTGPGLDRERLYWELSQLT
                                                         NSVTELGPYTLDRDSLYVNGFTHRSSVPTTSIPGTSAVHLETSGTPASLPGHT

APGPLLVPFTLNFTITNLQYEEDMRHPGSRKFSTTERVLQGLLKPLFKNTSVSSLYSGCRLTLLRPEKDGAATRVDAVCTHRPDPKSPGLDRERLYWKLSQLT
                                                         HGITELGPYTLDRHSLYVNGFTHQSSMTTTRTPDTSTMHLATSRTPASLSGPT

TASPLLVLFTINFTITNQRYEENMHHPGSRKFNTTERVLQGLLRPVFKNTSVGPLYSGCRLTLLRPKKDGAATKVDAICTYRPDPKSPGLDREQLYWELSQLT
                                                         HSITELGPYTQDRDSLYVNGFTHRSSVPTTSIPGTSAVHLETSGTPASLPGHT

APGPLLVPFTLNFTITNLQYEEDMRHPGSRKFNTTERVLQGLLKPLFKSTSVGPLYSGCRLTLLRPEKRGAATGVDTICTHRLDPLNPGLDREQLYWELSKLT
                                                         RGIIELGPYLLDRGSLYVNGFTHRTSVPTTSTPGTSTVDLGTSGTPFSLPSPA

XXXPLLXPFTLNFTITNLXYEEXMXXPGSRKFNTTERVLQTLLGPMFKNTSVGLLYSGCRLTLLRSEKDGAATGVDAICTHRLDPKSPGVDREQLYWELSQLT
                                                         NGIKELGPYTLDRNSLYVNGFTHWIPVPTSSTPGTSTVDLG.SGTPSLPSSPT

TAGPLLVPFTLNFTITNLKYEEDMHCPGSRKFNTTERVLQSLLGPMFKNTSVGPLYSGCRLTLLRSEKDGAATGVDAICTHRLDPKSPGVDREQLYWELSQLT
                                                         NGIKELGPYTLDRNSLYVNGFTHQTSAPNTSTPGTSTVDLGTSGTPSSLPSPT

XXXPLLXPFTLNFTITNLXYEEXMXXPGSRKFNTTERVLQGLLXPXFKXTSVGXLYSGCRLTLLRXEKXXAATXVDXXCXXXXDPXXPGLDREXLYWELSXLT
                                                         XXIXELGPYXLDRXSLYVNGFTHWIPVPTSSTPGTSTVDLG.SGTPSSLPSPT
```

TABLE 16-continued

CA125 Repeat Domains

TAGPLLVPFTLNFTITNLKYEEDMHCPGSRKFNTTERVLQSLLGPMFKNTSVGPLYSG<u>CRLTSLRSEKDGAATGVDAIC</u>THRVDPKSPFVDREQLYWELSQLT
NGIKELGPYTLDRNSLYVNGFTHQTSAPNTSTPGTSTVDLGTSGTPSSLPSPT

SAGPLLVPFTLNFTITNLQYEEDMHHPGSRKFNTTERVLQGLLGPMFKNTSVGLLYSG<u>CRLTLLRPEKNGAATGMDAIC</u>THRLDPKSPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLKPLFRNSSLEYLYSG<u>CRLASLRPEKDSSAMAVDAIC</u>THRPDPEDLGLDRERLYWELSNLT
NGIQELGPYTLDRNSLYVNGFTHRSSMPTTSTPGTSTVDVGTSGTPSSSPSPT

TAGPLLIPFTLNFTITNLQYGEDMGHPGSRKFNTTERVLQGLLGPIFKNTSVGPLYSG<u>CRLTSLRSEKDGAATCVDAIC</u>IHHLDPKSPGLNRERLYWELSQLT
NGIKELGPYTLDRNSLYVNGFTHRTSVPTTSTPGTSTVDLGTSGTPFSLPSPA

TAGPLLVLFTLNFTITNLKYEEDMHRPGSRKFNTTERVLQTLLGPMFKNTSVGLLYSG<u>CRLTLLRSEKDGAATGVDAIC</u>THRLDPKSPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLRPVFKNTSVGPLYSG<u>CRLTLLRPKKDGAATKVDAIC</u>TYRPDPKSPGLDREQLYWELSQLT
HSITELGPYTQDRDSLYVNGFTHRSSVPTTSIPGTSAVHLETTGTPSSFPGHT

EPGPLLIPFTFNFTITNLRYEENMQHPGSRKFNTTERVLQGLLTPLFKNTSVGPLYSG<u>CRLTLLRPEKQEAATGVDTIC</u>THRVDPIGPGLDRERLYWELSQLT
NSITELGPYTLDRDSLYVDGFNPWSSVPTTSTPGTSTVHLATSGTPSPLPGHT

APVPLLIPFTLNFTITDLHYEENMQHPGSRKFNTTERVLQGLLKPLFKSTSVGPLYSG<u>CRLTLLRPEKHGAATGVDAIC</u>TLRLDPTGPGLDRERLYWELSQLT
NSITELGPYTLDRDSLYVNGFNPWSSVPTTSTPGTSTVHLATSGTPSSLPGHT

TAGPLLVPFTLNFTITNLKYEEDMHCPGSRKFNTTERVLQSLHGPMFKNTSVGPLYSG<u>CRLTLLRSEKDGAATGVDAIC</u>THRLDPKSPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
NSITELGPYTLDRDSLYVNGFTHRSSMPTTSIPGTSAVHLETSGTPASLPGHT

APGPLLVPFTLNFTITNLQYEEDMRHPGSRKFNTTERVLQGLLKPLFKSTSVGPLYSG<u>CRLTLLRPEKRGAATGVDTIC</u>THRLDPLNPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFHPRSSVPTTSTPGTSTVHLATSGTPSSLPGHT

APVPLLIPFTLNFTITNLHYEENMQHPGSRKFNTTERVLQGLLGPMFKNTSVGLLYSG<u>CRLTLLRPEKNGAATGMDAIC</u>SHRLDPKSPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHQNSVPTTSTPGTSTVYWATTGTPSSFPGHT

EPGPLLIPFTFNFTITNLHYEENMQHPGSRKFNTTERVLQGLLTPLFKNTSVGPLYSG<u>CRLTLLRPEKQEAATGVDTIC</u>THRVDPIGPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHRSSVPTTSSPGTSTVHLATSGTPSSLPGHT

APVPLLIPFTLNFTITNLHYEENMQHPGSRKFNTTERVLQGLLKPLFKSTSVGPLYSG<u>CRLTLLRPEKHGAATGVDAIC</u>TLRLDPTGPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHRTSVPTTSTPGTSTVHLATSGTPSSLPGHT

APVPLLIPFTLNFTITNLQYEEDMHRPGSRKFNTTERVLQGLLSPIFKNSSVGPLYSG<u>CRLTSLRPEKDGAATGMDAVC</u>LYHPNPKRPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHWSSGLTTSTPWTSTVDLGTSGTPSPVPSPT

TAGPLLVPFTLNFTITNLQYEEDMHRPGSRKFNATERVLQGLLSPIFKNTSVGPLYSG<u>CRLTLLRPEKQEAATGVDTIC</u>THRVDPIGPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHRSFGLTTSTPWTSTVDLGTSGTPSPVPSPT

TAGPLLVPFTLNFTITNLQYEEDMHRPGSRKFNTTERVLQGLLTPLFRNTSVSSLYSG<u>CRLTLLRPEKDGAATRVDAVC</u>THRPDPKSPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHWIPVPTSSTPGTSTVDLG.SGTPXXLPSPT

TAGPLLVPFTLNFTITNLQYGEDMGHPGSRKFNTTERVLQGLLGPIFKNTSVGPLYSG<u>CRLTSLRSEKDGAATGVDAIC</u>IHHLDPKSPGLDREXLYWELSXLT
XXIXELGPYXLDRXSLYVNGFXXXXXXXXTSTPGTSXVXLXTSGTPXXXPXXT

XXXPLLXPFTLNFTITNLXYEEXMXXPGSRKFNTTERVLQGLLXPXFKXTSVGXLYSG<u>CRLTLLRXEKXXAATXVDXXC</u>XXXXDPXXPGLDREXLYWELSXLT
XXIXELGPYXLDRXSLYVNGFTHQTFAPNTSTPGTSTVDLGTSGTPSSLPSPT

TABLE 16-continued

CA125 Repeat Domains

```
SAGPLLVPFTLNFTITNLQYEEDMHHPGSRKFNTTERVLQGLLGPMFKNTSVGLLYSGCRLTLLRPEKNGAATRVDAVCTHRPDPKSPGLDREXLYWELSXLT
                                                    XXIXELGPYXLDRXSLYVNGFXXXXXXXXXTSTPGTSXVXLXTSGTPXXXPXXT

XXXPLLXPFTLNFTITNLXYEEXMXXPGSRKFNTTERVLQGLLKPLFKSTSVGPLYSGCRLTLLRPEKDGVATRVDAICTHRPDPKIPGLDRQQLYWELSQLT
                                                    HSITELGPYTLDRDSLYVNGFTQRSSVPTTSTPGTFTVQPETSETPSSLPGPT

ATGPVLLPFTLNFTITNLQYEEDMHRPGSRKFNTTERVLQGLLMPLFKNTSVSSLYSGCRLTLLRPEKDGAATRVDAVCTHRPDPKSPGLDRERLYWKLSQLT
                                                    HGITELGPYTLDRHSLYVNGFTHQSSMTTTRTPDTSTMHLATSRTPASLSGPT

TASPLLVLFTINFTITNLRYEENMHHPGSRKFNTTERVLQGLLRPVFKNTSVGPLYSGCRLTLLRPKKDGAATKVDAICTYRPDPKSPGLDREQLYWELSQLT
                                                    HSITELGPYTQDRDSLYNVGFTQRSSVPTTSVPGTPTVDLGTSGTPVSKPGPS

AASPLLVLFTLNGTITNLRYEENMQHPGSRKFNTTERVLQGLLRSLFKSTSVGPLYSGCRLTLLRPEKDGTATGVDAICTHHPDPKSPRLDREQLYWELSQLT
                                                    HNITELGHYALDNDSLFVNGFTHRSSVSTTSTPGTPTVYLGASKTPASIFGPS

AASHLLILFTLNFTITNLRYEENMW.PGSRKFNTTERVLQGLLRPLFKNTSVGPLYSGCRLTLLRPEKDGEATGVDAICTHRPDPTGPGLDREQLYLELSQLT
                                                    HSITELGPYTLDRDSLYVNGFTHRSSVPTTS.....................

TGVVSEEPFTLNFTINNLRYMADMGQPGSLKFNITDNVMKHLLSPLFQRSSLGARYTGCRVIALRSVKNGAETRVDLLCTYLQPLSGPGLPIKQVFHELSQQT
                                                    HGITRLGPYSLDKDSLYLNGYNEPGLDEPPTTPKPATTFLPPLSEATT.....

AMGYHLKTLTLNFTISNLQYSPDMGKGSATFNSTEGVLQHLLRPLFQKSSM.GPFYLGCQLISLRPEKDGAATGVDTTCTYHPDPVGPGLDIQQLYWELSQLT
                                                    HGVTQLGPYVLDRDSLFINGYAPQNLSIRGEYQINFHIVNWNLSNPDPTSSEY
```

TABLE 17

Carboxy Terminal Nucleotide Sequence

```
   1 GCCATGGGGT ACCACCTGAA GACCCTCACA CTCAACTTCA CCATCTCCAA (SEQ ID NO: 147)

51 TCTCCAGTAT TCACCAGATA TGGGCAAGGG CTCAGCTACA TTCAACTCCA

101 CCGAGGGGGT CCTTCAGCAC CTGCTCAGAC CCTTGTTCCA GAAGAGCAGC

151 ATGGGCCCCT CTACTTGGG TTGCCAACTG ATCTCCCTCA GGCCTGAGAA

201 GGATGGGCA GCCACTGGTG TGGACACCAC CTGCACCTAC CACCCTGACC

251 CTGTGGGCCC CGGGCTGGAC ATACAGCAGC TTTACTGGGA GCTGAGTCAG

301 CTGACCCATG GTGTCACCCA ACTGGGCTTC TATGTCCTGG ACAGGGATAG

351 CCTCTTCATC AATGGCTATG CACCCCAGAA TTTATCAATC CGGGGCGAGT

401 ACCAGATAAA TTTCCACATT GTCAACTGGA ACCTCAGTAA TCCAGACCCC

451 ACATCCTCAG AGTACATCAC CCTGCTGAGG GACATCCAGG ACAAGGTCAC

501 CACACTCTAC AAAGGCAGTC AACTACATGA CACATTCCGC TTCTGCCTGG

551 TCACCAACTT GACGATGGAC TCCGTGTTGG TCACTGTCAA GGCATTGTTC

601 TCCTCCAATT TGGACCCCAG CCTGGTGGAG CAAGTCTTTC TAGATAAGAC

651 CCTGAATGCC TCATTCCATT GGCTGGGCTC CACCTACCAG TTGGTGGACA

701 TCCATGTGAC AGAAATGGAG TCATCAGTTT ATCAACCAAC AAGCAGCTCC

751 AGCACCCAGC ACTTCTACCT GAATTTCACC ATCACCAACC TACCATATTC

801 CCAGGACAAA GCCCAGCCAG GCACCACCAA TTACCAGAGG AACAAAGGA

851 ATATTGAGGA TGCGCTCAAC CAACTCTTCC GAAACAGCAG CATCAAGAGT

901 TATTTTTCTG ACTGTCAAGT TTCAACATTC AGGTCTGTCC CAACAGGCA

951 CCACACCGGG GTGGACTCCC TGTGTAACTT CTCGCCACTG GCTCGGAGAG
                                                            *
1001 TAGACAGAGT TGCCATCTAT GAGGAATTTC TGCGGATGAC CCGGAATGGT

1051 ACCCAGCTGC AGAACTTCAC CCTGGACAGG AGCAGTGTCC TTGTGGATGG

1101 GTATTCTCCC AACAGAAATG AGCCCTTAAC TGGGAATTCT GACCTTCCCT
```

TABLE 17-continued

Carboxy Terminal Nucleotide Sequence

```
1151 TCTGGGCTGT CATCCTCATC GGCTTGGCAG GACTCCTGGG ACTCATCACA

1201 TGCCTGATCT GCGGTGTCCT GGTGACCACC CGCCGGCGGA AGAAGGAAGG

1251 AGAATACAAC GTCCAGCAAC AGTGCCCAGG CTACTACCAG TCACACCTAG

1301 ACCTGGAGGA TCTGCAATGA CTGGAACTTG CCGGTGCCTG GGGTGCCTTT

1351 CCCCCAGCCA GGGTCCAAAG AAGCTTGGCT GGGGCAGAAA TAAACCATAT

1401 TGGTCGGAAA AAAAAAAAA AA
```

TABLE 18

Carboxy Terminal Amino Acid Sequence

```
  1 AMGYHLKTLT LNFTISNLQY SPDMGKGSAT FNSTEGVLQH LLRPLFQKSS    (SEQ ID NO: 148)

51 MGPFYLGCQL ISLRPEKDGA ATGVDTTCTY HPDPVGPGLD IQQLYWELSQ

101 LTHGVTQLGF YVLDRDSLFI NGYAPQNLSI RGEYQINFHI VNWNLSNPDP
              *
151 TSSEYITLLR DIQDKVTTLY KGSQLHDTFR FCLVTNLTMD SVLVTVKALF

201 SSNLDPSLVE QVFLDKTLNA SFHWLGSTYQ LVDIHVTEME SSVYQPTSSS

251 STQHFYLNFT ITNLPYSQDK AQPGTTNYQR NKRNIEDALN QLFRNSSIKS

301 YFSDCQVSTF RSVPNRHHTG VDSLCNFSPL ARRVDRVAIY EEFLRMTRNG

351 TQLQNFTLDR SSVLVDGYSP NRNEPLTGNS DIPFWAVILI GLAGLLGLIT

401 CLICGVLVTT RRRKKEGEYN VQQQCPGYYQ SHLDLEDLQ
```

TABLE 19A

Serine/Threonine O-glycosylation Pattern Predicted for the Amino Terminal End of the CA125 Molecule
(SEQ ID NO: 149)

Length: 1799

| Sequence | Position | |
|---|---|---|
| RTDGIMEHITKIPNEAAHRGTIRPVKGPQTSTSPASPKGLHTGGTKRMETTTTALKTTTTALKTTSRATLTTSVYTPTLG | 80 | SEQ ID NO: 149 |
| TLTPLNASRQMASTILTEMMITTPYVFPDVPETTSSLATSLGAETSTALPRTTPSVLNRESETTASLVSRSGAERSPVIQ | 160 | |
| TLDVSSSEPDTTASWVIHPAETIPTVSKTTPNFFHSELDTVSSTATSHGADVSSAIPTNISPSELDALTPLVTISGTDTS | 240 | |
| TTFPTLTKSPHETETRTTWLTHPAETSSTIPRTIPNFSHHESDATPSIATSPGAETSSAIPIMTVSPGAEDLVTSQVTSS | 320 | |
| GTDRNMTIPTLTLSPGEPKTIASLVTHPEAQTSSAIPTSTISPAVSRLVTSMVTSLAAKTSTTNRALTNSPGEPATTVSL | 400 | |
| VTHPAQTSPTVPWTTSIFFHSKSDTTPSMTTSHGAESSSAVPTPTVSTEVPGVVTPLVTSSRAVISTTIPILTLSPGEPE | 480 | |
| TTPSMATSHGEEASSAIPTPTVSPGVPGVVTSLVTSSRAVTSTTIPILTFSLGEPETTPSMATSHGTEAGSAVPTVLPEV | 560 | |
| PGMVTSLVASSRAVTSTTLPTLTLSPGEPETTPSMATSHGAEASSTVPTVSPEVPGVVTSLVTSSSGVNSTSIPTLILSP | 640 | |
| GELETTPSMATSHGAEASSAVPTPTVSPGVSGVVTPLVTSSRAVTSTTIPILTLSSSEPETTPSMATSHGVEASSAVLTV | 720 | |
| SPEVPGMVTSLVTSSRAVTSTTIPTLTISSDEPETTTSLVTHSEAKMISAIPTLAVSPTVQGLVTSLVTSSGSETSAFSN | 800 | |
| LTVASSQPETIDSWVAHPGTEASSVVPTLTVSTGEPFTNISLVTHPAESSSTLPRTTSRFSHSELDTMPSTVTSPEAESS | 880 | |
| SAISTTISPGIPGVLTSLVTSSGRDISATFPTVPESPHESEATASWVTHPAVTSTTVPRTTPNYSHSEPDTTPSIATSPG | 960 | |
| AEATSDFPTITVSPDVPDMVTSQVTSSGTDTSITIPTLTLSSGEPETTTSFITYSETHTSSAIPTLPVSPGASKMLTSLV | 1040 | |
| ISSGTDSTTTFPTLTETPYEPETTAIQLIHPAETNTMVPRTTPKFSHSKSDTTLPVAITSPGPEASSAVSTTTISPDMSD | 1120 | |
| LVTSLVPSSGTDTSTTFPTLSETPYEPETTATWLTHPAETSTTVSGTIPNFSHRGSDTAPSMVTSPGVDTRSGVPTTTIP | 1200 | |

TABLE 19A-continued

Serine/Threonine O-glycosylation Pattern Predicted for the
Amino Terminal End of the CA125 Molecule
(SEQ ID NO: 149)

| | |
|---|---|
| PSIPGVVTSQVTSSATDTSTAIPTLTPSPGEPETTASSATHPGTQTGFTVPIRTVPSSEPDTMASWVTHPPQTSTPVSRT | 1280 |
| TSSFSHSSPDATPVMATSPRTEASSAVLTTISPGAPEMVTSQITSSGAATSTTVPTLTHSPGMPETTALLSTHPRTETSK | 1360 |
| TFPASTVFPQVSETTASLTIRPGAETSTALPTQTTSSLFTLLVTGTSRVDLSPTASPGVSAKTAPLSTHPGTETSTMIPT | 1440 |
| STLSLGLLETTGLLATSSSAETSTSTLTLTVSPAVSGLSSASITTDKPQTVTSWNTETSPSVTSVGPPEFSRTVTGTTMT | 1520 |
| LIPSEMPTPPKTSHGEGVSPTTILRTTMVEATNLATTGSSPTVAKTTTTFNTLAGSLFTPLTTPGMSTLASESVTSRTSY | 1600 |
| NHRSWISTTSSYNRRYWTPATSTPVTSTFSPGISTSSIPSSTAATVPFMVPFTLNFTITNLQYEEDMRHPGSRKFNATER | 1680 |
| ELQGLLKPLFRNSSLEYLYSGCRLASLRPEKDSSAMAVDAICTHRPDPEDLGLDRERLYWELSNLTNGIQELGPYTLDRN | 1760 |
| SLYVNGFTHRSSMPTTSTPGTSTVDVGTSGTPSSSPSPT | |

TABLE 19B

Serine/Threonine O-glycosylation Pattern Predicted for the
Amino Terminal End of the CA125 Molecule

| | |
|---|---|
| ....................T........TSTS................TTT....TTTT...TT.....TT...T.... | 80 |
| ...................................ST....TT.......................... | 160 |
| .....S.....T............T.S...........T.........S........S...........S.T..S | 240 |
| T...T.T................TSS....T.........S..T.S..TS......S......T.........T...TS. | 320 |
| ............T.S......T..S.........TSS...TST..............T......STT....T.S.....TT.S. | 400 |
| .T....TS.T...T.........S..T...TTS....SSS....T.T.ST....................T......T.S...... | 480 |
| TT.S..T......SS...T.T.S...........S......T...........T.S..TS......S...T..... | 560 |
| ..............T......T.S......TT.S..TS.....SST..T.S...........TS.S....T.......... | 640 |
| .....T.S..T.......SS...T.T.S...S..........S......T......T.SSS....T.S..TS......S..... | 720 |
| S............S......STT..T.T.SS.....TT..........S................T.......... | 800 |
| ....S..................SS.....T..............T....SSS....T.............ST.T......S | 880 |
| S...TT.S....................S....T......S..T....T....TSTT...TT....S.S....T.S..TS.. | 960 |
| ...TS......T.........T...TS.........T.T.SS.....T....T.....T.S...T................ | 1040 |
| .S..T.STTT..T.T.T.................T....TT.........S..........S......SS....TT....... | 1120 |
| .......S...T...STT..T.S.T......TT....T......ST.....................TS.......S.....TT.. | 1200 |
| .S......T....TS..T.TST...T.T.S.....TT.SS.T............T...SS...T...S...T....TST...S.T | 1280 |
| TSS.S.SS....T.....TS..T...SS....T.S..........T...TS....TSTT....T.S............ST...T...S. | 1360 |
| ....ST......S.TT...T.......ST...T.TT.S....................T.S...S.......ST...T...ST...T | 1440 |
| ST..............T...S..TSTS....T......S...S...S....T.....T.TS..T...S.S.TS......S.........T | 1520 |
| ...S...T.....S........T..............TT.SS.T.......................T....ST..S.......... | 1600 |
| ...................TST..TST.S...STSS...SST............................... | 1680 |
| ................................................................... | 1760 |
| ...............TTST...ST....TS.T.SSS.S.T | |

TABLE 20

Nucleotide and Amino Acid Sequences of Recombinant CA125 Repeat Showing Peptides (Underlined 1-4) which are Antigenically Matched for Immune Stimulation of Patients with the HLA-2 Histocompatibility Subtype
CA 125 Recombinant Nucleotide and Amino Acid Sequences
(SEQ ID NO: 151 and SEQ ID NO: 152, respectively)
CA 125 Recombinant Nucleotide (Anti-Sense Strand) Sequence (SEQ ID NO: 153)
Peptide 1 (SEQ ID NO: 154); Peptide 2 (SEQ ID NO: 155);
Peptide 3 (SEQ ID NO: 156) and Peptide 4 (SEQ ID NO: 157)

```
    ATGAGAGGATCGCATCACCATCACCATCACGGATCCATGGGCCACACAGAGCCTGGCCCT
1   ---------+---------+---------+---------+---------+---------+   60
    TACTCTCCTAGCGTAGTGGTAGTGGTAGTGCCTAGGTACCCGGTGTGTCTCGGACCGGGA
    M  R  G  S  H  H  H  H  H  H  G  S  M  G  H  T  E  P  G  P    -

CTCCTGATACCATTCACTTTCAACTTTACCATCACCAACCTGCATTATGAGGAAAACATG
61  ---------+---------+---------+---------+---------+---------+   120
    GAGGACTATGGTAAGTGAAAGTTGAAATGGTAGTGGTTGGACGTAATACTCCTTTTGTAC
     L  L  I  P  F  T  F  N  F  T  I  T  N  L  H  Y  E  E  N  M   -

CAACACCCTGGTTCCAGGAAGTTCAACACCACGGAGAGGGTTCTGCAGGGTCTGCTCAAG
121 ---------+---------+---------+---------+---------+---------+   180
    GTTGTGGGACCAAGGTCCTTCAAGTTGTGGTGCCTCTCCCAAGACGTCCCAGACGAGTTC
                                         3
    Q  H  P  G  S  R  K  F  N  T  T  E  R  V  L  Q  G  L  L  K    -

CCCTTGTTCAAGAACACCAGTGTTGGCCCTCTGTACTCTGGCTGCAGACTGACCTTGCTC
181 ---------+---------+---------+---------+---------+---------+   240
    GGGAACAAGTTCTTGTGGTCACAACCGGGAGACATGAGACCGACGTCTGACTGGAACGAG
    P  L  F  K  N  T  S  V  G  P  L  Y  S  G  C  R  L  T  L  L    -

AGACCTGAGAAGCATGAGGCAGCCACTGGAGTGGACACCATCTGTACCCACCGCGTTGAT
241 ---------+---------+---------+---------+---------+---------+   300
    TCTGGACTCTTCGTACTCCGTCGGTGACCTCACCTGTGGTAGACATGGGTGGCGCAACTA
    R  P  E  K  H  E  A  A  T  G  V  D  T  I  C  T  H  R  V  D    -

CCCATCGGACCTGGACTGGACAGAGAGCGGCTATACTGGGAGCTGAGCCAGCTGACCAAC
301 ---------+---------+---------+---------+---------+---------+   360
    GGGTAGCCTGGACCTGACCTGTCTCTCGCCGATATGACCCTCGACTCGGTCGACTGGTTG
                                 1                        4
    P  I  G  P  G  L  D  R  E  R  L  Y  W  E  L  S  Q  L  T  N    -

AGCATCACAGAGCTGGGACCCTACACCCTGGACAGGGACAGTCTCTATGTCAATGGCTTC
361 ---------+---------+---------+---------+---------+---------+   420
    TCGTAGTGTCTCGACCCTGGGATGTGGGACCTGTCCCTGTCAGAGATACAGTTACCGAAG
                                 2
    S  I  T  E  L  G  P  Y  T  L  D  R  D  S  L  Y  V  N  G  F    -

AACCCTCGGAGCTCTGTGCCAACCACCAGCACTCCTGGGACCTCCACAGTGCACCTGGCA
421 ---------+---------+---------+---------+---------+---------+   480
    TTGGGAGCCTCGAGACACGGTTGGTGGTCGTGAGGACCCTGGAGGTGTCACGTGGACCGT
    N  P  R  S  S  V  P  T  T  S  T  P  G  T  S  T  V  H  L  A    -

ACCTCTGGGACTCCATCCTCCCTGCCT
481 ---------+---------+-------                                    507
    TGGAGACCCTGAGGTAGGAGGGACGGA
    T  S  G  T  P  S  S  L  P
```

(SEQ ID NO: 154)
Peptide 1        RLYWELSQL (SEQ ID NO: 155)
Peptide 2        TLDRDSLYV (SEQ ID NO: 156)
Peptide 3        VLQGLLKPL (SEQ ID NO: 157)
Peptide 4        QLTNSITEL

TABLE 21

CA125 Protein Sequence

```
   1 MEHITKIPNE AAHRGTIRPV KGPQTSTSPA SPKGLHTGGT KRMETTTTAL           (SEQ ID NO: 162)
  51 KTTTTALKTT SRATLTTSVY TPTLGTLTPL NASRQMASTI LTEMMITTPY
 101 VFPDVPETTS SLATSLGAET STALPRTTPS VLNRESETTA SLVSRSGAER
 151 SPVIQTLDVS SSEPDTTASW VIHPAETIPT VSKTTPNFFH SELDTVSSTA
 201 TSHGADVSSA IPTNISPSEL DALTPLVTIS GTDTSTTFPT LTKSPHETET
 251 RTTWLTHPAE TSSTIPRTIP NFSHHESDAT PSIATSPGAE TSSAIPIMTV
 301 SPGAEDLVTS QVTSSGTDRN MTIPTLTLSP GEPKTIASLV THPEAQTSSA
 351 IPTSTISPAV SRLVTSMVTS LAAKTSTTNR ALTNSPGEPA TTVSLVTHPA
 401 QTSPTVPWTT SIFFHSKSDT TPSMTTSHGA ESSSAVPTPT VSTEVPGVVT
 451 PLVTSSRAVI STTIPILTLS PGEPETTPSM ATSHGEEASS AIPTPTVSPG
 501 VPGVVTSLVT SSRAVTSTTI PILTFSLGEP ETTPSMATSH GTEAGSAVPT
 551 VLPEVPGMVT SLVASSRAVT STTLPTLTLS PGEPETTPSM ATSHGAEASS
 601 TVPTVSPEVP GVVTSLVTSS SGVNSTSIPT LILSPGELET TPSMATSHGA
 651 EASSAVPTPT VSPGVSGVVT PLVTSSRAVT STTIPILTLS SSEPETTPSM
 701 ATSHGVEASS AVLTVSPEVP GMVTSLVTSS RAVTSTTIPT LTISSDEPET
 751 TTSLVTHSEA KMISAIPTLA VSPTVQGLVT SLVTSSGSET SAFSNLTVAS
 801 SQPETIDSWV AHPGTEASSV VPTLTVSTGE PFTNISLVTH PAESSSTLPR
 851 TTSRFSHSEL DTMPSTVTSP EAESSSAIST TISPGIFGVL TSLVTSSGRD
 901 ISATFPTVPE SPHESEATAS WVTHPAVTST TVPRTTPNYS HSEPDTTPSI
 951 ATSPGAEATS DFPTITVSPD VPDMVTSQVT SSGTDTSITI PTLTLSSGEP
1001 ETTTSFITYS ETHTSSAIPT LPVSPGASKM LTSLVISSGT DSTTTFPTLT
1051 ETPYEPETTA IQLIHPAETN TMVPRTTPKF SHSKSDTTLP VAITSPGPEA
1101 SSAVSTTTIS PDMSDLVTSL VPSSGTDTST TFPTLSETPY EPETTATWLT
1151 HPAETSTTVS GTIPNFSHRG SDTAPSMVTS PGVDTRSGVP TTTIPPSIPG
1201 VVTSQVTSSA TDTSTAIPTL TPSPGEPETT ASSATHPGTQ TGFTVPIRTV
1251 PSSEPDTMAS WVTHPPQTST PVSRTTSSFS HSSPDATPVM ATSPRTEASS
1301 AVLTTISPGA PEMVTSQITS SGAATSTTVP TLTHSPGMPE TTALLSTHPR
1351 TETSKTFPAS TVFPQVSETT ASLTIRPGAE TSTALPTQTT SSLFTLLVTG
1401 TSRVDLSPTA SPGVSAKTAP LSTHPGTETS TMIPTSTLSL GLLETTGLLA
1451 TSSSAETSTS TLTLTVSPAV SGLSSASITT DKPQTVTSWN TETSPSVTSV
1501 GPPEFSRTVT GTTMTLIPSE MPTPPKTSHG EGVSPTTILR TIMVEATNLA
1551 TTGSSPTVAK TTTTFNTLAG SLFTPLTTPG MSTLASESVT SRTSYNHRSW
1601 ISTTSSYNRR YWTPATSTPV TSTFSPGIST SSIPSSTA
                                         AT VPFMVPFTLN
1651 FTITNLQYEE DMRHFGSRKF NATERELQGL LKPLFRNSSL EYLYSGCRLA
1701 SLRPEKDSSA MAVDAICTHR PDPEDLGLDR ERLYWELSNL TNGIQELGPY
1751 TLDRNSLYVN GFTHRSSMPT TSTPGTSTVD VGTSGTPSSS PSPTAAGPLL
1801 MPFTLNFTIT NLQYEEDMRR TGSRKFNTME SVLQGLLKPL FKNTSVGPLY
1851 SGCRLTLLRP EKDGAATGVD AICTHRLDPK SPGLNREQLY WELSKLTNDI
```

TABLE 21-continued

CA125 Protein Sequence

1901 EELGPYTLDR NSLYVNGFTH QSSVSTTSTP GTSTVDLRTS GTPSSLSSPT

1951 IMAAGPLLVP FTLNFTITNL QYGEDMGHPG SRKFNTTERV LQGLLGPIFK

2001 NTSVGPLYSG CRLTSLRSEK DGAATGVDAI CIHHLDPKSP GLNRERLYWE

2051 LSQLTNGIKE LGPYTLDRNS LYVNGFTHRT SVPTSSTPGT STVDLGTSGT

2101 PFSLPSPATA GPLLVLFTLN FTITNLKYEE DMHRPGSRKF NTTERVLQTL

2151 LGPMFKNTSV GLLYSGCRLT LLRSEKDGAA TGVDAICTHR LDPKSPGLDR

2201 EQLYWELSQL TNGIKELGPY TLDRNSLYVN GFTHWIPVPT SSTPGTSTVD

2251 LGSGTPSSLP SPTAAGPLLV PFTLNFTITN LQYEEDMHHP GSRKFNTTER

2301 VLQGLLGPMF KNTSVGLLYS GCRLTLLRSE KDGAATGVDA ICTHRLDPKS

2351 PGVDREQLYW ELSQLTNGIK ELGPYTLDRN SLYVNGFTHQ TSAPNTSTPG R

2401 TSTVDLGTSG TPSSLPSPTS AGPLLVPFTL NFTITNLQYE EDMRHPGSRK e

2451 FNTTERVLQG LLKPLFKSTS VGPLYSGCRL TLLRSEKDGA ATGVDAICTH p

2501 RLDPKSPGVD REQLYWELSQ LTNGIKELGP YTLDRNSLYV NGFTHQTSAP e

2551 NTSTPGTSTV DLGTSGTPSS LPSPTSAGPL LVPFTLNFTI TNLQYEEDMH a

2601 HPGSRKFNTT ERVLQGLLGP MFKNTSVGLL YSGCRLTLLR PEKNGAATGM t

2651 DAICSHRLDP KSPGLNREQL YWELSQLTHG IKELGPYTLD RNSLYVNGFT

2701 HRSSVAPTST PGTSTVDLGT SGTPSSLPSP TTAVPLLVPF TLNFTITNLQ

2751 YGEDMRHPGS RKFNTTERVL QGLLGPLFKN SSVGPLYSGC RLISLRSEKD

2801 GAATGVDAIC THHLNPQSPG LDREQLYWQL SQMTNGIKEL GPYTLDRNSL D

2851 YVNGFTHRSS GLTTSTPWTS TVDLGTSGTP SPVPSPTTAG PLLVPFTLNF o

2901 TITNLQYEED MHRPGSRKFN ATERVLQGLL SPIFKNSSVG PLYSGCRLTS m

2951 LRPEKDGAAT GMDAVCLYHP NPKRPGLDRE QLYWELSQLT HNITELGPYS a

3001 LDRDSLYVNG FTHQNSVPTT STPGTSTVYW ATTGTPSSFP GHTEPGPLLI i

3051 PFTFNFTITN LHYEENMQHP GSRKFNTTER VLQGLLKPLF KNTSVGPLYS n

3101 GCRLTSLRPE KDGAATGMDA VCLYHPNPKR PGLDREQLYC ELSQLTHNIT

3151 ELGPYSLDRD SLYVNGFTHQ NSVFTTSTPG TSTVYWATTG TPSSFPGHTE

3201 PGPLLIPFTF NFTITNLHYE ENMQHPGSRK FNTTERVLQG LLKPLFKNTS

3251 VGPLYSGCRL TLLRPEKHEA ATGVDTICTH RVDPIGPGLD RERLYWELSQ

3301 LTNSITELGP YTLDRDSLYV NGFNPRSSVP TTSTPGTSTV HLATSGTPSS

3351 LPGHTAPVPL LIPFTLNFTI TNLHYEENMQ HPGSRKFNIT ERVLQGLLKP

3401 LFKNTSVGPL YSGCRLTLLR PEKHEAATGV DTICTHRVDP IGPGLDREXL

3451 YWELSXLTXX IXELGPYXLD RXSLYVNGFX XXXXXXXTST PGTSXVXLXT

3501 SGTPXXXPXX TSAGPLLVPF TLNFTITNLQ YEEDMHHPGS RKFNTTERVL

3551 QGLLGPMFKN TSVGLLYSGC RLTLLRPEKN GAATGMDAIC SHRLDPKSPG

3601 LDREQLYWEL SQLTHGIKEL GPYTLDRNSL YVNGFTHRSS VAPTSTPGTS

3651 TVDLGTSGTP SSLPSPTTAV PLLVPFTLNF TITNLQYGED MRHPGSRKFN

3701 TTERVLQGLL GPLFKNSSVG PLYSGCRLIS LRSEKDGAAT GVDAICTHHL

3751 NPQSPGLDRE QLYWQLSQMT NGIKELGPYT LDRNSLYVNG FTHRSSGLTT

3801 STPWTSTVDL GTSGTPSPVP SPTTAGPLLV PFTLNFTITN LQYEEDMHRP

TABLE 21-continued

CA125 Protein Sequence

```
3851 GSRKFNATER VLQGLLSPIF KNSSVGPLYS GCRLTSLRPE KDGAATGMDA
3901 VCLYHPNPKR PGLDREQLYW ELSQLTHNIT ELGPYSLDRD SLYVNGFTHQ
3951 SSMTTTRTPD TSTMHLATSR TPASLSGPTT ASPLLVLFTI NCTITNLQYE
4001 EDMRRTGSRK FNTMESVLQG LLKPLFKNTS VGPLYSGCRL TLLRPKKDGA
4051 ATGVDAICTH RLDPKSPGLN REQLYWELSK LTNDIEELGP YTLDRNSLYV
4101 NGFTHQSSVS TTSTPGTSTV DLRTSGTPSS LSSPTIMXXX PLLXPFTLNF
4151 TITNLXYEEX MXXPGSRKFN TTERVLQGLL RPLFKNTSVS SLYSGCRLTL
4201 LRPEKDGAAT RVDAACTYRP DPKSPGLDRE QLYWELSQLT HSITELGPYT
4251 LDRVSLYVNG FNPRSSVPTT STPGTSTVHL ATSGTPSSLP GHTXX XPLL
4301 XPFTLNFTIT NLXYEEXMXX PGSRKFNTTE RVLQGLLKPL FRNSSLEYLY
4351 SGCRLASLRP EKDSSAMAVD AICTHRPDPE DLGLDRERLY WELSNLTNGI
4401 QELGPYTLDR NSLYVNGFTH RSSFLTTSTP WTSTVDLGTS GTPSPVFSPT
4451 TAGPLLVPFT LNFTITNLQY EEDMHRPGSR RFNTTERVLQ GLLTPLFKNT R
4501 SVGPLYSGCR LTLLRPEKQE AATGVDTICT HRVDPIGPGL DRERLYWELS e
4551 QLTNSITELG PYTLDRDSLY VNGFNPWSSV PTTSTPGTST VHLATSGTPS p
4601 SLPGHTAPVP LLIPFTLNFT ITDLHYEENM QHPGSRKFNT TERVLQGLLK e
4651 PLFKSTSVGP LYSGCRLTLL RPEKHGAATG VDAICTLRLD PTGPGLDRER a
4701 LYWELSQLTN SVTELGPYTL DRDSLYVNGF THRSSVPTTS IPGTSAVHLE t
4751 TSGTPASLPG HTAPGPLLVF FTLNFTITNL QYEEDMRHPG SRKFSTTERV
4801 LQGLLKPLFK NTSVSSLYSG CRLTLLRPEK DGAATRVDAV CTHRPDPKSP
4851 GLDRERLYWK LSQLTHGITE LGPYTLDRHS LYVNGFTHQS SMTTTRTPDT
4901 STMHLATSRT PASLSGPTTA SPLLVLFTIN FTITNQRYEE NMHHPGSRKF
4951 NTTERVLQGL LRPVFKNTSV GPLYSGCRLT LLRPKKDGAA TKVDAICTYR D
5001 PDPKSPGLDR EQLYWELSQL TESITELGPY TQDRDSLYVN GFTWRSSVPT o
5051 TSIPGTSAVH LETSGTPASL PGHTAPGPLL VPFTLNFTIT NLQYEEDMRH m
5101 PGSRKFNTTE RVLQGLLKPL FKSTSVGPLY SGCRLTLLRP EKRGAATGVD a
5151 TICTHRLDPL NPGLDREQLY WELSELTEGI IELGPYLLDR GSLYVNGFTH i
5201 RTSVPTTSTP GTSTVDLGTS GTPFSLPSPA XXXPLLXPFT LNFTITNLXY n
5201 EEXMXXPGSR KFNTTERVLQ TLLGPMFKNT SVGLLYSGCR LTLLRSEKDG
5251 AATGVDAICT HRLDPKSPGV DREQLYWELS QLTNGIKELG PYTLDRNSLY
5301 VNGFTHWIPV PTSSTPGTST VDLGSGTPSL PSSPTTAGPL LVPFTLNFTI
5351 TNLKYEEDMH CPGSRKFNTT ERVLQSLLGP MFKNTSVGPL YSGCRLTLLR
5401 SEKDGAATGV DAICTHRLDP KSPGVDREQL YWELSQLTNG IKELGPYTLD
5451 RNSLYVNGFT HQTSAPNTST PGTSTVDLGT SGTPSSLPSP TXXXPLLXPF
5501 TLNFTITNLX YEEXMXXPGS RKFNTTERVL QGLLXPXFKX TSVGXLYSGC
5551 RLTLLRXEKX XAATXVDXXC XXXXDPXXPG LDREXLYWEL SXLTXXIXEL
5601 GPYXLDRXSL YVNGFTHWIP VPTSSTPGTS TVDLGSGTPS SLPSPTTAGP
5651 LLVPFTLNFT ITNLKYEEDM HCPGSRKFNT TERVLQSLLG PMFKNTSVGP
5701 LYSGCRLTSL RSEKDGAATG VDAICTHRVD PKSPGVDREQ LYWELSQLTN
```

TABLE 21-continued

CA125 Protein Sequence

```
5751 GIKELGPYTL DRNSLYVNGF THQTSAPNTS TPGTSTVDLG TSGTPSSLPS
5801 PTSAGPLLVP FTLNFTITNL QYEEDMHHPG SRKFNTTERV LQGLLGPMFK
5851 NTSVGLLYSG CRLTLLRPEK NGAATGMDAI CTHRLDPKSP GLDREXLYWE
5901 LSXLTXXIXE LGPYXLDRXS LYVNGFXXXX XXXXTSTPGT SXVXLXTSGT
5951 PXXXPXXTXX XPLLXPFTLN FTITNLXYEE XMXXPGSRKF NTTERVLQGL
6001 LKPLFRNSSL EYLYSGCRLA SLRPEKDSSA MAVDAICTHR PDPEDLGLDR
6051 ERLYWELSNL TNGIQELGPY TLDRNSLYVN GFTHRSSMPT TSTPGTSTVD
6101 VGTSGTPSSS PSPTTAGPLL IPFTLNFTIT NLQYGEDMGH PGSRKFNTTE
6151 RVLQGLLGPI FKNTSVGPLY SGCRLTSLRS EKDGAATGVD AICIHHLDPK
6201 SPGLNRERLY WELSQLTNGI KELGPYTLDR NSLYVNGFTH RTSVPTTSTP
6251 GTSTVDLGTS GTPFSLPSPA TAGPLLVLFT LNFTITNLKY EEDMHRPGSR
6301 KFNTTERVLQ TLLGPMFKNT SVGLLYSGCR LTLLRSEKDG AATGVDAICT
6351 HRLDPKSPGL DREXLYWELS XLTXXIXELG PYXLDRXSLY VNGFXXXXXXX
6401 XXTSTPGTSX VXLXTSGTPX XXPXXTXXXP LLXPFTLNFT ITNLXYEEXM
6451 XXPGSRKFNT TERVLQGLLR PVFKNTSVGP LYSGCRLTLL RFKKDGAATK
6501 VDAICTYRPD PKSPGLDREQ LYWELSQLTH SITELGPYTQ DRDSLYVNGF
6551 THRSSVPTTS IPGTSAVHLE TTGTPSSFPG HTEPGPLLIP FTFNFTITNL
6601 RYEENMQHPG SRKFNTTERV LQGLLTPLFK NTSVGPLYSG CRLTLLRPEK  R
6651 QEAATGVDTI CTHRVDPIGP GLDRERLYWE LSQLTNSITE LGPYTLDRDS  e
6701 LYVDGFNPWS SVPTTSTPGT STVHLATSGT PSPLPGHTAP VPLLIPFTLN  p
6751 FTITDLHYEE NMQHPGSRKF NTTERVLQGL LKPLFKSTSV GPLYSGCRLT  e
6801 LLRPEKHGAA TGVDAICTLR LDPTGPGLDR ERLYWELSQL TNSITELGPY  a
6851 TLDRDSLYVN GFNPWSSVPT TSTPGTSTVH LATSGTPSSL PGHTTAGPLL  t
6901 VPFTLNFTIT NLKYEEDMHC PGSRKFNTTE RVLQSLHGPM FKNTSVGPLY
6951 SGCRLTLLRS EKDGAATGVD AICTHRLDPK SPGLDREXLY WELSXLTXXI
7001 XELGPYXLDR XSLYVNGFXX XXXXXXTSTP GTSXVXLXTS GTPXXXPXXT
7051 XXXPLLXPFT LNFTITNLXY EEXMXXPGSR KFNTTERVLQ GLLXPXFKXT
7101 SVGXLYSGCR LTLLRXEKXX AATXVDXXCX XXXDPXXPGL DREXLYWELS  D
7151 XLTNSITELG PYTLDRDSLY VNGFTHRSSM PTTSIPGTSA VHLETSGTPA  o
7201 SLPGHTAPGP LLVPFTLNFT ITNLQYEEDM RHPGSRKFNT TERVLQGLLK  m
7251 PLFKSTSVGP LYSGCRLTLL RPEKRGAATG VDTICTHRLD PLNPGLDREX  a
7301 LYWELSXLTX XIXELGPYXL DRXSLYVNGF XXXXXXXXTS TPGTSXVXLX  i
7351 TSGTPXXXPX XTXXXPLLXP FTLNFTITNL XYEEXMXXPG SRKFNTTERV  n
7401 LQGLLXPXFK XTSVGXLYSG CRLTLLRXEK XXAATXVDXX CXXXXDPXXP
7451 GLDREXLYWE LSXLTXXIXE LGPYXLDRXS LYVNGFHPRS SVPTTSTPGT
7501 STVHLATSGT PSSLPGHTAP VPLIPFTLN FTITNLHYEE NMQHPGSRKF
7551 NTTERVLQGL LGPMFKNTSV GLLYSGCRLT LLRPEKNGAA TGMDAICSHR
7601 LDPKSPGLDR EXLYWELSXL TXXIXELGPY XLDRXSLYVN GFXXXXXXXXX
7651 TSTPGTSXVX LXTSGTPXXX PXXTXXXPLL XPFTLNFTIT NLXYEEXMXX
```

TABLE 21-continued

| CA125 Protein Sequence |
| --- |

```
7701 PGSRKFNTTE RVLQGLLXPX FKXTSVGXLY SGCRLTLLRX EKXXAATXVD
7751 XXCXXXXDPX XPGLDREXLY WELSXLTXXI XELGPYXLDR XSLYVNGFTH
7801 QNSVPTTSTP GTSTVYWATT GTPSSFPGHT EPGPLLIPFT FNFTITNLHY
7851 EENMQHPGSR KFNTTERVLQ GLLTPLFKNT SVGPLYSGCR LTLLRPEKQE
7901 AATGVDTICT HRVDPIGPGL DREXLYWELS XLTXXIXELG PYXLDRXSLY
7951 VNGFXXXXXX XXTSTPGTSX VXLXTSGTPX XXPXXTXXXP LLXPFTLNFT
8001 ITNLXYEEXM XXPGSRKFNT TERVLQGLLX PXFKXTSVGX LYSGCRLTLL
8051 RXEKXXAATX VDXXCXXXXD PXXPGLDREX LYWELSXLTX XIXELGPYXL
8101 DRXSLYVNGF THRSSVPTTS SPGTSTVHLA TSGTPSSLPG HTAPVPLLIP
8151 FTLNFTITNL HYEENMQHPG SRKFNTTERV LQGLLKPLFK STSVGPLYSG
8201 CRLTLLRPEK HGAATGVDAI CTLRLDPTGP GLDREXLYWE LSXLTXXIXE
8251 LGPYXLDRXS LYVNGFXXXX XXXXXTSTPGT SXVXLXTSGT PXXXPXXTXX
8301 XPLLXPFTLN FTITNLXYEE XMXXPGSRKF NTTERVLQGL LXPXFKXTSV
8351 GXLYSGCRLT LLRXEKXXAA TXVDXXCXXX XDPXXPGLDR EXLYWELSXL
8401 TXXIXELGPY XLDRXSLYVN GFTHRTSVPT TSTPGTSTVH LATSGTPSSL
8451 PGHTAPVPLL IPFTLNFTIT NLQYEEDMHR PGSRKFNTTE RVLQGLLSPI
8501 FKNSSVGPLY SGCRLTSLRP EKDGAATGMD AVCLYHPNPK RPGLDREQLY
8551 CELSQLTHNI TELGPYSLDR DSLYVNGFTH QNSVPTTSTP GTSTVYWATT
8601 GTPSSFPGHT XXXPLLXPFT LNFTITNLXY EEXMXXPGSR KFNTTERVLQ
8651 GLLXPXFKXT SVGXLYSGCR LTLLRXEKXX AATXVDXXCX XXXDPXXPGL
8701 DREXLYWELS XLTXXIXELG PYXLDRXSLY VNGFTHWSSG LTTSTPWTST
8751 VDLGTSGTPS PVPSPTTAGP LLVPFTLNFT ITNLQYEEDM HRPGSRKFNA
8801 TERVLQGLLS PIFKNTSVGP LYSGCRLTLL RPEKQEAATG VDTICTHRVD
8851 PIGPGLDREX LYWELSXLTX XIXELGPYXL DRXSLYVNGF XXXXXXXXTS
8901 TPGTSXVXLX TSGTPXXXPX XTXXXPLLXP FTLNFTITNL XYEEXMXXPG
8951 SRKFNTTERV LQGLLXPXFK XTSVGXLYSG CRLTLLRXEK XXAATXVDXX
9001 CXXXXDPXXP GLDREXLYWE LSXLTXXIXE LGPYXLDRXS LYVNGFTHRS
9051 FGLTTSTPWT STVDLGTSGT PSPVPSPTTA GPLLVPFTLN FTITNLQYEE
9101 DMHRPGSRKF NTTERVLQGL LTPLFRNTSV SSLYSGCRLT LLRPEKDGAA
9151 TRVDAVCTHR PDPKSPGLDR EXLYWELSXL TXXIXELGPY XLDRXSLYVN R
9201 GFXXXXXXXX TSTPGTSXVX LXTSGTSXVX LXTSGTPXXX PXXTXXXPLL e
     XPFTLNFTIT
9251 NLXYEEXMXX PGSRKFNTTE RVLQGLLXPX FKXTSVGXLY SGCRLTLLRX p
9301 EKXXAATXVD XXCXXXXDPX XPGLDREXLY WELSXLTXXI XELGPYXLDR e
9351 XSLYVNGFTH WIPVPTSSTP GTSTVDLGSG TPSSLPSPTT AGPLLVPFTL a
9401 NFTITNLQYG EDMGHPGSRK FNTTERVLQG LLGPIFKNTS VGPLYSGCRL t
9451 TSLRSEKDGA ATGVDAICIH HLDPKSPGLD REXLYWELSX LTXXIXELGP
9501 YXLDRXSLYV NGFXXXXXXX XTSTPGTSXV XLXTSGTPXX XPXXTXXXPL
9551 LXPFTLNFTI TNLXYEEXMX XPGSRKFNTT ERVLQGLLXP XFKXTSVGXL
```

TABLE 21-continued

CA125 Protein Sequence

```
 9601  YSGCRLTLLR XEKXXAATXV DXXCXXXXDP XXPGLDREXL YWELSXLTXX
 9651  IXELGPYXLD RXSLYVNGFT HQTFAPNTST PGTSTVDLGT SGTPSSLPSP  D
 9701  TSAGPLLVPF TLNFTITNLQ YEEDMHHPGS RKFNTTERVL QGLLGPMFKN  o
 9751  TSVGLLYSGC RLTLLRPEKN GAATRVDAVC THRPDPKSPG LDREXLYWEL  m
 9801  SXLTXXIXEL GPYXLDRXSL YVNGFXXXXX XXXTSTPGTS XVXLXTSGTP  a
 9851  XXXPXXTAPV PLLIPFTLNF TITNLHYEEN MQHPGSRKFN TTERVLQGLL  i
 9901  RPLFKSTSVG PLYSGCRLTL LRPEKHGAAT GVDAICTLRL DPTGPGLDRE  n
 9951  RLYWELSQLT NSVTELGPYT LDRDSLYVNG FTQRSSVPTT SIPGTSAVHL
10001  ETSGTPASLP GHTAPGPLLV PFTLNFTITN LQYEVDMRHP GSRKFNTTER
10051  VLQGLLKPLF KSTSVGPLYS GCRLTLLRPE KRGAATGVDT ICTHRLDPLN
10101  PGLDREQLYW ELSKLTRGII ELGPYLLDRG SLYVNGFTHR NFVPITSTPG
10151  TSTVHLGTSE TPSSLPRPIV PGPLLVPFTL NFTITNLQYE EAMRHPGSRK
10201  FNTTERVLQG LLRPLFKNTS IGPLYSSCRL TLLRPEKDKA ATRVDAICTH
10251  HPDPQSPGLN REQLYWELSQ LTHGITELGP YTLDRDSLYV DGFTHWSPIP
10301  TTSTPGTSIV NLGTSGIPPS LPETTXXXPL LXPFTLNFTI TNLXYEEXMX
10351  XPGSRKFNTT ERVLQGLLKP LFKSTSVGPL YSGCRLTLLR PEKDGVATRV
10401  DAICTHRPDP KIPGLDRQQL YWELSQLTHS ITELGPYTLD RDSLYVNGFT
10451  QRSSVPTTST PGTFTVQPET SETPSSLPGP TATGPVLLPF TLNFTITNLQ
10501  YEEDMHRPGS RKFNTTERVL QGLLMPLFKN TSVSSLYSGC RLTLlRPEKD
10551  GAATRVDAVC THRPDPKSPG LDRERLYWKL SQLTHGITEL GPYTLDRHSL
10601  YVNGFTHQSS MTTTRTPDTS TMHLATSRTP ASLSGPTTAS PLLVLFTINF
10651  TITNLRYEEN MHHPGSRKFN TTERVLQGLL RPVFKNTSVG PLYSGCRLTL
10701  LRPKKDGAAT KVDAICTYRP DPKSPGLDRE QLYWELSQLT HSITELGPYT
10751  QDRDSLYNVG FTQRSSVPTT SVPGTPTVDL GTSGTPVSKP GPSAASPLLV
10801  LFTLNGTITN LRYEENMQHP GSRKFNTTER VLQGLLRSLF KSTSVGPLYS
10851  GCRLTLLRPE KDGTATGVDA ICTHHPDPKS PRLDREQLYW ELSQLTHNIT
10901  ELGHYALDND SLFVNGFTHR SSVSTTSTPG TPTVYLGASK TPASIFGPSA
10951  ASHLLILFTL NFTITNLRYE ENMWPGSRKF NTTERVLQGL LRPLFKNTSV
11001  GPLYSGSRLT LLRPEKDGEA TGVDAICTHR PDPTGPGLDR EQLYLELSQL
11051  THSITELGPY TLDRDSLYVN GFTHRSSVPT TSTGVVSEEP FTLNFTINNL
11101  RYMADMGQPG SLKFNITDNV MKHLLSPLFQ RSSLGARYTG CRVIALRSVK
11151  NGAETRVDLL CTYLQPLSGP GLPIKQVFHE LSQQTHGITR LGPYSLDKDS
11201  LYLNGYNEPG LDEPPTTPKP ATTFLPPLSE ATTAMGYHLK TLTLNFTISN
11251  LQYSPDMGKG SATFNSTEGV LQHLLRPLFQ KSSMGPFYLG CQLISLRPEK
11301  DGAATGVDTT CYHPDPVGP GLDIQQLYWE LSQLTHGVTQ LGFYVLDRDS
11351  LFINGYAPQN LSIRGEYQIN FHIVNWNLSN PDPTSSEY
                                                              C  T  D
                                                         IT LLRDIQDKVT  a  e  o
11451  TLYKGSQLHD TFRFCLVTNL TMDSVLVTVK ALFSSNLDPS LVEQVFLDKT  .  r  r  m
```

TABLE 21-continued

CA125 Protein Sequence

```
11501 LNASFHWLGS TYQLVDIHVT EMESSVYQPT SSSSTQHFYL NFTITNLPYS . b m a
11551 QDKAQPGTTN YQRNKRNIED ALNQLFRNSS IKSYFSDCQV STFRSVPNRH . o i i
11601 HTGVDSLCNF SPLARRVDRV AIYEEFLRMT RNGTQLQNFT LDRSSVLVDG . x n n
11651 YSPNRNEPLT GNSDLPFWAV ILIGLAGLLG LITCLICGVL VTTRRRKKEG . Y a
11701 EYNVQQQCPG YYQSHLDLED LQ                                    l
```

TABLE 22

CA125 Repeat Nucleotide Sequence

```
  1 ACTGCTGGCC CTCTCCTGGT GCCATTCACC CTCAACTTCA CCATCACCAA (SEQ ID NO: 307)
 51 CCTGCAGTAT GAGGAGGACA TGCATCGCCC TGGATCTAGG AAGTTCAACA
101 CCACAGAGAG GGTCCTGCAG GGTCTGCTTA GTCCCATATT CAAGAACACC
151 AGTGTTGGCC CTCTGTACTC TGGCTGCAGA CTGACCTCTC TCAGGTCTGA
201 GAAGGATGGA GCAGCCACTG GAGTGGATGC CATCTGCATC CATCATCTTG
251 ACCCCAAAAG CCCTGGACTC AACAGAGAGC GGCTGTACTG GGAGCTGAGC
301 CGACTGACCA ATGGCATCAA AGAGCTGGGC CCCTACACCC TGGACAGGAA
351 CAGTCTCTAT GTCAATGGTT TCACCCATCG GACCTCTGTG CCCACCACCA
401 GCACTCCTGG GACTCCACA GTGGACCTTG GAACCTCAGG GACTCCATTC
451 TCCCTCCCAA GCCCCGCA
```

TABLE 23

CA125 Repeat Amino Acid Sequence

```
  1 TAGPLLVPFT LNFTITNLQY EEDMHRPGSR KFNTTERVLQ GLLSPIFKNT (SEQ ID NO: 308)
 51 SVGPLYSGCR LTSLRSEKDG AATGVDATCI HHLDPKSPGL NRERLYWELS
101 RLTNGIKELG PYTLDRNSLY VNGFTHRTSV PTTSTPGTST VDLGTSGTPF
151 SLPSPA
```

We claim:

1. An isolated recombinant polypeptide consisting of SEQ ID NO:162.

* * * * *